US007655770B1

(12) United States Patent
Cheikh et al.

(10) Patent No.: US 7,655,770 B1
(45) Date of Patent: Feb. 2, 2010

(54) NUCLEIC ACID MOLECULES AND OTHER MOLECULES ASSOCIATED WITH THE PHOSPHOGLUCONATE PATHWAY

(75) Inventors: Nordine Cheikh, Manchester, MO (US); Jingdong Liu, Ballwin, MO (US); Virginia M. Peschke, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 786 days.

(21) Appl. No.: 09/300,482

(22) Filed: Apr. 28, 1999

Related U.S. Application Data

(60) Provisional application No. 60/083,390, filed on Apr. 29, 1998.

(51) Int. Cl.
*C07H 21/00* (2006.01)
*C07K 1/00* (2006.01)
*A61K 38/00* (2006.01)

(52) U.S. Cl. ....................... 536/23.1; 530/300; 530/350

(58) Field of Classification Search ................ 536/23.1, 536/24.1, 24.7; 435/6, 69.1, 69.3, 320.1, 435/940, 7.1; 514/44; 702/20; 530/350
See application file for complete search history.

(56) References Cited

U.S. PATENT DOCUMENTS

| | | | | |
|---|---|---|---|---|
| 5,726,053 | A * | 3/1998 | Picataggio et al. | 435/252.3 |
| 5,912,169 | A * | 6/1999 | Schmidt et al. | 435/320.1 |
| 6,030,807 | A * | 2/2000 | De Lencastre et al. | 435/69.1 |

FOREIGN PATENT DOCUMENTS

WO WO 9737028 A2 * 10/1997

OTHER PUBLICATIONS

Gerhold et al., "It's the genes! EST access to human genome content", BioEssays vol. 18 No. 12, pp. 973-981.*
Wells et al., "The chemokine information source: identification and characterization of novel chemokines using the WorldWideWeb and Expressed Sequence Tag Databases", Journal of Leukocyte Biology vol. 61 No. 5, May 1997 pp. 545-550.*
Russell et al., "Structural Features can be Unconserved in Proteins with Similar Folds", J. Mol. Biol. (1994) 244, pp. 332-350.*
Attwood, "The Babel of Bioingormatics", Science vol. 290, Oct. 20, 2000.*
Katsurada, "Tezukayama-Gakuin Junior College Annual Report of Scientific Studies", (1996) No. 44 pp. 89-104.*
Katsurada, Tezukayma-Gakuin Junior Collgeg Annual Report of Scientific Studies, (1997) No. 45, pp. 58-73.*
Lal et al., "Cloning and Characterizaton of an Anaerobically Induced cDNA Encoding Glucose-6-Phosphate Isomerase from Maize", Plan Physiol. (1995) vol. 108 pp. 1295-1296.*
AB007907, GenBank, Oct. 14, 1997.*
AF037030, GenBank, Nov. 26, 1998.*
Accession D43256, GenBank, May 4, 1998.*
Accession AJ000265, GenBank, Aug. 25, 1998.*
Accession AB007907, GenBank, Oct. 15, 1997.*
Baker et al., "Proein Structure Prediction and Structural Genomics", Science vol. 294 No. 5 (Oct. 2001),pp. 93-96.*
NCBI GI # 3107516, Sequence Revision History Page for AN# D43256, seen at www.ncbi.nlm.nih.gov.*
Bouvier et al. NCBI accession No. Y15781, first seen Sep. 9, 1998.*
Walbot, V. NCBI accession No. AI586588, first seen Apr. 7, 1999.*
Meinkoth et al. Hybridization of nucleic acids immobilized on solid supports. Ananlytical Biochemistry. (1984) vol. 138, pp. 267-284.*
de Vetten et al. NCBI accession No. S77133, Sep. 22, 1995.*
Fahrendorf et al. NCBI accession No. U18238, Jan. 30, 1997.*
Moehs et al. NCBI accession No. U95923, May 11, 1997.*
Sasaki, T. NCBI accession No. C73011, Sep. 22, 1997.*
Ashihara and Komamine, "Enzyme and Metabolite Profiles of the Pentose Phosphate Pathway in Hypocotyls of *Phaseolus mungo* Seedlings" Plant Sci. Lett. 2:331-337 (1974).
Fahrendorf et al., "Stress responses in alfalfa (*Medicago sativa* L.) XIX. Transcriptional activation of oxidative pentose phosphate pathway genes at the onset of the isoflavonoid phytoalexin response," Plant Molecular Biology 28: 885-900(1995).
Fristensky et al., Entrez, Accession No. AI352951.
Kohler et al., "Transaldolase genes from the cyanobacteria *Anabaena variabilis* and *Synechocystis* sp. PCC 6803: comparison with other eubacterial and eukaryotic homologues," Plant Molecular Biology 30: 213-218 (1996).
Kohler et al., Entrez, Accession No. AAC41527.
Kohler et al., Entrez, Accession No. L47327.
Kusian et al., "The Calvin Cycle Enzyme Pentose-5-Phosphate 3-Epimerase is Encoded within the *cfx* Operons of the Chemoautotroph *Alcaligenes eutrophus*," J. of Bacteriology 174:7337-7344 (1992).
Kusian et al., Entrez, Accession No. AAA21962.
Kusian et al., Entrez, Accession No. M64173.
Lin et al., Entrez, Accession No. AAD14543.
Lin et al., Entrez, Accession No. AC006200.

(Continued)

*Primary Examiner*—Eric S Dejong
(74) *Attorney, Agent, or Firm*—Matthew L. Madsen; Ying-Horng Liu; Arnold & Porter LLP

(57) ABSTRACT

The present invention is in the field of plant biochemistry. More specifically the invention relates to nucleic acid sequences from plant cells, in particular, nucleic acid sequences from maize and soybean associated with the phosphogluconate pathway enzymes. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

16 Claims, No Drawings

OTHER PUBLICATIONS

Ma et al., "Cloning and Characterization of the *Pseudomonas aeruginosa zwf* Gene Encoding Glucose-6-Phosphate Dehydrogenase, an Enzyme Important in Resistance to Methyl Viologen (Pharaquat)," J. Bacteriol. 180:1741-1749 (1998).

Ma et al., Entrez, Accession No. AAD22666.

Ma et al., Entrez, Accession No. AF029673.

Mandel et al., "*CLA1*, a novel gene required for chloroplast development, is highly conserved in evolution," Plant J. 9:649-658 (1996).

Mandel et al., Entrez, Accession No. U27099.

Marra et al., Entrez, Accession No. AA162843.

Moehs et al., "Cloning and expression of transaldolase from potato," Plant Mol. Biol. 32:447-452 (1996).

Redinbaugh et al., Entrez, Accession No. AAC27702.

Redinbaugh et al., Entrez, Accession No. AF061837.

Schnarrenberger et al., "Enzymatic Evidence for a Complete Oxidative Pentose Phosphate Pathway in Chloroplasts and an Incomplete Pathway in the Cytosol of Spinach Leaves," Plant Physiol. 108:609-614(1995).

Teige et al., "Chloroplast pentose-5-phosphate 3-epimerase from potato:cloning, cDNA sequence, and tissue-specific enzyme accumulation," FEBS Letters 377:349-352 (1995).

Williams, John F., "A critical examination of the evidence for the reactions of the pentose pathway in animal tissues," Trends in Biochemical Sciences 5: 315-320 (1980).

*Entrez Report*, Accession No. CAA52442, Sep. 21, 1994.

K. Graeve, et al., "Purification, characterization, and cDNA sequence of glucose-6-phosphate dehydrogenase from potato (*Solanum tuberosum* L.)," *The Plant Journal* 5 (3), 353-361 (1994).

*Entrez Report*, Accession No. CAA89415, Aug. 11, 1997.

C. Cziepluch, et al., "Sequencing analysis of a 40.2 kb fragment of yeast chromosome X reveals 19 open reading frames including URA2 (5' end), TRK1, PBS2, SPT10, GCD14, RPE1, PHO86, NCA3, ASF1, CCT7, GZF3, Two tRNA genes, three remnant delta elements and a Ty4 transposon," *Yeast* 12 (14) 1471-1474 (1996).

T. Miosga, et al., "Genetic and Function Analysis of the *Saccharomyces cerevisiae* Gene Ep11 Encoding Ribulose-5-Phosphat 3-Epimerase," *Yeast* 11,5500 (1995).

T. Miosga, et al., "Cloning and characterization of the first two genes of the non-oxidative part of the *Saccharomyces cerevisiae* pentose-phosphate pathway," *Curr. Genet.* 30 (5), 404-409 (1996).

*Entrez Report*, Accession No. Z46646, Feb. 6, 1995.

G. Bernacchia, et al., "The transketolase gene family of the resurrection plant *Craterostigma plantagineum*: differential expression during the rehydration phase," *EMBO Journal* 14 (3), 610-618 (1995).

*Entrez Report*, Accession No. AAB54016, May 11, 1997.

C. Moehs, et al., "Cloning and expression of transaldolase from potato," *Plant Molecular Biology* 32 (3), 447-452, (1996).

*Entrez Report*, Accession No. AAC75951, Dec. 1, 2000.

F. Blattner, et al., "The complete genome sequence of *Escherichia coli* K-12," *Science* 277 (5331), 1453-1474 (1997).

*Entrez Report*, Accession No. BAA02920, Feb. 3, 1999.

T. Sakamoto, et al., "Sequence analysis of a DNA fragment from *Synechocystis* PCC6803 containing genes homologous to cysE (serine acetyltransferase) and pgi (gucose-6-phosphate isomerase)," *Plant Mol. Biol.* 29, 187 (1995).

Venter, J. Craig, et al., The Sequence of the Human Genome, *Science*, 291: 1304-1351 (2001).

Woese, Carl R., et al., Conservation of Primary Structure in 16S rRNA, *Nature*, 254: 83-85 (1975).

* cited by examiner

NUCLEIC ACID MOLECULES AND OTHER MOLECULES ASSOCIATED WITH THE PHOSPHOGLUCONATE PATHWAY

CROSS REFERENCE TO RELATED APPLICATIONS

This application claims priority under 35 U.S.C. § 119(e) to application Ser. No. 60/083,390, filed Apr. 29, 1998, which is herein incorporated by reference in its entirety.

INCORPORATION OF SEQUENCE LISTING

A paper copy of the Sequence Listing and a computer readable form of the Sequence Listing on diskette, containing the file named "phosphoglucseq.rpt", which is 330,491 bytes in size (measured in MS-DOS), and which was created on Apr. 28, 1999, are herein incorporated by reference.

FIELD OF THE INVENTION

The present invention is in the field of plant biochemistry. More specifically the invention relates to nucleic acid sequences from plant cells, in particular, nucleic acid sequences from maize and soybean plants associated with the phosphogluconate pathway in plants. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

BACKGROUND OF THE INVENTION

I. Phosphogluconate Pathway

The phosphogluconate pathway (OPPP) (also known as the oxidative pentose phosphate pathway, pentose phosphate shunt, or Warburg-Dickens pathway) is one of the two major pathways in plants by which carbohydrates may be ultimately degraded into $CO_2$, the other being glycolysis followed by the TCA cycle (Brownleader et al., In: *Plant Biochemistry* Academic Press, New York, pp. 111-141, (1997), the entirety of which is herein incorporated by reference). It has been reported that the OPPP generally accounts for 10-15% of the carbohydrate oxidation in cells (apRees In: *The Biochemistry of Plants Vol* 3:1-42, (1980), the entirety of which is herein incorporated by reference). It has been reported that the primary purposes of the OPPP is production of NADPH for use in biosynthetic reactions and the production of a ribose-5-phosphate for use in nucleic acid biosynthesis (Turner and Turner, In: *Biochemistry of Plants—A Comprehensive Treatise Vol* 2:279-316, (1980), the entirety of which is herein incorporated by reference). The subcellular localization of this pathway has been reported to differ between species, cell type, and plastid type being investigated. For example, reported cellular fractionation experiments in spinach leaf cells showed all enzymes of the phosphogluconate pathway were found in chloroplasts, but that only the first two enzymes of that pathway are present in the cytosol (Schnarrenberger et al., *Plant Physiol.* 108:609-614, (1995), the entirety of which is herein incorporated by reference).

In general, OPPP can be divided into two parts, oxidative (the reactions leading up to ribulose-5-phosphate), and non-oxidative (e.g. Williams, *Trends Biochem. Sci.* 5:315-320, (1980); apRees, In: *Encyclopedia of Plant Physiology Vol* 18 pp. 391-417, (1985), all of which references are incorporated herein in their entirety).

The first reported reaction of OPPP is the conversion of glucose-6-phosphate by glucose-6-phosphate dehydrogenase (G6PDH; EC 1.1.1.49) to 6-phosphogluconolactone. The hydrolysis of 6-phosphogluconolactone to 6-phosphogluconate can occur in a nonenzymatically manner or be catalyzed by a lactonase. This reaction is not at equilibrium and is irreversible (Ashihara and Komamine, *Plant Sci. Lett.* 2:331-337 (1974), the entirety of which is herein incorporated by reference; Turner and Turner, In: *Biochemistry of Plants—A Comprehensive Treatise Vol* 2:279-316, (1980)). The hydrolysis of 6-phosphogluconolactone to 6-phosphogluconate is reported to be a critical regulatory step in the phosphogluconate pathway. The hydrolysis of 6-phosphogluconolactone to 6-phosphogluconate has been reported to respond to the concentration of glucose-6-phosphate as well as the NADPH/NADP+ ratio. Inhibition of the hydrolysis of 6-phosphogluconolactone to 6-phosphogluconate by NADPH is consistent with the function of OPPP to provide NADPH (apRees, In: *The Biochemistry of Plants Vol* 3:1-42, (1980)). cDNA clones for G6PDH have been isolated from several plants including alfalfa (Fahrendorf et al., *Plant Mol. Biol.* 28: 885-900, (1995), the entirety of which is herein incorporated by reference) and potato (Graeve et al., *Plant J.* 5:353-361, (1994), the entirety of which is herein incorporated by reference).

6-phosphogluconate is dehydrogenated to ribulose-5-phosphate, NADPH, and $CO_2$ in an irreversible reaction catalyzed by 6-phosphogluconate dehydrogenase (6PGDH; EC 1.1.1.44). A cDNA clone for 6PGDH has been isolated from alfalfa (Fahrendorf et al., *Plant Mol Biol* 28: 885-900, (1995)). The first two steps of the OPPP are the only reported oxidation reactions in that pathway. Other reactions within OPPP serve to regenerate glucose-6-phosphate, as well as producing intermediates such as ribose-5-phosphate that are utilized in nucleic acid biosynthesis.

Ribulose-5-phosphate may be metabolized in one of two pathways. Ribose-5-phosphate isomerase (EC 5.3.1.6) catalyzes the conversion of ribulose-5-phosphate to ribose-5-phosphate, while ribulose-5-phosphate-3-epimerase (also known as pentose-5-phosphate-3-epimerase; EC 5.1.3.1) catalyzes the conversion of ribulose-5-phosphate to xylulose-5-phosphate. Transketolase (EC 2.2.1.1) catalyzes the conversion of ribulose-5-phosphate and xylulose-5-phosphate into sedheptulose-7-phosphate and 3-phosphoglyceraldehyde. Transaldolase (EC 2.2.1.2) catalyzes the conversion of sedheptulose-7-phosphate and 3-phosphoglyceraldehyde into erythrose-4-phosphate and fructose-6-phosphate.

Erythrose-4-phosphate is a substrate associated with the biosynthesis of lignin (Salisbury and Ross, *Plant Physiology*, Wadsworth Publishing Company, Belmont Calif., (1978), the entirety of which is herein incorporated by reference), or the production of aromatic amino acids via the shikimate pathway (Schnarrenberger et al., *Plant Physiol.* 108:609-614, (1995), the entirety of which is herein incorporated by reference). Clones for potato transaldolase (Moehs et al., *Plant Mol. Biol.* 32:447-452, (1996), the entirety of which is herein incorporated by reference); spinach transketolase (Flechner et al., *Plant Mol. Biol.* 32:475-484, (1996), the entirety of which is herein incorporated by reference); potato ribulose-5-phosphate-3-epimerase (Teige et al., *FEBS Lett.* 377:349-352, (1995), the entirety of which is herein incorporated by reference); and spinach ribulose-5-phosphate-3-epimerase (Nowitzki et al., *Plant Mol. Biol.* 29:1279-1291, (1995), the entirety of which is herein incorporated by reference) have been reported.

Fructose-6-phosphate may enter glycolysis (apRees, In: *The Biochemistry of Plants Vol* 3:1-42, (1980)). Fructose-6-phosphate can also be converted to glucose-6-phosphate via phosphohexose isomerase (also known as phosphoglucoisomerase) (EC5.3.1.9). Glucose-6-phosphate can be recycled in the OPPP pathway or be utilized during the synthesis of polysaccharides.

Transketolase (EC2.2.1.1) can catalyze the conversion of erythrose-4-phosphate and xylulose-5-phosphate to fructose 6-phosphate and 3-phosphoglyceraledehyde. Likewise, fructose 6-phosphate and 3-phosphoglyceraledehyde may be used in reactions as described above.

II. Expressed Sequence Tag Nucleic Acid Molecules

Expressed sequence tags, or ESTs are randomly sequenced members of a cDNA library (or complementary DNA) (McCombie et al., *Nature Genetics* 1:124-130 (1992); Kurata et al., *Nature Genetics* 8: 365-372 (1994); Okubo, et al. *Nature Genetics* 2: 173-179 (1992), all of which references are incorporated herein in their entirety). The randomly selected clones comprise insets that can represent a copy of up to the full length of a mRNA transcript.

Using conventional methodologies, cDNA libraries can be constructed from the mRNA (messenger RNA) of a given tissue or organism using poly dT primers and reverse transcriptase (Efstratiadis et al., *Cell* 7:279-288 (1976), the entirety of which is herein incorporated by reference; Higuchi et al., *Proc. Natl. Acad. Sci.* (*U.S.A.*) 73:3146-3150 (1976), the entirety of which is herein incorporated by reference; Maniatis et al., *Cell* 8:163-182 (1976) the entirety of which is herein incorporated by reference; Land et al., *Nucleic Acids Res.* 9:2251-2266 (1981), the entirety of which is herein incorporated by reference; Okayama et al., *Mol. Cell. Biol.* 2:161-170 (1982), the entirety of which is herein incorporated by reference; Gubler et al., *Gene* 25:263-269 (1983), the entirety of which is herein incorporated by reference).

Several methods may be employed to obtain full-length cDNA constructs. For example, terminal transferase can be used to add homopolymeric tails of dC residues to the free 3' hydroxyl groups (Land et al., *Nucleic Acids Res.* 9:2251-2266 (1981), the entirety of which is herein incorporated by reference). This tail can then be hybridized by a poly dG oligo which can act as a primer for the synthesis of full length second strand cDNA. Okayama and Berg, *Mol. Cell. Biol.* 2: 161-170 (1982), the entirety of which is herein incorporated by reference, report a method for obtaining full length cDNA constructs. This method has been simplified by using synthetic primer-adapters that have both homopolymeric tails for priming the synthesis of the first and second strands and restriction sites for cloning into plasmids (Coleclough et al., *Gene* 34:305-314 (1985), the entirety of which is herein incorporated by reference) and bacteriophage vectors (Krawinkel et al., *Nucleic Acids Res.* 14:1913 (1986), the entirety of which is herein incorporated by reference; Han et al., *Nucleic Acids Res.* 15:6304 (1987), the entirety of which is herein incorporated by reference).

These strategies have been coupled with additional strategies for isolating rare mRNA populations. For example, a typical mammalian cell contains between 10,000 and 30,000 different mRNA sequences (Davidson, *Gene Activity in Early Development,* 2nd ed., Academic Press, New York (1976). The number of clones required to achieve a given probability that a low-abundance mRNA will be present in a cDNA library is $N=(1n(1-P))/(1n(1-1/n))$ where N is the number of clones required, P is the probability desired, and 1/n is the fractional proportion of the total mRNA that is represented by a single rare mRNA (Sambrook et al., *Molecular Cloning: A Laboratory Manual,* 2nd ed., Cold Spring Harbor Laboratory Press (1989), the entirety of which is herein incorporated by reference).

A method to enrich preparations of mRNA for sequences of interest is to fractionate by size. One such method is to fractionate by electrophoresis through an agarose gel (Pennica et al., *Nature* 301:214-221 (1983), the entirety of which is herein incorporated by reference). Another ilk such method employs sucrose gradient centrifugation in the presence of an agent, such as methylmercuric hydroxide, that denatures secondary structure in RNA (Schweinfest et al., *Proc. Natl. Acad. Sci.* (*U.S.A.*) 79:4997-5000 (1982), the entirety of which is herein incorporated by reference).

A frequently adopted method is to construct equalized or normalized cDNA libraries (Ko, *Nucleic Acids Res.* 18:5705-5711 (1990), the entirety of which is herein incorporated by reference; Patanjali, S. R. et al., *Proc. Natl. Acad. Sci.* (*U.S.A.*) 88:1943-1947 (1991), the entirety of which is herein incorporated by reference). Typically, the cDNA population is normalized by subtractive hybridization (Schmid et al., *J. Neurochem.* 48:307-312 (1987) the entirety of which is herein incorporated by reference; Fargnoli et al., *Anal. Biochem.* 187:364-373 (1990) the entirety of which is herein incorporated by reference; Travis et al., *Proc. Natl. Acad. Sci.* (*U.S.A.*) 85:1696-1700 (1988) the entirety of which is herein incorporated by reference; Kato, *Eur. J. Neurosci.* 2:704-711 (1990); and Schweinfest et al., *Genet. Anal. Tech. Appl.* 7:64-70 (1990), the entirety of which is herein incorporated by reference). Subtraction represents another method for reducing the population of certain sequences in the cDNA library (Swaroop et al., *Nucleic Acids Res.* 19:1954 (1991), the entirety of which is herein incorporated by reference).

ESTs can be sequenced by a number of methods. Two basic methods may be used for DNA sequencing, the chain termination method of Sanger et al., *Proc. Natl. Acad. Sci.* (*U.S.A.*) 74: 5463-5467 (1977), the entirety of which is herein incorporated by reference, and the chemical degradation method of Maxam and Gilbert, *Proc. Nat. Acad. Sci.* (*U.S.A.*) 74: 560-564 (1977), the entirety of which is herein incorporated by reference. Automation and advances in technology such as the replacement of radioisotopes with fluorescence-based sequencing have reduced the effort required to sequence DNA (Craxton, *Methods* 2: 20-26 (1991), the entirety of which is herein incorporated by reference; Ju et al., *Proc. Natl. Acad. Sci.* (*U.S.A.*) 92: 4347-4351 (1995), the entirety of which is herein incorporated by reference; Tabor and Richardson, *Proc. Natl. Acad. Sci.* (*U.S.A.*) 92: 6339-6343 (1995), the entirety of which is herein incorporated by reference). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, *Nucleic Acids Res.* 18:1415-1419 (1990); Smith, *Nature* 349:812-813 (1991); Luckey et al., *Methods Enzymol.* 218:154-172 (1993); Lu et al., *J. Chromatog. A.* 680:497-501 (1994); Carson et al., *Anal. Chem.* 65:3219-3226 (1993); Huang et al., *Anal. Chem.* 64:2149-2154 (1992); Kheterpal et al., *Electrophoresis* 17:1852-1859 (1996); Quesada and Zhang, *Electro-*

*phoresis* 17:1841-1851 (1996); Baba, *Yakugaku Zasshi* 117: 265-281 (1997), all of which are herein incorporated by reference in their entirety).

ESTs longer than 150 nucleotides have been found to be useful for similarity searches and mapping (Adams et al., *Science* 252:1651-1656 (1991), herein incorporated by reference). ESTs, which can represent copies of up to the full length transcript, may be partially or completely sequenced. Between 150-450 nucleotides of sequence information is usually generated as this is length of sequence information that is routinely and reliably produced using single run sequence data. Typically, only single run sequence data is obtained from the cDNA library (Adams et al., *Science* 252: 1651-1656 (1991). Automated single run sequencing typically results in an approximately 2-3% error or base ambiguity rate (Boguski et al., *Nature Genetics* 4:332-333 (1993), the entirety of which is herein incorporated by reference).

EST databases have been constructed or partially constructed from, for example, *C. elegans* (McCombrie et al., *Nature Genetics* 1: 124-131 (1992)), human liver cell line HepG2 (Okubo et al., *Nature Genetics* 2:173-179 (1992)), human brain RNA (Adams et al., *Science* 252:1651-1656 (1991)); Adams et al., *Nature* 355:632-635 (1992)), *Arabidopsis*, (Newman et al., *Plant Physiol.* 106:1241-1255 (1994)); and rice (Kurata et al., *Nature Genetics* 8:365-372 (1994)).

III. Sequence Comparisons

A characteristic feature of a protein or DNA sequence is that it can be compared with other known protein or DNA sequences. Sequence comparisons can be undertaken by determining the similarity of the test or query sequence with sequences in publicly available or proprietary databases ("similarity analysis") or by searching for certain motifs ("intrinsic sequence analysis") (e.g. cis elements) (Coulson, *Trends in Biotechnology* 12: 76-80 (1994), the entirety of which is herein incorporated by reference); Birren et al., *Genome Analysis* 1: Cold Spring Harbor Laboratory Press, Cold Spring Harbor, N.Y. 543-559 (1997), the entirety of which is herein incorporated by reference).

Similarity analysis includes database search and alignment. Examples of public databases include the DNA Database of Japan (DDBJ) (world wide web at ddbj.nig.ac jpx); Genebank and the European Molecular Biology Laboratory Nucleic Acid Sequence Database (EMBL) A number of different search algorithms have been developed, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology* 12: 76-80 (1994); Birren et al., *Genome Analysis* 1: Cold Spring Harbor Laboratory Press, Cold Spring Harbor, N.Y. 543-559 (1997)).

BLASTN takes a nucleotide sequence (the query sequence) and its reverse complement and searches them against a nucleotide sequence database. BLASTN was designed for speed, not maximum sensitivity, and may not find distantly related coding sequences. BLASTX takes a nucleotide sequence, translates it in three forward reading frames and three reverse complement reading frames, and then compares the six translations against a protein sequence database. BLASTX is useful for sensitive analysis of preliminary (single-pass) sequence data and is tolerant of sequencing errors (Gish and States, *Nature Genetics* 3: 266-272 (1993), the entirety of which is herein incorporated by reference). BLASTN and BLASTX may be used in concert for analyzing EST data (Coulson, *Trends in Biotechnology* 12: 76-80 (1994); Birren et al., *Genome Analysis* 1: 543-559 (1997)).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins* 17: 49-61 (1993), the entirety of which is herein incorporated by reference), which is currently the default choice for BLAST programs. BLOSUM62 is tailored for alignments of moderately diverged sequences and thus may not yield the best results under all conditions. Altschul, *J. Mol. Biol.* 36: 290-300 (1993), the entirety of which is herein incorporated by reference, describes a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package that performs progressive multiple sequence alignments based on the method of Feng and Doolittle, *J. Mol. Evol.* 25: 351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices, or supply their own scoring matrix for both pairwise alignments and multiple alignments. CLUSTAL W for UNIX and VMS systems is available at: ftp.ebi.ac.uk. Another program is MACAW (Schuler et al., *Proteins Struct. Func. Genet.* 9: 180-190 (1991), the entirety of which is herein incorporated by reference, for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of sequence motifs in the world is PROSITE (Bairoch and Bucher, *Nucleic Acid*

*Research* 22: 3583-3589 (1994), the entirety of which is herein incorporated by reference). PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by S. Henikoff, *Trends Biochem Sci.* 18:267-268 (1993), the entirety of which is herein incorporated by reference; Henikoff and Henikoff, *Nucleic Acid Research* 19:6565-6572 (1991), the entirety of which is herein incorporated by reference; Henikoff and Henikoff, *Proteins,* 17: 49-61 (1993). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein query or a nucleotide query can be submitted to the BLOCKS server; if a nucleotide sequence is submitted, the sequence is translated in all six reading frames and motifs are sought for these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches (such as GCG program ProfileSearch) and Hidden Markov Models (HMMs) (Krough. et al., *J. Mol. Biol.* 235:1501-1531, (1994); Eddy, *Current Opinion in Structural Biology,* 6:361-365, (1996), both of which are herein incorporated by reference in their entirety). In both cases, a large number of common protein domains have been converted into profiles, as present in the PROSITE library, or HHM models, as in the Pfam protein domain library (Sonnhammer et al., *Proteins* 28:405-420 (1997), the entirety of which is herein incorporated by reference). Pfam contains more than 500 HMM models for enzymes, transcription factors, signal transduction molecules, and structural proteins. Protein databases can be queried with these profiles or HMM models, which will identify proteins containing the domain of interest. For example, HMMSW or HMMFS, two programs in a public domain package called HMMER (Sonnhammer et al., *Proteins* 28:405-420, (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov et al. *Proc. Natl. Acad. Sci.* 91: 12091-12095 (1994), the entirety of which is herein incorporated by reference). On the basis of an aligned set of input sequences, a weight matrix is calculated by using one of four methods (selected by the user). A weight matrix is simply a representation, position by position of how likely a particular amino acid will appear. The calculated weight matrix is then used to search the databases. To increase sensitivity, newly found sequences are added to the original data set, the weight matrix is recalculated, and the search is performed again. This procedure continues until no new sequences are found.

SUMMARY OF THE INVENTION

The present invention provides a substantially purified nucleic acid molecule that encodes a maize or soybean phosphogluconate pathway enzyme or fragment thereof, wherein the maize or soybean phosphogluconate pathway enzyme is selected from the group consisting of: (a) glucose-6-phosphate-1-dehydrogenase; (b) 6-phosphogluconate dehydrogenase; (c) putative 6-phosphogluconate dehydrogenase; (d) D-ribulose-5-phosphate-3-epimerase; (e) ribose-5-phosphate isomerase; (f) putative ribose-5-phosphate isomerase; (g) transketolase; (h) putative transketolase; (i) transaldolase; (j) putative transaldolase; and (k) phosphoglucoisomerase.

The present invention also provides a substantially purified nucleic acid molecule that encodes a plant phosphogluconate pathway enzyme or fragment thereof, wherein the nucleic acid molecule is selected from the group consisting of a nucleic acid molecule that encodes a maize or soybean glucose-6-phosphate-1-dehydrogenase enzyme or fragment thereof; a nucleic acid molecule that encodes a maize or soybean 6-phosphogluconate dehydrogenase enzyme or fragment thereof; a nucleic acid molecule that encodes a putative maize or soybean 6-phosphogluconate dehydrogenase enzyme or fragment thereof; a nucleic acid molecule that encodes a maize or soybean D-ribulose-5-phosphate-3-epimerase enzyme or fragment thereof; a nucleic acid molecule that encodes a maize or soybean ribose-5-phosphate isomerase enzyme or fragment thereof; a nucleic acid molecule that encodes a putative maize or soybean ribose-5-phosphate isomerase enzyme or fragment thereof; a nucleic acid molecule that encodes a maize or soybean transketolase enzyme or fragment thereof; a nucleic acid molecule that encodes a putative maize or soybean transketolase enzyme or fragment thereof; a nucleic acid molecule that encodes a maize or soybean transaldolase enzyme or fragment thereof; a nucleic acid molecule that encodes a maize putative transaldolase enzyme or fragment thereof; and a nucleic acid molecule that encodes a maize or soybean phosphoglucoisomerase enzyme or fragment thereof.

The present invention also provides a substantially purified maize or soybean phosphogluconate pathway enzyme or fragment thereof, wherein the maize or soybean phosphogluconate pathway enzyme is selected from the group consisting of (a) glucose-6-phosphate-1-dehydrogenase or fragment thereof; (b) 6-phosphogluconate dehydrogenase or fragment thereof; (c) putative 6-phosphogluconate dehydrogenase or fragment thereof; (d) D-ribulose-5-phosphate-3-epimerase or fragment thereof; (e) ribose-5-phosphate isomerase or fragment thereof; (f) putative ribose-5-phosphate isomerase or fragment thereof; (g) transketolase or fragment thereof; (h) putative transketolase or fragment thereof; (i) transaldolase or fragment thereof; (j) putative transaldolase or fragment thereof; and (k) phosphoglucoisomerase or fragment thereof.

The present invention also provides a substantially purified maize or soybean phosphogluconate pathway enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 699.

The present invention also provides a substantially purified maize or soybean glucose-6-phosphate-1-dehydrogenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 3 and SEQ ID NO: 4 through SEQ ID NO: 11.

The present invention also provides a substantially purified maize or soybean glucose-6-phosphate-1-dehydrogenase enzyme or fragment thereof encoded by a nucleic acid sequence selected from the group consisting of SEQ ID NO: 1 through SEQ ID NO: 3 and SEQ ID NO: 4 through SEQ ID NO: 11.

The present invention also provides a substantially purified maize or soybean 6-phosphogluconate dehydrogenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 12 through SEQ ID NO: 21 and SEQ ID NO: 22 through SEQ ID NO: 103.

The present invention also provides a substantially purified maize or soybean 6-phosphogluconate dehydrogenase enzyme or fragment thereof encoded by a nucleic acid sequence selected from the group consisting of SEQ ID NO: 12 through SEQ ID NO:21 and SEQ ID NO: 22 through SEQ ID NO: 103.

The present invention also provides a substantially purified putative maize or soybean 6-phosphogluconate dehydrogenase enzyme or fragment thereof enzyme or fragment thereof encoded by a first nucleic acid molecule which specifically hybridizes to a second nucleic acid molecule, the second nucleic acid molecule having a nucleic acid sequence of a complement of SEQ ID NO: 104 through SEQ ID NO: 209 and SEQ ID NO: 210 through SEQ ID NO: 214.

The present invention also provides a substantially purified putative maize or soybean 6-phosphogluconate dehydrogenase enzyme or fragment thereof encoded by a nucleic acid sequence of SEQ ID NO: 104 through SEQ ID NO: 209 and SEQ ID NO: 210 through SEQ ID NO: 214.

The present invention also provides a substantially purified maize or soybean D-ribulose-5-phosphate-3-epimerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 215 through SEQ ID NO: 260 and SEQ ID NO: 261 through SEQ ID NO: 299.

The present invention also provides a substantially purified maize or soybean D-ribulose-5-phosphate-3-epimerase enzyme or fragment thereof encoded by a nucleic acid sequence selected from the group consisting of SEQ ID NO: 215 through SEQ ID NO: 260 and SEQ ID NO: 261 through SEQ ID NO: 299.

The present invention also provides a substantially purified maize or soybean ribose-5-phosphate isomerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 300 through SEQ ID NO: 306 and SEQ ID NO: 307 through SEQ ID NO: 311.

The present invention also provides a substantially purified maize or soybean ribose-5-phosphate isomerase enzyme or fragment thereof encoded by a nucleic acid sequence selected from the group consisting of SEQ ID NO: 300 through SEQ ID NO: 306 and SEQ ID NO: 307 through SEQ ID NO: 311.

The present invention also provides a substantially purified putative maize or soybean ribose-5-phosphate isomerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 312 through SEQ ID NO: 313 and SEQ ID NO: 314 through SEQ ID NO: 318.

The present invention also provides a substantially purified putative maize or soybean ribose-5-phosphate isomerase enzyme or fragment thereof encoded by a nucleic acid sequence selected from the group consisting of SEQ ID NO: 312 through SEQ ID NO: 313 and SEQ ID NO: 314 through SEQ ID NO: 318.

The present invention also provides a substantially purified maize or soybean transketolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 319 through SEQ ID NO: 356 and SEQ ID NO: 357 through SEQ ID NO: 437.

The present invention also provides a substantially purified maize or soybean transketolase enzyme or fragment thereof encoded by a nucleic acid sequence selected from the group consisting of SEQ ID NO: 319 through SEQ ID NO: 356 and SEQ ID NO: 357 through SEQ ID NO: 437.

The present invention also provides a substantially purified putative maize or soybean transketolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 438 through SEQ ID NO: 447 and SEQ ID NO: 448 through SEQ ID NO: 453.

The present invention also provides a substantially purified putative maize or soybean transketolase enzyme or fragment thereof encoded by a nucleic acid sequence selected from the group consisting of SEQ ID NO: 438 through SEQ ID NO: 447 and SEQ ID NO: 448 through SEQ ID NO: 453.

The present invention also provides a substantially purified maize or soybean transaldolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 454 through SEQ ID NO: 533 and SEQ ID NO: 534 through SEQ ID NO: 617.

The present invention also provides a substantially purified maize or soybean transaldolase enzyme or fragment thereof encoded by a nucleic acid sequence selected from the group consisting of SEQ ID NO: 454 through SEQ ID NO: 533 and SEQ ID NO: 534 through SEQ ID NO: 617.

The present invention also provides a substantially purified putative maize transaldolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 618.

The present invention also provides a substantially purified putative maize transaldolase enzyme or fragment thereof encoded by a nucleic acid sequence selected from the group consisting of SEQ ID NO: 618.

The present invention also provides a substantially purified maize or soybean phosphoglucoisomerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 619 through SEQ ID NO: 683 and SEQ ID NO: 684 through SEQ ID NO: 699.

The present invention also provides a substantially purified maize or soybean phosphoglucoisomerase enzyme or fragment thereof encoded by a nucleic acid sequence selected from the group consisting of SEQ ID NO: 619 through SEQ ID NO: 683 and SEQ ID NO: 684 through SEQ ID NO: 699.

The present invention also provides a purified antibody or fragment thereof which is capable of specifically binding to a maize or soybean phosphogluconate pathway enzyme or fragment thereof, wherein the maize or soybean phosphogluconate pathway enzyme or fragment thereof is encoded by a nucleic acid molecule comprising a nucleic acid sequence selected from the group consisting of SEQ ID NO: 1 through SEQ ID NO: 699.

The present invention also provides a substantially purified antibody or fragment thereof, the antibody or fragment thereof capable of specifically binding to a substantially purified maize or soybean glucose-6-phosphate-1-dehydrogenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 3 and SEQ ID NO: 4 through SEQ ID NO: 11.

The present invention also provides a substantially purified antibody or fragment thereof, the antibody or fragment thereof capable of specifically binding to a maize or soybean 6-phosphogluconate dehydrogenase enzyme or fragment thereof encoded by a first nucleic acid molecule which specifically hybridizes to a second nucleic acid molecule, the second nucleic acid molecule having a nucleic acid sequence consisting of a complement of SEQ ID NO: 12 through SEQ ID NO: 21 and SEQ ID NO: 22 through SEQ ID NO: 103.

The present invention also provides a substantially purified antibody or fragment thereof, the antibody or fragment thereof capable of specifically binding to a putative maize or soybean 6-phosphogluconate dehydrogenase enzyme or fragment thereof enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 104 through SEQ ID NO: 209 and SEQ ID NO: 210 through SEQ ID NO: 214.

The present invention also provides a substantially purified antibody or fragment thereof, the antibody or fragment thereof capable of specifically binding to a maize or soybean D-ribulose-5-phosphate-3-epimerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 215 through SEQ ID NO: 260 and SEQ ID NO: 261 through SEQ ID NO: 299.

The present invention also provides a substantially purified antibody or fragment thereof, the antibody or fragment thereof capable of specifically binding to a maize or soybean ribose-5-phosphate isomerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 300 through SEQ ID NO: 306 and SEQ ID NO: 307 through SEQ ID NO: 311.

The present invention also provides a substantially purified antibody or fragment thereof, the antibody or fragment thereof capable of specifically binding to a putative maize or soybean ribose-5-phosphate isomerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 312 through SEQ ID NO: 313 and SEQ ID NO: 314 through SEQ ID NO: 318.

The present invention also provides a substantially purified antibody or fragment thereof, the antibody or fragment thereof capable of specifically binding to a maize or soybean transketolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 319 through SEQ ID NO: 356 and SEQ ID NO: 357 through SEQ ID NO: 437.

The present invention also provides a substantially purified antibody or fragment thereof, the antibody or fragment thereof capable of specifically binding to a putative maize or soybean transketolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 438 through SEQ ID NO: 447 and SEQ ID NO: 448 through SEQ ID NO: 453.

The present invention also provides a substantially purified antibody or fragment thereof, the antibody or fragment thereof capable of specifically binding to a maize or soybean transaldolase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 454 through SEQ ID NO: 533 and SEQ ID NO: 534 through SEQ ID NO: 617.

The present invention also provides a substantially purified antibody or fragment thereof, the antibody or fragment thereof capable of specifically binding to a putative maize transaldolase enzyme or fragment thereof encoded by a first nucleic acid molecule which specifically hybridizes to a second nucleic acid molecule, the second nucleic acid molecule having a nucleic acid sequence consisting of a complement of SEQ ID NO: 618.

The present invention also provides a substantially purified antibody or fragment thereof, the antibody or fragment thereof capable of specifically binding to a maize or soybean phosphoglucoisomerase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 619 through SEQ ID NO: 683 and SEQ ID NO: 684 through SEQ ID NO: 699.

The present invention also provides a transformed plant having a nucleic acid molecule which comprises: (A) an exogenous promoter region which functions in a plant cell to cause the production of a mRNA molecule; (B) a structural nucleic acid molecule comprising a nucleic acid sequence selected from the group consisting of (a) a nucleic acid sequence which encodes for a glucose-6-phosphate-1-dehydrogenase enzyme or fragment thereof; (b) a nucleic acid sequence which encodes for a 6-phosphogluconate dehydrogenase enzyme or fragment thereof; (c) a nucleic acid sequence which encodes for a putative 6-phosphogluconate dehydrogenase enzyme or fragment thereof; (d) a nucleic acid sequence which encodes for a D-ribulose-5-phosphate-3-epimerase enzyme or fragment thereof; (e) a nucleic acid sequence which encodes for a ribose-5-phosphate isomerase enzyme or fragment thereof; (f) a nucleic acid sequence which encodes for a putative ribose-5-phosphate isomerase enzyme or fragment thereof; (g) a nucleic acid sequence which encodes for a transketolase enzyme or fragment thereof; (h) a nucleic acid sequence which encodes for a putative transketolase enzyme or fragment thereof; (i) a nucleic acid sequence which encodes for a transaldolase enzyme or fragment thereof; (j) a nucleic acid sequence which encodes for a putative transaldolase enzyme or fragment thereof; (k) a nucleic acid sequence which encodes for a phosphoglucoisomerase enzyme or fragment thereof and (l) a nucleic acid sequence which is complementary to any of the nucleic acid sequences of (a) through (k); and (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule encodes a plant phosphogluconate pathway enzyme or fragment thereof, the structural nucleic acid molecule comprising a nucleic acid sequence selected from the group consisting of SEQ ID NO: 1 through SEQ ID NO: 699 or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule is selected from the group consisting of a nucleic acid molecule that encodes for a glucose-6-phosphate-1-dehydrogenase enzyme or fragment thereof; a nucleic acid molecule that encodes for a 6-phosphogluconate dehydrogenase enzyme or fragment thereof; a nucleic acid molecule that encodes for a putative 6-phosphogluconate dehydrogenase enzyme or fragment thereof; a nucleic acid molecule that encodes for a D-ribulose-5-phosphate-3-epimerase enzyme or fragment thereof; a nucleic acid molecule that encodes for a ribose-5-phosphate isomerase enzyme or fragment thereof; a nucleic acid molecule that encodes for a putative ribose-5-phosphate isomerase enzyme or fragment thereof; a nucleic acid molecule that encodes for a transketolase enzyme or fragment thereof; a nucleic acid molecule that encodes for a putative transketolase enzyme or fragment thereof; a nucleic acid molecule that encodes for a transaldolase enzyme or fragment thereof; a nucleic acid molecule that encodes for a putative transaldolase enzyme or fragment thereof; and a nucleic acid molecule that encodes for a phosphoglucoisomerase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a transcribed nucleic acid molecule with a transcribed strand and a non-transcribed strand, wherein the transcribed strand is complementary to a nucleic acid molecule comprising a nucleic acid sequence selected from the group consisting of SEQ ID NO: 1 through SEQ ID NO: 699 or fragment thereof; which is linked to (C) a 3' non-translated sequence that functions in plant cells to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to: (B) a transcribed nucleic acid molecule with a transcribed strand and a non-transcribed strand, wherein a transcribed mRNA of the transcribed strand is complementary to an endogenous mRNA molecule having a nucleic acid sequence selected from the group consisting of an endogenous mRNA molecule that encodes a maize or soybean glucose-6-phosphate-1-dehydrogenase enzyme or fragment thereof; an endogenous mRNA molecule that encodes a maize or soybean 6-phosphogluconate dehydrogenase enzyme or fragment thereof; an endogenous mRNA molecule that encodes a putative maize or soybean 6-phosphogluconate dehydrogenase enzyme or fragment thereof; an endogenous mRNA molecule that encodes a maize or soybean D-ribulose-5-phosphate-3-epimerase enzyme or fragment thereof; an endogenous mRNA molecule that encodes a maize or soybean ribose-5-phosphate isomerase enzyme or fragment thereof; an endogenous mRNA molecule that encodes a putative maize or soybean ribose-5-phosphate isomerase enzyme or fragment thereof; an endogenous mRNA molecule that encodes a maize or soybean transketolase enzyme or fragment thereof; an endogenous mRNA molecule that encodes a putative maize or soybean transketolase enzyme or fragment thereof; an endogenous mRNA molecule that encodes a maize or soybean transaldolase enzyme or fragment thereof; an endogenous mRNA molecule that encodes a putative maize transaldolase enzyme or fragment thereof; and an endogenous mRNA molecule that encodes a maize or soybean phosphoglucoisomerase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a method for determining a level or pattern of a plant phosphogluconate pathway enzyme in a plant cell or plant tissue comprising: (A) incubating, under conditions permitting nucleic acid hybridization, a marker nucleic acid molecule, the marker nucleic acid molecule having a nucleic acid sequence selected from the group consisting of SEQ ID NO: 1 through SEQ ID NO: 699 or complements thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant phosphogluconate pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant phosphogluconate pathway enzyme.

The present invention also provides a method for determining a level or pattern of a plant phosphogluconate pathway enzyme in a plant cell or plant tissue comprising: (A) incubating, under conditions permitting nucleic acid hybridization, a marker nucleic acid molecule, the marker nucleic acid molecule comprising a nucleic acid molecule that encodes a maize or soybean glucose-6-phosphate-1-dehydrogenase enzyme or complement thereof or fragment of either; a nucleic acid molecule that encodes a maize or soybean 6-phosphogluconate dehydrogenase enzyme or complement thereof or fragment of either; a nucleic acid molecule that encodes a maize or soybean putative 6-phosphogluconate dehydrogenase enzyme or complement thereof or fragment of either; a nucleic acid molecule that encodes a maize or soybean D-ribulose-5-phosphate-3-epimerase enzyme or complement thereof or fragment of either; a nucleic acid molecule that encodes a maize or soybean ribose-5-phosphate isomerase enzyme or complement thereof or fragment of either; a nucleic acid molecule that encodes a putative maize or soybean ribose-5-phosphate isomerase enzyme or complement thereof or fragment of either; a nucleic acid molecule that encodes a maize or soybean transketolase enzyme or complement thereof or fragment of either; a nucleic acid molecule that encodes a putative maize or soybean transketolase enzyme or complement thereof or fragment of either; a nucleic acid molecule that encodes a maize or soybean transaldolase enzyme or complement thereof or fragment of either; a nucleic acid molecule that encodes a putative maize transaldolase enzyme or complement thereof or fragment of either; and a nucleic acid molecule that encodes a maize or soybean phosphoglucoisomerase enzyme or complement thereof or fragment of either; with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant phosphogluconate pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant phosphogluconate pathway enzyme.

The present invention also provides a method for determining a level or pattern of a plant phosphogluconate pathway enzyme in a plant cell or plant tissue under evaluation which comprises assaying the concentration of a molecule, whose concentration is dependent upon the expression of a gene, the gene specifically hybridizes to a nucleic acid molecule having a nucleic acid sequence selected from the group consisting of SEQ ID NO: 1 through SEQ ID NO: 699 or complements thereof, in comparison to the concentration of that molecule present in a reference plant cell or a reference plant tissue with a known level or pattern of the plant phosphogluconate pathway enzyme, wherein the assayed concentration of the molecule is compared to the assayed concentration of the molecule in the reference plant cell or reference plant tissue with the known level or pattern of the plant phosphogluconate pathway enzyme.

The present invention also provides a method for determining a level or pattern of a plant phosphogluconate pathway enzyme in a plant cell or plant tissue under evaluation which comprises assaying the concentration of a molecule, whose concentration is dependent upon the expression of a gene, the gene specifically hybridizes to a nucleic acid molecule selected from the group consisting of a nucleic acid molecule that encodes a maize or soybean glucose-6-phosphate-1-dehydrogenase enzyme; a nucleic acid molecule that encodes a maize or soybean 6-phosphogluconate dehydrogenase enzyme or complement thereof; a nucleic acid molecule that encodes a putative maize or soybean 6-phosphogluconate dehydrogenase enzyme or complement thereof; a nucleic acid molecule that encodes a maize or soybean D-ribulose-5-phosphate-3-epimerase enzyme or complement thereof; a nucleic acid molecule that encodes a maize or soybean ribose-5-phosphate isomerase enzyme or complement thereof; a nucleic acid molecule that encodes a putative maize or soybean ribose-5-phosphate isomerase enzyme or complement thereof; a nucleic acid molecule that encodes a maize or soybean transketolase enzyme or complement thereof; a nucleic acid molecule that encodes a putative maize or soybean transketolase enzyme or complement thereof; a nucleic acid molecule that encodes a maize or soybean transaldolase enzyme or complement thereof; a nucleic acid molecule that encodes a putative maize transaldolase enzyme or complement thereof; and a nucleic acid molecule that encodes a maize or soybean phosphoglucoisomerase enzyme or complement thereof; in comparison to the concentration of that molecule present in a reference plant cell or a reference plant tissue with a known level or pattern of the plant phosphogluconate pathway enzyme, wherein the assayed concentration of the molecule is compared to the assayed concentration of the molecule in the reference plant cell or the reference plant tissue with the known level or pattern of the plant phosphogluconate pathway enzyme.

The present invention provides a method of determining a mutation in a plant whose presence is predictive of a mutation affecting a level or pattern of a protein comprising the steps: (A) incubating, under conditions permitting nucleic acid hybridization, a marker nucleic acid, the marker nucleic acid selected from the group of marker nucleic acid molecules which specifically hybridize to a nucleic acid molecule having a nucleic acid sequence selected from the group of SEQ ID NO: 1 through SEQ ID NO: 699 or complements thereof or fragment of either and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant phosphogluconate pathway enzyme comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule having a nucleic acid sequence selected from the group consisting of SEQ ID NO: 1 through SEQ ID NO: 699 or complements thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant phosphogluconate pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant phosphogluconate pathway enzyme comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule selected from the group consisting of a nucleic acid molecule that encodes a maize or soybean glucose-6-phosphate-1-dehydrogenase enzyme or complement thereof; a nucleic acid molecule that encodes a maize or soybean 6-phosphogluconate dehydrogenase enzyme or complement thereof; a nucleic acid molecule that encodes a putative maize or soybean 6-phosphogluconate dehydrogenase enzyme or complement thereof; a nucleic acid molecule that encodes a maize or soybean D-ribulose-5-phosphate-3-epimerase enzyme or complement thereof; a nucleic acid molecule that encodes a maize or soybean ribose-5-phosphate isomerase enzyme or complement thereof; a nucleic acid molecule that encodes a putative maize or soybean ribose-5-phosphate isomerase enzyme or complement thereof; a nucleic acid molecule that encodes a maize or soybean transketolase enzyme or complement thereof; a nucleic acid molecule that encodes a putative maize or soybean transketolase enzyme or complement thereof; a nucleic acid molecule that encodes a maize or soybean transaldolase enzyme or complement thereof; a nucleic acid molecule that encodes a putative maize or soybean transaldolase enzyme or complement thereof; a nucleic acid molecule that encodes a maize or soybean phosphoglucoisomerase enzyme or complement thereof; and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant phosphogluconate pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method of producing a plant containing an overexpressed protein comprising: (A) transforming the plant with a functional nucleic acid molecule, wherein the functional nucleic acid molecule comprises a promoter region, wherein the promoter region is linked to a structural region, wherein the structural region has a nucleic acid sequence selected from group consisting of SEQ ID NO: 1 through SEQ ID NO: 699; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention also provides a method of producing a plant containing an overexpressed plant phosphogluconate pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 699 or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant phosphogluconate pathway enzyme; and (B) growing the transformed plant.

The present invention also provides a method of producing a plant containing an overexpressed plant phosphogluconate pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule selected from the group consisting of a nucleic acid molecule that encodes a maize or soybean glucose-6-phosphate-1-dehydrogenase enzyme or fragment thereof; a nucleic acid molecule that encodes a maize or soybean 6-phosphogluconate dehydrogenase enzyme or fragment thereof; a nucleic acid molecule that encodes a putative maize or soybean 6-phosphogluconate dehydrogenase enzyme or fragment thereof; a nucleic acid molecule that encodes a maize or soybean D-ribulose-5-phosphate-3-epimerase enzyme or fragment thereof; a nucleic acid molecule that encodes a maize or soybean ribose-5-phosphate isomerase enzyme or fragment thereof; a nucleic acid molecule that encodes a putative maize or soybean ribose-5-phosphate isomerase enzyme or fragment thereof; a nucleic acid molecule that encodes a maize or soybean transketolase enzyme or fragment thereof; a nucleic acid molecule that encodes a putative maize or soybean transketolase enzyme or fragment thereof; a nucleic acid molecule that encodes a maize or soybean transaldolase enzyme or fragment thereof; a nucleic acid molecule that encodes a putative maize transaldolase enzyme or fragment thereof; a nucleic acid molecule that encodes a maize or soybean phosphoglucoisomerase enzyme or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant phosphogluconate pathway enzyme; and (B) growing the transformed plant.

The present invention also provides a method of producing a plant containing reduced levels of a plant phosphogluconate pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 699; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant phosphogluconate pathway enzyme; and (B) growing the transformed plant.

The present invention also provides a method of producing a plant containing reduced levels of a plant phosphogluconate pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of a nucleic acid molecule that encodes a maize or soybean glucose-6-phosphate-1-dehydrogenase enzyme or fragment thereof; a nucleic acid molecule that encodes a maize or soybean 6-phosphogluconate dehydrogenase enzyme or fragment thereof; a nucleic acid molecule that encodes a maize or soybean putative 6-phosphogluconate dehydrogenase enzyme or fragment thereof; a nucleic acid molecule that encodes a maize or soybean D-ribulose-5-phosphate-3-epimerase enzyme or fragment thereof; a nucleic acid molecule that encodes a maize or soybean ribose-5-phosphate isomerase enzyme or fragment thereof; a nucleic acid molecule that encodes a putative maize or soybean ribose-5-phosphate isomerase enzyme or fragment thereof; a nucleic acid molecule that encodes a maize or soybean transketolase enzyme or fragment thereof; a nucleic acid molecule that encodes a putative maize or soybean transketolase enzyme or fragment thereof; a nucleic acid molecule that encodes a maize or soybean transaldolase enzyme or fragment thereof; a nucleic acid molecule that encodes a putative maize transaldolase enzyme or fragment thereof; a nucleic acid molecule that encodes a maize or soybean phosphoglucoisomerase enzyme or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant phosphogluconate pathway enzyme; and (B) growing the transformed plant.

The present invention also provides a method for reducing expression of a plant phosphogluconate pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein the transcribed strand is complementary to a nucleic acid molecule having a nucleic acid sequence selected from the group consisting of SEQ ID NO: 1 through SEQ ID NO: 699 or complements thereof or fragments of either and the transcribed strand is complementary to an endogenous mRNA molecule; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method for reducing expression of a plant phosphogluconate pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein a transcribed mRNA of the transcribed strand is complementary to a nucleic acid molecule selected from the group consisting of an endogenous mRNA molecule that encodes a maize or soybean glucose-6-phosphate-1-dehydrogenase enzyme or fragment thereof; an endogenous mRNA molecule that encodes a maize or soybean 6-phosphogluconate dehydrogenase enzyme or fragment thereof; an endogenous mRNA molecule that encodes a putative maize or soybean 6-phosphogluconate dehydrogenase enzyme or fragment thereof; an endogenous mRNA molecule that encodes a maize or soybean D-ribulose-5-phosphate-3-epimerase enzyme or fragment thereof; an endogenous mRNA molecule that encodes a maize or soybean ribose-5-phosphate isomerase enzyme or fragment thereof; an endogenous mRNA molecule that encodes a putative maize or soybean ribose-5-phosphate isomerase enzyme or fragment thereof; an endogenous mRNA molecule that encodes a maize or soybean transketolase enzyme or fragment thereof; an endogenous mRNA molecule that encodes a putative maize or soybean transketolase enzyme or fragment thereof; an endogenous mRNA molecule that encodes a maize or soybean transaldolase enzyme or fragment thereof; an endogenous mRNA molecule that encodes a putative maize transaldolase enzyme or fragment thereof; an endogenous mRNA molecule that encodes a maize or soybean phosphoglucoisomerase enzyme or fragment thereof; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method of determining an association between a polymorphism and a plant trait comprising: (A) hybridizing a nucleic acid molecule specific for the polymorphism to genetic material of a plant, wherein the nucleic acid molecule has a nucleic acid sequence selected from the group consisting of SEQ ID NO: 1 through SEQ ID NO: 699 or complements thereof or fragment of either; and (B) calculating the degree of association between the polymorphism and the plant trait.

The present invention also provides a method of determining an association between a polymorphism and a plant trait comprising: (A) hybridizing a nucleic acid molecule specific for the polymorphism to genetic material of a plant, wherein the nucleic acid molecule is selected from the group consisting of a nucleic acid molecule that encodes a maize or soybean glucose-6-phosphate-1-dehydrogenase enzyme or complement thereof or fragment of either; a nucleic acid molecule that encodes a maize or soybean 6-phosphogluconate dehydrogenase enzyme or complement thereof or fragment of either; a nucleic acid molecule that encodes a putative maize or soybean 6-phosphogluconate dehydrogenase enzyme or complement thereof or fragment of either; a nucleic acid molecule that encodes a maize or soybean D-ribulose-5-phosphate-3-epimerase enzyme or complement thereof or fragment of either; a nucleic acid molecule that encodes a maize or soybean ribose-5-phosphate isomerase enzyme or complement thereof or fragment of either; a nucleic acid molecule that encodes a putative maize or soybean ribose-5-phosphate isomerase enzyme or complement thereof or fragment of either; a nucleic acid molecule that encodes a maize or soybean transketolase enzyme or complement thereof or fragment of either; a nucleic acid molecule that encodes a putative maize or soybean transketolase enzyme or complement thereof or fragment of either; a nucleic acid molecule that encodes a maize or soybean transaldolase enzyme or complement thereof or fragment of either; a nucleic acid molecule that encodes a putative maize transaldolase enzyme or complement thereof or fragment of either; and a nucleic acid molecule that encodes a maize or soybean phosphoglucoisomerase enzyme or complement thereof or fragment of either; and (B) calculating the degree of association between the polymorphism and the plant trait.

The present invention also provides a method of isolating a nucleic acid that encodes a plant phosphogluconate pathway enzyme or fragment thereof comprising: (A) incubating under conditions permitting nucleic acid hybridization, a first nucleic acid molecule comprising a nucleic acid sequence selected from the group consisting of SEQ ID NO: 1 through SEQ ID NO: 699 or complements thereof or fragment of either with a complementary second nucleic acid molecule obtained from a plant cell or plant tissue; (B) permitting hybridization between the first nucleic acid molecule and the second nucleic acid molecule obtained from the plant cell or plant tissue; and (C) isolating the second nucleic acid molecule.

The present invention also provides a method of isolating a nucleic acid molecule that encodes a plant phosphogluconate pathway enzyme or fragment thereof comprising: (A) incubating under conditions permitting nucleic acid hybridization, a first nucleic acid molecule selected from the group consisting of a nucleic acid molecule that encodes a maize or soybean glucose-6-phosphate-1-dehydrogenase enzyme or complement thereof or fragment of either; a nucleic acid molecule that encodes a maize or soybean 6-phosphogluconate dehydrogenase enzyme or complement thereof or fragment of either; a nucleic acid molecule that encodes a putative maize or soybean 6-phosphogluconate dehydrogenase enzyme or complement thereof or fragment of either; a nucleic acid molecule that encodes a maize or soybean D-ribulose-5-phosphate-3-epimerase enzyme or complement thereof or fragment of either; a nucleic acid molecule that encodes a maize or soybean ribose-5-phosphate isomerase enzyme or complement thereof or fragment of either; a nucleic acid molecule that encodes a putative maize or soybean ribose-5-phosphate isomerase enzyme or complement thereof or fragment of either; a nucleic acid molecule that encodes a maize or soybean transketolase enzyme or complement thereof or fragment of either; a nucleic acid molecule that encodes a putative maize or soybean transketolase enzyme or complement thereof or fragment of either; a nucleic acid molecule that encodes a maize or soybean transaldolase enzyme or complement thereof or fragment of either; a nucleic acid molecule that encodes a putative maize transaldolase enzyme or complement thereof or fragment of either; and a nucleic acid molecule that encodes a maize or soybean phosphoglucoisomerase enzyme or complement thereof or fragment of either; with a complementary second nucleic acid molecule obtained from a plant cell or plant tissue; (B) permitting hybridization between the plant phosphogluconate pathway enzyme nucleic acid molecule and the complementary nucleic acid molecule obtained from the plant cell or plant tissue; and (C) isolating the second nucleic acid molecule.

DETAILED DESCRIPTION OF THE INVENTION

Definitions and Agents of the Present Invention

Definitions

As used herein, a phosphogluconate pathway enzyme is any enzyme that is associated with the synthesis, oxidation, hydrolysis, or modification of phosphogluconate compounds.

As used herein, a phosphogluconate synthesis enzyme is any enzyme that is associated with the synthesis of phosphogluconate.

As used herein, a phosphogluconate oxidation enzyme is any enzyme that is associated with the oxidation of phosphogluconate.

As used herein, a phosphogluconate hydrolysis enzyme is any enzyme that is associated with the hydrolysis of phosphogluconate.

As used herein, a phosphogluconate modification enzyme is any enzyme that is associated with the modification of phosphogluconate compounds.

As used herein, glucose-6-phosphate dehydrogenase is any enzyme that catalyzes the conversion of glucose-6-phosphate to 6-phosphoglyconolactone.

As used herein, 6-phosphogluconate dehydrogenase is any enzyme that catalyzes the conversion of 6-phosphogluconate to ribulose-5-phosphate.

As used herein, ribose-5-phosphate isomerase is any enzyme that catalyzes the conversion of ribulose-5-phosphate to ribose-5-phosphate.

As used herein, ribulose-5-phosphate-3-epimerase is any enzyme that catalyzes the conversion of ribulose-5-phosphate to xylulose-5-phosphate.

As used herein, transketolase is any enzyme that catalyzes the conversion of ribose-5-phosphate and xylulose-5-phosphate to sedheptulose-7-phosphate and 3-phosphoglyceraldehyde.

As used herein, transaldolase is any enzyme that catalyzes the conversion of sedheptulose-7-phosphate and 3-phosphoglyceraldehyde to erythrose-4-phosphate and fructose-6-phosphate.

As used herein, phosphohexose isomerase (phosphoglucoisomerase) is any enzyme that catalyzes the conversion of fructose-6-phosphate to glucose-6-phosphate.

Agents (a) Nucleic Acid Molecules

Agents of the present invention include plant nucleic acid molecules and more preferably include maize and soybean nucleic acid molecules and more preferably include nucleic acid molecules of the maize genotypes B73 (Illinois Foundation Seeds, Champaign, Ill. U.S.A.), B73×Mol7 (Illinois Foundation Seeds, Champaign, Illinois U.S.A.), DK604 (Dekalb Genetics, Dekalb, Illinois U.S.A.), H99 (Illinois Foundation Seeds, Champaign, Illinois U.S.A.), RX601 (Asgrow Seed Company, Des Moines, Iowa), Mol7 (Illinois Foundation Seeds, Champaign, Illinois U.S.A.), and soybean types Asgrow 3244 (Asgrow Seed Company, Des Moines, Iowa), C 1944 (United States Department of Agriculture (USDA) Soybean Germplasm Collection, Urbana, Ill. U.S.A.), Cristalina (USDA Soybean Germplasm Collection, Urbana, Ill. U.S.A.), FT108 (Monsoy, Brazil), Hartwig (USDA Soybean Germplasm Collection, Urbana, Ill. U.S.A.), BW211S Null (Tohoku University, Morioka, Japan), P1507354 (USDA Soybean Germplasm Collection, Urbana, Ill. U.S.A.), Asgrow A4922 (Asgrow Seed Company, Des Moines, Iowa U.S.A.), P1227687 (USDA Soybean Germplasm Collection, Urbana, Ill. U.S.A.), P1229358 (USDA Soybean Germplasm Collection, Urbana, Ill. U.S.A.) and Asgrow A3237 (Asgrow Seed Company, Des Moines, Iowa U.S.A.).

A subset of the nucleic acid molecules of the present invention includes nucleic acid molecules that are marker molecules. Another subset of the nucleic acid molecules of the present invention include nucleic acid molecules that encode a protein or fragment thereof. Another subset of the nucleic acid molecules of the present invention are EST molecules.

Fragment nucleic acid molecules may encode significant portion(s) of, or indeed most of, these nucleic acid molecules. Alternatively, the fragments may comprise smaller oligonucleotides (having from about 15 to about 250 nucleotide residues and more preferably, about 15 to about 30 nucleotide residues).

The term "substantially purified", as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

It is understood that the agents of the present invention may be labeled with reagents that facilitate detection of the agent (e.g. fluorescent labels, Prober et al., *Science* 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448, all of which are hereby incorporated by reference in their entirety).

It is further understood, that the present invention provides recombinant bacterial, mammalian, microbial, insect, fungal and plant cells and viral constructs comprising the agents of the present invention. (See, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells)

Nucleic acid molecules or fragments thereof of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985), the entirety of which is herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 699 or complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO: 1 through SEQ ID NO: 699 or complements thereof under high stringency conditions such as 0.2×SSC and about 65° C.

In one aspect of the present invention, the nucleic acid molecules of the present invention have one or more of the nucleic acid sequences set forth in SEQ ID NO: 1 through SEQ ID NO: 699 or complements thereof. In another aspect of the present invention, one or more of the nucleic acid molecules of the present invention share between 100% and 90% sequence identity with one or more of the nucleic acid sequences set forth in SEQ ID NO: 1 through SEQ ID NO: 699 or complements thereof. In a further aspect of the present invention, one or more of the nucleic acid molecules of the present invention share between 100% and 95% sequence identity with one or more of the nucleic acid sequences set forth in SEQ ID NO: 1 through SEQ ID NO: 699 or complements thereof. In a more preferred aspect of the present invention, one or more of the nucleic acid molecules of the present invention share between 100% and 98% sequence identity with one or more of the nucleic acid sequences set forth in SEQ ID NO: 1 through SEQ ID NO: 699 or complements thereof. In an even more preferred aspect of the present invention, one or more of the nucleic acid molecules of the present invention share between 100% and 99% sequence identity with one or more of the sequences set forth in SEQ ID NO: 1 through SEQ ID NO: 699 or complements thereof.

In a further more preferred aspect of the present invention, one or more of the nucleic acid molecules of the present invention exhibit 100% sequence identity with a nucleic acid molecule present within MONN01, SATMON001, SATMON003 through SATMON014, SATMON016, SATMON017, SATMON019 through SATMON031, SATMON033, SATMON034, SATMONN01, SATMONN04 through SATMONN06, LIB36, LIB83 through LIB84, CMz029 through CMz031, CMz033 through CMz037, CMz039 through CMz042, CMz044 through CMz045, CMz047 through CMz050, SOYMON001 through SOYMON038, Soy51 through Soy56, Soy58 through Soy62, Soy65 through Soy77, LIB3054, LIB3087, and LIB3094 (Monsanto Company, St. Louis, Mo. U.S.A.).

(i) Nucleic Acid Molecules Encoding Proteins or Fragments Thereof

Nucleic acid molecules of the present invention can comprise sequences that encode a phosphogluconate pathway enzyme or fragment thereof. Such phosphogluconate pathway enzymes or fragments thereof include homologues of known phosphogluconate pathway enzymes in other organisms.

In a preferred embodiment of the present invention, a maize or soybean phosphogluconate pathway enzyme or fragment thereof of the present invention is a homologue of another plant phosphogluconate pathway enzyme. In another preferred embodiment of the present invention, a maize or soybean phosphogluconate pathway enzyme or fragment thereof of the present invention is a homologue of a fungal phosphogluconate pathway enzyme. In another preferred embodiment of the present invention, a maize or soybean phosphogluconate pathway enzyme or fragment thereof of the present invention is a homologue of a bacterial phosphogluconate pathway enzyme. In another preferred embodiment of the present invention, a soybean phosphogluconate pathway enzyme or fragment thereof of the present invention is a homologue of a maize phosphogluconate pathway enzyme. In another preferred embodiment of the present invention, a maize phosphogluconate pathway enzyme homologue or fragment thereof of the present invention is a homologue of a soybean phosphogluconate pathway enzyme. In another preferred embodiment of the present invention, a maize or soybean phosphogluconate pathway enzyme homologue or fragment thereof of the present invention is a homologue of an *Arabidopsis thaliana* phosphogluconate pathway enzyme.

In a preferred embodiment of the present invention, the nucleic molecule of the present invention encodes a maize or soybean phosphogluconate pathway enzyme or fragment thereof where a maize or soybean phosphogluconate pathway enzyme exhibits a BLAST probability score of greater than 1E-12, preferably a BLAST probability score of between about 1E-30 and about 1E-12, even more preferably a BLAST probability score of greater than 1E-30 with its homologue.

In another preferred embodiment of the present invention, the nucleic acid molecule encoding a maize or soybean phosphogluconate pathway enzyme or fragment thereof exhibits a % identity with its homologue of between about 25% and about 40%, more preferably of between about 40 and about 70%, even more preferably of between about 70% and about 90% and even more preferably between about 90% and 99%. In another preferred embodiment of the present invention, a maize or soybean phosphogluconate pathway enzyme or fragments thereof exhibits a % identity with its homologue of 100%.

In a preferred embodiment of the present invention, the nucleic molecule of the present invention encodes a maize or soybean phosphogluconate pathway enzyme or fragment thereof where a maize or soybean phosphogluconate pathway enzyme exhibits a BLAST score of greater than 120, preferably a BLAST score of between about 1450 and about 120, even more preferably a BLAST score of greater than 1450 with its homologue.

Nucleic acid molecules of the present invention also include non-maize, non-soybean homologues. Preferred non-maize, non-soybean homologues are selected from the group consisting of alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm and *Phaseolus*.

In a preferred embodiment, nucleic acid molecules having SEQ ID NO: 1 through SEQ ID NO: 699 or complements and fragments of either can be utilized to obtain such homologues.

The degeneracy of the genetic code, which allows different nucleic acid sequences to code for the same protein or peptide, is known in the literature. (U.S. Pat. No. 4,757,006, the entirety of which is herein incorporated by reference).

In an aspect of the present invention, one or more of the nucleic acid molecules of the present invention differ in nucleic acid sequence from those encoding a maize or soybean phosphogluconate pathway enzyme or fragment thereof in SEQ ID NO: 1 through SEQ ID NO: 699 due to the degeneracy in the genetic code in that they encode the same phosphogluconate pathway enzyme but differ in nucleic acid sequence.

In another further aspect of the present invention, one or more of the nucleic acid molecules of the present invention differ in nucleic acid sequence from those encoding a maize or soybean phosphogluconate pathway enzyme or fragment thereof in SEQ ID NO: 1 through SEQ ID NO: 699 due to fact that the different nucleic acid sequence encodes a phosphogluconate pathway enzyme having one or more conservative amino acid residue. Examples of conservative substitutions are set forth in Table 1. It is understood that codons capable of coding for such conservative substitutions are known in the art.

TABLE 1

| Original Residue | Conservative Substitutions |
|---|---|
| Ala | Ser |
| Arg | Lys |
| Asn | Gln; His |
| Asp | Glu |
| Cys | Ser; Ala |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In a further aspect of the present invention, one or more of the nucleic acid molecules of the present invention differ in nucleic acid sequence from those encoding a maize or soybean phosphogluconate pathway enzyme or fragment thereof set forth in SEQ ID NO: 1 through SEQ ID NO: 699 or fragment thereof due to the fact that one or more codons encoding an amino acid has been substituted for a codon that encodes a nonessential substitution of the amino acid originally encoded.

Agents of the present invention include nucleic acid molecules that encode a maize or soybean phosphogluconate pathway enzyme or fragment thereof and particularly substantially purified nucleic acid molecules selected from the group consisting of a nucleic acid molecule that encodes a maize or soybean glucose-6-phosphate-1-dehydrogenase enzyme or fragment thereof; a nucleic acid molecule that encodes a maize or soybean 6-phosphogluconate dehydrogenase enzyme or fragment thereof; a nucleic acid molecule that encodes a putative maize or soybean 6-phosphogluconate dehydrogenase enzyme or fragment thereof; a nucleic acid molecule that encodes a maize or soybean D-ribulose-5-phosphate-3-epimerase enzyme or fragment thereof; a nucleic acid molecule that encodes a maize or soybean ribose-5-phosphate isomerase enzyme or fragment thereof; a nucleic acid molecule that encodes a putative maize or soybean ribose-5-phosphate isomerase enzyme or fragment thereof; a nucleic acid molecule that encodes a maize or soybean transketolase enzyme or fragment thereof; a nucleic acid molecule that encodes a putative maize or soybean transketolase enzyme or fragment thereof; a nucleic acid molecule that encodes a maize or soybean transkealdolase enzyme or fragment thereof a nucleic acid molecule that encodes a putative maize transaldolase enzyme or fragment thereof; a nucleic acid molecule that encodes a maize or soybean phosphoglucoisomerase enzyme or fragment thereof.

Non-limiting examples of such nucleic acid molecules of the present invention are nucleic acid molecules comprising: SEQ ID NO: 1 through SEQ ID NO: 699 or fragment thereof that encode for a plant phosphogluconate pathway enzyme or fragment thereof, SEQ ID NO: 1 through SEQ ID NO: 3 and SEQ ID NO: 4 through SEQ ID NO: 11 or fragment thereof that encodes for a maize or soybean glucose-6-phosphate-1-dehydrogenase enzyme or fragment thereof; SEQ ID NO: 12 through SEQ ID NO: 21 and SEQ ID NO: 22 through SEQ ID NO: 103 or fragment thereof that encodes for a maize or soybean 6-phosphogluconate dehydrogenase enzyme or fragment thereof; SEQ ID NO: 104 through SEQ ID NO: 209 and SEQ ID NO: 210 through SEQ ID NO: 214 or fragment thereof that encodes for a putative maize or soybean 6-phosphogluconate dehydrogenase enzyme or fragment thereof; SEQ ID NO: 215 through SEQ ID NO: 260 and SEQ ID NO: 261 through SEQ ID NO: 299 or fragment thereof that encodes for a maize or soybean D-ribulose-5-phosphate-3-epimerase enzyme or fragment thereof; SEQ ID NO: 300 through SEQ ID NO: 306 and SEQ ID NO: 307 through SEQ ID NO: 311 or fragment thereof that encodes for a maize or soybean ribose-5-phosphate isomerase enzyme or fragment thereof; SEQ ID NO: 312 through SEQ ID NO: 313 and SEQ ID NO: 314 through SEQ ID NO: 318 or fragment thereof that encodes for a putative maize or soybean ribose-5-phosphate isomerase enzyme or fragment thereof; SEQ ID NO: 319 through SEQ ID NO: 356 and SEQ ID NO: 357 through SEQ ID NO: 437 or fragment thereof that encodes for a maize or soybean transketolase enzyme or fragment thereof; SEQ ID NO: 438 through SEQ ID NO: 447 and SEQ ID NO: 448 through SEQ ID NO: 453 or fragment thereof that encodes for a putative maize or soybean transketolase enzyme or fragment thereof; SEQ ID NO: 454 through SEQ ID NO: 533 and SEQ ID NO: 534 through SEQ ID NO: 617 or fragment thereof that encodes for a maize or soybean transaldolase enzyme or fragment thereof; SEQ ID NO: 618 or fragment thereof that encodes for a putative maize transaldolase enzyme or fragment thereof; and SEQ ID NO: 619 through SEQ ID NO: 683 and SEQ ID NO: 684 through SEQ ID NO: 699 or fragment thereof that encodes for a maize or soybean phosphoglucoisomerase enzyme or fragment thereof.

A nucleic acid molecule of the present invention can also encode an homologue of a maize or soybean glucose-6-phosphate-1-dehydrogenase enzyme or fragment thereof; a maize or soybean 6-phosphogluconate dehydrogenase enzyme or fragment thereof; a putative maize or soybean 6-phosphogluconate dehydrogenase enzyme or fragment thereof; a maize or soybean D-ribulose-5-phosphate-3-epimerase enzyme or fragment thereof; a maize or soybean ribose-5-phosphate isomerase enzyme or fragment thereof; a putative maize or soybean ribose-5-phosphate isomerase enzyme or fragment thereof; a maize or soybean transketolase enzyme or fragment thereof; a putative maize or soybean transketolase enzyme or fragment thereof; a maize or soybean transaldolase enzyme or fragment thereof; a putative maize transaldolase enzyme or fragment thereof; and a maize or soybean phosphoglucoisomerase enzyme or fragment thereof. As used herein a homologue protein molecule or fragment thereof is a counterpart protein molecule or fragment thereof in a second species (e.g., maize copalyl diphosphate synthase is a homologue of *Arabidopsis* copalyl diphosphate synthase).

(ii) Nucleic Acid Molecule Markers and Probes

One aspect of the present invention concerns markers that include nucleic acid molecules SEQ ID NO: 1 through SEQ ID NO: 699 or complements thereof or fragments of either that can act as markers or other nucleic acid molecules of the present invention that can act as markers. Genetic markers of the present invention include "dominant" or "codominant" markers "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g. absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

SNPs are single base changes in genomic DNA sequence. They occur at greater frequency and are spaced with a greater uniformly throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a results of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980), the entirety of which is herein incorporated reference; Konieczny and Ausubel, *Plant J.* 4:403-410 (1993), the entirety of which is herein incorporated by reference), enzymatic and chemical mismatch assays (Myers et al., *Nature* 313:495-498 (1985), the entirety of which is herein incorporated by reference), allele-specific PCR (Newton et al., *Nucl. Acids Res.* 17:2503-2516 (1989), the entirety of which is herein incorporated by reference; Wu et al., *Proc. Natl. Acad. Sci.* (*U.S.A.*) 86:2757-2760 (1989), the entirety of which is herein incorporated by reference), ligase chain reaction (Barany, *Proc. Natl. Acad. Sci.* (*U.S.A.*) 88:189-193 (1991), the entirety of which is herein incorporated by reference), single-strand conformation polymorphism analysis (Labrune et al., *Am. J. Hum. Genet.* 48: 1115-1120 (1991), the entirety of which is herein incorporated by reference), primer-directed nucleotide incorporation assays (Kuppuswami et al., *Proc. Natl. Acad. Sci. USA* 88:1143-1147 (1991), the entirety of which is herein incorporated by reference), dideoxy fingerprinting (Sarkar et al., *Genomics* 13:441-443 (1992), the entirety of which is herein incorporated by reference), solid-phase ELISA-based oligonucleotide ligation assays (Nikiforov et al., *Nucl Acids Res.* 22:4167-4175 (1994), the entirety of which is herein incorporated by reference), oligonucleotide fluorescence-quenching assays (Livak et al., *PCR Methods Appl.* 4:357-362 (1995), the entirety of which is herein incorporated by reference), 5'-nuclease allele-specific hybridization TaqMan assay (Livak et al., *Nature Genet.* 9:341-342 (1995), the entirety of which is herein incorporated by reference), template-directed dye-terminator incorporation (TDI) assay (Chen and Kwok, *Nucl. Acids Res.* 25:347-353 (1997), the entirety of which is herein incorporated by reference), allele-specific molecular beacon assay (Tyagi et al., *Nature Biotech.* 16: 49-53 (1998), the entirety of which is herein incorporated by reference), PinPoint assay (Haff and Smirnov, *Genome Res.* 7: 378-388 (1997), the entirety of which is herein incorporated by reference) and dCAPS analysis (Neff et al., *Plant J.* 14:387-392 (1998), the entirety of which is herein incorporated by reference).

Additional markers, such as AFLP markers, RFLP markers and RAPD markers, can be utilized (Walton, *Seed World* 22-29 (July, 1993), the entirety of which is herein incorporated by reference; Burow and Blake, *Molecular Dissection of Complex Traits,* 13-29, Paterson (ed.), CRC Press, New York (1988), the entirety of which is herein incorporated by reference). DNA markers can be developed from nucleic acid molecules using restriction endonucleases, the PCR and/or DNA sequence information. RFLP markers result from single base changes or insertions/deletions. These codominant markers are highly abundant in plant genomes, have a medium level of polymorphism and are developed by a combination of restriction endonuclease digestion and Southern blotting hybridization. CAPS are similarly developed from restriction nuclease digestion but only of specific PCR products. These markers are also codominant, have a medium level of polymorphism and are highly abundant in the genome. The CAPS result from single base changes and insertions/deletions.

Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant are highly abundant in genomes and exhibit a medium level of polymorphism.

SSRs require DNA sequence information. These codominant markers result from repeat length changes, are highly polymorphic and do not exhibit as high a degree of abundance in the genome as CAPS, AFLPs and RAPDs SNPs also require DNA sequence information. These codominant markers result from single base substitutions. They are highly abundant and exhibit a medium of polymorphism (Rafalski et al., In: *Nonmammalian Genomic Analysis*, Birren and Lai (ed.), Academic Press, San Diego, Calif., pp. 75-134 (1996), the entirety of which is herein incorporated by reference). It is understood that a nucleic acid molecule of the present invention may be used as a marker.

A PCR probe is a nucleic acid molecule capable of initiating a polymerase activity while in a double-stranded structure to with another nucleic acid. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS Pipeline), or GeneUp (Pesole et al., *BioTechniques* 25:112-123 (1998) the entirety of which is herein incorporated by reference), for example, can be used to identify potential PCR primers.

It is understood that a fragment of one or more of the nucleic acid molecules of the present invention may be a probe and specifically a PCR probe.

(b) Protein and Peptide Molecules

A class of agents comprises one or more of the protein or fragments thereof or peptide molecules encoded by SEQ ID NO: 1 through SEQ ID NO: 699 or one or more of the protein or fragment thereof and peptide molecules encoded by other nucleic acid agents of the present invention. As used herein, the term "protein molecule" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acids and "amino acids" refer to all naturally occurring L-amino acids. This definition is meant to include norleucine, ornithine, homocysteine and homoserine.

Non-limiting examples of the protein or fragment thereof of the present invention include a maize or soybean phosphogluconate pathway enzyme or fragment thereof; a maize or soybean glucose-6-phosphate-1-dehydrogenase enzyme or fragment thereof; a maize or soybean 6-phosphogluconate dehydrogenase enzyme or fragment thereof; a putative maize or soybean 6-phosphogluconate dehydrogenase enzyme or fragment thereof; a maize or soybean D-ribulose-5-phosphate-3-epimerase enzyme or fragment thereof; a maize or soybean ribose-5-phosphate isomerase enzyme or fragment thereof; a putative maize or soybean ribose-5-phosphate isomerase enzyme or fragment thereof; a maize or soybean transketolase enzyme or fragment thereof; a putative maize or soybean transketolase enzyme or fragment thereof; a maize or soybean transaldolase enzyme or fragment thereof; a putative maize transaldolase enzyme or fragment thereof; and a maize or soybean phosphoglucoisomerase enzyme or fragment thereof.

Non-limiting examples of the protein or fragment molecules of the present invention are a phosphogluconate pathway enzyme or fragment thereof encoded by: SEQ ID NO: 1 through SEQ ID NO: 699 or fragment thereof that encode for a phosphogluconate pathway enzyme or fragment thereof, SEQ ID NO: 1 through SEQ ID NO: 3 and SEQ ID NO: 4 through SEQ ID NO: 11 or fragment thereof that encodes for a maize or soybean glucose-6-phosphate-1-dehydrogenase enzyme or fragment thereof; SEQ ID NO: 12 through SEQ ID NO: 21 and SEQ ID NO: 22 through SEQ ID NO: 103 or fragment thereof that encodes for a maize or soybean 6-phosphogluconate dehydrogenase enzyme or fragment thereof; SEQ ID NO: 104 through SEQ ID NO: 209 and SEQ ID NO: 210 through SEQ ID NO: 214 or fragment thereof that encodes for a putative maize or soybean 6-phosphogluconate dehydrogenase enzyme or fragment thereof; SEQ ID NO: 215 through SEQ ID NO: 260 and SEQ ID NO: 261 through SEQ ID NO: 299 or fragment thereof that encodes for a putative maize or soybean D-ribulose-5-phosphate-3-epimerase enzyme or fragment thereof; SEQ ID NO: 300 through SEQ ID NO: 306 and SEQ ID NO: 307 through SEQ ID NO: 311 or fragment thereof that encodes for a maize or soybean ribose-5-phosphate isomerase enzyme or fragment thereof; SEQ ID NO: 312 through SEQ ID NO: 313 and SEQ ID NO: 314 through SEQ ID NO: 318 or fragment thereof that encodes for a putative maize or soybean ribose-5-phosphate isomerase enzyme or fragment thereof; SEQ ID NO: 319 through SEQ ID NO: 356 and SEQ ID NO: 357 through SEQ ID NO: 437 or fragment thereof that encodes for a maize or soybean transketolase enzyme or fragment thereof; SEQ ID NO: 438 through SEQ ID NO: 447 and SEQ ID NO: 448 through SEQ ID NO: 453 or fragment thereof that encodes for a putative maize or soybean transketolase enzyme or fragment thereof; SEQ ID NO: 454 through SEQ ID NO: 533 and SEQ ID NO: 534 through SEQ ID NO: 617 or fragment thereof that encodes for a maize or a soybean transaldolase enzyme or fragment thereof; SEQ ID NO: 618 or fragment thereof that encode for a putative maize transaldolase enzyme or fragment thereof; and SEQ ID NO: 619 through SEQ ID NO: 683 and SEQ ID NO: 684 through SEQ ID NO: 699 or fragment thereof that encodes for a maize or soybean phosphoglucoisomerase enzyme or fragment thereof.

One or more of the protein or fragment of peptide molecules may be produced via chemical synthesis, or more preferably, by expressing in a suitable bacterial or eucaryotic host. Suitable methods for expression are described by Sambrook et al., (In: *Molecular Cloning, A Laboratory Manual,* 2nd Edition, Cold Spring Harbor Press, Cold Spring Harbor, N.Y. (1989)), or similar texts. For example, the protein may be expressed in, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the present invention are preferably produced via recombinant means.

Another class of agents comprise protein or peptide molecules or fragments or fusions thereof encoded by SEQ ID NO: 1 through SEQ ID NO: 699 or complements thereof in which conservative, non-essential or non-relevant amino acid residues have been added, replaced or deleted. Computerized means for designing modifications in protein structure are known in the art (Dahiyat and Mayo, *Science* 278:82-87 (1997), the entirety of which is herein incorporated by reference).

The protein molecules of the present invention include plant homologue proteins. An example of such a homologue is a homologue protein of a non-maize or non-soybean plant species, that include but not limited to alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus* etc. Particularly preferred non-maize or non-soybean for use for the isolation of homologs would include, *Arabidopsis*, barley, cotton, oat, oilseed rape, rice, canola, ornamentals, sugarcane, sugarbeet, tomato, potato, wheat and turf grasses. Such a homologue can be obtained by any of a variety of methods. Most preferably, as indicated above, one or more of the disclosed sequences (SEQ ID NO: 1 through SEQ ID NO: 699 or complements thereof) will be used to define a pair of primers that may be used to isolate the homologue-encoding nucleic acid molecules from any desired species. Such molecules can be expressed to yield homologues by recombinant means.

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal and may comprise intact immunoglobulins, or antigen binding portions of immunoglobulins fragments (such as (F(ab'), $F(ab')_2$), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988), the entirety of which is herein incorporated by reference).

Murine monoclonal antibodies are particularly preferred. BALB/c mice are preferred for this purpose, however, equivalent strains may also be used. The animals are preferably immunized with approximately 25 μg of purified protein (or fragment thereof) that has been emulsified in a suitable adjuvant (such as TiterMax adjuvant (Vaxcel, Norcross, Ga.)). Immunization is preferably conducted at two intramuscular sites, one intraperitoneal site and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-protein or peptide antibodies. Preferably, a direct binding Enzyme-Linked Immunoassay (ELISA) is employed for this purpose.

More preferably, the mouse having the highest antibody titer is given a third i.v. injection of approximately 25 μg of the same protein or fragment. The splenic leukocytes from this animal may be recovered 3 days later and then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs"), preferably by direct ELISA.

In one embodiment, anti-protein or peptide monoclonal antibodies are isolated using a fusion of a protein or peptide of the present invention, or conjugate of a protein or peptide of the present invention, as immunogens. Thus, for example, a group of mice can be immunized using a fusion protein emulsified in Freund's complete adjuvant (e.g. approximately 50 μg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding the protein or peptide can also be obtained using this method.

In a preferred procedure for obtaining monoclonal antibodies, the spleens of the above-described immunized mice are removed, disrupted and immune splenocytes are isolated over a ficoll gradient. The isolated splenocytes are fused, using polyethylene glycol with BALB/c-derived HGPRT (hypoxanthine guanine phosphoribosyl transferase) deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2-3 weeks.

Hybridoma cells that arise from such incubation are preferably screened for their capacity to produce an immunoglobulin that binds to a protein of interest. An indirect ELISA may be used for this purpose. In brief, the supernatants of hybridomas are incubated in microtiter wells that contain immobilized protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbor cells. Desirably, the fusion plates are screened several times since the rates of hybridoma growth vary. In a preferred sub-embodiment, a different antigenic form may be used to screen the hybridoma. Thus, for example, the splenocytes may be immunized with one immunogen, but the resulting hybridomas can be screened using a different immunogen. It is understood that any of the protein or peptide molecules of the present invention may be used to raise antibodies.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

Uses of the Agents of the Invention

Nucleic acid molecules and fragments thereof of the present invention may be employed to obtain other nucleic acid molecules from the same species (e.g., ESTs or fragment thereof from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries obtained from maize or soybean. Methods for forming such libraries are well known in the art.

Nucleic acid molecules and fragments thereof of the present invention may also be employed to obtain nucleic acid homologues. Such homologues include the nucleic acid molecule of other plants or other organisms (e.g., alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus*, etc.) including the nucleic acid molecules that encode, in whole or in part, protein homologues of other plant species or other organisms, sequences of genetic elements such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homologue molecules may differ in their nucleotide sequences from those found in one or more of SEQ ID NO: 1 through SEQ ID NO: 699 or complements thereof because complete complementarity is not needed for stable hybridization. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143-4146 (1986), the entirety of which is herein incorporated by reference; Goodchild et al., *Proc. Natl. Acad. Sci.* (*U.S.A.*) 85:5507-5511 (1988), the entirety of which is herein incorporated by reference; Wickstrom et al., *Proc. Natl. Acad. Sci.* (*U.S.A.*) 85:1028-1032 (1988), the entirety of which is herein incorporated by reference; Holt et al., *Molec. Cell. Biol.* 8:963-973 (1988), the entirety of which is herein incorporated by reference; Gerwirtz et al., *Science* 242:1303-1306 (1988), the entirety of which is herein incorporated by reference; Anfossi et al., *Proc. Natl. Acad. Sci.* (*U.S.A.*) 86:3379-3383 (1989), the entirety of which is herein incorporated by reference; Becker et al., *EMBO J.* 8:3685-3691 (1989); the entirety of which is herein incorporated by reference). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194, all of which are herein incorporated by reference in their entirety) to amplify and obtain any desired nucleic acid molecule or fragment.

Promoter sequence(s) and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating EST nucleic acid molecules or preferably fragments thereof with members of genomic libraries (e.g. maize and soybean) and recovering clones that hybridize to the EST nucleic acid molecule or fragment thereof. In a second embodiment, methods of "chromosome walking," or inverse PCR may be used to obtain such sequences (Frohman et al., *Proc. Natl. Acad. Sci.* (*U.S.A.*) 85:8998-9002 (1988); Ohara et al., *Proc. Natl. Acad. Sci.* (*U.S.A.*) 86:5673-5677 (1989); Pang et al., *Biotechniques* 22:1046-1048 (1977); Huang et al., *Methods Mol. Biol.* 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996), all of which are herein incorporated by reference in their entirety).

The nucleic acid molecules of the present invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA,* 1, (1997), Cold Spring Harbor Laboratory Press, Cold Spring Harbor, N.Y., the entirety of which is herein incorporated by reference). Promoters obtained utilizing the nucleic acid molecules of the present invention could also be modified to affect their control characteristics. Examples of such modifications would include but are not limited to enhanced sequences as reported in Uses of the Agents of the Invention, Section (a) Plant Constructs and Plant Transformants. Such genetic elements could be used to enhance gene expression of new and existing traits for crop improvements.

In one sub-aspect, such an analysis is conducted by determining the presence and/or identity of polymorphism(s) by one or more of the nucleic acid molecules of the present invention and more preferably one or more of the EST nucleic acid molecule or fragment thereof which are associated with a phenotype, or a predisposition to that phenotype.

Any of a variety of molecules can be used to identify such polymorphism(s). In one embodiment, one or more of the EST nucleic acid molecules (or a sub-fragment thereof) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., PCT Patent Application WO91/14003; Jeffreys, European Patent Application 370,719; Jeffreys, U.S. Pat. No. 5,175,082; Jeffreys et al., *Amer. J Hum. Genet.* 39:11-24 (1986); Jeffreys et al., *Nature* 316:76-79 (1985); Gray et al., *Proc. R. Acad. Soc. Lond.* 243:241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124:783-789 (1990), all of which are herein incorporated by reference in their entirety).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction ("PCR") (Mullis et al., *Cold Spring Harbor Symp. Quant. Biol.* 51:263-273 (1986); Erlich et al., European Patent Appln. 50,424; European Patent Appln. 84,796; European Patent Application 258,017; European Patent Appln. 237,362; Mullis, European Patent Appln. 201,184; Mullis et al., U.S. Pat. No. 4,683,202; Erlich, U.S. Pat. No. 4,582,788; and Saiki et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci.* (*U.S.A.*) 88:189-193 (1991), the entirety of which is herein incorporated by reference). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069, the entirety of which is herein incorporated by reference).

The "Oligonucleotide Ligation Assay" ("OLA") may alternatively be employed (Landegren et al., *Science* 241:1077-1080 (1988), the entirety of which is herein incorporated by reference). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al., have described a nucleic acid detection assay that combines attributes of PCR and OLA (Nickerson et al., *Proc. Natl. Acad. Sci.* (*U.S.A.*) 87:8923-8927 (1990), the entirety of which is herein incorporated by reference). In this method, PCR is used to achieve the exponential amplification of target DNA, which is then detected using OLA. In addition to requiring multiple and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu et al., *Genomics* 4:560-569 (1989), the entirety of which is herein incorporated by reference) and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek et al., U.S. Pat. No. 5,130,238; Davey et al., European Patent Application 329,822; Schuster et al., U.S. Pat. No. 5,169,766; Miller et al., PCT Patent Application WO 89/06700; Kwoh et al., *Proc. Natl. Acad. Sci.* (*U.S.A.*) 86:1173-1177 (1989); Gingeras et al., PCT Patent Application WO 88/10315; Walker et al., *Proc. Natl. Acad. Sci.* (*U.S.A.*) 89:392-396 (1992), all of which are herein incorporated by reference in their entirety).

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and plant genetic analyses (Glassberg, UK Patent Application 2135774; Skolnick et al., *Cytogen. Cell Genet.* 32:58-67 (1982); Botstein et al., *Ann. J Hum. Genet.* 32:314-331 (1980); Fischer et al., (PCT Application WO90/13668); Uhlen, PCT Application WO90/11369).

Polymorphisms can also be identified by Single Strand Conformation Polymorphism (SSCP) analysis. SSCP is a method capable of identifying most sequence variations in a single strand of DNA, typically between 150 and 250 nucleotides in length (Elles, *Methods in Molecular Medicine Molecular Diagnosis of Genetic Diseases*, Humana Press (1996), the entirety of which is herein incorporated by reference); Orita et al., *Genomics* 5.874-879 (1989), the entirety of which is herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to, Lee et al., *Anal. Biochem.* 205:289-293 (1992), the entirety of which is herein incorporated by reference; Suzuki et al., *Anal. Biochem.* 192.82-84 (1991), the entirety of which is herein incorporated by reference; Lo et al., *Nucleic Acids Research* 20:1005-1009 (1992), the entirety of which is herein incorporated by reference; Sarkar et al., *Genomics* 13:441-443 (1992), the entirety of which is herein incorporated by reference. It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407-4414 (1995), the entirety of which is herein incorporated by reference). This method allows for the specific co-amplification of high numbers of restriction fragments, which can be visualized by PCR without knowledge of the nucleic acid sequence.

AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel.

AFLP analysis has been performed on *Salix* (Beismann et al., *Mol. Ecol.* 6:989-993 (1997), the entirety of which is herein incorporated by reference), *Acinetobacter* (Janssen et al., *Int. J. Syst. Bacteriol.* 47:1179-1187 (1997), the entirety of which is herein incorporated by reference), *Aeromonas popoffi* (Huys et al., *Int. J. Syst. Bacteriol.* 47:1165-1171 (1997), the entirety of which is herein incorporated by reference), rice (McCouch et al., *Plant Mol. Biol.* 35:89-99 (1997), the entirety of which is herein incorporated by reference; Nandi et al., *Mol. Gen. Genet.* 255:1-8 (1997), the entirety of which is herein incorporated by reference; Cho et al., *Genome* 39:373-378 (1996), the entirety of which is herein incorporated by reference), barley (*Hordeum vulgare*) (Simons et al., *Genomics* 44:61-70 (1997), the entirety of which is herein incorporated by reference; Waugh et al., *Mol. Gen. Genet.* 255:311-321 (1997), the entirety of which is herein incorporated by reference; Qi et al., *Mol. Gen. Genet.* 254:330-336 (1997), the entirety of which is herein incorporated by reference; Becker et al., *Mol. Gen. Genet.* 249:65-73 (1995), the entirety of which is herein incorporated by reference), potato (Van der Voort et al., *Mol. Gen. Genet.* 255:438-447 (1997), the entirety of which is herein incorporated by reference;

Meksem et al., *Mol. Gen. Genet.* 249:74-81 (1995), the entirety of which is herein incorporated by reference), *Phytophthora infestans* (Van der Lee et al., *Fungal Genet. Biol.* 21:278-291 (1997), the entirety of which is herein incorporated by reference), *Bacillus anthracis* (Keim et al., *J. Bacteriol.* 79:818-824 (1997), the entirety of which is herein incorporated by reference), *Astragalus cremnophylax* (Travis et al., *Mol. Ecol.* 5:735-745 (1996), the entirety of which is herein incorporated by reference), *Arabidopsis* (Cnops et al., *Mol. Gen. Genet.* 253:32-41 (1996), the entirety of which is herein incorporated by reference), *Escherichia coli* (Lin et al., *Nucleic Acids Res.* 24:3649-3650 (1996), the entirety of which is herein incorporated by reference), *Aeromonas* (Huys et al., *Int. J. Syst. Bacteriol.* 46:572-580 (1996), the entirety of which is herein incorporated by reference), nematode (Folkertsma et al., *Mol. Plant Microbe Interact.* 9:47-54 (1996), the entirety of which is herein incorporated by reference), tomato (Thomas et al., *Plant J.* 8:785-794 (1995), the entirety of which is herein incorporated by reference) and human (Latorra et al., *PCR Methods Appl.* 3:351-358 (1994), the entirety of which is herein incorporated by reference). AFLP analysis has also been used for fingerprinting mRNA (Money et al., *Nucleic Acids Res.* 24:2616-2617 (1996), the entirety of which is herein incorporated by reference; Bachem et al., *Plant J.* 9:745-753 (1996), the entirety of which is herein incorporated by reference). It is understood that one or more of the nucleic acids of the present invention, may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990), the entirety of which is herein incorporated by reference) and cleaveable amplified polymorphic sequences (CAPS) (Lyamichev et al., *Science* 260:778-783 (1993), the entirety of which is herein incorporated by reference). It is understood that one or more of the nucleic acid molecules of the present invention, may be utilized as markers or probes to detect polymorphisms by RAPD or CAPS analysis.

Through genetic mapping, a fine scale linkage map can be developed using DNA markers and, then, a genomic DNA library of large-sized fragments can be screened with molecular markers linked to the desired trait. Molecular markers are advantageous for agronomic traits that are otherwise difficult to tag, such as resistance to pathogens, insects and nematodes, tolerance to abiotic stress, quality parameters and quantitative traits such as high yield potential.

The essential requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) the entirety of which is herein incorporated by reference and further described by Arús and Moreno-González, *Plant Breeding*, Hayward et al., (eds.) Chapman & Hall, London, pp. 314-331 (1993), the entirety of which is herein incorporated by reference.

Additional models can be used. Many modifications and alternative approaches to interval mapping have been reported, including the use non-parametric methods (Kruglyak and Lander, *Genetics* 139.1421-1428 (1995), the entirety of which is herein incorporated by reference). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994), both of which is herein incorporated by reference in their entirety). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), the entirety of which is herein incorporated by reference and Zeng, *Genetics* 136:1457-1468 (1994) the entirety of which is herein incorporated by reference. Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), the entirety of which is herein incorporated by reference, thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995), the entirety of which is herein incorporated by reference).

Selection of an appropriate mapping populations is important to map construction. The choice of appropriate mapping population depends on the type of marker systems employed (Tanksley et al., *Molecular mapping plant chromosomes. Chromosome structure and function: Impact of new concepts*, Gustafson and Appels (eds.), Plenum Press, New York, pp 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, *Measurement of Linkage in Heredity*, Methuen and Co., (1938), the entirety of which is herein incorporated by reference). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequillibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (*U.S.A.*) 89:1477-1481 (1992), the entirety of which is herein incorporated by reference). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., *Proc. Natl. Acad. Sci.* (*U.S.A.*) 88:9828-9832 (1991), the entirety of which is herein incorporated by reference). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

It is understood that one or more of the nucleic acid molecules of the present invention may be used as molecular markers. It is also understood that one or more of the protein molecules of the present invention may be used as molecular markers.

In accordance with this aspect of the present invention, a sample nucleic acid is obtained from plants cells or tissues. Any source of nucleic acid may be used. Preferably, the nucleic acid is genomic DNA. The nucleic acid is subjected to restriction endonuclease digestion. For example, one or more nucleic acid molecule or fragment thereof of the present invention can be used as a probe in accordance with the above-described polymorphic methods. The polymorphism obtained in this approach can then be cloned to identify the mutation at the coding region which alters the protein's structure or regulatory region of the gene which affects its expression level.

In an aspect of the present invention, one or more of the nucleic molecules of the present invention are used to determine the level (i.e., the concentration of mRNA in a sample, etc.) in a plant (preferably maize or soybean) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue). As used herein, the Expression Response manifested by a cell or tissue is said to be "altered" if it differs from the Expression Response of cells or tissues of plants not exhibiting the phenotype. To determine whether an Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention, preferably one or more of the EST nucleic acid molecules or fragments thereof of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A principle of in situ hybridization is that a labeled, single-stranded nucleic acid probe will hybridize to a complementary strand of cellular DNA or RNA and, under the appropriate conditions, these molecules will form a stable hybrid. When nucleic acid hybridization is combined with histological techniques, specific DNA or RNA sequences can be identified within a single cell. An advantage of in situ hybridization over more conventional techniques for the detection of nucleic acids is that it allows an investigator to determine the precise spatial population (Angerer et al., *Dev. Biol.* 101:477-484 (1984), the entirety of which is herein incorporated by reference; Angerer et al., *Dev. Biol.* 112:157-166 (1985), the entirety of which is herein incorporated by reference; Dixon et al., *EMBO J.* 10:1317-1324 (1991), the entirety of which is herein incorporated by reference). In situ hybridization may be used to measure the steady-state level of RNA accumulation. It is a sensitive technique and RNA sequences present in as few as 5-10 copies per cell can be detected (Hardin et al., *J. Mol. Biol.* 202:417-431 (1989), the entirety of which is herein incorporated by reference). A number of protocols have been devised for in situ hybridization, each with tissue preparation, hybridization and washing conditions (Meyerowitz, *Plant Mol. Biol. Rep.* 5:242-250 (1987), the entirety of which is herein incorporated by reference; Cox and Goldberg, In: *Plant Molecular Biology: A Practical Approach*, Shaw (ed.), pp 1-35, IRL Press, Oxford (1988), the entirety of which is herein incorporated by reference; Raikhel et al., *In situ RNA hybridization in plant tissues*, In: *Plant Molecular Biology Manual*, vol. B9: 1-32, Kluwer Academic Publisher, Dordrecht, Belgium (1989), the entirety of which is herein incorporated by reference).

In situ hybridization also allows for the localization of proteins within a tissue or cell (Wilkinson, *In Situ Hybridization*, Oxford University Press, Oxford (1992), the entirety of which is herein incorporated by reference; Langdale, *In Situ Hybridization* In: *The Maize Handbook*, Freeling and Walbot (eds.), pp 165-179, Springer-Verlag, New York (1994), the entirety of which is herein incorporated by reference). It is understood that one or more of the molecules of the present invention, preferably one or more of the EST nucleic acid molecules or fragments thereof of the present invention or one or more of the antibodies of the present invention may be utilized to detect the level or pattern of a phosphogluconate pathway enzyme or mRNA thereof by in situ hybridization.

Fluorescent in situ hybridization allows the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 17:101-109 (1991), the entirety of which is herein incorporated by reference; Gustafson et al., *Proc. Natl. Acad. Sci.* (*U.S.A.*) 87:1899-1902 (1990), herein incorporated by reference; Mukai and Gill, *Genome* 34:448-452 (1991), the entirety of which is herein incorporated by reference; Schwarzacher and Heslop-Harrison, *Genome* 34:317-323 (1991); Wang et al., *Jpn. J. Genet.* 66:313-316 (1991), the entirety of which is herein incorporated by reference; Parra and Windle, *Nature Genetics* 5:17-21 (1993), the entirety of which is herein incorporated by reference). It is understood that the nucleic acid molecules of the present invention may be used as probes or markers to localize sequences along a chromosome.

Another method to localize the expression of a molecule is tissue printing. Tissue printing provides a way to screen, at the same time on the same membrane many tissue sections from different plants or different developmental stages. Tissue-printing procedures utilize films designed to immobilize proteins and nucleic acids. In essence, a freshly cut section of a tissue is pressed gently onto nitrocellulose paper, nylon membrane or polyvinylidene difluoride membrane. Such membranes are commercially available (e.g. Millipore, Bedford, Mass. U.S.A.). The contents of the cut cell transfer onto the membrane and the contents and are immobilized to the membrane. The immobilized contents form a latent print that can be visualized with appropriate probes. When a plant tissue print is made on nitrocellulose paper, the cell walls leave a physical print that makes the anatomy visible without further treatment (Varner and Taylor, *Plant Physiol.* 91:31-33 (1989), the entirety of which is herein incorporated by reference).

Tissue printing on substrate films is described by Daoust, *Exp. Cell Res.* 12:203-211 (1957), the entirety of which is herein incorporated by reference, who detected amylase, protease, ribonuclease and deoxyribonuclease in animal tissues using starch, gelatin and agar films. These techniques can be applied to plant tissues (Yomo and Taylor, *Planta* 112:35-43 (1973); the entirety of which is herein incorporated by reference; Harris and Chrispeels, *Plant Physiol.* 56:292-299 (1975), the entirety of which is herein incorporated by reference). Advances in membrane technology have increased the range of applications of Daoust's tissue-printing techniques allowing (Cassab and Varner, *J. Cell. Biol.* 105:2581-2588 (1987), the entirety of which is herein incorporated by reference) the histochemical localization of various plant enzymes and deoxyribonuclease on nitrocellulose paper and nylon (Spruce et al., *Phytochemistry* 26:2901-2903 (1987), the entirety of which is herein incorporated by reference; Barres et al., *Neuron* 5:527-544 (1990), the entirety of which is herein incorporated by reference; Reid and Pont-Lezica, *Tissue Printing. Tools for the Study of Anatomy, Histochemistry and Gene Expression*, Academic Press, New York, N.Y. (1992), the entirety of which is herein incorporated by reference; Reid et al., *Plant Physiol.* 93: 160-165 (1990), the entirety of which is if herein incorporated by reference; Ye et al., *Plant J.* 1:175-183 (1991), the entirety of which is herein incorporated by reference).

It is understood that one or more of the molecules of the present invention, preferably one or more of the EST nucleic acid molecules or fragments thereof of the present invention or one or more of the antibodies of the present invention may be utilized to detect the presence or quantity of a phosphogluconate pathway enzyme by tissue printing.

Further it is also understood that any of the nucleic acid molecules of the present invention may be used as marker nucleic acids and or probes in connection with methods that require probes or marker nucleic acids. As used herein, a probe is an agent that is utilized to determine an attribute or feature (e.g. presence or absence, location, correlation, etc.) of a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

A microarray-based method for high-throughput monitoring of plant gene expression may be utilized to measure gene-specific hybridization targets. This 'chip'-based approach involves using microarrays of nucleic acid molecules as gene-specific hybridization targets to quantitatively measure expression of the corresponding plant genes (Schena et al., *Science* 270:467-470 (1995), the entirety of which is herein incorporated by reference; Shalon, Ph.D. Thesis, Stanford University (1996), the entirety of which is herein incorporated by reference). Every nucleotide in a large sequence can be queried at the same time. Hybridization can be used to efficiently analyze nucleotide sequences.

Several microarray methods have been described. One method compares the sequences to be analyzed by hybridization to a set of oligonucleotides representing all possible subsequences (Bains and Smith, *J. Theor. Biol.* 135:303-307 (1989), the entirety of which is herein incorporated by reference). A second method hybridizes the sample to an array of oligonucleotide or cDNA molecules. An array consisting of oligonucleotides complementary to subsequences of a target sequence can be used to determine the identity of a target sequence, measure its amount and detect differences between the target and a reference sequence. Nucleic acid molecule microarrays may also be screened with protein molecules or fragments thereof to determine nucleic acid molecules that specifically bind protein molecules or fragments thereof.

The microarray approach may be used with polypeptide targets (U.S. Pat. No. 5,445,934; U.S. Pat. No. 5,143,854; U.S. Pat. No. 5,079,600; U.S. Pat. No. 4,923,901, all of which are herein incorporated by reference in their entirety). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides. (Fodor et al., *Science* 251:767-773 (1991), the entirety of which is herein incorporated by reference). It is understood that one or more of the nucleic acid molecules or protein or fragments thereof of the present invention may be utilized in a microarray based method.

In a preferred embodiment of the present invention microarrays may be prepared that comprise nucleic acid molecules where such nucleic acid molecules encode at least one, preferably at least two, more preferably at least three phosphogluconate pathway enzymes, more preferably at least four phosphogluconate pathway enzymes, more preferably at least five phosphogluconate pathway enzymes, more preferably at least six phosphogluconate pathway enzymes, more preferably at least seven phosphogluconate pathway enzymes, more preferably at least eight phosphogluconate pathway enzymes, more preferably at least nine phosphogluconate pathway enzymes, more preferably at least ten phosphogluconate pathway enzymes, and even more preferably at least eleven phosphogluconate pathway enzymes.

In a preferred embodiment the nucleic acid molecules are selected from the group consisting of a nucleic acid molecule that encodes a maize or soybean glucose-6-phosphate-1-dehydrogenase enzyme or fragment thereof; a nucleic acid molecule that encodes a maize or soybean 6-phosphogluconate dehydrogenase enzyme or fragment thereof; a nucleic acid molecule that encodes a putative maize or soybean 6-phosphogluconate dehydrogenase enzyme or fragment thereof; a nucleic acid molecule that encodes a maize or soybean D-ribulose-5-phosphate-3-epimerase enzyme or fragment thereof; a nucleic acid molecule that encodes a maize or soybean ribose-5-phosphate isomerase enzyme or fragment thereof; a nucleic acid molecule that encodes a putative maize or soybean ribose-5-phosphate isomerase enzyme or fragment thereof; a nucleic acid molecule that encodes a maize or soybean transketolase enzyme or fragment thereof; a nucleic acid molecule that encodes a putative maize or soybean transketolase enzyme or fragment thereof; a nucleic acid molecule that encodes a maize or soybean transaldolase enzyme or fragment thereof; a nucleic acid molecule that encodes a putative maize transaldolase enzyme or fragment thereof; and a nucleic acid molecule that encodes a maize or soybean phosphoglucoisomerase enzyme or fragment thereof.

Site directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site directed mutagenesis are often employed. These are cassette mutagenesis (Wells et al., *Gene* 34:315-323 (1985), the entirety of which is herein incorporated by reference), primer extension (Gilliam et al., *Gene* 12:129-137 (1980), the entirety of which is herein incorporated by reference; Zoller and Smith, *Methods Enzymol.* 100:468-500 (1983), the entirety of which is herein incorporated by reference; Dalbadie-McFarland et al., *Proc. Natl. Acad. Sci.* (*U.S.A.*) 79:6409-6413 (1982), the entirety of which is herein incorporated by reference) and methods based upon PCR (Scharf et al., *Science* 233:1076-1078 (1986), the entirety of which is herein incorporated by reference; Higuchi et al., *Nucleic Acids Res.* 16:7351-7367 (1988), the entirety of which is herein incorporated by reference). Site directed mutagenesis approaches are also described in European Patent 0 385 962, the entirety of which is herein incorporated by reference; European Patent 0 359 472, the entirety of which is herein incorporated by reference; and PCT Patent Application WO 93/07278, the entirety of which is herein incorporated by reference.

Site directed mutagenesis strategies have been applied to plants for both in vitro as well as in vivo site directed mutagenesis (Lanz et al., *J. Biol. Chem.* 266:9971-9976 (1991), the entirety of which is herein incorporated by reference; Kovgan and Zhdanov, *Biotekhnologiya* 5:148-154; No. 207160n, Chemical Abstracts 110:225 (1989), the entirety of which is herein incorporated by reference; Ge et al., *Proc. Natl. Acad. Sci.* (*U.S.A.*) 86:4037-4041 (1989), the entirety of which is herein incorporated by reference; Zhu et al., *J. Biol. Chem.* 271:18494-18498 (1996), the entirety of which is herein incorporated by reference; Chu et al., *Biochemistry* 33:6150-6157 (1994), the entirety of which is herein incorporated by reference; Small et al., *EMBO J.* 11:1291-1296 (1992), the entirety of which is herein incorporated by reference; Cho et al., *Mol. Biotechnol.* 8:13-16 (1997), the entirety of which is herein incorporated by reference; Kita et al., *J. Biol. Chem.* 271:26529-26535 (1996), the entirety of which is herein incorporated by reference, Jin et al., *Mol. Microbiol.* 7:555-562 (1993), the entirety of which is herein incorporated by reference; Hatfield and Vierstra, *J. Biol. Chem.* 267:14799-14803 (1992), the entirety of which is herein incorporated by reference; Zhao et al., *Biochemistry* 31:5093-5099 (1992), the entirety of which is herein incorporated by reference).

Any of the nucleic acid molecules of the present invention may either be modified by site directed mutagenesis or used as, for example, nucleic acid molecules that are used to target other nucleic acid molecules for modification. It is understood that mutants with more than one altered nucleotide can be constructed using techniques that practitioners are familiar with such as isolating restriction fragments and ligating such fragments into an expression vector (see, for example, Sambrook et al., *Molecular Cloning: A Laboratory Manual*, Cold Spring Harbor Press (1989)).

Sequence-specific DNA-binding proteins play a role in the regulation of transcription. The isolation of recombinant cDNAs encoding these proteins facilitates the biochemical analysis of their structural and functional properties. Genes encoding such DNA-binding proteins have been isolated using classical genetics (Vollbrecht et al., *Nature* 350: 241-243 (1991), the entirety of which is herein incorporated by reference) and molecular biochemical approaches, including the screening of recombinant cDNA libraries with antibodies (Landschulz et al., *Genes Dev.* 2:786-800 (1988), the entirety of which is herein incorporated by reference) or DNA probes (Bodner et al., *Cell* 55:505-518 (1988), the entirety of which is herein incorporated by reference). In addition, an in situ screening procedure has been used and has facilitated the isolation of sequence-specific DNA-binding proteins from various plant species (Gilmartin et al., *Plant Cell* 4:839-849 (1992), the entirety of which is herein incorporated by reference; Schindler et al., *EMBO J.* 11:1261-1273 (1992), the entirety of which is herein incorporated by reference). An in situ screening protocol does not require the purification of the protein of interest (Vinson et al., *Genes Dev.* 2:801-806 (1988), the entirety of which is herein incorporated by reference; Singh et al., *Cell* 52:415-423 (1988), the entirety of which is herein incorporated by reference).

Two steps may be employed to characterize DNA-protein interactions. The first is to identify promoter fragments that interact with DNA-binding proteins, to titrate binding activity, to determine the specificity of binding and to determine whether a given DNA-binding activity can interact with related DNA sequences (Sambrook et al., *Molecular Cloning: A Laboratory Manual,* 2nd edition, Cold Spring Harbor Laboratory Press, Cold Spring Harbor, New York (1989)). Electrophoretic mobility-shift assay is a widely used assay. The assay provides a rapid and sensitive method for detecting DNA-binding proteins based on the observation that the mobility of a DNA fragment through a nondenaturing, low-ionic strength polyacrylamide gel is retarded upon association with a DNA-binding protein (Fried and Crother, *Nucleic Acids Res.* 9:6505-6525 (1981), the entirety of which is herein incorporated by reference). When one or more specific binding activities have been identified, the exact sequence of the DNA bound by the protein may be determined. Several procedures for characterizing protein/DNA-binding sites are used, including methylation and ethylation interference assays (Maxam and Gilbert, *Methods Enzymol.* 65:499-560 (1980), the entirety of which is herein incorporated by reference; Wissman and Hillen, *Methods Enzymol.* 208:365-379 (1991), the entirety of which is herein incorporated by reference), footprinting techniques employing DNase I (Galas and Schmitz, *Nucleic Acids Res.* 5:3157-3170 (1978), the entirety of which is herein incorporated by reference), 1,10-phenanthroline-copper ion methods (Sigman et al., *Methods Enzymol.* 208:414-433 (1991), the entirety of which is herein incorporated by reference) and hydroxyl radicals methods (Dixon et al., *Methods Enzymol.* 208:414-433 (1991), the entirety of which is herein incorporated by reference). It is understood that one or more of the nucleic acid molecules of the present invention may be utilized to identify a protein or fragment thereof that specifically binds to a nucleic acid molecule of the present invention. It is also understood that one or more of the protein molecules or fragments thereof of the present invention may be utilized to identify a nucleic acid molecule that specifically binds to it.

A two-hybrid system is based on the fact that many cellular functions are carried out by proteins, such as transcription factors, that interact (physically) with one another. Two-hybrid systems have been used to probe the function of new proteins (Chien et al., *Proc. Natl. Acad. Sci.* (*U.S.A.*) 88:9578-9582 (1991) the entirety of which is herein incorporated by reference; Durfee et al., *Genes Dev.* 7:555-569 (1993) the entirety of which is herein incorporated by reference; Choi et al., *Cell* 78:499-512 (1994), the entirety of which is herein incorporated by reference; Kranz et al., *Genes Dev.* 8:313-327 (1994), the entirety of which is herein incorporated by reference).

Interaction mating techniques have facilitated a number of two-hybrid studies of protein-protein interaction. Interaction mating has been used to examine interactions between small sets of tens of proteins (Finley and Brent, *Proc. Natl. Acad. Sci.* (*U.S.A.*) 91:12098-12984 (1994), the entirety of which is herein incorporated by reference), larger sets of hundreds of proteins (Bendixen et al., *Nucl. Acids Res.* 22:1778-1779 (1994), the entirety of which is herein incorporated by reference) and to comprehensively map proteins encoded by a small genome (Bartel et al., *Nature Genetics* 12:72-77 (1996), the entirety of which is herein incorporated by reference). This technique utilizes proteins fused to the DNA-binding domain and proteins fused to the activation domain. They are expressed in two different haploid yeast strains of opposite mating type and the strains are mated to determine if the two proteins interact. Mating occurs when haploid yeast strains come into contact and result in the fusion of the two haploids into a diploid yeast strain. An interaction can be determined by the activation of a two-hybrid reporter gene in the diploid strain. An advantage of this technique is that it reduces the number of yeast transformations needed to test individual interactions. It is understood that the protein-protein interactions of protein or fragments thereof of the present invention may be investigated using the two-hybrid system and that any of the nucleic acid molecules of the present invention that encode such proteins or fragments thereof may be used to transform yeast in the two-hybrid system.

(a) Plant Constructs and Plant Transformants

One or more of the nucleic acid molecules of the present invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. Such genetic material may be transferred into either monocotyledons and dicotyledons including, but not limited to maize (pp 63-69), soybean (pp 50-60), *Arabidopsis* (p 45), *phaseolus* (pp 47-49), peanut (pp 49-50), alfalfa (p 60), wheat (pp 69-71), rice (pp 72-79), oat (pp 80-81), sorghum (p 83), rye (p 84), tritordeum (p 84), millet (p85), fescue (p 85), perennial ryegrass (p 86), sugarcane (p87), cranberry (p101), papaya (pp 101-102), banana (p 103), banana (p 103), muskmelon (p 104), apple (p 104), cucumber (p 105), dendrobium (p 109), gladiolus (p 110), chrysanthemum (p 110), liliacea (p 111), cotton (pp 113-114), eucalyptus (p 115), sunflower (p 118), canola (p 118), turfgrass (p121), sugarbeet (p 122), coffee (p 122) and dioscorea (p 122) (Christou, In: *Particle Bombardment for Genetic Engineering of Plants*, Biotechnology Intelligence Unit. Academic Press, San Diego, Calif. (1996), the entirety of which is herein incorporated by reference).

Transfer of a nucleic acid that encodes for a protein can result in overexpression of that protein in a transformed cell or transgenic plant. One or more of the proteins or fragments thereof encoded by nucleic acid molecules of the present invention may be overexpressed in a transformed cell or transformed plant. Particularly, any of the phosphogluconate pathway enzymes or fragments thereof may be overexpressed in a transformed cell or transgenic plant. Such overexpression may be the result of transient or stable transfer of the exogenous genetic material.

Exogenous genetic material may be transferred into a plant cell and the plant cell by the use of a DNA vector or construct designed for such a purpose. Design of such a vector is generally within the skill of the art (See, *Plant Molecular Biology: A Laboratory Manual*, Clark (ed.), Springier, N.Y. (1997), the entirety of which is herein incorporated by reference).

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci.* (*U.S.A.*) 84:5745-5749 (1987), the entirety of which is herein incorporated by reference), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), the entirety of which is herein incorporated by reference) and the CAMV 35S promoter (Odell et al., *Nature* 313:810-812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (*U.S.A.*) 84:6624-6628 (1987), the entirety of which is herein incorporated by reference), the sucrose synthase promoter (Yang et al., *Proc. Natl. Acad. Sci.* (*U.S.A.*) 87:4144-4148 (1990), the entirety of which is herein incorporated by reference), the R gene complex promoter (Chandler et al., *The Plant Cell* 1:1175-1183 (1989), the entirety of which is herein incorporated by reference) and the chlorophyll a/b binding protein gene promoter, etc. These promoters have been used to create DNA constructs which have been expressed in plants; see, e.g., PCT publication WO 84/02913, herein incorporated by reference in its entirety.

Promoters which are known or are found to cause transcription of DNA in plant cells can be used in the present invention. Such promoters may be obtained from a variety of sources such as plants and plant viruses. It is preferred that the particular promoter selected should be capable of causing sufficient expression to result in the production of an effective amount of the phosphogluconate pathway enzyme to cause the desired phenotype. In addition to promoters that are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci.* (*U.S.A.*) 87:3459-3463 (1990), herein incorporated by reference in its entirety), the chloroplast fructose-1,6-biphosphatase (FBPase) promoter from wheat (Lloyd et al., *Mol. Gen. Genet.* 225:209-216 (1991), herein incorporated by reference in its entirety), the nuclear photosynthetic ST-LS1 promoter from potato (Stockhaus et al., *EMBO J.* 8:2445-2451 (1989), herein incorporated by reference in its entirety), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994), herein incorporated by reference in its entirety), the promoter for the Cab-1 gene from wheat (Fejes et al., *Plant Mol. Biol.* 15:921-932 (1990), herein incorporated by reference in its entirety), the promoter for the CAB-1 gene from spinach (Lubberstedt et al., *Plant Physiol.* 104:997-1006 (1994), herein incorporated by reference in its entirety), the promoter for the cab1R gene from rice (Luan et al., *Plant Cell.* 4:971-981 (1992), the entirety of which is herein incorporated by reference), the pyruvate, orthophosphate dikinase (PPDK) promoter from maize (Matsuoka et al., *Proc. Natl. Acad. Sci.* (*U.S.A.*) 90: 9586-9590 (1993), herein incorporated by reference in its entirety), the promoter for the tobacco Lhcb1*2 gene (Cerdan et al., *Plant Mol. Biol.* 33:245-255 (1997), herein incorporated by reference in its entirety), the *Arabidopsis thaliana* SUC2 sucrose-H+ symporter promoter (Truernit et al., *Planta.* 196:564-570 (1995), herein incorporated by reference in its entirety) and the promoter for the thylakoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (*Sinapis alba*; Kretsch et al., *Plant Mol. Biol.* 28:219-229 (1995), the entirety of which is herein incorporated by reference).

For the purpose of expression in sink tissues of the plant, such as the tuber of the potato plant, the fruit of tomato, or the seed of maize, wheat, rice and barley, it is preferred that the promoters utilized in the present invention have relatively high expression in these specific tissues. A number of promoters for genes with tuber-specific or -enhanced expression are known, including the class I patatin promoter (Bevan et al., *EMBO J.* 8:1899-1906 (1986); Jefferson et al., *Plant Mol. Biol.* 14:995-1006 (1990), both of which are herein incorporated by reference in its entirety), the promoter for the potato tuber ADPGPP genes, both the large and small subunits, the sucrose synthase promoter (Salanoubat and Belliard, *Gene.* 60:47-56 (1987), Salanoubat and Belliard, *Gene.* 84:181-185 (1989), both of which are incorporated by reference in their entirety), the promoter for the major tuber proteins including the 22 kd protein complexes and proteinase inhibitors (Hannapel, *Plant Physiol.* 101:703-704 (1993), herein incorporated by reference in its entirety), the promoter for the granule bound starch synthase gene (GBSS) (Visser et al., *Plant Mol. Biol.* 17:691-699 (1991), herein incorporated by reference in its entirety) and other class I and II patatins promoters (Koster-Topfer et al., *Mol Gen Genet.* 219:390-396 (1989); Mignery et al., *Gene.* 62:27-44 (1988), both of which are herein incorporated by reference in their entirety).

Other promoters can also be used to express a phosphogluconate pathway enzyme or fragment thereof in specific tissues, such as seeds or fruits. The promoter for β-conglycinin (Chen et al., *Dev. Genet.* 10: 112-122 (1989), herein incorporated by reference in its entirety) or other seed-specific promoters such as the napin and phaseolin promoters, can be used. The zeins are a group of storage proteins found in maize endosperm. Genomic clones for zein genes have been isolated (Pedersen et al., *Cell* 29:1015-1026 (1982), herein incorporated by reference in its entirety) and the promoters from these clones, including the 15 kD, 16 kD, 19 kD, 22 kD, 27 kD and γ genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell. Biol.* 13:5829-5842 (1993), herein incorporated by reference in its entirety). Examples of promoters suitable for expression in wheat include those promoters for the ADP glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene (Samac et al., *Plant Mol. Biol.* 25:587-596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci. (U.S.A.)* 86:7890-7894 (1989), herein incorporated by reference in its entirety). Other root cell specific promoters include those reported by Conkling et al. (Conkling et al., *Plant Physiol.* 93:1203-1211 (1990), the entirety of which is herein incorporated by reference).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are herein incorporated in their entirety. In addition, a tissue specific enhancer may be used (Fromm et al., *The Plant Cell* 1:977-984 (1989), the entirety of which is herein incorporated by reference).

Constructs or vectors may also include with the coding region of interest a nucleic acid sequence that acts, in whole or in part, to terminate transcription of that region. For example, such sequences have been isolated including the Tr7 3' sequence and the NOS 3' sequence (Ingelbrecht et al., *The Plant Cell* 1:671-680 (1989), the entirety of which is herein incorporated by reference; Bevan et al., *Nucleic Acids Res.* 11:369-385 (1983), the entirety of which is herein incorporated by reference), or the like.

A vector or construct may also include regulatory elements. Examples of such include the Adh intron 1 (Callis et al., *Genes and Develop.* 1:1183-1200 (1987), the entirety of which is herein incorporated by reference), the sucrose synthase intron (Vasil et al., Plant Physiol. 91:1575-1579 (1989), the entirety of which is herein incorporated by reference) and the TMV omega element (Gallie et al., *The Plant Cell* 1:301-311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985), the entirety of which is herein incorporated by reference) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988), the entirety of which is herein incorporated by reference) which encodes glyphosate resistance; a nitrilase gene which confers resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500-12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996), the entirety of which is herein incorporated by reference.

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987), the entirety of which is herein incorporated by reference; Jefferson et al., *EMBO J.* 6:3901-3907 (1987), the entirety of which is herein incorporated by reference); an R-locus gene, which encodes a product that regulates the production of anthocyanin pigments (red color) in plant tissues (Dellaporta et al., Stadler Symposium 11:263-282 (1988), the entirety of which is herein incorporated by reference); a β-lactamase gene (Sutcliffe et al., *Proc. Natl. Acad. Sci.* (U.S.) 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234:856-859 (1986), the entirety of which is herein incorporated by reference); a xylE gene (Zukowsky et al., *Proc. Natl. Acad. Sci. (U.S.A.)* 80:1101-1105 (1983), the entirety of which is herein incorporated by reference) which encodes a catechol diozygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205-225 (1991), the entirety of which is herein incorporated by reference; Vasil, *Plant Mol. Biol.* 25:925-937 (1994), the entirety of which is herein incorporated by reference). For example, electroporation has been used to transform maize protoplasts (Fromm et al., *Nature* 312:791-793 (1986), the entirety of which is herein incorporated by reference).

Other vector systems suitable for introducing transforming DNA into a host plant cell include but are not limited to binary artificial chromosome (BIBAC) vectors (Hamilton et al., *Gene* 200:107-116 (1997), the entirety of which is herein incorporated by reference); and transfection with RNA viral vectors (Della-Cioppa et al., *Ann. N.Y. Acad. Sci.* (1996), 792 (Engineering Plants for Commercial Products and Applications), 57-61, the entirety of which is herein incorporated by reference). Additional vector systems also include plant selectable YAC vectors such as those described in Mullen et al., *Molecular Breeding* 4:449-457 (1988), the entirety of which is herein incorporated by reference).

Technology for introduction of DNA into cells is well known to those of skill in the art. Four general methods for delivering a gene into cells have been described: (1) chemical methods (Graham and van der Eb, *Virology* 54:536-539 (1973), the entirety of which is herein incorporated by reference); (2) physical methods such as microinjection (Capecchi, *Cell* 22:479-488 (1980), the entirety of which is herein incorporated by reference), electroporation (Wong and Neumann, *Biochem. Biophys. Res. Commun.* 107:584-587 (1982); Fromm et al., *Proc. Natl. Acad. Sci.* (*U.S.A.*) 82:5824-5828 (1985); U.S. Pat. No. 5,384,253, all of which are herein incorporated in their entirety); and the gene gun (Johnston and Tang, *Methods Cell Biol.* 43:353-365 (1994), the entirety of which is herein incorporated by reference); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988), all of which are herein incorporated in their entirety); and (4) receptor-mediated mechanisms (Curiel et al., *Hum. Gen. Ther.* 3:147-154 (1992), Wagner et al., *Proc. Natl. Acad. Sci.* (*USA*) 89:6099-6103 (1992), both of which are incorporated by reference in their entirety).

Acceleration methods that may be used include, for example, microprojectile bombardment and the like. One example of a method for delivering transforming nucleic acid molecules to plant cells is microprojectile bombardment. This method has been reviewed by Yang and Christou (eds.), *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671-674 (1988), the entirety of which is herein incorporated by reference) nor the susceptibility of *Agrobacterium* infection are required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990), the entirety of which is herein incorporated by reference). The screen disperses the tungsten nucleic acid particles so that they are not delivered to the recipient cells in large aggregates. A particle delivery system suitable for use with the present invention is the helium acceleration PDS-1000/He gun is available from Bio-Rad Laboratories (Bio-Rad, Hercules, Calif.) (Sanford et al., *Technique* 3:3-16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci.* (*U.S.A.*) 87:8526-8530 (1990); Svab and Maliga, *Proc. Natl. Acad. Sci.* (*U.S.A.*) 90:913-917 (1993); Staub and Maliga, *EMBO J.* 12:601-606 (1993); U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol.* 153:253-277 (1987), both of which are herein incorporated by reference in their entirety. Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179-203 (1985), the entirety of which is herein incorporated by reference. Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988), all of which are herein incorporated by reference in their entirety).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor Appl. Genet.* 205:34 (1986); Yamada et al., *Plant Cell Rep.* 4:85 (1986); Abdullah et al., *Biotechnolog* 4:1087 (1986), all of which are herein incorporated by reference in their entirety).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988), the entirety of which is herein incorporated by reference). In addition, "particle gun" or high-velocity microprojectile technology can be utilized (Vasil et al., *Bio/Technology* 10:667 (1992), the entirety of which is herein incorporated by reference).

Using the latter technology, DNA is carried through the cell wall and into the cytoplasm on the surface of small metal particles as described (Klein et al., *Nature* 328:70 (1987); Klein et al., *Proc. Natl. Acad. Sci.* (*U.S.A.*) 85:8502-8505 (1988); McCabe et al., *Bio/Technology* 6:923 (1988), all of which are herein incorporated by reference in their entirety). The metal particles penetrate through several layers of cells and thus allow the transformation of cells within tissue explants.

Other methods of cell transformation can also be used and include but are not limited to introduction of DNA into plants by direct DNA transfer into pollen (Zhou et al., *Methods Enzymol.* 101.433 (1983); Hess et al., *Intern Rev. Cytol.* 107:367 (1987); Luo et al., *Plant Mol Biol. Reporter* 6.165 (1988), all of which are herein incorporated by reference in their entirety), by direct injection of DNA into reproductive organs of a plant (Pena et al., *Nature* 325:274 (1987), the entirety of which is herein incorporated by reference), or by direct injection of DNA into the cells of immature embryos followed by the rehydration of desiccated embryos (Neuhaus et al., *Theor. Appl. Genet.* 75:30 (1987), the entirety of which is herein incorporated by reference).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908, all of which are herein incorporated by reference in their entirety); soybean (U.S. Pat. No. 5,569,834; U.S. Pat. No. 5,416,011; McCabe et. al., *Biotechnology* 6:923 (1988); Christou et al., *Plant Physiol.* 87:671-674 (1988); all of which are herein incorporated by reference in their entirety); *Brassica* (U.S. Pat. No. 5,463,174, the entirety of which is herein incorporated by reference); peanut (Cheng et al., *Plant Cell Rep.* 15:653-657 (1996), McKently et al., *Plant Cell Rep.* 14.699-703 (1995), all of which are herein incorporated by reference in their entirety); papaya; and pea (Grant et al., *Plant Cell Rep.* 15:254-258 (1995), the entirety of which is herein incorporated by reference).

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*USA*) 84:5354 (1987), the entirety of which is herein incorporated by reference); barley (Wan and Lemaux, *Plant Physiol* 104:37 (1994), the entirety of which is herein incorporated by reference); maize (Rhodes et al., *Science* 240:204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995); all of which are herein incorporated by reference in their entirety); oat (Somers et al., *Bio/Technology* 10:1589 (1992), the entirety of which is herein incorporated by reference); orchard grass (Horn et al., *Plant Cell Rep.* 7:469 (1988), the entirety of which is herein incorporated by reference); rice (Toriyama et al., *Theor Appl. Genet.* 205:34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991), all of which are herein incorporated by reference in their entirety); rye (De la Pena et al., *Nature* 325:274 (1987), the entirety of which is herein incorporated by reference); sugarcane (Bower and Birch, *Plant J.* 2:409 (1992), the entirety of which is herein incorporated by reference); tall fescue (Wang et al., *Bio/Technology* 10:691 (1992), the entirety of which is herein incorporated by reference) and wheat (Vasil et al., *Bio/Technology* 10:667 (1992), the entirety of which is herein incorporated by reference; U.S. Pat. No. 5,631,152, the entirety of which is herein incorporated by reference.)

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988), the entirety of which is herein incorporated by reference; Marcotte et al., *Plant Cell* 1.523-532 (1989), the entirety of which is herein incorporated by reference; McCarty et al., *Cell* 66:895-905 (1991), the entirety of which is herein incorporated by reference; Hattori et al., *Genes Dev.* 6:609-618 (1992), the entirety of which is herein incorporated by reference; Goff et al., *EMBO J.* 9:2517-2522 (1990), the entirety of which is herein incorporated by reference). Transient expression systems may be used to functionally dissect gene constructs (see generally, Mailga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters, enhancers etc. Further, any of the nucleic acid molecules of the present invention may be introduced into a plant cell in a manner that allows for overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990), the entirety of which is herein incorporated by reference; van der Krol et al., *Plant Cell* 2:291-299 (1990), the entirety of which is herein incorporated by reference). Cosuppression may result from stable transformation with a single copy nucleic acid molecule that is homologous to a nucleic acid sequence found with the cell (Prolls and Meyer, *Plant J.* 2:465-475 (1992), the entirety of which is herein incorporated by reference) or with multiple copies of a nucleic acid molecule that is homologous to a nucleic acid sequence found with the cell (Mittlesten et al., *Mol. Gen. Genet.* 244.325-330 (1994), the entirety of which is herein incorporated by reference). Genes, even though different, linked to homologous promoters may result in the cosuppression of the linked genes (Vaucheret, *C. R. Acad. Sci. III* 316.1471-1483 (1993), the entirety of which is herein incorporated by reference).

This technique has, for example, been applied to generate white flowers from red petunia and tomatoes that do not ripen on the vine. Up to 50% of petunia transformants that contained a sense copy of the glucoamylase (CHS) gene produced white flowers or floral sectors; this was as a result of the post-transcriptional loss of mRNA encoding CHS (Flavell, *Proc. Natl. Acad. Sci.* (*U.S.A.*) 91:3490-3496 (1994), the entirety of which is herein incorporated by reference); van Blokland et al., *Plant J.* 6:861-877 (1994), the entirety of which is herein incorporated by reference). Cosuppression may require the coordinate transcription of the transgene and the endogenous gene and can be reset by a developmental control mechanism (Jorgensen, *Trends Biotechnol.* 8:340-344 (1990), the entirety of which is herein incorporated by reference; Meins and Kunz, In: *Gene Inactivation and Homologous Recombination in Plants*, Paszkowski (ed.), pp. 335-348, Kluwer Academic, Netherlands (1994), the entirety of which is herein incorporated by reference).

It is understood that one or more of the nucleic acids of the present invention may be introduced into a plant cell and transcribed using an appropriate promoter with such transcription resulting in the cosuppression of an endogenous phosphogluconate pathway enzyme.

Antisense approaches are a way of preventing or reducing gene function by targeting the genetic material (Mol et al., *FEBS Lett.* 268:427-430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569-597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990), the entirety of which is herein incorporated by reference). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a phosphogluconate pathway enzyme in a plant cell may be reduced or depressed by growing a transformed plant cell containing a nucleic acid molecule whose non-transcribed strand encodes a phosphogluconate pathway enzyme or fragment thereof.

Antibodies have been expressed in plants (Hiatt et al., *Nature* 342:76-78 (1989), the entirety of which is herein incorporated by reference; Conrad and Fielder, *Plant Mol. Biol.* 26:1023-1030 (1994), the entirety of which is herein incorporated by reference). Cytoplamsic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16.4489-4496 (1997), the entirety of which is herein incorporated by reference; Marion-Poll, *Trends in Plant Science* 2:447-448 (1997), the entirety of which is herein incorporated by reference). For example, expressed anti-abscisic antibodies have been reported to result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15.1313-1315 (1997), the entirety of which is herein incorporated by reference; Baca et al., *Ann. Rev. Biophys. Biomol. Struct.* 26:461-493 (1997), the entirety of which is herein incorporated by reference). The catalytic abilities of abzymes may be enhanced by site directed mutagenesis. Examples of abzymes are, for example, set forth in U.S. Pat. No. 5,658,753; U.S. Pat. No. 5,632,990; U.S. Pat. No. 5,631,137; U.S. Pat. No. 5,602,015; U.S. Pat. No. 5,559,538; U.S. Pat. No. 5,576,174; U.S. Pat. No. 5,500,358; U.S. Pat. No. 5,318,897; U.S. Pat. No. 5,298,409; U.S. Pat. No. 5,258,289 and U.S. Pat. No. 5,194,585, all of which are herein incorporated in their entirety.

It is understood that any of the antibodies of the present invention may be expressed in plants and that such expression can result in a physiological effect. It is also understood that any of the expressed antibodies may be catalytic.

(b) Fungal Constructs and Fungal Transformants

The present invention also relates to a fungal recombinant vector comprising exogenous genetic material. The present invention also relates to a fungal cell comprising a fungal recombinant vector. The present invention also relates to methods for obtaining a recombinant fungal host cell comprising introducing into a fungal host cell exogenous genetic material.

Exogenous genetic material may be transferred into a fungal cell. In a preferred embodiment the exogenous genetic material includes a nucleic acid molecule of the present invention having a sequence selected from the group consisting of SEQ ID NO: 1 through SEQ ID NO: 699 or complements thereof or fragments of either or other nucleic acid molecule of the present invention. The fungal recombinant vector may be any vector which can be conveniently subjected to recombinant DNA procedures. The choice of a vector will typically depend on the compatibility of the vector with the fungal host cell into which the vector is to be introduced. The vector may be a linear or a closed circular plasmid. The vector system may be a single vector or plasmid or two or more vectors or plasmids which together contain the total DNA to be introduced into the genome of the fungal host.

The fungal vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the fungal cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the fungal host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the fungal host cell and, furthermore, may be non-encoding or encoding sequences.

For autonomous replication, the vector may further comprise an origin of replication enabling the vector to replicate autonomously in the host cell in question. Examples of origin of replications for use in a yeast host cell are the 2 micron origin of replication and the combination of CEN3 and ARS 1. Any origin of replication may be used which is compatible with the fungal host cell of choice.

The fungal vectors of the present invention preferably contain one or more selectable markers which permit easy selection of transformed cells. A selectable marker is a gene the product of which provides, for example biocide or viral resistance, resistance to heavy metals, prototrophy to auxotrophs and the like. The selectable marker may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase) and sC (sulfate adenyltransferase) and trpC (anthranilate synthase). Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, the entirety of which is herein incorporated by reference. A nucleic acid sequence of the present invention may be operably linked to a suitable promoter sequence. The promoter sequence is a nucleic acid sequence which is recognized by the fungal host cell for expression of the nucleic acid sequence. The promoter sequence contains transcription and translation control sequences which mediate the expression of the protein or fragment thereof.

A promoter may be any nucleic acid sequence which shows transcriptional activity in the fungal host cell of choice and may be obtained from genes encoding polypeptides either homologous or heterologous to the host cell. Examples of suitable promoters for directing the transcription of a nucleic acid construct of the invention in a filamentous fungal host are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase and hybrids thereof. In a yeast host, a useful promoter is the *Saccharomyces cerevisiae* enolase (eno-1) promoter. Particularly preferred promoters are the TAKA amylase, NA2-tpi (a hybrid of the promoters from the genes encoding *Aspergillus niger* neutral alpha-amylase and *Aspergillus oryzae* triose phosphate isomerase) and glaA promoters.

A protein or fragment thereof encoding nucleic acid molecule of the present invention may also be operably linked to a terminator sequence at its 3' terminus. The terminator sequence may be native to the nucleic acid sequence encoding the protein or fragment thereof or may be obtained from foreign sources. Any terminator which is functional in the fungal host cell of choice may be used in the present invention, but particularly preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase and *Saccharomyces cerevisiae* enolase.

A protein or fragment thereof encoding nucleic acid molecule of the present invention may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the fungal host cell of choice may be used in the present invention, but particularly preferred leaders are obtained from the genes encoding *Aspergillus oryzae* TAKA amylase and *Aspergillus oryzae* triose phosphate isomerase.

A polyadenylation sequence may also be operably linked to the 3' terminus of the nucleic acid sequence of the present invention. The polyadenylation sequence is a sequence which when transcribed is recognized by the fungal host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention, but particularly preferred polyadenylation sequences are obtained from the genes encoding *Aspergillus oryzae* TAKA amylase, *Aspergillus niger* glucoamylase, *Aspergillus nidulans* anthranilate synthase and *Aspergillus niger* alpha-glucosidase.

To avoid the necessity of disrupting the cell to obtain the protein or fragment thereof and to minimize the amount of possible degradation of the expressed protein or fragment thereof within the cell, it is preferred that expression of the protein or fragment thereof gives rise to a product secreted outside the cell. To this end, a protein or fragment thereof of the present invention may be linked to a signal peptide linked to the amino terminus of the protein or fragment thereof. A signal peptide is an amino acid sequence which permits the secretion of the protein or fragment thereof from the fungal host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof. Alternatively, the 5' end of the coding sequence may contain a signal peptide coding region which is foreign to that portion of the coding sequence which encodes the secreted protein or fragment thereof. The foreign signal peptide may be required where the coding sequence does not normally contain a signal peptide coding region. Alternatively, the foreign signal peptide may simply replace the natural signal peptide to obtain enhanced secretion of the desired protein or fragment thereof. The foreign signal peptide coding region may be obtained from a glucoamylase or an amylase gene from an *Aspergillus* species, a lipase or proteinase gene from *Rhizomucor miehei*, the gene for the alpha-factor from *Saccharomyces cerevisiae*, or the calf preprochymosin gene. An effective signal peptide for fungal host cells is the *Aspergillus oryzae* TAKA amylase signal, *Aspergillus niger* neutral amylase signal, the *Rhizomucor miehei* aspartic proteinase signal, the *Humicola lanuginosus* cellulase signal, or the *Rhizomucor miehei* lipase signal. However, any signal peptide capable of permitting secretion of the protein or fragment thereof in a fungal host of choice may be used in the present invention.

A protein or fragment thereof encoding nucleic acid molecule of the present invention may also be linked to a propeptide coding region. A propeptide is an amino acid sequence found at the amino terminus of a proprotein or proenzyme. Cleavage of the propeptide from the proprotein yields a mature biochemically active protein. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme. The propeptide coding region may be native to the protein or fragment thereof or may be obtained from foreign sources. The foreign propeptide coding region may be obtained from the *Saccharomyces cerevisiae* alpha-factor gene or *Myceliophthora thermophila* laccase gene (WO 95/33836, the entirety of which is herein incorporated by reference).

The procedures used to ligate the elements described above to construct the recombinant expression vector of the present invention are well known to one skilled in the art (see, for example, Sambrook et al., *Molecular Cloning, A Laboratory Manual,* 2nd ed., Cold Spring Harbor, N.Y., (1989)).

The present invention also relates to recombinant fungal host cells produced by the methods of the present invention which are advantageously used with the recombinant vector of the present invention. The cell is preferably transformed with a vector comprising a nucleic acid sequence of the invention followed by integration of the vector into the host chromosome. The choice of fungal host cells will to a large extent depend upon the gene encoding the protein or fragment thereof and its source. The fungal host cell may, for example, be a yeast cell or a filamentous fungal cell.

"Yeast" as used herein includes *Ascosporogenous* yeast (*Endomycetales*), *Basidiosporogenous* yeast and yeast belonging to the *Fungi Imperfecti* (*Blastomycetes*). The *Ascosporogenous* yeasts are divided into the families Spermophthoraceae and Saccharomycetaceae. The latter is comprised of four subfamilies, Schizosaccharomycoideae (for example, genus *Schizosaccharomyces*), Nadsonioideae, Lipomycoideae and Saccharomycoideae (for example, genera *Pichia, Kluyveromyces* and *Saccharomyces*). The *Basidiosporogenous* yeasts include the genera *Leucosporidim, Rhodosporidium, Sporidiobolus, Filobasidium* and *Filobasidiella*. Yeast belonging to the *Fungi Imperfecti* are divided into two families, Sporobolomycetaceae (for example, genera *Sorobolomyces* and *Bullera*) and Cryptococcaceae (for example, genus *Candida*). Since the classification of yeast may change in the future, for the purposes of this invention, yeast shall be defined as described in Biology and Activities of Yeast (Skinner et al., *Soc. App. Bacteriol. Symposium Series* No. 9, (1980), the entirety of which is herein incorporated by reference). The biology of yeast and manipulation of yeast genetics are well known in the art (see, for example, *Biochemistry and Genetics of Yeast*, Bacil et al. (ed.), 2nd edition, 1987*; The Yeasts*, Rose and Harrison (eds.), 2nd ed., (1987); and *The Molecular Biology of the Yeast Saccharomyces*, Strathem et al. (eds.), (1981), all of which are herein incorporated by reference in their entirety).

"Fungi" as used herein includes the phyla Ascomycota, Basidiomycota, Chytridiomycota and Zygomycota (as defined by Hawksworth et al., In: Ainsworth and Bisby's *Dictionary of The Fungi,* 8th edition, 1995, CAB International, University Press, Cambridge, UK; the entirety of which is herein incorporated by reference) as well as the Oomycota (as cited in Hawksworth et al., In: Ainsworth and Bisby's *Dictionary of The Fungi,* 8th edition, 1995, CAB International, University Press, Cambridge, UK) and all mitosporic fungi (Hawksworth et al., In: Ainsworth and Bisby's *Dictionary of The Fungi,* 8th edition, 1995, CAB International, University Press, Cambridge, UK). Representative groups of Ascomycota include, for example, *Neurospora, Eupenicillium* (=*Penicillium*), *Emericella* (=*Aspergillus*), *Eurotiun* (=*Aspergillus*) and the true yeasts listed above. Examples of Basidiomycota include mushrooms, rusts and smuts. Representative groups of Chytridiomycota include, for example, Allomyces, Blastocladiella, Coelomomyces and aquatic fungi. Representative groups of Oomycota include, for example, Saprolegniomycetous aquatic fungi (water molds) such as *Achlya*. Examples of mitosporic fungi include *Aspergillus, Penicilliun, Candida* and *Alternaria*. Representative groups of Zygomycota include, for example, *Rhizopus* and *Mucor.*

"Filamentous fungi" include all filamentous forms of the subdivision Eumycota and Oomycota (as defined by Hawksworth et al., In: Ainsworth and Bisby's *Dictionary of The Fungi,* 8th edition, 1995, CAB International, University Press, Cambridge, UK). The filamentous fungi are characterized by a vegetative mycelium composed of chitin, cellulose, glucan, chitosan, mannan and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In one embodiment, the fungal host cell is a yeast cell. In a preferred embodiment, the yeast host cell is a cell of the species of *Candida, Kluyveromyces, Saccharomyces, Schizosaccharomyces, Pichia* and *Yarrowia*. In a preferred embodiment, the yeast host cell is a *Saccharomyces cerevisiae* cell, a *Saccharomyces carlsbergensis, Saccharomyces diastaticus* cell, a *Saccharomyces douglasii* cell, a *Saccharomyces kluyveri* cell, a *Saccharomyces norbensis* cell, or a *Saccharomyces oviformis* cell. In another preferred embodiment, the yeast host cell is a *Kluyveromyces lactis* cell. In another preferred embodiment, the yeast host cell is a *Yarrowia lipolytica* cell.

In another embodiment, the fungal host cell is a filamentous fungal cell. In a preferred embodiment, the filamentous fungal host cell is a cell of the species of, but not limited to, *Acremonium, Aspergillus, Fusarium, Humicola, Myceliophthora, Mucor, Neurospora, Penicillium, Thielavia, Tolypocladium* and *Trichoderma* In a preferred embodiment, the filamentous fungal host cell is an *Aspergillus* cell. In another preferred embodiment, the filamentous fungal host cell is an *Acremonium* cell. In another preferred embodiment, the filamentous fungal host cell is a *Fusarium* cell. In another preferred embodiment, the filamentous fungal host cell is a *Humicola* cell. In another preferred embodiment, the filamentous fungal host cell is a *Myceliophthora* cell. In another even preferred embodiment, the filamentous fungal host cell is a *Mucor* cell. In another preferred embodiment, the filamentous fungal host cell is a *Neurospora* cell. In another preferred embodiment, the filamentous fungal host cell is a *Penicillium* cell. In another preferred embodiment, the filamentous fungal host cell is a *Thielavia* cell. In another preferred embodiment, the filamentous fungal host cell is a *Tolypocladiun* cell. In another preferred embodiment, the filamentous fungal host cell is a *Trichoderma* cell. In a preferred embodiment, the filamentous fungal host cell is an *Aspergillus oryzae* cell, an *Aspergillus niger* cell, an *Aspergillus foetidus* cell, or an *Aspergillus japonicus* cell. In another preferred embodiment, the filamentous fungal host cell is a *Fusarium oxysporum* cell or a *Fusarium graminearum* cell. In another preferred embodiment, the filamentous fungal host cell is a *Humicola insolens* cell or a *Humicola lanuginosus* cell. In another preferred embodiment, the filamentous fungal host cell is a *Myceliophthora thermophila* cell. In a most preferred embodiment, the filamentous fungal host cell is a *Mucor miehei* cell. In a most preferred embodiment, the filamentous fungal host cell is a *Neurospora crassa* cell. In a most preferred embodiment, the filamentous fungal host cell is a *Penicillium purpurogenum* cell. In another most preferred embodiment, the filamentous fungal host cell is a *Thielavia terrestris* cell. In another most preferred embodiment, the

*Trichoderma* cell is a *Trichoderma reesei* cell, a *Trichoderma viride* cell, a *Trichoderma longibrachiatum* cell, a *Trichoderma harzianum* cell, or a *Trichoderma koningii* cell. In a preferred embodiment, the fungal host cell is selected from an *A. nidulans* cell, an *A. niger* cell, an *A. oryzae* cell and an *A. sojae* cell. In a further preferred embodiment, the fungal host cell is an *A. nidulans* cell.

The recombinant fungal host cells of the present invention may further comprise one or more sequences which encode one or more factors that are advantageous in the expression of the protein or fragment thereof, for example, an activator (e.g., a trans-acting factor), a chaperone and a processing protease. The nucleic acids encoding one or more of these factors are preferably not operably linked to the nucleic acid encoding the protein or fragment thereof. An activator is a protein which activates transcription of a nucleic acid sequence encoding a polypeptide (Kudla et al., *EMBO* 9:1355-1364 (1990); Jarai and Buxton, *Current Genetics* 26:2238-244 (1994); Verdier, *Yeast* 6:271-297 (1990), all of which are herein incorporated by reference in their entirety). The nucleic acid sequence encoding an activator may be obtained from the genes encoding *Saccharomyces cerevisiae* heme activator protein 1 (hap 1), *Saccharomyces cerevisiae* galactose metabolizing protein 4 (gal4) and *Aspergillus nidulans* ammonia regulation protein (areA). For further examples, see Verdier, *Yeast* 6:271-297 (1990); MacKenzie et al., *Journal of Gen. Microbiol.* 139:2295-2307 (1993), both of which are herein incorporated by reference in their entirety). A chaperone is a protein which assists another protein in folding properly (Hartl et al., *TIBS* 19:20-25 (1994); Bergeron et al., *TIBS* 19:124-128 (1994); Demolder et al., *J. Biotechnology* 32:179-189 (1994); Craig, *Science* 260:1902-1903 (1993); Gething and Sambrook, *Nature* 355:33-45 (1992); Puig and Gilbert, *J. Biol. Chem.* 269:7764-7771 (1994); Wang and Tsou, *FASEB Journal* 7:1515-11157 (1993); Robinson et al., *Bio/Technology* 1:381-384 (1994), all of which are herein incorporated by reference in their entirety). The nucleic acid sequence encoding a chaperone may be obtained from the genes encoding *Aspergillus oryzae* protein disulphide isomerase, *Saccharomyces cerevisiae* calnexin, *Saccharomyces cerevisiae* BiP/GRP78 and *Saccharomyces cerevisiae* Hsp70. For further examples, see Gething and Sambrook, *Nature* 355:33-45 (1992); Hartl et al., *TIBS* 19:20-25 (1994). A processing protease is a protease that cleaves a propeptide to generate a mature biochemically active polypeptide (Enderlin and Ogrydziak, *Yeast* 10:67-79 (1994); Fuller et al., *Proc. Natl. Acad. Sci.* (*U.S.A.*) 86:1434-1438 (1989); Julius et al., *Cell* 37:1075-1089 (1984); Julius et al., *Cell* 32:839-852 (1983), all of which are incorporated by reference in their entirety). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2 and *Yarrowia lipolytica* dibasic processing endoprotease (xpr6). Any factor that is functional in the fungal host cell of choice may be used in the present invention.

Fungal cells may be transformed by a process involving protoplast formation, transformation of the protoplasts and regeneration of the cell wall in a manner known per se. Suitable procedures for transformation of *Aspergillus* host cells are described in EP 238 023 and Yelton et al., *Proc. Natl. Acad. Sci.* (*U.S.A.*) 81:1470-1474 (1984), both of which are herein incorporated by reference in their entirety. A suitable method of transforming *Fusarium* species is described by Malardier et al., *Gene* 78:147-156 (1989), the entirety of which is herein incorporated by reference. Yeast may be transformed using the procedures described by Becker and Guarente, In: Abelson and Simon, (eds.), *Guide to Yeast Genetics and Molecular Biology, Methods Enzymol.* Volume 194, pp 182-187, Academic Press, Inc., New York; Ito et al., *J. Bacteriology* 153:163 (1983); Hinnen et al., *Proc. Natl. Acad. Sci.* (*U.S.A.*) 75:1920 (1978), all of which are herein incorporated by reference in their entirety.

The present invention also relates to methods of producing the protein or fragment thereof comprising culturing the recombinant fungal host cells under conditions conducive for expression of the protein or fragment thereof. The fungal cells of the present invention are cultivated in a nutrient medium suitable for production of the protein or fragment thereof using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the protein or fragment thereof to be expressed and/or isolated. The cultivation takes place in a suitable nutrient medium comprising carbon and nitrogen sources and inorganic salts, using procedures known in the art (see, e.g., Bennett and LaSure (eds.), *More Gene Manipulations in Fungi*, Academic Press, CA, (1991), the entirety of which is herein incorporated by reference). Suitable media are available from commercial suppliers or may be prepared according to published compositions (e.g., in catalogues of the American Type Culture Collection, Manassas, Va.). If the protein or fragment thereof is secreted into the nutrient medium, a protein or fragment thereof can be recovered directly from the medium. If the protein or fragment thereof is not secreted, it is recovered from cell lysates.

The expressed protein or fragment thereof may be detected using methods known in the art that are specific for the particular protein or fragment. These detection methods may include the use of specific antibodies, formation of an enzyme product, or disappearance of an enzyme substrate. For example, if the protein or fragment thereof has enzymatic activity, an enzyme assay may be used. Alternatively, if polyclonal or monoclonal antibodies specific to the protein or fragment thereof are available, immunoassays may be employed using the antibodies to the protein or fragment thereof. The techniques of enzyme assay and immunoassay are well known to those skilled in the art.

The resulting protein or fragment thereof may be recovered by methods known in the arts. For example, the protein or fragment thereof may be recovered from the nutrient medium by conventional procedures including, but not limited to, centrifugation, filtration, extraction, spray-drying, evaporation, or precipitation. The recovered protein or fragment thereof may then be further purified by a variety of chromatographic procedures, e.g., ion exchange chromatography, gel filtration chromatography, affinity chromatography, or the like.

(c) Mammalian Constructs and Transformed Mammalian Cells

The present invention also relates to methods for obtaining a recombinant mammalian host cell, comprising introducing into a mammalian host cell exogenous genetic material. The present invention also relates to a mammalian cell comprising a mammalian recombinant vector. The present invention also relates to methods for obtaining a recombinant mammalian host cell, comprising introducing into a mammalian cell exogenous genetic material. In a preferred embodiment the exogenous genetic material includes a nucleic acid molecule of the present invention having a sequence selected from the group consisting of SEQ ID NO: 1 through SEQ ID NO: 699 or complements thereof or fragments of either or other nucleic acid molecule of the present invention.

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include viral promoters such as that from Simian Virus 40 (SV40) (Fiers et al., *Nature* 273: 113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells may include viral replicons, or sequences which insure integration of the appropriate sequences encoding HCV epitopes into the host genome. For example, another vector used to express foreign DNA is vaccinia virus. In this case, for example, a nucleic acid molecule encoding a protein or fragment thereof is inserted into the vaccinia genome. Techniques for the insertion of foreign DNA into the vaccinia virus genome are known in the art and may utilize, for example, homologous recombination. Such heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, *J Virol.* 49:857 (1984); Chakrabarti et al., *Mol. Cell. Biol.* 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety). Expression of the HCV polypeptide then occurs in cells or animals which are infected with the live recombinant vaccinia virus.

The sequence to be integrated into the mammalian sequence may be introduced into the primary host by any convenient means, which includes calcium precipitated DNA, spheroplast fusion, transformation, electroporation, biolistics, lipofection, microinjection, or other convenient means. Where an amplifiable gene is being employed, the amplifiable gene may serve as the selection marker for selecting hosts into which the amplifiable gene has been introduced. Alternatively, one may include with the amplifiable gene another marker, such as a drug resistance marker, e.g. neomycin resistance (G418 in mammalian cells), hygromycin in resistance etc., or an auxotrophy marker (HIS3, TRP1, LEU2, URA3, ADE2, LYS2, etc.) for use in yeast cells.

Depending upon the nature of the modification and associated targeting construct, various techniques may be employed for identifying targeted integration. Conveniently, the DNA may be digested with one or more restriction enzymes and the fragments probed with an appropriate DNA fragment which will identify the properly sized restriction fragment associated with integration.

One may use different promoter sequences, enhancer sequences, or other sequence which will allow for enhanced levels of expression in the expression host. Thus, one may combine an enhancer from one source, a promoter region from another source, a 5'-noncoding region upstream from the initiation methionine from the same or different source as the other sequences and the like. One may provide for an intron in the non-coding region with appropriate splice sites or for an alternative 3'-untranslated sequence or polyadenylation site. Depending upon the particular purpose of the modification, any of these sequences may be introduced, as desired.

Where selection is intended, the sequence to be integrated will have with it a marker gene, which allows for selection. The marker gene may conveniently be downstream from the target gene and may include resistance to a cytotoxic agent, e.g. antibiotics, heavy metals, or the like, resistance or susceptibility to HAT, gancyclovir, etc., complementation to an auxotrophic host, particularly by using an auxotrophic yeast as the host for the subject manipulations, or the like. The marker gene may also be on a separate DNA molecule, particularly with primary mammalian cells. Alternatively, one may screen the various transformants, due to the high efficiency of recombination in yeast, by using hybridization analysis, PCR, sequencing, or the like.

For homologous recombination, constructs can be prepared where the amplifiable gene will be flanked, normally on both sides with DNA homologous with the DNA of the target region. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. Where modeling of the gene is intended, homology will usually be present proximal to the site of the mutation. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., *E. coli* and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary mammalian host.

In the case of the primary mammalian host, a replicating vector may be used. Usually, such vector will have a viral replication system, such as SV40, bovine papilloma virus, adenovirus, or the like. The linear DNA sequence vector may also have a selectable marker for identifying transfected cells. Selectable markers include the neo gene, allowing for selection with G418, the herpes tk gene for selection with HAT medium, the gpt gene with mycophenolic acid, complementation of an auxotrophic host, etc.

The vector may or may not be capable of stable maintenance in the host. Where the vector is capable of stable maintenance, the cells will be screened for homologous integration of the vector into the genome of the host, where various techniques for curing the cells may be employed. Where the vector is not capable of stable maintenance, for example, where a temperature sensitive replication system is employed, one may change the temperature from the permissive temperature to the non-permissive temperature, so that the cells may be cured of the vector. In this case, only those cells having integration of the construct comprising the amplifiable gene and, when present, the selectable marker, will be able to survive selection.

Where a selectable marker is present, one may select for the presence of the targeting construct by means of the selectable marker. Where the selectable marker is not present, one may select for the presence of the construct by the amplifiable gene. For the neo gene or the herpes tk gene, one could employ a medium for growth of the transformants of about 0.1-1 mg/ml of G418 or may use HAT medium, respectively. Where DHFR is the amplifiable gene, the selective medium may include from about 0.01-0.5 μM of methotrexate or be deficient in glycine-hypoxanthine-thymidine and have dialysed serum (GHT media).

The DNA can be introduced into the expression host by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming mammalian cells are well known (see Keown et al., *Methods Enzymol.* (1989); Keown et al., *Methods Enzymol.* 185:527-537 (1990); Mansour et al., *Nature* 336:348-352, (1988); all of which are herein incorporated by reference in their entirety).

(d) Insect Constructs and Transformed Insect Cells

The present invention also relates to an insect recombinant vectors comprising exogenous genetic material. The present invention also relates to an insect cell comprising an insect recombinant vector. The present invention also relates to methods for obtaining a recombinant insect host cell, comprising introducing into an insect cell exogenous genetic material. In a preferred embodiment the exogenous genetic material includes a nucleic acid molecule of the present invention having a sequence selected from the group consisting of SEQ ID NO: 1 through SEQ ID NO: 699 or complements thereof or fragments of either or other nucleic acid molecule of the present invention.

The insect recombinant vector may be any vector which can be conveniently subjected to recombinant DNA procedures and can bring about the expression of the nucleic acid sequence. The choice of a vector will typically depend on the compatibility of the vector with the insect host cell into which the vector is to be introduced. The vector may be a linear or a closed circular plasmid. The vector system may be a single vector or plasmid or two or more vectors or plasmids which together contain the total DNA to be introduced into the genome of the insect host. In addition, the insect vector may be an expression vector. Nucleic acid molecules can be suitably inserted into a replication vector for expression in the insect cell under a suitable promoter for insect cells. Many vectors are available for this purpose and selection of the appropriate vector will depend mainly on the size of the nucleic acid molecule to be inserted into the vector and the particular host cell to be transformed with the vector. Each vector contains various components depending on its function (amplification of DNA or expression of DNA) and the particular host cell with which it is compatible. The vector components for insect cell transformation generally include, but are not limited to, one or more of the following: a signal sequence, origin of replication, one or more marker genes and an inducible promoter.

The insect vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the insect cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the insect host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the insect host cell and, furthermore, may be non-encoding or encoding sequences.

Baculovirus expression vectors (BEVs) have become important tools for the expression of foreign genes, both for basic research and for the production of proteins with direct clinical applications in human and veterinary medicine (Doerfler, *Curr. Top. Microbiol. Immunol.* 131:51-68 (1968); Luckow and Summers, *Bio/Technology* 6:47-55 (1988a); Miller, *Annual Review of Microbiol.* 42:177-199 (1988); Summers, *Curr. Comm. Molecular Biology*, Cold Spring Harbor Press, Cold Spring Harbor, N.Y. (1988); all of which are herein incorporated by reference in their entirety). BEVs are recombinant insect viruses in which the coding sequence for a chosen foreign gene has been inserted behind a baculovirus promoter in place of the viral gene, e.g., polyhedrin (Smith and Summers, U.S. Pat. No. 4,745,051, the entirety of which is incorporated herein by reference).

The use of baculovirus vectors relies upon the host cells being derived from Lepidopteran insects such as *Spodoptera frugiperda* or *Trichoplusia ni*. The preferred *Spodoptera frugiperda* cell line is the cell line Sf9. The *Spodoptera frugiperda* Sf9 cell line was obtained from American Type Culture Collection (Manassas, Va.) and is assigned accession number ATCC CRL 1711 (Summers and Smith, *A Manual of Methods for Baculovirus Vectors and Insect Cell Culture Procedures*, Texas Ag. Exper. Station Bulletin No. 1555 (1988), the entirety of which is herein incorporated by reference). Other insect cell systems, such as the silkworm *B. mori* may also be used.

The proteins expressed by the BEVs are, therefore, synthesized, modified and transported in host cells derived from Lepidopteran insects. Most of the genes that have been inserted and produced in the baculovirus expression vector system have been derived from vertebrate species. Other baculovirus genes in addition to the polyhedrin promoter may be employed to advantage in a baculovirus expression system. These include immediate-early (alpha), delayed-early (β), late (γ), or very late (delta), according to the phase of the viral infection during which they are expressed. The expression of these genes occurs sequentially, probably as the result of a "cascade" mechanism of transcriptional regulation. (Guarino and Summers, *J. Virol.* 57:563-571 (1986); Guarino and Summers, *J. Virol.* 61:2091-2099 (1987); Guarino and Summers, *Virol.* 162:444-451 (1988); all of which are herein incorporated by reference in their entirety).

Insect recombinant vectors are useful as intermediates for the infection or transformation of insect cell systems. For example, an insect recombinant vector containing a nucleic acid molecule encoding a baculovirus transcriptional promoter followed downstream by an insect signal DNA sequence is capable of directing the secretion of the desired biologically active protein from the insect cell. The vector may utilize a baculovirus transcriptional promoter region derived from any of the over 500 baculoviruses generally infecting insects, such as for example the Orders Lepidoptera, Diptera, Orthoptera, Coleoptera and Hymenoptera, including for example but not limited to the viral DNAs of *Autographa californica* MNPV, *Bombyx mori* NPV, *Trichoplusia ni* MNPV, *Rachiplusia ou* MNPV or *Galleria mellonella* MNPV, wherein said baculovirus transcriptional promoter is a baculovirus immediate-early gene IE1 or IEN promoter; an immediate-early gene in combination with a baculovirus delayed-early gene promoter region selected from the group consisting of 39K and a HindIII-k fragment delayed-early gene; or a baculovirus late gene promoter. The immediate-early or delayed-early promoters can be enhanced with transcriptional enhancer elements. The insect signal DNA sequence may code for a signal peptide of a Lepidopteran adipokinetic hormone precursor or a signal peptide of the *Manduca sexta* adipokinetic hormone precursor (Summers, U.S. Pat. No. 5,155,037; the entirety of which is herein incorporated by reference). Other insect signal DNA sequences include a signal peptide of the Orthoptera Schistocerca *gregaria* locust adipokinetic hormone precurser and the *Drosophila melanogaster* cuticle genes CP1, CP2, CP3 or CP4 or for an insect signal peptide having substantially a similar chemical composition and function (Summers, U.S. Pat. No. 5,155,037).

Insect cells are distinctly different from animal cells. Insects have a unique life cycle and have distinct cellular properties such as the lack of intracellular plasminogen activators in which are present in vertebrate cells. Another difference is the high expression levels of protein products ranging from 1 to greater than 500 mg/liter and the ease at which cDNA can be cloned into cells (Frasier, *In Vitro Cell. Dev. Biol.* 25:225 (1989); Summers and Smith, In: *A Manual of Methods for Baculovirus Vectors and Insect Cell Culture Procedures*, Texas Ag. Exper. Station Bulletin No. 1555 (1988), both of which are incorporated by reference in their entirety).

Recombinant protein expression in insect cells is achieved by viral infection or stable transformation. For viral infection, the desired gene is cloned into baculovirus at the site of the wild-type polyhedron gene (Webb and Summers, *Technique* 2:173 (1990); Bishop and Posse, *Adv. Gene Technol.* 1:55 (1990); both of which are incorporated by reference in their entirety). The polyhedron gene is a component of a protein coat in occlusions which encapsulate virus particles. Deletion or insertion in the polyhedron gene results the failure to form occlusion bodies. Occlusion negative viruses are morphologically different from occlusion positive viruses and enable one skilled in the art to identify and purify recombinant viruses.

The vectors of present invention preferably contain one or more selectable markers which permit easy selection of transformed cells. A selectable marker is a gene the product of which provides, for example biocide or viral resistance, resistance to heavy metals, prototrophy to auxotrophs and the like. Selection may be accomplished by co-transformation, e.g., as described in WO 91/17243, a nucleic acid sequence of the present invention may be operably linked to a suitable promoter sequence. The promoter sequence is a nucleic acid sequence which is recognized by the insect host cell for expression of the nucleic acid sequence. The promoter sequence contains transcription and translation control sequences which mediate the expression of the protein or fragment thereof. The promoter may be any nucleic acid sequence which shows transcriptional activity in the insect host cell of choice and may be obtained from genes encoding polypeptides either homologous or heterologous to the host cell.

For example, a nucleic acid molecule encoding a protein or fragment thereof may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the insect host cell of choice may be used in the present invention.

A polyadenylation sequence may also be operably linked to the 3' terminus of the nucleic acid sequence of the present invention. The polyadenylation sequence is a sequence which when transcribed is recognized by the insect host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention.

To avoid the necessity of disrupting the cell to obtain the protein or fragment thereof and to minimize the amount of possible degradation of the expressed polypeptide within the cell, it is preferred that expression of the polypeptide gene gives rise to a product secreted outside the cell. To this end, the protein or fragment thereof of the present invention may be linked to a signal peptide linked to the amino terminus of the protein or fragment thereof. A signal peptide is an amino acid sequence which permits the secretion of the protein or fragment thereof from the insect host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof.

At present, a mode of achieving secretion of a foreign gene product in insect cells is by way of the foreign gene's native signal peptide. Because the foreign genes are usually from non-insect organisms, their signal sequences may be poorly recognized by insect cells and hence, levels of expression may be suboptimal. However, the efficiency of expression of foreign gene products seems to depend primarily on the characteristics of the foreign protein. On average, nuclear localized or non-structural proteins are most highly expressed, secreted proteins are intermediate and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5' to 3') the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene.

Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optimal, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

Another exemplary insect signal sequence is the sequence encoding for *Drosophila* cuticle proteins such as CP1, CP2, CP3 or CP4 (Summers, U.S. Pat. No. 5,278,050; the entirety of which is herein incorporated by reference). Most of a 9 kb region of the *Drosophila* genome containing genes for the cuticle proteins has been sequenced. Four of the five cuticle genes contains a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes.

Standard methods of insect cell culture, cotransfection and preparation of plasmids are set forth in Summers and Smith (Summers and Smith, *A Manual of Methods for Baculovirus Vectors and Insect Cell Culture Procedures*, Texas Agricultural Experiment Station Bulletin No. 1555, Texas A&M University (1987)). Procedures for the cultivation of viruses and cells are described in Volkman and Summers, *J. Virol* 19:820-832 (1975) and Volkman et al., *J. Virol* 19:820-832 (1976); both of which are herein incorporated by reference in their entirety.

(e) Bacterial Constructs and Transformed Bacterial Cells

The present invention also relates to a bacterial recombinant vector comprising exogenous genetic material. The present invention also relates to a bacteria cell comprising a bacterial recombinant vector. The present invention also relates to methods for obtaining a recombinant bacteria host cell, comprising introducing into a bacterial host cell exogenous genetic material. In a preferred embodiment the exogenous genetic material includes a nucleic acid molecule of the present invention having a sequence selected from the group consisting of SEQ ID NO: 1 through SEQ ID NO: 699 or complements thereof or fragments of either or other nucleic acid molecule of the present invention.

The bacterial recombinant vector may be any vector which can be conveniently subjected to recombinant DNA procedures. The choice of a vector will typically depend on the compatibility of the vector with the bacterial host cell into which the vector is to be introduced. The vector may be a linear or a closed circular plasmid. The vector system may be a single vector or plasmid or two or more vectors or plasmids which together contain the total DNA to be introduced into the genome of the bacterial host. In addition, the bacterial vector may be an expression vector. Nucleic acid molecules encoding protein homologues or fragments thereof can, for example, be suitably inserted into a replicable vector for expression in the bacterium under the control of a suitable promoter for bacteria. Many vectors are available for this purpose and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2:95 (1977); the entirety of which is herein incorporated by reference). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Nucleic acid molecules encoding protein or fragments thereof may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous protein homologue or fragment thereof produce a protein conferring drug resistance and thus survive the selection regimen.

The expression vector for producing a protein or fragment thereof can also contains an inducible promoter that is recognized by the host bacterial organism and is operably linked to the nucleic acid encoding, for example, the nucleic acid molecule encoding the protein homologue or fragment thereof of interest. Inducible promoters suitable for use with bacterial hosts include the β-lactamase and lactose promoter systems (Chang et al., *Nature* 275:615 (1978); Goeddel et al., *Nature* 281:544 (1979); both of which are herein incorporated by reference in their entirety), the arabinose promoter system (Guzman et al., *J. Bacteriol.* 174:7716-7728 (1992); the entirety of which is herein incorporated by reference), alkaline phosphatase, a tryptophan (trp) promoter system (Goeddel, *Nucleic Acids Res.* 8:4057 (1980); EP 36,776; both of which are herein incorporated by reference in their entirety) and hybrid promoters such as the tac promoter (deBoer et al., *Proc. Natl. Acad. Sci.* (*USA*) 80:21-25 (1983); the entirety of which is herein incorporated by reference). However, other known bacterial inducible promoters are suitable (Siebenlist et al., *Cell* 20:269 (1980); the entirety of which is herein incorporated by reference).

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, encoding an *A. nidulans* protein homologue or fragment thereof homologue, may be ligated into the vector in frame with sequences for the amino-terminal Met and the subsequent 7 residues of β-galactosidase so that a hybrid protein is produced; pIN vectors (Van Heeke and Schuster, *J. Biol. Chem.* 264:5503-5509 (1989), the entirety of which is herein incorporated by reference); and the like. pGEX vectors (Promega, Madison Wis. U.S.A.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

Suitable host bacteria for a bacterial vector include archaebacteria and eubacteria, especially eubacteria and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla* and *Paracoccus*. Suitable *E. coli* hosts include *E. coli* W3110 (American Type Culture Collection (ATCC) 27,325, Manassas, Va. U.S.A.), *E. coli* 294 (ATCC 31,446), *E. coli* B and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. *E. coli* strain W3110 is a preferred host or parent host because it is a common host strain for recombinant DNA product fermentations. Preferably, the host cell should secrete minimal amounts of proteolytic enzymes.

Host cells are transfected and preferably transformed with the above-described vectors and cultured in conventional nutrient media modified as appropriate for inducing promoters, selecting transformants, or amplifying the genes encoding the desired sequences.

Numerous methods of transfection are known to the ordinarily skilled artisan, for example, calcium phosphate and electroporation. Depending on the host cell used, transformation is done using standard techniques appropriate to such cells. The calcium treatment employing calcium chloride, as described in section 1.82 of Sambrook et al., *Molecular Cloning: A Laboratory Manual*, New York: Cold Spring Harbor Laboratory Press, (1989), is generally used for bacterial cells that contain substantial cell-wall barriers. Another method for transformation employs polyethylene glycol/DMSO, as described in Chung and Miller (Chung and Miller, Nucleic Acids Res. 16:3580 (1988); the entirety of which is herein incorporated by reference). Yet another method is the use of the technique termed electroporation.

Bacterial cells used to produce the polypeptide of interest for purposes of this invention are cultured in suitable media in which the promoters for the nucleic acid encoding the heterologous polypeptide can be artificially induced as described generally, e.g., in Sambrook et al., *Molecular Cloning: A Laboratory Manual*, New York: Cold Spring Harbor Laboratory Press, (1989). Examples of suitable media are given in U.S. Pat. Nos. 5,304,472 and 5,342,763; both of which are incorporated by reference in their entirety.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

(f) Computer Readable Media

The nucleotide sequence provided in SEQ ID NO: 1 through SEQ ID NO: 699 or fragment thereof, or complement thereof, or a nucleotide sequence at least 90% identical, preferably 95%, identical even more preferably 99% or 100% identical to the sequence provided in SEQ ID NO: 1 through SEQ ID NO: 699 or fragment thereof, or complement thereof, can be "provided" in a variety of mediums to facilitate use. Such a medium can also provide a subset thereof in a form that allows a skilled artisan to examine the sequences.

A preferred subset of nucleotide sequences are those nucleic acid sequences that encode a first nucleic acid molecule selected from the group consisting of a nucleic acid molecule that encodes a maize or soybean glucose-6-phosphate-1-dehydrogenase enzyme or complement thereof or fragment of either; a nucleic acid molecule that encodes a maize or soybean 6-phosphogluconate dehydrogenase enzyme or complement thereof or fragment of either; a nucleic acid molecule that encodes a putative maize or soybean 6-phosphogluconate dehydrogenase enzyme or complement thereof or fragment of either; a nucleic acid molecule that encodes a maize or soybean D-ribulose-5-phosphate-3-epimerase enzyme or complement thereof or fragment of either; a nucleic acid molecule that encodes a maize or soybean ribose-5-phosphate isomerase enzyme or complement thereof or fragment of either; a nucleic acid molecule that encodes a putative maize or soybean ribose-5-phosphate isomerase enzyme or complement thereof or fragment of either; a nucleic acid molecule that encodes a maize or soybean transketolase enzyme or complement thereof or fragment of either; a nucleic acid molecule that encodes a putative maize or soybean transketolase enzyme or complement thereof or fragment of either; a nucleic acid molecule that encodes a maize or soybean transaldolase enzyme or complement thereof or fragment of either; a nucleic acid molecule that encodes a putative maize transaldolase enzyme or complement thereof or fragment of either; and a nucleic acid molecule that encodes a maize or soybean phosphoglucoisomerase enzyme or complement thereof or fragment of either.

A further preferred subset of nucleic acid sequences is where the subset of sequences which encode two proteins or fragments thereof, more preferably three proteins or fragments thereof more preferable four proteins or fragments thereof more preferably five proteins or fragments thereof, more preferably six proteins or fragments thereof, more preferably seven proteins or fragments thereof, more preferably eight proteins or fragments thereof, more preferably nine proteins or fragments thereof, more preferably ten proteins or fragments thereof, and even more preferably eleven proteins or fragments thereof. These nucleic acid sequences are selected from the group that encodes a maize or soybean glucose-6-phosphate-1-dehydrogenase enzyme or complement thereof or fragment of either; a nucleic acid molecule that encodes a maize or soybean 6-phosphogluconate dehydrogenase enzyme or complement thereof or fragment of either; a nucleic acid molecule that encodes a putative maize or soybean 6-phosphogluconate dehydrogenase enzyme or complement thereof or fragment of either; a nucleic acid molecule that encodes a maize or soybean D-ribulose-5-phosphate-3-epimerase enzyme or complement thereof or fragment of either; a nucleic acid molecule that encodes a maize or soybean ribose-5-phosphate isomerase enzyme or complement thereof or fragment of either; a nucleic acid molecule that encodes a putative maize or soybean ribose-5-phosphate isomerase enzyme or complement thereof or fragment of either; a nucleic acid molecule that encodes a maize or soybean transketolase enzyme or complement thereof or fragment of either; a nucleic acid molecule that encodes a putative maize or soybean transketolase enzyme or complement thereof or fragment of either; a nucleic acid molecule that encodes a maize or soybean transaldolase enzyme or complement thereof or fragment of either; a nucleic acid molecule that encodes a putative maize transaldolase enzyme or complement thereof or fragment of either; and a nucleic acid molecule that encodes a maize or soybean phosphoglucoisomerase enzyme or complement thereof or fragment of either.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410 (1990), the entirety of which is herein incorporated by reference) and BLAZE (Brutlag et al., *Comp. Chem.* 17:203-207 (1993), the entirety of which is herein incorporated by reference) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification and DNA replication, restriction, modification, recombination and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means and data storage means used to analyze the nucleotide sequence information of the present invention. The minimum hardware means of the computer-based systems of the present invention comprises a central processing unit (CPU), input means, output means and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used as the search means for the computer-based systems of the present invention.

Having now generally described the invention, the same will be more readily understood through reference to the following examples which are provided by way of illustration and are not intended to be limiting of the present invention, unless specified.

Example 1

The MONN01 cDNA library is a normalized library generated from maize (DK604, Dekalb Genetics, Dekalb, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when maize plants are at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON001 cDNA library is generated from maize (B73, Illinois Foundation Seeds, Champaign, Ill. U.S.A.) immature tassels at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tassel tissue from maize plants is collected at the V6 stage. At that stage the tassel is an immature tassel of about 2-3 cm in length. Tassels are removed and frozen in liquid nitrogen. The harvested tissue is then stored at −80° C. until RNA preparation. The RNA is purified from the stored tissue and the cDNA library is constructed as described in Example 2.

The SATMON003 library is generated from maize (B73×Mol7, Illinois Foundation Seeds, Champaign, Ill. U.S.A.) roots at the V6 developmental stage. Seeds are planted at a depth of approximately 3 cm into 2-3 inch peat pots containing Metro 200 growing medium. After 2-3 weeks growth, the seedlings are transplanted into 10 inch pots containing the Metro 200 growing medium. Plants are watered daily before transplantation and approximately 3 times a week after transplantation. Peters 15-16-17 fertilizer is applied approximately three times per week after transplanting at a concentration of 150 ppm N. Two to three times during the life time of the plant from transplanting to flowering a total of approximately 900 mg Fe is added to each pot. Maize plants are grown in a green house in approximately 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6 leaf development stage. The root system is cut from maize plant and washed with water to free it from the soil. The tissue is then immediately frozen in liquid nitrogen. The harvested tissue is then stored at −80° C. until RNA preparation. The RNA is purified from the stored tissue and the cDNA library is constructed as described in Example 2.

The SATMON004 cDNA library is generated from maize (B73×Mol7, Illinois Foundation Seeds, Champaign, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON005 cDNA library is generated from maize (B73×Mol7, Illinois Foundation Seeds, Champaign Ill., U.S.A.) root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation. The RNA is purified from the stored tissue and the cDNA library is constructed as described in Example 2.

The SATMON006 cDNA library is generated from maize (B73×Mol7, Illinois Foundation Seeds, Champaign Ill., U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON007 cDNA library is generated from the primary root tissue of 5 day old maize (DK604, Dekalb Genetics, Dekalb, Ill. U.S.A.) seedlings. Seeds are planted on a moist filter paper on a covered tray that is kept in the dark until germination (one day). After germination, the trays, along with the moist paper, are moved to a greenhouse where the maize plants are grown in the greenhouse in 15 hr day/9 hr night cycles for approximately 5 days. The daytime temperature is approximately 80° F. and the nighttime temperature is approximately 70° F. Supplemental lighting is provided by 1000 W sodium vapor lamps. The primary root tissue is collected when the seedlings are 5 days old. At this stage, the primary root (radicle) is pushed through the coleorhiza which itself is pushed through the seed coat. The primary root, which is about 2-3 cm long, is cut and immediately frozen in liquid nitrogen and then stored at −80° C. until RNA preparation. The RNA is purified from the stored tissue and the cDNA library is constructed as described in Example 2.

The SATMON008 cDNA library is generated from the primary shoot (coleoptile 2-3 cm) of maize (DK604, Dekalb Genetics, Dekalb, Ill. U.S.A.) seedlings which are approximately 5 days old. Seeds are planted on a moist filter paper on a covered tray that is kept in the dark until germination (one day). Then the trays containing the seeds are moved to a greenhouse at 15 hr daytime/9 hr nighttime cycles and grown until they are 5 days post germination. The daytime temperature is approximately 80° F. and the nighttime temperature is approximately 70° F. Tissue is collected when the seedlings are 5 days old. At this stage, the primary shoot (coleoptile) is pushed through the seed coat and is about 2-3 cm long. The coleoptile is dissected away from the rest of the seedling, immediately frozen in liquid nitrogen and then stored at −80° C. until RNA preparation. The RNA is purified from the stored tissue and the cDNA library is constructed as described in Example 2.

The SATMON009 cDNA library is generated from maize (DK604, Dekalb Genetics, Dekalb, Ill. U.S.A.) leaves at the 8 leaf stage (V8 plant development stage). Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 8-leaf development stage. The older more juvenile leaves, which are in a basal position, as well as the younger more adult leaves, which are more apical, are cut at the base of the leaves. The leaves are then pooled and then immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON010 cDNA library is generated from maize (DK604, Dekalb Genetics, Dekalb, Ill. U.S.A.) root tissue at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the V8 development stage. The root system is cut from this mature maize plant and washed with water to free it from the soil. The tissue is immediately frozen in liquid nitrogen. The harvested tissue is then stored at −80° C. until RNA preparation. The RNA is purified from the stored tissue and the cDNA library is constructed as described in Example 2.

The SATMON011 cDNA library is generated from undeveloped maize (DK604, Dekalb Genetics, Dekalb, Ill. U.S.A.) leaf at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The second youngest leaf which is at the base of the apical leaf of V6 stage maize plant is cut at the base and immediately transferred to liquid nitrogen containers in which the leaf is crushed. The harvested tissue is then stored at −80° C. until RNA preparation. The RNA is purified from the stored tissue and the cDNA library is constructed as described in Example 2.

The SATMON012 cDNA library is generated from 2 day post germination maize (DK604, Dekalb Genetics, Dekalb, Ill. U.S.A.) seedlings. Seeds are planted on a moist filter paper on a covered tray that is kept in the dark until germination (one day). Then the trays containing the seeds are moved to the greenhouse and grown at 15 hr daytime/9 hr nighttime cycles until 2 days post germination. The daytime temperature is approximately 80° F. and the nighttime temperature is approximately 70° F. Tissue is collected when the seedlings are 2 days old. At the two day stage, the coleorhiza is pushed through the seed coat and the primary root (the radicle) is pierced the coleorhiza but is barely visible. Also, at this two day stage, the coleoptile is just emerging from the seed coat. The 2 days post germination seedlings are then immersed in liquid nitrogen and crushed. The harvested tissue is stored at −80° C. until preparation of total RNA. The RNA is purified from the stored tissue and the cDNA library is constructed as described in Example 2.

The SATMON013 cDNA library is generated from apical maize (DK604, Dekalb Genetics, Dekalb, Ill. U.S.A.) meristem founder at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, the plant is at the 4 leaf stage. The lead at the apex of the V4 stage maize plant is referred to as the meristem founder. This apical meristem founder is cut, immediately frozen in liquid nitrogen and crushed. The harvested tissue is then stored at −80° C. until RNA preparation. The RNA is purified from the stored tissue and the cDNA library is constructed as described in Example 2.

The SATMON014 cDNA library is generated from maize (DK604, Dekalb Genetics, Dekalb, Ill. U.S.A.) endosperm at fourteen days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, ear shoots are ready for fertilization. At this stage, the ear shoots are enclosed in a paper bag before silk emergence to withhold the pollen. The ear shoots are pollinated and 14 days after pollination, the ears are pulled out and then the kernels are plucked out of the ears. Each kernel is then dissected into the embryo and the endosperm and the aleurone layer is removed. After dissection, the endosperms are immediately frozen in liquid nitrogen and then stored at −80° C. until RNA preparation. The RNA is purified from the stored tissue and the cDNA library is constructed as described in Example 2.

The SATMON016 cDNA library is generated from maize (DK604, Dekalb Genetics, Dekalb, Ill. U.S.A.) sheath tissue collected at the V8 developmental stage. Seeds are planted in a depth of approximately 3 cm in solid into 2-3 inch pots containing Metro growing medium. After 2-3 weeks growth, they are transplanted into 10" pots containing the same. Plants are watered daily before transplantation and approximately the times a week after transplantation. Peters 15-16-17 fertilizer is applied approximately three times per week after transplanting, at a strength of 150 ppm N. Two to three times during the life time of the plant from transplanting to flowering, a total of approximately 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. When the maize plants are at the V8 stage the $5^{th}$ and $6^{th}$ leaves from the bottom exhibit fully developed leaf blades. At the base of these leaves, the ligule is differentiated and the leaf blade is joined to the sheath. The sheath is dissected away from the base of the leaf then the sheath is frozen in liquid nitrogen and crushed. The tissue is then stored at −80° C. until RNA preparation. The RNA is purified from the stored tissue and the cDNA library is constructed as described in Example 2.

The SATMON017 cDNA library is generated from maize (DK604, Dekalb Genetics, Dekalb, Ill. U.S.A.) embryo collected from plants at twenty one days after pollination. Seeds are planted at a depth of approximately 3 cm into 2-3 inch peat pots containing Metro 200 growing medium. After 2-3 weeks growth the seeds are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of maize plant, which are ready for fertilization, are enclosed in a paper bag before silk emergence to withhold the pollen. The ear shoots are fertilized and 21 days after pollination, the ears are pulled out and the kernels are plucked out of the ears. Each kernel is then dissected into the embryo and the endosperm and the aleurone layer is removed. After dissection, the embryos are immediately frozen in liquid nitrogen and then stored at −80° C. until RNA preparation. The RNA is purified from the stored tissue and the cDNA library is constructed as described in Example 2.

The SATMON019 cDNA library is generated from maize (DK604, Dekalb Genetics, Dekalb, Ill. U.S.A.) culm (stem) at the V8 developmental stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. When the maize plant is at the V8 stage, the 5th and 6th leaves from the bottom have fully developed leaf blades. The region between the nodes of the 5th and the sixth leaves from the bottom is the region of the stem that is collected. The leaves are pulled out and the sheath is also torn away from the stem. This stem tissue is completely free of any leaf and sheath tissue. The stem tissue is then frozen in liquid nitrogen and stored at −80° C. until RNA preparation. The RNA is purified from the stored tissue and the cDNA library is constructed as described in Example 2.

The SATMON020 cDNA library is from a maize (DK604, Dekalb Genetics, Dekalb, Ill. U.S.A.) Hill Type II-Initiated Callus. Petri plates containing approximately 25 ml of Type II initiation media are prepared. This medium contains N6 salts and vitamins, 3% sucrose, 2.3 g/liter proline 0.1 g/liter enzymatic casein hydrolysate, 2 mg/liter 2,4-dichloro phenoxyacetic acid (2,4, D), 15.3 mg/liter $AgNO_3$ and 0.8% bacto agar and is adjusted to pH 6.0 before autoclaving. At 9-11 days after pollination, an ear with immature embryos measuring approximately 1-2 mm in length is chosen. The husks and silks are removed and then the ear is broken into halves and placed in an autoclaved solution of Clorox/TWEEN 20 sterilizing solution. Then the ear is rinsed with deionized water. Then each embryo is extracted from the kernel. Intact embryos are placed in contact with the medium, scutellar side up). Multiple embryos are plated on each plate and the plates are incubated in the dark at 25° C. Type II calluses are friable, can be subcultured with a spatula, frequently regenerate via somatic embryogenesis and are relatively undifferentiated. As seen in the microscope, the Tape II calluses show color ranging from translucent to light yellow and heterogeneity on with respect to embryoid structure as well as stage of embryoid development. Once Type II callus are formed, the calluses is transferred to type II callus maintenance medium without $AgN0_3$. Every 7-10 days, the callus is subcultured. About 4 weeks after embryo isolation the callus is removed from the plates and then frozen in liquid nitrogen. The harvested tissue is stored at −80° C. until RNA preparation. The RNA is purified from the stored tissue and the cDNA library is constructed as described in Example 2.

The SATMON021 cDNA library is generated from the immature maize (DK604, Dekalb Genetics, Dekalb Ill., U.S.A.) tassel at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. As the maize plant enters the V8 stage, tassels which are 15-20 cm in length are collected and frozen in liquid nitrogen. The harvested tissue is stored at −80° C. until RNA preparation. The RNA is purified from the stored tissue and the cDNA library is constructed as described in Example 2.

The SATMON022 cDNA library is generated from maize (DK604, Dekalb Genetics, Dekalb, Ill. U.S.A.) immature ear at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the plant is in the V8 stage. At this stage, some immature ear shoots are visible. The immature ear shoots (approximately 3-4 cm in length) are pulled out, frozen in liquid nitrogen and then stored at −80° C. until RNA preparation. The RNA is purified from the stored tissue and the cDNA library is constructed as described in Example 2.

The SATMON023 cDNA library is generated from maize (DK604, Dekalb Genetics, Dekalb, Ill. U.S.A.) ear (growing silk) at the V8 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. When the tissue is harvested at the V8 stage, the length of the ear that is harvested is about 10-15 cm and the silks are just exposed (approximately 1 inch). The ear along with the silks is frozen in liquid nitrogen and then the tissue is stored at −80° C. until RNA preparation. The RNA is purified from the stored tissue and the cDNA library is constructed as described in Example 2.

The SATMON024 cDNA library is generated from the immature maize (DK604, Dekalb Genetics, Dekalb, Ill. U.S.A.) tassel at the V9 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. As a maize plant enters the V9 stage, the tassel is rapidly developing and a 37 cm tassel along with the glume, anthers and pollen is collected and frozen in liquid nitrogen. The harvested tissue is stored at −80° C. until RNA preparation. The RNA is purified from the stored tissue and the cDNA library is constructed as described in Example 2.

The SATMON025 cDNA library is from maize (DK604, Dekalb Genetics, Dekalb, Ill. U.S.A.) Hill Type II-Regenerated Callus. Type II callus is grown in initiation media as described for SATMON020 and then the embryoids on the surface of the Type II callus are allowed to mature and germinate. The 1-2 gm fresh weight of the soft friable type callus containing numerous embryoids are transferred to 100×15 mm petri plates containing 25 ml of regeneration media. Regeneration media consists of Murashige and Skoog (MS) basal salts, modified White's vitamins (0.2 g/liter glycine and 0.5 g/liter myo-inositoland 0.8% bacto agar (6SMS0D)). The plates are then placed in the dark after covering with parafilm. After 1 week, the plates are moved to a lighted growth chamber with 16 hr light and 8 hr dark photoperiod. Three weeks after plating the Type II callus to 6SMS0D, the callus exhibit shoot formation. The callus and the shoots are transferred to fresh 6SMS0D plates for another 2 weeks. The callus and the shoots are then transferred to petri plates with reduced sucrose (3SMS0D). Upon distinct formation of a root and shoot, the newly developed green plants are then removed out with a spatula and frozen in liquid nitrogen containers. The harvested tissue is then stored at −80° C. until RNA preparation. The RNA is purified from the stored tissue and the cDNA library is constructed as described in Example 2.

The SATMON026 cDNA library is generated from maize (DK604, Dekalb Genetics, Dekalb, Ill. U.S.A.) juvenile/adult shift leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plants are at the 8-leaf development stage. Leaves are founded sequentially around the meristem over weeks of time and the older, more juvenile leaves arise earlier and in a more basal position than the younger, more adult leaves, which are in a more apical position. In a V8 plant, some leaves which are in the middle portion of the plant exhibit characteristics of both juvenile as well as adult leaves. They exhibit a yellowing color but also exhibit, in part, a green color. These leaves are termed juvenile/adult shift leaves. The juvenile/adult shift leaves (the 4th, 5th leaves from the bottom) are cut at the base, pooled and transferred to liquid nitrogen in which they are then crushed. The harvested tissue is then stored at −80° C. until RNA preparation. The RNA is purified from the stored tissue and the cDNA library is constructed as described in Example 2.

The SATMON027 cDNA library is generated from maize (DK604, Dekalb Genetics, Dekalb, Ill. U.S.A.) leaves from plants at the V8 developmental stage that are subject to six days water stress. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The older, more juvenile leaves, which are in a basal position, as well as the younger, more adult leaves, which are more apical, are all cut at the base of the leaves. All the leaves exhibit significant wilting. The leaves are then pooled and immediately transferred to liquid nitrogen containers in which the pooled leaves are then crushed. The harvested tissue is then stored at −80° C. until RNA preparation. The RNA is purified from the stored tissue and the cDNA library is constructed as described in Example 2.

The SATMON028 cDNA library is generated from maize (DK604, Dekalb Genetics, Dekalb, Ill. U.S.A.) roots at the V8 developmental stage that are subject to six days water stress. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The root system is cut, shaken and washed to remove soil. Root tissue is then pooled and immediately transferred to liquid nitrogen containers in which the pooled leaves are then crushed. The harvested tissue is then stored at −80° C. until RNA preparation. The RNA is purified from the stored tissue and the cDNA library is constructed as described in Example 2.

The SATMON029 cDNA library is generated from maize (DK604, Dekalb Genetics, Dekalb, Ill. U.S.A.) seedlings at the etiolated stage. Seeds are planted on a moist filter paper on a covered tray that is kept in the dark for 4 days at approximately 70° F. Tissue is collected when the seedlings are 4 days old. By 4 days, the primary root has penetrated the coleorhiza and is about 4-5 cm and the secondary lateral roots have also made their appearance. The coleoptile has also pushed through the seed coat and is about 4-5 cm long. The seedlings are frozen in liquid nitrogen and crushed. The RNA is purified from the stored tissue and the cDNA library is constructed as described in Example 2.

The SATMON030 cDNA library is generated from maize (DK604, Dekalb Genetics, Dekalb, Ill. U.S.A.) root tissue at the V4 plant development stage. Seeds are planted at a depth of approximately 3 cm into 2-3 inch peat pots containing Metro 200 growing medium. After 2-3 weeks growth, they are transplanted into 10 inch pots containing the same. Plants are watered daily before transplantation and approximately 3 times a week after transplantation. Peters 15-16-17 fertilizer is applied approximately three times per week after transplanting, at a strength of 150 ppm N. Two to three times during the life time of the plant, from transplanting to flowering, a total of approximately 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 sodium vapor lamps. Tissue is collected when the maize plant is at the 4 leaf development stage. The root system is cut from the mature maize plant and washed with water to free it from the soil. The tissue is then immediately frozen in liquid nitrogen. The harvested tissue is then stored at −80° C. until RNA preparation. The RNA is purified from the stored tissue and the cDNA library is constructed as described in Example 2.

The SATMON031 cDNA library is generated from the maize (DK604, Dekalb Genetics, Dekalb, Ill. U.S.A.) leaf tissue at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is 80° F. and the nighttime temperature is 70° F. Supplemental lighting is provided by 1000 W sodium vapor lamps. Tissue is collected when the maize plant is at the 4-leaf development stage. The third leaf from the bottom is cut at the base and immediately frozen in liquid nitrogen and crushed. The tissue is immediately frozen in liquid nitrogen. The harvested tissue is then stored at −80° C. until RNA preparation. The RNA is purified from the stored tissue and the cDNA library is constructed as described in Example 2.

The SATMON033 cDNA library is generated from maize (DK604, Dekalb Genetics, Dekalb, Ill. U.S.A.) embryo tissue from plants at 13 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 13 days after pollination, the ears are pulled out and then the kernels are plucked cut of the ears. Each kernel is then dissected into the embryo and the endosperm and the aleurone layer is removed. After dissection, the embryos are immediately frozen in liquid nitrogen and then stored at −80° C. until RNA preparation. The RNA is purified from the stored tissue and the cDNA library is constructed as described in Example 2.

The SATMON034 cDNA library is generated from cold stressed maize (DK604, Dekalb Genetics, Dekalb, Ill. U.S.A.) seedlings. Seeds are planted on a moist filter paper on a covered tray that is kept on at 10° C. for 7 days. After 7 days, the temperature is shifted to 15° C. for one day until germination of the seed. Tissue is collected once the seedlings are 1 day old. At this point, the coleorhiza has just pushed out of the seed coat and the primary root is just making its appearance.

The coleoptile has not yet pushed completely through the seed coat and is also just making its appearance. These 1 day old cold stressed seedlings are frozen in liquid nitrogen and crushed. The harvested tissue is then stored at −80° C. until RNA preparation. The RNA is purified from the stored tissue and the cDNA library is constructed as described in Example 2.

The SATMONN01 cDNA library is a normalized library generated from maize (B73, Illinois Foundation Seeds, Champaign, Ill. U.S.A.) immature tassels at the V6 plant development stage normalized tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation. The RNA is purified from the stored tissue and the normalized cDNA library is constructed as described in Example 2.

The SATMONN04 cDNA library is a normalized library generated from maize (B73×Mol7, Illinois Foundation Seeds, Champaign, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the normalized cDNA library is constructed as described in Example 2.

The SATMONN05 cDNA library is a normalized library generated from maize (B73×Mol7, Illinois Foundation Seeds, Champaign Ill., U.S.A.) root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation. The RNA is purified from the stored tissue and the normalized cDNA library is constructed as described in Example 2.

The SATMONN06 cDNA library is a normalized library generated from maize (B73×Mol7, Illinois Foundation Seeds, Champaign Ill., U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the normalized cDNA library is constructed as described in Example 2.

LIB36 is a normalized cDNA library prepared from maize (DK604, Dekalb Genetics, Dekalb, Ill. U.S.A) leaves harvested from V8 stage plants. Seeds are planted at a depth of approximately 3 cm in soil into 2"-3" peat pots containing Metro 200 growing medium. After 2-3 weeks growth, they are transplanted into 10" pots containing the same. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a green house in 15 hr day/9 hr night cycles. The daytime temperature is 80° F. and the night time temperature is 70° F. Lighting is provided by 1000 W sodium vapor lamps. Tissue is collected from V8 stage plants. The older more juvenile leaves which are in a basal position as well as the younger more adult leaves which are more apical were all cut at the base of the leaves. The leaves are then pooled and then immediately transferred to liquid nitrogen containers in which the pooled leaves are then crushed. The harvested tissue is then stored at −80° C. until RNA preparation.

For the construction of a cDNA library, the Superscript™ Plasmid System for cDNA synthesis and Plasmid Cloning (Gibco BRL, Life Technologies, Gaithersburg, Md.) or similar system, following the conditions suggested by the manufacturer, is used. Poly A+ mRNA is purified from the total RNA preparation using Dynabeads® Oligo $(dT)_{25}$ (Dynal Inc., Lake Success, N.Y.), or equivalent methods. Clones are selected and the plasmid DNA is isolated using a commercially available kit for normalizing the cDNA library.

LIB83 is a normalized cDNA library prepared from maize (DK604, Dekalb Genetics, Dekalb, Ill. U.S.A) leaves harvested from V8 stage plants. Seeds are planted at a depth of approximately 3 cm in soil into 2"-3" peat pots containing Metro 200 growing medium. After 2-3 weeks growth, they are transplanted into 10" pots containing the same. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Plants are grown in a greenhouse in 15 hr day/9 hr night cycles. The daytime temperature is 80° F. and the night time temperature was 70° F. Lighting was provided by 1000 W sodium vapor lamps. Tissue is collected from V8 stage plants. The older more juvenile leaves which are in a basal position as well as the younger more adult leaves which are more apical were all cut at the base of the leaves. The leaves are then pooled and then immediately transferred to liquid nitrogen containers in which the pooled leaves are then crushed The harvested tissue is then stored at −80° C. until RNA preparation.

For the construction of a cDNA library, the Superscript™ Plasmid System for cDNA synthesis and Plasmid Cloning (Gibco BRL, Life Technologies, Gaithersburg, Md.) or similar system, following the conditions suggested by the manufacturer, is used. Poly A+ mRNA is purified from the total RNA preparation using Dynabeads™ Oligo $(dT)_{25}$ (Dynal Inc., Lake Success, N.Y.), or equivalent methods. Clones are selected and the plasmid DNA is isolated using a commercially available kit for normalizing the cDNA library.

LIB84 a normalized cDNA library is prepared from maize (DK604, Dekalb Genetics, Dekalb, Ill. U.S.A) leaves harvested from V8 stage plants. Seeds are planted at a depth of approximately 3 cm in soil into 2"-3" peat pots containing Metro 200 growing medium. After 2-3 weeks growth, they are transplanted into 10" pots containing the same. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Plants were grown in a greenhouse in 15 hr day/9 hr night cycles. The daytime temperature was 80° F. and the night time temperature was 70° F. Lighting was provided by 1000 W sodium vapor lamps. Tissue was collected from V8 stage plants. The older more juvenile leaves which are in a basal position as well as the younger more adult leaves which are more apical were all cut at the base of the leaves. The leaves are then pooled and then immediately transferred to liquid nitrogen containers in which the pooled leaves are then crushed. The harvested tissue is then stored at −80° C. until RNA preparation.

For the construction of a cDNA library, the Superscript™ Plasmid System for cDNA synthesis and Plasmid Cloning (Gibco BRL, Life Technologies, Gaithersburg, Md.) or similar system, following the conditions suggested by the manufacturer, is used. Poly A+ mRNA is purified from the total RNA preparation using Dynabeads® Oligo $(dT)_{25}$ (Dynal Inc., Lake Success, N.Y.), or equivalent methods. Clones are selected and the plasmid DNA is isolated using a commercially available kit for normalizing the cDNA library.

The CMz029 (SATMON036) cDNA library is generated from maize (DK604, Dekalb Genetics, Dekalb, Ill. U.S.A.) endosperm 22 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 22 days after pollination, the ears are pulled out and then the kernels are plucked out of the ears. Each kernel is then dissected into the embryo and the endosperm and the alurone layer is removed. After dissection, the endosperms are immediately frozen in liquid nitrogen and then stored at −80° C. until RNA preparation. The RNA is purified from the stored tissue and the cDNA library is constructed as described in Example 2.

The CMz030 (Lib143) cDNA library is generated from maize (DK604, Dekalb Genetics, Dekalb, Ill. U.S.A.) seedling tissue two days post germination. Seeds are planted on a moist filter paper on a covered try that is keep in the dark until germination. The trays are then moved to the bench top at 15 hr daytime/9 hr nighttime cycles for 2 days post-germination. The day time temperature is 80° F. and the nighttime temperature is 70° F. Tissue is collected when the seedlings are 2 days old. At this stage, the colehrhiza has pushed through the seed coat and the primary root (the radicle) is just piercing the colehrhiza and is barely visible. The seedlings are placed at 42° C. for 1 hour. Following the heat shock treatment, the seedlings are immersed in liquid nitrogen and crushed. The harvested tissue is stored at −80° until RNA preparation. The RNA is purified from the stored tissue and the cDNA library is constructed as described in Example 2.

The CMz031 (Lib148) cDNA library is generated from maize (DK604, Dekalb Genetics, Dekalb, Ill. U.S.A.) pollen tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag to withhold pollen. Twenty-one days after pollination, prior to removing the ears, the paper bag is shaken to collect the mature pollen. The mature pollen is immediately frozen in liquid nitrogen containers and the pollen is crushed. The harvested tissue is then stored at −80° C. until RNA preparation. The RNA is purified from the stored tissue and the cDNA library is constructed as described in Example 2.

The CMz033 (Lib189) cDNA library is generated from maize (RX601 Asgrow, Asgrow Seed Company, Des Moines, Iowa U.S.A.) pooled leaf tissue harvested from field grown plants at Asgrow research stations. Leaves are harvested at anthesis from open pollinated plants in a field (multiple row) setting. The ear leaves from 10-12 plants are harvested, pooled, frozen in liquid nitrogen and then frozen at −80 C where they are stored until RNA preparation. The RNA is purified from the stored tissue and the cDNA library is constructed as described in Example 2.

The CMz034 (Lib3060) cDNA library is generated from maize (DK604, Dekalb Genetics, Dekalb, Ill. U.S.A.) senescing leaves from plants at 40 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from leaves located two leaves below the ear leaf. This sample represents those genes expressed during onset and early stages of leaf senescence. The leaves are pooled and immediately transferred to liquid nitrogen. The harvested tissue is then stored at −80° C. until RNA preparation. The RNA is purified from the stored tissue and the cDNA library is constructed as described in Example 2.

The CMz035 (Lib3061) cDNA library is generated from maize (DK604, Dekalb Genetics, Dekalb, Ill. U.S.A.) endosperm tissue from plants at 32 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag prior to silk emergence to withhold pollen. Thirty-two days after pollination, the ears are pulled out and the kernels are removed from the cob. Each kernel is dissected into the embryo and the endosperm and the aleurone layer is removed. After dissection, the endosperms are immediately transferred to liquid nitrogen. The harvested tissue is then stored at 80° C. until RNA preparation. The RNA is purified from the stored tissue and the cDNA library is constructed as described in Example 2.

The CMz036 (Lib3062) cDNA library is generated from maize (H99, USDA Maize Germplasm Collection, Urban, Ill. U.S.A.) husk tissue from 8 week old plants. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from 8 week old plants. The husk is separated from the ear and immediately transferred to liquid nitrogen containers. The harvested tissue is then stored at −80° C. until RNA preparation. The RNA is purified from the stored tissue and the cDNA library is constructed as described in Example 2.

The CMz037 (Lib3059) cDNA library is generated from maize (RX601 Asgrow, Asgrow Seed Company, Des Moines, Iowa U.S.A) pooled kernels from plants at 12-15 days after pollination. Sample are collected from field grown material. Whole kernels from hand pollinated (control pollination) are harvested as whole ears and immediately frozen on dry ice. Kernels from 10-12 ears are pooled and ground together in liquid nitrogen. The harvested tissue is then stored at −80° C. until RNA preparation. The RNA is purified from the stored tissue and the cDNA library is constructed as described in Example 2.

The CMz039 (Lib3066) cDNA library is generated from maize (H99 USDA Maize Germplasm Collection, Urban, Ill. U.S.A.) immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately frozen in liquid nitrogen. The harvested tissue is then stored at −80° C. until RNA preparation. The RNA is purified from the stored tissue and the cDNA library is constructed as described in Example 2.

The CMz040 (Lib3067) cDNA library is generated from maize (MO17 USDA Maixe Germplasm Collection, Urbana, Ill. U.S.A.) kernel tissue from plants at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag before silk emergence to withhold pollen. Five to eight days after controlled pollination. The ears are pulled and the kernels removed. The kernels are immediately frozen in liquid nitrogen. This sample represents genes expressed in early kernel development, during periods of cell division, amyloplast biogenesis and early carbon flow across the material to filial tissue. The harvested kernels tissue is then stored at −80° C. until RNA preparation. The RNA is purified from the stored tissue and the cDNA library is constructed as described in Example 2.

The CMz041 (Lib3068) cDNA library is generated from maize pollen germinating silk tissue from plants at the V10+ plant development stage. Maize MO17 and H99 (USDA Maize Germplasm Collection, Urbana, Ill. U.S.A.) seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants when the ear shoots are ready for fertilization at the silk emergence stage. The H99 emerging silks are pollinated with an excess of MO17 pollen under controlled pollination conditions in the green house. Eighteen hours after pollination the silks are removed from the ears and immediately frozen in liquid nitrogen. This sample represents genes expressed in both pollen and silk tissue early in pollination. The harvested tissue is then stored at −80° C. until RNA preparation. The RNA is purified from the stored tissue and the cDNA library is constructed as described in Example 2.

The CMz042 (Lib3069) cDNA library is generated from maize ear tissue excessively pollinated at the V10+ plant development stage. Maize MO17 and H99 (USDA Maize Germplasm Collection, Urbana, Ill. U.S.A.) seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants and the ear shoots which are ready for fertilization are at the silk emergence stage. The H99 immature ears are pollinated with an excess of MO17 pollen under controlled pollination conditions. Eighteen hours post-pollination, the ears are removed and immediately transferred to liquid nitrogen containers. The harvested tissue is then stored at −80° C. until RNA preparation. The RNA is purified from the stored tissue and the cDNA library is constructed as described in Example 2.

The CMz044 (Lib3075) cDNA library is generated from maize (H99, USDA Maize Germplasm Collection, Urbana, Ill. U.S.A.) microspore tissue from plants at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature anthers from 7 week old tassels. The immature anthers are first dissected from the 7 week old tassel with a scalpel on a glass slide covered with water. The microspores (immature pollen) are released into the water and are recovered by centrifugation. The microspore suspension is immediately frozen in liquid nitrogen. The harvested tissue is then stored at −80° C. until RNA preparation. The RNA is purified from the stored tissue and the cDNA library is constructed as described in Example 2.

The CMz045 (Lib3076) cDNA library is generated from maize (H99 USDA Maize Germplasm Collection, Urbana, Ill. U.S.A.) immature ear megaspore tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. The immature ears are harvested from the 7 week old plants and are approximately 2.5 to 3 cm in length. The kernels are removed from the cob immediately frozen in liquid nitrogen. The harvested tissue is then stored at −80° C. until RNA preparation. The RNA is purified from the stored tissue and the cDNA library is constructed as described in Example 2.

The CMz047 (Lib3078) cDNA library is generated from maize (RX601, Asgrow Seed Company, Des Moines, Iowa, U.S.A.) $CO_2$ treated high-exposure shoot tissue at the V10+ plant development stage. RX601 maize seeds are sterilized for 1 minute with a 10% Clorox solution. The seeds are rolled in germination paper, and germinated in 0.5 mM calcium sulfate solution for two days at 30° C. The seedlings are planted at a depth of approximately 3 cm into 2-3 inch peat pots containing Metro 200 growing medium at a rate of 2-3 seedlings per pot. Twenty pots are placed into a high $CO_2$ environment (approximately 1000 ppm $CO_2$). Twenty plants were grown under ambient greenhouse $CO_2$ (approximately 450 ppm $CO_2$). Plants are hand watered. Peters 20-20-20 fertilizer is also lightly applied. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. At ten days post planting, the shoots from both atmosphere are frozen in liquid nitrogen and lightly ground. The roots are washed in deionized water to remove the support media and the tissue is immediately transferred to liquid nitrogen containers. The harvested tissue is then stored at −80° C. until RNA preparation. The RNA is purified from the stored tissue and the cDNA library is constructed as described in Example 2.

The CMz048 (Lib3079) cDNA library is generated from maize (MO17USDA Maize Germplasm Collection, Urbana, Ill. U.S.A) basal endosperm transfer layer tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ maize plants. The ear shoots, which are ready for fertilization, are enclosed in a paper bag prior to silk emergence, to withhold the pollen. Kernels are harvested at 12 days post-pollination and placed on wet ice for dissection. The kernels are cross sectioned laterally, dissecting just above the pedicel region, including 1-2 mm of the lower endosperm and the basal endosperm transfer region. The pedicel and lower endosperm region containing the basal endosperm transfer layer is pooled and immediately frozen in liquid nitrogen. The harvested tissue is then stored at −80° C. until RNA preparation. The RNA is purified from the stored tissue and the cDNA library is constructed as described in Example 2.

The CMz049(Lib3088) cDNA library is generated from maize (H99, USDA Maize Germplasm Collection, Urbana, Ill. U.S.A) immature anther tissue from 8 weeks old plants. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Ears were harvested from 8 week old plants and were approximately 3.5-4.5 cm long. Kernels were dissected away from cob, frozen in liquid nitrogen and stored at −80 C until preparation of RNA. The RNA is purified from the stored tissue and the cDNA library is constructed as described in Example 2.

The CMz050 (Lib3114) cDNA library is generated from silks from maize (B73, Illinois Foundation Seeds, Champaign, Ill. U.S.A.) plants at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is beyond the 10-leaf development stage and the ear shoots are approximately 15-20 cm in length. The ears are pulled and silks are separated from the ears and immediately transferred to liquid nitrogen containers. The harvested tissue is then stored at −80° C. until RNA preparation. The RNA is purified from the stored tissue and the cDNA library is constructed as described in Example 2.

The SOYMON001 cDNA library is generated from soybean cultivar Asgrow 3244 (Asgrow Seed Company, Des Moines, Iowa U.S.A.) total leaf tissue at the V4 plant development stage. Leaf tissue from 38, field grown V4 stage plants is harvested from the $4^{th}$ node. Leaf tissue is removed from the plants and immediately frozen in dry-ice. The harvested tissue is then stored at −80° C. until RNA preparation. The RNA is purified from the stored tissue and the cDNA library is constructed as described in Example 2.

The SOYMON002 cDNA library is generated from soybean cultivar Asgrow 3244 (Asgrow Seed Company, Des Moines, Iowa U.S.A.) root tissue at the V4 plant development stage. Root tissue from 76, field grown V4 stage plants is harvested. The root systems is cut from the soybean plant and washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON003 cDNA library is generated from soybean cultivar Asgrow 3244 (Asgrow Seed Company, Des Moines, Iowa U.S.A.) seedling hypocotyl axis tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation. The RNA is purified from the stored tissue and the cDNA library is constructed as described in Example 2.

The SOYMON004 cDNA library is generated from soybean cultivar Asgrow 3244 (Asgrow Seed Company, Des Moines, Iowa U.S.A.) seedling cotyledon tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation. The RNA is purified from the stored tissue and the cDNA library is constructed as described in Example 2.

The SOYMON005 cDNA library is generated from soybean cultivar Asgrow 3244 (Asgrow Seed Company, Des Moines, Iowa U.S.A.) seedling hypocotyl axis tissue harvested 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after the start of imbibition. The 6 hours after imbibition samples are separated into 3 collections after removal of any adhering seed coat. The 6 hours after imbibition sample is collected over the course of approximately 2 hours starting at 6 hours post imbibition. At the 6 hours after imbibition stage, not all cotyledons have become fully hydrated and germination, or radicle protrusion, has not occurred. The seedlings are washed in water to remove soil, hypocotyl axis harvested and immediately frozen in liquid nitrogen. The harvested tissue is then stored at −80° C. until RNA preparation. The RNA is purified from the stored tissue and the cDNA library is constructed as described in Example 2.

The SOYMON006 cDNA library is generated from soybean cultivar Asgrow 3244 (Asgrow Seed Company, Des Moines, Iowa U.S.A.) seedling cotyledons tissue harvested 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after imbibition. The 6 hours after imbibition samples are separated into 3 collections after removal of any adhering seed coat. The 6 hours after imbibition sample is collected over the course of approximately 2 hours starting at 6 hours post-imbibition. At the 6 hours after imbibition, not all cotyledons have become fully hydrated and germination or radicle protrusion, have not occurred. The seedlings are washed in water to remove soil, cotyledon harvested and immediately frozen in liquid nitrogen. The harvested tissue is then stored at −80° C. until RNA preparation. The RNA is purified from the stored tissue and the cDNA library is constructed as described in Example 2.

The SOYMON007 cDNA library is generated from soybean cultivar Asgrow 3244 (Asgrow Seed Company, Des Moines, Iowa U.S.A.) seed tissue harvested 25 and 35 days post-flowering. Seed pods from field grown plants are harvested 25 and 35 days after flowering and the seeds extracted from the pods. Approximately 4.4 g and 19.3 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON008 cDNA library is generated from soybean cultivar Asgrow 3244 (Asgrow Seed Company, Des Moines, Iowa U.S.A.) leaf tissue harvested from 25 and 35 days post-flowering plants. Total leaf tissue is harvested from field grown plants. Approximately 19 g and 29 g of leaves are harvested from the fourth node of the plant 25 and 35 days post-flowering and immediately frozen in dry ice. The harvested tissue is then stored at −80° C. until RNA preparation. The RNA is purified from the stored tissue and the cDNA library is constructed as described in Example 2.

The SOYMON009 cDNA library is generated from soybean cultivar C1944 (USDA Soybean Germplasm Collection, Urbana, Ill. U.S.A.) pod and seed tissue harvested 15 days post-flowering. Pods from field grown plants are harvested 15 days post-flowering. Approximately 3 g of pod tissue is harvested and immediately frozen in dry-ice. The harvested tissue is then stored at −80° C. until RNA preparation. The RNA is purified from the stored tissue and the cDNA library is constructed as described in Example 2.

The SOYMON010 cDNA library is generated from soybean cultivar C1944 (USDA Soybean Germplasm Collection, Urbana, Ill. U.S.A.) seed tissue harvested 40 days post-flowering. Pods from field grown plants are harvested 40 days post-flowering. Pods and seeds are separated, approximately 19 g of seed tissue is harvested and immediately frozen in dry-ice. The harvested tissue is then stored at −80° C. until RNA preparation. The RNA is purified from the stored tissue and the cDNA library is constructed as described in Example 2.

The SOYMON011 cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation. The RNA is purified from the stored tissue and the cDNA library is constructed as described in Example 2.

The SOYMON012 cDNA library is generated from soybean cultivar Asgrow 3244 (Asgrow Seed Company, Des Moines, Iowa U.S.A.) leaf tissue. Leaves from field grown plants are harvested from the fourth node 15 days post-flowering. Approximately 12 g of leaves are harvested and immediately frozen in dry ice. The harvested tissue is then stored at −80° C. until RNA preparation. The RNA is purified from the stored tissue and the cDNA library is constructed as described in Example 2.

The SOYMON013 cDNA library is generated from soybean cultivar Asgrow 3244 (Asgrow Seed Company, Des Moines, Iowa U.S.A.) root and nodule tissue. Approximately, 28 g of root tissue from field grown plants is harvested 15 days post-flowering. The root system is cut from the soybean plant, washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON014 cDNA library is generated from soybean cultivar Asgrow 3244 (Asgrow Seed Company, Des Moines, Iowa U.S.A.) seed tissue harvested 25 and 35 days after flowering. Seed pods from field grown plants are harvested 15 days after flowering and the seeds extracted from the pods. Approximately 5 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON015 cDNA is generated from soybean cultivar Asgrow 3244 (Asgrow Seed Company, Des Moines, Iowa U.S.A.) seed tissue harvested 45 and 55 days post-flowering. Seed pods from field grown plants are harvested 45 and 55 days after flowering and the seeds extracted from the pods. Approximately 19 g and 31 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON016 cDNA library is generated from soybean cultivar Asgrow 3244 (Asgrow Seed Company, Des Moines, Iowa U.S.A.) root tissue. Approximately, 61 g and 38 g of root tissue from field grown plants is harvested 25 and 35 days post-flowering is harvested. The root system is cut from the soybean plant and washed with water to free it from the soil. The tissue is placed in 14 ml polystyrene tubes and immediately frozen in dry-ice. The harvested tissue is then stored at −80° C. until RNA preparation. The RNA is purified from the stored tissue and the cDNA library is constructed as described in Example 2.

The SOYMON017 cDNA library is generated from soybean cultivar Asgrow 3244 (Asgrow Seed Company, Des Moines, Iowa U.S.A.) root tissue. Approximately 28 g of root tissue from field grown plants is harvested 45 and 55 days post-flowering. The root system is cut from the soybean plant, washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON018 cDNA is generated from soybean cultivar Asgrow 3244 (Asgrow 1) Seed Company, Des Moines, Iowa U.S.A.) leaf tissue harvested 45 and 55 days post-flowering. Leaves from field grown plants are harvested 45 and 55 days after flowering from the fourth node. Approximately 27 g and 33 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON019 cDNA library is generated from soybean cultivars Cristalina (USDA Soybean Germplasm Collection, Urbana, Ill. U.S.A.) and FT108 (Monsoy, Brazil) (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation. The RNA is purified from the stored tissue and the cDNA library is constructed as described in Example 2.

The SOYMON020 cDNA is generated from soybean cultivar Asgrow 3244 (Asgrow Seed Company, Des Moines, Iowa U.S.A.) seed tissue harvested 65 and 75 days post-flowering. Seed pods from field grown plants are harvested 45 and 55 days after flowering and the seeds extracted from the pods. Approximately 14 g and 31 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON021 cDNA library is generated from Soybean Cyst Nematode-resistant soybean cultivar Hartwig (USDA Soybean Germplasm Collection, Urbana, Ill. U.S.A.) root tissue. Plants are grown in tissue culture at room temperature. At approximately 6 weeks post-germination, the plants are exposed to sterilized Soybean Cyst Nematode eggs. Infection is then allowed to progress for 10 days. After the 10 day infection process, the tissue is harvested. Agar from the culture medium and nematodes are removed and the root tissue is immediately frozen in dry ice. The harvested tissue is then stored at −80° C. until RNA preparation. The RNA is purified from the stored tissue and the cDNA library is constructed as described in Example 2.

The SOYMON022 (Lib3030) cDNA library is generated from soybean cultivar Asgrow 3244 (Asgrow Seed Company, Des Moines, Iowa U.S.A.) partially opened flower tissue. Partially to fully opened flower tissue is harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. A total of 3 g of flower tissue is harvested and immediately frozen in dry ice. The harvested tissue is then stored at −80° C. until RNA preparation. The RNA is purified from the stored tissue and the cDNA library is constructed as described in Example 2.

The SOYMON023 cDNA library is generated from soybean genotype BW211S Null (Tohoku University, Morioka, Japan) seed tissue harvested 15 and 40 days post-flowering. Seed pods from field grown plants are harvested 15 and 40 days post-flowering and the seeds extracted from the pods. Approximately 0.7 g and 14.2 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON024 cDNA library is generated from soybean cultivar Asgrow 3244 (Asgrow Seed Company, Des Moines, Iowa U.S.A.) internode-2 tissue harvested 18 days post-imbibition. Seeds are planted at a depth of approximately 2 cm into 2-3 inch peat pots containing Metromix 350 medium. The plants are grown in a greenhouse for 18 days after the start of imbibition at ambient temperature. Soil is checked and watered daily to maintain even moisture conditions. Stem tissue is harvested 18 days after the start of imbibition. The samples are divided into hypocotyl and internodes 1 through 5. The fifth internode contains some leaf bud material. Approximately 3 g of each sample is harvested and immediately frozen in dry ice. The harvested tissue is then stored at −80° C. until RNA preparation. The RNA is purified from the stored tissue and the cDNA library is constructed as described in Example 2.

The SOYMON025 cDNA library is generated from soybean cultivar Asgrow 3244 (Asgrow Seed Company, Des Moines, Iowa U.S.A.) leaf tissue harvested 65 days post-flowering. Leaves are harvested from the fourth node of field grown plants 65 days post-flowering. Approximately 18.4 g of leaf tissue is harvested and immediately frozen in dry ice. The harvested tissue is then stored at −80° C. until RNA preparation. The RNA is purified from the stored tissue and the cDNA library is constructed as described in Example 2.

SOYMON026 cDNA library is generated from soybean cultivar Asgrow 3244 (Asgrow Seed Company, Des Moines, Iowa U.S.A.) root tissue harvested 65 and 75 days post-flowering. Approximately 27 g and 40 g of root tissue from field grown plants is harvested 65 and 75 days post-flowering. The root system is cut from the soybean plant, washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON027 cDNA library is generated from soybean cultivar Asgrow 3244 (Asgrow Seed Company, Des Moines, Iowa U.S.A.) pod tissue, without seeds, harvested 25 days post-flowering. Seed pods from field grown plants are harvested 25 days post-flowering and the seeds extracted from the pods. Approximately 17 g of seed pod tissue is harvested and immediately frozen in dry ice. The harvested tissue is then stored at −80° C. until RNA preparation. The RNA is purified from the stored tissue and the cDNA library is constructed as described in Example 2.

The SOYMON028 cDNA library is generated from soybean cultivar Asgrow 3244 (Asgrow Seed Company, Des Moines, Iowa U.S.A.) drought-stressed root tissue. The plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of development, water is withheld from half of the plant collection (drought stressed population). After 3 days, half of the plants from the drought stressed condition and half of the plants from the control population are harvested. After another 3 days (6 days post drought induction) the remaining plants are harvested. A total of 27 g and 40 g of root tissue is harvested and immediately frozen in dry ice. The harvested tissue is then stored at −80° C. until RNA preparation. The RNA is purified from the stored tissue and the cDNA library is constructed as described in Example 2.

The SOYMON029 cDNA library is generated from Soybean Cyst Nematode-resistant soybean cultivar P107354 (USDA Soybean Germplasm Collection, Urbana, Ill. U.S.A.) root tissue. Late fall to early winter greenhouse grown plants are exposed to Soybean Cyst Nematode eggs. At 10 days post-infection, the plants are uprooted, rinsed briefly and the roots frozen in liquid nitrogen. Approximately 20 grams of root tissue is harvested from the infected plants. The harvested tissue is then stored at −80° C. until RNA preparation. The RNA is purified from the stored tissue and the cDNA library is constructed as described in Example 2.

The SOYMON030 cDNA library is generated from soybean cultivar Asgrow 3244 (Asgrow Seed Company, Des Moines, Iowa U.S.A.) flower bud tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. A total of 100 mg of flower buds are harvested and immediately frozen in liquid nitrogen. The harvested tissue is then stored at −80° C. until RNA preparation. Total RNA is prepared from 50 mg of tissue and used directly to generate a library using the Clonetech SMART™ PCR cDNA (Palo Alto, Calif. (U.S.A.) library construction kit. The EcoRI/XhoI adaptors are used in this library construction. The cDNA is ligated into the pINCY vector.

The SOYMON031 cDNA library is generated from soybean cultivar Asgrow 3244 (Asgrow Seed Company, Des Moines, Iowa U.S.A.) carpel and stamen tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. Flowers are dissected to separate petals, sepals and reproductive structures (carpels and stamens). A total of 300 mg of carpel and stamen tissue are harvested and immediately frozen in liquid nitrogen. The harvested tissue is then stored at −80° C. until RNA preparation. Total RNA is prepared from 150 mg of tissue and used directly to generate a library using the Clonetech SMART™ PCR cDNA (Palo Alto, Calif. (U.S.A.) library construction kit. The EcoRI/XhoI adaptors are used in this library construction. The cDNA is ligated into the pINCY vector.

The SOYMON032 cDNA library is prepared from the Asgrow cultivar A 4922 (Asgrow Seed Company, Des Moines, Iowa U.S.A.) rehydrated dry soybean seed meristem tissue. Surface sterilized seeds are germinated in liquid media for 24 hours. The seed axis is then excised from the barely germinating seed, placed on tissue culture media and incubated overnight at 20° C. in the dark. The supportive tissue is removed from the explant prior to harvest. Approximately 570 mg of tissue is harvested and frozen in liquid nitrogen. The harvested tissue is then stored at −80° C. until RNA preparation. The RNA is purified from the stored tissue and the cDNA library is constructed as described in Example 2.

The SOYMON033 cDNA library is generated from soybean cultivar Asgrow 3244 (Asgrow Seed Company, Des Moines, Iowa U.S.A.) heat-shocked seedling tissue without cotyledons. Seeds are imbibed and germinated in vermiculite for 2 days under constant illumination. After 48 hours, the seedlings are transferred to an incubator set at 40° C. under constant illumination. After 30, 60 and 180 minutes seedlings are harvested and dissected. A portion of the seedling consisting of the root, hypocotyl and apical hook is frozen in liquid nitrogen and stored at −80° C. The seedlings after 2 days of imbibition are beginning to emerge from the vermiculite surface. The apical hooks are dark green in appearance. Total RNA and poly $A^+$ RNA is prepared from equal amounts of pooled tissue. The RNA is purified from the stored tissue and the cDNA library is constructed as described in Example 2.

The SOYMON034 cDNA library is generated from soybean cultivar Asgrow 3244 (Asgrow Seed Company, Des Moines, Iowa U.S.A.) cold-shocked seedling tissue without cotyledons. Seeds are imbibed and germinated in vermiculite for 2 days under constant illumination. After 48 hours, the seedlings are transferred to a cold room set at 5° C. under constant illumination. After 30, 60 and 180 minutes seedlings are harvested and dissected. The seedlings after 2 days of imbibition are beginning to emerge from the vermiculite surface. The apical hooks are dark green in appearance. A portion of the seedling consisting of the root, hypocotyl and apical hook is frozen in liquid nitrogen and stored at −80° C. The RNA is purified from the stored tissue and the cDNA library is constructed as described in Example 2.

The SOYMON035 cDNA library is generated from soybean cultivar Asgrow 3244 (Asgrow Seed Company, Des Moines, Iowa U.S.A.) seed coat tissue. Seeds are planted at a depth of approximately 2 cm into 2-3 inch peat pots containing Metromix 350 medium and the plants are grown in an environmental chamber under 12 hr daytime/122 hr nighttime cycles. The daytime temperature is approximately 29° C. and the nighttime temperature 24° C. Soil is checked and watered daily to maintain even moisture conditions. Seeds are harvested from mid to nearly full maturation (seed coats are not yellowing). The entire embryo proper is removed from the seed coat sample and the seed coat tissue are harvested and immediately frozen in liquid nitrogen. The harvested tissue is then stored at −80° C. until RNA preparation. The RNA is purified from the stored tissue and the cDNA library is constructed as described in Example 2.

The SOYMON036 cDNA library is generated from soybean cultivars PI171451, PI227687 and PI229358 (USDA Soybean Germplasm Collection, Urbana, Ill. U.S.A.) insect challenged leaves. Plants from each of the three cultivars are grown in screenhouse conditions. The screenhouse is divided in half and one half of the screenhouse is infested with soybean looper and the other half infested with velvetbean caterpillar. A single leaf is taken from each of the representative plants at 3 different time points, 11 days after infestation, 2 weeks after infestation and 5 weeks after infestation and immediately frozen in liquid nitrogen. The harvested tissue is then stored at −80° C. until RNA preparation. Total RNA and poly A+ RNA is isolated from pooled tissue consisting of equal quantities of all 18 samples (3 genotypes X 3 sample times X 2 insect genotypes). The RNA is purified from the stored tissue and the cDNA library is constructed as described in Example 2.

The SOYMON037 cDNA library is generated from soybean cultivar A3244 (Asgrow Seed Company, Des Moines, Iowa U.S.A.) etiolated axis and radical tissue. Seeds are planted in moist vermiculite, wrapped and kept at room temperature in complete darkness until harvest. Etiolated axis and hypocotyl tissue is harvested at 2, 3 and 4 days post-planting. A total of 1 gram of each tissue type is harvested at 2, 3 and 4 days after planting and immediately frozen in liquid nitrogen. The harvested tissue is then stored at −80° C. until RNA preparation. The RNA is purified from the stored tissue and the cDNA library is constructed as described in Example 2.

The SOYMON038 cDNA library is generated from soybean variety Asgrow A3237 (Asgrow Seed Company, Des Moines, Iowa U.S.A.) rehydrated dry seeds. Explants are prepared for transformation after germination of surface-sterilized seeds on solid tissue media. After 6 days, at 28° C. and 18 hours of light per day, the germinated seeds are cold shocked at 4° C. for 24 hours. Meristemic tissue and part of the hypocotyl is remove and cotyledon excised. The prepared explant is then wounded for *Agrobacterium* infection. The 2 grams of harvested tissue is frozen in liquid nitrogen and stored at −80° C. until RNA preparation. The RNA is purified from the stored tissue and the cDNA library is constructed as described in Example 2.

The Soy51 (LIB3027) normalized cDNA library is prepared from pooled seeds from SOYMON007, SOYMON015 and SOYMON020. Equal amounts of SOYMON007, SOYMON015, and SOYMON020 in the form of single stranded DNA, are mixed and used as the starting material for normalization. The normalized cDNA library is constructed as described in Example 2.

The Soy52 (LIB3028) normalized cDNA library is generated from flowers collected from soybean cultivar Asgrow 3244 (Asgrow Seed Company, Des Moines, Iowa U.S.A.) plants. The tissue descriptions for this library are identical to that for Soy35 (SOYMON022). The RNA is purified from the stored tissue and the normalized cDNA library is constructed as described in Example 2.

The Soy53 (LIB3039) cDNA library is generated from soybean cultivar Asgrow 3244 (Asgrow Seed Company, Des Moines, Iowa U.S.A.) seedling shoot apical meristem tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Apical tissue is harvested from seedling shoot meristem tissue, 7-8 days after the start of imbibition. The apex of each seedling is dissected to include the fifth node to the apical meristem. The fifth node corresponds to the third trifoliate leaf in the very early stages of development. Stipules completely envelop the leaf primordia at this time. A total of 200 mg of apical tissue is harvested and immediately frozen in liquid nitrogen. The harvested tissue is then stored at −80° C. until RNA preparation. The RNA is purified from the stored tissue and the cDNA library is constructed as described in Example 2.

The Soy54 (LIB3040) cDNA library is generated from soybean cultivar Asgrow 3244 (Asgrow Seed Company, Des Moines, Iowa U.S.A.) heart to torpedo stage embryo tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected and embryos removed from surrounding endosperm and maternal tissues. Embryos from globular to young torpedo stages (by corresponding analogy to *Arabidopsis*) are collected with a bias towards the middle of this spectrum. Embryos which are beginning to show asymmetric development of cotyledons are considered the upper developmental boundary for the collection and are excluded. A total of 12 mg embryo tissue is frozen in liquid nitrogen. The harvested tissue is stored at −80° C. until RNA preparation. Total RNA is prepared from 100 mg of tissue and used directly to generate a library using the Clonetech SMART™ PCR cDNA (Palo Alto, Calif. (U.S.A.)) library construction kit. The SalI adaptors are used in this library construction. The cDNA is ligated into the pSPORT vector.

Soy55 (LIB3049) cDNA library is generated from soybean cultivar Asgrow 3244 (Asgrow Seed Company, Des Moines, Iowa U.S.A.) young seed tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected from very young pods (5 to 15 days after flowering). A total of 100 mg of seeds are harvested and frozen in liquid nitrogen. The harvested tissue is stored at −80° C. until RNA preparation. Total RNA is prepared from 100 mg of tissue and used directly to generate a library using the Clonetech SMART™ PCR cDNA (Palo Alto, Calif. (U.S.A.)) library construction kit. The SalI adaptors are used in this library construction. The cDNA is ligated into the pSPORT vector.

Soy56 (LIB3029) cDNA library is prepared from pooled seeds from Soy19 (SOYMON007), Soy27 (SOYMON015) and Soy33 (SOYMON020). Equal amounts of Soy19, Soy27 and Soy33, in the form of single stranded DNA, are mixed in equimolar quantities. This mixture is used as a non-normalized control for comparison to Soy51. The cDNA library is constructed as described in Example 2.

The Soy58 (LIB3050) cDNA library is generated from soybean cultivar Asgrow 3244 (Asgrow Seed Company, Des Moines, Iowa U.S.A.) drought stressed root tissue subtracted from control root tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of the plant drought is induced by withholding water. After 3 and 6 days root tissue from both drought stressed and control (watered regularly) plants are collected and frozen in dry-ice. The harvested tissue is stored at −80° C. until RNA preparation. The RNA is prepared from the stored tissue and the subtracted cDNA library is constructed as described in Example 2.

The Soy59 (LIB3051) cDNA library is generated from soybean cultivar Asgrow 3244 (Asgrow Seed Company, Des Moines, Iowa U.S.A.) endosperm tissue. Seeds are germinated on paper towels under laboratory ambient light conditions. At 8, 10 and 14 hours after imbibition, the seed coats are harvested. The endosperm consists of a very thin layer of tissue affixed to the inside of the seed coat. The seed coat and endosperm are frozen immediately after harvest in liquid nitrogen. The harvested tissue is stored at −80° C. until RNA preparation. The RNA is prepared from the stored tissue and the cDNA library is constructed using the pSPORT cDNA synthesis kit from Life Technologies (Life Technologies, Gaithersburg, Md. U.S.A.). The resulting cDNA is ligated into the pSPORT.

The Soy60 (LIB3072) cDNA library is generated by subtracting the target cDNA, which is prepared from soybean cultivar Asgrow 3244 (Asgrow Seed Company, Des Moines, Iowa U.S.A.) seeds plus pods from drought stressed plants, from the driver cDNA, which is prepared from soybean cultivar Asgrow 3244 seeds plus pods from non drought-stressed (control) plants. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. The RNA is prepared from the stored tissue and the subtracted cDNA library is constructed as described in Example 2.

The Soy61 (LIB3073) cDNA library is generated by subtracting the target cDNA, which is prepared from soybean cultivar Asgrow 3244 (Asgrow Seed Company, Des Moines, Iowa U.S.A.) jasmonic acid treated seedling, from the driver cDNA, which is prepared from control buffer treated seedlings without cotyledon. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA is prepared from the stored tissue and the subtracted cDNA library is constructed as described in Example 2. For this library's construction, the eighth fraction of the cDNA size fractionation step was used for ligation.

The Soy62 (LIB3074) cDNA library is generated by subtracting the target cDNA, which is prepared from soybean cultivar Asgrow 3244 (Asgrow Seed Company, Des Moines, Iowa U.S.A.) jasmonic acid treated seedlings without cotyledon, from the driver cDNA, which is prepared from soybean cultivar Asgrow 3244 control buffer treated seedlings without cotyledon. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA is prepared from the stored tissue and the subtracted cDNA library is constructed as described in Example 2. For this library's construction, the ninth fraction of the cDNA size fractionation step was used for ligation.

The Soy65 (LIB3107) cDNA library is generated from soybean cultivar Asgrow 3244 (Asgrow Seed Company, Des Moines, Iowa U.S.A.) abscission zone tissue from drought-stressed plants. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Plants are irrigated with 15-16-17 Peter's Mix. At the R3 stage of development, drought is imposed by withholding water. At 3, 4, 5 and 6 days, tissue is harvested and wilting is not obvious until the fourth day. Abscission layers from reproductive organs are harvested by cutting less than one millimeter proximal and distal to the layer and immediately frozen in liquid nitrogen. The harvested tissue is stored at −80° C. until RNA preparation. The following tissues are combined for the single library: four day stress, all nodes; 5 day stress, all nodes The RNA is prepared from the stored tissue and the cDNA library is constructed as described in Example 2.

The Soy66 (LIB3109) cDNA library is generated from soybean cultivar Asgrow 3244 (Asgrow Seed Company, Des Moines, Iowa U.S.A.) abscission zone tissue from control (watered regularly) plants. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Plants are irrigated with 15-16-17 Peter's Mix. At 3, 4, 5 and 6 days (relative to drought stress induction in plants for soy65), abscission layer tissue is harvested. Abscission layers from reproductive organs are harvested by cutting less than one millimeter proximal and distal to the layer and immediately frozen in liquid nitrogen. The harvested tissue is stored at −80° C. until RNA preparation. The following samples are combined for this cDNA library: 4 day control, all nodes; 5 day control; all nodes. The RNA is prepared from the stored tissue and the cDNA library is constructed as described in Example 2.

Soy67 (LIB3065) normalized cDNA library is prepared from pooled seeds from SOYMON007, SOYMON015 and SOYMON020 prepared tissue. Equal amounts of Soy19 (SOYMON007), Soy27 (SOYMON015) and Soy33 (SOYMON020), in the form of single stranded DNA, are mixed and used as the starting material for normalization. The normalized cDNA library is constructed as described in Example 2.

Soy68 (LIB3052) normalized cDNA library is prepared from pooled seeds from SOYMON007, SOYMON015 and SOYMON020. Equal amounts of Soy19 (SOYMON007), Soy27 (SOYMON015) and Soy33 (SOYMON020), in the form of single stranded DNA, are mixed and used as the starting material for normalization. The normalized cDNA library is constructed as described in Example 2.

Soy69 (LIB3053) normalized cDNA library is generated from soybean cultivars Cristalina (USDA Soybean Germplasm Collection, Urbana, Ill. U.S.A.) and FT108 (Monsoy, Brazil) (tropical germ plasma) normalized leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the 4$^{th}$ node of each of the Cristalina and FT108 cultivars and immediately frozen in dry ice. The harvested tissue is then stored at −80° C. until RNA preparation. The RNA is prepared from the stored tissue and the normalized cDNA library is constructed as described in Example 2.

LIB3054 is a normalized cDNA library generated from roots from two exotic soybean cultivars Cristilliana and FT108 (Monsoy, Brazil, tropical germ plasma). The roots are harvested from plants grown an environmental chamber set to a 12 h day/12 h night cycle, 29° C. daytime temperature, 24° C. night temperature and 70% relative humidity. Daytime light levels are measured at 450 μEinsteins/m$^2$. Soil is checked and watered daily to maintain even moisture conditions. Approximately 50 g and 56 g of roots are collected from each of the Cristilliana and FT108 cultivars. The plants are uprooted and the roots quickly rinsed in a pail of water. The root tissue is then cut from the plants, placed immediately in 14 ml polystyrene tubes and immersed in dry-ice. The tissue is then transferred to a −80° C. freezer for storage. Total RNA is prepared from the combination of equal amounts of root tissue from each cultivar. The RNA is prepared from the stored tissue and the normalized cDNA library is constructed as described in Example 2.

Soy70 (LIB3055) cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the 4$^{th}$ node of each of the Cristalina and FT108 cultivars and immediately frozen in dry ice. The harvested tissue is then stored at −80° C. until RNA preparation. The RNA is prepared from the stored tissue and the cDNA library is constructed as described in Example 2.

Soy71 (LIB3056) cDNA library is generated from soybean cultivars Cristalina and FT108 (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation. The RNA is prepared from the stored tissue and the cDNA library is constructed as described in Example 2.

LIB3087 is a cDNA library that is generated from soybean cultivar Asgrow 3244 (Asgrow Seed Company, Des Moines, Iowa U.S.A). Seeds are imbibed in water for 4 hours at 30° C., and then the seed coat is removed. For the 4 hr timepoint, axis tissue is immediately harvested, and flash-frozen in liquid nitrogen. For 8 and 12 hr timepoints, decoated seeds are transferred to cotton saturated with water and incubated at 30° C. for the remainder of the incubation period. Axis tissue is then excised and frozen in liquid nitrogen. Equal numbers of axes from each timepoint is pooled for RNA isolation. The collected tissue is stored at −80° C. Axis tissue consists of unexpanded root, hypocotyl, epicotyl and apex. The RNA is purified from the stored tissue and the cDNA library is constructed as described in Example 2.

LIB3092 (Soy75) cDNA library is generated from soybean cultivar Asgrow 3244 (Asgrow Seed Company, Des Moines, Iowa U.S.A.) drought stressed leaf that is subtracted from a control. Seeds are planted in moist Metromix 350 medium at a depth of approximately 2 cm. Trays are placed in an environmental chamber set to a 12 h day/12 h night cycle, 26° C. daytime temperature, 21° C. night temperature and 70% relative humidity. Daytime light levels are measured at 300 mEinsteins/m$^2$. Soil is checked and watered daily to maintain even moisture conditions. At the R3 stage of the plant, drought is induced by withholding water. After 3 and 6 days tissue is harvested. Leaves from both drought stressed and control (watered regularly) plants are collected from the fifth and sixth node and frozen in dry-ice. The tissue is then transferred to a −80° C. freezer for storage. For subtraction, a standard cDNA library is constructed in the pSPORT vector. Driver first strand cDNA is covalently linked to Dynabeads following a protocol similar to that described in the Dynal literature. The target library is then heat denatured and hybridized to the driver cDNA in 400 ml 4×SSPE for five rounds of hybridization at 68° C. and 20 hours. After each hybridization, the hybridization solution is removed from the system and the hybridized target cDNA removed from the driver by heat denaturation in water. The refreshed driver is then reintroduced to the hybridization for the next round of hybridization. The remaining cDNA in the hybridization solution is then used to transform *E. Coli* for sequencing.

Soy74 (LIB3093) cDNA library is generated from soybean cultivar Asgrow 3244 (Asgrow Seed Company, Des Moines, Iowa U.S.A.) leaves collected from control (watered regularly) plants. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue from control plants is stored at −80° C. until RNA preparation. The RNA is prepared from the stored tissue and the cDNA library is constructed as described in Example 2.

LIB3094 is a normalized cDNA library that is generated from soybean cultivar Asgrow 3244 (Asgrow Seed Company, Des Moines, Iowa U.S.A). Seeds are imbibed in water for 4 hours at 30° C., and then the seed coat is removed. For the 4 hr timepoint, axis tissue is immediately harvested, and flash-frozen in liquid nitrogen. For 8 and 12 hr timepoints, decoated seeds are transferred to cotton saturated with water and incubated at 30° C. for the remainder of the incubation period. Axis tissue is then excised and frozen in liquid nitrogen. Equal numbers of axes from each timepoint is pooled for RNA isolation. The collected tissue is stored at −80° C. Axis tissue consists of unexpanded root, hypocotyl, epicotyl and apex. The RNA is purified from the stored tissue and the cDNA library is constructed as described in Example 2.

The Soy76 (Lib3106) cDNA library is generated from soybean cultivar Asgrow 3244 (Asgrow Seed Company, Des Moines, Iowa U.S.A.) jasmonic acid and arachidonic treated seedlings. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints from the jasmonic acid treated seedlings are combined and ground. RNA from the arachidonic acid treated seedlings is isolated separately. Poly $A^+$ RNA is extracted from each total RNA sample separately and combined to make a cDNA library using approximately equal amounts of mRNA from each treatment. The cDNA library is constructed as described in Example 2. For the construction of this cDNA library, fraction 10 of the size fractionated cDNA is ligated into the pSPORT vector (Invitrogen, Carlsbad Calif. U.S.A.) in order to capture some of the smaller transcripts characteristic of antifungal proteins.

Soy77 (LIB3108) cDNA library is generated from soybean cultivar Asgrow 3244 (Asgrow Seed Company, Des Moines, Iowa U.S.A.) control buffer (0.1% Tween-20) treated seedlings. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints from control buffer treated seedlings are combined and ground. The RNA is prepared from the stored tissue and the cDNA library is constructed as described in Example 2. For the construction of this cDNA library, fraction 10 of the size fractionated cDNA is ligated into the pSPORT vector in order to capture some of the smaller transcripts characteristic of antifungal proteins.

Soy72 (LIB3138) normalized cDNA library is generated from equal amounts of Soy5 (SOYMON001), Soy20 (SOYMON008) and Soy24 (SOYMON012), Soy28 (SOYMON018) and Soy38 (SOYMON025) in the form of double stranded DNA. These DNAs are mixed and used as the starting material for normalization. The tissue descriptions for these libraries are found above. The RNA is purified from the stored tissue and the cDNA library is constructed as described in Example 2.

Soy73 (LIB3139) normalized cDNA library is generated from equal amounts of Soy6 (SOYMON002), Soy25 (SOYMON013) and Soy29 (SOYMON016), Soy31 (SOYMON017) and Soy39 (SOYMON026) in the form of double stranded DNA. These DNAs are mixed and used as the starting material for normalization. The tissue descriptions for these libraries are found above. The RNA is purified from the stored tissue and the cDNA library is constructed as described in Example 2.

Example 2

The stored RNA is purified using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) is used, following the conditions suggested by the manufacturer.

Normalized libraries are made using essentially the Soares procedure (Soares et al., *Proc. Natl. Acad. Sci.* (*U.S.A.*) 91:9228-9232 (1994), the entirety of which is herein incorporated by reference). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected and clones for rare transcripts are effectively increased in abundance.

Normalized libraries are prepared from single-stranded and double-stranded DNA. Single-stranded and double-stranded DNA representing approximately $1\times10^6$ colony forming units are isolated using standard protocols. RNA, complementary to the single-stranded DNA, is synthesized using the double stranded DNA as a template. Biotinylated dATP is incorporated into the RNA during the synthesis reaction. The single-stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single-stranded molecules remaining after hybrid capture are converted to double stranded form and represent the primary normalized library.

For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 μl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

Example 3

The cDNA libraries are plated on LB agar containing the appropriate antibiotics for selection and incubated at 37° for a sufficient time to allow the growth of individual colonies. Single colonies are individually placed in each well of a 96-well microtiter plates containing LB liquid including the selective antibiotics. The plates are incubated overnight at approximately 37° C. with gentle shaking to promote growth of the cultures. The plasmid DNA is isolated from each clone using Qiaprep plasmid isolation kits, using the conditions recommended by the manufacturer (Qiagen Inc., Santa Clara, Calif. U.S.A.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif. U.S.A.).

Example 4

Nucleic acid sequences that encode for the following phosphogluconate pathway enzymes: glucose-6-phosphate-1-dehydrogenase; 6-phosphogluconate dehydrogenase; putative 6-phosphogluconate dehydrogenase; D-ribulose-5-phosphate-3-epimerase; ribose-5-phosphate isomerase; putative ribose-5-phosphate isomerase; transketolase; putative transketolase; transaldolase; putative transaldolase; and phosphoglucoisomerase; are identified from the Monsanto EST PhytoSeq database using TBLASTN (default values) (TBLASTN compares a protein query against the six reading frames of a nucleic acid sequence). Matches found with BLAST P values equal or less than 0.001 (probability) or BLAST Score of equal or greater than 90 are classified as hits. If the program used to determine the hit is HMMSW then the score refers to HMMSW score.

In addition, the GenBank database is searched with BLASTN and BLASTX (default values) using ESTs as queries. EST that pass the hit probability threshold of $10e^{-8}$ for the following enzymes are combined with the hits generated by using TBLASTN (described above) and classified by enzyme (see Table A below).

A cluster refers to a set of overlapping clones in the PhytoSeq database. Such an overlapping relationship among clones is designated as a "cluster" when BLAST scores from pairwise sequence comparisons of the member clones meets a predetermined minimum value or product score of 50 or more (Product Score=(BLAST SCORE×Percentage Identity)/(5×minimum [length (Seq1), length (Seq2)])).

Since clusters are formed on the basis of single-linkage relationships, it is possible for two non-overlapping clones to be members of the same cluster if, for instance, they both overlap a third clone with at least the predetermined minimum BLAST score (stringency). A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. Clones grouped in a cluster in most cases represent a contiguous sequence.

TABLE A*

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| | | MAIZE GLUCOSE-6-PHOSPHATE 1-DEHYDROGENASE | | | | | | |
| 1 | −700047645 | 700047645H1 | SATMON003 | g471345 | BLASTX | 193 | 1e-21 | 58 |
| 2 | −700210379 | 700210379H1 | SATMON016 | g1480344 | BLASTX | 103 | 1e-10 | 85 |
| 3 | 9135 | 700203121H1 | SATMON003 | g1166405 | BLASTX | 108 | 1e-10 | 78 |
| | | SOYBEAN GLUCOSE-6-PHOSPHATE 1-DEHYDROGENASE | | | | | | |
| 4 | −700869140 | 700869140H1 | SOYMON016 | g2829880 | BLASTX | 164 | 1e-15 | 44 |
| 5 | −701065174 | 701065174H1 | SOYMON034 | g603219 | BLASTX | 86 | 1e-9 | 76 |
| 6 | −701130434 | 701130434H1 | SOYMON037 | g1197385 | BLASTX | 189 | 1e-19 | 55 |
| 7 | −701149522 | 701149522H1 | SOYMON031 | g603219 | BLASTX | 99 | 1e-8 | 71 |
| 8 | 26484 | 701003905H1 | SOYMON019 | g1197385 | BLASTX | 138 | 1e-15 | 81 |
| 9 | 9136 | 701038169H1 | SOYMON029 | g603219 | BLASTX | 139 | 1e-21 | 73 |
| 10 | 9136 | 700903571H1 | SOYMON022 | g603219 | BLASTX | 144 | 1e-20 | 81 |
| 11 | 9136 | 701045122H1 | SOYMON032 | g603219 | BLASTX | 100 | 1e-13 | 79 |
| | | MAIZE 6-PHOSPHOGLUCONATE DEHYDROGENASE | | | | | | |
| 12 | −L30686779 | LIB3068-060-Q1-K1-G12 | LIB3068 | g603221 | BLASTX | 186 | 1e-34 | 78 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 13 | 416 | LIB3066-006-Q1-K1-H7 | LIB3066 | g2529228 | BLASTN | 865 | 1e-63 | 72 |
| 14 | 4882 | LIB3059-023-Q1-K1-E8 | LIB3059 | g2529228 | BLASTN | 1058 | 1e-79 | 72 |
| 15 | 4882 | LIB3069-050-Q1-K1-H6 | LIB3069 | g2529229 | BLASTX | 252 | 1e-69 | 83 |
| 16 | 4882 | LIB3066-024-Q1-K1-G4 | LIB3066 | g2529229 | BLASTX | 256 | 1e-60 | 79 |
| 17 | 4882 | LIB143-002-Q1-E1-A7 | LIB143 | g2529228 | BLASTN | 794 | 1e-57 | 74 |
| 18 | 4882 | LIB3069-043-Q1-K1-E1 | LIB3069 | g2529228 | BLASTN | 749 | 1e-52 | 73 |
| 19 | 4882 | LIB189-026-Q1-E1-G9 | LIB189 | g2529228 | BLASTN | 566 | 1e-36 | 75 |
| 20 | 4882 | LIB3069-054-Q1-K1-H7 | LIB3069 | g2529228 | BLASTN | 510 | 1e-31 | 75 |
| 21 | 4882 | LIB3062-033-Q1-K1-B9 | LIB3062 | g603221 | BLASTX | 151 | 1e-29 | 70 |
| | | SOYBEAN 6-PHOSPHOGLUCONATE DEHYDROGENASE | | | | | | |
| 22 | −700660509 | 700660509H1 | SOYMON004 | g2529228 | BLASTN | 641 | 1e-58 | 82 |
| 23 | −700851941 | 700851941H1 | SOYMON023 | g2529228 | BLASTN | 363 | 1e-20 | 94 |
| 24 | −700988668 | 700988668H1 | SOYMON009 | g2529228 | BLASTN | 221 | 1e-27 | 99 |
| 25 | −701065575 | 701065575H1 | SOYMON034 | g2529228 | BLASTN | 375 | 1e-20 | 95 |
| 26 | −701097417 | 701097417H1 | SOYMON028 | g2529228 | BLASTN | 229 | 1e-20 | 90 |
| 27 | −701097624 | 701097624H1 | SOYMON028 | g2529228 | BLASTN | 596 | 1e-40 | 70 |
| 28 | −701108654 | 701108654H1 | SOYMON036 | g2529228 | BLASTN | 817 | 1e-59 | 85 |
| 29 | −701127281 | 701127281H1 | SOYMON037 | g2529228 | BLASTN | 209 | 1e-8 | 90 |
| 30 | 1015 | 701136806H1 | SOYMON038 | g2529228 | BLASTN | 1221 | 1e-92 | 96 |
| 31 | 1015 | 701135971H1 | SOYMON038 | g2529228 | BLASTN | 971 | 1e-72 | 92 |
| 32 | 1015 | 700996470H1 | SOYMON018 | g2529228 | BLASTN | 940 | 1e-71 | 95 |
| 33 | 1015 | 700737338H1 | SOYMON010 | g2529228 | BLASTN | 469 | 1e-30 | 91 |
| 34 | 12395 | 700900348H1 | SOYMON027 | g2529228 | BLASTN | 1313 | 1e-100 | 97 |
| 35 | 12395 | 701099109H1 | SOYMON028 | g2529228 | BLASTN | 1252 | 1e-95 | 98 |
| 36 | 12395 | 701138412H1 | SOYMON038 | g2529228 | BLASTN | 1205 | 1e-91 | 95 |
| 37 | 12395 | 700995812H1 | SOYMON011 | g2529228 | BLASTN | 863 | 1e-85 | 95 |
| 38 | 12395 | 701097095H1 | SOYMON028 | g2529228 | BLASTN | 641 | 1e-84 | 95 |
| 39 | 12395 | 700667386H1 | SOYMON006 | g2529228 | BLASTN | 1082 | 1e-81 | 96 |
| 40 | 14379 | 701098379H1 | SOYMON028 | g2529228 | BLASTN | 1258 | 1e-96 | 99 |
| 41 | 14379 | 700667507H1 | SOYMON006 | g2529228 | BLASTN | 764 | 1e-54 | 94 |
| 42 | 14813 | 700790407H2 | SOYMON011 | g2529228 | BLASTN | 726 | 1e-60 | 82 |
| 43 | 14813 | 700790454H2 | SOYMON011 | g2529228 | BLASTN | 297 | 1e-43 | 84 |
| 44 | 23322 | 701056256H1 | SOYMON032 | g2529228 | BLASTN | 1079 | 1e-99 | 97 |
| 45 | 23322 | 701006115H1 | SOYMON019 | g2529228 | BLASTN | 828 | 1e-97 | 97 |
| 46 | 23322 | 701046496H1 | SOYMON032 | g2529228 | BLASTN | 753 | 1e-71 | 91 |
| 47 | 23322 | 701127189H1 | SOYMON037 | g2529228 | BLASTN | 440 | 1e-42 | 94 |
| 48 | 23861 | 701123687H1 | SOYMON037 | g2529228 | BLASTN | 995 | 1e-81 | 93 |
| 49 | 23861 | 700562186H1 | SOYMON002 | g2529228 | BLASTN | 787 | 1e-56 | 95 |
| 50 | 25330 | 701155571H1 | SOYMON031 | g2529228 | BLASTN | 922 | 1e-86 | 95 |
| 51 | 25330 | 701151123H1 | SOYMON031 | g2529228 | BLASTN | 1147 | 1e-86 | 99 |
| 52 | 25330 | 700869362H1 | SOYMON016 | g2529228 | BLASTN | 569 | 1e-75 | 94 |
| 53 | 2704 | 700651490H1 | SOYMON003 | g2529228 | BLASTN | 1482 | 1e-126 | 98 |
| 54 | 2704 | 700746336H1 | SOYMON013 | g2529228 | BLASTN | 1221 | 1e-105 | 99 |
| 55 | 2704 | 701127584H1 | SOYMON037 | g2529228 | BLASTN | 973 | 1e-100 | 97 |
| 56 | 2704 | 701062890H1 | SOYMON033 | g2529228 | BLASTN | 1173 | 1e-99 | 97 |
| 57 | 2704 | 701070368H1 | SOYMON034 | g2529228 | BLASTN | 686 | 1e-97 | 95 |
| 58 | 2704 | 700848709H1 | SOYMON021 | g2529228 | BLASTN | 1277 | 1e-97 | 98 |
| 59 | 2704 | 700904479H1 | SOYMON022 | g2529228 | BLASTN | 1281 | 1e-97 | 99 |
| 60 | 2704 | 700748881H1 | SOYMON013 | g2529228 | BLASTN | 1264 | 1e-96 | 96 |
| 61 | 2704 | 700746110H1 | SOYMON013 | g2529228 | BLASTN | 1257 | 1e-95 | 97 |
| 62 | 2704 | 701036989H1 | SOYMON029 | g2529228 | BLASTN | 1090 | 1e-94 | 95 |
| 63 | 2704 | 700986972H1 | SOYMON009 | g2529228 | BLASTN | 1173 | 1e-93 | 96 |
| 64 | 2704 | 700832482H1 | SOYMON019 | g2529228 | BLASTN | 1202 | 1e-93 | 98 |
| 65 | 2704 | 701209853H1 | SOYMON035 | g2529228 | BLASTN | 1210 | 1e-92 | 97 |
| 66 | 2704 | 700981060H1 | SOYMON009 | g2529228 | BLASTN | 1198 | 1e-91 | 93 |
| 67 | 2704 | 700730187H1 | SOYMON009 | g2529228 | BLASTN | 1182 | 1e-89 | 99 |
| 68 | 2704 | 701010566H1 | SOYMON019 | g2529228 | BLASTN | 649 | 1e-88 | 90 |
| 69 | 2704 | 701008609H1 | SOYMON019 | g2529228 | BLASTN | 1124 | 1e-88 | 91 |
| 70 | 2704 | 700727312H1 | SOYMON009 | g2529228 | BLASTN | 1171 | 1e-88 | 94 |
| 71 | 2704 | 700750187H1 | SOYMON013 | g2529228 | BLASTN | 1059 | 1e-84 | 94 |
| 72 | 2704 | 700747389H1 | SOYMON013 | g2529228 | BLASTN | 614 | 1e-82 | 92 |
| 73 | 2704 | 700988527H1 | SOYMON009 | g2529228 | BLASTN | 781 | 1e-81 | 92 |
| 74 | 2704 | 700836168H1 | SOYMON019 | g2529228 | BLASTN | 1079 | 1e-81 | 93 |
| 75 | 2704 | 700904775H1 | SOYMON022 | g2529228 | BLASTN | 491 | 1e-80 | 95 |
| 76 | 2704 | 700566794H1 | SOYMON002 | g2529228 | BLASTN | 1045 | 1e-78 | 96 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 77 | 2704 | 700764571H1 | SOYMON022 | g2529228 | BLASTN | 1028 | 1e-76 | 91 |
| 78 | 2704 | 701047371H1 | SOYMON032 | g2529228 | BLASTN | 995 | 1e-74 | 96 |
| 79 | 2704 | 700727986H1 | SOYMON009 | g2529228 | BLASTN | 619 | 1e-73 | 92 |
| 80 | 2704 | 701009981H2 | SOYMON019 | g2529228 | BLASTN | 840 | 1e-71 | 93 |
| 81 | 2704 | 701049731H1 | SOYMON032 | g2529228 | BLASTN | 965 | 1e-71 | 98 |
| 82 | 2704 | 701105763H1 | SOYMON036 | g2529228 | BLASTN | 603 | 1e-70 | 92 |
| 83 | 2704 | 701214664H1 | SOYMON035 | g2529228 | BLASTN | 876 | 1e-64 | 93 |
| 84 | 2704 | 700889079H1 | SOYMON024 | g2529228 | BLASTN | 376 | 1e-43 | 92 |
| 85 | 2704 | 701037615H1 | SOYMON029 | g2529228 | BLASTN | 450 | 1e-28 | 85 |
| 86 | 502 | 700742139H1 | SOYMON012 | g2309076 | BLASTX | 179 | 1e-17 | 82 |
| 87 | 502 | 700743132H1 | SOYMON012 | g1573539 | BLASTX | 141 | 1e-12 | 87 |
| 88 | 6991 | 701048543H1 | SOYMON032 | g10409 | BLASTX | 116 | 1e-8 | 46 |
| 89 | 7306 | 700728579H1 | SOYMON009 | g2529228 | BLASTN | 797 | 1e-60 | 86 |
| 90 | 7306 | 700852657H1 | SOYMON023 | g2529228 | BLASTN | 739 | 1e-56 | 86 |
| 91 | 7306 | 700954712H1 | SOYMON022 | g2529228 | BLASTN | 700 | 1e-53 | 86 |
| 92 | 7306 | 700830929H1 | SOYMON019 | g2529228 | BLASTN | 693 | 1e-48 | 87 |
| 93 | 7306 | 700946027H1 | SOYMON024 | g2529228 | BLASTN | 681 | 1e-47 | 86 |
| 94 | 7306 | 701109643H1 | SOYMON036 | g2529228 | BLASTN | 566 | 1e-41 | 88 |
| 95 | 7306 | 700670024H1 | SOYMON006 | g2529228 | BLASTN | 478 | 1e-35 | 88 |
| 96 | 7306 | 700561367H1 | SOYMON002 | g2529228 | BLASTN | 274 | 1e-25 | 80 |
| 97 | 9847 | 700849887H1 | SOYMON021 | g2529228 | BLASTN | 246 | 1e-9 | 72 |
| 98 | −GM11339 | LIB3049-022-Q1-E1-H3 | LIB3049 | g2529228 | BLASTN | 1360 | 1e-111 | 86 |
| 99 | 14379 | LIB3050-022-Q1-K1-H11 | LIB3050 | g2529228 | BLASTN | 1793 | 1e-143 | 96 |
| 100 | 14379 | LIB3049-022-Q1-E1-H2 | LIB3049 | g2529228 | BLASTN | 1080 | 1e-137 | 97 |
| 101 | 16 | LIB3040-004-Q1-E1-H4 | LIB3040 | g2529228 | BLASTN | 290 | 1e-36 | 96 |
| 102 | 23322 | LIB3050-010-Q1-E1-D7 | LIB3050 | g2529228 | BLASTN | 726 | 1e-95 | 97 |
| 103 | 2704 | LIB3039-020-Q1-E1-G6 | LIB3039 | g2529228 | BLASTN | 1060 | 1e-116 | 92 |
| MAIZE PUTATIVE 6-PHOSPHOGLUCONATE DEHYDROGENASE | | | | | | | | |
| 104 | −700159280 | 700159280H1 | SATMON012 | g3342801 | BLASTN | 677 | 1e-58 | 86 |
| 105 | −700259383 | 700259383H1 | SATMON017 | g3342803 | BLASTN | 1210 | 1e-94 | 94 |
| 106 | −700336103 | 700336103H1 | SATMON019 | g3342801 | BLASTN | 777 | 1e-93 | 96 |
| 107 | −700347721 | 700347721H1 | SATMON023 | g3342799 | BLASTN | 282 | 1e-25 | 69 |
| 108 | −700451974 | 700451974H1 | SATMON028 | g2529229 | BLASTX | 159 | 1e-15 | 60 |
| 109 | −700549549 | 700549549H1 | SATMON022 | g3342799 | BLASTN | 1144 | 1e-86 | 86 |
| 110 | −700570587 | 700570587H1 | SATMON030 | g3342801 | BLASTN | 780 | 1e-80 | 80 |
| 111 | −701165285 | 701165285H1 | SATMONN04 | g3342801 | BLASTN | 469 | 1e-68 | 96 |
| 112 | 1485 | 700072738H1 | SATMON007 | g3342799 | BLASTN | 1670 | 1e-130 | 100 |
| 113 | 1485 | 700102916H1 | SATMON010 | g3342801 | BLASTN | 667 | 1e-107 | 97 |
| 114 | 1485 | 700075367H1 | SATMON007 | g3342799 | BLASTN | 1355 | 1e-104 | 100 |
| 115 | 1485 | 700215789H1 | SATMON016 | g3342799 | BLASTN | 1355 | 1e-104 | 100 |
| 116 | 1485 | 700618992H1 | SATMON034 | g3342799 | BLASTN | 926 | 1e-102 | 99 |
| 117 | 1485 | 700236444H1 | SATMON010 | g3342801 | BLASTN | 1237 | 1e-94 | 98 |
| 118 | 1485 | 701182383H1 | SATMONN06 | g3342801 | BLASTN | 707 | 1e-93 | 97 |
| 119 | 1485 | 700243716H1 | SATMON010 | g3342799 | BLASTN | 1233 | 1e-93 | 98 |
| 120 | 1485 | 700017132H1 | SATMON001 | g3342801 | BLASTN | 650 | 1e-84 | 100 |
| 121 | 1485 | 700000601H1 | SATMON001 | g3342801 | BLASTN | 1125 | 1e-84 | 100 |
| 122 | 1485 | 700000606H1 | SATMON001 | g3342801 | BLASTN | 1100 | 1e-82 | 100 |
| 123 | 1485 | 700473536H1 | SATMON025 | g3342799 | BLASTN | 1079 | 1e-81 | 97 |
| 124 | 1485 | 700000638H1 | SATMON001 | g3342801 | BLASTN | 1045 | 1e-78 | 100 |
| 125 | 1485 | 700000634H1 | SATMON001 | g3342801 | BLASTN | 1050 | 1e-78 | 100 |
| 126 | 1485 | 700000685H1 | SATMON001 | g3342801 | BLASTN | 1030 | 1e-77 | 100 |
| 127 | 1485 | 700620501H1 | SATMON034 | g3342801 | BLASTN | 834 | 1e-60 | 96 |
| 128 | 1485 | 700423115H1 | SATMONN01 | g3342801 | BLASTN | 718 | 1e-51 | 99 |
| 129 | 1485 | 700159096H1 | SATMON012 | g3342801 | BLASTN | 416 | 1e-48 | 84 |
| 130 | 1485 | 700450859H1 | SATMON028 | g3342799 | BLASTN | 414 | 1e-25 | 88 |
| 131 | 1485 | 700472336H1 | SATMON025 | g3342799 | BLASTN | 371 | 1e-22 | 90 |
| 132 | 17367 | 700615074H1 | SATMON033 | g3342802 | BLASTX | 120 | 1e-22 | 68 |
| 133 | 17367 | 700223083H1 | SATMON011 | g2529229 | BLASTX | 117 | 1e-18 | 58 |
| 134 | 20418 | 700142466H1 | SATMON012 | g3342801 | BLASTN | 586 | 1e-40 | 99 |
| 135 | 20418 | 700156495H1 | SATMON012 | g3342801 | BLASTN | 436 | 1e-27 | 97 |
| 136 | 416 | 700211273H1 | SATMON016 | g3342799 | BLASTN | 1536 | 1e-119 | 98 |
| 137 | 416 | 700085942H1 | SATMON011 | g3342799 | BLASTN | 1508 | 1e-116 | 99 |
| 138 | 416 | 700074747H1 | SATMON007 | g3342801 | BLASTN | 1018 | 1e-110 | 97 |
| 139 | 416 | 700572331H1 | SATMON030 | g3342799 | BLASTN | 1205 | 1e-108 | 98 |
| 140 | 416 | 700075257H1 | SATMON007 | g3342799 | BLASTN | 801 | 1e-105 | 98 |
| 141 | 416 | 700581966H1 | SATMON031 | g3342799 | BLASTN | 1330 | 1e-102 | 98 |
| 142 | 416 | 700220231H1 | SATMON011 | g3342801 | BLASTN | 1336 | 1e-102 | 99 |
| 143 | 416 | 700220126H1 | SATMON011 | g3342801 | BLASTN | 1327 | 1e-101 | 99 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 144 | 416 | 700238542H1 | SATMON010 | g3342801 | BLASTN | 1299 | 1e-99 | 98 |
| 145 | 416 | 700166459H1 | SATMON013 | g3342799 | BLASTN | 1217 | 1e-92 | 99 |
| 146 | 416 | 700221262H1 | SATMON011 | g3342801 | BLASTN | 1107 | 1e-83 | 90 |
| 147 | 416 | 700165558H1 | SATMON013 | g3342799 | BLASTN | 1061 | 1e-79 | 94 |
| 148 | 416 | 700449887H2 | SATMON028 | g3342799 | BLASTN | 986 | 1e-77 | 97 |
| 149 | 416 | 700460574H1 | SATMON030 | g3342799 | BLASTN | 702 | 1e-71 | 84 |
| 150 | 416 | 700220154H1 | SATMON011 | g3342801 | BLASTN | 917 | 1e-67 | 98 |
| 151 | 416 | 700614034H1 | SATMON033 | g3342799 | BLASTN | 666 | 1e-46 | 98 |
| 152 | 4839 | 700072438H2 | SATMON007 | g3342799 | BLASTN | 973 | 1e-103 | 96 |
| 153 | 4839 | 700021163H1 | SATMON001 | g3342799 | BLASTN | 853 | 1e-92 | 96 |
| 154 | 4839 | 700030139H1 | SATMON003 | g3342799 | BLASTN | 851 | 1e-91 | 98 |
| 155 | 4839 | 700021353H1 | SATMON001 | g3342799 | BLASTN | 866 | 1e-83 | 99 |
| 156 | 4839 | 700581184H1 | SATMON031 | g3342799 | BLASTN | 899 | 1e-73 | 95 |
| 157 | 4839 | 700219274H1 | SATMON011 | g3342801 | BLASTN | 518 | 1e-54 | 87 |
| 158 | 4839 | 700153705H1 | SATMON007 | g3342801 | BLASTN | 695 | 1e-52 | 87 |
| 159 | 4839 | 700341982H1 | SATMON020 | g3342799 | BLASTN | 360 | 1e-46 | 99 |
| 160 | 4839 | 700341234H1 | SATMON020 | g3342801 | BLASTN | 569 | 1e-38 | 89 |
| 161 | 4839 | 700343990H1 | SATMON021 | g3342799 | BLASTN | 366 | 1e-21 | 91 |
| 162 | 4882 | 700206482H1 | SATMON003 | g3342799 | BLASTN | 1592 | 1e-123 | 98 |
| 163 | 4882 | 700091812H1 | SATMON011 | g3342799 | BLASTN | 1546 | 1e-120 | 97 |
| 164 | 4882 | 700446652H1 | SATMON027 | g3342801 | BLASTN | 1455 | 1e-112 | 98 |
| 165 | 4882 | 700104823H1 | SATMON010 | g3342801 | BLASTN | 896 | 1e-111 | 98 |
| 166 | 4882 | 700356053H1 | SATMON024 | g3342801 | BLASTN | 1368 | 1e-105 | 97 |
| 167 | 4882 | 700219471H1 | SATMON011 | g3342801 | BLASTN | 920 | 1e-104 | 100 |
| 168 | 4882 | 700077133H1 | SATMON007 | g3342801 | BLASTN | 770 | 1e-102 | 97 |
| 169 | 4882 | 700208920H1 | SATMON016 | g3342801 | BLASTN | 701 | 1e-101 | 98 |
| 170 | 4882 | 700342808H1 | SATMON021 | g3342801 | BLASTN | 1170 | 1e-101 | 97 |
| 171 | 4882 | 700151209H1 | SATMON007 | g3342801 | BLASTN | 1321 | 1e-101 | 97 |
| 172 | 4882 | 700333146H1 | SATMON019 | g3342801 | BLASTN | 1011 | 1e-99 | 99 |
| 173 | 4882 | 700239943H1 | SATMON010 | g3342801 | BLASTN | 1295 | 1e-99 | 98 |
| 174 | 4882 | 700354623H1 | SATMON024 | g3342799 | BLASTN | 846 | 1e-98 | 98 |
| 175 | 4882 | 700348987H1 | SATMON023 | g3342801 | BLASTN | 997 | 1e-97 | 99 |
| 176 | 4882 | 700354655H1 | SATMON024 | g3342799 | BLASTN | 854 | 1e-94 | 96 |
| 177 | 4882 | 700075354H1 | SATMON007 | g3342801 | BLASTN | 1035 | 1e-93 | 100 |
| 178 | 4882 | 700351460H1 | SATMON023 | g3342801 | BLASTN | 946 | 1e-92 | 98 |
| 179 | 4882 | 700574482H1 | SATMON030 | g3342801 | BLASTN | 954 | 1e-92 | 97 |
| 180 | 4882 | 700455406H1 | SATMON029 | g3342801 | BLASTN | 663 | 1e-86 | 95 |
| 181 | 4882 | 700261343H1 | SATMON017 | g3342801 | BLASTN | 882 | 1e-81 | 93 |
| 182 | 4882 | 700156333H1 | SATMON007 | g3342801 | BLASTN | 1055 | 1e-79 | 100 |
| 183 | 4882 | 700152511H1 | SATMON007 | g3342801 | BLASTN | 786 | 1e-77 | 99 |
| 184 | 4882 | 700152557H1 | SATMON007 | g3342801 | BLASTN | 939 | 1e-74 | 97 |
| 185 | 4882 | 701176801H1 | SATMONN05 | g3342801 | BLASTN | 985 | 1e-73 | 100 |
| 186 | 4882 | 700242384H1 | SATMON010 | g3342801 | BLASTN | 676 | 1e-64 | 94 |
| 187 | 4882 | 700258317H1 | SATMON017 | g3342801 | BLASTN | 373 | 1e-61 | 98 |
| 188 | 4882 | 700377763H1 | SATMON019 | g3342801 | BLASTN | 615 | 1e-61 | 97 |
| 189 | 4882 | 700473877H1 | SATMON025 | g3342801 | BLASTN | 605 | 1e-46 | 100 |
| 190 | 4882 | 700076402H1 | SATMON007 | g3342801 | BLASTN | 256 | 1e-28 | 98 |
| 191 | 4882 | 700152333H1 | SATMON007 | g3342801 | BLASTN | 450 | 1e-28 | 100 |
| 192 | 4882 | 700155664H1 | SATMON007 | g3342801 | BLASTN | 260 | 1e-23 | 100 |
| 193 | 4882 | 700473648H1 | SATMON025 | g3342799 | BLASTN | 272 | 1e-16 | 91 |
| 194 | 4882 | 700548356H1 | SATMON022 | g3342799 | BLASTN | 290 | 1e-15 | 95 |
| 195 | 5830 | 700088306H1 | SATMON011 | g3342799 | BLASTN | 1604 | 1e-124 | 97 |
| 196 | 5830 | 700096066H1 | SATMON008 | g3342799 | BLASTN | 1575 | 1e-122 | 98 |
| 197 | 5830 | 700571406H1 | SATMON030 | g3342799 | BLASTN | 921 | 1e-118 | 96 |
| 198 | 5830 | 700075112H1 | SATMON007 | g3342799 | BLASTN | 1504 | 1e-116 | 95 |
| 199 | 5830 | 700050136H1 | SATMON003 | g3342799 | BLASTN | 1201 | 1e-91 | 97 |
| 200 | 5830 | 700028323H1 | SATMON003 | g3342799 | BLASTN | 1075 | 1e-90 | 97 |
| 201 | 5830 | 700076449H1 | SATMON007 | g3342799 | BLASTN | 1176 | 1e-89 | 94 |
| 202 | 5830 | 700352064H1 | SATMON023 | g3342799 | BLASTN | 1111 | 1e-86 | 96 |
| 203 | 5830 | 700346689H1 | SATMON021 | g3342799 | BLASTN | 1010 | 1e-75 | 96 |
| 204 | 5830 | 700217673H1 | SATMON016 | g3342799 | BLASTN | 1010 | 1e-75 | 97 |
| 205 | 5830 | 700350270H1 | SATMON023 | g3342799 | BLASTN | 405 | 1e-72 | 96 |
| 206 | 5830 | 700466829H1 | SATMON025 | g3342799 | BLASTN | 609 | 1e-50 | 96 |
| 207 | 5830 | 700220161H1 | SATMON011 | g3342799 | BLASTN | 590 | 1e-40 | 94 |
| 208 | 5830 | 700220192H1 | SATMON011 | g3342799 | BLASTN | 551 | 1e-37 | 96 |
| 209 | 5830 | 700453728H1 | SATMON029 | g3342799 | BLASTN | 491 | 1e-32 | 90 |
| | | SOYBEAN PUTATIVE 6-PHOSPHOGLUCONATE DEHYDROGENASE | | | | | | |
| 210 | 17920 | 700889178H1 | SOYMON024 | g3342801 | BLASTN | 480 | 1e-30 | 71 |
| 211 | 17920 | 700976950H1 | SOYMON009 | g3342801 | BLASTN | 303 | 1e-16 | 67 |
| 212 | 489 | 700744939H1 | SOYMON013 | g3342804 | BLASTX | 250 | 1e-29 | 79 |
| 213 | 489 | 700748139H1 | SOYMON013 | g3342800 | BLASTX | 150 | 1e-27 | 65 |
| 214 | 5856 | 701070317H1 | SOYMON034 | g3342800 | BLASTX | 132 | 1e-21 | 73 |

TABLE A*-continued

| Seq No. | Cluster ID | CloneID | Library | NCBI gi | Method | Score | P-value | % Ident |
|---|---|---|---|---|---|---|---|---|
| | | PHOSPHOGLUCONATE PATHWAY ENZYMES | | | | | | |
| | | MAIZE D-RIBULOSE-5-PHOSPHATE-3-EPIMERASE | | | | | | |
| 215 | −700222465 | 700222465H1 | SATMON011 | g1162980 | BLASTX | 149 | 1e-27 | 84 |
| 216 | −700618106 | 700618106H1 | SATMON033 | g902739 | BLASTX | 80 | 1e-25 | 76 |
| 217 | 10201 | 700101610H1 | SATMON009 | g902738 | BLASTN | 1009 | 1e-75 | 80 |
| 218 | 10201 | 700098237H1 | SATMON009 | g902738 | BLASTN | 1000 | 1e-74 | 80 |
| 219 | 10201 | 700209605H1 | SATMON016 | g1162979 | BLASTN | 976 | 1e-72 | 78 |
| 220 | 10201 | 700101988H1 | SATMON009 | g902738 | BLASTN | 626 | 1e-69 | 80 |
| 221 | 10201 | 700091966H1 | SATMON011 | g902738 | BLASTN | 905 | 1e-66 | 80 |
| 222 | 10201 | 700101445H1 | SATMON009 | g1162979 | BLASTN | 844 | 1e-61 | 80 |
| 223 | 10201 | 700159349H1 | SATMON012 | g902738 | BLASTN | 681 | 1e-48 | 73 |
| 224 | 10201 | 700380926H1 | SATMON023 | g902738 | BLASTN | 463 | 1e-45 | 81 |
| 225 | 17215 | 700048475H1 | SATMON003 | g1008313 | BLASTX | 177 | 1e-17 | 61 |
| 226 | 17215 | 700105805H1 | SATMON010 | g1008313 | BLASTX | 123 | 1e-10 | 59 |
| 227 | 1795 | 700432796H1 | SATMONN01 | g902739 | BLASTX | 139 | 1e-12 | 93 |
| 228 | 6043 | 700104089H1 | SATMON010 | g1162979 | BLASTN | 583 | 1e-39 | 79 |
| 229 | 6043 | 700099362H1 | SATMON009 | g1162980 | BLASTX | 156 | 1e-29 | 71 |
| 230 | 6043 | 700042321H1 | SATMON004 | g1162979 | BLASTN | 271 | 1e-27 | 79 |
| 231 | 6043 | 700457795H1 | SATMON029 | g902739 | BLASTX | 132 | 1e-25 | 64 |
| 232 | 6043 | 700096215H1 | SATMON008 | g1162980 | BLASTX | 120 | 1e-19 | 65 |
| 233 | 6043 | 700378379H1 | SATMON019 | g1162980 | BLASTX | 119 | 1e-17 | 86 |
| 234 | 6043 | 700239692H1 | SATMON010 | g1162980 | BLASTX | 167 | 1e-16 | 63 |
| 235 | 6043 | 700093535H1 | SATMON008 | g1162980 | BLASTX | 120 | 1e-13 | 61 |
| 236 | 6043 | 700098183H1 | SATMON009 | g1162980 | BLASTX | 121 | 1e-13 | 60 |
| 237 | 6043 | 700093175H1 | SATMON008 | g902739 | BLASTX | 126 | 1e-12 | 59 |
| 238 | 6043 | 700098056H1 | SATMON009 | g1162980 | BLASTX | 120 | 1e-9 | 57 |
| 239 | 6043 | 700101650H1 | SATMON009 | g1162980 | BLASTX | 120 | 1e-9 | 57 |
| 240 | 6043 | 700053356H1 | SATMON009 | g1162980 | BLASTX | 121 | 1e-9 | 57 |
| 241 | 6043 | 700099441H1 | SATMON009 | g902739 | BLASTX | 122 | 1e-9 | 58 |
| 242 | 7043 | 700162921H1 | SATMON013 | g1008313 | BLASTX | 130 | 1e-17 | 60 |
| 243 | 7043 | 700552657H1 | SATMON022 | g902739 | BLASTX | 154 | 1e-16 | 51 |
| 244 | −L1891463 | LIB189-001-Q1-E1-F4 | LIB189 | g1162979 | BLASTN | 596 | 1e-39 | 78 |
| 245 | −L30781313 | LIB3078-002-Q1-K1-A2 | LIB3078 | g1162979 | BLASTN | 440 | 1e-25 | 79 |
| 246 | 10201 | LIB3078-034-Q1-K1-E8 | LIB3078 | g1162979 | BLASTN | 1271 | 1e-97 | 78 |
| 247 | 10201 | LIB189-018-Q1-E1-G1 | LIB189 | g902738 | BLASTN | 1263 | 1e-96 | 79 |
| 248 | 10201 | LIB3060-022-Q1-K1-G2 | LIB3060 | g902738 | BLASTN | 1228 | 1e-93 | 76 |
| 249 | 10201 | LIB3060-034-Q1-K1-D3 | LIB3060 | g902738 | BLASTN | 1205 | 1e-91 | 79 |
| 250 | 10201 | LIB36-007-Q1-E1-D10 | LIB36 | g1162979 | BLASTN | 989 | 1e-83 | 78 |
| 251 | 10201 | LIB3078-053-Q1-K1-F4 | LIB3078 | g1162979 | BLASTN | 850 | 1e-62 | 68 |
| 252 | 10201 | LIB189-034-Q1-E1-B12 | LIB189 | g902738 | BLASTN | 761 | 1e-53 | 74 |
| 253 | 1795 | LIB3067-056-Q1-K1-A4 | LIB3067 | g902738 | BLASTN | 645 | 1e-43 | 80 |
| 254 | 6043 | LIB189-017-Q1-E1-F12 | LIB189 | g1162979 | BLASTN | 842 | 1e-61 | 78 |
| 255 | 6043 | LIB36-012-Q1-E1-H11 | LIB36 | g1162979 | BLASTN | 742 | 1e-51 | 78 |
| 256 | 6043 | LIB3060-018-Q1-K1-B5 | LIB3060 | g1162979 | BLASTN | 653 | 1e-43 | 77 |
| 257 | 6043 | LIB3062-015-Q1-K1-A11 | LIB3062 | g1162979 | BLASTN | 637 | 1e-42 | 77 |
| 258 | 6043 | LIB189-031-Q1-E1-D1 | LIB189 | g1162979 | BLASTN | 532 | 1e-33 | 76 |
| 259 | 6043 | LIB3060-013-Q1-K1-A2 | LIB3060 | g1162979 | BLASTN | 466 | 1e-27 | 75 |
| 260 | 7043 | LIB148-032-Q1-E1-A4 | LIB148 | g2564973 | BLASTX | 238 | 1e-42 | 48 |
| | | SOYBEAN D-RIBULOSE-5-PHOSPHATE-3-EPIMERASE | | | | | | |
| 261 | −700677209 | 700677209H1 | SOYMON007 | g1162980 | BLASTX | 130 | 1e-30 | 85 |
| 262 | 10469 | 700971857H1 | SOYMON005 | g1008313 | BLASTX | 208 | 1e-27 | 55 |
| 263 | 10469 | 701064495H1 | SOYMON034 | g1008313 | BLASTX | 208 | 1e-27 | 56 |
| 264 | 10469 | 701007767H1 | SOYMON019 | g1008313 | BLASTX | 129 | 1e-25 | 54 |
| 265 | 10469 | 700656367H1 | SOYMON004 | g1008313 | BLASTX | 182 | 1e-22 | 57 |
| 266 | 15209 | 700791582H1 | SOYMON011 | g2388956 | BLASTX | 129 | 1e-10 | 66 |
| 267 | 15209 | 701001180H1 | SOYMON018 | g1008313 | BLASTX | 122 | 1e-9 | 65 |
| 268 | 18337 | 700739263H1 | SOYMON012 | g902738 | BLASTN | 481 | 1e-50 | 82 |

TABLE A*-continued

| Seq No. | Cluster ID | CloneID | Library | NCBI gi | Method | Score | P-value | % Ident |
|---|---|---|---|---|---|---|---|---|
| PHOSPHOGLUCONATE PATHWAY ENZYMES | | | | | | | | |
| 269 | 18337 | 700681545H1 | SOYMON008 | g1162979 | BLASTN | 342 | 1e-44 | 83 |
| 270 | 18818 | 700866167H1 | SOYMON016 | g1162979 | BLASTN | 853 | 1e-62 | 89 |
| 271 | 18818 | 700983968H1 | SOYMON009 | g1162979 | BLASTN | 422 | 1e-55 | 76 |
| 272 | 5784 | 700999796H1 | SOYMON018 | g1162979 | BLASTN | 535 | 1e-43 | 78 |
| 273 | 5784 | 700788240H1 | SOYMON011 | g902738 | BLASTN | 455 | 1e-36 | 77 |
| 274 | 5784 | 701000905H1 | SOYMON018 | g902738 | BLASTN | 501 | 1e-36 | 77 |
| 275 | 5784 | 701040171H1 | SOYMON029 | g902738 | BLASTN | 510 | 1e-33 | 78 |
| 276 | 5784 | 700754807H1 | SOYMON014 | g902738 | BLASTN | 447 | 1e-31 | 72 |
| 277 | 5784 | 700904930H1 | SOYMON022 | g902738 | BLASTN | 465 | 1e-29 | 77 |
| 278 | 5784 | 700739828H1 | SOYMON012 | g902738 | BLASTN | 455 | 1e-28 | 76 |
| 279 | 5784 | 700741008H1 | SOYMON012 | g1162980 | BLASTX | 142 | 1e-16 | 81 |
| 280 | 5784 | 700738184H1 | SOYMON012 | g1162980 | BLASTX | 167 | 1e-16 | 81 |
| 281 | 5784 | 700790753H1 | SOYMON011 | g1162980 | BLASTX | 149 | 1e-15 | 79 |
| 282 | 5784 | 701110183H1 | SOYMON036 | g1162980 | BLASTX | 161 | 1e-15 | 81 |
| 283 | 5784 | 700876264H1 | SOYMON018 | g1162980 | BLASTX | 140 | 1e-12 | 87 |
| 284 | 5784 | 700787492H2 | SOYMON011 | g1162980 | BLASTX | 141 | 1e-12 | 76 |
| 285 | 5784 | 700788242H1 | SOYMON011 | g1162980 | BLASTX | 80 | 1e-11 | 89 |
| 286 | 5784 | 700741612H1 | SOYMON012 | g1162980 | BLASTX | 103 | 1e-11 | 78 |
| 287 | 5784 | 700789926H2 | SOYMON011 | g1162980 | BLASTX | 119 | 1e-11 | 74 |
| 288 | 5784 | 701105542H1 | SOYMON036 | g1162980 | BLASTX | 117 | 1e-10 | 66 |
| 289 | 5784 | 700741161H1 | SOYMON012 | g1162980 | BLASTX | 101 | 1e-8 | 63 |
| 290 | 5784 | 700877044H1 | SOYMON018 | g902738 | BLASTN | 236 | 1e-8 | 73 |
| 291 | 9624 | 700659817H1 | SOYMON004 | g1162979 | BLASTN | 959 | 1e-71 | 85 |
| 292 | 9624 | 700558457H1 | SOYMON001 | g1162979 | BLASTN | 533 | 1e-64 | 81 |
| 293 | 9624 | 700898624H1 | SOYMON027 | g1162979 | BLASTN | 867 | 1e-63 | 83 |
| 294 | 9624 | 700848716H1 | SOYMON021 | g1162979 | BLASTN | 680 | 1e-61 | 83 |
| 295 | 9624 | 700990488H1 | SOYMON011 | g1162979 | BLASTN | 763 | 1e-54 | 83 |
| 296 | 9624 | 700980873H1 | SOYMON009 | g1162979 | BLASTN | 722 | 1e-51 | 77 |
| 297 | 9624 | 700654880H1 | SOYMON004 | g1162979 | BLASTN | 473 | 1e-36 | 71 |
| 298 | 10469 | LIB3040-057-Q1-E1-C5 | LIB3040 | g1008313 | BLASTX | 205 | 1e-60 | 54 |
| 299 | 9624 | LIB3030-001-Q1-B1-F10 | LIB3030 | g1162979 | BLASTN | 1185 | 1e-90 | 80 |
| MAIZE RIBOSE-5-PHOSPHATE ISOMERASE | | | | | | | | |
| 300 | 5053 | 700206243H1 | SATMON003 | g1669358 | BLASTX | 165 | 1e-20 | 59 |
| 301 | 5053 | 700157368H1 | SATMON012 | g1001678 | BLASTX | 188 | 1e-19 | 59 |
| 302 | −L30672312 | LIB3067-007-Q1-K1-C3 | LIB3067 | g1789280 | BLASTX | 114 | 1e-24 | 54 |
| 303 | −L841459 | LIB84-028-Q1-E1-A11 | LIB84 | g1789280 | BLASTX | 117 | 1e-25 | 53 |
| 304 | 5053 | LIB3078-033-Q1-K1-A2 | LIB3078 | g1001678 | BLASTX | 217 | 1e-42 | 50 |
| 305 | 5053 | LIB3060-054-Q1-K1-G1 | LIB3060 | g2649655 | BLASTX | 100 | 1e-34 | 48 |
| 306 | 5053 | LIB3078-054-Q1-K1-B9 | LIB3078 | g1669358 | BLASTX | 65 | 1e-24 | 40 |
| SOYBEAN RIBOSE-5-PHOSPHATE ISOMERASE | | | | | | | | |
| 307 | 17047 | 700737894H1 | SOYMON012 | g1001678 | BLASTX | 93 | 1e-14 | 62 |
| 308 | 17047 | 700790677H2 | SOYMON011 | g2649655 | BLASTX | 68 | 1e-9 | 47 |
| 309 | 17047 | 700891079H1 | SOYMON024 | g1001678 | BLASTX | 122 | 1e-9 | 56 |
| 310 | 8783 | 701120985H1 | SOYMON037 | g1789280 | BLASTX | 115 | 1e-9 | 51 |
| 311 | 8783 | 700745725H1 | SOYMON013 | g1789280 | BLASTX | 113 | 1e-8 | 51 |
| MAIZE PUTATIVE RIBOSE-5-PHOSPHATE ISOMERASE | | | | | | | | |
| 312 | −700622640 | 700622640H1 | SATMON034 | g3257798 | BLASTX | 128 | 1e-10 | 63 |
| 313 | 5053 | 700213140H1 | SATMON016 | g500774 | BLASTX | 195 | 1e-20 | 43 |
| SOYBEAN PUTATIVE RIBOSE-5-PHOSPHATE ISOMERASE | | | | | | | | |
| 314 | −700840778 | 700840778H1 | SOYMON020 | g500774 | BLASTX | 203 | 1e-21 | 51 |
| 315 | −700898355 | 700898355H1 | SOYMON027 | g3257798 | BLASTX | 108 | 1e-17 | 60 |
| 316 | 16333 | 700562390H1 | SOYMON002 | g500774 | BLASTX | 211 | 1e-22 | 44 |
| 317 | 16333 | 700961206H1 | SOYMON022 | g500774 | BLASTX | 145 | 1e-14 | 51 |
| 318 | 8873 | 701120413H1 | SOYMON037 | g3257798 | BLASTX | 134 | 1e-11 | 48 |
| MAIZE TRANSKETOLASE | | | | | | | | |
| 319 | −700097383 | 700097383H1 | SATMON009 | g664902 | BLASTN | 1029 | 1e-76 | 80 |
| 320 | −701159054 | 701159054H1 | SATMONN04 | g2529342 | BLASTX | 214 | 1e-27 | 79 |
| 321 | −701184582 | 701184582H1 | SATMONN06 | g1658321 | BLASTN | 745 | 1e-53 | 74 |
| 322 | 1244 | 700553205H1 | SATMON022 | g1658321 | BLASTN | 816 | 1e-59 | 75 |
| 323 | 1244 | 700473792H1 | SATMON025 | g1658321 | BLASTN | 826 | 1e-59 | 75 |
| 324 | 1244 | 700405168H1 | SATMON028 | g1658321 | BLASTN | 805 | 1e-58 | 75 |
| 325 | 1244 | 700089307H1 | SATMON011 | g1658321 | BLASTN | 743 | 1e-53 | 74 |
| 326 | 1244 | 700355533H1 | SATMON024 | g1658321 | BLASTN | 589 | 1e-51 | 76 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 327 | 1244 | 700085136H1 | SATMON011 | g1658321 | BLASTN | 690 | 1e-48 | 76 |
| 328 | 1244 | 700382850H1 | SATMON024 | g664900 | BLASTN | 537 | 1e-47 | 72 |
| 329 | 1244 | 700454437H1 | SATMON029 | g1658321 | BLASTN | 655 | 1e-45 | 75 |
| 330 | 1244 | 700150022H1 | SATMON007 | g1658321 | BLASTN | 606 | 1e-41 | 76 |
| 331 | 1244 | 700212701H1 | SATMON016 | g1658321 | BLASTN | 507 | 1e-40 | 74 |
| 332 | 1244 | 700438654H1 | SATMON026 | g2529342 | BLASTX | 160 | 1e-24 | 89 |
| 333 | 1244 | 700458530H1 | SATMON029 | g2529342 | BLASTX | 177 | 1e-20 | 87 |
| 334 | 2946 | 700262031H1 | SATMON017 | g1658321 | BLASTN | 467 | 1e-30 | 74 |
| 335 | 3403 | 700075930H1 | SATMON007 | g664900 | BLASTN | 968 | 1e-71 | 81 |
| 336 | 3403 | 700381012H1 | SATMON023 | g1658321 | BLASTN | 949 | 1e-70 | 80 |
| 337 | 3403 | 700243701H1 | SATMON010 | g1658321 | BLASTN | 874 | 1e-63 | 80 |
| 338 | 3403 | 700220485H1 | SATMON011 | g664900 | BLASTN | 666 | 1e-54 | 74 |
| 339 | 3403 | 700045165H1 | SATMON004 | g664900 | BLASTN | 734 | 1e-52 | 73 |
| 340 | 3403 | 701185190H1 | SATMONN06 | g664900 | BLASTN | 709 | 1e-50 | 77 |
| 341 | 3403 | 700552475H1 | SATMON022 | g664900 | BLASTN | 591 | 1e-49 | 81 |
| 342 | 3403 | 700044755H1 | SATMON004 | g664900 | BLASTN | 690 | 1e-48 | 72 |
| 343 | 3403 | 700051910H1 | SATMON003 | g664900 | BLASTN | 671 | 1e-47 | 77 |
| 344 | 3403 | 700027425H1 | SATMON003 | g664900 | BLASTN | 675 | 1e-47 | 71 |
| 345 | 3403 | 700048347H1 | SATMON003 | g664900 | BLASTN | 662 | 1e-46 | 71 |
| 346 | 3403 | 700380608H1 | SATMON021 | g1658321 | BLASTN | 623 | 1e-43 | 82 |
| 347 | 3403 | 700448484H1 | SATMON027 | g664900 | BLASTN | 522 | 1e-33 | 71 |
| 348 | 3403 | 700184906H1 | SATMON014 | g2529342 | BLASTX | 251 | 1e-27 | 77 |
| 349 | 3403 | 700048819H1 | SATMON003 | g664900 | BLASTN | 453 | 1e-27 | 74 |
| 350 | 3403 | 701167994H1 | SATMONN05 | g2529342 | BLASTX | 193 | 1e-19 | 76 |
| 351 | 8097 | 700084375H1 | SATMON011 | g664900 | BLASTN | 855 | 1e-76 | 79 |
| 352 | 8097 | 700445226H1 | SATMON027 | g664900 | BLASTN | 464 | 1e-60 | 79 |
| 353 | 8097 | 700240770H1 | SATMON010 | g664900 | BLASTN | 750 | 1e-60 | 80 |
| 354 | 8097 | 700045122H1 | SATMON004 | g664900 | BLASTN | 638 | 1e-54 | 80 |
| 355 | 3403 | LIB3060-013-Q1-K1-A12 | LIB3060 | g664900 | BLASTN | 1052 | 1e-78 | 72 |
| 356 | 3403 | LIB3078-007-Q1-K1-G3 | LIB3078 | g664900 | BLASTN | 629 | 1e-41 | 69 |

SOYBEAN TRANSKETOLASE

| Seq No. | Cluster ID | CloneID | Library | NCBI gi | Method | Score | P-value | % Ident |
|---|---|---|---|---|---|---|---|---|
| 357 | −700646481 | 700646481H1 | SOYMON013 | g1658321 | BLASTN | 967 | 1e-71 | 83 |
| 358 | −700734535 | 700734535H1 | SOYMON010 | g1658321 | BLASTN | 822 | 1e-59 | 82 |
| 359 | −700865886 | 700865886H1 | SOYMON016 | g1658321 | BLASTN | 568 | 1e-38 | 82 |
| 360 | −700943688 | 700943688H1 | SOYMON024 | g1658321 | BLASTN | 902 | 1e-66 | 82 |
| 361 | −700954594 | 700954594H1 | SOYMON022 | g2529342 | BLASTX | 172 | 1e-16 | 75 |
| 362 | −701064360 | 701064360H1 | SOYMON034 | g664901 | BLASTX | 179 | 1e-17 | 80 |
| 363 | 1039 | 700662776H1 | SOYMON005 | g1658321 | BLASTN | 755 | 1e-78 | 83 |
| 364 | 1039 | 700663764H1 | SOYMON005 | g1658321 | BLASTN | 839 | 1e-61 | 82 |
| 365 | 1039 | 700952282H1 | SOYMON022 | g1658321 | BLASTN | 785 | 1e-56 | 81 |
| 366 | 1039 | 700835426H1 | SOYMON019 | g1658321 | BLASTN | 748 | 1e-53 | 81 |
| 367 | 1039 | 700738038H1 | SOYMON012 | g1658321 | BLASTN | 559 | 1e-37 | 80 |
| 368 | 1040 | 700606230H1 | SOYMON008 | g1658321 | BLASTN | 532 | 1e-69 | 82 |
| 369 | 1040 | 700681196H2 | SOYMON008 | g1658321 | BLASTN | 866 | 1e-63 | 80 |
| 370 | 1040 | 700876408H1 | SOYMON018 | g1658321 | BLASTN | 475 | 1e-60 | 82 |
| 371 | 1040 | 700901259H1 | SOYMON027 | g1658321 | BLASTN | 821 | 1e-59 | 81 |
| 372 | 1040 | 700996991H1 | SOYMON018 | g1658321 | BLASTN | 450 | 1e-58 | 80 |
| 373 | 1040 | 700876984H1 | SOYMON018 | g1658321 | BLASTN | 807 | 1e-58 | 81 |
| 374 | 1040 | 700871885H1 | SOYMON018 | g1658321 | BLASTN | 812 | 1e-58 | 81 |
| 375 | 1040 | 700740158H1 | SOYMON012 | g1658321 | BLASTN | 767 | 1e-55 | 78 |
| 376 | 1040 | 700787592H1 | SOYMON011 | g1658321 | BLASTN | 770 | 1e-55 | 80 |
| 377 | 1040 | 700789355H2 | SOYMON011 | g1658321 | BLASTN | 727 | 1e-51 | 81 |
| 378 | 1040 | 700786173H2 | SOYMON011 | g1658321 | BLASTN | 523 | 1e-47 | 79 |
| 379 | 1040 | 700987027H1 | SOYMON009 | g1658321 | BLASTN | 680 | 1e-47 | 78 |
| 380 | 1040 | 700683335H1 | SOYMON008 | g1658321 | BLASTN | 567 | 1e-38 | 80 |
| 381 | 1040 | 700742402H1 | SOYMON012 | g1658321 | BLASTN | 521 | 1e-34 | 78 |
| 382 | 1040 | 700682934H1 | SOYMON008 | g1658322 | BLASTX | 111 | 1e-22 | 79 |
| 383 | 1040 | 701001535H1 | SOYMON018 | g664900 | BLASTN | 337 | 1e-18 | 85 |
| 384 | 1381 | 701002017H1 | SOYMON018 | g1658321 | BLASTN | 860 | 1e-62 | 81 |
| 385 | 1381 | 700680946H1 | SOYMON008 | g1658321 | BLASTN | 848 | 1e-61 | 75 |
| 386 | 1381 | 700785920H2 | SOYMON011 | g1658321 | BLASTN | 715 | 1e-60 | 80 |
| 387 | 1381 | 700741325H1 | SOYMON012 | g1658321 | BLASTN | 836 | 1e-60 | 81 |
| 388 | 1381 | 700737257H1 | SOYMON010 | g1658321 | BLASTN | 783 | 1e-56 | 83 |
| 389 | 1381 | 700743637H1 | SOYMON012 | g1658321 | BLASTN | 456 | 1e-47 | 79 |
| 390 | 1381 | 700683536H1 | SOYMON008 | g1658321 | BLASTN | 682 | 1e-47 | 82 |
| 391 | 1381 | 700899577H1 | SOYMON027 | g1658321 | BLASTN | 632 | 1e-43 | 73 |
| 392 | 1381 | 700655539H1 | SOYMON004 | g1658321 | BLASTN | 399 | 1e-32 | 77 |
| 393 | 1381 | 700743117H1 | SOYMON012 | g664901 | BLASTX | 144 | 1e-12 | 88 |
| 394 | 1381 | 701047167H1 | SOYMON032 | g1658321 | BLASTN | 147 | 1e-10 | 88 |
| 395 | 1694 | 700557862H1 | SOYMON001 | g1658321 | BLASTN | 918 | 1e-67 | 81 |
| 396 | 1694 | 701124388H1 | SOYMON037 | g1658321 | BLASTN | 884 | 1e-64 | 84 |
| 397 | 1694 | 700977906H1 | SOYMON009 | g1658321 | BLASTN | 741 | 1e-60 | 81 |

TABLE A*-continued

| Seq No. | Cluster ID | CloneID | Library | NCBI gi | Method | Score | P-value | % Ident |
|---|---|---|---|---|---|---|---|---|
| | | PHOSPHOGLUCONATE PATHWAY ENZYMES | | | | | | |
| 398 | 1694 | 700741633H1 | SOYMON012 | g1658321 | BLASTN | 753 | 1e-60 | 83 |
| 399 | 20534 | 701214424H1 | SOYMON035 | g1658321 | BLASTN | 855 | 1e-62 | 80 |
| 400 | 20534 | 701214345H1 | SOYMON035 | g1658321 | BLASTN | 845 | 1e-61 | 81 |
| 401 | 20534 | 700737144H1 | SOYMON010 | g1658321 | BLASTN | 743 | 1e-53 | 79 |
| 402 | 20534 | 700737045H1 | SOYMON010 | g1658321 | BLASTN | 716 | 1e-50 | 80 |
| 403 | 2081 | 700684191H1 | SOYMON008 | g1658321 | BLASTN | 243 | 1e-11 | 68 |
| 404 | 2081 | 700871634H1 | SOYMON018 | g1658321 | BLASTN | 243 | 1e-9 | 65 |
| 405 | 2081 | 700896859H1 | SOYMON027 | g1658321 | BLASTN | 243 | 1e-9 | 65 |
| 406 | 2081 | 700741968H1 | SOYMON012 | g1658321 | BLASTN | 243 | 1e-9 | 65 |
| 407 | 2081 | 700743285H1 | SOYMON012 | g1658321 | BLASTN | 234 | 1e-8 | 65 |
| 408 | 2081 | 701105794H1 | SOYMON036 | g1658321 | BLASTN | 236 | 1e-8 | 65 |
| 409 | 2081 | 700646243H1 | SOYMON012 | g1658321 | BLASTN | 236 | 1e-8 | 65 |
| 410 | 2081 | 701104160H1 | SOYMON036 | g1658321 | BLASTN | 236 | 1e-8 | 65 |
| 411 | 2081 | 700741863H1 | SOYMON012 | g1658321 | BLASTN | 238 | 1e-8 | 65 |
| 412 | 2091 | 700651076H1 | SOYMON003 | g1658321 | BLASTN | 1055 | 1e-79 | 79 |
| 413 | 2091 | 700874803H1 | SOYMON018 | g1658321 | BLASTN | 888 | 1e-65 | 82 |
| 414 | 2091 | 700988611H1 | SOYMON009 | g1658321 | BLASTN | 419 | 1e-61 | 79 |
| 415 | 2091 | 700657810H1 | SOYMON004 | g1658321 | BLASTN | 805 | 1e-58 | 81 |
| 416 | 2091 | 700739094H1 | SOYMON012 | g1658321 | BLASTN | 425 | 1e-54 | 82 |
| 417 | 2091 | 700962626H1 | SOYMON022 | g1658321 | BLASTN | 742 | 1e-52 | 78 |
| 418 | 2091 | 700990046H1 | SOYMON011 | g1658321 | BLASTN | 376 | 1e-34 | 79 |
| 419 | 3782 | 700870543H1 | SOYMON018 | g1658322 | BLASTX | 157 | 1e-25 | 68 |
| 420 | 4096 | 700556949H1 | SOYMON001 | g664901 | BLASTX | 188 | 1e-18 | 92 |
| 421 | 4096 | 700877014H1 | SOYMON018 | g664901 | BLASTX | 188 | 1e-18 | 92 |
| 422 | 4096 | 700877022H1 | SOYMON018 | g664901 | BLASTX | 188 | 1e-18 | 92 |
| 423 | 4096 | 700999039H1 | SOYMON018 | g664901 | BLASTX | 169 | 1e-16 | 91 |
| 424 | 7870 | 700998419H1 | SOYMON018 | g1658321 | BLASTN | 430 | 1e-51 | 80 |
| 425 | 7870 | 700557019H1 | SOYMON001 | g1658321 | BLASTN | 685 | 1e-48 | 80 |
| 426 | 7870 | 700786020H2 | SOYMON011 | g1658321 | BLASTN | 531 | 1e-41 | 78 |
| 427 | 7870 | 700740475H1 | SOYMON012 | g1658321 | BLASTN | 609 | 1e-41 | 74 |
| 428 | 7870 | 700875020H1 | SOYMON018 | g1658321 | BLASTN | 525 | 1e-34 | 79 |
| 429 | 7870 | 700674249H1 | SOYMON007 | g1658321 | BLASTN | 510 | 1e-33 | 82 |
| 430 | 7870 | 700658256H1 | SOYMON004 | g2529342 | BLASTX | 178 | 1e-22 | 61 |
| 431 | 7870 | 700677401H1 | SOYMON007 | g664901 | BLASTX | 158 | 1e-14 | 91 |
| 432 | 9031 | 700874020H1 | SOYMON018 | g1658321 | BLASTN | 789 | 1e-56 | 79 |
| 433 | 9031 | 700726463H1 | SOYMON009 | g1658321 | BLASTN | 758 | 1e-54 | 76 |
| 434 | 9031 | 700869017H1 | SOYMON016 | g664900 | BLASTN | 743 | 1e-53 | 77 |
| 435 | 9031 | 700566216H1 | SOYMON002 | g664901 | BLASTX | 201 | 1e-20 | 92 |
| 436 | 1039 | LIB3051-053-Q1-K2-F1 | LIB3051 | g1658321 | BLASTN | 1326 | 1e-101 | 80 |
| 437 | 9031 | LIB3039-045-Q1-E1-D1 | LIB3039 | g1658321 | BLASTN | 1033 | 1e-77 | 79 |
| | | MAIZE PUTATIVE TRANSKETOLASE | | | | | | |
| 438 | −700045462 | 700045462H1 | SATMON004 | g2612940 | BLASTN | 1219 | 1e-92 | 89 |
| 439 | −700223919 | 700223919H1 | SATMON011 | g2612940 | BLASTN | 1025 | 1e-76 | 87 |
| 440 | −700256830 | 700256830H1 | SATMON017 | g2612940 | BLASTN | 1029 | 1e-76 | 87 |
| 441 | −701169515 | 701169515H1 | SATMONN05 | g2612940 | BLASTN | 327 | 1e-40 | 92 |
| 442 | 23377 | 700263420H1 | SATMON017 | g2612940 | BLASTN | 489 | 1e-31 | 75 |
| 443 | 23377 | 701185311H1 | SATMONN06 | g2612940 | BLASTN | 460 | 1e-27 | 78 |
| 444 | 7446 | 700624329H1 | SATMON034 | g2612940 | BLASTN | 1046 | 1e-87 | 88 |
| 445 | 7446 | 700159091H1 | SATMON012 | g2612940 | BLASTN | 898 | 1e-77 | 89 |
| 446 | −L30626416 | LIB3062-048-Q1-K1-D12 | LIB3062 | g2612940 | BLASTN | 808 | 1e-74 | 86 |
| 447 | −L30684293 | LIB3068-046-Q1-K1-B2 | LIB3068 | g2612940 | BLASTN | 846 | 1e-90 | 87 |
| | | SOYBEAN PUTATIVE TRANSKETOLASE | | | | | | |
| 448 | 19183 | 700907766H1 | SOYMON022 | g2612940 | BLASTN | 395 | 1e-30 | 68 |
| 449 | −700764341 | 700764341H1 | SOYMON021 | g2612941 | BLASTX | 247 | 1e-39 | 75 |
| 450 | −700888745 | 700888745H1 | SOYMON024 | g2612941 | BLASTX | 237 | 1e-27 | 76 |
| 451 | −700909473 | 700909473H1 | SOYMON022 | g2612941 | BLASTX | 114 | 1e-16 | 53 |
| 452 | 7224 | 700681472H2 | SOYMON008 | g2612941 | BLASTX | 107 | 1e-12 | 72 |
| 453 | 19325 | 700751059H1 | SOYMON014 | g2244912 | BLASTX | 160 | 1e-15 | 78 |
| | | MAIZE TRANSALDOLASE | | | | | | |
| 454 | −700074081 | 700074081H1 | SATMON007 | g2078350 | BLASTX | 199 | 1e-26 | 79 |
| 455 | −700087740 | 700087740H1 | SATMON011 | g2078349 | BLASTN | 651 | 1e-45 | 68 |
| 456 | 10709 | 700049020H1 | SATMON003 | g2078350 | BLASTX | 131 | 1e-10 | 67 |
| 457 | 143 | 700207653H1 | SATMON016 | g2078349 | BLASTN | 911 | 1e-67 | 76 |
| 458 | 143 | 700099852H1 | SATMON009 | g2078349 | BLASTN | 889 | 1e-65 | 75 |
| 459 | 143 | 700268119H1 | SATMON017 | g2078349 | BLASTN | 872 | 1e-63 | 76 |
| 460 | 143 | 700211193H1 | SATMON016 | g2078349 | BLASTN | 848 | 1e-61 | 76 |
| 461 | 143 | 700454251H1 | SATMON029 | g2078349 | BLASTN | 829 | 1e-60 | 78 |
| 462 | 143 | 700204216H1 | SATMON003 | g2078349 | BLASTN | 801 | 1e-57 | 76 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 463 | 143 | 700333262H1 | SATMON019 | g2078349 | BLASTN | 691 | 1e-56 | 74 |
| 464 | 143 | 700618845H1 | SATMON034 | g2078349 | BLASTN | 781 | 1e-56 | 76 |
| 465 | 143 | 700239238H1 | SATMON010 | g2078349 | BLASTN | 776 | 1e-55 | 76 |
| 466 | 143 | 700205539H1 | SATMON003 | g2078349 | BLASTN | 754 | 1e-54 | 73 |
| 467 | 143 | 700344192H1 | SATMON021 | g2078349 | BLASTN | 756 | 1e-54 | 75 |
| 468 | 143 | 700239126H1 | SATMON010 | g2078349 | BLASTN | 733 | 1e-52 | 73 |
| 469 | 143 | 700207418H1 | SATMON016 | g2078349 | BLASTN | 736 | 1e-52 | 70 |
| 470 | 143 | 700575204H1 | SATMON030 | g2078349 | BLASTN | 741 | 1e-52 | 71 |
| 471 | 143 | 700442682H1 | SATMON026 | g2078349 | BLASTN | 725 | 1e-51 | 74 |
| 472 | 143 | 700343686H1 | SATMON021 | g2078349 | BLASTN | 556 | 1e-49 | 74 |
| 473 | 143 | 700241386H1 | SATMON010 | g2078349 | BLASTN | 694 | 1e-49 | 75 |
| 474 | 143 | 700209193H1 | SATMON016 | g2078349 | BLASTN | 704 | 1e-49 | 72 |
| 475 | 143 | 700549360H1 | SATMON022 | g2078349 | BLASTN | 689 | 1e-48 | 77 |
| 476 | 143 | 700213668H1 | SATMON016 | g2078349 | BLASTN | 690 | 1e-48 | 72 |
| 477 | 143 | 700099381H1 | SATMON009 | g2078349 | BLASTN | 691 | 1e-48 | 73 |
| 478 | 143 | 700241472H1 | SATMON010 | g2078349 | BLASTN | 507 | 1e-47 | 76 |
| 479 | 143 | 700158253H1 | SATMON012 | g2078349 | BLASTN | 670 | 1e-47 | 76 |
| 480 | 143 | 700243043H1 | SATMON010 | g2078349 | BLASTN | 680 | 1e-47 | 73 |
| 481 | 143 | 700077153H1 | SATMON007 | g2078350 | BLASTX | 238 | 1e-46 | 74 |
| 482 | 143 | 700094547H1 | SATMON008 | g2078349 | BLASTN | 659 | 1e-46 | 73 |
| 483 | 143 | 700237891H1 | SATMON010 | g2078349 | BLASTN | 638 | 1e-44 | 71 |
| 484 | 143 | 700142446H1 | SATMON012 | g2078349 | BLASTN | 625 | 1e-43 | 75 |
| 485 | 143 | 700440545H1 | SATMON026 | g2078349 | BLASTN | 626 | 1e-43 | 71 |
| 486 | 143 | 700622336H1 | SATMON034 | g2078349 | BLASTN | 633 | 1e-43 | 72 |
| 487 | 143 | 700082380H1 | SATMON011 | g2078349 | BLASTN | 610 | 1e-42 | 70 |
| 488 | 143 | 700171422H1 | SATMON013 | g2078349 | BLASTN | 602 | 1e-41 | 77 |
| 489 | 143 | 700449973H1 | SATMON028 | g2078349 | BLASTN | 609 | 1e-41 | 70 |
| 490 | 143 | 701182293H1 | SATMONN06 | g2078349 | BLASTN | 480 | 1e-40 | 72 |
| 491 | 143 | 700154086H1 | SATMON007 | g2078349 | BLASTN | 592 | 1e-40 | 71 |
| 492 | 143 | 700018427H1 | SATMON001 | g2078349 | BLASTN | 593 | 1e-40 | 78 |
| 493 | 143 | 700615631H1 | SATMON033 | g2078349 | BLASTN | 608 | 1e-40 | 71 |
| 494 | 143 | 700550235H1 | SATMON022 | g2078350 | BLASTX | 237 | 1e-38 | 78 |
| 495 | 143 | 700203959H1 | SATMON003 | g2078349 | BLASTN | 571 | 1e-38 | 73 |
| 496 | 143 | 700152039H1 | SATMON007 | g2078349 | BLASTN | 532 | 1e-35 | 72 |
| 497 | 143 | 700207472H1 | SATMON016 | g2078350 | BLASTX | 168 | 1e-34 | 67 |
| 498 | 143 | 700580755H1 | SATMON031 | g2078350 | BLASTX | 202 | 1e-33 | 73 |
| 499 | 143 | 700477590H1 | SATMON025 | g2078349 | BLASTN | 365 | 1e-32 | 74 |
| 500 | 143 | 700083979H1 | SATMON011 | g2078349 | BLASTN | 517 | 1e-32 | 70 |
| 501 | 143 | 700569751H1 | SATMON030 | g2078350 | BLASTX | 161 | 1e-30 | 63 |
| 502 | 143 | 700239239H1 | SATMON010 | g2078350 | BLASTX | 182 | 1e-30 | 69 |
| 503 | 143 | 700469525H1 | SATMON025 | g2078350 | BLASTX | 270 | 1e-30 | 64 |
| 504 | 143 | 700242890H1 | SATMON010 | g2078349 | BLASTN | 451 | 1e-28 | 71 |
| 505 | 143 | 700168126H1 | SATMON013 | g2078349 | BLASTN | 448 | 1e-27 | 71 |
| 506 | 143 | 700338361H1 | SATMON020 | g2078349 | BLASTN | 441 | 1e-26 | 72 |
| 507 | 143 | 700337834H1 | SATMON020 | g2078349 | BLASTN | 444 | 1e-26 | 73 |
| 508 | 143 | 700339742H1 | SATMON020 | g2078349 | BLASTN | 434 | 1e-25 | 71 |
| 509 | 143 | 700205161H1 | SATMON003 | g2078350 | BLASTX | 171 | 1e-22 | 69 |
| 510 | 143 | 700171567H1 | SATMON013 | g2078350 | BLASTX | 212 | 1e-21 | 86 |
| 511 | 143 | 700202495H1 | SATMON003 | g2078350 | BLASTX | 195 | 1e-19 | 80 |
| 512 | 143 | 700266495H1 | SATMON017 | g2078350 | BLASTX | 175 | 1e-16 | 73 |
| 513 | 143 | 701173375H2 | SATMONN05 | g2078350 | BLASTX | 112 | 1e-13 | 78 |
| 514 | 143 | 700404964H1 | SATMON027 | g2078350 | BLASTX | 133 | 1e-11 | 77 |
| 515 | 143 | 700430542H1 | SATMONN01 | g2078350 | BLASTX | 137 | 1e-11 | 77 |
| 516 | 143 | 701181429H1 | SATMONN06 | g2078349 | BLASTN | 238 | 1e-8 | 74 |
| 517 | 14658 | 700622708H1 | SATMON034 | g4602 | BLASTX | 144 | 1e-20 | 40 |
| 518 | 14658 | 700196413H1 | SATMON014 | g1574680 | BLASTX | 118 | 1e-9 | 43 |
| 519 | 15681 | 700261694H1 | SATMON017 | g4602 | BLASTX | 80 | 1e-10 | 35 |
| 520 | 143 | LIB3062-030-Q1-K1-A8 | LIB3062 | g2078349 | BLASTN | 878 | 1e-80 | 74 |
| 521 | 143 | LIB3060-017-Q1-K1-G11 | LIB3060 | g2078349 | BLASTN | 1041 | 1e-77 | 73 |
| 522 | 143 | LIB3060-002-Q1-K2-A11 | LIB3060 | g2078349 | BLASTN | 1009 | 1e-75 | 73 |
| 523 | 143 | LIB3069-030-Q1-K1-A11 | LIB3069 | g2078349 | BLASTN | 877 | 1e-68 | 71 |
| 524 | 143 | LIB3060-032-Q1-K1-C7 | LIB3060 | g2078349 | BLASTN | 660 | 1e-66 | 72 |
| 525 | 143 | LIB3059-017-Q1-K1-B4 | LIB3059 | g2078349 | BLASTN | 885 | 1e-64 | 73 |
| 526 | 143 | LIB3066-053-Q1-K1-G10 | LIB3066 | g2078349 | BLASTN | 833 | 1e-60 | 69 |
| 527 | 143 | LIB3060-017-Q1-K1-G12 | LIB3060 | g2078349 | BLASTN | 756 | 1e-53 | 73 |
| 528 | 143 | LIB143-027-Q1-E1-B11 | LIB143 | g2078350 | BLASTX | 246 | 1e-42 | 75 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 529 | 143 | LIB3059-016-Q1-K1-H12 | LIB3059 | g2078350 | BLASTX | 138 | 1e-36 | 59 |
| 530 | 15681 | LIB3062-027-Q1-K1-H4 | LIB3062 | g1786189 | BLASTX | 112 | 1e-32 | 42 |
| 531 | 19642 | LIB143-006-Q1-E1-H7 | LIB143 | g1574680 | BLASTX | 91 | 1e-26 | 41 |
| 532 | 29728 | LIB3079-007-Q1-K1-G3 | LIB3079 | g2078350 | BLASTX | 238 | 1e-41 | 68 |
| 533 | 29728 | LIB3069-033-Q1-K1-E2 | LIB3069 | g2078350 | BLASTX | 96 | 1e-25 | 65 |
| | | SOYBEAN TRANSALDOLASE | | | | | | |
| 534 | −700557848 | 700557848H1 | SOYMON001 | g1786189 | BLASTX | 138 | 1e-12 | 62 |
| 535 | −700898220 | 700898220H1 | SOYMON027 | g2078350 | BLASTX | 96 | 1e-13 | 79 |
| 536 | −701053141 | 701053141H1 | SOYMON032 | g2078350 | BLASTX | 190 | 1e-24 | 63 |
| 537 | 12032 | 701209342H1 | SOYMON035 | g2078349 | BLASTN | 882 | 1e-64 | 79 |
| 538 | 12032 | 700566011H1 | SOYMON002 | g2078349 | BLASTN | 521 | 1e-43 | 79 |
| 539 | 12032 | 700957709H1 | SOYMON022 | g2078349 | BLASTN | 607 | 1e-41 | 72 |
| 540 | 16286 | 701014315H1 | SOYMON019 | g2078349 | BLASTN | 632 | 1e-43 | 75 |
| 541 | 16286 | 700733731H1 | SOYMON010 | g2078350 | BLASTX | 171 | 1e-27 | 64 |
| 542 | 16286 | 700978907H1 | SOYMON009 | g2078349 | BLASTN | 452 | 1e-27 | 75 |
| 543 | 16286 | 700675063H1 | SOYMON007 | g2078350 | BLASTX | 159 | 1e-23 | 66 |
| 544 | 18022 | 700963175H1 | SOYMON022 | g2078349 | BLASTN | 771 | 1e-55 | 80 |
| 545 | 18022 | 700892251H1 | SOYMON024 | g2078349 | BLASTN | 519 | 1e-34 | 81 |
| 546 | 18700 | 700741418H1 | SOYMON012 | g2078349 | BLASTN | 440 | 1e-26 | 75 |
| 547 | 18700 | 701210709H1 | SOYMON035 | g2078350 | BLASTX | 227 | 1e-24 | 90 |
| 548 | 18700 | 700867261H1 | SOYMON016 | g2078350 | BLASTX | 158 | 1e-14 | 85 |
| 549 | 18700 | 700867361H1 | SOYMON016 | g2078349 | BLASTN | 179 | 1e-11 | 79 |
| 550 | 3993 | 700893136H1 | SOYMON024 | g2078349 | BLASTN | 725 | 1e-51 | 78 |
| 551 | 3993 | 700747125H1 | SOYMON013 | g2078349 | BLASTN | 613 | 1e-49 | 79 |
| 552 | 3993 | 701044349H1 | SOYMON032 | g2078349 | BLASTN | 630 | 1e-43 | 74 |
| 553 | 3993 | 700832771H1 | SOYMON019 | g2078349 | BLASTN | 608 | 1e-41 | 74 |
| 554 | 3993 | 700975359H1 | SOYMON009 | g2078349 | BLASTN | 449 | 1e-28 | 71 |
| 555 | 3993 | 700970463H1 | SOYMON005 | g2078350 | BLASTX | 83 | 1e-22 | 74 |
| 556 | 3993 | 701012833H1 | SOYMON019 | g2078350 | BLASTX | 207 | 1e-21 | 52 |
| 557 | 3993 | 700794982H1 | SOYMON017 | g2078349 | BLASTN | 335 | 1e-19 | 75 |
| 558 | 3993 | 701012461H1 | SOYMON019 | g2078350 | BLASTX | 189 | 1e-18 | 50 |
| 559 | 3993 | 700982758H1 | SOYMON009 | g2078349 | BLASTN | 337 | 1e-17 | 75 |
| 560 | 3993 | 701102424H1 | SOYMON028 | g2078350 | BLASTX | 161 | 1e-15 | 70 |
| 561 | 3993 | 700746415H1 | SOYMON013 | g2078349 | BLASTN | 320 | 1e-15 | 74 |
| 562 | 3993 | 700897055H1 | SOYMON027 | g2078349 | BLASTN | 289 | 1e-13 | 73 |
| 563 | 3993 | 700967006H1 | SOYMON029 | g2078349 | BLASTN | 289 | 1e-13 | 73 |
| 564 | 3993 | 701100750H1 | SOYMON028 | g2078349 | BLASTN | 182 | 1e-12 | 78 |
| 565 | 3993 | 701055410H1 | SOYMON032 | g2078350 | BLASTX | 120 | 1e-11 | 60 |
| 566 | 3993 | 701040696H1 | SOYMON029 | g2078349 | BLASTN | 263 | 1e-11 | 72 |
| 567 | 3993 | 701211427H1 | SOYMON035 | g2078350 | BLASTX | 73 | 1e-10 | 50 |
| 568 | 3993 | 700963010H1 | SOYMON022 | g2078350 | BLASTX | 73 | 1e-10 | 50 |
| 569 | 3993 | 701099581H1 | SOYMON028 | g2078350 | BLASTX | 97 | 1e-10 | 50 |
| 570 | 3993 | 700888568H1 | SOYMON024 | g2078350 | BLASTX | 112 | 1e-10 | 47 |
| 571 | 3993 | 701011889H1 | SOYMON019 | g2078350 | BLASTX | 124 | 1e-10 | 48 |
| 572 | 3993 | 700726386H1 | SOYMON009 | g2078350 | BLASTX | 90 | 1e-9 | 48 |
| 573 | 3993 | 700943367H1 | SOYMON024 | g2078349 | BLASTN | 242 | 1e-9 | 72 |
| 574 | 3993 | 700650311H1 | SOYMON003 | g2078349 | BLASTN | 242 | 1e-9 | 72 |
| 575 | 3993 | 701008074H1 | SOYMON019 | g2078350 | BLASTX | 83 | 1e-8 | 48 |
| 576 | 3993 | 700955316H1 | SOYMON022 | g2078349 | BLASTN | 155 | 1e-8 | 72 |
| 577 | 3993 | 701043442H1 | SOYMON029 | g2078349 | BLASTN | 234 | 1e-8 | 73 |
| 578 | 3993 | 700905939H1 | SOYMON022 | g2078349 | BLASTN | 234 | 1e-8 | 73 |
| 579 | 3993 | 700728911H1 | SOYMON009 | g2078349 | BLASTN | 234 | 1e-8 | 73 |
| 580 | 4079 | 700565922H1 | SOYMON002 | g2078349 | BLASTN | 574 | 1e-72 | 83 |
| 581 | 4079 | 700991339H1 | SOYMON011 | g2078349 | BLASTN | 918 | 1e-67 | 81 |
| 582 | 4079 | 700746817H1 | SOYMON013 | g2078349 | BLASTN | 902 | 1e-66 | 81 |
| 583 | 4079 | 701007939H1 | SOYMON019 | g2078349 | BLASTN | 877 | 1e-64 | 80 |
| 584 | 4079 | 701015475H1 | SOYMON019 | g2078349 | BLASTN | 843 | 1e-61 | 82 |
| 585 | 4079 | 701097904H1 | SOYMON028 | g2078349 | BLASTN | 826 | 1e-60 | 81 |
| 586 | 4079 | 700744275H1 | SOYMON013 | g2078349 | BLASTN | 833 | 1e-60 | 80 |
| 587 | 4079 | 700907055H1 | SOYMON022 | g2078349 | BLASTN | 624 | 1e-59 | 82 |
| 588 | 4079 | 701102453H1 | SOYMON028 | g2078349 | BLASTN | 453 | 1e-58 | 80 |
| 589 | 4079 | 700795760H1 | SOYMON017 | g2078349 | BLASTN | 804 | 1e-58 | 80 |
| 590 | 4079 | 700837515H1 | SOYMON020 | g2078349 | BLASTN | 811 | 1e-58 | 84 |
| 591 | 4079 | 700943689H1 | SOYMON024 | g2078349 | BLASTN | 782 | 1e-56 | 81 |
| 592 | 4079 | 701009626H1 | SOYMON019 | g2078349 | BLASTN | 715 | 1e-55 | 85 |
| 593 | 4079 | 700978865H1 | SOYMON009 | g2078349 | BLASTN | 334 | 1e-51 | 81 |
| 594 | 4079 | 700731620H1 | SOYMON010 | g2078349 | BLASTN | 400 | 1e-51 | 79 |
| 595 | 4079 | 700891691H1 | SOYMON024 | g2078349 | BLASTN | 713 | 1e-50 | 80 |
| 596 | 4079 | 700957819H1 | SOYMON022 | g2078349 | BLASTN | 677 | 1e-47 | 79 |

TABLE A*-continued

| Seq No. | Cluster ID | CloneID | Library | NCBI gi | Method | Score | P-value | % Ident |
|---|---|---|---|---|---|---|---|---|
| | | PHOSPHOGLUCONATE PATHWAY ENZYMES | | | | | | |
| 597 | 4079 | 700563553H1 | SOYMON002 | g2078349 | BLASTN | 547 | 1e-46 | 77 |
| 598 | 4079 | 700846208H1 | SOYMON021 | g2078349 | BLASTN | 524 | 1e-45 | 79 |
| 599 | 4079 | 700965218H1 | SOYMON022 | g2078349 | BLASTN | 622 | 1e-43 | 80 |
| 600 | 4079 | 700897435H1 | SOYMON027 | g2078349 | BLASTN | 633 | 1e-43 | 80 |
| 601 | −GM20444 | LIB3056-010-Q1-N1-B6 | LIB3056 | g2078349 | BLASTN | 837 | 1e-71 | 74 |
| 602 | 12032 | LIB3056-013-Q1-N1-E12 | LIB3056 | g2078349 | BLASTN | 722 | 1e-94 | 78 |
| 603 | 16286 | LIB3029-008-Q1-B1-B11 | LIB3029 | g2078349 | BLASTN | 1047 | 1e-78 | 74 |
| 604 | 18700 | LIB3051-043-Q1-K1-C2 | LIB3051 | g2078349 | BLASTN | 626 | 1e-41 | 75 |
| 605 | 3993 | LIB3051-038-Q1-K1-G6 | LIB3051 | g2078349 | BLASTN | 651 | 1e-56 | 75 |
| 606 | 3993 | LIB3051-077-Q1-K1-B8 | LIB3051 | g2078349 | BLASTN | 807 | 1e-56 | 75 |
| 607 | 3993 | LIB3051-115-Q1-K1-B3 | LIB3051 | g2078349 | BLASTN | 511 | 1e-54 | 75 |
| 608 | 3993 | LIB3051-054-Q1-K2-C5 | LIB3051 | g2078349 | BLASTN | 755 | 1e-52 | 75 |
| 609 | 3993 | LIB3040-029-Q1-E1-B10 | LIB3040 | g2078350 | BLASTX | 117 | 1e-43 | 61 |
| 610 | 3993 | LIB3040-059-Q1-E1-F9 | LIB3040 | g2078350 | BLASTX | 217 | 1e-42 | 57 |
| 611 | 3993 | LIB3051-087-Q1-K1-A8 | LIB3051 | g2078349 | BLASTN | 368 | 1e-38 | 75 |
| 612 | 3993 | LIB3056-001-Q1-B1-C11 | LIB3056 | g2078349 | BLASTN | 520 | 1e-32 | 72 |
| 613 | 3993 | LIB3051-112-Q1-K1-H9 | LIB3051 | g2078349 | BLASTN | 393 | 1e-30 | 71 |
| 614 | 4079 | LIB3056-008-Q1-N1-H10 | L183056 | g2078349 | BLASTN | 1357 | 1e-104 | 81 |
| 615 | 4079 | LIB3050-022-Q1-K1-B11 | LIB3050 | g2078349 | BLASTN | 1338 | 1e-102 | 81 |
| 616 | 4079 | LIB3051-094-Q1-K1-B8 | LIB3051 | g2078349 | BLASTN | 1088 | 1e-81 | 80 |
| 617 | 4079 | LIB3050-021-Q1-K1-G2 | LIB3050 | g2078349 | BLASTN | 673 | 1e-49 | 77 |
| | | MAIZE PUTATIVE TRANSALDOLASE | | | | | | |
| 618 | 15681 | 700429804H1 | SATMONN01 | g1323043 | BLASTX | 100 | 1e-11 | 37 |
| | | MAIZE PHOSPHOGLUCOISOMERASE | | | | | | |
| 619 | −700086021 | 700086021H1 | SATMON011 | g1100771 | BLASTX | 225 | 1e-28 | 51 |
| 620 | −700169489 | 700169489H1 | SATMON013 | g1100771 | BLASTX | 152 | 1e-13 | 59 |
| 621 | −700222638 | 700222638H1 | SATMON011 | g1100771 | BLASTX | 256 | 1e-28 | 60 |
| 622 | −700445574 | 700445574H1 | SATMON027 | g1100771 | BLASTX | 143 | 1e-12 | 54 |
| 623 | −700475232 | 700475232H1 | SATMON025 | g596022 | BLASTN | 845 | 1e-61 | 90 |
| 624 | −700612774 | 700612774H1 | SATMON033 | g596022 | BLASTN | 1574 | 1e-122 | 95 |
| 625 | 14393 | 700222547H1 | SATMON011 | g1100771 | BLASTX | 239 | 1e-25 | 60 |
| 626 | 14393 | 700220357H1 | SATMON011 | g1100771 | BLASTX | 218 | 1e-23 | 68 |
| 627 | 14393 | 700050317H1 | SATMON003 | g1100771 | BLASTX | 120 | 1e-22 | 63 |
| 628 | 14393 | 700163544H1 | SATMON013 | g1100771 | BLASTX | 214 | 1e-22 | 62 |
| 629 | 15724 | 700207164H1 | SATMON017 | g1100771 | BLASTX | 135 | 1e-17 | 67 |
| 630 | 15724 | 700552402H1 | SATMON022 | g1100771 | BLASTX | 135 | 1e-11 | 60 |
| 631 | 15724 | 700086085H1 | SATMON011 | g1100771 | BLASTX | 137 | 1e-11 | 45 |
| 632 | 20643 | 700577051H1 | SATMON031 | g1100771 | BLASTX | 241 | 1e-26 | 66 |
| 633 | 20643 | 700201592H1 | SATMON003 | g1100771 | BLASTX | 113 | 1e-19 | 45 |
| 634 | 20643 | 700576644H1 | SATMON030 | g1100771 | BLASTX | 113 | 1e-17 | 43 |
| 635 | 2351 | 700208928H1 | SATMON016 | g1100771 | BLASTX | 274 | 1e-43 | 73 |
| 636 | 2351 | 700240758H1 | SATMON010 | g1100771 | BLASTX | 283 | 1e-43 | 79 |
| 637 | 2351 | 700352502H1 | SATMON023 | g1100771 | BLASTX | 197 | 1e-36 | 70 |
| 638 | 2351 | 700581930H1 | SATMON031 | g1100771 | BLASTX | 164 | 1e-34 | 72 |
| 639 | 2351 | 700028642H1 | SATMON003 | g1100771 | BLASTX | 294 | 1e-33 | 65 |
| 640 | 2351 | 700106092H1 | SATMON010 | g1100771 | BLASTX | 294 | 1e-33 | 62 |
| 641 | 2351 | 700082102H1 | SATMON011 | g1100771 | BLASTX | 300 | 1e-33 | 62 |
| 642 | 2351 | 700083446H1 | SATMON011 | g1100771 | BLASTX | 274 | 1e-30 | 65 |
| 643 | 2351 | 700580585H1 | SATMON031 | g1100771 | BLASTX | 163 | 1e-29 | 69 |
| 644 | 2351 | 700550608H1 | SATMON022 | g1100771 | BLASTX | 265 | 1e-29 | 61 |
| 645 | 2351 | 700106079H1 | SATMON010 | g1100771 | BLASTX | 261 | 1e-28 | 54 |
| 646 | 2351 | 700244248H1 | SATMON010 | g1100771 | BLASTX | 238 | 1e-25 | 67 |
| 647 | 2351 | 700152233H1 | SATMON007 | g1100771 | BLASTX | 167 | 1e-22 | 72 |
| 648 | 2351 | 700455043H1 | SATMON029 | g1100771 | BLASTX | 168 | 1e-21 | 68 |
| 649 | 2351 | 700615809H1 | SATMON033 | g1100771 | BLASTX | 207 | 1e-21 | 66 |
| 650 | 2351 | 701165320H1 | SATMONN04 | g1100771 | BLASTX | 122 | 1e-14 | 63 |

TABLE A*-continued

PHOSPHOGLUCONATE PATHWAY ENZYMES

| Seq No. | Cluster ID | CloneID | Library | NCBI gi | Method | Score | P-value | % Ident |
|---|---|---|---|---|---|---|---|---|
| 651 | 32930 | 700042996H1 | SATMON004 | g596022 | BLASTN | 476 | 1e-95 | 98 |
| 652 | 4222 | 700222539H1 | SATMON011 | g596022 | BLASTN | 1160 | 1e-87 | 100 |
| 653 | 4222 | 700104023H1 | SATMON010 | g596022 | BLASTN | 1060 | 1e-84 | 100 |
| 654 | 4222 | 700101580H1 | SATMON009 | g596022 | BLASTN | 871 | 1e-74 | 99 |
| 655 | 4222 | 700473395H1 | SATMON025 | g596022 | BLASTN | 368 | 1e-46 | 95 |
| 656 | 4222 | 700800179H1 | SATMON036 | g596022 | BLASTN | 240 | 1e-11 | 100 |
| 657 | 8858 | 700221523H1 | SATMON011 | g1100771 | BLASTX | 278 | 1e-31 | 59 |
| 658 | 895 | 700100965H1 | SATMON009 | g596022 | BLASTN | 1611 | 1e-125 | 99 |
| 659 | 895 | 700620985H1 | SATMON034 | g596022 | BLASTN | 1418 | 1e-114 | 98 |
| 660 | 895 | 700082062H1 | SATMON011 | g596022 | BLASTN | 1365 | 1e-110 | 97 |
| 661 | 895 | 700573782H1 | SATMON030 | g596022 | BLASTN | 920 | 1e-107 | 98 |
| 662 | 895 | 700236138H1 | SATMON010 | g596022 | BLASTN | 1395 | 1e-107 | 100 |
| 663 | 895 | 700086336H1 | SATMON011 | g596022 | BLASTN | 1370 | 1e-105 | 100 |
| 664 | 895 | 700801467H1 | SATMON036 | g596022 | BLASTN | 1249 | 1e-99 | 95 |
| 665 | 895 | 700801458H1 | SATMON036 | g596022 | BLASTN | 1245 | 1e-98 | 100 |
| 666 | 895 | 700475024H1 | SATMON025 | g596022 | BLASTN | 1162 | 1e-97 | 93 |
| 667 | 895 | 700243164H1 | SATMON010 | g596022 | BLASTN | 1105 | 1e-96 | 100 |
| 668 | 895 | 700804665H1 | SATMON036 | g596022 | BLASTN | 1266 | 1e-96 | 99 |
| 669 | 895 | 700021931H1 | SATMON001 | g596022 | BLASTN | 1126 | 1e-84 | 99 |
| 670 | 895 | 700805540H1 | SATMON036 | g596022 | BLASTN | 776 | 1e-55 | 99 |
| 671 | 895 | 700172576H1 | SATMON013 | g596022 | BLASTN | 571 | 1e-38 | 98 |
| 672 | 895 | 700105116H1 | SATMON010 | g596022 | BLASTN | 558 | 1e-37 | 99 |
| 673 | 895 | 700472931H1 | SATMON025 | g596022 | BLASTN | 379 | 1e-31 | 97 |
| 674 | 20643 | LIB3069-009-Q1-K1-B3 | LIB3069 | g1100771 | BLASTX | 215 | 1e-44 | 50 |
| 675 | 2351 | LIB3079-007-Q1-K1-C11 | LIB3079 | g1100771 | BLASTX | 304 | 1e-77 | 72 |
| 676 | 32930 | LIB189-001-Q1-E1-E4 | LIB189 | g596022 | BLASTN | 794 | 1e-115 | 95 |
| 677 | 4222 | LIB3079-001-Q1-K1-H7 | LIB3079 | g596022 | BLASTN | 1132 | 1e-101 | 89 |
| 678 | 895 | LIB148-049-Q1-E1-D6 | LIB148 | g596022 | BLASTN | 2194 | 1e-178 | 97 |
| 679 | 895 | LIB3066-052-Q1-K1-G8 | LIB3066 | g596022 | BLASTN | 2178 | 1e-172 | 97 |
| 680 | 895 | LIB148-016-Q1-E1-G5 | LIB148 | g596022 | BLASTN | 1567 | 1e-161 | 99 |
| 681 | 895 | LIB143-032-Q1-E1-E10 | LIB143 | g596022 | BLASTN | 1914 | 1e-155 | 99 |
| 682 | 895 | LIB3061-013-Q1-K1-F7 | LIB3061 | g596022 | BLASTN | 1738 | 1e-136 | 88 |
| 683 | 895 | LIB143-047-Q1-E1-D4 | LIB143 | g596022 | BLASTN | 1490 | 1e-119 | 88 |
| SOYBEAN PHOSPHOGLUCOISOMERASE | | | | | | | | |
| 684 | −700568558 | 700568558H1 | SOYMON002 | g1369950 | BLASTX | 165 | 1e-15 | 80 |
| 685 | −700845275 | 700845275H1 | SOYMON021 | g1100771 | BLASTX | 124 | 1e-10 | 53 |
| 686 | −700960755 | 700960755H1 | SOYMON022 | g1100771 | BLASTX | 153 | 1e-14 | 52 |
| 687 | 18663 | 700838363H1 | SOYMON020 | g1100771 | BLASTX | 215 | 1e-22 | 63 |
| 688 | 18663 | 700838355H1 | SOYMON020 | g1100771 | BLASTX | 155 | 1e-14 | 81 |
| 689 | 19355 | 700897450H1 | SOYMON027 | g1100771 | BLASTX | 273 | 1e-31 | 74 |
| 690 | 19355 | 700744258H1 | SOYMON013 | g1100771 | BLASTX | 207 | 1e-29 | 69 |
| 691 | 19355 | 701153832H1 | SOYMON031 | g1100771 | BLASTX | 226 | 1e-23 | 58 |
| 692 | 20088 | 700856114H1 | SOYMON023 | g1100771 | BLASTX | 176 | 1e-33 | 75 |
| 693 | 20088 | 700670380H1 | SOYMON006 | g1100771 | BLASTX | 207 | 1e-33 | 71 |
| 694 | 20088 | 700788785H2 | SOYMON011 | g1100771 | BLASTX | 120 | 1e-32 | 74 |
| 695 | 20088 | 700847659H1 | SOYMON021 | g1100771 | BLASTX | 192 | 1e-31 | 84 |
| 696 | 20088 | 701136417H1 | SOYMON038 | g1100771 | BLASTX | 169 | 1e-27 | 66 |
| 697 | 31255 | 701207622H1 | SOYMON035 | g1100771 | BLASTX | 168 | 1e-29 | 61 |
| 698 | 20088 | LIB3051-014-Q1-E1-G3 | LIB3051 | g1100771 | BLASTX | 400 | 1e-68 | 73 |
| 699 | 31255 | LIB3056-008-Q1-N1-G8 | LIB3056 | g1100771 | BLASTX | 188 | 1e-52 | 62 |

*Table Headings

Cluster ID

A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. The cluster ID entries in the table refer to the cluster with which the particular clone in each row is associated.

Clone ID

The clone ID number refers to the particular clone in the PhytoSeq database. Each clone ID entry in the table refers to the clone whose sequence is used for (1) the sequence comparison whose scores are presented and/or (2) assignment to the particular cluster which is presented. Note that a clone may be included in this table even if its sequence comparison scores fail to meet the minimum standards for similarity. In such a case, the clone is included due solely to its association with a particular cluster for which sequences of one or more other member clones possess the required level of similarity.

Library

The library ID refers to the particular cDNA library from which a given clone is obtained. Each cDNA library is associated with the particular tissue(s), line(s) and developmental stage(s) from which it is isolated.

NCBI gi

Each sequence in the GenBank public database is arbitrarily assigned a unique NCBI gi (National Center for Biotechnology Information GenBank Identifier) number. In this table, the NCBI gi number which is associated (in the same row) with a given clone refers to the particular GenBank sequence which is used in the sequence comparison. This entry is omitted when a clone is included solely due to its association with a particular cluster.

Method

The entry in the "Method" column of the table refers to the type of BLAST search that is used for the sequence comparison. "CLUSTER" is entered when the sequence comparison scores for a given clone fail to meet the minimum values required for significant similarity. In such cases, the clone is listed in the table solely as a result of its association with a given cluster for which sequences of one or more other member clones possess the required level of similarity.

Score

Each entry in the "Score" column of the table refers to the BLAST score that is generated by sequence comparison of the designated clone with the designated GenBank sequence using the designated BLAST method. This entry is omitted when a clone is included solely due to its association with a particular cluster. If the program used to determine the hit is HMMSW then the score refers to HMMSW score.

P-Value

The entries in the P-Value column refer to the probability that such matches occur by chance.

% Ident

The entries in the "% Ident" column of the table refer to the percentage of identically matched nucleotides (or residues) that exist along the length of that portion of the sequences which is aligned by the BLAST comparison to generate the statistical scores presented. This entry is omitted when a clone is included solely due to its association with a particular cluster.

We claim:

1. A substantially purified nucleic acid molecule that encodes a maize or soybean phosphogluconate pathway enzyme or fragment thereof, wherein said maize or soybean phosphogluconate pathway enzyme is selected from the group consisting of:

(a) glucose-6-phosphate-1-dehydrogenase;

(b) D-ribulose-5-phosphate-3-epimerase; and (c) phosphoglucoisomerase;

wherein said substantially purified nucleic acid molecule comprises a nucleic acid sequence selected from the group consisting of SEQ ID NOs: 1, 225, 619 and complements thereof.

2. An isolated nucleic acid molecule, wherein said isolated nucleic acid molecule comprises a nucleic acid sequence selected from the group consisting of SEQ ID NOs: 1, 4, 14, 27, 225, 298, 311, 356, 569, and 619 or complements thereof.

3. The isolated nucleic acid molecule according to claim 2, wherein said isolated nucleic acid molecule comprises a nucleic acid sequence of SEQ ID NO: 1 or complement thereof.

4. The isolated nucleic acid molecule according to claim 2, wherein said isolated nucleic acid molecule comprises a nucleic acid sequence of SEQ ID NO: 4 or complement thereof.

5. The isolated nucleic acid molecule according to claim 2, wherein said isolated nucleic acid molecule comprises a nucleic acid sequence of SEQ ID NO: 27 or complement thereof.

6. The isolated nucleic acid molecule according to claim 2, wherein said isolated nucleic acid molecule comprises a nucleic acid sequence of SEQ ID NO: 225 or complement thereof.

7. The isolated nucleic acid molecule according to claim 2, wherein said isolated nucleic acid molecule comprises a nucleic acid sequence of SEQ ID NO: 298 or complement thereof.

8. The isolated nucleic acid molecule according to claim 2, wherein said isolated nucleic acid molecule comprises a nucleic acid sequence of SEQ ID NO: 311 or complement thereof.

9. The isolated nucleic acid molecule according to claim 2, wherein said isolated nucleic acid molecule comprises a nucleic acid sequence of SEQ ID NO: 356 or complement thereof.

10. The isolated nucleic acid molecule according to claim 2, wherein said isolated nucleic acid molecule comprises a nucleic acid sequence of SEQ ID NO: 569 or complement thereof.

11. The isolated nucleic acid molecule according to claim 2, wherein said isolated nucleic acid molecule comprises a nucleic acid sequence of SEQ ID NO: 619 or complement thereof.

12. A substantially purified nucleic acid molecule that encodes a maize or soybean 6-phosphogluconate dehydrogenase or fragment thereof, comprising a nucleic acid sequence selected from the group consisting of SEQ ID NOs: 14, 27 and complements thereof.

13. A substantially purified nucleic acid molecule that encodes a maize or soybean phosphogluconate pathway enzyme or fragment thereof, wherein said maize or soybean phosphogluconate pathway enzyme is selected from the group consisting of:

(a) glucose-6-phosphate-1-dehydrogenase;

(b) D-ribulose-5-phosphate-3-epimerase;

(c) ribose-5-phosphate isomerase; and (d) transaldolase;

wherein said substantially purified nucleic acid molecule comprises a nucleic acid sequence selected from the group consisting of SEQ ID NOs: 4, 298, 311, 569 and complements thereof.

14. A substantially purified nucleic acid molecule that encodes a maize transketolase enzyme or fragment thereof comprising a nucleic acid sequence of SEQ ID NO: 356 or complement thereof.

15. The isolated nucleic acid molecule according to claim 2, wherein said isolated nucleic acid molecule comprises a nucleic acid sequence of SEQ ID NO: 14 or complement thereof.

16. An isolated nucleic acid molecule, wherein said nucleic acid molecule consists of a nucleic acid sequence selected from the group consisting of SEQ ID NOs: 1, 4, 14, 27, 225, 298, 311, 356, 569, and 619 or complements thereof.

* * * * *

SEQUENCE LISTING

```
<160> NUMBER OF SEQ ID NOS: 699

<210> SEQ ID NO 1
<211> LENGTH: 233
<212> TYPE: DNA
<213> ORGANISM: Zea mays

<400> SEQUENCE: 1

gtttttgcag ttagtagaat atgttagtgg ctcctatgat agggtggaag gatttgagtt      60

attgaatgag gcaatctctg agtatgagac ttcagaaaac aatgactcgg gaagctaccg     120

cagattattt tatttggcat tgcctccatc agtctaccca tcagtatgcg agatgataag     180

atcatattgc atgagtccat cttcacacac cggttggaca agggttattg ttg            233


<210> SEQ ID NO 2
<211> LENGTH: 180
<212> TYPE: DNA
<213> ORGANISM: Zea mays

<400> SEQUENCE: 2

tcgttcggca gcagcaacga ggtgctggat gggacgccga cgggagatgg ggcaccgggg      60

caggggcagc ggggagcgag caccgtcagc atcacggtcg tcggcgcctc cggcgacctc     120

gccaagaaga agatcttccc ggccctcttc gccttgttct acgagggctg gctcccggag     180


<210> SEQ ID NO 3
<211> LENGTH: 137
<212> TYPE: DNA
<213> ORGANISM: Zea mays

<400> SEQUENCE: 3

cacagatctt gatagggcca ctaatgagct tgtgatacgt gtgcaaccgg atgaagcaat      60

ttacctaaag attaacaaca agattcctgg tctcggtatg cgactagata ggagtaactt     120
```

-continued

```
gaatctccat tatgccg                                                   137


<210> SEQ ID NO 4
<211> LENGTH: 263
<212> TYPE: DNA
<213> ORGANISM: Glycine max
<220> FEATURE:
<223> OTHER INFORMATION: unsure at all n locations

<400> SEQUENCE: 4

gaagcacttt tggatgttgc gtcatgtctt gcaagcagtg ctcagaccca gaagggatgg     60

aatcgcataa tatttgagaa gccatttggc tttgatgcac tttcttccca taggctgaca    120

caatatcttc tttcaaactt tcaggaaaag caaatatata gaattganca tctactagga    180

aggaatcnca gtnaaaatcc tncaggttta agggtttcaa annnagnttt tgagccacct    240

tngagnngna cntnnnnnga nna                                            263


<210> SEQ ID NO 5
<211> LENGTH: 259
<212> TYPE: DNA
<213> ORGANISM: Glycine max
<220> FEATURE:
<223> OTHER INFORMATION: unsure at all n locations

<400> SEQUENCE: 5

ctgtgttgag ttttcnancc ttaaaaagac tntctcttct ctctcgtctc tttctctccc     60

tgangcanna nancattagc atgcanancc agagtggttc tagtaatccg gtgctgctag    120

aggntgggaa ctagtgaatg gcatatcgag cgaagatcta gcttcggcac tgaatncccc    180

ttagcaatan aggcangcca tgtgnctgaa actngtcact ctctattgtn gtgcttggcg    240

cttntgggga tcttgctaa                                                 259


<210> SEQ ID NO 6
<211> LENGTH: 284
<212> TYPE: DNA
<213> ORGANISM: Glycine max
<220> FEATURE:
<223> OTHER INFORMATION: unsure at all n locations

<400> SEQUENCE: 6

tggaatcgca taatatttga naagccattt ggctttgatg cactttcttc ccataggctg     60

acacaatatc ttctttcaaa ctttcaggaa aagcanatat atagaattga tcanctacta    120

ggaaggaatc ncattgnaaa tcttacagtt tnaaggtttt caaatctagt ttttgagcca    180

ctttggagtc gtacttanat aagataatgt agcaggncat ttatcagagg ncttggctgt    240

gcatcctggg aagntattcn ntggctatgg gatnatccgt ganc                     284


<210> SEQ ID NO 7
<211> LENGTH: 253
<212> TYPE: DNA
<213> ORGANISM: Glycine max
<220> FEATURE:
<223> OTHER INFORMATION: unsure at all n locations

<400> SEQUENCE: 7

gagtgcgtga agaaaacacc aactgttttn agttttccaa ccttaaaaag annnnnnnnn     60

nnnnnnnnnn nnnnnnnnnn nnngaagcaa aanaanatta gcatcaaaac cagagtggtt    120

ctagtaatcc ggngctgcta gaggatggga actagtnaat ggcatatcga gcgaagatct    180

agcttcggca ctgaatcccc cttagcaaga gaggcaggaa atgtgcctga aactgggtca    240
```

-continued

```
ctctctattg ttg                                                          253


<210> SEQ ID NO 8
<211> LENGTH: 137
<212> TYPE: DNA
<213> ORGANISM: Glycine max

<400> SEQUENCE: 8

ccaggcagta tataagacat ggacagttga tattctcaga agattttggc actgaaggac     60

gtggcgggta ctttgaccat tatggtatca tgagagacat tatgcagaat catttacttc    120

aaatactagc actcttt                                                   137


<210> SEQ ID NO 9
<211> LENGTH: 287
<212> TYPE: DNA
<213> ORGANISM: Glycine max
<220> FEATURE:
<223> OTHER INFORMATION: unsure at all n locations

<400> SEQUENCE: 9

caaccttaaa agactctctt ttctctctct gaactctgaa gcaaaacaac attaccagag     60

tggttctagt aattcagtgc tgctagaaga tggaaactag tgaatggcat atcgagcgaa    120

gatctagctt cggctctgaa tcccccttag caaganangc aggaaatgtg cctganactg    180

ggtcactctc tattgtggtg cttggngctt ctggtgatct tgctaagaag aagacatttc    240

ctgcactttt ccacctatac ctggcaggga ttcttaccac cagatga                  287


<210> SEQ ID NO 10
<211> LENGTH: 251
<212> TYPE: DNA
<213> ORGANISM: Glycine max
<220> FEATURE:
<223> OTHER INFORMATION: unsure at all n locations

<400> SEQUENCE: 10

cttttctctc tctgaactct gaagcnaaac aacattacca gagtggttct agtaattcag     60

tgctgctaga agatggaaac tagtgaatgg catatcgagc gaagatctag cttcggctct    120

gaatccccct agcaagagag gcaggaaatg tgcctgaaac tgggtcactc tctattgtgg    180

tgcttggtgc ttctggtgat cttgctaaga agaagacatt tcctgcactt ttccacctat    240

acctgngnta c                                                         251


<210> SEQ ID NO 11
<211> LENGTH: 193
<212> TYPE: DNA
<213> ORGANISM: Glycine max
<220> FEATURE:
<223> OTHER INFORMATION: unsure at all n locations

<400> SEQUENCE: 11

gtttcagcta actctgcttc acttggtaat tgagtggttc tagtaatccg gtgctgctag     60

aggatgggaa ctagtgaatg gcatatcgag cgaagatcta gcttcggcac tgaatccccc    120

ttagcaagat atgcaggaan tgtgcctgaa actgggtcac tctctattgt tgtgcttggc    180

gcttctgggg atc                                                       193


<210> SEQ ID NO 12
<211> LENGTH: 318
<212> TYPE: DNA
```

-continued

<213> ORGANISM: Zea mays
<220> FEATURE:
<223> OTHER INFORMATION: unsure at all n locations

<400> SEQUENCE: 12
gcgagccaag agcgtggaga ntngatggaa ccttaacctc gcagagcttg ccaggatntg 60
gaagggcggc tgcattatcc gtgcgaggtt ccttgatagg atcaagagcg cgtacgacag 120
gaatcctgag ctcgccaatg gcgcagccat ttgaggaatt ggttggtatg agcagggatg 180
ttttctgctt tgggtgattt ctctctgtgg gttatctttc cttttactat tgttatcttt 240
atgcttctag atccaagtcg agtacttcga ataatgctgt actgtatggt tggcaagtga 300
agaacattgt gtagcttc 318

<210> SEQ ID NO 13
<211> LENGTH: 467
<212> TYPE: DNA
<213> ORGANISM: Zea mays
<220> FEATURE:
<223> OTHER INFORMATION: unsure at all n locations

<400> SEQUENCE: 13
ggccaagagc gcggagaaag gctgggggct caacccgctc gtccttcagc ccgctcagga 60
acctcgagtc caaggacgcc tcgatcgtag gagcggccac cgacagctcg gcggcctgct 120
gcaccgtcca cttccctgtc cctttcatcc cggtcttgtc aaggaccttg tccaccaggt 180
agccatcgcc atgctcgtcc ttgatgccaa agatgtcggc cgtgatctcn atcaagaagc 240
tcaggagctc gcccttgttc cactcggaga acacctggtg cagctcactg ttggtgagct 300
taccgaccga cttgagaacg tcgtatgcct nggaaatcaa ctgcatatcg gcatactcga 360
ttccgttggt gaaccatttt nacaaaantt ncccgatnca nctttngcca agtacgtnaa 420
acaaangggc cactttttaa ggggccttta anaaancncc tttnnng 467

<210> SEQ ID NO 14
<211> LENGTH: 410
<212> TYPE: DNA
<213> ORGANISM: Zea mays
<220> FEATURE:
<223> OTHER INFORMATION: unsure at all n locations

<400> SEQUENCE: 14
cccacgcgtc cgcggtcatg ggcagaacc ttgccctcaa cattgcagag aaagggttcc 60
ccatctctgt gtacaacagg acaacctcca aggtggacga gaccgtgcag cgtgccaagg 120
cagaaggaaa ccttcccgtc tacggcttcc atgaccccgc gtcctttgtg aagtccattc 180
agaagccacg ggtggtgatc atgctcgtca aggccggcgc gccagttgac cagaccatcg 240
cgacgctcgc agctcacttg gagcagggcg actgcatcat cgatgggggg aacgagtggt 300
acgagaacac ggagaggagg gagaaggcca tggaggagcg cggcctnctg tatcttggca 360
tgggtgtctc tggaggaaag gagggtgccc gcaacggccc gtccttgatg 410

<210> SEQ ID NO 15
<211> LENGTH: 449
<212> TYPE: DNA
<213> ORGANISM: Zea mays

<400> SEQUENCE: 15
cccacgcgtc cgcccacgcg ttcgggtggt ttgacggtgc tggcatcgcc aattcaactc 60
cgcatctgca tcggcagcgc gccagctcca tagtgtagga ggagatggcg ctcacaagaa 120

-continued

```
tcggtcttgc tggccttgcg gtcatggggc agaaccttgc cctcaacatt gcagagaaag    180

ggttccccat ctctgtgtac aacaggacaa ccttcaaggt ggacgagacc gtgcagcgtg    240

ccaaggcaga aggaaacctt cccgtctacg gcttccatga ccccgcgtcc tttgtgaagt    300

ccattcagaa gccacgggtg gtgatcatgc tcgtcaaggc cggcgcgcca gttgaccaga    360

ccatcgcgac gctcgcagct cacttggagc agggcgactg catcatcgat agggggaacg    420

agtggtacga gaacacggag aggagggag                                      449
```

<210> SEQ ID NO 16
<211> LENGTH: 410
<212> TYPE: DNA
<213> ORGANISM: Zea mays

<400> SEQUENCE: 16

```
ggcactttcc ctgcctgatt ggcgatttaa gcggtggggg agggaaggcc gatggtcagt     60

gaaagagagt aggtggacgg acggtgctgg catcgccaat tcaactccgc atctgcatcg    120

gcagcgcgcc agctccatag tgtaggagga gatggcgctc acaagaatcg gtcttgctgg    180

ccttgcggtc atggggcaga accttgccct caacattgca gagaaagggt tccccatctc    240

tgtgtacaac aggacaacct ccaaggtgga cgagaccgtg cagcgtgcca aggcagaagg    300

aaaccttccc gtctacggct tccatgaccc cgcgtccttt gtgaagtcca ttcagaagcc    360

acgggtggtg atcatgctcg tcaaggccgg cgcgccagtt gaccagacca               410
```

<210> SEQ ID NO 17
<211> LENGTH: 409
<212> TYPE: DNA
<213> ORGANISM: Zea mays

<400> SEQUENCE: 17

```
aggtggccgg acggtggtgg catcgccaat tcaactccgc atctgaatcg gcactcggca     60

gcgcgccagc tccatagtgt aggaggagga gatggcgctc acaagaatcg gtcttgctgg    120

ccttgcggtc atggggcaga accttgccct caacattgca gagaaagggt tccccatctc    180

tgtgtacaac aggacaacct ccaaggtgga cgagaccgtg cagcgtgcca aggcagaagg    240

aaaccttccc gtctacggct tccatgaccc cgcgtccttt gtgaactcca ttcagaagcc    300

acgggtggtg atcatgctcg tcaaggccgg cgcgccagtt gaccagacca tcgcgacgct    360

cgcagctcac ttggagcagg gcgactgcat catcgaatgg gggaacgag                409
```

<210> SEQ ID NO 18
<211> LENGTH: 420
<212> TYPE: DNA
<213> ORGANISM: Zea mays

<400> SEQUENCE: 18

```
ggtggacgga cggtgctggc atcgccaatt caacttcgca tctgcatcgg cagcgcgcca     60

gctccatagg aggagatggc gctcacaaga atcggtcttg ctggccttgc ggtcatgggg    120

cagaaccttg ccctcaacat tgcagagaaa gggttcccca tctctgtgta caacaggaca    180

acctccaagg tggacgagac cgtgcagcgt gccaaggcag aaggaaacct tcccgtctac    240

ggcttccatg accccgcgtc ctttgtgaag tccattcaga agccacgggt ggtgatcatg    300

ctcgtcaagg ccggcgcgcc agttgaccag accatcgcga cgctcgcagc tcacttggag    360

cagggcgact gcatcatcga tagggggaac gagtggtacg aggacacgga gaggagggag    420
```

-continued

<210> SEQ ID NO 19
<211> LENGTH: 403
<212> TYPE: DNA
<213> ORGANISM: Zea mays

<400> SEQUENCE: 19
agcggacgcg tgggggacgg acggtgctgg catcgccaat tcaactccgc atctgcatcg 60
gcagcgcgcc agctccatag tgtaggagga gatggcgctc acaagaatcg gtcttgctgg 120
ccttgcggtc atggggcaga accttgccct caacattgca gagaaagggt tccccatctc 180
tgtgtacaac aggacaacct ccaaggtgga cgagaccgtg cagcgtgcca aggcagaagg 240
aaaccttccc gtctacggct tccatgaccc cgcgtccttt gtgaagtcca ttcagaagcc 300
acgggtggtg atcatgctcg tcaaggccgg cgcgccagtt gaccagacca tcgcgacgct 360
cgcagctcac tttgagcagg gcgactgcat catcgatggg ggg 403

<210> SEQ ID NO 20
<211> LENGTH: 433
<212> TYPE: DNA
<213> ORGANISM: Zea mays

<400> SEQUENCE: 20
ggcactttcc ctgcctgatt ggcgatttat agcggtgggg gagggaaggc cgatggtcag 60
ggaaagagag taggtggacg gacggtgctg gcatcgccaa ttcaactccg catctgcatc 120
ggcagcgcgc cagctccata ggaggagatg gcgctcacaa gaatcggtct tgctggcctt 180
gcggtcatgg ggcagaacct tgccctcaac attgcagaga aagggttccc catctctgtg 240
tacaacagga caacctccaa ggtggacgag accgtgcagc gtgccaaggc agaaggaaac 300
cttcccgtct acggcttcca tgaccccgcg tcctttgtga agtccattca gaagccacgg 360
gtggtgatca tgctcgtcaa ggccggcgcg ccagttgacc agaccatcgc gacgctcgca 420
gctcacttgg agc 433

<210> SEQ ID NO 21
<211> LENGTH: 209
<212> TYPE: DNA
<213> ORGANISM: Zea mays
<220> FEATURE:
<223> OTHER INFORMATION: unsure at all n locations

<400> SEQUENCE: 21
gcatctgcat cggcagcgcg ncagnngnat aggaggagat ggcgctcaca agaatcggtn 60
ttgctggcct tgcggncatg gggcagaacc ttgccctnaa cattgcagag aaagggnnan 120
ccatatgtgt gnacaacagg acaacctgca aggtngacna gaccgtncag ngngncnagg 180
cagaangana ccttangntt tannnattg 209

<210> SEQ ID NO 22
<211> LENGTH: 271
<212> TYPE: DNA
<213> ORGANISM: Glycine max
<220> FEATURE:
<223> OTHER INFORMATION: unsure at all n locations

<400> SEQUENCE: 22
caagaaggaa accttcctgt ntatggctac cataacccta aattctttgt ccaatccatt 60
cancaagcca agggtcataa taatgcttgt caaggctgnt gcacctgttg accaaaccat 120
caagaccctc tcagcacact tnnccaaggg tgattgcatc attgatggtg gcaatgagtg 180

```
gtatgagaac actgagagaa gagagaaagc gatgtccgaa ttgggtcttc tctaccttgn    240

ggatgggagt ttcaggtggt gaagaaggtg c                                   271

<210> SEQ ID NO 23
<211> LENGTH: 240
<212> TYPE: DNA
<213> ORGANISM: Glycine max

<400> SEQUENCE: 23

tctcgagcga atcggctcgg aggctactta aagggcttgg aatgaagaaa ggaaataatt    60

gatcaccaat ctgcctggag gagagttgtt tgccttgcta tcaattccgg tattagcact   120

ccaggttatt tcagggatag gattttgttc ctgactgtat tgcagtcacc gaatatggag   180

caactaagga cggatatttg ggggtatatt atgggcaacg agaggttgga tgcgaattac   240

<210> SEQ ID NO 24
<211> LENGTH: 242
<212> TYPE: DNA
<213> ORGANISM: Glycine max
<220> FEATURE:
<223> OTHER INFORMATION: unsure at all n locations

<400> SEQUENCE: 24

ctgctctacc ttgggatggg agtttctggt ggtgaggaag gtgctctaat ggtccctctt    60

tgatgcctgg tggtcgttga ggcttcaaat acatagaaga tattcttctc aaggtgcagc   120

tcaagtcctg acagtggtct tgcgtactat atnnnaaggt gnctggtaat ttgtcnatga   180

tcacatggac gattgtgnat nantatgcaa ggcatattnt gagcatagca gtgcaataga   240

tc                                                                   242

<210> SEQ ID NO 25
<211> LENGTH: 263
<212> TYPE: DNA
<213> ORGANISM: Glycine max

<400> SEQUENCE: 25

cctgagttga gtttacatag ccacaacgtg gtgaagtttt atttatatta tttccaactg    60

aattgcttga tagtttgttt tccaactatg ttgtatcttt gctgatcatg ctttgtgctt   120

gatacaaaat tgtccagctc atggtgcctt tttaattttc acattttgat aagatttcct   180

tcagcgtcat ggatacatgt tatgttacac caggagttga aatttttaca tttattgtta   240

acttgttgag tttaatgttg atc                                           263

<210> SEQ ID NO 26
<211> LENGTH: 253
<212> TYPE: DNA
<213> ORGANISM: Glycine max

<400> SEQUENCE: 26

ctctcaaata catagaagat attcttctca atgtggcagc tcaagtacct gacagtggtc    60

cttgcgtgac ttatcttggt aaaggtgggt ctggtaattt tgtgagagag attcaacaat   120

ggaatgagta atggtgaatt cagctgaatt ccaaaggctt ataaggtccg gaattcagtt   180

ggaaagtggt caattgagga ctaacaaggg gcctcctcgg attggaccaa ggaagacctc   240

cgaagttccc gga                                                      253

<210> SEQ ID NO 27
```

-continued

<211> LENGTH: 229
<212> TYPE: DNA
<213> ORGANISM: Glycine max

<400> SEQUENCE: 27
cagaccttat tttttctgtc atttgcttca aatttcagga gattaattat gcgctcaacc 60
cacaacaaga ataggccttg ctggattggc tgttaatggg caaaatctgg cactcaatat 120
tgcttgaaaa gggcttccca attccggtta acaacggaac catttccaag gttattgggc 180
cataagacga agcaaaccag gaaggaaacc ttcaatttat ggggaacaa 229

<210> SEQ ID NO 28
<211> LENGTH: 250
<212> TYPE: DNA
<213> ORGANISM: Glycine max

<400> SEQUENCE: 28
aatgaatctg atcagggcaa agagcattga gaaaggttgg gacttgaagt tgggggaact 60
tgcaaggatt tggaaagggg gttgcatcat aagagcaata tttttggaca gaatcaagaa 120
agcatacgac agaaatccta accttgcaaa ccttcttgtg gatccagaat ttgcaaagga 180
aatagtggat agacaatctg catggagaag agttgtgtgt cttgctatca actatggcac 240
tagcacacca 250

<210> SEQ ID NO 29
<211> LENGTH: 87
<212> TYPE: DNA
<213> ORGANISM: Glycine max

<400> SEQUENCE: 29
ggctcgaggg ggtcttacca cactgagtgg ttcaagcttg ccaaacagtc aagaaattag 60
agtactgtag tgcagccaat caggatc 87

<210> SEQ ID NO 30
<211> LENGTH: 256
<212> TYPE: DNA
<213> ORGANISM: Glycine max

<400> SEQUENCE: 30
attcttctca aggtggcagc tcaagtccct gacagtggtc cttgcgtgac ttatattggt 60
aaaggtggct ctggtaattt tgtgaaaatg atccacaatg gcatcgaata tggtgacatg 120
cagctgattg cagaggccta tgatgtgctg aagtcagttg gaaagttgtc aaatgaggaa 180
ctacaaagtg tcttctcaga atggaacaag ggagaacttc tgagtttcct gattgaaatc 240
actgcagata tatttg 256

<210> SEQ ID NO 31
<211> LENGTH: 213
<212> TYPE: DNA
<213> ORGANISM: Glycine max

<400> SEQUENCE: 31
gcgtgactta tattggtaaa ggtggctctg gtaattttgt gacaatgatc cacaatggca 60
tcgaatctgg tgacatgcag ctgattgcag aggcctatga tgtgctgaag tcagttggaa 120
agttgtcaaa tgaggaacta caaagtgtct tctcagaatg gaacaaggga gaacttctcg 180
agtttcctga ttgacatcac tgcagatata ttt 213

-continued

<210> SEQ ID NO 32
<211> LENGTH: 268
<212> TYPE: DNA
<213> ORGANISM: Glycine max
<220> FEATURE:
<223> OTHER INFORMATION: unsure at all n locations

<400> SEQUENCE: 32
gtggcagctc aagtccctga cagtggtcct tgcgtgactt atattggtaa aggtggctct 60
ggtaattttg tgaaaatgat ccacaatggc atcgaatatg gtgacatgca gctgattgca 120
gaggcctatg atgtgctgaa gtcagttgga aagttgtcaa atgaggaact acaaagtgtc 180
tcctcagaat ggaacaaggg agaattctga gtttccgatt ganatcatgc agatatattg 240
gattcangag ataagggaga nggatacc 268

<210> SEQ ID NO 33
<211> LENGTH: 109
<212> TYPE: DNA
<213> ORGANISM: Glycine max

<400> SEQUENCE: 33
aaattttgtg aaaatgatcc acaatggaat tgagtatggt gacatgcagc tcattgctga 60
ggcctatgat gtgctaaagt cggttggaaa gttgtcaaat gaggagctg 109

<210> SEQ ID NO 34
<211> LENGTH: 277
<212> TYPE: DNA
<213> ORGANISM: Glycine max

<400> SEQUENCE: 34
gggcactggt aagtggactg ttcagcaagg tgctgaatta tcaattgctg ctcccactat 60
tgaagcatca ttggatgcaa ggttcctgag tgggttgaag gaggaaagag ttgaagctgc 120
aaaggtcttt aaatcaggtg gtattggtga tatcgtgact gatcaacctg tagacaagaa 180
aaaattggtt gatgatgtta ggaaggctct ttatgcagcc aaaatctgta gttatgcaca 240
gggaatgaat ttgatccgtg caaagagtat tgaaaag 277

<210> SEQ ID NO 35
<211> LENGTH: 252
<212> TYPE: DNA
<213> ORGANISM: Glycine max

<400> SEQUENCE: 35
gcaaggttcc tgagtgggtt gaaggaggaa agagttgaag ctgcaaaggt ctttaaatca 60
ggtggcattg gtgatattgt gactgatcaa cctgtagaca agcagaagtt gattgatgat 120
gttaggaagg ctctttatgc agccagaatc tgtagttatg cacagggaat gaatttgatc 180
cgtgcaaaga gtattgaaaa gggttgggat ttgaagttgg gtgaactggc ccggatttgg 240
aaagggggtt gc 252

<210> SEQ ID NO 36
<211> LENGTH: 262
<212> TYPE: DNA
<213> ORGANISM: Glycine max

<400> SEQUENCE: 36
cttgttgaca aggtcctaga caagactggc atgaagggca ctggtcaagt ggactgggca 60
gcaagctgct gaattatcaa ttgctgctcc cactattgaa gcatcattgg atgcaaggtt 120

-continued

```
cctgagtggg ttgaaggagg aaagacttga agctgcaaag gtctttaaat caggtggtat    180

tgctgatatc gtgactgatc aacctgtaga caagaaaaaa ttggttgatg atgttaggaa    240

ggctctttat gcagccaaaa tc                                             262
```

<210> SEQ ID NO 37
<211> LENGTH: 241
<212> TYPE: DNA
<213> ORGANISM: Glycine max
<220> FEATURE:
<223> OTHER INFORMATION: unsure at all n locations

<400> SEQUENCE: 37

```
tttggaatta aggatgataa gggagatgga tatcttgttg acaaggtcct agacaagact     60

ggcatgaagg gcactggtaa gtggactgtt cagcaagctg ctgaattatc aattgctgct    120

cccactattg angcatcatt ggatgcaagg ttcctgagtg ggttgaagga ggaagagttg    180

aagctgcaaa ggtctttaaa tcaggtggta ttggtgatat cgtgactgat caacctgtag    240

a                                                                    241
```

<210> SEQ ID NO 38
<211> LENGTH: 239
<212> TYPE: DNA
<213> ORGANISM: Glycine max

<400> SEQUENCE: 38

```
aaagtgtctt ctcagaatgg aacaagggag aacttctgag tttcctgatt gaaatcactg     60

cagatatatt tggaattaag gatgataagg gagatggata tcttgttgac aagcgtccta    120

gacaagactg gcatgaaggg cactggtaag tggactgttc agcaagctgc tgaattatca    180

attgctgctc ccactattga agcatcattg gatgcaaggg tcctgagtgg ggtgaagga     239
```

<210> SEQ ID NO 39
<211> LENGTH: 252
<212> TYPE: DNA
<213> ORGANISM: Glycine max

<400> SEQUENCE: 39

```
ggagatggat tcttgttgac aaggtcctag acaagactgg catgaagggc actggtaagt     60

ggactgttca gcaagctgct gaattatcaa ttgctgctcc cactattgaa gcatcattgg    120

atgcaaggtt cctgagtggg ttgaaggagg aaagagttga agctgcaaag gtctttaaat    180

caggtggtat tggtgatatc gtgactgatc aacctgtaga caagaaaaaa ttggttgata    240

tgttaggaag gc                                                        252
```

<210> SEQ ID NO 40
<211> LENGTH: 262
<212> TYPE: DNA
<213> ORGANISM: Glycine max

<400> SEQUENCE: 40

```
ctcgagccgt tcttagacag aatcaagcag gcatatgaaa gaacccctaa tctggcaaac     60

cttcttgtgg atccagagtt tgcaaaggaa ataattgatt accaatctgc ctggaggaga    120

gttgtttgcc ttgctatcaa ttctggtatt agcactccag gtatgtctgc tagtcttgct    180

tattttgaca cttacagaag ggaaaggttg ccagctaatt tggtgcaagc tcaacgagac    240

tactttggtg ctcatacata tg                                             262
```

-continued

<210> SEQ ID NO 41
<211> LENGTH: 167
<212> TYPE: DNA
<213> ORGANISM: Glycine max
<220> FEATURE:
<223> OTHER INFORMATION: unsure at all n locations

<400> SEQUENCE: 41
accttcttgt ggatccagag tttgcaangg aaataatcga tcgccaatct gcctggagga 60
gagttgtttg ccttgctatc aattctggta tcagcactcc aggtatgtct gctagtctng 120
cttatnttga cacttacaga agggaaaggt nnccagctaa tttggtg 167

<210> SEQ ID NO 42
<211> LENGTH: 230
<212> TYPE: DNA
<213> ORGANISM: Glycine max

<400> SEQUENCE: 42
gtgatagcga tgtccgaatt gggtcttctc taccttggga tgggagtttc aggtggtgaa 60
gaaggtgcaa gacatggtcc ctctttgatg cctggtggtt cattcgagga ctacaagtac 120
atagaagaca ttctcctcaa ggtagacgca caagtccctg atagtggtca ttgtgtgacc 180
tacatcggca aaggtggatc aggaaatttt gtgaaaatga tccacaatgg 230

<210> SEQ ID NO 43
<211> LENGTH: 245
<212> TYPE: DNA
<213> ORGANISM: Glycine max

<400> SEQUENCE: 43
gtgaaagcga tgtccgaatt gggtcttctc taccttggga tgggagtttc aggaggtgaa 60
gaaggtgcaa gacatggtcc ctctttgatg cctggtggtt cattcgaggc ctacaagtac 120
atagaagaca ttctcctcaa ggtggccgca caagtccctg atagtggtcc ttgtgtgacc 180
tacatcggca aaggtggatc aggaaatttt gtgaaaatga tccacaatgg aattgagtat 240
ggtga 245

<210> SEQ ID NO 44
<211> LENGTH: 289
<212> TYPE: DNA
<213> ORGANISM: Glycine max

<400> SEQUENCE: 44
atctgcctgg aggagagttg tttgccttgc tatcaattct ggtattagca ctccaggtat 60
gtctgctagt cttgcttatt ttgacactta cagaagggaa aggttgccag ctaatttggt 120
gcaagctcaa cgagactact ttggtgctca tacatatgaa agggttgaca tagaggggtc 180
ttaccatact gagtggttca agcttgccaa acagtcaaga aattagatta ctgtatttga 240
gccatcagga ttttcctaat aaatgtaata ttgtctgctc agactgtat 289

<210> SEQ ID NO 45
<211> LENGTH: 272
<212> TYPE: DNA
<213> ORGANISM: Glycine max

<400> SEQUENCE: 45
tcaggtatgt ctgctagtct tgcttatttt gacacttaca gaagggaaag gttgccagct 60
aatttggtgc aagctcaacg agactacttt ggtgctcata catatgaaag ggttgacata 120

-continued gaggggtctt accatactga gtggttcaag cttgccaaac agtcaagaaa ttagattact 180
gtatttgagc caatcaggat tttcctaata aatgtaatat tttctgctca gactgtatgc 240
tgagttgagt ttgcatatcc acaatgtggt ga 272

<210> SEQ ID NO 46
<211> LENGTH: 246
<212> TYPE: DNA
<213> ORGANISM: Glycine max

<400> SEQUENCE: 46
ctaagataca acatagttgg aaaacaaact atcaagcaat tcagttggaa ataatataaa 60
taaaacttca ccacgttgtg gctatgtaaa ctcaactcag catacagtct gagcagaaaa 120
cattacattt attaggaaaa tcctgattgg ttcaaataca gtaatctaaa ttctagactg 180
tttggcaagc ttgaaccact cagtatggta agaccccctct atgtcaacca ttcatatgta 240
tgagca 246

<210> SEQ ID NO 47
<211> LENGTH: 156
<212> TYPE: DNA
<213> ORGANISM: Glycine max

<400> SEQUENCE: 47
ggggtcttac catactgagt ggttcaagct tgccaaacag tcaagaaatt agattactgt 60
atttgagcca atcaggattt tcctaataaa tgtaatattt tctgctcaga ctgtatgctg 120
agttgagttt gccaagcaat tcagttggaa ataatg 156

<210> SEQ ID NO 48
<211> LENGTH: 250
<212> TYPE: DNA
<213> ORGANISM: Glycine max

<400> SEQUENCE: 48
tatggctacc atgaccccga agcttttgtt cattccattc aaaagcctag ggtgataata 60
atgcttgtta aggctggggc acctgttgac cagaccatta agaccctatc tgcatacatg 120
gaaaaaggtg actgcataat tgatggtggt aacgaatggt acgagaacac cgaaaggaga 180
gagaaatcgg tggctgaatt gggtctgctc taccttggga tgggagtttc tggtggtgag 240
gaaagtgctc 250

<210> SEQ ID NO 49
<211> LENGTH: 170
<212> TYPE: DNA
<213> ORGANISM: Glycine max

<400> SEQUENCE: 49
ggcacctgtt gaccagacca ttaagaccct atctgcatac atggaaaaag gtgactgcat 60
aattgatggt ggtaacgaat ggtacgagaa caccgaaaga agagagaaat cggtggctga 120
attgggtctg ctctaccttg ggatgggagt ttctggtggt gaggaaggtg 170

<210> SEQ ID NO 50
<211> LENGTH: 275
<212> TYPE: DNA
<213> ORGANISM: Glycine max

<400> SEQUENCE: 50
gacgacagaa gggagaaatc ggtggctgaa ttgggtctgc tctacctcgg gatgggagtt 60

-continued tctggtggtg aggaaggtgc tcgtaatggt ccctctttga tgcctggtgg ttcgtttgag 120
gctttcaaat acatagaaga tattcttctc aaggtggcag ctcaagtccc tgacagtggt 180
ccttgcgtga cttatattgg taaaggtggc tctggtaatt ttgtgaaaat gatccacaat 240
ggcatcgaat atggtgacat gcagctgatt gcaga 275

<210> SEQ ID NO 51
<211> LENGTH: 256
<212> TYPE: DNA
<213> ORGANISM: Glycine max

<400> SEQUENCE: 51
acggctgcga gaagacgaca gaagggggaa aaaggtgact gtataattga tggtggtaac 60
gaatggtatg agaacactga aagaagagag aaagaggtgg ctgaattggg tctgctctac 120
cttgggatgg gagtttctgg tggtgaggaa ggtgctcgta atggtccctc tttgatgcct 180
ggtggttcgt ttgaggcttt caaatacata gaagatattc ttctcaaggt ggcagctcaa 240
gtacctgaca gtggtc 256

<210> SEQ ID NO 52
<211> LENGTH: 252
<212> TYPE: DNA
<213> ORGANISM: Glycine max

<400> SEQUENCE: 52
gactgccata ttgatggtgg taacgaatgg tacgagaaca ccgaaagaag agagaaatcg 60
gtggctgaat tgggtctgct ctaccttggg atgggagttt ctggtggtga ggaaggtgct 120
cgtaatggtc ctctttgatg cctggtggtt cgtttgaggc tttcaaatac atagaagata 180
ttcttctcaa ggtggcagct caagtccctg acagtggtcc ttgcgtgact tatattggta 240
aaggtggctc tg 252

<210> SEQ ID NO 53
<211> LENGTH: 346
<212> TYPE: DNA
<213> ORGANISM: Glycine max

<400> SEQUENCE: 53
gtgaagttaa ggaaatcaat tatggctcaa ccctcaacaa gaatagggcc ttgctggact 60
ggctgttatg ggccaaaatc tagcactcaa tattgctgag aaaggctttc ccatttctgt 120
ttataaccga accacttcca aggttgatga gactgtagaa cgagcaaaac aagaaggaaa 180
tcttccagtt tatggctacc atgaccccga agcttttgtt cattccattc aaaagcctag 240
ggtgataata atgcttgtta aggctggggc atctgttgac cagaccatta agaccctatc 300
tgcatacatg gaaaaaggtg actgcataat tgatggtggt aacgaa 346

<210> SEQ ID NO 54
<211> LENGTH: 283
<212> TYPE: DNA
<213> ORGANISM: Glycine max

<400> SEQUENCE: 54
ccagacctta atttttctct cattcgcttc aaatttcagg aaatcaatta tggctcaacc 60
ctcaacaaga ataggccttg ctggactggc tgttatgggc caaaatctag cactcaatat 120
tgctgagaaa ggctttccca tttctgttta taaccgaacc acttccaagg ttgatgagac 180

-continued

```
tgtagaacga gcaaaacaag aaggaaatct tccagtttat ggctaccatg accccgaagc    240

ttttgtcatt ccattcaaaa gcctagggtg ataataatgc ttg                      283


<210> SEQ ID NO 55
<211> LENGTH: 276
<212> TYPE: DNA
<213> ORGANISM: Glycine max

<400> SEQUENCE: 55

caaatttcag gaaatcaatt atggctcaac cctcaacaag aataggcctt gctggactgg     60

ctgttatggg ccaaaatcta gcactcaata ttgctgagaa aggctttccc atttctgttt    120

ataaccgaac cacttccaag gttgatgaga ctgtagaacg agcaaaacag gaaggaaatc    180

ttccagttta tggctaccat gaccccgaag cttttgttca ttccattcaa aagcctaggg    240

tgataataat gcttgttaag gctggggcac ctgttg                              276


<210> SEQ ID NO 56
<211> LENGTH: 289
<212> TYPE: DNA
<213> ORGANISM: Glycine max

<400> SEQUENCE: 56

cagaccttaa ttgttctctc attcgcttca aatttcagga aatcaattat ggctcaaccc     60

tcaacaagaa taggccttgc tggactggct gttatgggcc aaaatctagc actcaatatt    120

gctgagaaag gctttcccat ttctgtttat aaccgaacca cttccaaggt tgatgagact    180

gtagaacgag caaaacaaga aggaaatctt ccagtttatg gctaccatga ccccgaagct    240

tttgttcatt ccattcaaaa gcctagggtg ataataatgc ttgttaagg                289


<210> SEQ ID NO 57
<211> LENGTH: 267
<212> TYPE: DNA
<213> ORGANISM: Glycine max

<400> SEQUENCE: 57

cctcattcgc ttcaaatttc aggaaatcaa ttatggctca accctcaaca agaataggcc     60

ttgctggact ggctgttatg ggccaaaatc tagcactcaa tattgctgag aaaggctttc    120

ccatttctgt ttaaccgaa ccacttccaa ggttgatgag actgtagaac gagcaaaaca     180

agaaggaaat cttccagttt atggctacca tgaccccgaa gcttttgttc attccattca    240

aaagcctagg gtgataataa tgcttgt                                        267


<210> SEQ ID NO 58
<211> LENGTH: 260
<212> TYPE: DNA
<213> ORGANISM: Glycine max

<400> SEQUENCE: 58

ccagacctta atttttctct cattcgcttc aaatttcagg aaatcaatta tggctcaacc     60

ctcaacaaga ataggccttg ctggactggc tgttatgggc caaaatctag cactcaatat    120

tgctgagaaa ggctttccca tttctgttta taaccgaacc acttccaagg ttgatgagac    180

tgtagaacga gcaaaacaag aaggaaatct tccagtttat ggctaccatg accccgaagc    240

ttttgttcat tccattcaaa                                                260


<210> SEQ ID NO 59
<211> LENGTH: 260
```

-continued

```
<212> TYPE: DNA
<213> ORGANISM: Glycine max

<400> SEQUENCE: 59

tgtgattcca gaccttaatt tttctctcat tcgcttcaaa tttcaggaaa tcaattatgg      60

ctcaaccctc aacaagaata ggccttgctg gactggctgt tatgggccaa aatctagcac     120

tcaatattgc tgagaaaggc tttcccattt ctgtttataa ccgaaccact tccaaggttg     180

atgagactgt agaacgagca aaacaagaag gaaatcttcc agtttatggc taccatgacc     240

ccgaagcttt tgttcattcc                                                  260


<210> SEQ ID NO 60
<211> LENGTH: 265
<212> TYPE: DNA
<213> ORGANISM: Glycine max

<400> SEQUENCE: 60

cagaccttaa tttttctctc attcgcttca aatttcaggg gatcaattat ggctcaaccc      60

tcaacaagaa tatgccttgc tggactggct gttatgggcc agaatctagc actcaatatt     120

gctgagaaag gctttcgcat ttctgtttat aaccgaacca cttccaaggt tgatgagact     180

gtagaacgag caaaacaaga aggaaatctt ccagtttatg gctaccatga ccccgaagct     240

tttgttcatt ccattcaaaa gccta                                            265


<210> SEQ ID NO 61
<211> LENGTH: 263
<212> TYPE: DNA
<213> ORGANISM: Glycine max
<220> FEATURE:
<223> OTHER INFORMATION: unsure at all n locations

<400> SEQUENCE: 61

ctagacctta atttttctct cattcgcttc aaatttcagg aaatcaatta tggctcaacc      60

ctcaacaaga ataggccttg ctggactggc tgttatgggt ccaaatctag cactcaatat     120

tgctgagaaa ggctttccca tttctgttta taaccgaacc acttccaagg ttgatgagac     180

tgtagaacta gcannacaag aaggaaatct tccagtttat ggctaccatg accccgaagc     240

ttttgttcat tccattcaaa agc                                              263


<210> SEQ ID NO 62
<211> LENGTH: 279
<212> TYPE: DNA
<213> ORGANISM: Glycine max

<400> SEQUENCE: 62

tgctctgtga ttccagacct taatttttcc ctcattcgct tcaaatttca ggaaatcaat      60

tatggctcaa ccctcaacaa gaataggcct tgcacctctg gctgttatgg gccaaaatct     120

agcactcaat attgctgaga aaggctttcc catttctgtt tataaccgaa ccacttccaa     180

ggttgatgag actgtagaac gagcaaaaca agaaggaaat cttccagttt atggctacca     240

tgaccccgaa gcttttgttc attccattca aacgcctag                             279


<210> SEQ ID NO 63
<211> LENGTH: 284
<212> TYPE: DNA
<213> ORGANISM: Glycine max
<220> FEATURE:
<223> OTHER INFORMATION: unsure at all n locations
```

-continued

<400> SEQUENCE: 63

```
tgattccaga ccttaatttt tctctcattc gcttcaaatt tcaggaaatc aattatggct     60

caaccctcaa caagaatagg ccttgctgga ctggctgtta tgggccaaaa tctagcactc    120

natattgctg agaaaggctt tcccatttct gnttataacc gnaccacttc caaggntgat    180

gagactgtag nacgagcnaa acaggaagga aatcttccag tttatggcta ccatgacccc    240

gnagctttgt tcattccatt caaaagctag ggtgataata atgc                     284
```

<210> SEQ ID NO 64
<211> LENGTH: 256
<212> TYPE: DNA
<213> ORGANISM: Glycine max

<400> SEQUENCE: 64

```
gtgattccag accttaattt ttctctcatt cgcttcaaat ttcaggaaat caattatggc     60

tcaaccctca acaagaatag gccttgctgg actggctgtt atgggccaaa atctagcact    120

caatattgct gagaaaggct ttcccatttc tgtttataac cgaaccactt ccaaggttga    180

tgagactgta gaacgagcaa aacaggaagg aaatcttcca gtttatggct accatgaccc    240

cgaagctttt gttcat                                                    256
```

<210> SEQ ID NO 65
<211> LENGTH: 265
<212> TYPE: DNA
<213> ORGANISM: Glycine max

<400> SEQUENCE: 65

```
ccgtgctctg tgattccaga ccttaatttt tctctcattc ccttcaaatt tcaggaaatc     60

aattatggct caaccctcaa caagaatagg ccttgctgga ctggctgtta tgggccaaaa    120

tctagcactc aatattgctg agaaaggctt tcccatttct gtttataacc gaaccacttc    180

caaggttgat gagactgtag aacgagcaaa acaagaagga aatcttccag tttatggcta    240

ccatgacccc gaagcttttg ttcat                                          265
```

<210> SEQ ID NO 66
<211> LENGTH: 275
<212> TYPE: DNA
<213> ORGANISM: Glycine max
<220> FEATURE:
<223> OTHER INFORMATION: unsure at all n locations

<400> SEQUENCE: 66

```
gtgattccca gaccttattt nttctgtcat ttgcttcaaa tttcaggaga ttaattatgg     60

ctcaacccan aacaagaata ggccttnctg gattggctgt tatgggccaa aatctggcac    120

tcaatattgc tgagaaaggc ttncccattt ctgtttacaa ccgaaccact tccaaggttg    180

atgagacagt agaacgagca aaacaagaag gaaatcttcc agtttatggc taccatgacc    240

ctgaagcttt tgttcattcc attcaanagc ctagg                               275
```

<210> SEQ ID NO 67
<211> LENGTH: 236
<212> TYPE: DNA
<213> ORGANISM: Glycine max

<400> SEQUENCE: 67

```
cagaccttaa tttttctctc attcgcttca aatttcagga aatcaattat ggctcaaccc     60

tcaacaagaa taggccttgc tggactggct gttatgggcc aaaatctagc actcaatatt    120
```

-continued

```
gctgagaaag gctttcccat ttctgtttat aaccgaacca cttccaaggt tgatgagact    180

gtagaacgag caaaacagga aggaaatctt ccagtttatg gctaccatga ccccga        236


<210> SEQ ID NO 68
<211> LENGTH: 280
<212> TYPE: DNA
<213> ORGANISM: Glycine max

<400> SEQUENCE: 68

cacagacctt atgatttctg tcatttacat caaatttcag gagattaatt atggctcaac     60

ccataacaag aataggcctt gctggattgg ctgttatggg ccaaaatctg gcactcaata    120

ttgctgagaa aggctttccc attctgttta caaccgaacc acttccaagg ttgatgagac    180

agtagaacga gcaaaacaag aaggaaatct tccagtttat ggctaccatg accctgaagc    240

ttttgttcat tccattcaaa agcctagggt gatactaatg                          280


<210> SEQ ID NO 69
<211> LENGTH: 281
<212> TYPE: DNA
<213> ORGANISM: Glycine max

<400> SEQUENCE: 69

ctgtgattcc cagaccttat tttttctgtc atttgcttca agtctcagga gattgattat     60

ggctcaaccc acaacaagaa taggccttgc tggattggct gttatgggcc aaaatctggc    120

actcaatatt gctgagaaag gctttcccat ttctgtttac aaccgaacca cttccaaggt    180

tgatgagaca gtagaacgag caaaacaaga aggaaatctt ccagtttatg gctaccatga    240

ccctgaagct tttgttcatt ccattcaaaa gcctagggtg a                        281


<210> SEQ ID NO 70
<211> LENGTH: 261
<212> TYPE: DNA
<213> ORGANISM: Glycine max

<400> SEQUENCE: 70

gattcccaga ccttattttt tctgtcattt gcttcaaatt tcaggagatt aattatggct     60

caacccacaa caagaatagg ccttgctgga ttggctgtta tgggccaaaa tctggcactc    120

aatattgctg agaaaggctt tcccatttct gtttacaacc gaaccacttc caaggttgat    180

gagacagtag aacgagcaaa acaagaagga aatcttccag tttatggcta ccatgaccct    240

gaagcttttg ttcattccat t                                              261


<210> SEQ ID NO 71
<211> LENGTH: 225
<212> TYPE: DNA
<213> ORGANISM: Glycine max

<400> SEQUENCE: 71

cttaatttgt ctctcattcg cttcaaattt caggaaatca attatggctc gaccctcgac     60

aagaataggc cttgctggac tggctgttat ggggcaaaat ctagcactca atattgctga    120

gaaaggcttt cccatttctg tttataaccg aaccacttcc aaggttgatg agactgtaga    180

acgagcaaaa caagaaggaa atcttccagt ttatggctac catga                    225


<210> SEQ ID NO 72
<211> LENGTH: 265
<212> TYPE: DNA
```

-continued

<213> ORGANISM: Glycine max

<400> SEQUENCE: 72
ccagacctta atttttctct cattcgcttc agctttcagg aaatcaatta tggctcaacc 60
ctcaacaaga ataggccttg ctggactggc tgttatgggc caaaatctag cactcaatat 120
tactgagaaa ggctgtccca tttctgttta taaccgaacc acttccaagg ttgatgagac 180
tgcagaacga gcaaaacaag aaggacatct tccagtttat ggctaccatg accccgaagc 240
ttttgttcat tccattcaaa agccc 265

<210> SEQ ID NO 73
<211> LENGTH: 288
<212> TYPE: DNA
<213> ORGANISM: Glycine max
<220> FEATURE:
<223> OTHER INFORMATION: unsure at all n locations

<400> SEQUENCE: 73
cccgcatctt ttgatccgtg ctctgtgatt cccagacctt atttntnctg tcatttgctt 60
caaatntcag gagattaatt atggctcaac ccacaacaag aataggcctt gctggattgg 120
gctgttatgg gccaaaatct ggcactcaat attgctgaga aaggctttcc catttctgtt 180
tacanccgaa ccacttccaa ggttgatgag acagtagaac gagcaaanca aganggaaat 240
cttccagttt atggctacca tgaccctgaa gcttttgttc nttccatt 288

<210> SEQ ID NO 74
<211> LENGTH: 259
<212> TYPE: DNA
<213> ORGANISM: Glycine max

<400> SEQUENCE: 74
gatccgtgct ctgtgattcc cagaccttat tttttctctc atttgcttca aatttcagga 60
gattaattat ggctcaaccc acaacaagaa taggccttgc tggattggct gttatgggcc 120
aaaatctggc actcaatatt gctgagaaag gctttcccat ttctgtttac aaccgaacca 180
cttccaaggt tgatgagaca gtagaacgag caaaacaaga aggaaatctt ccagtttatg 240
gctaccatga ccctgaagc 259

<210> SEQ ID NO 75
<211> LENGTH: 250
<212> TYPE: DNA
<213> ORGANISM: Glycine max

<400> SEQUENCE: 75
tccagacctt aatttttctc tcattcgctt caaatttcag gaaatcaatt atggctcaac 60
cctcaacaag aataggcctt gctggactgg ctgttatggg ccaatatcta gcactcaata 120
ttgctgagaa aggtttccca tttctgttta taaccgaacc acttccaagg ttgatgagac 180
tgtagaacga gcaaaacaag aaggaaatct tccagtttat ggctaccatg accccgaagc 240
ttttgttcat 250

<210> SEQ ID NO 76
<211> LENGTH: 220
<212> TYPE: DNA
<213> ORGANISM: Glycine max
<220> FEATURE:
<223> OTHER INFORMATION: unsure at all n locations

<400> SEQUENCE: 76

-continued

```
cnagacctta atttttctct cattcgcttc aaatttcagg aaatcaatta tggctcaacc     60

ctcaacaaga ataggccttg ctggactggc tgttatgggc caaaatctag cactcaatat    120

tgctgagaaa ggctttccca tttcgncnta taaccgaacc acttccaagg ttgatgagac    180

tgtagaacga gcaaaacaag aaggaaatct tccagtttnt                          220
```

<210> SEQ ID NO 77
<211> LENGTH: 230
<212> TYPE: DNA
<213> ORGANISM: Glycine max

<400> SEQUENCE: 77

```
tgtgattcca gaccttaatt tttctctcat tcgcttcaaa tgtcaggaaa tcaagtatgg     60

ctcaaccctc cacaagagta ggccttgctg gactggctgt tatgggccca aatctagcac    120

tcaatattgc tgagaaaggc tttcccattt ctgtttataa ccgaaccact tccaaggttg    180

atgagactgt agaacgagca aaacctgaag gcaatcttcc agtttatggc               230
```

<210> SEQ ID NO 78
<211> LENGTH: 259
<212> TYPE: DNA
<213> ORGANISM: Glycine max

<400> SEQUENCE: 78

```
cttatttttt ctgtcatttg cttcaaattt caggagatta attatagctc aacccacaac     60

aagaataggc cttgctggat tggctgttat gggccaaaat ctggcactca atattgctga    120

gaaaggcttt cccatttctg tttacaaccg aaccacttcc aaggttgatg agacagtaga    180

acgagcaaaa caagaaggaa atcttccagt ttatggctac catgaccctg aagcttttgt    240

tcattccatt caaaagcct                                                 259
```

<210> SEQ ID NO 79
<211> LENGTH: 256
<212> TYPE: DNA
<213> ORGANISM: Glycine max

<400> SEQUENCE: 79

```
cttttgatcc gtgctctgtg attcccagac cttatttttt ctgtcatttg cttcaaattt     60

caggagatta attatggctc aacccacaac aagaataggc cttgctggat tggctgttat    120

gggccaaaac tggcactcaa tattgctgag aaaggctttc ccatttctgt ttacaaccga    180

accacttcca aggttgatga gacagtagaa cgagcaaaac aagaaggaaa tcttccagtt    240

tatggctacc atgacc                                                    256
```

<210> SEQ ID NO 80
<211> LENGTH: 253
<212> TYPE: DNA
<213> ORGANISM: Glycine max

<400> SEQUENCE: 80

```
cccagacctt attttttctg tcatttgctt caaatttcag gagataatta tggctcaacc     60

cacaacaaga ataggccttg ctggattggc tgttatgggc caaaatctgg cactcaatat    120

tgctgagaaa ggctttccca tttctgttta caaccgaacc acttccaagg ttgatgagac    180

agtagaacga gcataacaag aaggaaatct tccagtttat ggctaccatg accctgaagc    240

ttttgttcat tcc                                                       253
```

-continued

<210> SEQ ID NO 81
<211> LENGTH: 198
<212> TYPE: DNA
<213> ORGANISM: Glycine max

<400> SEQUENCE: 81
ccagacctta atttttctct cattcgcttc aaatttcagg aaatcaatta tggctcaacc 60
ctcaacaaga ataggccttg ctggactggc tgttatgggc caaaatctag cactcaatat 120
tgctgagaaa ggctttccca tttctgttta taaccgaacc acttccaagg ttgatgagac 180
tgtagaccga gcaaaaca 198

<210> SEQ ID NO 82
<211> LENGTH: 281
<212> TYPE: DNA
<213> ORGANISM: Glycine max

<400> SEQUENCE: 82
atataatata catacatata tatataactt attccccgc atcttttgat ccgtgctctg 60
tgattcccag accttatttt ttctgtcatt tgcttcaaat ttcaggagat taattatggc 120
tcaacccaca acaagaatag gccttgctgg attggctgtt atgggccaaa atctggcact 180
caatattgct gagaaaggct ttcccatttc tgtttacaac cgaaccactt ccaaggttga 240
tgagacagta gaacgagcaa aacaagaagg aaatcttcca g 281

<210> SEQ ID NO 83
<211> LENGTH: 245
<212> TYPE: DNA
<213> ORGANISM: Glycine max

<400> SEQUENCE: 83
tcgatcgggt atcacatctg aattgggact gctcctattc tgggtactat tctgagaata 60
attatggctc aacccacaac aagaataggc cttgctggat tggctgttat gggccaaaat 120
ctggcactca atattgctga gaaaggcttt cccatttctg tttacaaccg aaccacttcc 180
aaggttgatg agacagtaga acgagcaaaa caagaaggaa atcttccagt ttatggctac 240
catga 245

<210> SEQ ID NO 84
<211> LENGTH: 230
<212> TYPE: DNA
<213> ORGANISM: Glycine max

<400> SEQUENCE: 84
aaccgaacca cttccaaggt tgtaaacaga aatgggaaag cctttctcag caatattgag 60
tgccagattt tggcccataa cagccaatcc agcaaggcct attcttgttg tgggttgagc 120
cataattaat ctcctgaaat ttgaagcaaa tgacagaaaa aataaggtct gggaatcaca 180
gagcacggat caaaagatgc gggggaataa gttatatata tatgtatgta 230

<210> SEQ ID NO 85
<211> LENGTH: 88
<212> TYPE: DNA
<213> ORGANISM: Glycine max

<400> SEQUENCE: 85
ggctcgagct cagtcgcttc aaatttcagg aaatcaatta tggctcaacc ctcaacaaga 60
ataggccttg ctggactggc tgttatgg 88

-continued

<210> SEQ ID NO 86
<211> LENGTH: 202
<212> TYPE: DNA
<213> ORGANISM: Glycine max

<400> SEQUENCE: 86
caaaaagcaa tctagctttg catactctac ctctacttca cctcgttacc aaaactagca 60
atcatgtctg tcgagcccaa gggagatgtc ggactcattg gtctggccgt tatgggtcaa 120
aacctgatcc tcaacatgaa cgacaagggt ttcaccgtcg tcgcctacaa ccgaaccacc 180
tccaaggtcg accacttcct gg 202

<210> SEQ ID NO 87
<211> LENGTH: 173
<212> TYPE: DNA
<213> ORGANISM: Glycine max

<400> SEQUENCE: 87
caaaaagcaa tctagctttg catactctac ctctacttca cctcgttacc aaaactagca 60
atcatgtctg tcgagcccaa gggagatgtc ggactcattg gtctggccgt tatgggtcaa 120
aacctgatcc tcaacatgaa cgacaagggt ttcaccgtcg tcgcctacaa ccg 173

<210> SEQ ID NO 88
<211> LENGTH: 237
<212> TYPE: DNA
<213> ORGANISM: Glycine max

<400> SEQUENCE: 88
aggaaacgcc tttcctgaga agtcggaagg aagagagtga gagtgagagt gagagtgaga 60
gagatggagt ttggattttt gggtttgggg ataatgggta aggctatggc aatcaatctg 120
ctacgccatg gcttcaaggt cactatttgg aacagaaccc tctccaagtg tgatgaactc 180
gtgcaacatg gtgcttcagt tggagaaacc ccagcaactg tagtcaagaa atgcaag 237

<210> SEQ ID NO 89
<211> LENGTH: 255
<212> TYPE: DNA
<213> ORGANISM: Glycine max

<400> SEQUENCE: 89
gattggtggt acactggaaa ttaaccatgg ctcaacctgc aagcctcaca agaataggcc 60
ttgctggcct ggctgtgatg ggccaaaacc ttgctctcaa cattgctgag aaaggctttc 120
ccatttctgt ctacaaccgg accgcgtcca aggttgatga gacagttgaa agagcaaaac 180
aagaaggaaa ccttcctgtg tatggctacc atgaccctaa attctttgtc caatccattc 240
aaaagccaag ggtca 255

<210> SEQ ID NO 90
<211> LENGTH: 256
<212> TYPE: DNA
<213> ORGANISM: Glycine max

<400> SEQUENCE: 90
ctttctcgca tgaattttcg aacattgaac aggaaattaa ccatggctca acctgcaagc 60
ctcacaagaa taggccttgc tggcctggct gtgatgggcc aaaaccttgc tctcaacatt 120
gctgagaaag gctttcccat ttctgtctac aaccggaccg cgtccaaggt tgatgagaca 180

-continued

```
gttgaaagag caaaacaaga aggaaacctt cctgtgtatg gctaccatga ccctaaattc    240

tttgtccaat ccattc                                                    256


<210> SEQ ID NO 91
<211> LENGTH: 256
<212> TYPE: DNA
<213> ORGANISM: Glycine max

<400> SEQUENCE: 91

cacccagatc tcaattttct gcaatttcac tcagaccagg aaattaacca tggctcaacc     60

tgcaagcctc acaagaatag gccttgctgg cctggctgtg atgggccaaa accttgctct    120

caacattgct gagaaaggct ttcccatttc tgtctacaac cggaccgcgt ccaaggttga    180

tgagacagtt gaaagagcaa aacaagaagg aaaccttcct gtgtatggct accataaccc    240

taaattcttt gtccaa                                                    256


<210> SEQ ID NO 92
<211> LENGTH: 249
<212> TYPE: DNA
<213> ORGANISM: Glycine max

<400> SEQUENCE: 92

cgatgccaca acttctgtgt tggattggtg gtacactgga aattaaccat ggctcaaaca     60

acaagcctca caagaatagg ccttgctggc ctggctgtga tgggccaaaa ccttgctctc    120

aacattgctg agaaaggctt tcccatttct gtctacaacc ggaccgcgtc caaggttgat    180

gagacagttg aaagagcaaa acaagaagga aaccttcctg tgtatggcta ccatgaccct    240

aaattcttt                                                            249


<210> SEQ ID NO 93
<211> LENGTH: 250
<212> TYPE: DNA
<213> ORGANISM: Glycine max

<400> SEQUENCE: 93

ccagatctca attttctgca atttcactca gaccaggacc ttaaccatgg ctcaacctgc     60

aagcctcaca agaataggcc ttgctggcct ggctgtgatg ggccaaaacc ttgctctcaa    120

cattgctgac aaaggctttc ccatttctgt ctacaaccgg accgcgtcca aggttgatga    180

gacagttgaa agagcaaaac aagaaggaaa ccttcctgtg tatggctacc ataacctcaa    240

attctttgtc                                                           250


<210> SEQ ID NO 94
<211> LENGTH: 273
<212> TYPE: DNA
<213> ORGANISM: Glycine max

<400> SEQUENCE: 94

gttaatttgc accttttgtt tctctctaga aattagaagt tcatgcttaa actttacctt     60

gatacttctt tctcgcatga attttcgaac attgaacagg aaattaacca tggctcaacc    120

tgcaagcctc acaagaatag gccttgctgg cctggctgtg atgggccaaa accttgctct    180

caacattgct gagaaaggct ttcccatttc tgtctacaac cggaccgcgt ccaaggttga    240

tgagacagtt gaaagagcaa aacaagaagg aaa                                 273


<210> SEQ ID NO 95
<211> LENGTH: 250
```

-continued

<212> TYPE: DNA
<213> ORGANISM: Glycine max

<400> SEQUENCE: 95
gttaatttgc accttttgtt tctctctaga aattagaagt tcatgcttaa actttacctt 60
gatacttctt tctcgcatga attttcgaac attgaacagg aaattaacca tggctcaacc 120
tgcaagcctc acaagaatag gccttgctgg cctggctgtg atgggccaaa accttgctct 180
caacattgct gagaaaggct ttcccatttc tgtctacaac cggaccgcgt ccaaggttga 240
tgagacagtt 250

<210> SEQ ID NO 96
<211> LENGTH: 307
<212> TYPE: DNA
<213> ORGANISM: Glycine max

<400> SEQUENCE: 96
caacagtgca tgcttgcaat tcaacttagt ctacagtgtc cttgtatatt actcttttgt 60
ccttgctcac ttgatgcttt ctacaatctc tgggacaccc agatctcaat tttctgcaat 120
ttcactcaga ccaggaaatt aaccatggct caacctgcaa gcctcacaag aataggcctg 180
ctggcctggg ctgtgatggg ccaaaacctt gctctcaaca ttgctgagaa aggctttccc 240
atttcgtcta caaccggacc gcgtccaagg ttgatgagac agttgaaaga gcaaacaaga 300
aggaact 307

<210> SEQ ID NO 97
<211> LENGTH: 241
<212> TYPE: DNA
<213> ORGANISM: Glycine max

<400> SEQUENCE: 97
ctaaaaagca cttcttagtt ctccctctcc cactaaaaac catagtactc tagataataa 60
ttaacatcaa ccctcactcc ttcgcacacc aaacccttcc ttcctatctc tcactaatct 120
aatggaatcc gcagcactgt cgcgcatagg cctggcgggc ctggcggtga tgggccaaaa 180
cctagcccta gacatcgcag aaaaggggtt cccgatctcc gtgtacaacc gcacggcctc 240
t 241

<210> SEQ ID NO 98
<211> LENGTH: 401
<212> TYPE: DNA
<213> ORGANISM: Glycine max

<400> SEQUENCE: 98
gcgtccatac gactgcgaga agacgacaga aggggatgtt aagaaggctc tttatgcagc 60
caaaatctgt agttatgcac agggaatgaa tttgatccgt gcaaacagta ttgagcgggg 120
ttgggatttg aagttgggtg aactggcccg gatttggaaa gggggttgca ttattagagc 180
aatattctta gacagaatca agcaggcata tgaaagaaac cctaatctgg caaaccttct 240
tgtggatcca gagtttgcac aggaaatcat tgattaccaa tctgcctgca ggagagttgt 300
ttgccttgct atcaattctg gtattagcac tccaggtatg tctgctaatc ttgcttattt 360
tgacacttac agaaaggaac agtttccagc caatttggtg c 401

<210> SEQ ID NO 99
<211> LENGTH: 435
<212> TYPE: DNA

-continued

<213> ORGANISM: Glycine max

<400> SEQUENCE: 99
cccacgcgtc cgtacggctg cgagaagacg acagaaggga gaaaaaattg gttgatgatg 60
ttaggaaggc tctttatgca gccaaaatct gtagttatgc acagggaatg aatttgatcc 120
gtgcaaagag tattgaaaag ggttgggatt tgaagttggg tgaactggcc cggatttgga 180
aaggtggttg catcattaga gcaatattct tagacagaat caagcaagcg tatgatagaa 240
accctaatct ggcaaacctt cttgtggatc cagagtttgc aaaggaaata atcgatcgcc 300
aatctgcctg gaggagagtt gtttgccttg ctatcaattc tggtatcagc actccaggta 360
tgtctgctag tcttgcttat tttgacactt acagaaggga aaggttgcca gctaatttgg 420
tgcaagctca acgag 435

<210> SEQ ID NO 100
<211> LENGTH: 376
<212> TYPE: DNA
<213> ORGANISM: Glycine max

<400> SEQUENCE: 100
cacgcgtcca tacggctgcg agaagacgac agaaggggat gttaggaagg ctctttatgc 60
agccaaaatc tgtagttatg cacagggaat gaatttgatc cgtgcaaaga gtattgaaaa 120
gggttgggat ttgaagttgg gtgaactggc ccggatttgg aaagggggtt gcattattag 180
agcaatattc ttagacagaa tcaagcaggc atatgaaaga aaccctaatc tggcaaacct 240
tcttgtggat ccagagtttg caaaggaaat aattgattac caatctgcct ggaggagagt 300
tgtttgcctt gctatcaatt ctggtattag cactccaggt atgtctgcta gtcttgctta 360
gtttgacact tacaga 376

<210> SEQ ID NO 101
<211> LENGTH: 340
<212> TYPE: DNA
<213> ORGANISM: Glycine max
<220> FEATURE:
<223> OTHER INFORMATION: unsure at all n locations

<400> SEQUENCE: 101
acgcgtccgc ccacgcgtcc gtacggctgc gagaagacga cagaaggggg atccgtgctc 60
tgtgattcca gaccttaatt tttctctcat tcgcttcaaa tttcnggaaa tcaattatgg 120
ctcaaccctc aacaagaata ggccttgctg gactggctgt tatgggccaa aatctagcac 180
tcaatattgc tgagaaaggc tttcccattt ctgtttataa ccgaaccact tccaaggttg 240
atgagactgt agaacgagca aaacaagaag gaaatcttcc agtttatggc taccatgacc 300
ccgaagcttt tgttcattcc attcaaaaac ctaaggtgat 340

<210> SEQ ID NO 102
<211> LENGTH: 354
<212> TYPE: DNA
<213> ORGANISM: Glycine max

<400> SEQUENCE: 102
agtacggctg cgagaagacg acagaagggg ttgccagcta atttggtgca agctcaacga 60
gactactttg gtgctcatac atatgaaagg gttgacatag aggggtctta ccatactgag 120
tggttcaagc ttgccaaaca gtctagaatt tagattactg tatttgaacc aatcaggatt 180
ttcctaataa atgtaatgtt ttctgctcag actgtatgct gagttgagtt tacatagcca 240

-continued

```
caacgtggtg aagttttatg tatattattt ccaactgaat tgcatgatag tttgttttcc    300

aactatgttg tatctttgct gattatgctt tgtgcttgat acaaaattgt ccca          354


<210> SEQ ID NO 103
<211> LENGTH: 399
<212> TYPE: DNA
<213> ORGANISM: Glycine max
<220> FEATURE:
<223> OTHER INFORMATION: unsure at all n locations

<400> SEQUENCE: 103

aggctgcgag aagacgacag aagggggtgc tctatgattc ccagacctta ttttttctgt     60

catttgcttc aaatttcagg gagattaatt atggctcaac ccacaacaag aataggcctt    120

gctggattgg ctgttatggg ccaaaatctg gcactcaata ttgctgagaa aggctttccc    180

atttctgttt acaaccgaac cacttccaag gttgatgaga cagtagaacg agcaaaacaa    240

gaaggaaatc ttccagttta tggctaccat gaccctgaag cttttgttca ttccattcaa    300

aagcctaagg tgataataat gcttgttaag gctggggcac ctgttgacca gaccattaag    360

aacctatctg cgtacatgga anaaagtgac tgtataatt                            399


<210> SEQ ID NO 104
<211> LENGTH: 179
<212> TYPE: DNA
<213> ORGANISM: Zea mays

<400> SEQUENCE: 104

gagctgtcgg tggccgctcc tacgatcgag gcgtccttgg actcgaggtt cctgagcggg     60

ctgaaggacg agcgggtgga tgcctccaag atcttccatg gtgactacta ctccaccggc    120

tcgccggtgg acaaggcgca ctggttggag gacgtgatgc aggccctgta cgcgtccaa     179


<210> SEQ ID NO 105
<211> LENGTH: 270
<212> TYPE: DNA
<213> ORGANISM: Zea mays

<400> SEQUENCE: 105

tagcgcgacg gccgcccttt tttttttttt ttgagaatca tcatagcaat tgcataccaa     60

aattaagaga atcaaactgt gcgtacctac atcacagtaa aactgaagct acacaatgtt    120

cttcacttgc caaccataca gtacagcatt atttgaagta ctcgacttgg atctagaagc    180

ataaagataa caatagtaaa acaaaagata acccacagag agacatcaca caaagcagac    240

aacatcactt ctcataccaa ccaattcctc                                      270


<210> SEQ ID NO 106
<211> LENGTH: 291
<212> TYPE: DNA
<213> ORGANISM: Zea mays
<220> FEATURE:
<223> OTHER INFORMATION: unsure at all n locations

<400> SEQUENCE: 106

ccgcaacgnn cncgtccttg atgcccggan gctcgttcga cgcttacaag tacgtcgaag     60

acattgttct caaggtggct gctcaggtcc ctgacagtgg cccgtgtgtn acgtacattg    120

gcaaaggtgg atcgggcaac tttgtcaaga tggttcacaa cggaatcgag tatgggcgat    180

atgcagctga tttccgaggc ttacgacgtt ctcaagtcgg tcggtaagct caccaacagt    240
```

-continued gagctgcacc aggtgttctc cgagtggaac aagggcgagt cctgagttct t 291

<210> SEQ ID NO 107
<211> LENGTH: 287
<212> TYPE: DNA
<213> ORGANISM: Zea mays
<220> FEATURE:
<223> OTHER INFORMATION: unsure at all n locations

<400> SEQUENCE: 107
cgcagacgga ggacggcgcc tgcgtcacct tcgtcgggcc cggcggcgcc ggcaacttcg 60
tcaagatggt gcacaacggg ancgagtacg gcgacatgca gcaccatcgc cgaggcgtac 120
gacgtgctcc gcaggctcgg gggcctgtcc aactccgaga tcgccgatgt cttcgctgag 180
tggaacaggg gggagctcga gagcttcctg gtcnagatca ccgccgacat tttcaccgtg 240
gctgacccgt tggacgggag cgggagtggc ggcggggcgt ggttgat 287

<210> SEQ ID NO 108
<211> LENGTH: 192
<212> TYPE: DNA
<213> ORGANISM: Zea mays

<400> SEQUENCE: 108
cggcgacatg cagctcatcg ccgaagcgta cgacgtgctc cgcaggctcg ggggcctgtc 60
caactccgag atcgccgacg tcttcgcgga gtggaacagg ggggagctcg agagcttcct 120
ggtccagatc atcgccgaca ttttcatcgt gctgacccgt tagactggag ctggatcggc 180
ggtcaggacg ct 192

<210> SEQ ID NO 109
<211> LENGTH: 281
<212> TYPE: DNA
<213> ORGANISM: Zea mays

<400> SEQUENCE: 109
gatggctgct caggtacctg ttagcggccc gtgcgtcaca tgtattggca aatgtggatc 60
agggaacttc gtcaagatgc ttcacaattg aattgagtat ggttgcatgc aacttatcga 120
cgaggcttat gatttactca agtcggtgag taagctcatc aacagcgagc tgcatcaggt 180
attctctgag tgtgaatcaa ggtgagctcc tcagtatctt gattaagatc acggccgaca 240
tcgttggtat ctaggatcac aagggtgaat gctacctcgt c 281

<210> SEQ ID NO 110
<211> LENGTH: 325
<212> TYPE: DNA
<213> ORGANISM: Zea mays

<400> SEQUENCE: 110
tagcgctcac aagaatcggt cttgctgagc ctgcgtgtca tggcggcaga aacttgccct 60
caacattgca gaggaagggt tccccatctc tgtgtacaac aggagaagct ccaaggtgga 120
cgagaccgtg ccacgtgcca acgcagtacg aaaccttccc gtctagggct tccatgaccc 180
cgcgttcgtt gtgaagtcca ttcagaagcc acgggtggtg atcatgctcg tcaaagccgg 240
cgcgcagttg accagaccat cgcgactctc gcagctcact tggagcaggg cgactgcatc 300
atcgctcgtg ggaacgagtg gtacg 325

<210> SEQ ID NO 111
<211> LENGTH: 222

-continued

<212> TYPE: DNA
<213> ORGANISM: Zea mays

<400> SEQUENCE: 111
aaagggacag ggaagtggac ggtgcagcag gccgccgagc tgtcggtggc cgctcctacg 60
atcgaagcgt tcttggactc gaggttcctg agcgggctga aggacgagcg ggtggaggcc 120
tccaagatct tccagggtga ctactactcc accggctcgc cggtggacaa ggcgcagctg 180
gtggaggacg tgaggcaggc cctgtacgcg tacaagatct gc 222

<210> SEQ ID NO 112
<211> LENGTH: 334
<212> TYPE: DNA
<213> ORGANISM: Zea mays

<400> SEQUENCE: 112
tgactactcc actggcctac cggtggacaa ggcacagctg atcgaggacg tgaggcaagc 60
tctatatgcc tccaagatct gcagttacgc gcagggcatg aacatcatca aggccaagag 120
ctcagagaaa ggatggggcc tcaaccttgg tgagctagcg aggatctgga agggagggtg 180
catcatccgt gccatcttcc tcgaccgcat caagaaggcg tacgatagga accctaacct 240
tgccaacctc ctcgttgacc ccgagttcgc ccaggagatc atagacaggc aagctgcctg 300
gcgcagggtt gtctgccttg ccatcaacaa tggc 334

<210> SEQ ID NO 113
<211> LENGTH: 314
<212> TYPE: DNA
<213> ORGANISM: Zea mays

<400> SEQUENCE: 113
gaggcctcca agatcttcca gggtgactac tactccaccg gctcgccggt ggacaaggcg 60
cactgagtgg aggacgtgag gcaggccctg tacgcgtcca agatctgcag ctacgcgcag 120
ggcatgaaca tcatcaaggc caagagcgcg gagaaaggct ggggcgtcga cctcggcgaa 180
ctggcacagg atctagaagg gcgggtgcat catccgcgcc atcttcctgg accgcatcaa 240
gaaggcctac gacaggaacc cgggcctcgc cagcctgctc gtagaccccg agttcgcgca 300
ggagatcatg gaca 314

<210> SEQ ID NO 114
<211> LENGTH: 271
<212> TYPE: DNA
<213> ORGANISM: Zea mays

<400> SEQUENCE: 114
gaggcaagct ctatatgcct ccaagatctg cagttacgcg cagggcatga acatcatcaa 60
ggccaagagc tcagagaaag gatggggcct caaccttggt gagctagcga ggatctggaa 120
gggagggtgc atcatccgtg ccatcttcct cgaccgcatc aagaaggcgt acgataggaa 180
ccctaacctt gccaacctcc tcgttgaccc cgagttcgcc caggagatca tagacaggca 240
agctgcctgg cgcagggttg tctgccttgc c 271

<210> SEQ ID NO 115
<211> LENGTH: 271
<212> TYPE: DNA
<213> ORGANISM: Zea mays

<400> SEQUENCE: 115

-continued

```
ctccactggc ctaccggtgg acaaggcaca gctgatcgag gacgtgaggc aagctctata     60

tgcctccaag atctgcagtt acgcgcaggg catgaacatc atcaaggcca agagctcaga    120

gaaaggatgg ggcctcaacc ttggtgagct agcgaggatc tggaagggag ggtgcatcat    180

ccgtgccatc ttcctcgacc gcatcaagaa ggcgtacgat aggaacccta accttgccaa    240

cctcctcgtt gaccccgagt tcgcccagga g                                   271


<210> SEQ ID NO 116
<211> LENGTH: 289
<212> TYPE: DNA
<213> ORGANISM: Zea mays

<400> SEQUENCE: 116

gaggacgtga ggcaagctct atatgcctcc aagatctgca gttacgcgca gggcatgaac     60

atcatcaagg ccaagagctc agagaaagga tggggcctca accttggtga gctagcgagg    120

atctggaagg gagggtgcat catccgtgcc atcttcctcg accgcatcaa gaaggcgtac    180

gataggaacc ctaaccttgc caacctcctc gttgaccccg agttcgccca ggagatcata    240

gacaggcaag ctgcctggcg cagggttgtc tgccttgcca tcaacaatg                289


<210> SEQ ID NO 117
<211> LENGTH: 266
<212> TYPE: DNA
<213> ORGANISM: Zea mays

<400> SEQUENCE: 117

ctacgcgcag ggcatgaaca tcatcaaggc caagagcgcg gagaaaggct gggggctcaa     60

cctcggcgag ctggccagga tctggaaggg cgggtgcatc atccgcgcca tcttcctgga    120

ccgcatcaag aaggcctacg acaggaaccc gggcctcgcc agcctgctcg tagaccccga    180

gttcgcgcag gagatcatgg acaggcaggc ggcgtggcgc agggtggtgt gcctcgccat    240

caacaacggc gtcagacccc gggaat                                         266


<210> SEQ ID NO 118
<211> LENGTH: 264
<212> TYPE: DNA
<213> ORGANISM: Zea mays

<400> SEQUENCE: 118

cgccacgccg cctgcctgtc catgatctcc tgcgcgaact cggggtctac gagcaggctg     60

gcgaggcccg ggttcctgtc gtaggccttc ttgatgcggt ccaggaagat ggcgcggatg    120

atgcacccgc ccttccagat cctggccagc tcgccgaggt tgagccccca gcctttctcc    180

gcgctcttgg ccttgatgat gttcatgccc tgcgcgtagt gcagatcttg gacgcgtaca    240

gggcctgcct cacgtcctcc acca                                           264


<210> SEQ ID NO 119
<211> LENGTH: 254
<212> TYPE: DNA
<213> ORGANISM: Zea mays

<400> SEQUENCE: 119

cggacgcgtg gcggaccgtg gggacgtga ggcaagctct atatgcctcc aagatctgca     60

gttacgcgca aggcatgaac agcatcaagg ccaagagctc agagaaagga tggggcctca    120

accttggtga gctagcgagg atctggaagg gagggtgcat catccgtgcc atcttcctcg    180

accgcatcaa gaaggcgtac gataggaacc ctaaccttgc caacctcctc gttgaccccg    240
```

-continued

```
agttcgccca ggag                                                      254

<210> SEQ ID NO 120
<211> LENGTH: 242
<212> TYPE: DNA
<213> ORGANISM: Zea mays

<400> SEQUENCE: 120

gcacgagctt ggactcgagg ttcctgagcg ggctgaagga cgagcgggtg gaggcctcca     60

agatcttcca gggtgactac tactccaccg gctcgccggt ggacaaggcg cactggtgga    120

ggacgtgagg caggccctgt acgcgtccaa gatctgcagc tacgcgcagg gcatgaacat    180

catcaaggcc aagagcgcgg agaaaggctg ggggctcaac ctcggcgagc tggccaggat    240

ct                                                                   242

<210> SEQ ID NO 121
<211> LENGTH: 225
<212> TYPE: DNA
<213> ORGANISM: Zea mays

<400> SEQUENCE: 121

acgcgtccaa gatctgcagc tacgcgcagg gcatgaacat catcaaggcc aagagcgcgg     60

agaaaggctg ggggctcaac ctcggcgagc tggccaggat ctggaagggc gggtgcatca    120

tccgcgccat cttcctggac cgcatcaaga aggcctacga caggaacccg ggcctcgcca    180

gcctgctcgt agaccccgag ttcgcgcagg agatcatgga caggc                    225

<210> SEQ ID NO 122
<211> LENGTH: 220
<212> TYPE: DNA
<213> ORGANISM: Zea mays

<400> SEQUENCE: 122

acgcgtccaa gatctgcagc tacgcgcagg gcatgaacat catcaaggcc aagagcgcgg     60

agaaaggctg ggggctcaac ctcggcgagc tggccaggat ctggaagggc gggtgcatca    120

tccgcgccat cttcctggac cgcatcaaga aggcctacga caggaacccg ggcctcgcca    180

gcctgctcgt agaccccgag ttcgcgcagg agatcatgga                          220

<210> SEQ ID NO 123
<211> LENGTH: 248
<212> TYPE: DNA
<213> ORGANISM: Zea mays

<400> SEQUENCE: 123

gtgcatcatc cgtgccatct tcctcgaccg catcaagaag gcgtacgata ggaaccctaa     60

ccttgccaac ctcctcgttg accccgagtt cgcccaggag atcatagaca ggcaagctgc    120

ctggcgcagg gttgtctgcc ttgccatcaa caatggcgtt agcaccccag gcatgtctgc    180

aagtctggcc tacttcgact cgtaccgaag agttaggttt cgcgaaactg tggtggaggc    240

tcagagag                                                             248

<210> SEQ ID NO 124
<211> LENGTH: 209
<212> TYPE: DNA
<213> ORGANISM: Zea mays

<400> SEQUENCE: 124
```

```
acgcgtccaa gatctgcagc tacgcgcagg gcatgaacat catcaaggcc aagagcgcgg      60

agaaaggctg ggggctcaac ctcggcgagc tggccaggat ctggaagggc gggtgcatca     120

tccgcgccat cttcctggac cgcatcaaga aggcctacga caggaacccg ggcctcgcca     180

gcctgctcgt agaccccgag ttcgcgcag                                       209
```

<210> SEQ ID NO 125
<211> LENGTH: 210
<212> TYPE: DNA
<213> ORGANISM: Zea mays

<400> SEQUENCE: 125

```
acgcgtccaa gatctgcagc tacgcgcagg gcatgaacat catcaaggcc aagagcgcgg      60

agaaaggctg ggggctcaac ctcggcgagc tggccaggat ctggaagggc gggtgcatca     120

tccgcgccat cttcctggac cgcatcaaga aggcctacga caggaacccg ggcctcgcca     180

gcctgctcgt agaccccgag ttcgcgcagg                                      210
```

<210> SEQ ID NO 126
<211> LENGTH: 206
<212> TYPE: DNA
<213> ORGANISM: Zea mays

<400> SEQUENCE: 126

```
acgcgtccaa gatctgcagc tacgcgcagg gcatgaacat catcaaggcc aagagcgcgg      60

agaaaggctg ggggctcaac ctcggcgagc tggccaggat ctggaagggc gggtgcatca     120

tccgcgccat cttcctggac cgcatcaaga aggcctacga caggaacccg ggcctcgcca     180

gcctgctcgt agaccccgag ttcgcg                                          206
```

<210> SEQ ID NO 127
<211> LENGTH: 176
<212> TYPE: DNA
<213> ORGANISM: Zea mays

<400> SEQUENCE: 127

```
gcgccatctt cctggaccgc atcaagaagg cctacgacag gaacccgggc ctcgccagcc      60

tgctcgtaga ccccgagttc gcgcaggaga tcatggacag gcaggcagcg tggcgcaggg     120

tggtgtgcct cgccatcaac aacggcgtca caccccggga atgtccgcta gcctgg         176
```

<210> SEQ ID NO 128
<211> LENGTH: 146
<212> TYPE: DNA
<213> ORGANISM: Zea mays

<400> SEQUENCE: 128

```
cgtgaggcag gccctgtacg cgtccaagat ctgcagctac gcgcagggca tgaacatcat      60

caaggccaag agcgcggaga aaggctgggg gctcaacctc ggcgagctgg ccaggatctg     120

gaagggcggg tgcatcatcc gcgcca                                          146
```

<210> SEQ ID NO 129
<211> LENGTH: 187
<212> TYPE: DNA
<213> ORGANISM: Zea mays

<400> SEQUENCE: 129

```
tggtggagga cgtgaggcag gccctgtacg cgtccaagat ctgcagctac gcgcagggca      60

tgaacatcat caaggccaag agcgcggaga aaggcttggg gctcggcctc ggcgagctgg     120
```

-continued ccaggatctg gaagggcggg tgcatcatcc gcgccatctt cctggaccgc atcaagaatg 180
cctacga 187

<210> SEQ ID NO 130
<211> LENGTH: 123
<212> TYPE: DNA
<213> ORGANISM: Zea mays

<400> SEQUENCE: 130
gcctcaacct tggtgagcta gcgacgatct ggaaaggagg gtgcatcatc cgtgtaatct 60
tcctcgaccg catcaagaag gcgtacgata ggaaccctaa ccttgccaac ctcctcgttg 120
acc 123

<210> SEQ ID NO 131
<211> LENGTH: 83
<212> TYPE: DNA
<213> ORGANISM: Zea mays

<400> SEQUENCE: 131
gtgcatcatc cgtgccatct tcctcgaacg catcgagaag gcgtacgata ggaaccctaa 60
ccttgccaac ctcctcgttg acg 83

<210> SEQ ID NO 132
<211> LENGTH: 270
<212> TYPE: DNA
<213> ORGANISM: Zea mays

<400> SEQUENCE: 132
caggattctg gacaagactg ggatgaaggg gaccgggaaa tggaccgtgc agcaggcggc 60
ggacttgcgg tggcagcgcc acgattgccg cgtcgctgga cgggaggtac ctctcagggt 120
tgaaggacga acgggtcgca gccgctgggg tgctggagga agaggggatg ccggcagcct 180
gttggagacg gttaatgtcg acaagaaggt gctggtggat acggtcaggc aagcgctcta 240
cgcctccaag atttgcagct atgcgcaggg 270

<210> SEQ ID NO 133
<211> LENGTH: 258
<212> TYPE: DNA
<213> ORGANISM: Zea mays

<400> SEQUENCE: 133
cggacgcgtg ggggaaccgt gcagcaggcg gcggacttgc ggtggcagcg cccacgattg 60
ccgcgtcgca ggacgggagg tacctctcag ggttgaagga cgaacgggtc gcagccgctg 120
gggtgctgga ggaagagggg atgccggcag gcctgttgga gacggttaat gtcgacaaga 180
aggtgctggt ggatagggtc aggcaagcgc tctacgcctc caagatttgc agctatgcgc 240
agggaatgaa tctgctgc 258

<210> SEQ ID NO 134
<211> LENGTH: 119
<212> TYPE: DNA
<213> ORGANISM: Zea mays

<400> SEQUENCE: 134
atgcccggtg ttgactactc cagtcggtaa tgagatttcc tgcaggaact tgtctattga 60
tctttgtaag ttaattattt atatgaataa aataagagca aacatgcttg tgtttgggc 119

-continued

<210> SEQ ID NO 135
<211> LENGTH: 87
<212> TYPE: DNA
<213> ORGANISM: Zea mays

<400> SEQUENCE: 135
atgcccggtg ttgactactc cagtcggtaa tgagatttcc tgcaggaact tgtctattga 60
tctttgtaag ttaattattt atatgaa 87

<210> SEQ ID NO 136
<211> LENGTH: 312
<212> TYPE: DNA
<213> ORGANISM: Zea mays

<400> SEQUENCE: 136
atgtcctgga caagaccggg atgaatggaa ctgggaaatg gacagtccag caggctgctg 60
agctttctgt agctgctcct acaatcgagg cgtccttgga ctccaggttc ctcagcggtc 120
tgaaggacga gcgcgttgag gcttccaaaa tcttccaagg tgactactcc actggcctac 180
cggtggacaa ggcacagctg atcgaggacg tgaggcaagc tctatatgcc tccaagatct 240
gcagttacgc gcagggcatg aacatcatca aggccaagag ctcagagaaa ggatggggcc 300
tcaaccttgg tg 312

<210> SEQ ID NO 137
<211> LENGTH: 307
<212> TYPE: DNA
<213> ORGANISM: Zea mays

<400> SEQUENCE: 137
gatcaggcaa cttcgtcaag atggttcaca atggaattga atatggtgac atgcaactta 60
tcgccgaggc ttatgatgtt ctcaagtcgg tgggtaagct cacaaacagc gagctgcatc 120
aggtgttctc tgagtggaac aagggtgagc tcctcagttt cttgattgag atcacggccg 180
acatctttgg tatcaaggat gacaagggtg aaggctacct ggtcgacaag gtcctggaca 240
agaccgggat gaagggaact gggaaatgga cagtccagca ggctgctgag ctttctgtag 300
ctgctcc 307

<210> SEQ ID NO 138
<211> LENGTH: 305
<212> TYPE: DNA
<213> ORGANISM: Zea mays
<220> FEATURE:
<223> OTHER INFORMATION: unsure at all n locations

<400> SEQUENCE: 138
cgatatgcag ctgatttccg aggcttacga cgttctcaag tcggtcggta agctcaccaa 60
cagtgagctg caccaggtgt tctccgagtg gaacaagggg cgagctcctg agcttcttga 120
tcganatcac ggccgacatc tttggcatca aggacgagca tggcgatggc tacctagtgg 180
acaaggtcct tgacaagacc gggatgaaag ggacagggaa gtggacggtg cagcaggccg 240
ccgagctgtc ggtggccgct cctacgatcg angcgtcctt ggactcgagg ttcctgagcg 300
ggctg 305

<210> SEQ ID NO 139
<211> LENGTH: 356
<212> TYPE: DNA
<213> ORGANISM: Zea mays

-continued

<220> FEATURE:
<223> OTHER INFORMATION: unsure at all n locations

<400> SEQUENCE: 139

```
tgttctcaag tcggtgggta agctaacaaa cagcgagctg catcaggtgt tctctgagtg     60

gaacaagggt gagctcctca gtttcttgat tgagatcacg gccgacatct ttggtatcaa    120

ggatgacaag ggtgaaggct acctggtcga caaggtcctg gacaagaccg ggatgaaggg    180

aactgggaaa tggacagtcc agcaggctgc tgagctttct gtagctgctc ctacaatcga    240

ggcgtccttg gactccaggt tcctcagcgg tctaaggacg agcgcgttga ggcttccana    300

atcttccaag gtgactactc cactgagcct acggtgngac aaggcacagc tgatcg        356
```

<210> SEQ ID NO 140
<211> LENGTH: 312
<212> TYPE: DNA
<213> ORGANISM: Zea mays
<220> FEATURE:
<223> OTHER INFORMATION: unsure at all n locations

<400> SEQUENCE: 140

```
ctctgagtgg aacaagggtg agctcctcag tttcttgatt gagatcacgg ccgacatctt     60

tggtatcaag gatgacaagg gtgaaggcta cctggtcgac aaggtcctgg acaagaccgg    120

gatgaaggga actgggnaat ggacagtcca gcaagctgct gaacttcctg tagctgctcc    180

tacaatcaag gcgtccttgg actccaggtc cctcagcggt ctgaatgacg accgcgttga    240

ggcttccaaa atcttccaag gtgactactc cactggccta ccggtggaca aggcacagct    300

gatggaggac gt                                                        312
```

<210> SEQ ID NO 141
<211> LENGTH: 275
<212> TYPE: DNA
<213> ORGANISM: Zea mays

<400> SEQUENCE: 141

```
gtggatcagg caactttgtc aagatggttc acaatgggat tgaatatggt gacatgcaac     60

ttatcgctga ggcttatgat gttctcaagt cggtgggtaa gctaacaaac agcgagctgc    120

atcaggtgtt ctctgagtgg aacaagggtg agctcctcag tttcttgatt gagatcacgg    180

ccgacatctt tggtatcaag gatgacaagg gtgaaggcta cctggtcgac aaggtcctgg    240

acaagaccgg gatgaaggga actgggaaat ggaca                               275
```

<210> SEQ ID NO 142
<211> LENGTH: 268
<212> TYPE: DNA
<213> ORGANISM: Zea mays

<400> SEQUENCE: 142

```
tgttctccga gtggaacaag ggcgagctcc tgagcttctt gatcgagatc acggccgaca     60

tctttggcat caaggacgag catggcgatg gctacctggt ggataaggtc cttgacaaga    120

ccgggatgaa agggacaggg aagtggacgg tgcagcaggc cgccgagctg tcggtggccg    180

ctcctacgat cgaggcgtcc ttggactcga ggttcctgag cgggctgaag gacgagcggg    240

tggaggcctc caagatcttc cagggtga                                       268
```

<210> SEQ ID NO 143
<211> LENGTH: 269
<212> TYPE: DNA

<213> ORGANISM: Zea mays

<400> SEQUENCE: 143
cgacgttctc aagtcggtcg gtaagctcac caacagtgag ctgcaccagg tgttctccga 60
gtggaacaag ggcgagctcc tgagcttctt gatcgagatc acggccgaca tctttggcat 120
caaggacgag catggcgatg gctacctggt ggacaaggtc cttgacaaga ccgggatgaa 180
agggacaggg aagtggacgg tgcagcaggc cgccgagctg tcggtggccg ctcctacgat 240
cgaggcgtcc ttggactcga ggttcctga 269

<210> SEQ ID NO 144
<211> LENGTH: 267
<212> TYPE: DNA
<213> ORGANISM: Zea mays

<400> SEQUENCE: 144
ggcaaaggtg gatcgggcaa ctttgtcaag atggttcaca acggaatcga gtatggcgat 60
atgcagctga tttccgaggc ttacgacgtt ctcaagtcgg tcggtaagct caccaacagt 120
gagctgcacc aggtgttctc cgagtggaac aagggcgagc tcctgagctt cttgatcgag 180
atcacggccg acatctttgg catcaaggac gagcatggcg atggctacct agtggacaag 240
gtccttgaca agaccgggat gaaaggg 267

<210> SEQ ID NO 145
<211> LENGTH: 247
<212> TYPE: DNA
<213> ORGANISM: Zea mays

<400> SEQUENCE: 145
gagatcacgg ccgacatctt tggtatcaag gatgacaagg gtgaaggcta cctggtcgac 60
aaggtcctgg acaagaccgg gatgaaggga actgggaaat ggacagtcca gcaggctgct 120
gagctttctg tagctgctcc tacaatcgag gcgtccttgg actccaggtt cctcagcggt 180
ctgaaggacg agcgcgttga ggcttccaaa atcttccaag gtgactactc cactggccta 240
ccggtgg 247

<210> SEQ ID NO 146
<211> LENGTH: 265
<212> TYPE: DNA
<213> ORGANISM: Zea mays
<220> FEATURE:
<223> OTHER INFORMATION: unsure at all n locations

<400> SEQUENCE: 146
cgtacnnttn gcanangtgg atcgggcaac tttgtcaaga tggtncacaa cggaatcgag 60
tatggcgata tgcagctgat ttccgangct tacgacgttc tcaagtcggt cggtaagctc 120
accaacagtg agnngcacca ngtgttctcc gantggaaca anggnnagct cctgngcttc 180
ttgatcgnga tnncggccga natcnttggc atcaaggacg agcatggcga tggctaccta 240
ntggncaagg tccntgacaa gaccg 265

<210> SEQ ID NO 147
<211> LENGTH: 216
<212> TYPE: DNA
<213> ORGANISM: Zea mays

<400> SEQUENCE: 147
gtccagcagg ctgctgagct ttctgtagct gctcctacaa tccaggcgtc cttggactcc 60

-continued

```
aggttcctca gcggtctgaa ggactagcgc gttgaggctt ccagaatctt ccaaggtgac    120

tactccactg gcctaccggt ggacaatgca cagctgatcg aggacgtgag gcaagctcta    180

tatgcctcca ggatctgcag ttacgcgcag ggcatg                              216


<210> SEQ ID NO 148
<211> LENGTH: 256
<212> TYPE: DNA
<213> ORGANISM: Zea mays

<400> SEQUENCE: 148

caagggtgag ctcctcagtt tcttgattga gatcacggcc gacatctttg gtatcaagga     60

tgacaagggt gaaggctacc tggtcgacaa ggtcctggac aagaccggga tgaagggaac    120

tgggaaatgg acagtccagc aggctgctga gctttctgta gctgctccta caatcgaggc    180

gtccttggac tccaggttcc tcaccgtctt aaaggacgac cgcgttgagg cttccaaaat    240

cttccaaggt ggatat                                                    256


<210> SEQ ID NO 149
<211> LENGTH: 176
<212> TYPE: DNA
<213> ORGANISM: Zea mays

<400> SEQUENCE: 149

aaacagcgag ctgcatcagg tgttctctga gtggaacaag ggtgagctcc tcagtttctt     60

gattgagatc acggccgaca tctttggtat caaggatgac aagggtgaag gctacctggt    120

cgacaaggtc ctggacaagc cgggatgaag ggaactggga aatggacact ccaaca        176


<210> SEQ ID NO 150
<211> LENGTH: 185
<212> TYPE: DNA
<213> ORGANISM: Zea mays

<400> SEQUENCE: 150

cgacgttctc aagtcggtcg gtaagctcac caacagtgag ctgcaccagg tgttctccga     60

gtggaacaag ggcgagctcc tgagcttctt gatcgagatc acggccgaca tctttggcat    120

caaggacgag catggcgatg gctacctggt ggacaaggtc cttgacaaga ccgggatgaa    180

aggga                                                                185


<210> SEQ ID NO 151
<211> LENGTH: 136
<212> TYPE: DNA
<213> ORGANISM: Zea mays

<400> SEQUENCE: 151

caaacagcga gctgcatcag gtgttctctg agtggaacaa ggggcggctc ctcagtttct     60

tgattgagat cacggccgac atctttggta tcaaggatga caagggtgaa ggctacctgg    120

tcgacaaggt cctgga                                                    136


<210> SEQ ID NO 152
<211> LENGTH: 282
<212> TYPE: DNA
<213> ORGANISM: Zea mays

<400> SEQUENCE: 152

cggcgctcac acgtacgaga gggacaggct tcccgccaac ctggtgcagg ctcagagaga     60
```

-continued

```
ctacttcggc gctcacacgt acgagagggt tgacatgcct ggttctttcc acaccgagtg    120

gttcaagatt gcgcgcaact ccaagatctg aacatggcct cgtgtttgca tatgccagta    180

tgccaccgtg tcgagtaatc actcatatta ctgcttgcag ggaggaactg tgtttgattt    240

ttattttcca tgcgcaatgc ttaatttagg tcaggaagtc ca                        282


<210> SEQ ID NO 153
<211> LENGTH: 248
<212> TYPE: DNA
<213> ORGANISM: Zea mays

<400> SEQUENCE: 153

gcacgagcag ggataggctt cccgccaacc tggtgcaggc tcagagagac tacttcggcg     60

ctcacacgta cgagagggtt gacatgcctg gttctttcca caccgagtgg ttcaagattg    120

cgcgcaactc caagatctga acatggcctc gtgtttgcat atgccagtat gccaccgtgt    180

cgagtaatca atcatattac tgcttgcagg gaggaactgt gtttgatttt tattttccat    240

gcgcaatg                                                              248


<210> SEQ ID NO 154
<211> LENGTH: 254
<212> TYPE: DNA
<213> ORGANISM: Zea mays

<400> SEQUENCE: 154

gcgcgcaact ccaagatctg aacatggcct cgtgtttgca tatgccagta tgccaccgtg     60

tcgagtaatc aatcatatta ctgcttgcag ggaggaactg tgtttgattt ttattttcca    120

tgcgcaatgc ttaatttagg tcaggaagtc caaagtctct cccattgttt tcctgtaaga    180

gctaagcagt accagatgga gaaccttata tttgctggaa catgaataga agcatttgac    240

atgcttgtgc ttac                                                       254


<210> SEQ ID NO 155
<211> LENGTH: 236
<212> TYPE: DNA
<213> ORGANISM: Zea mays

<400> SEQUENCE: 155

gcacgagatt gcgcgcaact ccaagatctg aacatggcct cgtgtttgca tatgccagta     60

tgccaccgtg tcgagtaatc aatcatatta ctgcttgcag ggaggaactg tgtttgattt    120

ttattttcca tgcgcaatgc ttaatttagg tcaggaagtc caaagtctct cccattgttt    180

tcctgtaaga gctaagcagt accagatgga gaaccttata tttgctggaa catgaa        236


<210> SEQ ID NO 156
<211> LENGTH: 197
<212> TYPE: DNA
<213> ORGANISM: Zea mays

<400> SEQUENCE: 156

agacaggcaa gctgcctggc gcagggttgt ctgccttgcc atcaacaatg gcgttagcac     60

cccaggcatg tctgcaagtc tggcctactt cgactcgtac cgcagggaca ggcttcccgc    120

caacctggtg caggctcaga gagactactt cggcgctccc acgtacgaga gggttgacat    180

gcctggttct ttccaca                                                    197


<210> SEQ ID NO 157
<211> LENGTH: 281
```

-continued

<212> TYPE: DNA
<213> ORGANISM: Zea mays

<400> SEQUENCE: 157
cggacgcgtg ggcggacgcg tgggcggacg cgtgggggca agctgcctgg cgcagggttg 60
tctgccttgc cactcaacaa tggcagttac accccaggca tgtctgcaca gtctggccta 120
cttcgactcg taccgcagga caggcttccc gccaacctgg tgcaggctca gagagactac 180
ttcggcgctc acacgtacga gagggttgac atgcctggtt ctttccacac cgagtggttc 240
aagattgcgc gcaactccaa gatctgaaca tggcctcgtg t 281

<210> SEQ ID NO 158
<211> LENGTH: 249
<212> TYPE: DNA
<213> ORGANISM: Zea mays

<400> SEQUENCE: 158
cttgccatca acaatggcgt tacaccccag gcatgtctgc aagtctggcc tacttcgact 60
cgtaccgcag gacaggcttc ccgccaacct ggtgcaggct cagagagact acttcggcgc 120
tcacacgtac gagagggttg acatgcctgg ttctttccac accgagtggt tcaagattgc 180
gcgcaactcc aagatctgaa catggcctcg tgtttgcata tgccagtatg ccaccgtgtc 240
gagtaatca 249

<210> SEQ ID NO 159
<211> LENGTH: 150
<212> TYPE: DNA
<213> ORGANISM: Zea mays

<400> SEQUENCE: 159
gggaggaact gtgtttgatt tttattttcc atgcgcaatg cttaatttag gtcaggaagt 60
ccaaagtctc tcccattgtt ttcctgtaag agctaagcag taccagatgg agaaccttat 120
atttgctgga acatgaataa aagcatttga 150

<210> SEQ ID NO 160
<211> LENGTH: 133
<212> TYPE: DNA
<213> ORGANISM: Zea mays

<400> SEQUENCE: 160
gtaagtctgg cctacttcga ctcgtaccgc agggacaggc ttcccgccaa cctggtgcag 60
gctcagagag actacttcgg cgctcacacg tacgagaggg ttgacatgcc tggttctttc 120
cacaccgaat ggt 133

<210> SEQ ID NO 161
<211> LENGTH: 72
<212> TYPE: DNA
<213> ORGANISM: Zea mays

<400> SEQUENCE: 161
attgcgcgca actccaagat ctgaacatgg cctcgtgttt gcatatgcca gtatgccacc 60
gtgtcgagta at 72

<210> SEQ ID NO 162
<211> LENGTH: 327
<212> TYPE: DNA
<213> ORGANISM: Zea mays
<220> FEATURE:

-continued

<223> OTHER INFORMATION: unsure at all n locations

<400> SEQUENCE: 162
atcaggggga ctgtatcgtc gatggtggca acgagtggta cgagaacacg gagaggaggg 60
agaaggcgat ggaggagcgc gggctcctat atcttggcat gggcgtctcc ggaggagagg 120
agggtgcccg caatggcccg tccttgatgc ccgggggctc cttcgaggca tacaagtaca 180
ttgaagatat tcttctcaag gtggctgctc aggtacctga cagcggcccg tgcgtcacat 240
atattggcaa aagtggatca ggcaacttcg tcaagatggt tcacaatgga attgaatatg 300
gtgacatgcn acttatcgcc gaggctt 327

<210> SEQ ID NO 163
<211> LENGTH: 331
<212> TYPE: DNA
<213> ORGANISM: Zea mays
<220> FEATURE:
<223> OTHER INFORMATION: unsure at all n locations

<400> SEQUENCE: 163
cgagtggtac gagaacacgg agaggangga gaaggcgatg gaggagcgcg ggctcctata 60
tcttggcatg ggcgtctccg gaggagagga nggtgcccgc aatggcccgt ccttgatgcc 120
cgggggctcc ttcgaggcat acaagtacat tgaagatatt cttctcaagg tggctgctca 180
ggtacctgac agcggcccgt gcgtcacata tattggcaaa ggtggatcag gcaactttgt 240
caagatggtt cacaatggga ttgaatatgg tgacatgcaa cttatcgctg aggcttatga 300
tgttctcaag tcggtgggta actaacaaac a 331

<210> SEQ ID NO 164
<211> LENGTH: 297
<212> TYPE: DNA
<213> ORGANISM: Zea mays
<220> FEATURE:
<223> OTHER INFORMATION: unsure at all n locations

<400> SEQUENCE: 164
cacggagagg agggagaagg ccatggagga gcgcggcctc ctgtatcttg gcatgggtgt 60
ctctggagga gagganggtg cccgcaacgg cccgtccttg atgcccggag gctcgttcga 120
ggcttacaag tacgtcgaag acattgtcct caaggtggct gctcaggtcc ctgacagtgg 180
cccgtgtgtc acgtacattg gcaaaggtgg atcgggcaac tttgtcaaga tggttcacaa 240
cggaatcgag tatggcgata tgcagctgat ttccgaggca tacgacgttc tcaagtc 297

<210> SEQ ID NO 165
<211> LENGTH: 324
<212> TYPE: DNA
<213> ORGANISM: Zea mays

<400> SEQUENCE: 165
ggtggccgga cggtggtggc atcgccaatt caactccgca tctgaatcgg cactcggcag 60
cgcgccagtc catagtgtag gaggaggaga tggcgctcac aagaatcggt cttgctggcc 120
ttgcggtcat ggggcagaac ccttgcctca agcattgcag agaaagggtt ccccatctct 180
gtgtacaaca ggacaacctc caaggtggac gagaccgtgc agcgtgccaa ggcagaagga 240
aaccttcccg tctacggctt ccatgacccc gcgtcctttg tgaactccat tcagaagcca 300
cgggtggtga tcatgctcgt caag 324

-continued

<210> SEQ ID NO 166
<211> LENGTH: 287
<212> TYPE: DNA
<213> ORGANISM: Zea mays

<400> SEQUENCE: 166
gccacgggtg gtgatcatgc tcgtcaaggc cggcgacaca gttgtgcaga ccatcgcgac 60
gctcgcagct cacttggagc agggcgactg cgtcatcgat ggggggaacg agtggtacga 120
gaacacggag aggagggaga aggccatgga ggagcgcggc ctcctgtatc ttggcatggg 180
tgtctctgga ggagaggagg gtgcccgcaa cggcccgtcc ttgatgcccg gaggctcgtt 240
cgaggcttac aagtacgtcg aagacattgt cctcaaggtg gctgctc 287

<210> SEQ ID NO 167
<211> LENGTH: 283
<212> TYPE: DNA
<213> ORGANISM: Zea mays

<400> SEQUENCE: 167
ccgcatctga atcggcactc ggcagcgcgc cactccatag tgtaggagga gatggcgctc 60
acaagaatcg gtcttgctgg ccttgcggtc atggggcaga accttgccct caacattgca 120
gagaaagggt tccccatctc tgtgtacaac aggacaacct ccaaggtgga cgagaccgtg 180
cagcgtgcca aggcagaagg aaaccttccc gtctacggct tccatgaccc cgcgtccttt 240
gtgaagtcca ttcagaagcc acgggtggtg atcatgctcg tca 283

<210> SEQ ID NO 168
<211> LENGTH: 285
<212> TYPE: DNA
<213> ORGANISM: Zea mays

<400> SEQUENCE: 168
ggtggacgag accgtgcagc gtgccaaggc agaaggaaac cttcccgtct acggcttcca 60
tgaccccgcg tcctttgtga agtccattca gaagccacgg gtggtgatca tgctcgtcaa 120
ggccggcgcg ccagttgacc agaccatcgc gacgctcgca gctcacttgg agcagggcga 180
ctgcatcatc gatgggggga acgagtggta cgagaacacg gagatgaggg agaaggccat 240
ggaggatcgc ggcctcctgt atcttggcat gggtgtctct ggagg 285

<210> SEQ ID NO 169
<211> LENGTH: 311
<212> TYPE: DNA
<213> ORGANISM: Zea mays

<400> SEQUENCE: 169
gccggaggtg gtggcatcgc aattcaactc cgcatctgaa tcggcactcg gcagcgcgcc 60
actccatagt gtaggaggag gagatggcgc tcacaagaat cggtcttgct ggccttgcgg 120
tcatggggca gaaccttgcc ctcaacattg cagagaaagg gttccccatc tctgtgtaca 180
acaggacaac ctccaaggtg gacgagaccg tgcagcgtgc caaggcagaa ggaaaccttc 240
ccgtctacgg cttccatgac cccgcgtcct ttgtgaactc cattcagaag ccacgggtgg 300
tgatcatgct c 311

<210> SEQ ID NO 170
<211> LENGTH: 290
<212> TYPE: DNA
<213> ORGANISM: Zea mays

-continued

<400> SEQUENCE: 170
aattcaactc cgcatctgaa tcggcactcg gcagcgcgcc agctccatag cgaggagatg 60
gcgctcacaa gaatcggtct tgctggcctt gcggtcatgg ggcagaacct tgccctcaac 120
attgcagaga tagggttccc catctctgtg tacaacagga caacctccaa ggtggacgag 180
accgtgcagc gtgccaaggc agaaggaaac cttcccgtct acggcttcca tgaccccgcg 240
tcctttgtga agtccattca gaagccacgg gtggtgatca tgctcgtcaa 290

<210> SEQ ID NO 171
<211> LENGTH: 275
<212> TYPE: DNA
<213> ORGANISM: Zea mays

<400> SEQUENCE: 171
gccacgggtg gtgatcatgc tcgtcaaggc cggcgcgcca gttgaccaga ccatcgcgac 60
gctcgcagct cacttggagc agggcgactg catcatcgat ggggggaacg agtggtacga 120
gaacacggag aggagggaga aggccatgga ggagcgcggc ctcttgtatc ttggcatggg 180
tgtctctgga ggagaggagg gtgcccgcaa cggcccgtcc ttgatgcccg gatgctcgtt 240
cgacgcttac aagtacgtcg aagacattgt tctca 275

<210> SEQ ID NO 172
<211> LENGTH: 296
<212> TYPE: DNA
<213> ORGANISM: Zea mays

<400> SEQUENCE: 172
gagaggtagg tggccggacg gtggtggcat cgccaattca actccgcatc tgaatcggca 60
ctcggcagcg cgccactcca tagtgtagga ggaggagatg gcgctcacaa gaatcggtct 120
tgctggcctt gcggtcatgg ggcagaacct tgccctcaac attgcagaga aagggttccc 180
catctctgtg tacaacagga caacctccaa ggtggacgag accgtgcagc gtgccaaggc 240
agaaggaaac cttcccgtct acggcttcca tgaccccgcg tcctttgtga actcca 296

<210> SEQ ID NO 173
<211> LENGTH: 268
<212> TYPE: DNA
<213> ORGANISM: Zea mays

<400> SEQUENCE: 173
gcgactgcat catcgatggg gggaacgagt ggtacgagaa cacggagagg agggagaagg 60
ccatggagga gcgcggcctc ttgtatcttg gcatgggtgt ctctggagga gaggagggtg 120
cccgcaacgg cccgtccttg atgcccggag gctcgttcga cgcttacaag tacgtcgaag 180
acattgttct caaggtggct gctcaggtcc ctgacagtgg cccgtgtgtc acgtacattg 240
gcaaaggtgg atcgggcaac tttgtcaa 268

<210> SEQ ID NO 174
<211> LENGTH: 276
<212> TYPE: DNA
<213> ORGANISM: Zea mays
<220> FEATURE:
<223> OTHER INFORMATION: unsure at all n locations

<400> SEQUENCE: 174
acaagtacat tgaagatatt cttctcaagg tggctgctca ggtacctgac agcggcccgt 60
gcgtcacata tattggcaaa ggtggatcag gcaacttcgt caagatggtt cacaatggaa 120

-continued

```
ttgaatatgg tgacatgcaa cttatcgccg aggcttatga tgttctcaag ttcggtgggt    180

aagctcacaa acngcgagct gcatcaggtg ttctctgagt ggaacaaggg tgagctcctc    240

agtttcttga ttgagatcac ggccgacatc ttggta                              276


<210> SEQ ID NO 175
<211> LENGTH: 297
<212> TYPE: DNA
<213> ORGANISM: Zea mays

<400> SEQUENCE: 175

gtaggtggcc ggacggtggt gggctcgcca attcaactcc gcatctgaat cggcactcgg     60

cagcgcgcca gctccatagt gtaggaggag gtgatggcgc tcacaagaat cggtcttgct    120

ggccttgcgg tcatggggca gaaccttgcc ctcaacattg cagagaaagg gttccccatc    180

tctgtgtaca acaggacaac ctccaaggtg gacgagaccg tgcagcgtgc caaggcagaa    240

ggaaaccttc ccgtctacgg cttccatgac cccgcgtcct ttgtgaactc cattcag       297


<210> SEQ ID NO 176
<211> LENGTH: 274
<212> TYPE: DNA
<213> ORGANISM: Zea mays
<220> FEATURE:
<223> OTHER INFORMATION: unsure at all n locations

<400> SEQUENCE: 176

acaagtacat tgaagatatt cttctcaagg tggctgctca ggtacctgac agcggcccgt     60

gcgtcacata tattggcaaa ggtggatcag gcaacttcgt caagatggtt cacaatggaa    120

ttgaatatgg tgacatgcaa cttatcgccg aggcttatga tgttctcaag tccggtgggt    180

aagctcacaa acngcgagct gcatcaggtg ttctctgagt ggaacaaggg tgagctcctc    240

agtttctgat tgagatcacg gccgacatct tggt                                274


<210> SEQ ID NO 177
<211> LENGTH: 274
<212> TYPE: DNA
<213> ORGANISM: Zea mays

<400> SEQUENCE: 177

ggtggccgga cggtggtggc atcgccaatt caactccgca tctgaatcgg cactcggcag     60

cgcgccactc catagtgtag gaggagatgg cgctcacaag aatcggtctt gctggccttg    120

cggtcatggg gcagaacctt gccctcaaca ttgcagagaa agggttcccc atctctgtgt    180

acaacaggac aacctccaag gtggacgaga ccgtgcagcg tgccaaggca gaaggaaacc    240

ttcccgtcta cggcttccat gaccccgcgt cctt                                274


<210> SEQ ID NO 178
<211> LENGTH: 271
<212> TYPE: DNA
<213> ORGANISM: Zea mays

<400> SEQUENCE: 178

cggtggccgg acggtggtgg catcgccaat tcaactccgc atctgaatcg gcactcggca     60

gcgcgccact ccatagtgta ggaggaggag atggcgctca caagaatcgg tcttgctggc    120

cttgcggtca tggggcagaa ccttgccctc aacattgcag agaaagggtt ccccatctct    180

gtgtacaaca ggacaacctc caaggtggac gagaccgtgc agcgtgccaa ggcagaagga    240
```

-continued

```
aaccttcccg tctacggctt ccatgacccc g                                 271


<210> SEQ ID NO 179
<211> LENGTH: 258
<212> TYPE: DNA
<213> ORGANISM: Zea mays

<400> SEQUENCE: 179

gggttcccca tctctgtgta caacaggaca acctccaagg tggacgagac cgtgcagcgt     60

gccaaggcag aaggaaacct tcccgtctac ggcttccatg accccgcgtc ctttgtgaac    120

tccattcaga agccacgggt ggtgatcatg ctcgtcaagg ccggcgcgcc agttgaccag    180

atcatcgcga cgctcgcagc tcacttggag cagggcgact gcatcatcga tggggggaac    240

gagtggtacg agaacacg                                                  258


<210> SEQ ID NO 180
<211> LENGTH: 270
<212> TYPE: DNA
<213> ORGANISM: Zea mays

<400> SEQUENCE: 180

ggccggcgcg ccagttgacc agaccatcgc gacgctcgca gctcacttgg agcagggcga     60

ctgcatcatc gatgggggga acgagtggta cgagaacacg gagaggaggg agaaggccat    120

ggaggagcgc ggcctcttgt atcttggcat gggtgtctct ggaggagagg agggtgcccg    180

caacggcccg tccttgatgc ccggaggtcg ttcgacgctt acaagtacgt cgagacattg    240

ttctcaaggt ggctgctcag gtccctgaca                                     270


<210> SEQ ID NO 181
<211> LENGTH: 251
<212> TYPE: DNA
<213> ORGANISM: Zea mays

<400> SEQUENCE: 181

gtgatcatgc tcgtcaaggc cggcgcgcca gtagaccaga ccatcgcgac gctcgcagct     60

cacttggagc agggcgactg catcatcgat ggggggaacg agtggtacga gaacacggag    120

aggagggaga aggccatgga ggagcgcggc ctcttgtatc ttggcatggg tgtctcttga    180

ggagaagaag gtgcccgcaa cggcccgtcc ttgatgcccg ggagctcgtt cgacgcttac    240

aagtacgtcg a                                                         251


<210> SEQ ID NO 182
<211> LENGTH: 224
<212> TYPE: DNA
<213> ORGANISM: Zea mays

<400> SEQUENCE: 182

gccggaggtg gtggcatcgc caattcaact ccgcatctga atcggcactc ggcagcgcgc     60

cagctccata gtgtaggagg agatggcgct cacaagaatc ggtcttgctg gccttgcggt    120

catggggcag aaccttgccc tcaacattgc agagaaaggg ttccccatct ctgtgtacaa    180

caggacaacc tccaaggtgg acgagaccgt gcagcgtgcc aagg                     224


<210> SEQ ID NO 183
<211> LENGTH: 233
<212> TYPE: DNA
<213> ORGANISM: Zea mays

<400> SEQUENCE: 183
```

-continued gccggaggtg gtggcatcgc caattcaact ccgcatctga atcggcactc ggcagcgcgc 60
cactccatag tgtaggagga ggagatggcg ctcacaagaa tcggtcttgc tggccttgcg 120
gtcatggggc agaaccttgc cctcaacatt gcagagaaag ggttccccat ctctgtgtac 180
aacaggacaa cctccaaggt ggacgagacc gtgcagcgtg ccaaggcaga agg 233

<210> SEQ ID NO 184
<211> LENGTH: 235
<212> TYPE: DNA
<213> ORGANISM: Zea mays

<400> SEQUENCE: 184
ggccggacgg tggtggcatc gccaattcaa ctccgcatct gaatcggcac tcggcagcgc 60
gccagtccat agtgtatgag gagatggcgc tcacaagaat cggtcttgct ggccttgcgg 120
tcatggggca gaaccttgcc ctcaacattg cagagaaagg gttccccatc tctgtgtaca 180
acaggacaac ctccaaggtg gacgagaccg tggcacgtgc caaggcagaa ggaaa 235

<210> SEQ ID NO 185
<211> LENGTH: 263
<212> TYPE: DNA
<213> ORGANISM: Zea mays

<400> SEQUENCE: 185
cttccctgcc cgattggcga tttaagtggt gggggaggga aggacgatgg tcagtgaaag 60
agaggtaggt ggccggacgg tggtggcatc gccaattcaa ctccgcatct gaatcggcac 120
tcggcagcgc gccagctcca tagtgtagga ggagatggcg ctcacaagaa tcggtcttgc 180
tggccttgcg gttatggggc agaaccttgc cctcaacatt gcagagaaag ggttccccat 240
ctctgtgtac aacaggacaa cct 263

<210> SEQ ID NO 186
<211> LENGTH: 221
<212> TYPE: DNA
<213> ORGANISM: Zea mays

<400> SEQUENCE: 186
ggccggacgg tggtggcatc gccaattcaa ctccgcatct gaatcggcac tcggcagcgc 60
gccagctcca taggaggagg agatggcgct cacaagaatc ggtcttgctg gccttgcggt 120
catggggcag aaccttgccc tcaacattgc agagaaaggg ttccccatct ctgtgtacaa 180
caggacaacc tccaaggtgg acgagaccgt gcaaggtgcc a 221

<210> SEQ ID NO 187
<211> LENGTH: 294
<212> TYPE: DNA
<213> ORGANISM: Zea mays

<400> SEQUENCE: 187
cccgaaagcc gccaagcggc tgctgcgcaa ggagcgaaag gcacttccct acccgattgg 60
cgatttaagt ggtgggggag ggaaggccga tggtcagtga aagagaggta ggtggccgga 120
cggaggtggc atcgccaatt caactccgca tctgaatcgg cactcggcag cgcgccagca 180
ccataggagg agatggcgct cacaagaatc ggtcttgctg gccttgcggt catggggcag 240
aaccttgccc tcaacattgc agagaaaggg ttcccgatct ctgtgtacaa cagg 294

<210> SEQ ID NO 188

-continued

<211> LENGTH: 200
<212> TYPE: DNA
<213> ORGANISM: Zea mays

<400> SEQUENCE: 188
ggccggacgg tggtggcatc gccaattcaa ctccgcatct gaatcggcac tcggcagcgc 60
gccagctcca taggaggagg agatggcgct cacaagaatc ggtcttgctg gccttgcggt 120
catgtggcag aaccttgccc tcaacattgc agagaaaggg ttccccatct ctgtgtacaa 180
caggacaacc tccaaggtgg 200

<210> SEQ ID NO 189
<211> LENGTH: 154
<212> TYPE: DNA
<213> ORGANISM: Zea mays

<400> SEQUENCE: 189
ctccgcatct gcatcggcag cgcgccagct ccataggagg agatggcgct cacaagaatc 60
ggtcttgctg gccttgcggt catggggcag aaccttgccc tcaacattgc agagaaaggg 120
ttccccatct ctgtgtacaa caggacaacc tcca 154

<210> SEQ ID NO 190
<211> LENGTH: 127
<212> TYPE: DNA
<213> ORGANISM: Zea mays

<400> SEQUENCE: 190
ggtaggtggc cggacggtgg tggcatcgcc agttcaactc cgcatctgaa tcggcactcg 60
gcagcgcgcc actccatagg aggagatggc gctcacaaga atcggtcttg ctggccttgc 120
ggtcatg 127

<210> SEQ ID NO 191
<211> LENGTH: 104
<212> TYPE: DNA
<213> ORGANISM: Zea mays

<400> SEQUENCE: 191
gccggacggt ggtggcatcg ccaattcaac tccgcatctg aatcggcact cggcagcgcg 60
ccagctccat agtgtaggag gagatggcgc tcacaagaat cggt 104

<210> SEQ ID NO 192
<211> LENGTH: 162
<212> TYPE: DNA
<213> ORGANISM: Zea mays

<400> SEQUENCE: 192
ggcaccttcc ctgcccgatt ggcgatttaa gtggtggggg agggaaggcc gatggtcagt 60
gaaagagagg taggtggccg gacggtggtg gcatcgccaa ttcaactccg catctgaatc 120
ggcactcggc agcgcgccag ctccatagtg atagaggagg ag 162

<210> SEQ ID NO 193
<211> LENGTH: 87
<212> TYPE: DNA
<213> ORGANISM: Zea mays

<400> SEQUENCE: 193
gcatacaagt acattgaaga tattcttctc aaggtggctg ctcaggtacc tgacagcggc 60
cgtgcgtcac atatatggca aggtgga 87

-continued

<210> SEQ ID NO 194
<211> LENGTH: 91
<212> TYPE: DNA
<213> ORGANISM: Zea mays

<400> SEQUENCE: 194
cgggtggctg ctcaggtacc tgaccgcggc ccgtgcgtca catatattgg caaaggtgcc 60
tcaggcaact tcgtcaagat ggttcacaat c 91

<210> SEQ ID NO 195
<211> LENGTH: 330
<212> TYPE: DNA
<213> ORGANISM: Zea mays

<400> SEQUENCE: 195
ccgcgctgca ggggcgacgc aaggccgagc gctcctcgat ccagatccaa ggtaggagat 60
ggctctcacg agaattggcc tcgccggcct cgcggtcatg ggacagaacc ttgccctcaa 120
catcgcggag aaagggttcc ccatctcggt ctacaacagg acaacctcca aggttgatga 180
gaccgtgcag cgtgccaagg tcgaaggaaa cctcccagtg tttggtttcc acgaccccgc 240
gtccttcgtg agctccatcc agaagccccg tgtcgtcatc atgctcgtca aggctggggc 300
gccggtggac cagaccattg ccacgctcgc 330

<210> SEQ ID NO 196
<211> LENGTH: 323
<212> TYPE: DNA
<213> ORGANISM: Zea mays

<400> SEQUENCE: 196
tccagatcca aggtaggaga tggctctcac gagaattggc ctcgccggcc tcgcggtcat 60
gggacagaac cttgccctca acatcgcgga gaaagggttc cccatctcgg tctacaacag 120
gacaacctcc aaggttgatg agaccgtgca gcgtgccaag gtcgaaggaa acctcccagt 180
gtttggtttc cacgaccccg cgtccttcgt gagctccatc cagaagcccc gtgtcgtcat 240
catgctcgtc aaggctgggg cgccggtgga ccagaccatt gccacgctcg cggcgcacct 300
tgatcagggg gactgtatcg tcg 323

<210> SEQ ID NO 197
<211> LENGTH: 350
<212> TYPE: DNA
<213> ORGANISM: Zea mays

<400> SEQUENCE: 197
agcgtgccaa ggtcgaagga aacctcccag tgtttggttt ccacgacccc gcgtccttcg 60
tgagctccat ccagaagccc cgtgtcgtca tcatgctcgt caaggctggg gcgccggtgg 120
accagaccat tgccacgctc gcggcgcacc ttgatcaggg ggactgtatc gtcgatggtg 180
gcaacagtgg tacgagaaca cggagaagag ggagaaggcg atggaagagc gcgggctcct 240
atatcttggc atgggcgtct ccggaggaga ggacggtgcc cgcaatggct cgtccttgat 300
gcccgggggc tccttcgagg catacaagta cattgaagat attcttctca 350

<210> SEQ ID NO 198
<211> LENGTH: 317
<212> TYPE: DNA
<213> ORGANISM: Zea mays

-continued

<400> SEQUENCE: 198
gcaaggccga gcgctcctcg atccagatcc aaggtaggag atggctctca cgagaattgg 60
cctcgccggc ctcgcggtca tgggacagaa ccttgccctc aacatcgcgg agaaagggtt 120
ccccatctcg gtctacaaca ggacaacctc caaggttgat gagaccgtgc agcgtgccaa 180
ggtcgaagga aacctcccag tgtttggttt ccacgacccc gcgtccttcg tgagctccat 240
ccagaagccc cgtgtcgtca tcatgctcgt caaagctggg gcgccggtgg accagaccat 300
tgccacgctc gcggcgc 317

<210> SEQ ID NO 199
<211> LENGTH: 299
<212> TYPE: DNA
<213> ORGANISM: Zea mays

<400> SEQUENCE: 199
ctctcgcctc ggcttggcag tcggcactcc ctctccaccg cgctgcaggg gcgacgcaag 60
gccgagcgct cctcgatcca gatccaaggt aggagatggc tctcacgaga attggcctcg 120
ccggcctcgc ggtcatggga cagaaccttg ccctcaacat cgcggagaaa gggttcccca 180
tctcggtcta caacaggaca acctccaagg ttgatgagac cgtgcagcgt gccaaggtcg 240
aaggaaacct cacagtgttt ggtttccacg accccgcgtc cttcgtgagc tccatccag 299

<210> SEQ ID NO 200
<211> LENGTH: 279
<212> TYPE: DNA
<213> ORGANISM: Zea mays

<400> SEQUENCE: 200
tgtcggcact ccctctccac cgcgctgcag gggcgacgca aggccgagcg ctcctcgatc 60
cagatccaag gtaggagatg gctctcacga gaattggcct cgccggcctc gcggtcatgg 120
gacagaacct tgccctcaac atcgcggaga aagggttccc catctcggtc tacaacagga 180
caacctccaa ggttgatgag accgtgcagc gtgccaaggt cgaaggaaac ctcccagtgt 240
ttggtttcca cgaccccgcg tccttcgtga gctccatcc 279

<210> SEQ ID NO 201
<211> LENGTH: 321
<212> TYPE: DNA
<213> ORGANISM: Zea mays

<400> SEQUENCE: 201
gtaggctggc gctgcagatc aaaaggctct cgcctcggct tggcagtcgg cactccctct 60
ccaccgcgct gcaggggcga cgcaaggccg agcggtcctc gatccaggtc caaggtagga 120
gatggctctc acgaggaatg gcctcgccgg cctcgcggtc atgggacaga accttgccct 180
caacatcgcg gagaaagggt tccccatctc ggtctacaac aggacaacct ccaaggttga 240
tgagaccgtg cagcgtgcca aggtcgaaag aaacctccca gtgtttggtt tccacgaccc 300
cgcgtccttc gtgagctcca t 321

<210> SEQ ID NO 202
<211> LENGTH: 267
<212> TYPE: DNA
<213> ORGANISM: Zea mays

<400> SEQUENCE: 202
cccatctcgg tctacaacag gacgacctcc aaggttgatg agaccgtgca gcgtgccaag 60
gtcgaaggaa acctccccgt gtttggtctc cacgaccccg cgtccttcgt gagctccatc 120
cagaagcccc gtgtcgtcat catgctcgtc aaggctgggg cgccggtgga ccagaccatt 180
gccacgctcg cggcgcacct ggatcagggg gactgtatcg tcgatggtgg caacgagtgg 240
tacgagaaca cggagaggaa ggagaag 267

<210> SEQ ID NO 203
<211> LENGTH: 266
<212> TYPE: DNA
<213> ORGANISM: Zea mays

<400> SEQUENCE: 203
gctgcagatc aaaaggctct cgcctcggct tggcagtcgg cactccctct ccaccgcgct 60
gcaggggcga cgcaaggccg agcgctcctc gatccagatc caaggtagga gatgtgtctc 120
acgagaattg gcctcgccgg cctcgcggtc atgggacaga accttgccct caacatcgcg 180
gagaaagggt tccccatctc ggtctacaac aggacgacct ccaaggttgg gaagaccgtg 240
cagcgtgcca aggtcgaagg aaacct 266

<210> SEQ ID NO 204
<211> LENGTH: 264
<212> TYPE: DNA
<213> ORGANISM: Zea mays

<400> SEQUENCE: 204
cgctgcagat caaaaggctc tcgcctcggc ttggcagtcg gcactccctc tccaccgcgc 60
tgcaggggcg acgcaaggcc gagcgctcct cgatccagat ccaaggtagg agatggctct 120
cacgagaatt ggcctcgccg gcctcgcggt catgggacag aaccttgccc tcaacatcgc 180
ggagaaaggg ttccccatct cggtctacaa caggacaacc tccaaggttg atgagaccgt 240
gcagcgtgcc aaggtcgaag gaaa 264

<210> SEQ ID NO 205
<211> LENGTH: 294
<212> TYPE: DNA
<213> ORGANISM: Zea mays

<400> SEQUENCE: 205
aacgtaggct ggcgctgcag atcaaaaggc tctcgcctcg gcttggcagt cggcactccc 60
tctccaccgc gctgcagggg cgacgcaagg ccgagcgctc ctcgatccag atccaaggta 120
ggagatggct ctcacgagaa tgcgcctcgc cggcctcgcg gtcatgggac agaaccttgc 180
cctcaacatc gcggagaaag ggttccccat ctcggtctac aacaggacaa cctccaaggt 240
tgatgagacc gtgcagcgtg ccaaggtcga aggaaacctc ccagtgtttg gttt 294

<210> SEQ ID NO 206
<211> LENGTH: 150
<212> TYPE: DNA
<213> ORGANISM: Zea mays

<400> SEQUENCE: 206
cagaactccg tgtcgtcata tgctcgtcaa ggctggggcg ccggtggacc agaccattgc 60
cacgctcgcg gcgcaccttg atcaggggga ctgtatcgtc gatggtggca acgagtggta 120
cgagaacacg gagaggaggg agaaggcgat 150

<210> SEQ ID NO 207

-continued

<211> LENGTH: 161
<212> TYPE: DNA
<213> ORGANISM: Zea mays

<400> SEQUENCE: 207
caaaaggctc tcgcctcggc ttggcagtcg gcactccctc tccaccgcgc tgcaggggcg 60
acgcaaggcc gagcgctcct cgatccagat ccaaggtagg agatggctct cacgagaatt 120
ggcctcgccg gcctcgcggt catgggacag aaccttgccc t 161

<210> SEQ ID NO 208
<211> LENGTH: 161
<212> TYPE: DNA
<213> ORGANISM: Zea mays

<400> SEQUENCE: 208
caaaaggctc tcgcctcggc ttggcagtcg gcactccctc tccaccgcgc tgcaggggcg 60
acgcaaggcc gagcgctcct cgatccagat ccaaggtagg agatggctct cacgagaatt 120
ggcctcgccg gcatcgcggt catgggacag aaccttgccc t 161

<210> SEQ ID NO 209
<211> LENGTH: 205
<212> TYPE: DNA
<213> ORGANISM: Zea mays

<400> SEQUENCE: 209
accttgccct caacatcgcg gagaaagggt tccccatctc ggtctacaac aggacgacct 60
ccaaggttga tgagaccgtg cagcgtgcca aggtcgaagg aaacctcccc gtgtttggtt 120
tccacgaccc cgcgtccttc gtgagctccc atccagaagc cccgtgtcgt catcatgctc 180
gtcaaggctg gggcgccggt ggacc 205

<210> SEQ ID NO 210
<211> LENGTH: 270
<212> TYPE: DNA
<213> ORGANISM: Glycine max

<400> SEQUENCE: 210
ggccggcgcc cccgtcgacc aaaccatcgc cgccctctcc gaccacctcg accccggcga 60
ctgcatcatc gacggcggca acgagtggta cgagaacacc gagcgccgca tgagcctcgt 120
cgccgacaaa ggcctcctct acctcggcat gggcgtctcc ggcggcgaag acggcgcacg 180
ccacggcccc tccctcatgc ccggtgggtc ccaccaggcc tactccaacg tccaggacat 240
cctccacaaa atcgccgccc aggtcgacga 270

<210> SEQ ID NO 211
<211> LENGTH: 165
<212> TYPE: DNA
<213> ORGANISM: Glycine max
<220> FEATURE:
<223> OTHER INFORMATION: unsure at all n locations

<400> SEQUENCE: 211
angagtgnnt acgagaacac cgagcgccgc atgaacctcg tcgccgacaa aggcctcctc 60
tanctcggca tgggcgtctc cggcggcgaa gacggcgcac gccacggccc ctccctcatg 120
cccggtgggt cccaccatgc ctactccaac gtgccagnac atcct 165

<210> SEQ ID NO 212
<211> LENGTH: 248

-continued

<212> TYPE: DNA
<213> ORGANISM: Glycine max

<400> SEQUENCE: 212
ggcgtatgca agggaaatgg tgtatagaca ggctgcgtgg catagaatcg tggggttggc 60
ggtttcggct gggattagta ctagcggaat gtgtgccagt cttgcttggt ttgataccta 120
tcggagggca agacttccgg caaaccttgt ccaggctcag agggacttgt ttggggcgca 180
tacttacgag agggttgatc gccctggggc ttttcatacc gagtggacga aactcgctcg 240
caatagtg 248

<210> SEQ ID NO 213
<211> LENGTH: 251
<212> TYPE: DNA
<213> ORGANISM: Glycine max

<400> SEQUENCE: 213
ggagtttgca agggaaatgg tgcagagaca ggctgcgtgg atgagggttg tggggttggc 60
ggtttcggct gggattagta ctcccggaat gtgtgccagt cttgcttact ttgataccta 120
tcggagggca agacttccgg caaaccttgt ccaggctcag agggacttgt ttggggcgca 180
tacttacgag agggttgatc gccctggggc ttttcatacc gagtggacga aactcgctcg 240
caatagtggg g 251

<210> SEQ ID NO 214
<211> LENGTH: 272
<212> TYPE: DNA
<213> ORGANISM: Glycine max

<400> SEQUENCE: 214
gataagaagc agttgatcga tgacgtcagg caggctctga atgcttccaa gattagcagt 60
tatgctcagg ggatgaattt gttgagggct aagagtaatg agaaaggatg gaacttgaat 120
ttgggggagt tagctaggat tggaagggag ggtgcatcat aagggccgtg ttcttggacc 180
ggatcaagaa ggcttatcag aggaacccta atttggcgag tttgattgtg gacccggagt 240
atgcaaggcg aatagtccag agacacgctg cg 272

<210> SEQ ID NO 215
<211> LENGTH: 196
<212> TYPE: DNA
<213> ORGANISM: Zea mays

<400> SEQUENCE: 215
gccacgcgtc cgcggacgcg tggattccat gtgagggcat cagctcgggt tgacaaattc 60
tcaaagagtg acatcatcgt gtccccttcg attctgtctg caaactttgc gaagcttggt 120
gatcaggtaa aagctgtgga ggtggcagga tgcgactgga ttcatgtcga tgtcatggac 180
gggcgctttg tgccaa 196

<210> SEQ ID NO 216
<211> LENGTH: 353
<212> TYPE: DNA
<213> ORGANISM: Zea mays
<220> FEATURE:
<223> OTHER INFORMATION: unsure at all n locations

<400> SEQUENCE: 216
tgcgtcatct acgcgcagga aggcgttcca agtgagggca tcagctcggg ttgacaagtt 60

-continued

```
ctcaaagagt gatatcaggg tngtcccttc gcatctgtct ggaaactgtc gcaaagctat    120

gttgatcagg tagaagcgtg ggaggtggca agatgtgact ggattctgtc gatgtcatgg    180

acgggcgctg tgtgcgaaat atcacaattg gacctgtggt tgttgatgct ctgcgtcctg    240

tgactgatct tccattggat gtacatctga tgattgtgga acctgagcag cgagtcactg    300

attgtatcaa ggcangtgct gatattgtta gtgtccactg tgaacagaca tcg           353
```

<210> SEQ ID NO 217
<211> LENGTH: 312
<212> TYPE: DNA
<213> ORGANISM: Zea mays

<400> SEQUENCE: 217

```
agcgactcca ctcactgcaa ttgattatgt tcttgatgtt gttgacctgg tgctgattat     60

gtctgtgaat cctgggtttg gtggccagag ctttatcgag agtcaagtaa agaaaattgc    120

agaactgaga aggttatgtg cagagaaggg agtgaacccc tggattgagg ttgatggtgg    180

tgttggtccg aaaaatgcct acaaggttat tgaagctggc gcaaatgcca ttgtcgcagg    240

ttctgcagtt tttggggctc cagactacgc tgaagctatc aaaggaataa agaccagcca    300

aagacctcta gc                                                        312
```

<210> SEQ ID NO 218
<211> LENGTH: 312
<212> TYPE: DNA
<213> ORGANISM: Zea mays

<400> SEQUENCE: 218

```
gctctgcgtc cagtgactga tcttccgttg gatgtacatc tgatgattgt ggaacctgag     60

cagcgagtcc ccgattttat caaggcaggt gctgatattg ttagtgtcca ctgtgaacag    120

acatcgacca tccatttgca ccgaacagtc aatcagatta aaagtctagg agcaaaggca    180

ggagttgttt tgaatccagc gactccactc actgcaattg attatgttct tgatgttgtt    240

gacctggtgc tgattatgtc tgtgaatcct gggtttggtg gccagagctt tatcgagagt    300

caagtaaaga aa                                                        312
```

<210> SEQ ID NO 219
<211> LENGTH: 314
<212> TYPE: DNA
<213> ORGANISM: Zea mays

<400> SEQUENCE: 219

```
cctgagcagc gagtccccga ttttatcaag gcaggtgctg atattgttag tgtccactgt     60

gaacagacat cgaccatcca tttgcaccga acagtcaatc agattaaaag tctaggagca    120

aaggcaggag ttgttttgaa tccagcgact ccactcactg caattgatta tgttcttgat    180

gttgttgacc tggtgctgat tatgtctgtg aatcctgggt ttggtggcca gagctttatc    240

gagagtcaag taaagaaaat tgcagaactg agagagttat gtgcagagaa gggagtgaac    300

ccctggattg aggt                                                      314
```

<210> SEQ ID NO 220
<211> LENGTH: 305
<212> TYPE: DNA
<213> ORGANISM: Zea mays

<400> SEQUENCE: 220

```
ggcaggtgct gatattgtta gtgtccactg tgaacagaca tcgaccatcc atttgcaccg     60
```

-continued

```
aacagtcaat cagattaaaa gtctaggagc aaaggcagga gttgtttgaa tccagcgact    120

ccactcactg caattgatta tgttcttgat gttgttgacc tggtgctgat tatgtctgtg    180

aatcctgggt ttggtggcca gagctttatc gagagtcaag taaagaaaat tgcagaactg    240

agaaggttat gtgcagagaa gggagtgaac ccctggattg aggttgatgg tggtgttggt    300

ccgaa                                                                305
```

<210> SEQ ID NO 221
<211> LENGTH: 280
<212> TYPE: DNA
<213> ORGANISM: Zea mays

<400> SEQUENCE: 221

```
atccatttgc accgaacagt caatcagatt aaaagtctag gagcaaaggc aggagttgtt     60

ttgaatccag cgactccact cactgcaatt gattatgttc ttgatgttgt tgacctggtg    120

ctgattatgt ctgtgaatcc tgggtttggt ggccagagct ttatcgagag tcaagtaaag    180

aaaattgcag aactgagaag gttatgtgca gagaagggag tgaacccctg gattgaggtt    240

gatggtggtg ttggtccgaa aaatgcctac aaggttattg                          280
```

<210> SEQ ID NO 222
<211> LENGTH: 284
<212> TYPE: DNA
<213> ORGANISM: Zea mays

<400> SEQUENCE: 222

```
ctgtctgcaa actttgcgaa cgttggtgat caggtaaaag ctgtggaggt ggcaggatgc     60

gactggattc atgtcgatgt catggacggg cgctttgtgc caaacatcac aattggaccc    120

ttggttgttg atgctctgcg tccagtgact gatcttccgt tggatgtaca tctgatgatt    180

gtggaacctg agcagcgagt ccccgatttt atcaaggcag gtgctgatat tgttagtgtc    240

cactgtgaac agacatcgac catccatttg caccgaacag tcaa                      284
```

<210> SEQ ID NO 223
<211> LENGTH: 218
<212> TYPE: DNA
<213> ORGANISM: Zea mays

<400> SEQUENCE: 223

```
tgttagtgtc cactgtgaac agacatcgac catccatttg caccgaacag tcaatcagat     60

taaaagtcta ggagcaaagg caggagttgt tttgaatcca gcgactccac tcactgcaat    120

tgattaggtt cttgatgtgg ttgacctggt gctgattatg tctgtgaatc ctgggtttgg    180

tggccagagc tttatcgaga gtcaggtaaa gaaaattg                            218
```

<210> SEQ ID NO 224
<211> LENGTH: 249
<212> TYPE: DNA
<213> ORGANISM: Zea mays

<400> SEQUENCE: 224

```
tatcaaggca ggtgctgata ttgttagtgt ccactgtgaa cagacatcga ccatccattt     60

gcaccgaaca gtcaatcaga ttaaaagtct aggagcaaag gcaggagttg ttttgaatcc    120

agcgactcca ctcactgcaa ttgattatgt tcttgatgtt gtcgccctgg tgctgattat    180

gtctgtaaat cctgggtttg gtggccagag ctttatcgag agtcaagtaa agaaaattgc    240
```

-continued agaactgag 249

<210> SEQ ID NO 225
<211> LENGTH: 316
<212> TYPE: DNA
<213> ORGANISM: Zea mays

<400> SEQUENCE: 225

| gataaggtgc gcacactgag aaagaagtac ccttcccttg acatagaggt tgatggtggt | 60 |
| ctaggtcctt caaccataga cgtggccgca tctgctgggg ccaattgcat cgtcgctgga | 120 |
| agctctatat ttggcgctgc ggacccagga gccatcatat ctgtgctgag gaagagcgtc | 180 |
| gagggctctc agaacaaaaa ctgattttgg tgtttctgct gtaaagtact ccctccgttt | 240 |
| ttttttattc gtcgcgtttt agttcaaaca tgaactagcg gacgactgat attcgagaat | 300 |
| ggagggagta cttcga | 316 |

<210> SEQ ID NO 226
<211> LENGTH: 301
<212> TYPE: DNA
<213> ORGANISM: Zea mays

<400> SEQUENCE: 226

| ggttgatggt ggtctaggtc cttcaaccat agacgtggcc gcatctgctg gggccaattg | 60 |
| catcgtcgct ggaagctcta tatttggcgc tgcggaccca ggagccatca tatctgtgct | 120 |
| gaggaagagc gtcgagggct ctcagaacaa aaactgattt tggtgtttct gctgtaaagt | 180 |
| actccctccg ttttttttatt cgtcgcgttt tagttcaaac atgaactagc ggacgactga | 240 |
| tattcgagaa tggagggatt acttcgaccc tgcacgtcag atgagctgat cctcacattg | 300 |
| c | 301 |

<210> SEQ ID NO 227
<211> LENGTH: 247
<212> TYPE: DNA
<213> ORGANISM: Zea mays

<400> SEQUENCE: 227

| cggttattga agctggcgca aatgccattg tcgcaggttc tgcagttttt gcggtgtcca | 60 |
| gactaacact gcagctatca aaggaataca gaccagccaa agacctctag ctgtagccgc | 120 |
| ataaggcgct ggacgtgtaa tcatttactc tgtgcaagtt taccagtgat gcgatctgta | 180 |
| tagttgtgtg tcttgtccaa ccatacgtat accgagatga aaagagacgg aggcagtgaa | 240 |
| gaactat | 247 |

<210> SEQ ID NO 228
<211> LENGTH: 319
<212> TYPE: DNA
<213> ORGANISM: Zea mays

<400> SEQUENCE: 228

| attgagagag ccagagaggt gggcagatgg cgacaccgtc gtcgtcgctt tgctccagct | 60 |
| tcgcctccct gcggaccgcc tccatcggcc accccgcgg catcgcgtca tctacgccca | 120 |
| ggaaggcgtt ccaagtgagg gcatcagctc gggttgacaa gttctcaaag agtgatatca | 180 |
| ttgtgtcccc ttcgattctg tctgcaaact tcgccaagct tggtgatcag gtaaaagccg | 240 |
| tggaggtggc aggatgtgac tggattcatg tcgatgtcat ggacgggcgc tttgtgccaa | 300 |
| atatcacaat tggaccttt | 319 |

-continued

<210> SEQ ID NO 229
<211> LENGTH: 301
<212> TYPE: DNA
<213> ORGANISM: Zea mays

<400> SEQUENCE: 229
gagagaggcg cgcagatggc gacgccgtcg tcgtcgcttt gctccagctt cgcctccctg 60
cggaccgcct ccatcggcca cccccgtggc atcgcctcct ccacgcccag gaaggcattc 120
catgtgaggg catcagctcg ggttgacaaa ttctcaaaga gtgacatcat cgtgtcccct 180
tcgattctgt ctgcaaactt tgcgaacttg gtgatcaggt aaaagctgtg gaggtggcag 240
gatgcgactg gattcatgtc gatgtcatgg acgggcgctt tgtgccaaac atcacaattg 300
g 301

<210> SEQ ID NO 230
<211> LENGTH: 268
<212> TYPE: DNA
<213> ORGANISM: Zea mays

<400> SEQUENCE: 230
cgcagatggc gacgccgtcg tcgtcgcttt gctccagctt cgcctccctg cggaccgcct 60
ccatcggcca cccccgtggc atcgcctcct ccacgcccag gaaggcattc catgtgaggg 120
catcagctcg ggttgacaag ttctcaaaga gtgacatcat cgtgtcccct tcgattctgt 180
ctgcaaactt tgcgaacttc ggtgatcagg taaaagctgt ggaggtggca ggatgcgact 240
ggattcatgt cgatgtcatg gatgggcg 268

<210> SEQ ID NO 231
<211> LENGTH: 256
<212> TYPE: DNA
<213> ORGANISM: Zea mays

<400> SEQUENCE: 231
aagcgtcgtc gtcgctttgc tccagcttcg cctccctgcg gaccgcctcc atcggccacc 60
cccgtggcat cgcctcctcc acgcccagga aggcattcca tgtgagggca tcagctcggg 120
ttgacaaatt ctcaaagagt gacatcatcg tgtccccttc gattctgtct gcaaactttg 180
cgaagcttgg tgatcaggta aaagctgtgg aggtggcagg cggcgactgg attcatgtcg 240
atgtcatgga cgggcg 256

<210> SEQ ID NO 232
<211> LENGTH: 319
<212> TYPE: DNA
<213> ORGANISM: Zea mays

<400> SEQUENCE: 232
gctcttgcaa caagccaaac aacccagtgg ctgctagccg agacagggga tagattgaga 60
gagaggcgcg cagatggcga cgccgtcgtc gtcgctttgc tccagcttcg cctccctgcg 120
gaccgcctcc atcggccacc cccgtggcat cgcctcctcc acgcccagga aggcattcca 180
tgtgagggca tcagctcggg ttgacaaatt ctcaaagagt gacatcatcg tgtccccttc 240
gattctgtct gcaaactttg cgaactctgg tgatcaggta aaagctgtgg aggtggcagg 300
atgcgactgg attcatgtc 319

<210> SEQ ID NO 233

-continued

<211> LENGTH: 287
<212> TYPE: DNA
<213> ORGANISM: Zea mays
<220> FEATURE:
<223> OTHER INFORMATION: unsure at all n locations

<400> SEQUENCE: 233
ccagtggctg ctagccgaga cggggataga ttgacagaca ggcgcgcaga tcgcgacgcc 60
gtcgtcgtcg ctttgctcca gcttcgcctc cctgcggacc gcctccatcg gccacccccg 120
tggcatcgcc tcctccacgc ccagtcaagg cattccatgt gagggcatca gctcgggttc 180
acaaattctc aaagagtgac atcatcgtgt ccccttcgat tctgtctgca aactttgcga 240
acttggtgat caggtanaag ctgtggaggt ggcaggatgc gactgga 287

<210> SEQ ID NO 234
<211> LENGTH: 261
<212> TYPE: DNA
<213> ORGANISM: Zea mays

<400> SEQUENCE: 234
agaggggata gattgagaga gccagagagg tgggcagatg gcgacaccgt cgtcgtcgct 60
ttgctccagc ttcgcctccc tgcggaccgc ctccatcggc cacccccgcg gcatcgcgtc 120
atctacaccc aggaaggcgt tccaagtgag ggcatcagct cgggttgaca agttctcaaa 180
gagtgatatc attgtgtccc cttcgattct gtctgcaaac ttcgccaagc ttggtgatca 240
ggtaaaagcc gtggaggtgg c 261

<210> SEQ ID NO 235
<211> LENGTH: 299
<212> TYPE: DNA
<213> ORGANISM: Zea mays

<400> SEQUENCE: 235
gctcttgcaa caagccaaac aacccagtgg ctgctagccg agacagggga tagattgaga 60
gagaggcgcg cagatggcga cgccgtcgtc gtcgctttgc tccagcttcg cctccctgcg 120
gaccgcctcc atcggccacc cccgtggcat cgcctcctcc acgcccagga aggcattcca 180
tgtgagggca tcagctcggg ttgacaaatt ctcaaagagt gacatcatcg tgtccccttc 240
gattctgtct gcaaactttg cgaacgttgg tgatcaggta aaagctgtgg aggtggcag 299

<210> SEQ ID NO 236
<211> LENGTH: 241
<212> TYPE: DNA
<213> ORGANISM: Zea mays

<400> SEQUENCE: 236
attgacagac aggcgcgcag atggcgacgc cgtcgtcgtc gctttgctcc agcttcgcct 60
ccctgcggac cgcctccatc ggccaccccc gtggcatcgc ctcctccacg cccaggaagg 120
cattccatgt gagggcatca gctcgggttg acaaattctc aaagagtgac atcatcgtgt 180
ccccttcgat tctgtctgca aactttgcga agcttggtga tcaggtaaaa gctgtggagg 240
t 241

<210> SEQ ID NO 237
<211> LENGTH: 293
<212> TYPE: DNA
<213> ORGANISM: Zea mays

<400> SEQUENCE: 237

-continued

```
ctcttgcaac aagccaaaca acccagtggc tgctagccga gacaggggat agattgagag     60

agaggcgcgc agatggcgac gccgtcgtcg tcgctttgct ccagcttcgc ctccctgcgg    120

accgcctcca tcggccaccc ccgtggcatc gcctcctcca cgcccaggaa ggcattccat    180

gtgagggcat cagctcgggt tgacaaattc tcaaagagtg acatcatcgt gtccccttcg    240

attctgtctg caaactttgc gaactgtggt gatcaggtaa aagctgtgga ggt           293


<210> SEQ ID NO 238
<211> LENGTH: 325
<212> TYPE: DNA
<213> ORGANISM: Zea mays

<400> SEQUENCE: 238

accaaatcgc ttaccgcccc cgaagcgtct cggttcgcat agcagagctg ctcttgcaac     60

aagccaaaca acccagtggc tgctagccga gacaggggat agattgagag agaggcgcgc    120

agatggcgac gccgtcgtcg tcgctttgct ccagcttcgc ctccctgcgg accgcctcca    180

tcggccaccc ccgtggcatc gcctcctcca cgcccaggaa ggcattccat gtgagggcat    240

cagctcgggt tgacaaattc tcaaagagtg acatcatcgt gtccccttcg attctgtctg    300

caaactttgc gaacgttggt gatca                                          325


<210> SEQ ID NO 239
<211> LENGTH: 301
<212> TYPE: DNA
<213> ORGANISM: Zea mays

<400> SEQUENCE: 239

cgaagctctc ggttcgcata gcagagctgc tcttgcaaca agccaaacaa cccagtggct     60

gctagccgag acaggggata gattgagaga gaggcgcgca gatggcgacg ccgtcgtcgt    120

cgctttgctc cagcttcgcc tccctgcgga ccgcctccat cggccacccc cgtggcatcg    180

cctcctccac gcccaggaag ggattccatg tgagggcatc agctcgggtt gacaaattct    240

caaagagtga catcatcgtg tccccttcga ttctgtctgc aaactttgcg aagcttggtg    300

a                                                                    301


<210> SEQ ID NO 240
<211> LENGTH: 288
<212> TYPE: DNA
<213> ORGANISM: Zea mays

<400> SEQUENCE: 240

agcagagctg ctcttgcaac aagccaaaca acccagtggc tgctagccga gacaggggat     60

agattgagag agaggcgcgc agatggcgac gccgtcgtcg tcgctttgct ccagcttcgc    120

ctccctgcgg accgcctcca tcggccaccc ccgtggcatc gcctcctcca cgcccaggaa    180

ggcattccat gtgagggcat cagctcgggt tgacaaattc tcaaagagtg acatcatcgt    240

gtccccttcg attctgtctg caaactttgc gaactgtggt gatcaggt                 288


<210> SEQ ID NO 241
<211> LENGTH: 304
<212> TYPE: DNA
<213> ORGANISM: Zea mays

<400> SEQUENCE: 241

aatcgcttac cgcccccgaa gcgtctcggt tcgcatagca gagctgctct tgcaacaagc     60
```

-continued

```
caaacaaccc agtggctgct agccgagaca ggggatagat tgagagagag gcgcgcagat    120

ggcgacgccg tcgtcgtcgc tttgctccag cttcgcctcc ctgcggaccg cctccatcgg    180

ccaccccgt ggcatcgcct cctccacgcc caggaaggca ttccatgtga gggcatcagc    240

tcgggttgac aaattctcaa agagtgacat catcgtgtcc ccttcgattc tgtctgcaaa    300

cttt                                                                 304


<210> SEQ ID NO 242
<211> LENGTH: 229
<212> TYPE: DNA
<213> ORGANISM: Zea mays
<220> FEATURE:
<223> OTHER INFORMATION: unsure at all n locations

<400> SEQUENCE: 242

cataactact ctgccaccaa tccggggagg aatcaaccta gcggtaagcg gacatggcgg     60

cggcgaagat agcgccgtcg atgctctcgt cggactttgc caacctcgct tcggaggctg    120

agcgcatggt ccgcctaggc gccgactggc tacatatgga catcatggat gggcacttcg    180

ttcctaacct gactattggg gctccggtga tccagangct tgagaaata                229


<210> SEQ ID NO 243
<211> LENGTH: 269
<212> TYPE: DNA
<213> ORGANISM: Zea mays

<400> SEQUENCE: 243

gctacatatg gacatcatgg atgggcactt cgttcctaac ctgactattg gggctccggt     60

gatccagagc ttgaggaaac ataccaaagc atatttggac tgccatctta tggtcacaaa    120

gccttcagat tacgtagaac catttggaaa ggctggcgct tctggattca cattccatat    180

agaagttgct agagacaact ggcaagatct catccaaagc attaaatcaa agggtatgcg    240

gcctggtgta tcattgaggc caggtactc                                      269


<210> SEQ ID NO 244
<211> LENGTH: 385
<212> TYPE: DNA
<213> ORGANISM: Zea mays

<400> SEQUENCE: 244

ccgggctcaa ccaacgcgtc aggatgtttt gaaccaacca acccaatcaa cggaaattga     60

taacttcctg gaggtggttg acctgtggcg gataaggtcg gtaaacccgg ggttgggggg    120

caaaacctta accaaaagtc aattaaagaa aattgcaaaa ctgaaaaggt aatgtgcaaa    180

aaagggagtg aaccccggga ttgaggttga tggtggtgtt ggtccgaaaa atgcctacaa    240

ggttattgaa gctggcgcaa atgccattgt cgcaagttct gcagtttttg gggctccaga    300

ctacgctgaa gctatcaaag gaataaagac cagccaaaga cctctagctg tagccgcata    360

aagagctgga cgtgtaatca tttac                                          385


<210> SEQ ID NO 245
<211> LENGTH: 389
<212> TYPE: DNA
<213> ORGANISM: Zea mays
<220> FEATURE:
<223> OTHER INFORMATION: unsure at all n locations

<400> SEQUENCE: 245

gaccaagccg tccaatcaag gtggaggcca tggatgggcc ctttgtgcca aacatcacaa     60
```

-continued

```
ttggaccctg gggtgttgat gctctgcgtc cagtgactga tcttccgttg gatgtacatc    120
tgatgattgt ggaacctgag cagcgagtcc ctgattttat caaggcaggt gctgatattg    180
ctagtgtcca ctgtgaacag acatcgacct tcatttgcac cgaacagtca atcagattaa    240
aagtctagga gcanaggcag ggattgttnt gaatccagcg actccactca ctgcaattga    300
ttacgttctt gatgttgttg acctggtgct gattatgtct gtgaatcctg ggtttgttgg    360
cagagcttta tcgagagtca agtaaggaa                                       389
```

```
<210> SEQ ID NO 246
<211> LENGTH: 412
<212> TYPE: DNA
<213> ORGANISM: Zea mays

<400> SEQUENCE: 246

gtgtcccctt cgattctgtc tgcaaacttt gcgaagcttg gtgatcaggt aaaagctgtg     60
gaggtggcag gatgcgactg gattcatgtc gatgtcatgg acgggcgctt tgtgccaaac    120
atcacaattg gacccttggt tgttgatgct ctgcgtccag tgactgatct tccgttggat    180
gtacatctga tgattgtgga acctgagcag cgagtccccg attttatcaa ggcaggtgct    240
gatattgtta gtgtccactg tgaacagaca tcgaccatcc atttgcaccg aacagtcaat    300
cagattaaaa gtctaggagc aaaggcagga gttgttttga atccagcgac tccactcact    360
gcaattgatt acgttcttga tgttgttgac ctggtgctga ttatgtctgt ga            412
```

```
<210> SEQ ID NO 247
<211> LENGTH: 397
<212> TYPE: DNA
<213> ORGANISM: Zea mays

<400> SEQUENCE: 247

gatgctctgc gtccagtgac tgatcttccg ttggatgtac atctgatgat tgtggaacct     60
gagcagcgag tccctgattt tatcaaggca ggtgctgata ttgttagtgt ccactgtgaa    120
cagacatcga ccatccattt gcaccgaaca gtcaatcaga ttaaaagtct aggagcaaag    180
gcaggagttg ttttgaatcc agcgactcca ctcactgcaa ttgattacgt tcttgatgtt    240
gttgacctgg tgctgattat gtctgtgaat cctgggtttg gtggccagag ctttatcgag    300
agtcaagtaa agaaaattgc agaactgaga aggttatgtg cagagaaggg agtgaacccc    360
tggattgagg ttgatggtgg tgttggtccg aaaaatg                              397
```

```
<210> SEQ ID NO 248
<211> LENGTH: 403
<212> TYPE: DNA
<213> ORGANISM: Zea mays

<400> SEQUENCE: 248

ggaggtggca ggatgcgact ggattcatgt cgatgtcatg gacgggcgct ttgtgccaaa     60
catcacaatt ggacccttgg ttgttgatgc tctgcgtcca gtgactgatc ttccgttgga    120
tgtacatctg atgattgtgg aacctgagca gcgagtcccc gattttatca aggcaggtgc    180
tgatattgtt agtgtccact gtgaacagac atcgaccatc catttgcacc gaacagtcaa    240
tcagattaaa agtctaagag caaaggcagg gaattgtttg aatccagcga cttcacttac    300
tggaattgat tatggtcctg atggtggtga cctggtgctg attatgtctg tgaatcctgg    360
gtttggtggc caaagcttta ttgagagtca agttaaggaa att                      403
```

-continued

<210> SEQ ID NO 249
<211> LENGTH: 419
<212> TYPE: DNA
<213> ORGANISM: Zea mays
<220> FEATURE:
<223> OTHER INFORMATION: unsure at all n locations

<400> SEQUENCE: 249
gtgaaagccg tggaggtggc aggatgttac tggattcatg tcgatgtcat ggacgggcgc 60
tttgtgccaa atatcacaat tggacctttg gttgttgatg ctctgcgtcc tgtgactgat 120
cttccattgg atgtacatct gatgattgtg gaacctgagc agcgagtccc tgattttatc 180
aaggcaggtg ctgatattgt tagtgtccac tgtgaacaaa catcgaccat ccatttgcac 240
agaacagtca atcagattaa aagtctagga gcaaaagcag gagttgtttt gaatccagcg 300
actccactca atgcaattga ttacattctt gatgttgttg acctggtgtt gattatgtct 360
gtgaatcctg ggtttggtgg ccagagcttt atcgagagtc aagtnaggaa aattgcaga 419

<210> SEQ ID NO 250
<211> LENGTH: 451
<212> TYPE: DNA
<213> ORGANISM: Zea mays

<400> SEQUENCE: 250
cgatgtcatg gacgggcgct ttgtgccaaa catcacaatt ggacccttgg ttgttgatgc 60
tctgcgtcca gtgactgatc ttccgttgga tgtacatctg atgattgtgg aacctgagca 120
gcgagtcccc gattttatca aggcaggtgc tgatattgtt agtgtccact gtgaacagac 180
atcgaccatc catttgcacc gaacagtcaa tcagattaaa agtctaggag caaaggcagg 240
agttgttttg aatccagcga ctccactcac tgcaattgat tatgttcttg atgttgttga 300
cctggtgctg attatgtctg tgaatcctgg gtttggtggc cagagcttta tcgagagtca 360
agtaaagaag attgcagaac tgagaaggtt atgtgcagag aagggagtga acccctggat 420
tgaggttgat ggtggtgttg gtcccaaaaa t 451

<210> SEQ ID NO 251
<211> LENGTH: 389
<212> TYPE: DNA
<213> ORGANISM: Zea mays

<400> SEQUENCE: 251
cttggtgatc aggtaaaagc tgtggaggtg gcatgatgcg actggattca tgttgatgtc 60
atggatgggc gctttgtggc aaacatcaca attggaccct tggttgttga tgctctgcgt 120
ccagtgactg atcttccgtt ggatgtacat ctgatgattg tggaacctga gcagcgagtc 180
cctgatttta tcaaggcagg tgctgatatt gatagtgtcc actgtgaaca gacatcgacc 240
attcatttgc accgaacagt caatcagatt aaaagtctat gagcaaaggc aggagttgtt 300
gtgaatccag cgactgcact cactgcaatt gattacgttc ttgatgatga tgacctggtg 360
ctgattatgt ctgtgaatcc tgggtttgg 389

<210> SEQ ID NO 252
<211> LENGTH: 426
<212> TYPE: DNA
<213> ORGANISM: Zea mays

<400> SEQUENCE: 252
ctatgaacag acatcgacca tccatttgca ccgaacaatc aatcagatta aaagtctagg 60

-continued

```
agcaaaggca ggagttgttt tgaatccagc gactccactc actgcaattg attaggggct    120

tgatgttgtt gacctggtgc tgattagggg ggtgaatcct gcgtttggtg gccagagctt    180

tatcgagagt caagtaaaga aaattgcaga actgagaagg ttatgtgcag agaagggagt    240

gaacccctgg attgaggttg atggtggtgt tggtccgaaa aatgcctaca aggttattga    300

agctggcgca aattctattt tctcaggttc tgcagttttt ggggctccag actacgctga    360

agctatcaaa tggaataaga ccatccaaag acctctagct gtagccgcat aaacaacttg    420

acgtgt                                                                426
```

<210> SEQ ID NO 253
<211> LENGTH: 380
<212> TYPE: DNA
<213> ORGANISM: Zea mays

<400> SEQUENCE: 253

```
cggacgcgtg ggcggacgcg tgggctgaga aggttatgtg cagagaaggg agtgaacccc     60

tggattgagg ttgatggtgg tgttggtccg aaaaatgcct acaaggttat tgaagctggc    120

gcaaatgcca ttgtcgcagg ttctgcagtt tttggggctc cagactacgc tgaagctatc    180

aaaggaataa agaccagcca aagacctcta gctgtagccg cataaggagc tggacgtgta    240

atcatttact ctgtgcaagt ttaccagtga tgcgatctgt atagatgtgt gtcttgtcca    300

gccatacgta taccggagat gaaaagagac ggaagcagtg aagaaatatc cttttttttt    360

cttctcattt ttcacgaaga                                                 380
```

<210> SEQ ID NO 254
<211> LENGTH: 375
<212> TYPE: DNA
<213> ORGANISM: Zea mays

<400> SEQUENCE: 254

```
agagagccag agaggtgggc agatggcgac accgtcgtcg tcgctttgct ccagcttcgc     60

ctccctgcgg accgcctcca tcggccaccc ccgcggcatc gcgtcatcta cgcccaggaa    120

ggcgttccaa gtgagggcat cagctcgggt tgacaagttc tcaaagagtg atatcattgt    180

gtccccttcg attctgtctg caaacttcgc caagcttggt gatcaggtaa aagccgtgga    240

ggtggcagga tgtgactgga ttcatgtcga tgtcatggac gggcgctttg tgccaaatat    300

cacaattgga cctttggttg ttgatgctct gcgtcctgtg actgatcttc cattggatgt    360

acatctgatg attgt                                                      375
```

<210> SEQ ID NO 255
<211> LENGTH: 429
<212> TYPE: DNA
<213> ORGANISM: Zea mays

<400> SEQUENCE: 255

```
cacacgcgtc cgcaacaagc caaacaaccc agtggctgct agccgagaca ggggatagat     60

tgagagagag gcgcgcagat ggcgacgccg tcgtcgtcgc tttgctccag cttcgcctcc    120

ctgcggaccg cctccatcgg ccacccccgt ggcatcgcct cctccacgcc caggaaggca    180

ttccatgtga gggcatcagc tcgggttgac aaattctcaa agagtgacat catcgtgtcc    240

ccttcgattc tgtctgcaaa ctttgcgaag cttggtgatc aggtaaaagc tgtggaggtg    300

gcaggatgcg actggattca tgtcgatgtc atggacgggc gctttgtgcc aaacatcaca    360
```

-continued attggaccct tggttgttga tgctctgcgt ccagtgactg atcttccgtt ggatgtacat 420
ctgatgatg 429

<210> SEQ ID NO 256
<211> LENGTH: 424
<212> TYPE: DNA
<213> ORGANISM: Zea mays

<400> SEQUENCE: 256
atcgcttacc gcccccgaag cgtctcggtt cgcatagcag agctgctctt gcaacaagcc 60
aaacaaccca gtggctgcta gccgagacag gggatagatt gagagagagg cgcgcagatg 120
gcgacgccgt cgtcgtcgct ttgctccagc ttcgcctccc tgcggaccgc ctccatcggc 180
cacccccgtg gcatcgcctc ctccacgccc aggaaggcat tccatgtgag ggcatcagct 240
cgggttgaca aattctcaaa gagtgacatc atcgtgtccc cttcgattct gtctgcaaac 300
tttgcgaagc ttggtgatca ggtaaaagct gtggaggtgg caggatgcga ctggattcat 360
gtcgatgtca tggacgggcg ctttgtgcca aacatcacaa ttggaccctt ggttgttgat 420
gctc 424

<210> SEQ ID NO 257
<211> LENGTH: 419
<212> TYPE: DNA
<213> ORGANISM: Zea mays
<220> FEATURE:
<223> OTHER INFORMATION: unsure at all n locations

<400> SEQUENCE: 257
cgcccccgaa gcgtctcggt tcgcatagca aagctgctct tgcaacaagc caaacaaggc 60
antggctgct agccgagaca ggggatagat tgagagagag gcgcgcagat ggcgacgccg 120
tcgtcgtcgc tttgctccag cttcgcctcc ctgcggaccg cctccatcgg ccacccccgt 180
ggcatcgcct cctccacgct caggaaggca ttccatgtga gggcatcagc tcgggttgac 240
aagttctcaa agagtgacat catcgtgtcc ccttcgattc tgtctgcaaa ctttgcgaag 300
cttggtgatc aggtaaaagc tgtggaggtg gcaggatgcg actggattca tgtcgatgtc 360
atggacgggc gctttgtgcc aaacatcaca attggaccct tggtttgtga tgctctgcg 419

<210> SEQ ID NO 258
<211> LENGTH: 416
<212> TYPE: DNA
<213> ORGANISM: Zea mays

<400> SEQUENCE: 258
agaaccaaat cgcttaccgc ccccgaagcg tctcggttcg catagcaaag ctgctcttgc 60
aacaagccaa acaacccagt ggctgctagc cgagacaggg gatagattga gagagaggcg 120
cgcagatggc gacgccgtcg tcgtcgcttt gctccagctt cgcctccctg cggaccgcct 180
ccatcggcca cccccgtggc atcgcctcct ccacgctcag gaaggcattc catgtgaggg 240
catcagctcg ggttgacaag ttctcaaaga gtgacatcat cgtgtcccct tcgattctgt 300
ctgcaaactt tgcgaagctt ggtgatcagg taaaagctgt ggaggtggca ggatgcgact 360
ggattcatgt cgatgtcatg gacgggcgct ttgtgccaaa catcacaatt ggaccc 416

<210> SEQ ID NO 259
<211> LENGTH: 390
<212> TYPE: DNA
<213> ORGANISM: Zea mays

-continued

<220> FEATURE:
<223> OTHER INFORMATION: unsure at all n locations

<400> SEQUENCE: 259
caacaagcca aacaacccag tggctgctag ccgagacagg ggatagattg agagagaggc 60
gcgcagatgg cgacgccgtc gtcgtcgctt tgctccagct tcgcctccct gcggaccgcc 120
tccatcggcc acccccgtgg catcgcctcc tccacgccca ggaaggcatt ccatgtgagg 180
gcatcagctc gggttgacaa attctcaaag agtgacatca tcgtgtcccc ttcgattctg 240
tctgcaaact ttgcgaagct tggtgatcag gtaaaagctg tggaagtggc aggatgcgac 300
tggattcatg tcgatgtcat ggacgggcgc tttgtgccaa acatcacaat tggacccttg 360
ngttgtgatg ctctgcgtcc agtgactgat 390

<210> SEQ ID NO 260
<211> LENGTH: 415
<212> TYPE: DNA
<213> ORGANISM: Zea mays

<400> SEQUENCE: 260
gttttgtttg ttgtccgcct ggcgcctggc cccataacta ctctgccaca atccggggaa 60
gaatcaacct agcggtaagc ggacatggcg gcggcgaaga tagcgccgtc gatgctctcg 120
tcggactttg ccaacctcgc ttcggaggct gagcgcatgg tccgcctagg cgccgactgg 180
ctacatatgg acatcatgga tgggcacttc gttcctaacc tgactattgg ggctccggtg 240
atccagagct tgaggaaaca taccaaagca tatttggact gccatcttat ggtcacaaag 300
ccttcagatt acgtagaacc atttggaaag gctggcgctt ctggattcac attccatata 360
gaagttgcta gagacaactg gcaagatctc atccaaagca ttaaatcaaa gggta 415

<210> SEQ ID NO 261
<211> LENGTH: 257
<212> TYPE: DNA
<213> ORGANISM: Glycine max

<400> SEQUENCE: 261
aaaatttcaa ccacagtgaa ggctacatct cgtgttgaca agttttcaaa aagcgatatc 60
attgtctctc catccattct ttctgcaaac tttgcaagat tgggacaaca ggtgaaagca 120
ctgcagttgg ctggttgtga ttggcttcac gttgatgtaa tggatggccg ttttgttcca 180
aatattacaa ttggacctct tgtcggctga tgcattgcgc cctgtgacag atcttccttt 240
ggatgtacac ctgatga 257

<210> SEQ ID NO 262
<211> LENGTH: 272
<212> TYPE: DNA
<213> ORGANISM: Glycine max
<220> FEATURE:
<223> OTHER INFORMATION: unsure at all n locations

<400> SEQUENCE: 262
gggagttgaa aganagaaag gaaggatggg agtgacaccg aaaattgctc cttcgatgct 60
ctcttccgac ttcgccaatt tggcttccga ggctcagcgc atgctccact tcggcgccga 120
ttggctccac atggacatca tggatgggca ttttgtcccc aatttaacta ttggcgctcc 180
agttattgaa agtttgagaa agcacacaaa gggatatttg gattgtcacc ttatggttac 240
aaatcctctt gattatgttg agnccttggc aa 272

-continued

<210> SEQ ID NO 263
<211> LENGTH: 260
<212> TYPE: DNA
<213> ORGANISM: Glycine max
<220> FEATURE:
<223> OTHER INFORMATION: unsure at all n locations

<400> SEQUENCE: 263
agttgaaaga nagaaaggaa ggatgggagt gacaccgaaa attgctcctt cgatgctctc 60
ttccgacttc gccaatttgg cttccgaggc tcagcgcatg ctccacttcg gcgccgattg 120
gctccacatg gacatcatgg atgggcattt tgtccccaat ttaactattg gcgctccagt 180
tattgaaagt ttgagaaagc acacaaaggg atatttggat tgtcacctta tggttacaaa 240
tcctcttgat tatgttgagc 260

<210> SEQ ID NO 264
<211> LENGTH: 266
<212> TYPE: DNA
<213> ORGANISM: Glycine max

<400> SEQUENCE: 264
caaggaagga tgggagtgac accgaaaatt gctccttcga tgctctcttc cgacttcgcc 60
aatttggctt ccgaggctca gcgcatgctc cacttcggcg ccgattggct ccacatggac 120
atcatggatg ggtcttttgt ccccaattta actattggcg ctccagttat tgaaagtttg 180
agaaagcaca caaagggata tttggattgt caccttatgg ttacaaatcc tcttgattat 240
gttgagccct tggcaaaagc tggtgc 266

<210> SEQ ID NO 265
<211> LENGTH: 228
<212> TYPE: DNA
<213> ORGANISM: Glycine max
<220> FEATURE:
<223> OTHER INFORMATION: unsure at all n locations

<400> SEQUENCE: 265
tgacaccgaa aattgctcct tcgatgctcn cttccgantt cgcnaatttg gcttccgagg 60
ctcagcgcat gctccacttc ggcgccgatt ggctccacat ggacatcatg gntgggnatt 120
ttgtccccaa tttaactatt ggcgctccag ttattganag tttgagaaag cacacaaagg 180
gatatttnng attgtcacct tatggttaca aatcctcttg attatgtt 228

<210> SEQ ID NO 266
<211> LENGTH: 243
<212> TYPE: DNA
<213> ORGANISM: Glycine max

<400> SEQUENCE: 266
caaccataga tgtggccgca tcagcagggg caaactgcat tgttgctgga agttcagtgt 60
ttggtgcccc tgagccagtt caagtaatat ccttactaag gaattctgtt gagaaagccc 120
agcaaacctt gatacagtaa aaaaaaaatg tcgttttaag ttgcagtaca cttcacaact 180
ttgcataaac aatatgctta atgtttaaca ttttccataa gttgaataaa agatcatgtg 240
act 243

<210> SEQ ID NO 267
<211> LENGTH: 266
<212> TYPE: DNA
<213> ORGANISM: Glycine max

<400> SEQUENCE: 267
agaggttgat ggtggtttag ggccttcaac catagacgtg gccgcatcag caggggcaaa 60
ttgcattgtt gctggaagtt ctgtttttgg tgcacctgag ccagctcaag taatatccta 120
ctgaggagtt ctgttgagaa agcccagcaa acctcgatac agtaaaacaa tgtcgtttta 180
agttgcagta tacttcacaa ctttacataa acaatatgct aatgttaaca tttcataagt 240
tgaataaaag atcaagtgct tgaaaa 266

<210> SEQ ID NO 268
<211> LENGTH: 229
<212> TYPE: DNA
<213> ORGANISM: Glycine max

<400> SEQUENCE: 268
gaaaatttct gacttgagaa gagtgtgcgc ggaaaaggga gtgaatccat ggattgaagt 60
agatggtgga gttggtccag caaatgctta caaggtgatt gaggctggag ccaatgctct 120
ggttgcaggc tctgcttgtt tggagctaaa gattatgccg aagctataag aggaatcaaa 180
accagcaaaa gacctgaagc agttgctgtg tgaaatgccc atgtggttc 229

<210> SEQ ID NO 269
<211> LENGTH: 266
<212> TYPE: DNA
<213> ORGANISM: Glycine max

<400> SEQUENCE: 269
cccccatccc caccccaact tgtatattgt gcataatatc tatctgcatt ctctctcttc 60
agggagtgaa tccatggatt gaagtagatg gtggagttgg tccagcaaat gcttacaagg 120
tgattgaggc tggagccaat gctctggttg caggctctgc tgtgtttgga gctaaagatt 180
atgccgaagc tataagagga atcaaaacca gcaaaagacc tgaagcagtt gctgtgtgaa 240
atgcccatgt ggttcaatat tcaccg 266

<210> SEQ ID NO 270
<211> LENGTH: 257
<212> TYPE: DNA
<213> ORGANISM: Glycine max

<400> SEQUENCE: 270
agcgatatca ttgtctctcc gtccattctt tctgcaaact tttcaaaatt gggagagcag 60
gtgaaagcag tggaattggc tggttgtgat tggattcacg ttgatgtaat ggatggtcgc 120
tttgttccaa atattacaat tggacctctt gtggttgatg cattgcgccc tgtgacagat 180
cttcctttgg atgtacacct gatgattgta gacctgaaca aagggtacca gattttatta 240
aggcaggagc tgatata 257

<210> SEQ ID NO 271
<211> LENGTH: 274
<212> TYPE: DNA
<213> ORGANISM: Glycine max
<220> FEATURE:
<223> OTHER INFORMATION: unsure at all n locations

<400> SEQUENCE: 271
caagttttca aaaagcgata tcattgtttc tccatccatt ctttctgcaa actttgcaaa 60
attgggaang cangtgaaag cagtggagtn gnnggntggt aatnggntca angtngatgt 120

-continued

```
aatggatggc cngtttngtn ccaaatatta caattggacc tcttgtggtt gatgcattgc    180

cgcccctgtg acagatcttc cttnggatgt acacctgatg attgtagacc ctgaacaaag    240

ggtaccagat tttattaagg caggagcccg atac                                274


<210> SEQ ID NO 272
<211> LENGTH: 281
<212> TYPE: DNA
<213> ORGANISM: Glycine max
<220> FEATURE:
<223> OTHER INFORMATION: unsure at all n locations

<400> SEQUENCE: 272

cttcttcctt gtgttcatcg accctccaat cccaaatcaa tggattctgc cttcacaaaa     60

cctctctttc ccatcctcgt tccctcactt tctccaggaa gaaaatttca accacagtga    120

aggctacatc tcgtgttgac aagttttcaa aaagcgatat cattgtttct ccatccattc    180

tttctgcaaa ctttgcaaaa ttgggagagc aggtgaaagc agtggagttg gctggttntg    240

atggattcac gttgatgtaa tggatgggcg tttgttccaa a                        281


<210> SEQ ID NO 273
<211> LENGTH: 256
<212> TYPE: DNA
<213> ORGANISM: Glycine max

<400> SEQUENCE: 273

gatggctgca acctcttcct tgtgctcatc gaccctccaa tcccagatca atggattctt     60

ccttcacaaa acctctcttt cccatactcc ttccctcact ttctccagga ggaaaatttc    120

aaccacagtg aaggctacat ctcgagtcga caagttttca aaaagcgata tcattgtctc    180

tccgtccatt ctttctgcaa acttttcaaa attggagagc aagtgaaagc agtagaattg    240

gctggttgtg attgga                                                    256


<210> SEQ ID NO 274
<211> LENGTH: 273
<212> TYPE: DNA
<213> ORGANISM: Glycine max
<220> FEATURE:
<223> OTHER INFORMATION: unsure at all n locations

<400> SEQUENCE: 274

gattgctgag tcaaacttga attgaaggtg aagaaggaga tggcagnaac ttcttccttg     60

tgttnatcga ncctncaatc ccaaatcaat ggattctgcn ttcacaaaac ctctntttcc    120

catcctcgtt ccctnacttt ctcnaggaag aaaatttcaa ccacagtgaa ggctacatct    180

cgtgttnaca agttttcaaa aagcgatatc attgtttctc catccattct ttntgcaaac    240

tttgcaaaat tgggagagca ggtgaaagca gtg                                 273


<210> SEQ ID NO 275
<211> LENGTH: 260
<212> TYPE: DNA
<213> ORGANISM: Glycine max
<220> FEATURE:
<223> OTHER INFORMATION: unsure at all n locations

<400> SEQUENCE: 275

ggtnangtaa acttganttg aagtgaagaa ggagatggct gcaacctctt ccttgtgctt     60

catcgaccct ccaatcccag atcaatggat tcttccttca caaaacctct ctttcccata    120

ctccttccct cactttctcc aggaggaaaa tttcaaccac agtgaaggct acatctcgag    180
```

-continued

```
tcgacaagtt ttcaaaaagc gatatcattg tctctccgtc cattctttct gcaaactttt    240

caaaattggg agagcaggtg                                                260


<210> SEQ ID NO 276
<211> LENGTH: 247
<212> TYPE: DNA
<213> ORGANISM: Glycine max

<400> SEQUENCE: 276

gtcaaacttg aattgaaggt gaagaaggag atggcagcaa cttcttcctt gtgttcatcg     60

accctccaat cccaaatcaa tggattctgc cttcacaaaa cctctctttc ccatcctcgt    120

tccctcactt tctccaggaa gaaaatttca accacagtga aggctacatc tcgtgttgac    180

aagttttcaa aaagcgatat cattgtttct ccatccattc tttctgcaaa ctttgcaaaa    240

ttgggag                                                              247


<210> SEQ ID NO 277
<211> LENGTH: 255
<212> TYPE: DNA
<213> ORGANISM: Glycine max

<400> SEQUENCE: 277

ggattggtga ggtaaacttg aattgaagtg aagaaggaga tggctgcaac ctcttccttg     60

tgctcatcga ccctccaatc ccagatcaat ggattcttcc ttcacaaaac ctctctttcc    120

catactcctt ccctcacttt ctccaggagg aaaatttcaa ccacagtgaa ggctacatct    180

cgagtcgaca agttttcaaa aagcgatatc attgtctctc cgtccattct ttctgcaaac    240

ttttcaaaat tggga                                                     255


<210> SEQ ID NO 278
<211> LENGTH: 254
<212> TYPE: DNA
<213> ORGANISM: Glycine max

<400> SEQUENCE: 278

cgattggtga ggtaaacttg aattgaagtg aagaaggaga tggctgcaac ctcttccttg     60

tgctcatcga ccctccaatc ccagatcaat ggattcttcc ttcacaaaac ctctctttcc    120

catacttctt ccctcacttt ctccaggagg aaaatttcaa ccacagtgaa ggctacatct    180

cgagtcgaca agttttcaaa aagcgatatc attgtctctc cgtccattct ttctgcaaac    240

ttttcaaaat tggg                                                      254


<210> SEQ ID NO 279
<211> LENGTH: 276
<212> TYPE: DNA
<213> ORGANISM: Glycine max

<400> SEQUENCE: 279

gcataggatt ggtgaggtaa acttgaattg aagtgaagaa ggagatggct gcaacctctt     60

ccttgtgctc atcgaccctc caatcccaga tcaatggatt cttccttcac aaaacctctc    120

tttcccatac tccttccctc actttctcca ggaggaattt caaccacagt gaaggctaca    180

tctcgagtcg acaagttttc aaaaagcgat atcattgtct ctccgtccat tctttctgca    240

aacttttcaa aattgggaga gcaggtgaaa gcagtg                              276


<210> SEQ ID NO 280
```

-continued

<211> LENGTH: 244
<212> TYPE: DNA
<213> ORGANISM: Glycine max

<400> SEQUENCE: 280
taggattggt gaggtaaact tgaattgaag tgaagaagga gatggctgca acctcttcct 60
tgtgctcatc gaccctccaa tcccagatca atggattctt ccttcacaaa acctctcttt 120
cccatactcc ttccctcact ttctccagga ggaaaatttc aaccacagtg aaggctacat 180
ctcgagtcga caagttttca aaaagcgata tcattgtctc tccgtccatt ctttctgcaa 240
actt 244

<210> SEQ ID NO 281
<211> LENGTH: 249
<212> TYPE: DNA
<213> ORGANISM: Glycine max

<400> SEQUENCE: 281
cttttgtgaa ggcctaggat tgctgagtca aacttgaatt gaaggtgaag aaggagatgg 60
cagcaacttc ttccttgtgt tcatcgaccc tccaatccca aatcaatgga ttctgccttc 120
acaaaacctc tctttcccat cctcgttccc tcactttctc caggaagaaa atttcaacca 180
cagtgaaggc tacatctcgt gttgacaagt tttcaaaaag cgatatcatt gtttctccat 240
ccattcttt 249

<210> SEQ ID NO 282
<211> LENGTH: 262
<212> TYPE: DNA
<213> ORGANISM: Glycine max

<400> SEQUENCE: 282
cacacacttt tttcaaggca taggattggt gaggcaaact tgaattgaag tgaagaagga 60
gatggctgca acctcttcct tgtgctcatc gaccctccaa tcccagatca atggattctt 120
ccttcacaaa acctctcttt cccatactcc ttccctcact ttctccagga ggaaaatttc 180
aaccacagtg aaggctacat ctcgagtcga caagttttca aaaagcgata tcattgtctc 240
tccgtccatt ctttctgcaa at 262

<210> SEQ ID NO 283
<211> LENGTH: 249
<212> TYPE: DNA
<213> ORGANISM: Glycine max

<400> SEQUENCE: 283
ttttgtcaag gcataggatt ggtgaggtaa acttgaattg aagtgaagaa ggagatggct 60
gcaacctctt ccttgtgctc atcgaccctc caatcccaga tcaatggatt cttccttcac 120
aaaaccttct ttcccatact ccttccctca ctttctccag gaggaaaatt tcaaccacag 180
tgaaggctac atctcgagtc gacaagtttt caaaaagcga tatcattgtc tctccgtcca 240
ttctttctg 249

<210> SEQ ID NO 284
<211> LENGTH: 265
<212> TYPE: DNA
<213> ORGANISM: Glycine max

<400> SEQUENCE: 284
cacacagtca cacttttgtg aaggcctagg attgctgagt caaacttgaa ttgaaggtga 60

-continued

```
cgaaggagat ggcagcaact tcttccttgt gttcatcgac cctccaatcc caaatcaatg    120

gattctgcct tcacaaaacc tctctttccc atcctcgttc cctcactttc tccaggaaga    180

aaatttcaac cacagtgaag gctacatctc gtgttgacaa gttttcaaaa agcgatatca    240

ttgtttctcc atccattctt tctgc                                          265


<210> SEQ ID NO 285
<211> LENGTH: 250
<212> TYPE: DNA
<213> ORGANISM: Glycine max

<400> SEQUENCE: 285

caaggcatag gatcggtgag gcaaacttga attgaagtga agaaggagat ggctgcaacc     60

tcttccttgt gctcatcgac cctccaatcc cagatcaatg gattcttcct tcacatcacc    120

tctcttcccc atactccttc cctcactttc tccaggagga aaatttcaac cacagtgaag    180

gctacatctc gagtcgacaa gttttcaaaa gcgatatcat tgtctctccg tccattcttt    240

ctgcaaattt                                                           250


<210> SEQ ID NO 286
<211> LENGTH: 251
<212> TYPE: DNA
<213> ORGANISM: Glycine max

<400> SEQUENCE: 286

cacacttttg tcaaggcata ggattggtga ggtaaacttg aattgaagtg aagaaggaga     60

tggctgcaac ctcttccttg tgctcatcga ccctccaatc ccagatcaat ggattcttcc    120

ttcacaaaac ctctctttcc catactcctt ccctcacttt ctccaggagg aaaatttcaa    180

ccacagtgaa ggctacatct cgagtcgaca agttttcaaa agcgatatca ttgtctctcc    240

gtccattctt t                                                         251


<210> SEQ ID NO 287
<211> LENGTH: 273
<212> TYPE: DNA
<213> ORGANISM: Glycine max

<400> SEQUENCE: 287

cttttgtgaa ggcctaggat tgctgagtca aacttgaatt gaagagtgaa gaaggagatg     60

gcagcaactt cttccttgtg ttcatcgacc ctccaatccc aaatcaatgg attctgcctt    120

cacaaaacct ctctttccca tcctcgttcc ctcactttct ccaggaagaa aatttcaacc    180

acagtgaagg ctacatctcg tgttgacaag ttttcaaaaa gcgatatcat tgtttctcca    240

tccattcttt ctgcaaactt tgcaaaattg ggg                                 273


<210> SEQ ID NO 288
<211> LENGTH: 273
<212> TYPE: DNA
<213> ORGANISM: Glycine max
<220> FEATURE:
<223> OTHER INFORMATION: unsure at all n locations

<400> SEQUENCE: 288

cacacacagt canactttng tgaaggccta ggattggtga gtcaaacttg aattgaaggt     60

gaagaaggag atggcagcaa cttcttcctt gtgttcatcg accctccaat cccaaatcaa    120

tggattctgc cttcacaaaa cctctctttc ccatcctcgt tccctcactt tctccaggaa    180
```

-continued

```
gaaaatttca accacagtga aggctacatc tcgtgttgac aagttttcaa aaagcggata    240

tcattgtttc tccatccatc tttctgcaaa ttt                                 273


<210> SEQ ID NO 289
<211> LENGTH: 259
<212> TYPE: DNA
<213> ORGANISM: Glycine max

<400> SEQUENCE: 289

cacagtcaca cttttgtgaa ggcctaggat tgctgagtca aacttgaatt gaaggtgaag     60

aaggagatgg cagcaacttc ttccttgtgt tcatcgaccc tccaatccca aatcaatgga    120

ttctgccttc acaaaacctc tctttcccat cctcgttccc tcactttctc caggaagaaa    180

atttcaacca cagtgaaggc tacatctcgt gttgacaagt tttcaaaaag cgatatcatt    240

gtttctccat ccattcttt                                                 259


<210> SEQ ID NO 290
<211> LENGTH: 246
<212> TYPE: DNA
<213> ORGANISM: Glycine max

<400> SEQUENCE: 290

tttcctcaag gcataggatt ggtgaggtaa acttgaattg aagtgaagaa ggagatggct     60

gcaacctctt ccttgtgctc atcgaccctc caatcccaga tcaatggatt cttgcttcac    120

aaaacctctc ttgctcatac tccttccctc actttctcca ggcggaaaat ttcaaccaca    180

gtgaaggcta catctcgagt cgacaagttt tcaaaaagcg atatcatgtg gtcgctccgt    240

ccattc                                                               246


<210> SEQ ID NO 291
<211> LENGTH: 262
<212> TYPE: DNA
<213> ORGANISM: Glycine max

<400> SEQUENCE: 291

gctggagttg tcttaaaccc cggtaccccc ttaagtgcaa tagaatatat ccttgatgtg     60

gttgatttgg tcttaattat gtccgtaaac cctggctttg gtggccagag ttttattgag    120

agtcaagtaa agaaaatttc tgatttgaga agattgtgtg cggagaaggg agtgaatcca    180

tggattgaag tagatggtgg agttggtcca gcaaatgcat acaaggtgat tgaggctgga    240

gccaatgcac tggttgctgg ct                                             262


<210> SEQ ID NO 292
<211> LENGTH: 282
<212> TYPE: DNA
<213> ORGANISM: Glycine max

<400> SEQUENCE: 292

agggtaccag attttattaa ggcaggagct gatatagtca gtgttcattg tgaacaatct     60

tccaccatcc atttgcatcg tactgttaat caagtgaaaa gtctgggagc taaagctgga    120

gttgtcttaa accctgctac ccccttaagt gcaatagaat atgtcctgat gtggtggatt    180

tggtcttaat tatgtccgta aaccctggct ttggtggcca gagttttatt gagagtcaag    240

taaagaaaat ttctgacttg agaagagtgt gcgcggaaaa gg                       282


<210> SEQ ID NO 293
<211> LENGTH: 249
```

-continued

<212> TYPE: DNA
<213> ORGANISM: Glycine max

<400> SEQUENCE: 293
gtcgctttgt tccaaatatt acaattggac ctcttgtggt tgatgcattg cgccctgtga 60
cagatcttcc tttggatgta cacctgatga ttgtagagcc tgaacaaagg gtaccagatt 120
ttattaaggc aggagctgat atagtcagtg ttcattgtga acaatcttcc accatccatt 180
tgcatcgtac agttaatcaa gtgaaaagtc tgggagctaa agctggagtt gtcttaaacc 240
ccggtaccc 249

<210> SEQ ID NO 294
<211> LENGTH: 264
<212> TYPE: DNA
<213> ORGANISM: Glycine max

<400> SEQUENCE: 294
ggtgaaagca gtagaattgg ctggttgtga ttggattcac gttgatgtaa tggatggtcg 60
ctttgttcca aatattacaa ttggacctct tgtggttgat gcattgcgcc ctgtgacaga 120
tcttcctttg gatgtacacc tgatgattgt agagcctgaa caaagggtac cagattttat 180
taaggcagga gctgatatag tcagtgttca ttgtgaacaa tcttccacca tccatttgca 240
tcgtacagtt aatcaagtga aaag 264

<210> SEQ ID NO 295
<211> LENGTH: 267
<212> TYPE: DNA
<213> ORGANISM: Glycine max
<220> FEATURE:
<223> OTHER INFORMATION: unsure at all n locations

<400> SEQUENCE: 295
gtcagtgttc attgtgaaca atcttccncc atccatttgc atcctacagt taacncaagt 60
gaaaagtctg ggagctaaag ctggagttgt cttaaacccc ggtacccccct taagtgcaat 120 agaatatatc cttgatgtgg ttgatttggt cttaattatg tccgtaaacc ctggctttgg 180
tggccagagt tttattgaga gtcaagtaaa gaaaatttct gatttgagaa gattgtgtgc 240
ggagaaggga gtgaatccat ggattga 267

<210> SEQ ID NO 296
<211> LENGTH: 277
<212> TYPE: DNA
<213> ORGANISM: Glycine max
<220> FEATURE:
<223> OTHER INFORMATION: unsure at all n locations

<400> SEQUENCE: 296
gtccaattgt aatatttgga acaaaacggc catccattac aattngacct cttgtggttg 60
atgcattgcg ccctgtgaca nctcttcctt tggatgtaca cctgatgatt gtacagcctg 120
aacaaagggt accagatttt attaaggcag gagctgatat agtcagtgtt cattgtgaac 180
aatcttccac catccatttg catcgtactg ttaatcaagt gaaaagtctg ggagctaaag 240
ctggagttgt ctaaaccctg ctacccccctt aagtgca 277

<210> SEQ ID NO 297
<211> LENGTH: 263
<212> TYPE: DNA
<213> ORGANISM: Glycine max
<220> FEATURE:

-continued

<223> OTHER INFORMATION: unsure at all n locations

<400> SEQUENCE: 297
ggctggagtt gtcttaaacc ccggtacccc cttaagtgca atagaatata tccttgatgt 60
ggttnatttg gtcttaattn tgtaccgtaa accctggctt tggtggccag agttttattg 120
agagtcaagt aaagaaattt ctgatttgag aagattgtgt gcggagaagg gagtgaatcc 180
atggattgaa gtagatggtg ggngttggtc cagcaaatgc atacaggtga tnggaggctg 240
gnagccaaac cntggtgcag gcc 263

<210> SEQ ID NO 298
<211> LENGTH: 388
<212> TYPE: DNA
<213> ORGANISM: Glycine max

<400> SEQUENCE: 298
ggagaaagaa agaaaagatg ggaatgacac cgaaaatagc tccttcgatg ctctcttccg 60
acttcgccaa tttggcttcc gaggctcagc gcatgctcca cttcggcgcc gattggctcc 120
acatggacat catggatggg cattttgtcc ccaatttaac tattggcgct ccagttattg 180
aaagtttgag aaagcacaca aaggcatatt tggattgtca ccttatggtt acaaatcctc 240
ttgattatgt tgaacccttg gcaaaagctg gtgcttctgg ttttacattt cacgtagaga 300
catcaaaaga taactggaaa gaacttatcc aaagaatcaa gtcacatggc atgattcctg 360
gtgtagcatt aaagcctggg accccccgt 388

<210> SEQ ID NO 299
<211> LENGTH: 368
<212> TYPE: DNA
<213> ORGANISM: Glycine max

<400> SEQUENCE: 299
gatggccgtt ttgttccaaa tattacaatt ggacctcttg tggttgatgc attgcgccct 60
gtgacagatc ttcctttgga tgtacacctg atgattgtac agcctgaaca aagggtacca 120
gattttagta aggcacgagc tgatatagtc agtgttcatt gtgaacaatc ttccaccatc 180
catttgcatc gtactgttaa tcaagtgaaa agtctgggag ctaaagctgg agttgtctta 240
aaccctgcta ccccccttaag tgcaatagaa tatgtccttg atgtggtgga tttggtccta 300
attaagtccg taaaccctgg ctttggtggc cacagtttta atgagagtca agtaaagaaa 360
atttctga 368

<210> SEQ ID NO 300
<211> LENGTH: 350
<212> TYPE: DNA
<213> ORGANISM: Zea mays
<220> FEATURE:
<223> OTHER INFORMATION: unsure at all n locations

<400> SEQUENCE: 300
cgccatcgac ggtgccgacg aggttgaccc tgaccttaac cttgtgaaag ggaggggtgg 60
tgctcttctt cgtgagaaga tggttgaggc agcatcggac aagtttattg ttattgttga 120
cgagacaaaa ctagttgatg ggttaggagg tagtggtcta gccatgccag tggaagttgt 180
gcagttctgc tggaagtaca accttgtaag attgcaggaa ctgtttaagg aggaaggagt 240
cgaggcaaag ctaaggtttg aaggcgacaa gccctatgtt actgacaact ncaactacat 300
cgtcgattta tacttcaaga cgccaatcaa ggatgcgttg gcagcaggac 350

-continued

<210> SEQ ID NO 301
<211> LENGTH: 264
<212> TYPE: DNA
<213> ORGANISM: Zea mays

<400> SEQUENCE: 301
ccgctctcca cgctcgacga caacccgctc atcgacctcg ccatcgacgg tgccgacgag 60
gttgaccctg acctcaacct tgtgaaaggg cggggtggtg ctcttcttcg tgagaagatg 120
gttgaggcag catcggacaa gtttattgtt attgttgacg agacaaaact agttgatggg 180
ttaggaggta gtggtctagc catgccagtg gaagttgtgc agttctgctg gaagtacaac 240
cttgtaagat tgcaggaact gttt 264

<210> SEQ ID NO 302
<211> LENGTH: 267
<212> TYPE: DNA
<213> ORGANISM: Zea mays

<400> SEQUENCE: 302
caaactgcgg ctgctgtaga tacgcgcgcc gtcactccaa ggtccaagcc tcccttgctc 60
ccgccaccgc ccctcaccat gggcagcgcc gccgcctctc cgcagccgtc tgggaatctg 120
acgcaggacg agctcaagcg cgtggcggcg caccgcgcgg tggagttcgt ggagcccggc 180
atgacgctgg gcctgggcac gggttccacg gccgcgcacg cgctggaccg tctgggctac 240
ctactccgcg tgggctcgct gtccggg 267

<210> SEQ ID NO 303
<211> LENGTH: 333
<212> TYPE: DNA
<213> ORGANISM: Zea mays

<400> SEQUENCE: 303
acgcccacgc gtccgtcccg ttcccgatcc tcatcacctc aaccccgcgc cgccccctcc 60
ccaccaccct cgccatggtc agcgccgccg cctcgccgcc gccgtccggg aagccgacgc 120
aggacgagct gaagcgcttg gcggcgcacc gcgcggtgga gctcgtggag cccggcatga 180
cgctgggcct gggcacgggc tccacggcgg cgcacgcgct ggaccgcctg ggcgacctcc 240
tccgcgcggg cgcgctgccg gggggtggccg gcgtgccgac ctcgctcaag acggatgcgc 300
aagcggcgcg cgtcggcatc ccgctgctcc cgc 333

<210> SEQ ID NO 304
<211> LENGTH: 420
<212> TYPE: DNA
<213> ORGANISM: Zea mays

<400> SEQUENCE: 304
ggcgtgccca catccaagcg caccttcgag caggcgcagt cgctcggcat cccgctctgg 60
acgctcgacg acaacccgct catcgacctc gccatcgacg gtgccgacga ggttgaccct 120
gacctcaacc ttgtgaaagg gcggggtggt gctcttcttc gtgagaagat ggttgaggca 180
gcatcggaca agtttattgt tattgttgac gagacaaaac tagttgatgg gttaggaggt 240
agtggtctag ccatgccagt ggaagttgtg cagttctgct ggaagtacaa ccttgtaaga 300
ttgcaggaac tgtttaagga ggaaggagtc gaggcaaagc taaggtttga aggcgacaag 360
ccctatgtta ctgacaactc aaactacatc gtcgatttat acttcaagac gccaatcaag 420

-continued

<210> SEQ ID NO 305
<211> LENGTH: 432
<212> TYPE: DNA
<213> ORGANISM: Zea mays

<400> SEQUENCE: 305

```
accttgtgaa agggcggggt ggtgctcttc ttcgtgagaa gatggttgag gcagcatcgg     60
acaagtttat tgttattgtt gacgagacaa aactagttga tgggttagga ggtagtggtc    120
tagccatgcc agtggaagtt gtgcagttct gctggaagta caaccttgta agattgcagg    180
aactgtttaa ggaggaagga gtcgaggcaa agctaaggtt tgaaggcgac aagccctatg    240
ttactgacaa ctcaaactac atcgtcgatt tatacttcaa gacgccaatc aaggatgcgt    300
tggcagcagg acaggaaatt gcagctctgg aaggagttgt tgaccatggg ttgttcttga    360
acatggcgag ttcagtgatc attgctggaa cggacggtgt cagtgtcaaa acgaagtgag    420
tttttgagtt gc                                                        432
```

<210> SEQ ID NO 306
<211> LENGTH: 461
<212> TYPE: DNA
<213> ORGANISM: Zea mays
<220> FEATURE:
<223> OTHER INFORMATION: unsure at all n locations

<400> SEQUENCE: 306

```
caccaagcat gccgcnnatg gggtgntgtt nttcgtgaga agatgggtga ggcagcatng     60
gacaagttta ntgttattgt tgacgagaca aaactagttg atgggttagg aggtagtggt    120
ctagccatgc cagtggaagt tgtgcagttc tgctggaagt acaaccttgt aagattgcag    180
gaactgttta aggaggaagg agtcgaggca aagctaaggt ttgaaggcga caagccctat    240
gttactgaca actcaaacta catcgtcgat ttatacttca agacgccaat caaggatgcc    300
gttggcagca ggacaggaaa ttgcagctct ggaaggagtt gttgaccatg ggttgttctt    360
gaacatggcg agttcagtga tcattgctgg aacggacggt gtcagtgtca aaacgaaatg    420
agtttttgag ttgctttgtt ggttgngttg aaattttttt t                        461
```

<210> SEQ ID NO 307
<211> LENGTH: 249
<212> TYPE: DNA
<213> ORGANISM: Glycine max

<400> SEQUENCE: 307

```
ctcgatctcg ccatcgacgg cgccgacgag gtcgaccccg acctcaacct cgtcaaaggc     60
cgcggcggcg ccctcctccg cgagaagatg gtcgaggccg cctccgacaa gttcgtcgtg    120
gtcgtcgacg acaccaagct cgtggacggc ctcggcggaa gcgggctggc catgccggtg    180
gaggtggtcc agttctgctg gaagtacaat ctggatcggc ttcaggagct tttcaaggaa    240
gaaggtgtg                                                            249
```

<210> SEQ ID NO 308
<211> LENGTH: 240
<212> TYPE: DNA
<213> ORGANISM: Glycine max

<400> SEQUENCE: 308

```
gtcgaccccg acctcaacct cgtcaaaggc cgcggcggcg ccctcctccg cgagaagatg     60
gtcgaggccg cctccgacaa gttcgtcgtg gtcgtcgacg acaccaagct cgtggacggc    120
```

-continued ctcgcggaag cgggctggcc atgccggtgg aggtggtcca gttctgctgg aagtacaatc 180
tggatcggct tcaggagctt ttcaaggaag aaggtgtgga agcaaaattg agattggagg 240

<210> SEQ ID NO 309
<211> LENGTH: 262
<212> TYPE: DNA
<213> ORGANISM: Glycine max

<400> SEQUENCE: 309
ggtcgacccc gacctcaacc tcgtcaaagg ccgcggcggc gccctcctcc gcgagaagat 60
ggtcgaggcc gcctccgaca agttcgtcgt ggtcgtcgac gacaccaagc tcgtggacgg 120
cctcggcgga agcgggctgg ccatgccggt ggaggtggtc cagatctgct ggaagtacaa 180
tctggatcgg cttcaggagc ttttcaagga agaaggtgtg gaagcaaaat tgagattgga 240
ggagagtggg aaccctacgt ca 262

<210> SEQ ID NO 310
<211> LENGTH: 263
<212> TYPE: DNA
<213> ORGANISM: Glycine max
<220> FEATURE:
<223> OTHER INFORMATION: unsure at all n locations

<400> SEQUENCE: 310
accacacatt caattttana cctctgggcg tggctagctt caacctttaa cattaacatg 60
gccattccct acccccattt catcgccacc gagaaagccg ccatggacgc cggcctcctc 120
cacccctcct ccccctccgt catcctcacc caagacgatt tgaagaaaat cgccgcctac 180
aaggccgtcg agtacgtgga gtccggcatg atcctcggcc tcggcaccgg ctccaccgcc 240
aagcatgccg tcgaccgcat cgg 263

<210> SEQ ID NO 311
<211> LENGTH: 274
<212> TYPE: DNA
<213> ORGANISM: Glycine max

<400> SEQUENCE: 311
cttacattcc tttctccacc acacattcaa ttttgaacct ctgggactgg ctagcttcaa 60
cctttaacat taacatggcc attccctacc cccatttcat cgccaccgag aaagccgcca 120
tggacgccgg cctcctccac ccctcctccc cctccgtcat cctcacccaa gacgatttga 180
agaaaatcgc cgcctacaag gccgtcgagt acgtggagtc cggcatggtc ctcggcctag 240
gcaccggctc caccgccaag catgccgtcg accg 274

<210> SEQ ID NO 312
<211> LENGTH: 333
<212> TYPE: DNA
<213> ORGANISM: Zea mays

<400> SEQUENCE: 312
ctcacctccc ctccactccc tttctcccct gactcctgct ctataggatc ctccgcctcc 60
atcgcctctc gcgcctccaa tcgccttcgg cgcttcgtcc gtcctgctcc acctcttctt 120
acgccggttg accctgacct caaccttgtg aaagggcggg gtggtgctct tcttcgtgag 180
aagatggttg aggcagcatc ggacaagttt attgttattg ttgacgagac aaaactagtt 240
gatgggttag gaggtagtgg tctagccatg ccagtggaag ttgtgcagtt ctgctggaag 300

-continued tacaaccttg taagattgca ggactgttaa gga 333

<210> SEQ ID NO 313
<211> LENGTH: 302
<212> TYPE: DNA
<213> ORGANISM: Zea mays

<400> SEQUENCE: 313
ggatggtgct cgggctcggg acgggctcca cggccgcctt cgccgtcgcc gagatcggcg 60
cgctcctggc cgcgggcaag ctcgagaaga tcgtcggcgt gcccacatcc aagcgcacct 120
tcgagcaggc gcagtcgctc ggcatcccgc tctccacgct cgacgacaac ccgctcatcg 180
acctcgccat cgacggtgcc gacgaggttg accctgacct caaccttgtg aaagggcggg 240
gtggtgctct tcttcgtgag aagatggttg aggcagcatc ggacaagttt attgttattg 300
tt 302

<210> SEQ ID NO 314
<211> LENGTH: 244
<212> TYPE: DNA
<213> ORGANISM: Glycine max

<400> SEQUENCE: 314
ctcaaggaca tcgtcggaat ccccacctcc acaaaaaccc acgaacaagc cctctccctc 60
gggatccccc tctccgatct cgacgcccac cccgccatcg atctcgccat cgacggcgcc 120
gacgaggtcg atcccttcct caacctcgtc aagggccgtg gcggctccct cctccgagaa 180
aaaatggtcg aaggcgcatg caagaagttc atcgtcatcg ttgatgagtc caagctcgta 240
aact 244

<210> SEQ ID NO 315
<211> LENGTH: 267
<212> TYPE: DNA
<213> ORGANISM: Glycine max

<400> SEQUENCE: 315
ccgccatcga tctcgccatc gacggcgccg acgaggtcga tcccttcctc aacctcgtca 60
agggccgtgg cggctccctc ctccgagaaa aaatggtcga aggcgcatgc aagaagttca 120
tcgtcatcgt tgatgagtcc aagctcgtaa actatttggg gggtagtggg ttggccatgc 180
ccgttgaggt tattaagttc tgttggaggt tcaccgcggc gaggttgcag aagcttcttg 240
aggaggctgg gtgcgttgcc aggctca 267

<210> SEQ ID NO 316
<211> LENGTH: 291
<212> TYPE: DNA
<213> ORGANISM: Glycine max
<220> FEATURE:
<223> OTHER INFORMATION: unsure at all n locations

<400> SEQUENCE: 316
gatttgaaga aaatcgcngc ctacaaggcc gtcgagtacg tggagtccgg catggtcctc 60
ggcctaggca ccggctccan cgccaagcat gccgtcganc gcatcggcga gctcctccgc 120
cagggcaagc tcaaggacat cgtcggaatc cccacctcca caaaaaccca cgaacaagcc 180
ctctccctcg ggatccccct ctccgatctc gacgcccacc ccgccatcga tctcgccatc 240
gacggcgccg acgaggtcga tcccttcctc aacctcgtca agggccgtgg g 291

-continued

<210> SEQ ID NO 317
<211> LENGTH: 265
<212> TYPE: DNA
<213> ORGANISM: Glycine max

<400> SEQUENCE: 317
agacgacctc aagaaaatcg ccgcctacaa ggccgtcgag tacgtcgagt ccggcatggt 60
cctcggcctc ggcaccggct ccactgccaa gcacgccgtc gaccgcatcg gcgagctcct 120
ccgccaagga aaactcaaag acatcgtcgg catccccacc tccaccaaaa cccacgacca 180
ggccctctcc ctcggcatcc ccctctccga tctcgactcc caccccaccg tcgatctcgc 240
catcgacggc gccgacgagg tcgat 265

<210> SEQ ID NO 318
<211> LENGTH: 265
<212> TYPE: DNA
<213> ORGANISM: Glycine max
<220> FEATURE:
<223> OTHER INFORMATION: unsure at all n locations

<400> SEQUENCE: 318
cacaccacna cgcctccacg ngccttattc nanncacccc taantngngt aaacngcgca 60
ctaccacncc actaccctcc ccgccatcng cgccatcacc ctcacccagg acgaccncaa 120
gagactcgcc gccgacaagg ccgtggagtc cgtcaagagc ggcatggtcc tcggcctagg 180
caccggctcc actgctgcct tcgtcgtcgc caagcttggc gcccttctcg cctccggcca 240
actctccgac atcgtcggtg tcccc 265

<210> SEQ ID NO 319
<211> LENGTH: 320
<212> TYPE: DNA
<213> ORGANISM: Zea mays

<400> SEQUENCE: 319
gagaagtcgg tcaacacgat ccggttcctg gccatcgacg ccgtcgagaa ggccaactcc 60
ggccacccgg gcctccccat gggctgcgcg cccatgggcc acgtcctcta cgacgaggtc 120
atgcgctaca accccaagaa cccctactgg ttcaaccgcg accgcttcgt cctctccgcc 180
ggccacggct gcatgctcca gtacgccctc ctccacctcg ccggttacga cagcgttaag 240
gaggaggact tgaagcagtt ctggcaatgg ggaagcagaa caccgggcca ccctgagaac 300
tttgagactc caggagttga 320

<210> SEQ ID NO 320
<211> LENGTH: 235
<212> TYPE: DNA
<213> ORGANISM: Zea mays

<400> SEQUENCE: 320
gtacaccatc tctgacaact ctaccggcaa caagccgggc atcattgtga tgggcaccgt 60
ctccgagctg tagatcgcgg ccaaggccgt cgacgagctg aggaaggagg ggaagacggt 120
ccgcgtcgtc tcgttcgtct cctgggaact ctttgatgag cagtcggatg agcacaagga 180
gatcgtcctc cctgccgccg tcacagcgag gatcagcatc gaagccgggt ccact 235

<210> SEQ ID NO 321
<211> LENGTH: 276
<212> TYPE: DNA
<213> ORGANISM: Zea mays

-continued

<400> SEQUENCE: 321
ccagattcgc ttaaggctga aaggcggatg gaagctctca tatagtcggt gaagacaaag 60
aacgttgcac aataaggtat cagaccaggg ctgtgaacag cgatgccatt cgaaatggca 120
cccatagcat gctctcgcac accgaagcga atgtttctct cttcaggagt atccctctgg 180
atttctccaa acttcttaag cagtgtcatg tttgacgttg cgagatccga actacctcca 240
agaaatccag gtattacttt ggcaagtgca ttcaag 276

<210> SEQ ID NO 322
<211> LENGTH: 292
<212> TYPE: DNA
<213> ORGANISM: Zea mays

<400> SEQUENCE: 322
gcaaccaggc agaaccttgg atggccctat gacacattct ttgtaccaga ggacgtcaag 60
agtcactgga gccgccacac acccgaaggt gctgcacttg aggctgattg gaacgctatg 120
tttgcagagt acgagaagaa gtatgcagat gatgcagcaa ccttgaaaag tatcatcacg 180
ggggagttac ccactggctg ggttgatgct cttcctaaat acactccaga gagcccagga 240
gatgccacca ggaacctctc ccagcagtgc ctgaacgcgc ttgctaatgt tg 292

<210> SEQ ID NO 323
<211> LENGTH: 295
<212> TYPE: DNA
<213> ORGANISM: Zea mays

<400> SEQUENCE: 323
tggaagtgca ctgggtgcca aagaggttga agcaaccagg cagaaccttg gatggcccta 60
cgacacattc tttgtaccag aggacgtcaa gagtcactgg agccgccaca cacccgaagg 120
tgctgcactt gaggctgatt ggaacgctaa gtttgcagag tacgagaaga agtatgcaga 180
tgatgcagca accttgaaaa gtatcatcac gggggagtta cccactggct gggttgatgc 240
tcttcctaaa tacactccag agagcccagg agatgccacc taggaactct cccag 295

<210> SEQ ID NO 324
<211> LENGTH: 285
<212> TYPE: DNA
<213> ORGANISM: Zea mays

<400> SEQUENCE: 324
agagtacgag aagaagtatg cagatgatgc agcaaccttg aaaagtatca tcacggggga 60
gttacccact ggctgggttg atgctcttcc taaatacact ccagagagcc caggagatgc 120
caccaggaac ctctcccagc agtgcctgaa cgcccttgct aatgttgtgc ctggtcttat 180
cggaggcagt gctgatcttg catcctccaa catgactctg ctgaagatgt ttggtgactt 240
ccagaaggat acagctgaag agcgcaatgt ccgcttcgga gtcag 285

<210> SEQ ID NO 325
<211> LENGTH: 296
<212> TYPE: DNA
<213> ORGANISM: Zea mays

<400> SEQUENCE: 325
ggccacagtc aaggagccgg acacaccgaa gcggagcacc tgaggccgat tggaacgcta 60
tgtttgcaga gtacgagaag aagtatgcag atgatgcagc aaccttgaaa agtatcatca 120
cgggggagtt acccactggc tgggttgatg ctcttcctaa atacactcca gagagcccag 180

-continued gagatgccac caggaacctc tcccagcagt gcctgaacgc gcttgctaat gttgtgcctg 240
gtcttattgg aggcagtgct gatcttgcat cctccaacat gactctgctg aagatg 296

<210> SEQ ID NO 326
<211> LENGTH: 293
<212> TYPE: DNA
<213> ORGANISM: Zea mays

<400> SEQUENCE: 326
caggagatgc caccaggaac ctctcccagc agtgcctgaa cgcgcttgct aatgttgtgc 60
ctggtcttat tggaggcagt gctgatcttg catcctccaa catgactctg ctgaagatgt 120
ttggtgactt ccagaaggat acagctgaag agcgcaatgt ccgctttgga gtcagagagc 180
acggaatggg cgccatttgc acaggcattg ctctgcacag cccagggttt gttccgtact 240
gtgctacagt ctttgtcttc actgtttaca tgagaggtgc catgaggatc tcg 293

<210> SEQ ID NO 327
<211> LENGTH: 271
<212> TYPE: DNA
<213> ORGANISM: Zea mays

<400> SEQUENCE: 327
gtcaagagtc actggagccg ccacacaccc gaaggtgctg cacttgaggc tgattggaac 60
gctatgtttg cagagtacga gaagaagtat gcagatgatg cagcaacctt gaaaagtatc 120
atcacggggg agttacccac tggctgggtt gatgctcttc ctaaatacac tccagagagc 180
ccaggagatg ccaccaggaa cctctcccag cagtgcctga acgcgcttgc taatgttgtg 240
cctggtctta ttggaggcag tgctgatctt g 271

<210> SEQ ID NO 328
<211> LENGTH: 285
<212> TYPE: DNA
<213> ORGANISM: Zea mays

<400> SEQUENCE: 328
ccaccaggac cctctcccag cagtgcctga acgcgcttgc taatgttgtg cctggtctta 60
ttggaggcag tgctgatctt gcatcctcca acatgactct gctgaagatg tttggagact 120
tccagaagga tacagctgaa gagcgcaatg tccgctttgg agtcagagag cacggaatgg 180
gcgccatttg caacggcatt gctctgcaca gcccagggtt tgttccgtac tgtgctacat 240
tctttgtctt cactgattac atgagaggtg ccatgaggat ctcgg 285

<210> SEQ ID NO 329
<211> LENGTH: 274
<212> TYPE: DNA
<213> ORGANISM: Zea mays

<400> SEQUENCE: 329
ctcgagcgaa tcggctcgag atcacggggg agttacccac tgcctgggtt gatgctcacc 60
ctaaatacac tccagagagc ccaggagatg ccaccaggaa cctctcccag cagtgcctga 120
acgcccttgc taatgttgtg cctggtctta tcggaggcag tgctgatctt gcatcctcca 180
acatgactct gctgaagatg tttggtgact tccagaagga tacagctgaa gagcgcaatg 240
tccgcttcgg agtcagagag cacggaatgg gcgc 274

<210> SEQ ID NO 330

-continued

<211> LENGTH: 187
<212> TYPE: DNA
<213> ORGANISM: Zea mays

<400> SEQUENCE: 330
ccactggctg ggttgatgct cttcctaaat acactccaga gagcccagga gatgccacca 60
ggaacctctc ccagcagtgc ctgaacgccc ttgctaatgt tgtgcctggt cttatcggag 120
gcagtgctga tcttgcatcc tccaacatga ctctgctgaa gatgtttggt gacttccaga 180
aggatac 187

<210> SEQ ID NO 331
<211> LENGTH: 219
<212> TYPE: DNA
<213> ORGANISM: Zea mays

<400> SEQUENCE: 331
gaagtatgca gatgatgcag caaccttgaa aagtatcatc acgggggagt tacccactgg 60
ctgggttgat gctcttccta aatacactcc agagagccca ggagatgcca ccaggaacct 120
ctcccagcag tgcctgaacg cgcttgctaa tgttgtgcct ggtcttattg gaggcagtgc 180
tgatcttgca tcttccaaca tgactctgct gaagatgtt 219

<210> SEQ ID NO 332
<211> LENGTH: 177
<212> TYPE: DNA
<213> ORGANISM: Zea mays

<400> SEQUENCE: 332
tcttattgga ggcagtgctg atcttgcatc ctccaacatg actctgctga agatgtgggg 60
tgactcccag aaggatacac tgaagagcgc aatgtccgct ttggagtcag agagcacgga 120
atgggcgcca tttgcaacgg cattgctctg cacagcccag ggtttgttcc gtactgt 177

<210> SEQ ID NO 333
<211> LENGTH: 261
<212> TYPE: DNA
<213> ORGANISM: Zea mays

<400> SEQUENCE: 333
cgctcgagcg catcggctcg agatcacggg ggagttaccc actggctggg ttgatgctat 60
tcctaaatac actccagaga gcccaggagc tgccacagga ccctctccca gcagtgcctg 120
aacgcccttg ctaatgttgt gcctggtctt atcggaggca gtgctgatct tgcatcctcc 180
aacatgactc tgctgaagat gtttggtgac ttccagaagg atacagctga agagcgccat 240
gtccgcttcg gagtcagaga g 261

<210> SEQ ID NO 334
<211> LENGTH: 203
<212> TYPE: DNA
<213> ORGANISM: Zea mays

<400> SEQUENCE: 334
caggggtctt ggcaagctga tagctttcta cgatgacaac cacatttcca tcgacggaga 60
cacggagatt gcattcacag aggacgtgag cacccgcttc gaggctcttg ggtggcacac 120
gatctgggtt aagaatggga acaccggata tgatgacatc cgcgcaccat taaggaggcg 180
aaggcagtca ctgacaagcc cac 203

-continued

<210> SEQ ID NO 335
<211> LENGTH: 289
<212> TYPE: DNA
<213> ORGANISM: Zea mays

<400> SEQUENCE: 335
gagcgcaatg tccgcttcgg agtcagagag cacggaatgg gcgccatttg caacggcatt 60
gctctgcaca gcccagggtt tgttccgtac tgtgctacat tctttgtctt cactgattac 120
atgagaggtg ccatgaggat ctcggccctg tctgaagccg gagtcatcta tgtcatgacc 180
cacgactcta ttggtctcgg agaagatggc ccgacccatc agcccatcga gcacctggtg 240
agcttccgtg cgatgccgaa catactgatg ctccgccctg ctgatggca 289

<210> SEQ ID NO 336
<211> LENGTH: 305
<212> TYPE: DNA
<213> ORGANISM: Zea mays

<400> SEQUENCE: 336
gatgtttggt gacttccaga aggatacagc tgaagagcgc aatgtccgct tcggagtcag 60
agagcacgga atgggcgcca tttgcaacgg cattgctctg cacagcccag ggtttgttcc 120
gtactgtgct acattctttg tcttcactga ttacatgaga ggtgccatga ggatctcggc 180
cctgtctgaa gccggagtca tctatgtcat gacccacgac tctattggtc tcggagaaga 240
tggcccgacc catcagccca tcgagcacct ggtgagcttc cgtgcgatgc cgaacatact 300
gatgc 305

<210> SEQ ID NO 337
<211> LENGTH: 275
<212> TYPE: DNA
<213> ORGANISM: Zea mays

<400> SEQUENCE: 337
attacatgag aggtgccatg aggatctcgg ccctgtctga agccggagtc atctatgtca 60
tgacccacga ctctattggt ctcggagaag atggcccgac ccatcagccc atcgagcacc 120
tggtgagctt ccgtgcgatg ccgaacatac tgatgctccg ccctgctgat ggcaacgaga 180
ctgccggagc atacaaagtc gcggtcctca acaggaagag gccgtccatc ctcgctctct 240
ccaggcaaaa gctccctcac ctgcctggca cctcg 275

<210> SEQ ID NO 338
<211> LENGTH: 288
<212> TYPE: DNA
<213> ORGANISM: Zea mays

<400> SEQUENCE: 338
agcacctggt gagcttccgt gcgatgccga acatactgat gctccgccct gctgatggca 60
acgagactgc cggagcatac aaagtcgcgg tcctcaacag gaagaggccg tccatcctcg 120
ctctctccag gcaaaagctc cctcacctgc ctggcacctc gatcgagggc gtggagaagg 180
gcgggtacac catctctgac aactcgaccg gcaacaagcc tgacatcatt gtgatgggca 240
ccggctccga gctggagatc gcggccaagg ccgccgacga gctgagga 288

<210> SEQ ID NO 339
<211> LENGTH: 280
<212> TYPE: DNA
<213> ORGANISM: Zea mays

-continued

<400> SEQUENCE: 339
ctgccggagc atacaaagtc gcggtcctca acaggaagag gccgtccatc ctcgctctct 60
ccaggcaaaa gctccctcac ctgcctggca cctcgatcga gggcgtggag aagggcgggt 120
acaccatctc tgacaactcg accggcaaca agcctgacat cattgtgatg ggcaccggct 180
ccgagctgga gatcgcggcc aaggccgccg acgagctgag gaaggagggg aagacggtcc 240
gcgtcgtctc gttcgtctcc tgggaactct ttgatgagca 280

<210> SEQ ID NO 340
<211> LENGTH: 255
<212> TYPE: DNA
<213> ORGANISM: Zea mays

<400> SEQUENCE: 340
gtctcggaga agatggcccg acccatcagc ccatcgagca cctggtgagc ttccgtgcga 60
tgccgaacat actgatgctc cgccctgctg atggcaacga gactgccgga gcatacaaag 120
tcgcggtcct caacaggaag aggccgtcca tcctcgctct ctccaggcaa aagctccctc 180
acctgcctgg cacctcgatc gagggcgtgg agaagggcgg gtacaccatc tctgacactc 240
gaccggcaac aagcc 255

<210> SEQ ID NO 341
<211> LENGTH: 254
<212> TYPE: DNA
<213> ORGANISM: Zea mays

<400> SEQUENCE: 341
catctatgtc atgacccacg actctattgg tctcggagaa gatggcccga cccatcagcc 60
catcgagcac ctggtgagct tccgtgcgat gccgaacata ctgatgctcc gccctgctga 120
tggcaacgag actgccggag catacaaagt cgcggtcctc aacaggaaga ggccgtccat 180
cctcgctctc tccaggcaaa agctccctca cctgcctggc acctcgatcg agggcgtgga 240
gaagggcggg taca 254

<210> SEQ ID NO 342
<211> LENGTH: 273
<212> TYPE: DNA
<213> ORGANISM: Zea mays

<400> SEQUENCE: 342
ggagatcgcg gccaaggccg ccgacgagct gaggaaggag gggaagacgg tccgcgtcgt 60
ctcgttcgtc tcctgggaac tctttgatga gcagtcggat gagtacaagg agagcgtcct 120
ccctgccgcc gtcacagcga ggatcagcat cgaggccggg tccactctcg gctggcagaa 180
gtacgtcgga gcccagggca aggccattgg catcgacaag ttcggcgcga gtgctcctgc 240
cgggacgatc tacaaggagt acggcatcac cgt 273

<210> SEQ ID NO 343
<211> LENGTH: 301
<212> TYPE: DNA
<213> ORGANISM: Zea mays

<400> SEQUENCE: 343
ctatgtcatg acccacgact ctattggtct cggagaggat ggcccgaccc atcagcccat 60
cgagcacctg gtgagcttcc gtgcgatgcc gaacatactg atgctccgcc ctgctgatgg 120
caacgagact gccggagcat acaaagtcgc ggtcctcaac aggaagaggc cgtccatcct 180

-continued cgctctctcc aggcaaaagc tccctcacct gcctggcacc tcgatcgacg gcgtggagaa 240
tggcgggtac accatctctg acaactcgac cggcaacaag cctgacctca ttgtgatggg 300
c 301

<210> SEQ ID NO 344
<211> LENGTH: 276
<212> TYPE: DNA
<213> ORGANISM: Zea mays

<400> SEQUENCE: 344
gcctgacatc attgtgatgg gcaccggctc cgagctggag atcgcggcca aggccgccga 60
cgagctgagg tcatgagggg aagacggtcc gcgtcgtctc gttcgtctcc tgggaactct 120
ttgatgagca gtcggatgag tacaaggaga gcgtcctccc tgccgccgtc acagcgagga 180
tcagcatcga ggccgggtcc actctcggct ggcagaagta cgtcggagcc cagggcaagg 240
ccattggcat cgacaagttc ggcgcgagtg ctcctg 276

<210> SEQ ID NO 345
<211> LENGTH: 300
<212> TYPE: DNA
<213> ORGANISM: Zea mays

<400> SEQUENCE: 345
cgacgagctg aggaaggagg ggaagacggt ccgcgtcgtc tcgttcgtct cctgggaact 60
ctttgatgag cagtcggatg agtacaagga gagcgtcctc cctgccgccg tcacagcgag 120
gatcagcatc gaggccgggt ccactctcgg ctggcagaag tacgtcggag cccagggcaa 180
ggccattggc atcgacaagt tcggcgcgag tgctcctgcc gggacgatct acaaggagta 240
cggcatcacc gtggagagca tcattgcagc tgccaagagc ttttaagagc taacaacggt 300

<210> SEQ ID NO 346
<211> LENGTH: 316
<212> TYPE: DNA
<213> ORGANISM: Zea mays

<400> SEQUENCE: 346
ggtgccatga ggatctcggc cctgtctgaa gccggagtca tctatgtcat gacccacgac 60
tctattggtc tcggagagga tggcccgacc catcagccca tcgagcacct ggtgagcttc 120
cgtgcgatgc cgaacatact gatgctccgc cctgctgatg gcaacgagac tgccggagca 180
tacatcgccg cggtcctcaa caggaagagg ccgtccatcc tcgctctctc caggcaaaag 240
ctccctcacc tgcctggcac ctcgatcgag ggcgtggaga agggcgggta caccatctct 300
gacaactcga ccggca 316

<210> SEQ ID NO 347
<211> LENGTH: 299
<212> TYPE: DNA
<213> ORGANISM: Zea mays

<400> SEQUENCE: 347
ctttgatgag cagtcggatg agtacaagga gagcgtcctc cctgctgccg tcacagcgag 60
gatcagcatc gaggccgggt ccactcttgg ctggcagaag tacgtcggag cccagggcaa 120
ggccattggc atcgacaagt tcggcgcgag tgctcctgcc gggacgatct acaaggagta 180
cggcatcacc gtggagagca tcattgcagc tgccaagagc ttttaagagc taacaacggt 240

-continued ctggagtttt ttttattgtc gtcgttgatg ccaaaggaac actgtacctt gaggacagt 299

<210> SEQ ID NO 348
<211> LENGTH: 242
<212> TYPE: DNA
<213> ORGANISM: Zea mays

<400> SEQUENCE: 348
caggcgtcct ccctgctgcc gtcacagcga ggatcagcat cgaggccggg tccactcttg 60
gctggcagaa gtacgtcgga gcccagggca aggccattgg catcgacaag ttcggcgcga 120
gtgctcctgc cgggacgatc tacaaggagt acggcatcac cgtggagagc atcattgcag 180
ctgccaagag cttttaagag ctaacaacgg tctggagttt tttttattgt cgtcgttgat 240
gc 242

<210> SEQ ID NO 349
<211> LENGTH: 287
<212> TYPE: DNA
<213> ORGANISM: Zea mays

<400> SEQUENCE: 349
tctcgagccg gtcctcaaca ggaagaggcc gtccatcctc gctctctcca ggcaaaagct 60
ccctcacctg cctggcacct cgatcgaggg cgtggagaag ggcgggtaca ccatctctga 120
caactcgacc ggcaacaagc ctgacatcat tgtgatgggc accggctccg agctggagat 180
cgcggccaag gccgccgacg agctgaggaa ggaggggaag acggtccgcg tcgtctcgtt 240
cgtctcctgg gaactctttg atgagcagtc ggatgagtac aaggaga 287

<210> SEQ ID NO 350
<211> LENGTH: 265
<212> TYPE: DNA
<213> ORGANISM: Zea mays

<400> SEQUENCE: 350
gtccactctc ggctggcaga agtacgtcgg agcccagggc aaggccattg gcatcgacaa 60
gttcggcgcg agtgctcctg ccgggacgat ctacaaggag tacggcatca ccgtggagag 120
catcattgca gctgccaaga gcctttaaga gctaacaacg gtctggagtt tttcttattg 180
tcgtcgttga tgccaaagga acactgtacc tagaggacat cctatgcctc ggagcttgga 240
ataatgatga tggagggagc ggaag 265

<210> SEQ ID NO 351
<211> LENGTH: 336
<212> TYPE: DNA
<213> ORGANISM: Zea mays

<400> SEQUENCE: 351
cttcgaggct cttgggtggc acacgatctg ggttaagaat gggaacaccg gatatgatga 60
catccgcgca ccattaagga ggcgaaggca gttactgaca agcccacctt gatcaaggtg 120
actaccacga tcggttttgg atctcccaac aaggccaact catacagtgt tcatggaagt 180
gcactgggtg ccaaatatggt tgaagcaacc aggcagaacc ttggatggcc ctatgacaca 240
ttctttgtac cagaggacgt caagagtcac tggagccgcc acacacccga aggtgctgca 300
cttgaggctg attggaacgc taagtttgca gagtac 336

<210> SEQ ID NO 352
<211> LENGTH: 275

-continued

<212> TYPE: DNA
<213> ORGANISM: Zea mays

<400> SEQUENCE: 352
tgatcacccg cttcgaggct cttgggtggc acactatctg ggttaagaat gggaacaccg 60
gatatgatga catccgcaca ccattaagga ggcgaaggca gttactgaca agcccacctt 120
gatcaaggtg actaccacat cggttttgga tctcccaaca aggccaactc atacagtgtt 180
tatggaagtg cactgggtgc caaagaggtt gaagcaacca ggcagaacct tggatggccc 240
tatgacacat tctctgtacc agaggacgtc aagag 275

<210> SEQ ID NO 353
<211> LENGTH: 286
<212> TYPE: DNA
<213> ORGANISM: Zea mays

<400> SEQUENCE: 353
ccggatatga tgacatccgc gcaccattaa ggaggcgaag gcagttactg acaagcccac 60
cttgatcaag gtgactacca cgatcggttt tggatctccc aacaaggcca actcatacag 120
tgttcatgga agtgcactgg gtgccaaaga ggttgaagca accaggcaga accttggatg 180
gccctatgac acattctttg taccagagga cgtcaagagt cactggagcc gccacacacc 240
cgaacgtgct gcacttgagg ctgattggaa cgctaagttt gcagag 286

<210> SEQ ID NO 354
<211> LENGTH: 249
<212> TYPE: DNA
<213> ORGANISM: Zea mays

<400> SEQUENCE: 354
cttgggtggc acacgatctg ggttaagaat gggaacaccg gatatgatga catccgcgca 60
ccattaagga ggcgaaggca gttactgaca agcccacctt gatcaaggtg actaccacga 120
tcggttttgg atctcccaac aaggccaact catacagtgt tcatggaagt gcactgggtg 180
ccaaagaggt tgaagcaacc aggcagaacc ttggatggcc ctatgacaca ttctttgtac 240
cagaggacg 249

<210> SEQ ID NO 355
<211> LENGTH: 423
<212> TYPE: DNA
<213> ORGANISM: Zea mays

<400> SEQUENCE: 355
agctccctca cctgcctggc acctcgatcg agggcgtgga gaagggcggg tacaccatgt 60
ctgacaactc gaccggcaac aagcctgacc tcattgtgat gggcaccggc tccgagctgg 120
agatcgcggc caaggccgcc gacgagctga ggaaggaggg caagacggtc cgcgtcgtct 180
cgttcgtctc ctgggaactc tttgatgagc agtcggatga gtacaaggag agcgtcctcc 240
ctgctgccgt cacagcgagg atcagcatcg aggccgggtc cactcttggc tggcagaagt 300
acgtcggagc ccagggcaag gccattggca tcgacaagtt cggcgcgagt gctcctgccg 360
ggacgatcta caaggagtac ggcatcaccg tggagagcat cattgcagct gccaagaagc 420
ttt 423

<210> SEQ ID NO 356
<211> LENGTH: 385
<212> TYPE: DNA

-continued

<213> ORGANISM: Zea mays

<400> SEQUENCE: 356
caaccggcac caagcctgac atcattgggt tgggcaccgg ctccgagctg gagatcgcgg 60
gcaatgcggc cgacgagctg aggaaggagg ggaagacggt ccgcgtcgtc tcgttcgtct 120
cctgggaact ctttgatgag cagtcggatg agtacaagga gagcgtcctc cctgccgacg 180
tcacagcgag gatcagcatc gaggccgggt ccactctcgg ctggcagaag tacgtcggag 240
cccaaggcaa ggccattggc atcgacaagt tcggcgcgag tgctcctgcc gggacgatct 300
acaaggagta cggcatcacc gtggagagca tcattgcaac tgccaagagc ttttaagagc 360
taacaacggt ctgggagttt ttttt 385

<210> SEQ ID NO 357
<211> LENGTH: 279
<212> TYPE: DNA
<213> ORGANISM: Glycine max

<400> SEQUENCE: 357
atgctaagtt tgctgagtat gaaaagaaat acaaggagga agctgcagaa ttgaaatcta 60
ttatcaatgg tgaattccct gctggttggg agaaagcact tccgacatac actccagaga 120
gcccagcgga tgccaccaga aacctgtctc aaacaaacct taatgccctt gcaaaggttc 180
ttcccggtct gcttggtggc agtgcagatc ttgcttcttc caacatgacc ttgctcaaaa 240
tgttcgggga cttccagaag gatactccag cagagcgta 279

<210> SEQ ID NO 358
<211> LENGTH: 246
<212> TYPE: DNA
<213> ORGANISM: Glycine max

<400> SEQUENCE: 358
ccttgctcaa aatgttcggg gacttccaaa aggatactcc agcagagcgt aatgttagat 60
tcggtgttag agaacacgga atgggagcta tctgcaacgg cattgctctt cacagccctg 120
gactgattcc atattgtgca accttctttg tattcactga ctacatgaga ggtgccataa 180
ggctttctgc gctgtctgag gctggggtta tttatgtcat gacccatgat tcaataggac 240
ttggag 246

<210> SEQ ID NO 359
<211> LENGTH: 220
<212> TYPE: DNA
<213> ORGANISM: Glycine max

<400> SEQUENCE: 359
caataaccag tgagagtcac aatcaaatag tagggaatgg gttaatcctt ggaacagggc 60
tgattccata ttgtgcaacc ttctttgtat tcactgacta catgagaggt gccataaggc 120
tttctgcgct gtctgaggct ggggttattt atgtcatgac ccatgattca ataggacttg 180
gagaagatgg gccaacccac cagcctattg agcacctagc 220

<210> SEQ ID NO 360
<211> LENGTH: 263
<212> TYPE: DNA
<213> ORGANISM: Glycine max

<400> SEQUENCE: 360
cagaaacctg tctcaaacaa accttaatgc ccttgcaaag gttcttcccg gtctgcttgg 60

-continued tggcagtgca gatcttgctt cttccaacat gaccttgctc aaaatgttcg gggacttcca 120
aaaggatact ccagcagagc gtaatgttag attcggtgtt agagaacacg gaatgggagc 180
tatctgcaat ggcattgctc ttcacagccc tggactgatt ccatattgtg caaccttctt 240
tgtattcact gactacatga gag 263

<210> SEQ ID NO 361
<211> LENGTH: 308
<212> TYPE: DNA
<213> ORGANISM: Glycine max

<400> SEQUENCE: 361
tccttcccat cattctctgg cctcaagtca cattctacat gcaaagcagc agcagccacg 60
tcctcgcgta gaaggggtgc ttgtccatcc accaacgttg ttcgagccgc tgcggttgag 120
acactcgacc aaaccaccga ggtttctctg gtggagaaat ccgtcaacac cattcggttt 180
ttggccattg atgcagttga gaaggccaac tctggtcacc ctggtctccc catggggtgt 240
gctccaatgg gtcacattct ctacgatgag ataatgaggt acaatcctaa gaaccccgtt 300
ggttcaac 308

<210> SEQ ID NO 362
<211> LENGTH: 263
<212> TYPE: DNA
<213> ORGANISM: Glycine max

<400> SEQUENCE: 362
tgctgtttca gccagagtta gcattgaggc aggatcaaca tttgggtggg agaaaattgt 60
tggagcaaaa gggaaaagca ataggcattg atcgttttgg agctagtgct ccagctggaa 120
gaatatacaa agaatttggt atcactaagg aagctgttgt tgctgcagct aaagagctta 180
tctagaactt ttgatttttt ttgccttctg gttttggttg agagcattcc atgtcatgaa 240
taagaaaaag gttaaatatc ctt 263

<210> SEQ ID NO 363
<211> LENGTH: 332
<212> TYPE: DNA
<213> ORGANISM: Glycine max
<220> FEATURE:
<223> OTHER INFORMATION: unsure at all n locations

<400> SEQUENCE: 363
aaccattggt tatggttctc ctaacaaggc taactcctac agtgtgcatg gaagtgcact 60
gggtgccaaa gaagttgang ccacaaggca gaaccttgga tggtcacatg agccattcca 120
cgtgcctgag gatgtcaaaa agcattggag tcgccacacc cctgagggtg ctgcacttga 180
agctgaatgg aatgctaagt ttgctgagta tgaaaagaat acaaggagga agctgcagaa 240
ttgaaatcta ttatcaatgg tgaattccct gctggttggg agaaagcact tccgacatac 300
actccagaga gcccacgggt gccaccagaa ac 332

<210> SEQ ID NO 364
<211> LENGTH: 247
<212> TYPE: DNA
<213> ORGANISM: Glycine max

<400> SEQUENCE: 364
aaccattggt tatggttctc ctaacaaggc taactcctac agtgtgcatg gaagtgcact 60

-continued gggtgccaaa gaagttgatg ccacaaggca gaaccttgga tggtcacatg agccattcca 120
cgtgcctgag gatgtcaaaa agcattggag tcgccacacc cctgagggtg ctgcacttga 180
agctgaatgg aatgctaagt ttgctgagta tgaaaagaaa tacaaggagg aagctgcaga 240
attgaaa 247

<210> SEQ ID NO 365
<211> LENGTH: 238
<212> TYPE: DNA
<213> ORGANISM: Glycine max

<400> SEQUENCE: 365
caaggctaac tcctacagtg tgcatggaag tgcactgggt gccaaagaag ttgatgccac 60
aaggcagaac cttggatggt cacatgagcc attccacgtg cctgaggatg tcaaaaagca 120
ttggagtcgc cacacccctg agggtgctgc acttgaagct gaatggaatg ctaagtttgc 180
tgagtatgaa aagaaataca aggaggaagc tgcagaattg aaatctatta tcaatggt 238

<210> SEQ ID NO 366
<211> LENGTH: 253
<212> TYPE: DNA
<213> ORGANISM: Glycine max

<400> SEQUENCE: 366
gggtgccaaa gaagttgatg ccacaaggca gaaccttgga tggtcacatg agccattcca 60
cgtgcctgag gatgtcaaaa agcattggag tcgccacacc cctgagggtg ctgcacttga 120
agctgagtgg aatgctaagt ttgctgagta tgaaaagaaa tacaaggagg aagctgcaga 180
attgaaatct attatcaatg gtgaattccc tgctggttgg gagaaagcac ttccgacata 240
cactccagag agc 253

<210> SEQ ID NO 367
<211> LENGTH: 171
<212> TYPE: DNA
<213> ORGANISM: Glycine max

<400> SEQUENCE: 367
gttctcctaa caaggctaac tcctacagtg tgcatggaag tgcactgggt gccaaagaag 60
ttgatgccac aaggcagaac cttggatggt cacatgagcc attccacgtg cctgaggatg 120
tcaaaaagca ttggagtcgc cacacccctg agggtgctgc acttgaagct g 171

<210> SEQ ID NO 368
<211> LENGTH: 277
<212> TYPE: DNA
<213> ORGANISM: Glycine max

<400> SEQUENCE: 368
atacgagcct ttccatgtgc cagaagatgt taaaaagcat tggagtcgcc ataccccctga 60 gggtgctaaa cttgaagctg agtggaatgc caagtttgca gaatatgaga agaaatacag 120
tgaggaagct gcagagctga aggctattat tactgtgaat taccagctgg ttgggagaaa 180
gcacttccga catacactcc agaaagccct gctgatgcta caagaaatct gtctcagcaa 240
aatctaaatg cccttgttaa ggttcttcct ggtctac 277

<210> SEQ ID NO 369
<211> LENGTH: 268
<212> TYPE: DNA
<213> ORGANISM: Glycine max -continued

<400> SEQUENCE: 369
gctacaagga agaatcttgg atggccatac gagcctttcc atgtgccaga agatgtcaag 60
aagcattgga gtcgccatac acctgagggt gctaaacttg aagctgagtg gaatgccaag 120
tttgtggaat atgagaagca atacagtgag gaagctgcag agctgaaggc tattattact 180
ggcgaattac cagcaagttg ggagaaagca cttccgacat acacaccaga aagccctgct 240
gatgctacaa gaaatctgtc tcagcaaa 268

<210> SEQ ID NO 370
<211> LENGTH: 258
<212> TYPE: DNA
<213> ORGANISM: Glycine max

<400> SEQUENCE: 370
taaagaagca aaggctgtca aagacaaacc cactttgatc aaggtaacca ctaccattgg 60
atttggttct ccaaacaagg ctaattccta cagtgttcat gggagtgcat taggtgctaa 120
agaagtggat gctacaagga agaatcttgg atggccatac gagcctttcc atgtgccaga 180
agatgtcaag aagcattgga gtcgccatac acctgagggt gctaaacttg aagctgagtg 240
gaatgccaag tttgtgga 258

<210> SEQ ID NO 371
<211> LENGTH: 247
<212> TYPE: DNA
<213> ORGANISM: Glycine max

<400> SEQUENCE: 371
gccatacccc tgagggtgct aaacttgaag ctgagtggaa tgccaagttt gcagaatatg 60
agaagaaata cagtgaggaa gctgcagagc tgaaggctat tattactggt gaattaccag 120
ctggttggga gaaagcactt ccgacataca ctccagaaag ccctgctgat gctacaagaa 180
atctgtctca gcaaaatcta aatgcccttg ttaaggttct tcctggtcta cttggtggca 240
gtgcaga 247

<210> SEQ ID NO 372
<211> LENGTH: 264
<212> TYPE: DNA
<213> ORGANISM: Glycine max
<220> FEATURE:
<223> OTHER INFORMATION: unsure at all n locations

<400> SEQUENCE: 372
ggagtcgcca tacacctgag ggtgctaaac ttgaagctga gtggtntgcc aagtttgtgg 60
aatatgagaa gcaatacagt gaggaagctg cagagctgaa ggctattatt actggcgaat 120
taccagctgg ttgggagaaa cacttccgac atacacacca gaaagccctg ctgatgctac 180
aagaaatctg tctcagcaaa atctaaatgc ccttgttaag gttcttcctg gtctacttgg 240
tggtagtgca gatcttgcct cttc 264

<210> SEQ ID NO 373
<211> LENGTH: 245
<212> TYPE: DNA
<213> ORGANISM: Glycine max

<400> SEQUENCE: 373
gtggaatgcg aagtttgcag aatatgagaa gacatacagt gaggaagctg cagagctgaa 60

-continued

```
ggctattatt actggtgaat taccagctgg ttgggagaaa gcacttccga catacactcc    120

agaaagccct gctgatgcta caagaaatct gtctcagcaa aatctaaatg cccttgttaa    180

ggttcttcct ggtctacttg gtggcagtgc agatcttgcc tcttccaaca tgaccttgtt    240

gaaat                                                                 245
```

<210> SEQ ID NO 374
<211> LENGTH: 242
<212> TYPE: DNA
<213> ORGANISM: Glycine max

<400> SEQUENCE: 374

```
tggaatgcca agtttgcaga atatgagaag aaatacagtg aggaagctgc agagctgaag     60

gctattatta ctggtgaatt accagctggt tgggagaaag cacttccgac atacactcca    120

gaaagccctg ctgatgctac aagaaatctg tctcagcaaa atctaaatgc ccttgttaag    180

gttcttcctg gtctacttgg tggcagtgca gatcttgcct cttccaacat gaccttgttg    240

aa                                                                    242
```

<210> SEQ ID NO 375
<211> LENGTH: 246
<212> TYPE: DNA
<213> ORGANISM: Glycine max

<400> SEQUENCE: 375

```
gcagaatatg agaagaaata cagtgaggaa gctgcagagc tgaaggctat tattactggt     60

gaattaccag ctggttggga gaaagcactt ccgacataca ctccagaaag ccctgctgat    120

gctacaagaa atctgtctca gcaaaatcta aatgcccttg ttaaggttct tcctggtcta    180

cttggtggca gtgcagatct tgcctcttcc aacatgacct tgttgaaatc atacggagat    240

ttccaa                                                                246
```

<210> SEQ ID NO 376
<211> LENGTH: 236
<212> TYPE: DNA
<213> ORGANISM: Glycine max

<400> SEQUENCE: 376

```
ggatgctaca aggaagaatc ttggatggcc atacgagcct ttccatgtgc cagaagatgt     60

caagaagcat tggagtcgcc atacacctga gggtgctaaa cttgaagctg agtggaatgc    120

caagtttgtg gaatatgaga agcaatacag tgaggaagct gcagagctga aggctattat    180

tactggcgaa ttaccagctg gttgggagaa agcacttccg acatacacac cagaaa        236
```

<210> SEQ ID NO 377
<211> LENGTH: 253
<212> TYPE: DNA
<213> ORGANISM: Glycine max

<400> SEQUENCE: 377

```
attggagtcg ccataccccct gagggtgcta aacttgaagc tgagtggaat gccaagtttg     60

cagaatatga gaagaaatac agtgaggaag ctgcagagct gaaggctatt attactggtg    120

aattaccagc tggttgggag aaagcacttc cgacatacac tccagaaagc cctgctgatg    180

ctacaagaaa tctgtctcag caaaatctaa atgccctttt aaggttcttc ctggtctact    240

tggtggcagt gca                                                        253
```

-continued

<210> SEQ ID NO 378
<211> LENGTH: 250
<212> TYPE: DNA
<213> ORGANISM: Glycine max

<400> SEQUENCE: 378
acagtgttca tgggagtgcg ttaggtgcta aagaagtgga tgctacaagg tagaatctgg 60
gatggccata cgagcctttc catgtgccag aacgtgtcaa gaagcattgg agtcgccata 120
cacctgaggg tgctaaactt gaagctgagt ggaatgccaa gtttgtggaa tatgagaagc 180
aatacagtga ggaagctgca gagctgaagg ctattattac tggcgaatta ccagctggtt 240
gggagaaagc 250

<210> SEQ ID NO 379
<211> LENGTH: 268
<212> TYPE: DNA
<213> ORGANISM: Glycine max
<220> FEATURE:
<223> OTHER INFORMATION: unsure at all n locations

<400> SEQUENCE: 379
aaacaaggct aattcctaca gtgttcatng gagtncatta ggtgctaaag aagncgatgc 60
tacaaggnag aatcttggat ggccatacga gcctttccat gtgccagang atgtcaagaa 120
gcattggagt cgccatacac ctgagggtgc taaacttgaa gctgagtgga atgccaagtt 180
tgtggaatat gagaagcaat acagtgaggn agctgcagag tgaaggctat tattactggc 240
gaattaccag ctggttggna nanancct 268

<210> SEQ ID NO 380
<211> LENGTH: 248
<212> TYPE: DNA
<213> ORGANISM: Glycine max

<400> SEQUENCE: 380
tgctaaagaa gtggatgcta caaggaagaa tcttggatgg ccatacgagc ctttccatgt 60
gccaacagat gtcaagaagc attggagtcg ccatacacct gagggtgcta aacttgaagc 120
tgagtggaat gccaagtttg tggaatatga gaagcaatac agtgaggaag ctgcagagct 180
gaaggctatt attactggcg aattaccagc tggttgggag aacgcacttc cgacatacac 240
accagaaa 248

<210> SEQ ID NO 381
<211> LENGTH: 167
<212> TYPE: DNA
<213> ORGANISM: Glycine max

<400> SEQUENCE: 381
tgcacttccg atctacacac cagatagccc tgctgatgct acaagaaatc tgtctcagca 60
aaatctaaat gcccttgtta aggttcttcc tggtctactt ggtggtagtg cagatcttgc 120
ctcttccaac atgaccttat tggaatcgta tggggatttc caaaaga 167

<210> SEQ ID NO 382
<211> LENGTH: 173
<212> TYPE: DNA
<213> ORGANISM: Glycine max

<400> SEQUENCE: 382
atgggagtgc attaggtgct aaagaagtgg atgctacaag gaagaatctt ggatggccat 60

-continued acgagccttt ccatgtgcca gaagatgtac aagagcattg gagtcgccat acacctgagg 120
gtgctaaact tgaagctagt ggaatgccaa gtttgtggaa tatgagaagc aat 173

<210> SEQ ID NO 383
<211> LENGTH: 298
<212> TYPE: DNA
<213> ORGANISM: Glycine max
<220> FEATURE:
<223> OTHER INFORMATION: unsure at all n locations

<400> SEQUENCE: 383
ttggatttgg ttctccaaac aagggctaat tcctacagtg ttcatgggag tgcattaggt 60
gctaaaagaa gtngatgcta caaggaagaa tcttggatgg ccatacgagc ctttccatgt 120
gccagaagat gtcaagaagc attggagtcg ccatacactg agggtgctaa acttgaagct 180
gagtggaatg ccaagtttgt ggaatatgag aagcaataca gtgaggaagc tgcagagctg 240
aaggctatta tactggcgat taccagctgg ttgggagaaa gcattccgac atacacac 298

<210> SEQ ID NO 384
<211> LENGTH: 273
<212> TYPE: DNA
<213> ORGANISM: Glycine max
<220> FEATURE:
<223> OTHER INFORMATION: unsure at all n locations

<400> SEQUENCE: 384
gttagatttg gtgttagtga acatggaatg ggagcaatct gtaatggtat tgctcttcat 60
agccccggat tcattccata ctgtgcaact ttctttgtct tcactgacta catgagagct 120
gccataagga tttctgcact gtgtgaagct ggagttatnc nagtgatgac tcatgattcg 180
attggacttg gagaggatgg accaactcat cagccaatag agcacttggc aagcttcagg 240
gcaatgccaa acatttgatg cttcgtccag ctg 273

<210> SEQ ID NO 385
<211> LENGTH: 295
<212> TYPE: DNA
<213> ORGANISM: Glycine max

<400> SEQUENCE: 385
gttaggtttg gtgttagaga acatggattg ggagcaatct gtaacggtat tgctcttcat 60
agttccggat tcattccata ctgtgcaact ttctttgtct tcactgacta tatgagagct 120
gccataagga tttctgcact gtgtcgggct ggagttattt atgtgatgac tcatcattcg 180
attggacttg gagaggatgg accaactcat cagccaatag agtatttggc aagcttcagg 240
gcaatgcctc acactttgat gcttcgtcca gctgatgtat atgaactgct ggatc 295

<210> SEQ ID NO 386
<211> LENGTH: 260
<212> TYPE: DNA
<213> ORGANISM: Glycine max

<400> SEQUENCE: 386
gcaaaatcta aatgcccttg ttaaggttct tcctggtcta cttggtggta gtgcagatct 60
tgcctcttcc aacatgacct tattgaaatc gtatggggat ttccaaaaga atactcccga 120
agagcgcaat gttaggtttg gtgttagaga acatggaatg ggagcaatct gtaacggtat 180
tgctcttcat agccccggat tcattccata ctgtgcaact ttctttgtct tcactgacta 240
tatgagagct tccataagga 260

-continued

<210> SEQ ID NO 387
<211> LENGTH: 249
<212> TYPE: DNA
<213> ORGANISM: Glycine max

<400> SEQUENCE: 387
gcctcttcca acatgacctt gttgaaatca tacggagatt tccaaaagaa tactcccgaa 60
gagcgcaatg ttagatttgg tgttagagaa catggaatgg gagcaatctg taatggtatt 120
gctcttcata gccccggatt cattccatac tgtgcaactt tctttgtctt cactgactac 180
atgagagctg ccataaggat ttctgcactg tgtgaagctg gagttattta tgtgatgact 240
catgattcg 249

<210> SEQ ID NO 388
<211> LENGTH: 252
<212> TYPE: DNA
<213> ORGANISM: Glycine max

<400> SEQUENCE: 388
gggatttcca aaagaatact cccgaagagc gcaatgttag gtttggtgtt agagaacatg 60
gaatgggagc aatctgtaac ggtattgctc ttcatagccc cggattcatt ccatactgtg 120
caactttctt tgtcttcact gactatatga gagctgccat aaggatttct gcactgtgtg 180
aagctggagt tatttatgtg atgactcatg attcgattgg acttggagag gatggaccaa 240
ctcatcagcc aa 252

<210> SEQ ID NO 389
<211> LENGTH: 255
<212> TYPE: DNA
<213> ORGANISM: Glycine max

<400> SEQUENCE: 389
agcagatctt gcctcttcca acatgacctt attgaaatcg tatggggatt tccaaaagaa 60
tactcccgaa gagcgcaatg ttaggtttgg tgttagagaa catggaatgg gagcaatctg 120
taacggtatt gctcttcata gccccggatt cattccatac tgtgcaactt tctttgtctt 180
cactgactat atgagagctg ccataaggat ttctgcactg tgtgaagctg gagttattta 240
tgtgatgact catga 255

<210> SEQ ID NO 390
<211> LENGTH: 260
<212> TYPE: DNA
<213> ORGANISM: Glycine max

<400> SEQUENCE: 390
gggagcaatc tgtaatggta ttgctcttca tagccccgga ttcattccat actgtgcaac 60 ttttttgtc ttcactgact acatgagagc tgccataagg atttctgcac tgtgtgaagc 120
tggagttatt tatgtgatga ctcatgattc gattggactt ggagaggatg gaccaactca 180
tcagccaata gagcacttgg caagcttcag ggcaatgcca aacactttga tgcttcgtcc 240
agctgatggt aatgaaactg 260

<210> SEQ ID NO 391
<211> LENGTH: 238
<212> TYPE: DNA
<213> ORGANISM: Glycine max -continued

<400> SEQUENCE: 391
ccggattcat tccatactgt gcaactttct ttgtcttcac tgactatatg agagctgcca 60
taaggatttc tgcactgtgt gaagctggag ttatttatgt gatgactcat gattcgattg 120
gacttggaga ggatggacca actcatcagc caatagagca tttggcaagc ttcagggcaa 180
tgccaaacac tttgatgctt cgtccagctg atggtaatga aactgctgga tcatacaa 238

<210> SEQ ID NO 392
<211> LENGTH: 248
<212> TYPE: DNA
<213> ORGANISM: Glycine max
<220> FEATURE:
<223> OTHER INFORMATION: unsure at all n locations

<400> SEQUENCE: 392
gcaaaatcta aatgcccttg ttaaggttct tcctggtcta cttggtgnnc gtgcagatct 60
tgcctcttcc aacanngacc ttgttgaaat catacggaga tttccaaaag aatactcccg 120
aagagcgcaa tgttagattt ggtgttagag aacatggaat gggagcaatc tgtaatggta 180
ttgcncttca tagccccgga ttcatccata ctgtgcaact tttnttgtct tcatggacta 240
catgagag 248

<210> SEQ ID NO 393
<211> LENGTH: 167
<212> TYPE: DNA
<213> ORGANISM: Glycine max

<400> SEQUENCE: 393
catgacctta ttgaaatcgt attgggattt ccaaaagact actcccgaag agcgcaatgt 60
taggtttggt gttagagaac atggaatggg agcaatctgt aacggtattg ctcttcatag 120
acccggattc attccatact gtgcaacttt ctttgtcttc actgact 167

<210> SEQ ID NO 394
<211> LENGTH: 91
<212> TYPE: DNA
<213> ORGANISM: Glycine max

<400> SEQUENCE: 394
gactacatga gagctgccat aaggatttct gcactgtgtg aaagctggag ttatttatgt 60
gatgactcat ggattcgatt ggacttggag a 91

<210> SEQ ID NO 395
<211> LENGTH: 288
<212> TYPE: DNA
<213> ORGANISM: Glycine max
<220> FEATURE:
<223> OTHER INFORMATION: unsure at all n locations

<400> SEQUENCE: 395
tgaattccga caatggggga gcaggactcc tggacatcct gagaactttg agacagttgg 60
aattgaagtg actacaggtc ctcttggtca gggcattgcc aatgctgttg ggttagcact 120
agctgagaaa cacttggctg cacgatttaa caagcctgac aatgagattg ttgaccatta 180
cacatatgtt atattgggtg atggttgtca aatggaggga atttcaaatg aagcatgctc 240
acttgccggt cactggggtc tagggaagct tatngcttta atgatgac 288

<210> SEQ ID NO 396
<211> LENGTH: 262

-continued

<212> TYPE: DNA
<213> ORGANISM: Glycine max

<400> SEQUENCE: 396
caagacctta aggaattccg acaatgggga agcagaactc ctggacatcc tgagaacttt 60
gagacccttg gagttgaagt gaccacaggt cctcttggtc agggcattgc caatgctgtt 120
ggattagcac tagctgagaa gcacttggct gcacgattta acaagcctga caatgagatt 180
gttgaccatt acacatatgt tatattgggt gatggttgtc aaatggaggg aatttcaaat 240
gaagcatgct cacttgccgg tc 262

<210> SEQ ID NO 397
<211> LENGTH: 279
<212> TYPE: DNA
<213> ORGANISM: Glycine max
<220> FEATURE:
<223> OTHER INFORMATION: unsure at all n locations

<400> SEQUENCE: 397
cgcttggntc aaccntgacc gtttcgttct ctctgctgga tctggctgca tgctccaata 60
tgctctcctt cancttgctg gctatnacac tgttcaggaa caagacctta aggaattccg 120
acaatgggga agcagaactc ctggacatcc tgagaacttt gagacccttg gagttgaagt 180
gaccacaggt cctcttggtc agggcattgc caatgctgtt ggattagcat agctgagaag 240
cacttggctg cacgattaac aagcctgaca atgagatgt 279

<210> SEQ ID NO 398
<211> LENGTH: 254
<212> TYPE: DNA
<213> ORGANISM: Glycine max

<400> SEQUENCE: 398
tgacactgtt caggaacaag accttaagga attccgacaa tggggaagca gaactcctgg 60
acatcctgag aactttgaga cccttggagt tgaagtgacc acaggtcctc ttggtcaggg 120
cattgccaat gctgttggat tagcactagc tgagaagcac ttggctgcac gatttaacaa 180
gcctgacaat gagattgttg accattacac atatgttaat tgggtgatgg ttgtcaaatg 240
gagggaattt caaa 254

<210> SEQ ID NO 399
<211> LENGTH: 264
<212> TYPE: DNA
<213> ORGANISM: Glycine max

<400> SEQUENCE: 399
gttgaaaagg gtggttacac catttcggac aactccactg gcaacaagcc tgatgtcatt 60
ttgatcggaa ctggttcgga attggaaatc gctgccaaag ctgctgatga cctaaggaag 120
gaagggaagg ctgttagagt tgtttccctt gtttcttggg aactttttga tgagcaatca 180
gaagcctaca aggagagtgt tttccctgct gctgtttcag ccagagttag cattgaggca 240
ggatcaacat ttgggtggga gaaa 264

<210> SEQ ID NO 400
<211> LENGTH: 258
<212> TYPE: DNA
<213> ORGANISM: Glycine max
<220> FEATURE:
<223> OTHER INFORMATION: unsure at all n locations -continued

<400> SEQUENCE: 400
gttgaaaagg gtggttacac catttcggac aactccactg gcaacaagcc tgatgtcatt 60
ttgatcggaa ctggttcgga attggaaatc gctgccaaag ctgctgatga cctaaggaag 120
gaagggaagg ctgttagagt tgtttccctt gtttcttggg aactttttga tgagcaatca 180
gnagcctaca aggagagtgt tttccctgct gctgtttcag ccagagttag cattgaggca 240
ggatcaacat ttgggtgg 258

<210> SEQ ID NO 401
<211> LENGTH: 249
<212> TYPE: DNA
<213> ORGANISM: Glycine max

<400> SEQUENCE: 401
gagttgaaaa gggtggttac accatttcgg acaactccac tggcaacaag cctgatgtca 60
ttttgatcgg aactggttcg gaattggaaa tcgctgccaa agctgctgat gacctaagga 120
aggaagggaa ggctgttaga gttgtttccc ttgtttcttg ggaacttttt gatgagcaat 180
cagaagccta caaggagagt gttttccctg ctgctgtttc agccagagtt agcattgagg 240
caggatcaa 249

<210> SEQ ID NO 402
<211> LENGTH: 273
<212> TYPE: DNA
<213> ORGANISM: Glycine max

<400> SEQUENCE: 402
gagttgaaaa gggtggttac accatttcgg acaactccac tggcaacaag cctgatgtca 60
ttttgatcgg aactggttcg gaattggaaa tcgctgccaa agctgctgat gacctaagga 120
aggaagggaa ggctgttaga gttgtttccc ttgtttcttg ggaacttttt gatgagcaat 180
cagaagccta caaggagagt gttttccctg ctgctgtttc agccagagtt agcattgagg 240
caggatcaac atttgggtgg gagaaaattg ttg 273

<210> SEQ ID NO 403
<211> LENGTH: 256
<212> TYPE: DNA
<213> ORGANISM: Glycine max

<400> SEQUENCE: 403
cactcttctt cttcttcttc ttcttcactc tacaaccact aaactaagtg gttggttttg 60
gtttagtttc atttttttga agctcttaaa cttaaggctt aagccatggc atcctcatcc 120
tctctgcatc tatctcaggc ccttctggca cgtgctgtgt accttcatgg ctcttcttct 180
tctgaccgtg tctcactctc cttcccatca ttctctggcc tcaagtcaca ttctgcatgc 240
tccaatatgc tctcct 256

<210> SEQ ID NO 404
<211> LENGTH: 233
<212> TYPE: DNA
<213> ORGANISM: Glycine max

<400> SEQUENCE: 404
ctaaactaag tggttggttt tggtttagtt tcattttttt gaagcgctta aacttaaggc 60
ttaagccatg gcatcctcat cctctctgca tctatctcag gcccttctgg cacgtgctgt 120
gtaccttcat ggctcttctt cttctgaccg tgtctcactc tccttcccat cattctctgg 180

-continued

```
cctcaagtca cattctacat gcaaagcagc agtagccacg tcctcgcgta gaa          233


<210> SEQ ID NO 405
<211> LENGTH: 247
<212> TYPE: DNA
<213> ORGANISM: Glycine max

<400> SEQUENCE: 405

aactaagtgg ttggttttgg tttagtttca tttttttgaa gctcttaaac ttaaggctta     60

agccatggca tcctcatcct ctctgcatct atctcaggcc cttctggcac gtgctgtgta    120

ccttcatggc tcttcttctt ctgaccgtgt ctcactctcc ttcccatcat tctctggcct    180

caagtcacat tctacatgca aagcagcagc agccacgtcc tcgcgtagaa ggggtgcttg    240

tccatcc                                                              247


<210> SEQ ID NO 406
<211> LENGTH: 243
<212> TYPE: DNA
<213> ORGANISM: Glycine max

<400> SEQUENCE: 406

aaacactctt cttcttcttc ttcttcttca ctctacaacc actaaactaa gtggttggtt     60

ttggtttagt ttcatttttt tgaagctctt aaacttaagg cttaagccat ggcatcctca    120

tcctctctgc atctatctca ggcccttctg gcacgtgctg tgtaccttca tggctcttct    180

tcttctgacc gtgtctcact ctccttccca tcattctctg gcctcaagtc acattctaca    240

tgc                                                                  243


<210> SEQ ID NO 407
<211> LENGTH: 215
<212> TYPE: DNA
<213> ORGANISM: Glycine max

<400> SEQUENCE: 407

ttttggttta gtttcattgt tctgaagctc ttaaacttaa ggcttaagcc atggcatcct     60

catcctctct gcatctatct caggcccttc tggcacgtgc tgtgtacctt catggctctt    120

cttctctgac cgtgtctcac tctccttccc atcattctct ggcctcaagt cacattctac    180

atgcaaagca gcagcagcca cgtcctcgcg tagaa                               215


<210> SEQ ID NO 408
<211> LENGTH: 276
<212> TYPE: DNA
<213> ORGANISM: Glycine max
<220> FEATURE:
<223> OTHER INFORMATION: unsure at all n locations

<400> SEQUENCE: 408

tcttcttctt cactctacaa ccactannct aagtggttgg ttttggttta gtttcatttt     60

tttgaagctc ttaaacttaa ggcttaagcc atggcatcct catcctctct gcatctatct    120

caggcccttc tggcacgtgc tgtgtacctt catggctctt cttcttctga ccgngtctca    180

ctctccttcc catcattctc tggcctcaag tcacattcta catgcaaagc agcancagcc    240

acgtcctcgc gtagaagggg tgcttgtcca tccacc                              276


<210> SEQ ID NO 409
<211> LENGTH: 289
<212> TYPE: DNA
```

<213> ORGANISM: Glycine max

<400> SEQUENCE: 409
tcttcttctt cttcttcttc actctacaac cactaaacta agtggttggt tttggtttag 60
tttcattttt ttgaagctct taaacttaag gcttaagcca tggcatcctc atcctctctg 120
catctatctc aggcccttct ggcacgtgct gtgtaccttc atggctcttc ttcttctgac 180
cgtgtctcac tctccttccc atcattctct ggcctcaagt cacattctac atgcaaagca 240
gcagcagcca cgtcctcgcg tagaaggggt gcttgtccat ccaccaacg 289

<210> SEQ ID NO 410
<211> LENGTH: 221
<212> TYPE: DNA
<213> ORGANISM: Glycine max
<220> FEATURE:
<223> OTHER INFORMATION: unsure at all n locations

<400> SEQUENCE: 410
tcttcttctt cactctacaa ccactaaact aagtggttgg ntttggttta gtttcatttt 60
tttgaagctc ttaaacttaa ggcttaagcc atggcatcct catcctctct gcatctatct 120
caggcccttc tggcacgtgc tgtgtacctt catggctctt cttcttctga ccgngtctca 180
ctctccttcc catcattctc tggcctcaag tcacattcta t 221

<210> SEQ ID NO 411
<211> LENGTH: 255
<212> TYPE: DNA
<213> ORGANISM: Glycine max

<400> SEQUENCE: 411
cttcttcttc ttcttcttct tcactctaca accactaaac taagtggttg gttttggttt 60
agtttcattt ttttgaagct cttaaactta aggcttaagc catggcatcc tcatcctctc 120
tgcatctatc tcaggccctt ctggcacgtg ctgtgtacct tcatggctct tcttcttctg 180
accgtgtctc actctccttc ccatcattct ctggcctcaa gtcacattct acatgcaaag 240
cagcagcagc cacgt 255

<210> SEQ ID NO 412
<211> LENGTH: 333
<212> TYPE: DNA
<213> ORGANISM: Glycine max
<220> FEATURE:
<223> OTHER INFORMATION: unsure at all n locations

<400> SEQUENCE: 412
anattgtaga ccantanaca tatgtnatat tnggtgatgg ntgtcaaatg gagggantnt 60
caaatgaagc atgctcactt gccggtcact ggggtctagg gaagcttatn gcttnatatg 120
atgacaacca catttccatt gatggggaca ctgagattgc attcactgag aatgttgatc 180
aacgttttga ggcacttggg tggcatgtaa tttgggtgaa gaatggaaat actggatatg 240
atgaaattcg tgcagccatt aaggaagcaa aggctgtcaa agacgaaccc actatgatcc 300
aggtaaccac taccattgga ttggttctcc aaa 333

<210> SEQ ID NO 413
<211> LENGTH: 260
<212> TYPE: DNA
<213> ORGANISM: Glycine max

<400> SEQUENCE: 413

-continued aacaagcctg acaatgagat tgttgaccat tacacatatg ttatattggg tgatggttgt 60
caaatggagg gaatttcaaa tgaagcttgc tcacttgccg gtcactgggg tctaggaaag 120
ctcattgctt tatatgatga caatcacatt tccattgatg gtgacactga gattgcattc 180
actgagaatg ttgatcagcg ttttgaagca cttggatggc atgtaatttg ggtgaagaat 240
ggaaatactg gatatgatga 260

<210> SEQ ID NO 414
<211> LENGTH: 288
<212> TYPE: DNA
<213> ORGANISM: Glycine max
<220> FEATURE:
<223> OTHER INFORMATION: unsure at all n locations

<400> SEQUENCE: 414
cacttggctg cacgatttaa caatcctgnc antgagattg ttgaccatta nacatatgtt 60
atattgggtg atggttgtca aatggaggga atttcaaatg aagcatgctc acttgccgnc 120
tcactggggt ctagggaagc ttattgcttt ntatgatgac aaccacattt ccattnctgg 180
ggacactgag attgcattca ctgagantgt tgatcaacgt ttgaggcact tgggtggcat 240
gtaatttggg tgaagaatgg anatactgga tatgatgaaa ttcgtgcg 288

<210> SEQ ID NO 415
<211> LENGTH: 242
<212> TYPE: DNA
<213> ORGANISM: Glycine max

<400> SEQUENCE: 415
gaatttcaaa tgaagcatgc tcacttgccg gtcactgggg tctagggaag cttattgctt 60
tatatgatga caaccacatt tccattgatg ggacactga gattgcattc actgagaatg 120
ttgatcaacg ttttgaggca cttgggtggc atgtaatttg ggtgaagaat ggaaatactg 180
gatatgatga aattcgtgca gccattaagg aagcaaaggc tgtcaaagac aaacccacta 240
tg 242

<210> SEQ ID NO 416
<211> LENGTH: 251
<212> TYPE: DNA
<213> ORGANISM: Glycine max

<400> SEQUENCE: 416
caaatggagg gaatttcaaa tgaagcatgc tcacttgccg gtcactgggg tctagggaag 60
cttattgctt tatatgatga caaccacatt tccattgatg gggacactga gattgcattc 120
actgagaatg tgatcaacgt tttgaggcac ttgagtggca tgtaatttgg gtgaagaatg 180
gaaatactgg atatgatgaa attcgtgcag ccattaagga agcaaaggct gtcaaagaca 240
cccactatga t 251

<210> SEQ ID NO 417
<211> LENGTH: 245
<212> TYPE: DNA
<213> ORGANISM: Glycine max

<400> SEQUENCE: 417
gcacgattta acaagcctga caatgagatt gttgaccatt acacatatgt tatattgggt 60
gatggttgtc aaatggaggg aatttcaaat gaagcatgct cacttgccgg tcactggggt 120

-continued ctagggaagc ttattgcttt atatgatgac aaccacattt ccattgatgg ggacactgag 180
attgcattca ctgagaatgt tgatcaacgt tttgaggcac ttgggtggca tgtaatttgg 240
gtgaa 245

<210> SEQ ID NO 418
<211> LENGTH: 249
<212> TYPE: DNA
<213> ORGANISM: Glycine max
<220> FEATURE:
<223> OTHER INFORMATION: unsure at all n locations

<400> SEQUENCE: 418
gttgatcang cgttttgnaa gcacttggat ggcatgtaat ttgggtgaag natggaaata 60
ctggatatga tgaaattgcg tgcagccatt aaagaagnaa aggctgtcaa agacaaaccc 120
actttgatca aggtanccac tagnattgga ttaggttctc caaacaaggc taattcncac 180
agtgttcatg ggncgtgcat taggtgctaa agaagtggat gctacnangn anaatnttgg 240 atggcnata 249

<210> SEQ ID NO 419
<211> LENGTH: 240
<212> TYPE: DNA
<213> ORGANISM: Glycine max

<400> SEQUENCE: 419
cattgatgca gttgagaagg ccaactctgg tcaccctggt ctccccatgg ggtgtgctct 60
aatgggctca cattctctac gatgagataa tgaggtacaa ttctaagaac cccgcttggt 120
tcaaccgtga cgtttcgttc tctctgctgg acatggctgc atgctccaat atgctctcct 180
tcaccttgct ggctatgaca ctgttcagga acaagacctt aaggaattcc gacaatgggg 240

<210> SEQ ID NO 420
<211> LENGTH: 283
<212> TYPE: DNA
<213> ORGANISM: Glycine max

<400> SEQUENCE: 420
caagattgtt ggaagcaaag gaaaggccat aggcattgat cgatttggag caagtgctcc 60
agctggaaaa atatacaagg agtttggtat caccaaggaa gctgttattg ctgctgccaa 120
agaactttcg tagatatatt tgttgagttt cttttatctc atctagaact tgtggttttc 180
acttgtggct ttgggttact gttacatgac ttgttttttg agatatcact ttagccacaa 240
taaggaagat tagatgttct gcatatgatt gtcagaggaa cca 283

<210> SEQ ID NO 421
<211> LENGTH: 259
<212> TYPE: DNA
<213> ORGANISM: Glycine max

<400> SEQUENCE: 421
caagattgtt ggaagcaaag gaaaggccat aggcattgat cgatttggag caagtgctcc 60
agctggaaaa atatacaagg agtttggtat caccaaggaa gctgttattg ctgctgccaa 120
agaactttcg tagatatatt tgttgagttt cttttatctc atctagaact tgtggttttc 180
acttgtggct ttgggttact gttacatgac ttgttttttg agatatcact ttagccacaa 240
taaggaagat tagattgtt 259

-continued

<210> SEQ ID NO 422
<211> LENGTH: 256
<212> TYPE: DNA
<213> ORGANISM: Glycine max

<400> SEQUENCE: 422
caagattgtt ggaagcaaag gaaaggccat aggcattgat cgatttggag caagtgctcc 60
agctggaaaa atatacaagg agtttggtat caccaaggaa gctgttattg ctgctgccaa 120
agaactttcg tagatatatt tgttgagttt cttttatctc atctagaact tgtggttttc 180
acttgtggct ttgggttact gttacatgac ttgtttttg agatatcact ttagccacaa 240
taaggaagat tagatt 256

<210> SEQ ID NO 423
<211> LENGTH: 271
<212> TYPE: DNA
<213> ORGANISM: Glycine max
<220> FEATURE:
<223> OTHER INFORMATION: unsure at all n locations

<400> SEQUENCE: 423
aaaggaaagg ccataggcat tgatcgattt ggagcaagtg ctccagctgg aaaaatatac 60
aaggagtttg gtatcaccaa ggaagctgtt attgctgctg ccaaagaact ttcgtaatat 120
atttgttgag tntcttttat ctcatctaga acttgtggtt ttcacttgtg gctttgggtt 180
actgttacat gacttgtttt ttgagatatc actttagcca caatanggaa gatagattgt 240
tcttgcatat gattgtcaga ggaaccactt a 271

<210> SEQ ID NO 424
<211> LENGTH: 258
<212> TYPE: DNA
<213> ORGANISM: Glycine max
<220> FEATURE:
<223> OTHER INFORMATION: unsure at all n locations

<400> SEQUENCE: 424
tctgcactgt gtgaagctgg agttatttat gtgatgactc atgattcgat tggacttgga 60
gaggatggac caactcatca gccaatagag catttggcaa gcttcagggc aatgccaaac 120
actttgatgc ttgtccagct gatggnaatg aaactgctgg atcatacaaa gttgctgtgg 180
ttaacaggaa gagaccctca attcttgcac tttctaggca aaagttgacc caacttccag 240
ganttctatt gagggagt 258

<210> SEQ ID NO 425
<211> LENGTH: 209
<212> TYPE: DNA
<213> ORGANISM: Glycine max

<400> SEQUENCE: 425
gctgatggta atgaaactgc tggatcatac aaagttgctg tggttaacag gaagagaccc 60
tcaattcttg cactttctag gcaaaagttg acccaacttc caggaacttc tattgaggga 120
gttgaaaagg gtggctacac catttcagac aactcatcag gtaacaagcc tgatgttatt 180
ttgattggaa ctggttctga gttggaaat 209

<210> SEQ ID NO 426
<211> LENGTH: 257
<212> TYPE: DNA
<213> ORGANISM: Glycine max -continued

<400> SEQUENCE: 426
cgaccaactc atcagccaat agagcatttg gcaagcttca gggcaatgcc aaacacttag 60
atgcttcgtc cagctgatgg taatgaaact gctggatcat acaaagttgc tgtggttaac 120
aggtagagac cctcaattct tgcactttct aggcaaaagt tgacccaact tccaggaact 180
tctattgagg gatttgaaaa gggtggctac accattctcg aacagctcat caggtaacaa 240
gccggatgtt attttga 257

<210> SEQ ID NO 427
<211> LENGTH: 246
<212> TYPE: DNA
<213> ORGANISM: Glycine max

<400> SEQUENCE: 427
gctgtggtta acaggaagag accctcaatt cttgcacttt ctaggcaaaa gttgacccaa 60
cttccaggaa cttctattga gggagttgaa aagggtggct acaccatttc agacaactca 120
tcaggtaaca agcctgatgt tattttgatt ggaactggtt ctgagttgga aattgctgct 180
gctgctgctg aggatctagg aaaggaagga aaagctgtta gagttgtttc ttttgttagc 240
tgggaa 246

<210> SEQ ID NO 428
<211> LENGTH: 168
<212> TYPE: DNA
<213> ORGANISM: Glycine max

<400> SEQUENCE: 428
gaccaactca tcagccaata gagcacttgg caagcttcag ggcaatgcca aacactttga 60
tgcttcgtcc agctgatggt aatgaaactg ctggatcata caaagttgct gtggttaaca 120
ggaagagacc ctcaattctt gcactttcta ggcaaaagtt gacccaac 168

<210> SEQ ID NO 429
<211> LENGTH: 168
<212> TYPE: DNA
<213> ORGANISM: Glycine max

<400> SEQUENCE: 429
aattcttgca ctttctaggc aaaagttgac ccaacttcca ggaacttcta ttgagggagt 60
tgaaaagggt ggctacacca tttcagacaa ctcatcaggt aacaagcctg atgttatttt 120
gattggaact ggttctgagt tggaaattgc tgctgctgct gctgagga 168

<210> SEQ ID NO 430
<211> LENGTH: 254
<212> TYPE: DNA
<213> ORGANISM: Glycine max
<220> FEATURE:
<223> OTHER INFORMATION: unsure at all n locations

<400> SEQUENCE: 430
ctcatgattc gattggactt gggagaggat ggaccaacta catcagccaa tagagcattt 60
ngcaagcttc agggcaatgc caaacacttn cntgcttcgt ccagctatgg taatgaaact 120
gctggatcat acaaagttgc tgtggttaac aggaagagac cctcaattct tgcactttct 180
agncaaaagt tgacccaact tccaggaact tctattggag gtgaaaaggg tggctacacc 240
atttcagana actc 254

-continued

<210> SEQ ID NO 431
<211> LENGTH: 117
<212> TYPE: DNA
<213> ORGANISM: Glycine max

<400> SEQUENCE: 431
aattcttgca cttgctaggc aaaagttgac ccagcttcca ggaacttcta ttgagggagt 60
tgaaaagggt ggctacacca tttcagacaa ctcatcaggt aacaagcctg atgttat 117

<210> SEQ ID NO 432
<211> LENGTH: 263
<212> TYPE: DNA
<213> ORGANISM: Glycine max

<400> SEQUENCE: 432
atgagaggtg ccataaagct ttctgcgctg tctgaggctg ggttatttta atgtcatgac 60
ccatgattca ataggacttg gagaagatgg gccaacccac cagcctattg agcacctagc 120
aagcttccgg gcaatgccaa acattttgat gcttcgtccc gccgacggta acgaaacagc 180
cggagcatac aaagtggccg tgctcaacag gaagagaccc tccattcttg ccctatccag 240
gcaaaaactg ccccagcttc ccg 263

<210> SEQ ID NO 433
<211> LENGTH: 257
<212> TYPE: DNA
<213> ORGANISM: Glycine max

<400> SEQUENCE: 433
cattttgatg cttcgtcctg ccgacggtaa cgaaacagcc ggagcataca aagtggccgt 60
gctcaacagg aagagaccct ccattcttgc cctatccagg caaaaactgc cccagcttcc 120
cggaacttcc attgaaggag ttgaaaaggg tggttacacc atttcggaca actccactgg 180
caacaagcct aatgacattt ggaccggaac tggttcggaa ttggaaatcg ctgccaaagc 240
tgctgatgac ctaagga 257

<210> SEQ ID NO 434
<211> LENGTH: 253
<212> TYPE: DNA
<213> ORGANISM: Glycine max

<400> SEQUENCE: 434
tcatgaccca tgattcaata ggacttggag aagatgggcc aacccaccag cctattgagc 60
acctagcaag cttccgggca atgccaaaca ttttgatgct tcgtcccgcc gacggtaacg 120
aaacagccgg agcatacaaa gtggccgtgc tcaacaggaa gagaccctcc attcttgccc 180
tatccaggca aaaactgccc cagcttcccg gaacttccat tgaaggagtt gaaaagggtg 240
gttacaccat ttc 253

<210> SEQ ID NO 435
<211> LENGTH: 134
<212> TYPE: DNA
<213> ORGANISM: Glycine max
<220> FEATURE:
<223> OTHER INFORMATION: unsure at all n locations

<400> SEQUENCE: 435
ttggagaaga tgggccaacc caccagccta ttgagcacct agnnagcttc cgggcaatgc 60
caaacatttt gatgcttcgt cccgccgacg gtaacgaaac agccgnagca taccaagtgg 120

-continued

```
ccgtgtcaac aggg                                                    134


<210> SEQ ID NO 436
<211> LENGTH: 387
<212> TYPE: DNA
<213> ORGANISM: Glycine max

<400> SEQUENCE: 436

cccacgcgtc cgcccacgcg tccgggtcac aacaaccatt ggttatggtt ctcctaacaa   60

ggctaactcc tacagtgtgc atggaagtgc actgggtgcc aaagaagttg atgccacaag  120

gcagaacctt ggatggtcac atgagccatt ccacgtgcct gaggatgtca aaaagcattg  180

gagtcgccac acccctgagg gtgctgcact tgaagctgaa tggaatgcta agtttgctga  240

gtatgaaaag aaatacaagg aggaagctgc agaattgaaa tctattatca atggtgaatt  300

ccctgctggt tgggagaaag cactttcgac atacactcca gagagcccag cggatgccac  360

cagaaacctg tctcaaacaa accttaa                                      387


<210> SEQ ID NO 437
<211> LENGTH: 316
<212> TYPE: DNA
<213> ORGANISM: Glycine max

<400> SEQUENCE: 437

ggggttattt atgtcatgac ccatgattca ataggacttg gagaagatgg gccaacccac   60

caccctattg agcacctagc aagcttccgg gcaatgccaa acattttgat gcttcgtccc  120

gccgacggta acgaaacagc cggagcatac aaagtggccg tgctcaacag gaagagaccc  180

tccattcttg ccctgtccag gcaaaaactg ccccagcttc ccggaacttc cattgaagga  240

gttgaaaagg gtggttacac catttcggac aactccactg gcaacaagcc tgatgtcatt  300

ttgatcggaa ctggtt                                                  316


<210> SEQ ID NO 438
<211> LENGTH: 301
<212> TYPE: DNA
<213> ORGANISM: Zea mays

<400> SEQUENCE: 438

gtcatcttcc acgtctccaa gaccggcggc cacctcgggt ccagcctcgg cgtggtggag   60

ctcaccgtcg cgctgcacta cgtcttcaac gcgccgcagg accgcatcct ctgggacgtc  120

ggccaccagt cgtacccgca caagatcctg acggggcggc gcgacaagat gccgacgatg  180

cggcagacca acggcctggc gggcttcccc aagcgcgccg agagcgagta cgacagcttc  240

ggcacgggcc acagctccac caccatctcc gcggcgctcg ggatggcggt gggccgggac  300

c                                                                  301


<210> SEQ ID NO 439
<211> LENGTH: 265
<212> TYPE: DNA
<213> ORGANISM: Zea mays

<400> SEQUENCE: 439

cggtgccgcc caactacaaa ggcactcccc tcgaggtcgg caaaggcagg atcctgcttg   60

agggcgaccg ggtggcgctg ctggggtacg ggtcggcagt gcagtactgc ctgactgccg  120

cgtccctggt gcagcgccac ggcctcaagg tcaccgtcgc cgacgcgagg ttctgcaagc  180

cgctggacca cgccctgatc aggagcctgg ccaagtccca cgaggtgctc atcaccgtgg  240
```

-continued

```
aggaaggctc catcggcggg ttcgg                                          265


<210> SEQ ID NO 440
<211> LENGTH: 245
<212> TYPE: DNA
<213> ORGANISM: Zea mays

<400> SEQUENCE: 440

gtgggccggg acctcaaggg cggcaagaac aacgtggtcg cggtgatcgg cgacggcgcc     60

atgacggccg ggcaggcgta cgaggccatg aacaacgccg ggtacctgga ctccgacatg    120

atcgtcatcc tcaacgacaa caagcaggtg tccttgccca cggcgacgct cgacgggccg    180

gtgccgcccg taggcgcgct cagcagcgac ctcagcaagc tgcagtcaag caggccgctc    240

aagga                                                                245


<210> SEQ ID NO 441
<211> LENGTH: 156
<212> TYPE: DNA
<213> ORGANISM: Zea mays

<400> SEQUENCE: 441

gaagcaggtc ggtggctcag tgcacgagct ggcggcgaag gtggacgagt acgcccgcgt     60

catgatcagc gggcccggct cctcgctctt cgaggagctc ggtctctact acatcggccc    120

cgtcgacggc cacaacatcg acgacctcat caccat                              156


<210> SEQ ID NO 442
<211> LENGTH: 271
<212> TYPE: DNA
<213> ORGANISM: Zea mays

<400> SEQUENCE: 442

gtgtacgtga cggtagccga cgcccggttc tgcaagccgc tggacacggc gctgatccgg     60

gagctcgccg ccgagcacga ggtgctgatc accgccgagg agggatccat cggcgggttc    120

ggctcccacg tcgcacacta cctcagcctg accggcctcc tggacgggcc cctcaaactg    180

agatccatgt tcctgccgga ccggtacatc gaccatggcg caccgcagga ccagatcgag    240

gattcagggc tgacgccgcg gcacatcgcc g                                   271


<210> SEQ ID NO 443
<211> LENGTH: 288
<212> TYPE: DNA
<213> ORGANISM: Zea mays

<400> SEQUENCE: 443

ccgacgcccg gttctgcaag ccgctggaca cggcgctgat ccgggagctc gccgccgagc     60

acgaggtgct gatcaccgcc gaggagggat ccatcggcgg gttcggctcc cacgtcgccc    120

actacctcag cctgaccggc ctcctggacg ggcccctcaa actgagatcc atgttcctgc    180

cggaccggta catcgaccat ggcgcaccgc aggaccagat cgatgaggca gggctgacgc    240

gcggcacatc gccgccaccg tgctgtccct gctggggagg ccattgga                 288


<210> SEQ ID NO 444
<211> LENGTH: 340
<212> TYPE: DNA
<213> ORGANISM: Zea mays

<400> SEQUENCE: 444
```

-continued

```
aagagcacca agaccaccgg ccccgtcctc atccacgtcg tcaccgagaa gggccgcggc     60

tacccctacg ccgagcgagc cgccgacaag taccacggtg tcgccaagtt tgatccggcg    120

accgggaagc agttcaagtc ccccgccaag acgctgtcct acaccaacta cttcgccgag    180

gcgctcatcg ccgaggcggg ccaggacagc aagatcgtgg ccatccacgc ggccatgggc    240

ggcggcacgg ggctcaacta cttcctccgc cgcttcccga accggtgctt cgacgtcggg    300

atcgcggaca gcacgccgtc acgttcgggc cggctggctg                          340
```

<210> SEQ ID NO 445
<211> LENGTH: 245
<212> TYPE: DNA
<213> ORGANISM: Zea mays

<400> SEQUENCE: 445

```
gtaccacggt gtcgccaagt ttgatccggc gaccgggaag cagttcaagt cccccgccaa     60

gacgctgtcc tacaccaact acttcgccga ggcgctcatc gccgaggcgg agcaggacag    120

caagatcgtg gccatccacg cggccatggg cggcggcacg gggctcaact acttcctccg    180

ccgcttcccg agccggtgct tcgacgtcgg gatcgcggag cagcacgccg tcacgttcgc    240

ggccg                                                                245
```

<210> SEQ ID NO 446
<211> LENGTH: 298
<212> TYPE: DNA
<213> ORGANISM: Zea mays
<220> FEATURE:
<223> OTHER INFORMATION: unsure at all n locations

<400> SEQUENCE: 446

```
cgatctgcag aagctaccgg taaggttcgt catggacagg gccgggctgg tcggcgcgga     60

cgggccgacc cactgcgggg cgttcgacgt cgcgtacatg gcctgcctgc ccaacatggt    120

cgtcatggcc ccgtccgacg aggccgagct ctgccacatg gtcgccaccg ccgcggcaat    180

cgacgaccgc ccgtcctgct tccgctaccc gagaggcaac ggcgttggcg tcccgttgcc    240

gnccaactac aaaggcactc ccctcgaggt cgggcaaagc aggatcctgc tggagggc      298
```

<210> SEQ ID NO 447
<211> LENGTH: 333
<212> TYPE: DNA
<213> ORGANISM: Zea mays
<220> FEATURE:
<223> OTHER INFORMATION: unsure at all n locations

<400> SEQUENCE: 447

```
cagggccggg ctggtcggcg cggacgggcc gacccactgc ggggcgttcg acgtcgcgtg     60

catggcctgc ctgcccaaca tggtcgtcat ggccccgtcc gacgaggccg agctctgcca    120

catggtcgcc accgccgcgg caatcgacga ccgcccgtcc tgcttccgct acccgagagg    180

caacggcgtt ggcgtcccgt tgccgcccaa ctacaaaggc actcccctcg aggtcggcaa    240

aggcaggatc ctgctggagg gcgacaccgg ggngctgctg gngtacgggt cgggagtgca    300

gnactggctg accgtcgcgt acctggtgca gcg                                 333
```

<210> SEQ ID NO 448
<211> LENGTH: 240
<212> TYPE: DNA
<213> ORGANISM: Glycine max

<400> SEQUENCE: 448

-continued caacaagcag gtttctttac caactgctac tcttgatgga cccataccac ctgtaggagc 60
cttgagtagc gctctcagta gattacaatc aaataggcct cttagagaat tgagagaggt 120
tgccaaggga gttcctaaac gaattggagg tcctatgcat gaattggctg caaaagttga 180
cgagtatgct cgtggcatga tcagtggttc tggatcatca ctttttgaag agcttggact 240

<210> SEQ ID NO 449
<211> LENGTH: 309
<212> TYPE: DNA
<213> ORGANISM: Glycine max

<400> SEQUENCE: 449
aatgcagggt accttgactc taacatgata attatactta atgacaacaa gcaagtttct 60
ttgcctactg ctactattga tggtcctgca actccaattg gagcccgcaa tagtgcctta 120
agcaaaattc aagcaagcac caaataccgc aaactgagag aagctgcgaa aggcatcaca 180
aagcagatag gaggaacaac acacaacttg cagcaaaggt agatgagtat gcaagaggta 240
tgatcagtgg ttctagtact acacttgttg aggagctcgg cttatactac atatgccctg 300
tggatggtc 309

<210> SEQ ID NO 450
<211> LENGTH: 233
<212> TYPE: DNA
<213> ORGANISM: Glycine max

<400> SEQUENCE: 450
aaaacaactg gtcctgtgct gctccatgtt gtcactgaaa aaggccatgg atatccatat 60
gcagaaagag cagcagatta gtaccatgga gttactaagt ttgatccatt aactggaaaa 120
caattcaaat tcaatgctgc cacccagtta tacacaacat actttgcaga ggctttaatt 180
tctgaagcgg aagcttacaa agacattgtc ggaatccatg ctgcaatggg agg 233

<210> SEQ ID NO 451
<211> LENGTH: 268
<212> TYPE: DNA
<213> ORGANISM: Glycine max

<400> SEQUENCE: 451
tgtgattctg tatgatagcc gtcactcttt acttccaaaa attgaggagg gcccaaagac 60
atttgtcaat gccctatcta gtaccctgag caagctccag tccagtaaat ctttccggag 120
atttagagaa gctgctaggg gtgttacgaa acgaattggt aggtctgcat gaattggcag 180
ctaaagtgga tgaatatgct cgtggtatga tgggtcctct aggtgctact ctttttgaag 240
agcttgggtt gtactacata ggcccagt 268

<210> SEQ ID NO 452
<211> LENGTH: 162
<212> TYPE: DNA
<213> ORGANISM: Glycine max

<400> SEQUENCE: 452
cttccttgtt ggaacatcat ggcttgcgcg caacagtggc tgatgcacgt ttctgcaagc 60
cattggaccg ttctcttatt cttagccttg cccaatcgca cgaggttttg atcactgtgg 120
aagaagggca ataggaggat tcggatctca tgttgttcag tt 162

<210> SEQ ID NO 453

-continued

<211> LENGTH: 232
<212> TYPE: DNA
<213> ORGANISM: Glycine max

<400> SEQUENCE: 453
gatctctccg ctctctcatc ataccgcact ctcgggtagt tacttcctct tccctctcac 60
tctcaatggg gtctccattt cctcgcccac gctcaccgcc tccaccagat gaagaaaagg 120
ccatgtgggg tatatgcatc cctctccgag agtggagagt attattccca ccgaccgcca 180
actcccctac tagacaccgt caactatcct attcatatga agaatctctc tg 232

<210> SEQ ID NO 454
<211> LENGTH: 280
<212> TYPE: DNA
<213> ORGANISM: Zea mays

<400> SEQUENCE: 454
gtgcaccgac caagaaaacc tcgcttcacg atctctacga gctccagggc ctctccccgt 60
ggtatgacaa cctctgccga cctgtcaccg acttgctgcc ccttatcgcc agctgtgttc 120
gtggagtcac cagcaaccct gcagtaatcc tccgtttcca ccttttgttt cttcgcttgc 180
atggttgctg cgcattcact cctgaccgtg tcctcgacgc aatgcagatt ttccagaagg 240
ccatctcatc ctccagcgca tatgatgatc agttcaagca 280

<210> SEQ ID NO 455
<211> LENGTH: 274
<212> TYPE: DNA
<213> ORGANISM: Zea mays

<400> SEQUENCE: 455
tgacactcaa ggaactgttg aggaggcaaa gtggttacac aaagtggtca accgccccaa 60
tgtctacata aagatccctg ctaccgcaga atgtgttcat tccatccgtg aagttatcgc 120
taatggcatt agcgtcaacg tcacgcttat attctctatt gcgagatacg aggctgtgat 180
tgatgcttac cttgatgggc tagaggcttc tggcttgagc gacttatctc gagttaccag 240
tgtcgcatcc ttctttgtca gtcgagtcga cacc 274

<210> SEQ ID NO 456
<211> LENGTH: 306
<212> TYPE: DNA
<213> ORGANISM: Zea mays

<400> SEQUENCE: 456
ccaacgagca aaccccccat ttgccaccaa ccccgacgag cggcgatgac cggcacgtgt 60
ctaagctggc ggcgccccgt ccggcggcac cgccgctccg gccggcgtcc ctccgcaccg 120
ccgccctcgc cttcgccccc tccgcgcgcc gggtccgcgt ctccgtcgcc gggcgagcca 180
ggagccccat cattgcgatg gcttcggcca aggaaggaaa tggtgcaccg accaagagga 240
ctgcgcttca tgatctctac gagctccagg gcctgtcccc gtggtacgac aacctatgcc 300
gccctg 306

<210> SEQ ID NO 457
<211> LENGTH: 330
<212> TYPE: DNA
<213> ORGANISM: Zea mays

<400> SEQUENCE: 457
ccaaggtggg aggcgttggc caagaaaggt gccaagaaac aaaggttgtt gtgggcatcc 60

-continued

```
accggtgtca agaacccagc ttatcctgac actctttatg tggacagtct catcggacct    120

gacacggtca acacgatgcc cgaccaagct ttgcaagcat tcatagacca cggcaccgtt    180

tcaaggacag ttgatgcgaa cgtgtctgag gcggaaggtg tatacagtgc cttggagaag    240

cttggcatcg actgggaaga ggttggaaag cagcttgagc tggaaggcgt ggactccttc    300

aagaagagct ttgacagcct actcgtgagc                                     330
```

```
<210> SEQ ID NO 458
<211> LENGTH: 317
<212> TYPE: DNA
<213> ORGANISM: Zea mays

<400> SEQUENCE: 458

gaaattctct ggcccgaggt gggaggcgtt ggccaagaaa ggtgccaaga aacagaggtt     60

gttgtgggca tccaccggtg tcaagaaccc agcttatccc gacactcttt acatcgacag    120

tctcattgga cctgacacgg tcaacacgat gcccgaccaa gctttgcacg cattcataga    180

ccacggcact gtctcgagga cagttgatgc gaatgtgtcc gaggcggaag gtgtatacag    240

cgccttggag aagcttggca ttgactgggg cgaggtcgga aagcagcttg agctggaagg    300

tgtggactcc ttcaaga                                                   317
```

```
<210> SEQ ID NO 459
<211> LENGTH: 306
<212> TYPE: DNA
<213> ORGANISM: Zea mays

<400> SEQUENCE: 459

cgggaggcgt tggccaagaa aggtgccaag aaacaaaggt tgttgtgggc atccaccggt     60

gtcaagaacc cagcttatcc tgacactctt tatgtggaca gtctcatcgg acctgacacg    120

gtcaacacga tgcccgacca agctttgcaa gcattcatag accacggcac cgtttcaagg    180

acagttgatg cgaatgtgtc tgaggcggaa ggtgtataca gcgccttgga gaagcttggc    240

atcgactggg aagaggttgg aaagcagctt gagctggaga gcgtggactc cttcaagaag    300

agcttt                                                               306
```

```
<210> SEQ ID NO 460
<211> LENGTH: 299
<212> TYPE: DNA
<213> ORGANISM: Zea mays

<400> SEQUENCE: 460

cttgagcgac ttatctcgag ttaccagtgt cgcatccttc tttgtcagtc gagtcgacac     60

ccttatcgac aaaatgcttg agaagattgg aacacctgag gcacttgcct tgagagggaa    120

ggctgccgtc gcacaggcca aactagcaaa tcggctctac cagaagaaat tctctggccc    180

gaagtgggag gcgttggcca agaaaggtgc caagaaacag aggttgttgt gggcgtccac    240

cggtgtcaag aacccagctt atcccgacac tctttacatc gacagtctca ttggacctg     299
```

```
<210> SEQ ID NO 461
<211> LENGTH: 282
<212> TYPE: DNA
<213> ORGANISM: Zea mays

<400> SEQUENCE: 461

agcaaatcgg ctctaccaga agaaattctc tggcccaagg tgggaggcgt tggccaagaa     60
```

-continued

```
aggtgccaag aaacaaaggt tgttgtgggc atccaccggt gtcaagaacc cagcttatcc    120

tgacactctt tatgtggaca gtctcatcgg acctgacacg gtcaacacga tgcccgacca    180

agctttgcaa gcattcatag accacggcac cgtttcaagg acagttgatg cgaacgtgtc    240

tgaggcggaa ggtgtataca gtgccttgga gaagcttggc at                       282
```

```
<210> SEQ ID NO 462
<211> LENGTH: 295
<212> TYPE: DNA
<213> ORGANISM: Zea mays

<400> SEQUENCE: 462

gcgacttatc tcgagttacc agtgtcgcat ccttctttgt cagccgagtc gacaccctta     60

tcgacaaaat gcttgagaag attggaacac ctgaggcact tgccttgaga gggaaggctg    120

ccgtcgcaca ggccaaacta gcaaatcggc tctaccagaa gaaattctct ggcccgaggt    180

gggaggcgtt ggccaagaaa ggtgccaaga aacagaggtt gttgtgggca tccaccggtg    240

tcaagaaccc agcttatccc gacactcttt acatcgacag tctcattgga cctga         295
```

```
<210> SEQ ID NO 463
<211> LENGTH: 313
<212> TYPE: DNA
<213> ORGANISM: Zea mays

<400> SEQUENCE: 463

tgaatgtgtt ccttccatcc aggaagttat cgctaatggc attagcgtca acgtcacgct     60

tattttctca attgcgagat atgaggctgt gattgatgct tacctcgatg ggctagaggc    120

ttctggactt gagtgactta tcccgagtta ctagcgttgc atccttcttt gtcagccgag    180

tggacaccct tattgacaaa atgcttgaca agattggaac acctgaggcc cttgccttga    240

gaggaaaggc tgcagtagcg caggccaaac tagcaaatcg gctctaccag aagaaattct    300

ctggcccaag gtg                                                       313
```

```
<210> SEQ ID NO 464
<211> LENGTH: 275
<212> TYPE: DNA
<213> ORGANISM: Zea mays

<400> SEQUENCE: 464

gaacacctga ggcccttgcc ttgagaggaa aggctgcagt agcacaggcc aaactagcaa     60

atcggctcta ccagaagaaa ttctctggcc caaggtggga ggcgttggcc aagaaaggtg    120

ccaagaaaca aaggttgttg tgggcatcca ccggtgtcaa gaacccagct tatcctgaca    180

ctctttatgt ggacagtctc atcggacctg acacggtcaa cacgatgccc gaccaagctt    240

tgcaagcatt catagaccac ggcaccgttt caagg                               275
```

```
<210> SEQ ID NO 465
<211> LENGTH: 286
<212> TYPE: DNA
<213> ORGANISM: Zea mays

<400> SEQUENCE: 465

cccacgcgtc cgcccacgcg tccggtgatt gatgcttacc ttgatgggct agaggcttct     60

ggcttgagcg acttatctcg agttaccagt gtcgcatcct tctttgtcag ccgagtcgac    120

acccttatcg acaaaatgct tgagaagatt ggaacacctg aggcacttgc cttgagaggg    180

aaggctgccg tcgcacaggc caaactagca aatcggctct accagaagaa attctctggc    240
```

-continued

```
ccgaggtggg aggcgttggc caagaaaggt gccaagaaac agaggt                    286


<210> SEQ ID NO 466
<211> LENGTH: 284
<212> TYPE: DNA
<213> ORGANISM: Zea mays

<400> SEQUENCE: 466

ctcaaggaac tgttgaagcg gcaaagtggt tacacaaagt ggtcaaccgc cccaatgtct      60

acataaagat cccagctact gcagaatgtg ttccttccat ccaggaagtt atcgctaatg     120

gcattagcgt caacgtcacg cttattttct caattgcgag atatgaggct gtgattgatg     180

cttacctcga tgggctagag gcttctggct tgagtgactt atcccgagtt actagcgttg     240

catccttctt tgtcagccga gtggacaccc ttattgacaa aatg                      284


<210> SEQ ID NO 467
<211> LENGTH: 277
<212> TYPE: DNA
<213> ORGANISM: Zea mays

<400> SEQUENCE: 467

aaccgcccca atgtctacat aaagatccct gctaccgccg aatgtgttcc ttccatccgg      60

gaagttatcg ctaatggcat tagcgtcaac gtcacgctta ttttctctat tgcgagatac     120

gaggctgtga ttgatgctta ccttgatggg ctagaggctt ctggcttgag cgacttatct     180

cgagttacca gtgtcgcatc cttctttgtc agccgagtcg acacccttat cgacaaaatg     240

cttgagaaga ttggaacacc tgaggcactt gccttga                              277


<210> SEQ ID NO 468
<211> LENGTH: 279
<212> TYPE: DNA
<213> ORGANISM: Zea mays

<400> SEQUENCE: 468

ttttgagcct atctacgatg agaccgatgg ggctgatggg tatgtctccg tggaggtgtc      60

tcctaggttg gcaaatgaca ctcaaggaac tgttgaggcc gcaaagtggt tacacaaagt     120

ggtcaaccgc cccaatgtct acataaagat ccctgctacc gccgaatgtg ttccttccat     180

ccgggaagtt atcgctaatg gcattagcgt caacgtcacg cttattttct ctattgcgag     240

atacgaggct gtgattgatg cttaccttga tgggctaga                            279


<210> SEQ ID NO 469
<211> LENGTH: 334
<212> TYPE: DNA
<213> ORGANISM: Zea mays

<400> SEQUENCE: 469

cggacgcgtg ggtccagcgc atatgatgat cagttcaagc agctcatttc ggctggaaag      60

gacgcggaga gcgcttactg ggaactcgtt ataaaggata tccaagatgc gtgcaaactt     120

tttgagccca tctacgatga gactgatggg gctgatgggt atgtctccgt agaggtgtct     180

cctaggttgg caaatgacac tcaaggaact gttgaagcgg caaagtggtt acacaaagtg     240

gtcaaccgcc ccaatgtcta cataaagatc ccagctactg cagaatgtgt tccttccatc     300

caggaagtta tcgctaatgg cattagcgtc aacg                                 334


<210> SEQ ID NO 470
```

-continued

<211> LENGTH: 322
<212> TYPE: DNA
<213> ORGANISM: Zea mays

<400> SEQUENCE: 470
tagcagctca tttcggcagg aaaggatgcg gagagcgctt actgggaact cgttataaag 60
gatatccaag atgcgtgcaa actttttgag cccatctacg acgagactga tggggctgat 120
gggtatgtct ccgtagaggt gtctcctagg ttggcaaatg acactcaagg aactgttgaa 180
gcggcaaagt ggttacacaa agtggtcaac cgccccaatg tctacataaa gatcccagct 240
actgcagaat gtgttccttc catccaggaa gttatcgcta atggcattag cgtcaacgtc 300
acgcttattt tctcaattgc ga 322

<210> SEQ ID NO 471
<211> LENGTH: 283
<212> TYPE: DNA
<213> ORGANISM: Zea mays

<400> SEQUENCE: 471
gttgttgtgg gcatccaccg gtgtcaagaa cccagcttat cccgacactc tttacatcga 60
cagtctcatt ggacctgaca cggtcaacac gatgcccgac caagctttgc acgcattcat 120
agaccacggc actgtctcga ggacagttga tgcgaatgtg tccgaggcgg aaggtgtata 180
cagcgccttg gagaagcttg gcattgactg gggcgaggtc ggaaagcagc ttgagctgga 240
aggtgtggac tccttcaaga agagctttga cagcctactc gtg 283

<210> SEQ ID NO 472
<211> LENGTH: 265
<212> TYPE: DNA
<213> ORGANISM: Zea mays

<400> SEQUENCE: 472
gccttatcga caaaatgctt gagaagattg gaacacctga ggcacttgcc ttgagaggga 60
aggctgccgt cgcacaggcc aaactagcaa atcggctcta ccagaagaaa ttctctggcc 120
cgaggtggga ggcgttggcc aagaaaggtg ccaagaaaca gaggttgttg tgggcatcca 180
ccggtgtcaa gaacccagct tatcccgaca ctctttacat cgacagtctc attggacctg 240
acacggtcaa cacgatgccc gacca 265

<210> SEQ ID NO 473
<211> LENGTH: 240
<212> TYPE: DNA
<213> ORGANISM: Zea mays

<400> SEQUENCE: 473
caagattgga acacctgagg cccttgcctt gagaggaaag gctgcagtag cacaggccaa 60
actagcaaat cggctctacc agaagaaatt ctctggccca aggtgggagg cgttggccaa 120
gaaaggtgcc aagaaacaaa ggttgttgtg ggcatccacc ggtgtcagga acccagctta 180
tcctgacact ctttatgtgg acagtctcat cggacctgac acggtcaaca cgatgcccga 240

<210> SEQ ID NO 474
<211> LENGTH: 301
<212> TYPE: DNA
<213> ORGANISM: Zea mays

<400> SEQUENCE: 474
ccgacaaggt ccgggacgcg tggctgggaa ctcgttataa aggatatcca agatgcgtgc 60

-continued aaacttttttg agcccatata cgatgagact gatagggctg atgggtatgt ctccgtagag 120
gtgtctccta ggttggcaaa tgacactcaa ggaactgttg aagcggcaaa gtggttacac 180
aaagtggtca accgccccaa tgtctacata aagatcccag ctactgcaga atgtgttcct 240
tccatccagg aagttatcgc taatggcatt agcgtcaacg tcacgcttat tttctcaatt 300
g 301

<210> SEQ ID NO 475
<211> LENGTH: 300
<212> TYPE: DNA
<213> ORGANISM: Zea mays

<400> SEQUENCE: 475
agaggcttct ggcttgagcg acttatctcg agttaccagt gtcgcatcct tctttgtcag 60
ccgagtcgac acccttatcg acaaaatgct tgagaagatt ggaacacctg aggcacttgc 120
cttgagaggg aaggctgccg tcgcacaggc caaactagca aatcggctct accagaagaa 180
attctctggc ccgaggtggg aggcgttggc caagaaaggt gccaagaaac agaggttgtt 240
gtgggcatcc accggtgtca agaacccagc ttatcccgac actctttaca tcgacagtct 300

<210> SEQ ID NO 476
<211> LENGTH: 267
<212> TYPE: DNA
<213> ORGANISM: Zea mays

<400> SEQUENCE: 476
ggcaaatgac actcaaggaa ctgttgaagc ggcaaagtgg ttacacaaag tggtcaaccg 60
ccccaatgtc tacataaaga tcccagctac tgcagaatgt gttccttcca tccaggaagt 120
tatcgctaat ggcattagcg tcaacgtcac gcttattttc tcaattgcaa gatatgaggc 180
tgtgattgat gcttacctcg atgggctaga ggcttctggc ttgagtgact tatcccgagt 240
tactagcgtt gcatccttct ttgtcag 267

<210> SEQ ID NO 477
<211> LENGTH: 293
<212> TYPE: DNA
<213> ORGANISM: Zea mays

<400> SEQUENCE: 477
cccacgcgtc cgcccacgcg tccgggaact cgttataaag gatatccaag atgcgtgcaa 60
actttttgag cccatctacg acgagactga tggggctgat gggtatgtct ccgtagaggt 120
gtctcctagg ttggcaaatg acactcaagg aactgttgaa gcggcaaagt ggttacacaa 180
agtggtcaac cgccccaatg tctacataaa gatcccagct actgcagaat gtgttccttc 240
catccaggaa gttatcgcta atggcattag cgtcaacgtc acgcttttct caa 293

<210> SEQ ID NO 478
<211> LENGTH: 257
<212> TYPE: DNA
<213> ORGANISM: Zea mays

<400> SEQUENCE: 478
gcgttggcca agaaaggtgc caagaaacag aggttgttgt gggcatccac cggtgtcaag 60
aacccagctt atcgcgacac tctttacatc gacagtctca ttggacctga cacggtcaac 120
acgatgcccg accaagcttt gcacgcattc atagaccacg gcactgtctc gaggacagtt 180

-continued

```
gatgcgaatg tgtccgaggc ggaaggtgta tacagcgcct tggagaagct tggcattgac    240

tggggcgagg tcggaaa                                                   257


<210> SEQ ID NO 479
<211> LENGTH: 229
<212> TYPE: DNA
<213> ORGANISM: Zea mays

<400> SEQUENCE: 479

cccttatcga caaaatgctt gagaagattg gaacacctga ggcacttgcc ttgagaggga     60

aggctgccgt cgcacaggcc aaactagcaa atcggctcta ccagaagaaa ttctctggcc    120

cgaggtggga ggcgttggcc aagaaaggtg ccaagaaaca gaggttgttg tgggcgtcca    180

ccggtgtcaa gaacccagct tatcccgaca ctctttacat cgacagtct                229


<210> SEQ ID NO 480
<211> LENGTH: 263
<212> TYPE: DNA
<213> ORGANISM: Zea mays

<400> SEQUENCE: 480

atggggctga tgggtatgtc tccgtagagg tgtctcctag gttggcaaat gacactcaag     60

gaactgttga agcggcaaag tggttacaca aagtggtcaa ccgcccccaat gtctacataa    120

agatcccagc tactgcagaa tgtgttcctt ccatccagga agttatcgct aatggcatta    180

gcgtcaacgt cacgcttatt ttctcaattg caagatatga ggctgtgatt gatgcttacc    240

tcgatgggct agaggcttct ggc                                            263


<210> SEQ ID NO 481
<211> LENGTH: 300
<212> TYPE: DNA
<213> ORGANISM: Zea mays

<400> SEQUENCE: 481

gccaaggaag gaagcggtgc accgaccaag aggactgcgc ttcatgatct ctacgagctc     60

cagggcctgt ccccgtggta cgacaaccta tgccgccctg tcacagactt gctgcccatt    120

atcgccagcg ggtccgtgga gtcaccagca acccaacgat tttccaaaag gccatttcat    180

cgtccagcgc atatgatgat cagttcaagc agctcatttc ggcaggaaag gatgcggaga    240

gcgcttactg ggaactcgtt ataaaggata tccaagatgc gtgcaaactt tttgagccca    300


<210> SEQ ID NO 482
<211> LENGTH: 312
<212> TYPE: DNA
<213> ORGANISM: Zea mays

<400> SEQUENCE: 482

tccaaccaag ggttcggaaa gtcaaggcta atttccccaa tgtgggaaac cgaggctggg     60

attgaggcta accttaatgg gcaaaaggct tctggcttga gcgacttatc tcgagttacc    120

agtgtcgcat ccttctttgt cagtcgagtc gacaccctta tcgacaaaat gcttgagaag    180

attggaacac ctgaggcact tgccttgaga gggaaggctg ccgtcgcaca ggccaaacta    240

gcaaatcggc tctaccagaa gaaattctct ggcccgaggt gggaggcgtt ggccaagaaa    300

ggtgccaaga aa                                                        312


<210> SEQ ID NO 483
<211> LENGTH: 264
```

-continued

<212> TYPE: DNA
<213> ORGANISM: Zea mays

<400> SEQUENCE: 483
gcaacccaac gattttccaa aaggccattt catcgtccag cgcatatgat gatcagttca 60
agcagctcat ttcggcagga aaggatgcgg agagcgctta ctgggaactc gttataaagg 120
atatccaaga tgcgtgcaaa ctttttgagc ccatctacga cgagactgat ggggctgatg 180
ggtatgtctc cgtagaggtg tctcctaggt tggcaaatga cactcaagga actgttgaag 240
cggcaaagtg gttacacaaa gtgg 264

<210> SEQ ID NO 484
<211> LENGTH: 232
<212> TYPE: DNA
<213> ORGANISM: Zea mays

<400> SEQUENCE: 484
ggtcaacacg atgcccgacc aagctttgca ggcattcata gaccacggca ctgtttcgag 60
gacagttgat gcgaatgtgt ccgaggcgga aggtgtatac agcgccttgg agaagcttgg 120
cattgactgg ggcgaggtcg gaaagcagct tgagctggaa ggtgtggact ccttcaagaa 180
gagctttgac agcctactcg tgagcctgca ggagaagggc aactagcctc aa 232

<210> SEQ ID NO 485
<211> LENGTH: 258
<212> TYPE: DNA
<213> ORGANISM: Zea mays

<400> SEQUENCE: 485
caaacttttt gagcccatct acgacgagac tgatggggct gatgggtatg tctccgtaga 60
ggtgtctcct aggttggcaa atgacactca aggaactgtt gaagcggcaa agtggttaca 120
caaagtggtc aaccgcccca atgtctacat aaagatccca gctactgcag aatgtgttcc 180
ttccatccag gaagttatcg ctaatggcat tagcgtcaac gtcacgctta ttttctcaat 240
tgcgagatat gaggctgt 258

<210> SEQ ID NO 486
<211> LENGTH: 328
<212> TYPE: DNA
<213> ORGANISM: Zea mays

<400> SEQUENCE: 486
aaagtggtta cacaaagtgg tcaaccgccc caatgtctac ataaagatcc ctgctaccgc 60
cgaatgtgtt cattccatcc gtgaagttat cgctaatggc attagcgtca acgtcacgct 120
tattttctct attgcgagat acgaggctgt gattgatgct taccttgatg ggctagaggc 180
ttctggcttg agcgacttat ctcgagttac cagtgtcgca tccttctttg tcagtcgagt 240
cgacaccctt atcgacaaaa tgttgagaag atggaacacc tgaggcattg ccttgagagg 300
gaaggtgccg tcgcacagcc aactagca 328

<210> SEQ ID NO 487
<211> LENGTH: 274
<212> TYPE: DNA
<213> ORGANISM: Zea mays

<400> SEQUENCE: 487
cccacgcgtc cggtcaccga cttgctgccc cttatcgcca gcggtgttcg tggagtcacc 60

-continued

```
agcaaccctg caattttcca gaaggccatc tcatcctcca gcgcatatga tgatcagttc    120

aagcagctca tttcgggcgg aaaggacgcg gagagcgctt actgggaact tgttataaag    180

gatatccaag acgcgtgcag tctttttgag cctatctacg atgagaccga tggggctgat    240

gggtatgtct ccgtggaggt gtctcctagg ttgg                                274


<210> SEQ ID NO 488
<211> LENGTH: 213
<212> TYPE: DNA
<213> ORGANISM: Zea mays

<400> SEQUENCE: 488

cggacggtgg gcgacaaaat gcttgagaag attggaacac ctgaggcact tgccttgaga     60

gggaaggctg agcgtcgcac aggccaaact agcaaatcgg ctctaccaga agaaattctc    120

tggcccgagg tgggaggcgt tggccaagaa aggtgccaag aaacagaggt tgttgtgggc    180

gtccaccggt gtcaagaacc cagcttatcc cga                                 213


<210> SEQ ID NO 489
<211> LENGTH: 262
<212> TYPE: DNA
<213> ORGANISM: Zea mays

<400> SEQUENCE: 489

tttcatcgtc cagcgcatat gatgatcagt tcaagcagct catttcggct ggaaaggacg     60

cggagagcgc ttactgggaa ctcgttataa aggatatcca agatgcgtgc aaactttttg    120

agcccatcta cgatgagact gatggggctg atgggtatgt ctccgtagag gtgtctccta    180

ggttggcaaa tgacactcaa ggaactgttg aagcggcaaa gtggttacac aaagtggtca    240

accgccccaa tgtctacata aa                                             262


<210> SEQ ID NO 490
<211> LENGTH: 252
<212> TYPE: DNA
<213> ORGANISM: Zea mays

<400> SEQUENCE: 490

cgatggggct gatgggtatg tctccgtgga ggtgtctcct aggttggcaa atgacactca     60

aggaactgtt gaggcggcaa agtggttaca caaagtggtc aaccgcccca atgtctacat    120

aaagatccct gctaccgccg aatgtgttcc ttccatccgg gaagttatcg ctaatggcat    180

tagcgtcaac gtcacgctta ttttctctat tgcgacatac gaggctgtga ttgatgctta    240

ccttgatggg ct                                                        252


<210> SEQ ID NO 491
<211> LENGTH: 239
<212> TYPE: DNA
<213> ORGANISM: Zea mays

<400> SEQUENCE: 491

cagcaaccca acgattttcc aaaaggccat ttcatcgtcc agcgcatatg atgatcagtt     60

caagcagctc atttcggctg gaaaggacgc ggagagcgct tactgggaac tcgttataaa    120

ggatatccaa gatgcgtgca aactttttga gcccatctac gatgagactg atggggctga    180

tgggtatgtc tccgtagagg tgtctcctag gttggcaaat gacactcaag gaactgttg     239


<210> SEQ ID NO 492
<211> LENGTH: 196
```

-continued

<212> TYPE: DNA
<213> ORGANISM: Zea mays

<400> SEQUENCE: 492
gaaaggtgcc aagaaacaaa ggttgttgtg ggcatccacc ggtgtcaaga acccagctta 60
tcctgacact ctttatgtgg acagtctcat cggacctgac acggtcaaca cgatgcccga 120
ccaagctttg caagcattca tagaccacgg caccgtttca aggacagttg atgcgaacgt 180
gtctgaggcg gaaggt 196

<210> SEQ ID NO 493
<211> LENGTH: 355
<212> TYPE: DNA
<213> ORGANISM: Zea mays
<220> FEATURE:
<223> OTHER INFORMATION: unsure at all n locations

<400> SEQUENCE: 493
atctctacga gctccagggc ctgtcaccgt ggtacgacaa cctatgccgc cctgtcacag 60
acttgctgcc cattatcgcc agcgaggtcc gtggagtcac cagcaatcca acgattttcc 120
anaaggccat ttcatcgtcc agcgcatatg atgatcagtt caagcagctc atttcggctg 180
gaaaggacgc ggagagcgct tactgggaac tcgttataaa ggatatccaa gatgcgtgca 240
aactttttga gcccatctac gatgagactg atggggctga tgggtatgtc tccgtagagg 300
tgtctcctag gttggcaaat gacactcaag gaactgttga agcggcatag tggtt 355

<210> SEQ ID NO 494
<211> LENGTH: 270
<212> TYPE: DNA
<213> ORGANISM: Zea mays

<400> SEQUENCE: 494
gactagttct agatcgccag cggcgtccgt ggagtcacca gcaacccaac gattttccaa 60
aaggccattt catcgtccag cgcatatgat gatcagttca agcagctcat ttcggcagga 120
aaggatgcgg agagcgctta ctgggaactc gttataaagg atatccaaga tgcgtgcaaa 180
ctttttgagc ccatctacga cgagactgat ggggctgatg ggtatgtctc cgtagaggtg 240
tctcctaggt tggcaaatga cactcaagga 270

<210> SEQ ID NO 495
<211> LENGTH: 226
<212> TYPE: DNA
<213> ORGANISM: Zea mays

<400> SEQUENCE: 495
gacgcggaga gcgcttactg ggaactcgtt ataaaggata tccaagatgc gtgcaaactt 60
tttgagccca tctacgatga gactgatggg gctgatgggt atgtctccgt agaggtgtct 120
cctaggttgg caaatgacac tcaaggaact gttgaagcgg caaagtggtt acacaaagtg 180
gtcaaccgcc ccaatgtcta cataaagatc ccagctactg cagaat 226

<210> SEQ ID NO 496
<211> LENGTH: 234
<212> TYPE: DNA
<213> ORGANISM: Zea mays

<400> SEQUENCE: 496
cccacgcgtc cgcccacgcg tccgggaaag gatgcggaga gcgcttactg ggaactcgtt 60

-continued

```
ataaaggata tccaagatgc gtgcaaactt tttgagccca tctacgacga gactgatggg    120

gctgatgggt atgtctccgt agaggtgtct cctaggttgg caaatgacac tcaaggaact    180

gttgaagcgg caaagtggtt acacaaagtg gtcaaccgcc ccaatgtcta cata          234
```

<210> SEQ ID NO 497
<211> LENGTH: 313
<212> TYPE: DNA
<213> ORGANISM: Zea mays

<400> SEQUENCE: 497

```
ccgagtccgc gtttccgtcg ccgggcgagc caggagcccc atcattgcga tggcttcggc     60

caaggaagga agcggtgcac cgaccaagag gactgcgctt catgatctct acgagctcca    120

gggcctgtcc ccgtggtacg acaacctatg ccgccctgtc acagacttgc tgcccattat    180

cgccagcggc gtccgtggag tcaccagcaa cccaacgatt ttccaaaagg ccatttcatc    240

gtccagcgca tatgatgatc agttcaagca gctcatttcg gcaggaaagg atgcggagag    300

cgcttactgg gaa                                                       313
```

<210> SEQ ID NO 498
<211> LENGTH: 243
<212> TYPE: DNA
<213> ORGANISM: Zea mays

<400> SEQUENCE: 498

```
ggatatgcaa gatgcgtgca aactttttga gcccatctat gacgagactg atggggctga     60

tgggtatgtc tccgtagagg ggtctcctag gttggctaat gacactcaat gtactgttga    120

agctgcaaag tggttacaca aagttgtcaa ccgccccaat gtctacataa agatcccagc    180

tactgcagaa tgtgttcctt ccatccagga agttatccct aatggcatta gcgtcaacgt    240

cac                                                                  243
```

<210> SEQ ID NO 499
<211> LENGTH: 281
<212> TYPE: DNA
<213> ORGANISM: Zea mays

<400> SEQUENCE: 499

```
cacgcttatt ttctctattg cgacatacga ggctgtgatt gatgcttacc ttgatgggct     60

agaagcttcg ggcttgagcg acttatctcg agttaccagt gtcgcatcct tctttgtcag    120

ccgagtcgac acccttatcg acaaaatgct gaaaatattg gaacacctga ggcacttgcc    180

ttgagaggga aggctgccgt cgcacaggcc aaactagcaa atcggctcta ccagaagaaa    240

ttctctggcc caaggtggga ggcgttggcc aagaaaggtg c                        281
```

<210> SEQ ID NO 500
<211> LENGTH: 320
<212> TYPE: DNA
<213> ORGANISM: Zea mays

<400> SEQUENCE: 500

```
gtctcgagga cagttccgtg gtctatgaat gcgtgcaaag cttggtcggg catcgtgttg     60

accacggcac tgtctcgagg acagttgatg cgaatgtgtc cgatgcggaa cgtgtataca    120

gcgccttgga gaatcttggc attgactggg gcgatgtcgg aaagcagctt gagctggaag    180

gtgtggactc cttcaagaag agctttgaca gcctactcgt gagcctacag gagaatggca    240

acagcctcaa gacggcaact gtgtaaaact gagaagattg ggtagcggcg ggtgaacgat    300
```

-continued tttactatat aaaatgctag 320

<210> SEQ ID NO 501
<211> LENGTH: 318
<212> TYPE: DNA
<213> ORGANISM: Zea mays

<400> SEQUENCE: 501
tgttggccaa gcaagagtgc caacgaaaca gcacgttcgc tgtagcgcat cccttggtgt 60
ccagaaccca gcttgtcccg cgactaccta catcgacagt ctcattgggc ctgacacggt 120
caacacgatg cccgaccaag ctttgcacgc attcatagac cacggcactg tctcgaggac 180
agttgatgcg aatgtgtccg aggcggaagg tgtatacagc gccttggaga agcttggcat 240
tgactcgggc gaggtcggaa agcagcttga gctggaaggt gtggactctt caagcagact 300
ttgacagcct actcgtga 318

<210> SEQ ID NO 502
<211> LENGTH: 283
<212> TYPE: DNA
<213> ORGANISM: Zea mays

<400> SEQUENCE: 502
cagacgcgtg gggtccgcgt ctccgtcgcc gggcgagcca ggagccccat cattgcgatg 60
gcttcggcca aggacggaaa tggtgcaccg accaagagga ctgcgcttca tgatctctac 120
gagctccagg gcctgtcccc gtggtacgac aacctatgcc gccctgtcac agacttgctg 180
cccattatcg ccagcggcgt ccgtggagtc accagcaacc caacgatttt ccaaaaggcc 240
atttcatcgt ccagcgcata tgatgatcag ttcaagcagc tca 283

<210> SEQ ID NO 503
<211> LENGTH: 275
<212> TYPE: DNA
<213> ORGANISM: Zea mays

<400> SEQUENCE: 503
atctcatcct ccagcgcata tgatggttat ctggaccatt gcagggttgc tggtgactcc 60
acgaacaccg ctattttcca gaaggtcatc tcatcctcca gcgcatatga tgatcagttc 120
aagcagctca tttcgggcgg aaatgacgcg gagagtgctt actgcgaact tgttatacag 180
gatatccaag acgcgtgcag tctttttgag cctatctacg atgagaccga tggggctgat 240
gggtatgtct ccgtggaggt gtctcctagg ttggc 275

<210> SEQ ID NO 504
<211> LENGTH: 184
<212> TYPE: DNA
<213> ORGANISM: Zea mays

<400> SEQUENCE: 504
accagcaacc ctacaatttt ccagaaggcc atctcatcct ccagcgcata tgatgatcag 60
ttcaagcagc tcatttcggg cggaaaggac gcggagagcg cttactggga actcgttata 120
aaggatatcc aagacgcgtg cagtcttttt gagcctatct acgatgagac cgatggggct 180
gatg 184

<210> SEQ ID NO 505
<211> LENGTH: 262
<212> TYPE: DNA

-continued

<213> ORGANISM: Zea mays
<220> FEATURE:
<223> OTHER INFORMATION: unsure at all n locations

<400> SEQUENCE: 505
cccacgcgtc cgatgtgtct gaggcggaag gtgtatacag cgccttggag aagcttggca 60
tcgactggga agaggttgga aagcagcttg agctggaagg cgtggactcc ttcaagaaga 120
gctttgacag cctactcgtg agcctgcagg agaagggcaa cagcctcaag atggcgagtg 180
tgtaaagctg agaagattgg gtacctgcga gtgaacgatt ttactanata naatgctagc 240
ttgctggctc tcctcttagt tt 262

<210> SEQ ID NO 506
<211> LENGTH: 291
<212> TYPE: DNA
<213> ORGANISM: Zea mays

<400> SEQUENCE: 506
cggctcgagg tttcaaggac agttgatgcg aacgtgtctg aggcggaagg tgtatacagt 60
gccttggaga agcttggcat cgactgggaa gaggttggaa agcagcttga gctggaaggc 120
gtggactcct tcaagaagag ctttgacagc ctactcgtga gcctgcagga gaagggcaac 180
agcctcaaga tggcgagtgt gtaaagctga gaagattggg tacctgcgag tgaacgattt 240
tactaaataa aatgctagct tgctggctct cctcttagtt tttacgctgt a 291

<210> SEQ ID NO 507
<211> LENGTH: 244
<212> TYPE: DNA
<213> ORGANISM: Zea mays

<400> SEQUENCE: 507
aaggcggaag gtgtatacag cgccttggag aagcttggca ttgactgggc cgaggtcgga 60
aagcagcttg agctggaagg tgtggactcc ttcaagaaga gctttgacag cctactcgtg 120
agcctgcagg agaagggcaa cagcctcaag acggcaactg tgtaaaactg agaagattgg 180
gtaccggcgg gtgaacgatt ttactaaata aaatgctagc ttgctggctc tcctaatttt 240
tacg 244

<210> SEQ ID NO 508
<211> LENGTH: 298
<212> TYPE: DNA
<213> ORGANISM: Zea mays

<400> SEQUENCE: 508
tgcgaacgtg tctgaggcgg aaggtgtata cagtgccttg gagaagcttg gcatcgactg 60
ggaagaggtt ggaaagcagc ttgagctgga aggcgtggac tccttcaaga agagctttga 120
cagcctactc gtgagcctgc aggagaaggg caacagcctc aagatggcga gtgtgtcaag 180
ctgagaagat tgggtacctg cgagtgaacg attttactaa ataaaatgct agcttgctag 240
ctctcctctt agtttttacg ctgtaccttt gctctcaatt ttctgagtcg gctttgta 298

<210> SEQ ID NO 509
<211> LENGTH: 241
<212> TYPE: DNA
<213> ORGANISM: Zea mays

<400> SEQUENCE: 509
gcagaatgtg ttccttccat ccaggaagtt atcgctaatg gcattagcgt caacgtcacg 60

-continued

```
cttattttct caattgcaag atatgaggct gtgattgatg cttacctcga tgggctagag    120

gcttctggct tgagtgaatt atcccgagtt actagcgttg catccttctt tgtcagccga    180

gtggacaccc ttattgacaa aatgcttgac aagattggaa cacctgaggc ccttgccttg    240

a                                                                    241


<210> SEQ ID NO 510
<211> LENGTH: 139
<212> TYPE: DNA
<213> ORGANISM: Zea mays

<400> SEQUENCE: 510

caagacgcgt gcagtctttt tgagcctatc tacgatgaga ccgatggggc tgatgggtat     60

gtctccgtgg aggtgtctcc taggttggca aatgacactc aaggaactgt tgaggccgca    120

aagtggttac acaaagtgg                                                 139


<210> SEQ ID NO 511
<211> LENGTH: 170
<212> TYPE: DNA
<213> ORGANISM: Zea mays
<220> FEATURE:
<223> OTHER INFORMATION: unsure at all n locations

<400> SEQUENCE: 511

cggcactgtc tcgaggacag ttgatgcgaa tgtgcccgac gcggaaggtg tatacagcgc     60

cttggagaag cttggcattg actgggccga ggtcggaaag cagcttgagc tggaaggtgt    120

ggactccttc acagagagca ttgacangct actcgtgagc ctgcaggaga               170


<210> SEQ ID NO 512
<211> LENGTH: 169
<212> TYPE: DNA
<213> ORGANISM: Zea mays

<400> SEQUENCE: 512

ctcgatgggc tagaggcttc tggcttgagt gacttatccc gagttactag cgttgcatcc     60

ttctttgtca gccgagtgga cacccttatt gacaaaatgc ttgacaagat tggaacacct    120

gaggcccttg ccttgagagg aaaggctgca gtagcgcagg ccaaactag                169


<210> SEQ ID NO 513
<211> LENGTH: 259
<212> TYPE: DNA
<213> ORGANISM: Zea mays

<400> SEQUENCE: 513

gcgccttgga gaagcttggc attgactggg gcgaggtcgg aaagcagctt gagctggaag     60

gtgtggactc cttcaagaag acgcggtgac agcctactcg tgagcctaca ggagaagggc    120

aacagcctca agacggcaac tgtgtaaaac tgagaagatt gggtaccggc gggtgaacaa    180

cattactaaa taaaatgcta gcttgctggc tctcttagtt tttacgatgt acctttgctc    240

tccattttct gaatcggga                                                 259


<210> SEQ ID NO 514
<211> LENGTH: 216
<212> TYPE: DNA
<213> ORGANISM: Zea mays
<220> FEATURE:
<223> OTHER INFORMATION: unsure at all n locations
```

-continued

<400> SEQUENCE: 514
ggaaagcagc ttgagctgga aggcgtggac tccttcaaga agagctttga cagcctactc 60
gtgagcctgc aggagaaggg caacagcctc aagatggcga gtgtgtaaag ctgagaagat 120
tgggtacctg cgagtgaacg attttactaa atanaatgct agcttgctgg ctctcctctt 180
agtttttacg ctgtactttg ctctcaattt tctgag 216

<210> SEQ ID NO 515
<211> LENGTH: 291
<212> TYPE: DNA
<213> ORGANISM: Zea mays

<400> SEQUENCE: 515
catcgactgg gaagaggttg gaaagcagct tgagctggaa ggcgtggact ccttcaagaa 60
gagctttgac agcctactcg tgagcctgca ggagaagggc aacagcctca agatggcgag 120
tgtgtaaagc tgagaagatt gggtacctgc gagtgaacga ttttactaaa taaaatgcta 180
gcttgctggc tctcctctta gtttttacgc tgtacctttg ctctcaattt tctgagtcgg 240
ctttgtatcc cagcttgcca gaacgtcatg tgtagccatg ttcatggctg t 291

<210> SEQ ID NO 516
<211> LENGTH: 260
<212> TYPE: DNA
<213> ORGANISM: Zea mays

<400> SEQUENCE: 516
gcgtggactc cttcaagaag agctttgaca gcctactcgt gagcctgcag gagaagggca 60
acagcctcaa gatggcgagt gtgtaaagct gagaagattg ggtacctgcg agtgaacgat 120
tttactaaat aaaatgctag cttgctggct ctcctcttag tttttacgct gtacctttgc 180
tctcaatttt ctgaatcggc tttgtatccc aggcttgcca gaacgtcatt gtgtagccac 240
tgttcatggc ttgtaattgc 260

<210> SEQ ID NO 517
<211> LENGTH: 327
<212> TYPE: DNA
<213> ORGANISM: Zea mays

<400> SEQUENCE: 517
cgacggaaat agatgctcgg ttagcttatg acacccaggg cataatccac agggtacatg 60
aactgttgaa tctatacaac caacatgatg tctcaactga ccgcctgtta ttcaaaattc 120
ctgctacatg gcaaggcata gaggcctcaa ggttgcttga atctgaagga attcaaacgc 180
atctatcatt tgtttacagt ttcgcacaag cggcagcggc agcacaagct ggtgcatctg 240
tagtacaaat gtttgtgggc cgattgcggg actgggcagg catcactctg gtgacccaga 300
gatagatgaa gctttgaaga atggaga 327

<210> SEQ ID NO 518
<211> LENGTH: 203
<212> TYPE: DNA
<213> ORGANISM: Zea mays

<400> SEQUENCE: 518
cagggcataa tccacagggt acatgaactg ttgaatctat acaaccaaca tgatgtctca 60
actgaccgcc tgttattcaa aattcctgct acatggcaag gcatagaggc ctcaaggttg 120
cttgaatctg aaggaattca aacgcatcta acatttgttt acagtttcgc acaagcggca 180

-continued gggtcagcac aagctggtgc atc 203

<210> SEQ ID NO 519
<211> LENGTH: 268
<212> TYPE: DNA
<213> ORGANISM: Zea mays

<400> SEQUENCE: 519
cctcaaggtt gcttgaatct gaaggaattc aaacgcatct aacatttgtt tacagtttcg 60
cacaagcgag cacggcagca caagctggtg catctgtagt acaaatgttt gtaggccgat 120
tgcgggactg ggcaaggcat cactctggtg acccagagat agatgaagct ttgaagaatg 180
gagaagatgc tgggctttct ttggcgaaga aagtatatgc ctatattcac aggaatgggt 240
acaaaacaaa gctgatggcc gctgccat 268

<210> SEQ ID NO 520
<211> LENGTH: 417
<212> TYPE: DNA
<213> ORGANISM: Zea mays

<400> SEQUENCE: 520
ggaacacctg aggcccttgc cttgagagga aaggctgcag tagcgcaggc cagactggca 60
aatcggctct ggcagaagaa attctctggc ccaaggtggg aggcgttggc caagaaaggt 120
gccaagaaac aaaggttgtt gtgggcatcc accggtgtca agaacccagc ttatcctgac 180
actctttatg tggacagtct catcggacct gacacggtca acacgatgcc cgaccaagct 240
ttgcaagcat tcatagacca cggcaccgtt tcaaggacag ttgatgcgaa tgtgtctgaa 300
gcggaaggtg tatacagcgc cttggagaag cttggcatcg actgggaaga ggttggaaag 360
cagcttgagc tggaaggcgt ggactccttc aagaagagct ttgacagcct actcgtg 417

<210> SEQ ID NO 521
<211> LENGTH: 424
<212> TYPE: DNA
<213> ORGANISM: Zea mays

<400> SEQUENCE: 521
aatcggctct accagaagaa attctctggc ccgaggtggg aggcgttggc caagaaaggt 60
gccatgaaac agaggttgtt gtgggcgttc accggtgtca agaacccagc ttatcccgac 120
actctttaca tcgactgtct cattggacct gacactgtca acacgatgcc cgaccaagct 180
ttgcaggcat tcatagacca cggcactgtt tcgaggacag ttgatgcgaa tgtgtacgag 240
gcggaaggtg tatacagcgc cttggacaat cttggcattg actggcgcga ggtcagaaag 300
cagcttgagc tggaaggtgt ggactccttc atgaagagct ttgacagcct actcgtgagc 360
ctgcaggaga tggtcaacat cctcaagacg gcatctgtgt aaaactgaga agattgtgta 420
ccgg 424

<210> SEQ ID NO 522
<211> LENGTH: 443
<212> TYPE: DNA
<213> ORGANISM: Zea mays

<400> SEQUENCE: 522
atttcggctg gaaaggacgc ggagagcgct tactgggaac tcgttataaa ggatatccag 60
gatgcgtgca aactttttga gcccatctac gatgagactg atggggctga tgggtatgtc 120

-continued

```
tccgtagagg tgtctcctag gttggcaaat gacactcaag gaactgttga agcggcaaag    180

tggttacaca aagtggtcaa ccgccccaat gtctacataa agatcccagc tactgcagaa    240

tgtgttcctt ccatccagga agttatcgct aatggcatta gcgtcaacgt cacgcttatt    300

ttctcaattg caagatatga ggctgtgatt gatgcttacc tcgatgggct agaggcttct    360

ggcttgagtg acttatcccg agttactagc gttgcatcct tctttgtcag ccgagtggac    420

acccttattg acaaaatgct tga                                            443


<210> SEQ ID NO 523
<211> LENGTH: 438
<212> TYPE: DNA
<213> ORGANISM: Zea mays
<220> FEATURE:
<223> OTHER INFORMATION: unsure at all n locations

<400> SEQUENCE: 523

gccagcggcg tccgtggagt caccttctac ccaacgattt tccaaaaggc catttgagtc     60

gtccagcgca tatgatgagc agttcaagca gctcatttcg gcaggaaagg atgcggagag    120

cgcttactgg gaactcgtta taaaggatat ccaagatgcg tgcaaacttt ttgagcccat    180

ctacgacgag actgatgggg ctgatgggta tgtctccgta gaggtgtctc ctaggttggc    240

aaatgacact caaggaactg ttgaagcggc aaagtggtta cacaaagtgg tcaaccgccc    300

caatgtctac ataaagatcc cagctactgc agaatgtgtt ccttccatcc aggaagttat    360

cgctaatggc attagcgtca acgtcacgct tatnntctca attgcgagat atgaggctgt    420

gattgatgct tacctcga                                                  438


<210> SEQ ID NO 524
<211> LENGTH: 369
<212> TYPE: DNA
<213> ORGANISM: Zea mays

<400> SEQUENCE: 524

gcgagatacg aggctgtgat tgatgcttac cttgatgggc tagaggctgg tggcttgagc     60

gacttatctt gagttaccag cgtcgcatgc ttctttgtca gtcgagtcta cacccttatc    120

gacaaaatgc ttgagaagat tggaacacct gaggcacttg ccttgagagg gaaggctgcc    180

gacgtacagg ccaaactagc aaatcggctc taccagaaga aattctctgg cccgaggtgg    240

gaagcgtctg ccaagaaagg tgccaagaaa cagatgttgt tgcgggcgtt cacccgtgtc    300

aagaacccag cttatcccga cactctttac atcgacagtc ttattggacc tgacacggtc    360

aacacgatt                                                            369


<210> SEQ ID NO 525
<211> LENGTH: 375
<212> TYPE: DNA
<213> ORGANISM: Zea mays

<400> SEQUENCE: 525

tgcttacctc gatgggctag aggcttctgg cttgagtgac ttatcccgag ttactagcgt     60

tgcgtccttc tttgtcagcc gagtggacac ccttattgac aaaatgcttg acaagattgg    120

aacacctgag gcccttgcct tgagaggaaa ggctgcagta gcacaggcca aactagcaaa    180

tcggctctac cagaagaaat tctctggccc aaggtgggag gcgttggcca agaaaggtgc    240

caagaaacaa aggttgttgt gggcatccac cggtgtcaag aacccagctt atcctgacac    300

tctggatgtg gacagtctca tctgacctga cacgttcaac acgatgcccg accaagcttt    360
```

-continued gcaagcattt catag 375

<210> SEQ ID NO 526
<211> LENGTH: 389
<212> TYPE: DNA
<213> ORGANISM: Zea mays

<400> SEQUENCE: 526
cccacgcgtc cgctgcgctt catgatctct acgagctcca gggcctgtcc ccgtggtacg 60
agaacctatg ccgccctgtc acagacttgc tgcccattat cgccagcggc gtccgtggag 120
tcaccagcaa cccaacgatt ttccaaaagg ccatttcatc gtccagcgca tatgatgatc 180
agttcaagca gctcatttcg gcaggaaagg atgcggagag cgcttactgg gaactcgtta 240
taaaggatat ccaagatgcg tgcaaacttt ttgagcccat ctacgacgag actgatgggg 300
ctgatgggta tgtctccgta gaggtgtctc ctaggttggc aaatgacact caaggaactg 360
ttgaagcggc aaagtggtta cacaaagtg 389

<210> SEQ ID NO 527
<211> LENGTH: 379
<212> TYPE: DNA
<213> ORGANISM: Zea mays
<220> FEATURE:
<223> OTHER INFORMATION: unsure at all n locations

<400> SEQUENCE: 527
aatcggctct accagaagaa attctctggc ccgaggtggg aggcgttggc cgagaagggt 60
gccatgaaac agaggttgtt gtgggcgtcc accggtgtca agaacccagc ttatcccgac 120
actctctaca tcgacagcct cattggacct gacacggtca acactatgcc cgtacaagct 180
ttgcatgcat tcatagacca cggcactgtt tcgaggacag ttgatgctaa tgtgtacgag 240
gcggaaggtg tatacagcgc cttggagaag cttggcattg actgnggcga ggtcggaaag 300
caacttgagc tggaaggtgt ggactccttc aagaagagct ttgacagcct actcgtgagc 360
ctgcatgaga agggcaaca 379

<210> SEQ ID NO 528
<211> LENGTH: 185
<212> TYPE: DNA
<213> ORGANISM: Zea mays

<400> SEQUENCE: 528
aggcctgtcc ccgtggtacg acaacctatg ccgccctgtc acagacttgc tgcccattat 60
cgccagcggc gtccgtggag tcaccagcaa cccaacgatt ttccaaaagg ccatttcatc 120
gtccagcgca tatgatgatc agttcaagca gctcatttcg gcaggaaagg atgcggagag 180
cgcta 185

<210> SEQ ID NO 529
<211> LENGTH: 374
<212> TYPE: DNA
<213> ORGANISM: Zea mays

<400> SEQUENCE: 529
gaggtacgcg tacgcgaaca cgatgcccga ccaagctttt caagcattca tagaccactg 60
caccgtttca aggacagttg atgcgaatgt gtctgaggcg gaaggtgtat acagcgcctt 120
ggagaagctt ggcatcgact gggaacaggt tggaaagcag cttgagctgg aacgcgtgga 180

-continued ctccttcaag aagagctttg acagcctact cgtgagcctg caggacaagg gcaacagtct 240
caagatggcg agtgtgtaaa gctgataaga ttgggtacct gccagtgaac gattttacta 300
aataaaatgc tagcttgctg gctcttctct tactatttac gctgtacctt tgctctcaat 360
tatctgaatc ggct 374

<210> SEQ ID NO 530
<211> LENGTH: 348
<212> TYPE: DNA
<213> ORGANISM: Zea mays

<400> SEQUENCE: 530
gtctcaactg accgcctgtt attcataatt cctgctacat ggcaaggcat agaggcctca 60
aggttgcttg aatctgaagg aattcaaacg catctaacat ttgtttacag tttcgcacta 120
aagcggcagc ggcagcacaa gctggtgcat ctgtagtaca aatgtttgtg ggccgattgc 180
gggactgggc aaggcatcac tctggtgacc cagagataga tgaagctttg aagaatggag 240
aagatgctgg gctttctttg gcgaagaaag tatatgccta tattcacagg aatgggtaca 300
aaacaaagct gatggccgct gccataccga acaagcagga cgtattta 348

<210> SEQ ID NO 531
<211> LENGTH: 525
<212> TYPE: DNA
<213> ORGANISM: Zea mays
<220> FEATURE:
<223> OTHER INFORMATION: unsure at all n locations

<400> SEQUENCE: 531
ggggggtggg gttgactgtc atgttcgcgt ggcggtacaa agtcgaaatt gnccgggcca 60
cccacgcaac cgcatcgcga ccgccaaagc ccgcgacttt cagcctacgg aggccacatc 120
tggccgcgcg ggccgccgct ggcaacgcac ccacgtcccc ggtccgcgag gtcgtcactg 180
agctcgacgc ggtcgccggc ttcagcgaga tcgtgccgga caccgtcgtg ttcgatgatt 240
tcgagaggtt cgcacccacg gcggccacag tgagctcgtc gctgctgctt gggatcactg 300
ggctcccaga cactaagttc aagagtgcga tagatactgc actggcagat ggtgagtgca 360
acgcactgga gaaggctgat gacatgatgt cctgttacct caccaaggct cttgcatatg 420
ttggcgctga actggctcat caagtccctg ggagagtttc gacggaaata gatgctcggt 480
tagcttatga cacccagggc ataatccaca gggtacatga actgt 525

<210> SEQ ID NO 532
<211> LENGTH: 423
<212> TYPE: DNA
<213> ORGANISM: Zea mays
<220> FEATURE:
<223> OTHER INFORMATION: unsure at all n locations

<400> SEQUENCE: 532
agagcctcca aaacctcgca acaaccccgt gacacccaca cccatccgcc ctgcgcctcc 60
tcgcgctccc caccaacccc gacgagcggc gatgaccggc acggtgtcca agctggcggc 120
gccccggcct gcggcgccac cgctccggcc ggcgtccctc cgcgccgccg caatcgcctt 180
cgccccctcc ccgcgccggg tccgcgtctc cgtcgccggg cgggccagga tcccctccgt 240
cattgcgatg gcttctgcca aggaaggaaa tggtgcaccg accaagaaaa cctcgcttca 300
cgatctctac gagctccagg gcctctcccc gtggtatgac aacctctgcc gacctgtcac 360
cgacttgctg ccccttatcg ccagcggtgt tcgtggagtc accagcaacc ctgcaattnt 420

-continued

```
cca                                                                  423


<210> SEQ ID NO 533
<211> LENGTH: 429
<212> TYPE: DNA
<213> ORGANISM: Zea mays

<400> SEQUENCE: 533

cggacgcgtg ggagcctcca aaacctcgca acaaccccgt gacacccaca cccatccgcg     60

ctgcccctcc tcgcgctccc caccaacccc gacgagcggc gatgaccggc acggtgtcca    120

agctggcggc gccccggcct gcggcgccac cgctccggcc ggcgtccctc cgcgccgccg    180

caatcgcctt cgccccctcc ccgcgccggg tccgcgtctc cgtcgccggg cgggccagga    240

tcccctccgt cattgcgatg gcttctgcca aggaaggaaa tggtgcaccg accaagaaaa    300

cctcgcttca cgatctctac gagctccagg gcctctcccc gtggtatgac aacctctgcc    360

gacctgtcac cgacttgctt gcccttatcg gcagcggtgt tcgtggagtc accagcaacc    420

ctacaattt                                                            429


<210> SEQ ID NO 534
<211> LENGTH: 283
<212> TYPE: DNA
<213> ORGANISM: Glycine max
<220> FEATURE:
<223> OTHER INFORMATION: unsure at all n locations

<400> SEQUENCE: 534

ctcttgggaa tatgtggcct tccanacacc atttttagga atgctgtgga aatggcttag     60

ctgattctga gtgttatgga cttgaaaatc ctaacgcgcg attgtcttgt tttgtcaaca    120

aggctttcgc gaatatcggt agtgacatgg caaagcttgt ccctggccgt gtttcgacag    180

aagtggatgc gcggcttgct tatgacacac atgccattat caggaaggtg catgacctgt    240

tgaagttgta catgatannt atgtacctcc gcaacgtctg ttg                      283


<210> SEQ ID NO 535
<211> LENGTH: 250
<212> TYPE: DNA
<213> ORGANISM: Glycine max

<400> SEQUENCE: 535

agtggacact ctcattgaca aggcccttga gaaaattggc accccagatg ctcttaatct     60

acgtgggaag gtaactgttt attgttttcc aaactaattt ctattcttgg ctttggattt    120

attacacttt caaatgtcaa atatgctctt cggattgcat attgaatttt acaggcagca    180

gtagcccaag cagcattggc ttaccagctc taccaaagga aattttctgg tcaaagtggg    240

aactctaagt                                                           250


<210> SEQ ID NO 536
<211> LENGTH: 333
<212> TYPE: DNA
<213> ORGANISM: Glycine max
<220> FEATURE:
<223> OTHER INFORMATION: unsure at all n locations

<400> SEQUENCE: 536

tgtttgatag aaataatgga tcggaacggg ccaaagatca naagtacaat tcttcaccat     60

ctctatgata agcagagaca gagcccttac tatgacaatc tctgtcgccc tgtttcagat    120
```

-continued

```
ttgcttccat ttattgccaa tgggatcaga ggtgtcacta ccaacccagc ggtactcact    180

actcagtttt ttcttcacct gaaaacatta ctcttctcca tttggtttta tttttatcta    240

gtttctgtgt gttggttata ataacttttc agtgttctca catcgcagat ttttgaaaga    300

gctatttcat cctcaaatgc ctacgatgat cag                                 333


<210> SEQ ID NO 537
<211> LENGTH: 280
<212> TYPE: DNA
<213> ORGANISM: Glycine max

<400> SEQUENCE: 537

ggacaccctc attgacaagg cccttgagaa aattggcacc ccagtggccc ttaatctacg     60

cgggaaggca gcggtagccc aagcagcatt ggcttaccag ctctaccaaa ggaaattttc    120

tggtccaagg tgggaagctc tagttaaaaa gggggccaag aagcaaaggc tcctctgggc    180

ctcaaccagt gtaaagaatc ctgcctattc tgacacctta tatgttgctc ctcttattgg    240

acccgacact gtatcaacaa tgccagacca agcccttcaa                          280


<210> SEQ ID NO 538
<211> LENGTH: 294
<212> TYPE: DNA
<213> ORGANISM: Glycine max
<220> FEATURE:
<223> OTHER INFORMATION: unsure at all n locations

<400> SEQUENCE: 538

gtgttgcctc tttctttgtc agtagagtgg acactctcca ttgacaaggc ccttgagaaa     60

attggcaccc cagaggctct taatctacgt gggaaggcag cagtagccca agcagcattg    120

gcttaccacc tctaccaaag gaaattttct ggtccaaggt gggaagctct agttaaaaag    180

ggggccaaga agcaaaggct ctttgggcct caaccagtgt aaagaaccct gcctattctg    240

acacntatat gttgctcctc tattggaccc gacatgatca accagccaga ccaa          294


<210> SEQ ID NO 539
<211> LENGTH: 221
<212> TYPE: DNA
<213> ORGANISM: Glycine max
<220> FEATURE:
<223> OTHER INFORMATION: unsure at all n locations

<400> SEQUENCE: 539

gtagagtgga caccctcatt gacaaggccc ttgagnaaat tggcacccca gtggccctta     60

atctacgcgg gaaggcagcg gtagcccaag cagcattggc ttaccagctc taccaaagga    120

aattttctgg tccaaggtgg gaagctctag ttaaaaaggg ggccaagaag caaaggctcc    180

tctgggcctc aaccagtgta aagaatcctg cctattctga c                        221


<210> SEQ ID NO 540
<211> LENGTH: 299
<212> TYPE: DNA
<213> ORGANISM: Glycine max

<400> SEQUENCE: 540

tattctcagt ttgcggtgtt tgatagaaat aatggatcgg aacgggccaa agatcaaaag     60

tacaattctt caccatctct atgagaagca gagacagagc ccttactatg acaatctctg    120

tcgccctgtt tcaggtttgc ttccatttat tgccaatggg atcagaggtg tcactaccaa    180

cccagcgatt tttgaaagag ctatttcatc ctcaaatgcc tacgatgatc agttgaggga    240
```

-continued attggtaggg gcagggaagg acatagaaag tgcttattgg gaattggttg tgaaggaca 299

<210> SEQ ID NO 541
<211> LENGTH: 240
<212> TYPE: DNA
<213> ORGANISM: Glycine max

<400> SEQUENCE: 541
gaagcagaga cagagccctt actatgacaa tctctgtcgc cctgtttcag atttgcttcc 60
atttattgcc aatgggatca gaggtgtcac taccaaccca gcgatttttg aaagagctat 120
ttcatcctca aaatgctacg atgatcagtt gagggaaatg gtcagggcca ggaaggacat 180
agaaagtgct tattgggaat tggttgtgaa ggacatacag gatacttgca aacttctgga 240

<210> SEQ ID NO 542
<211> LENGTH: 278
<212> TYPE: DNA
<213> ORGANISM: Glycine max
<220> FEATURE:
<223> OTHER INFORMATION: unsure at all n locations

<400> SEQUENCE: 542
tttcacttgc tctctctttg ctcttatccc ttttcctttn tctnctttc ctttgggttt 60 tctattctca gtttgcggtg tttgatagaa ataatggatc ggaaccggcc aaagatcaaa 120
agtacaattc ttcaccatct ctatgagaag cagagacaga gcccttacta tgacaatctc 180
tgtcgccctg tttcagattt gcttccattt attgccaatg ggatcagagg tgtcactacc 240
aacccagcga tttttganag agctatttca tcctcaag 278

<210> SEQ ID NO 543
<211> LENGTH: 254
<212> TYPE: DNA
<213> ORGANISM: Glycine max

<400> SEQUENCE: 543
atttttcttt tttcttcttt tcctttgggt tttctattct cagtttgcgg tgtttgatag 60
aaataatgga tcggaacggg ccaaagatca aaagtacaat tcttcaccat ctctatgaga 120
agcagagaca gagcccttac atgacaatct ctgtcgccct gtttcagatt tgcttccatt 180
tattgccaat gggatcagag gtgtcactac caacccagcg atttttgaaa gagctatttc 240
atcctcaaat gcct 254

<210> SEQ ID NO 544
<211> LENGTH: 236
<212> TYPE: DNA
<213> ORGANISM: Glycine max

<400> SEQUENCE: 544
caagaagcaa aggctccttt gggcctcaac cagtgtaaag aaccctgcct attctgacac 60
cttatatgtt gctcctctta ttggacccga cactgtatca accatgccag accaagccct 120
tcaagcattt attgatcatg gtaccgtatc caggacaata gactcaaatg catctgaagc 180
tgaaggaata tacaatgctc tccagaaatt gggtattgac tggagctttg ttggtt 236

<210> SEQ ID NO 545
<211> LENGTH: 260
<212> TYPE: DNA
<213> ORGANISM: Glycine max -continued

<400> SEQUENCE: 545
ggctcctttg ggcctcaacc agtgtaaaga accctgccta ttctgacacc ttatatgttg 60
ctcctcttat tggacccgac actgtatcaa ccatgccaga ccaagccctt caagcattta 120
ttgatcatgg taccgtatcc aggacaatag actcaatgca tctgaagctg aaggaatata 180
caatgctctc cagaaattgg gtattgactg gagctttgtt ggttcccagc ttgaacttga 240
aggagtggac tcgtttaaga 260

<210> SEQ ID NO 546
<211> LENGTH: 250
<212> TYPE: DNA
<213> ORGANISM: Glycine max

<400> SEQUENCE: 546
gaaggaatat acaatgctct ccagaaattg ggtattgact ggagctttgt tggttcccag 60
cttgaacttg aaggagtgga ctcgtttaag aagagctttg acagcctcct ggattctctg 120
caagagaagg caaactctct taagttggtc agccattgaa gtgtgaacgt catagttagt 180
aatgcagtgc tatgtatgaa gtgatttatg gattaataaa aggcagtggc tgtgcatttt 240
gtgctgctgt 250

<210> SEQ ID NO 547
<211> LENGTH: 265
<212> TYPE: DNA
<213> ORGANISM: Glycine max

<400> SEQUENCE: 547
ctcgagccgg gaatatacaa tgctctccag aaattgggta ttgactggag ctttgttgga 60
ctcccagctt gaacttgaag gagtggactc gtttaagaag agctttgaca gcctcctgga 120
ttctctgcaa gagaaggcaa actctcttaa gttggtcagc cactgaagtt tgaacgtcat 180
ggttagtaat gcagtgctgt gtatgatggc atctatggat taataaaagg cagcggctgt 240
gcattttgtg ctgctgcaaa tgtgc 265

<210> SEQ ID NO 548
<211> LENGTH: 228
<212> TYPE: DNA
<213> ORGANISM: Glycine max

<400> SEQUENCE: 548
cgtcatggtt gctcctctta ttggacccga cactgtatca accatgccag accaagccct 60
tcaagcattt attgatcatg gtaccgtatc caggacaata gactcaaatg tgcttcatgg 120
agtcatttat ttagacgata gtgatacaat gtaaatggga aaaattgtcc gcttcaagtc 180
aagcgttttg ttttttcccc actatacaat ggttgtgcgt ttatgttt 228

<210> SEQ ID NO 549
<211> LENGTH: 224
<212> TYPE: DNA
<213> ORGANISM: Glycine max

<400> SEQUENCE: 549
cgtcatggat gctcctctta ttggacccga cactgtatca accatgccag accaagccct 60
tcaagcattt attgatcatg gtaccgtatc caggacaata gactcaaatg tgcttcatgg 120
agtcatttat ttagacgata gtgatacaat gtacttggga aaaattgtcc gcttcaagtc 180
aagcgttttg ttttttcccc actatacaat ggttgtgcga ttat 224

-continued

<210> SEQ ID NO 550
<211> LENGTH: 238
<212> TYPE: DNA
<213> ORGANISM: Glycine max

<400> SEQUENCE: 550
gatcaaatgc tcccaaacag atgggaatgg aagtcctgca aagaggacag tgcttcatga 60
tctttatgag aaagaagggc agagtccatg gtatgataat ctctgcagac ctgttacaga 120
ccttcttcct cttatagcaa gtggtgtcag aggcgtcact agcaaccctg cgatttttca 180
gaaagctatc tcatcatcga atgcttacaa tgatcagttc agggaacttg tgcaagca 238

<210> SEQ ID NO 551
<211> LENGTH: 269
<212> TYPE: DNA
<213> ORGANISM: Glycine max

<400> SEQUENCE: 551
ggaatggaag tcctgcaaag aggacagtgc ttcatgatct ttatgagaaa gaagggcaga 60
gtccatggta tgataatctc tgcagacctg ttacagacct gcttcctctt atagcaagtg 120
gtgtcagagg cgtcactagc aaccctgcga tctttcagaa agctatctca tcatcgaatg 180
cttacaatga tcagttcagg gaacttgtgc aaacagggaa agacattgaa agtgcatatt 240
gggaacttgt agtgaaggat atccaagat 269

<210> SEQ ID NO 552
<211> LENGTH: 272
<212> TYPE: DNA
<213> ORGANISM: Glycine max

<400> SEQUENCE: 552
aattaacctc tccgcttccc tccgatccat tcactccctc cctcttaaaa cctccttgcg 60
gatcaaatgc tcccaaacag atgggaatgg aagtcctgca aagaggacag tgcttcatga 120
tctttatgag aaagaagggc agagtccatg gtatgataat ctctgcagac ctgttacaga 180
ccttcttcct cttatagcaa gtggtgtcag aggcgtcact agcaaccctg cgatttttca 240
gaaagctatc tcatcatcga atgcttacaa tg 272

<210> SEQ ID NO 553
<211> LENGTH: 231
<212> TYPE: DNA
<213> ORGANISM: Glycine max

<400> SEQUENCE: 553
gctccctctt aaaacctcct tacggatcaa atgctcccaa acagatggga atggaagtcc 60
tgcaaagagg acagtgcttc atgatcttta tgagaaagaa gggcagagtc catggtatga 120
taatctctgc agacctgtta cagacctgct tcctcttata gcaagtggtg tcagaggcgt 180
cactagcaac cctgcgatct ttcagaaagc tatctcatca tcgaatgctt a 231

<210> SEQ ID NO 554
<211> LENGTH: 237
<212> TYPE: DNA
<213> ORGANISM: Glycine max
<220> FEATURE:
<223> OTHER INFORMATION: unsure at all n locations

<400> SEQUENCE: 554

-continued tacaaaatta acctctccgc ttccaccnga tccattcact cactcnntct taaaanctcc 60
ttncggatca aatgctccca aacagatggg aatggaagtc ctgcaaagag gacagtgctt 120
catgatcttt atgagaaaga acngcagagt ccatggtatg ataatctctg cagacctgtt 180
acagaccttc ttcctcttat agcaagtggt gtcagaggng tcactagcaa ccctgng 237

<210> SEQ ID NO 555
<211> LENGTH: 270
<212> TYPE: DNA
<213> ORGANISM: Glycine max

<400> SEQUENCE: 555
taaaactaac ctatccgctt ccctccgatc cattcactcg ctccctctta aaacctcctt 60
acggatcaaa tgctcccaaa cagatgggaa tggaagtctg caaagaggac agtgcttcat 120
gatctttatg agaaagaagg gagagtccat ggtatgataa tctctgcaga cctgttacag 180
actgcttctc ttatagcaag tggtgtcaga ggcgtcatta gcaacctgcg catctttcag 240
aaagctatct catcatcgaa tgttacatga 270

<210> SEQ ID NO 556
<211> LENGTH: 292
<212> TYPE: DNA
<213> ORGANISM: Glycine max

<400> SEQUENCE: 556
ccattttcaa gctctcaacg ccatctccag ctgcttcctt atcagaagcg cttcgcccca 60
gagattctcg cttcctctcc ttcaatcctt cttccaacgc tattaattac aaaattaacc 120
tctccgcttc cctccgatcc attcactccc tccctcttaa aacctccttg cggatcaaat 180
gctcccaaac agatgggaat ggaagtcctg caaagaggac agtgcttcat gatctttatg 240
agaaagaagg gcagagtcca tggtatgata atctctgcag acctgttaca ga 292

<210> SEQ ID NO 557
<211> LENGTH: 165
<212> TYPE: DNA
<213> ORGANISM: Glycine max

<400> SEQUENCE: 557
caaaattaac ctctccgctt ccctccgatc cattcactcc ctccctctta aaacctcctt 60
gcggatcaaa tgctcccaaa cagatgggaa tggaagtcct gcaaagagga cagtgcttca 120
tgatctttat gagaaagaag ggcagagtcc atggtatgat aatct 165

<210> SEQ ID NO 558
<211> LENGTH: 289
<212> TYPE: DNA
<213> ORGANISM: Glycine max

<400> SEQUENCE: 558
cattttcaag ctctcaacgc catctccagc tgcttcctta tcagaagcgc ttcgccccag 60
agattctcgc ttcctctcct tcaatccttc ttccaacgct attaattaca aaattaacct 120
ctccgcttcc ctccgatcca ttcactccct ccctcttaaa acctccttgc ggatcacctg 180
ctcccaaaca gatgggaatg gaagtcctgc aaagaggaca gtgcttcatg atctttatga 240
gaaagaaggg cagagtccat ggtatgataa tctctgcaga cctgttaca 289

<210> SEQ ID NO 559
<211> LENGTH: 275

-continued

<212> TYPE: DNA
<213> ORGANISM: Glycine max
<220> FEATURE:
<223> OTHER INFORMATION: unsure at all n locations

<400> SEQUENCE: 559
ccattttcaa gctctcaacg ccatctccag ctgcttcctt atcagangcg cttcgcccca 60
gagattctcg cttcctctcc ttcaatcctt cttccaacgc tattaattac aaaattaacc 120
tctccgcttc cctccgatcc attcactccc tccctcttaa aacctccttg cggatcaaat 180
gctcccaaac agatgggaat ggaagtcctg caaagaggac agtgcttcat gatctttatg 240
aganagaagg gcagagtcca tggtatgata atctc 275

<210> SEQ ID NO 560
<211> LENGTH: 274
<212> TYPE: DNA
<213> ORGANISM: Glycine max

<400> SEQUENCE: 560
attttcaagc tctcaacgcc atctccagct gcttccttat cagaagcgct tcgccccaga 60
gattctcgct tcctctcctt caatccttct tccaacgcta ttaattacaa aattaacctc 120
tccgcttccc tccgatccat tcactcctcc ctcttaaaac ctccttgcgg atcaaatgct 180
cccaaacaga tgggaatgga agtcctgcaa agaggacagt gcttcatgat ctttatgaga 240
aagaagggca gagtccatgg tatgataatc tctg 274

<210> SEQ ID NO 561
<211> LENGTH: 270
<212> TYPE: DNA
<213> ORGANISM: Glycine max

<400> SEQUENCE: 561
ccattttcaa gctctcaacg ccatctccag ctgcttcctt atcagaagcg cttcgcccca 60
gagattctcg cttcctctcc ttcaatcctt cttccaacgc tattaattac aaaattaacc 120
tctccgcttc cctccgatca ttcactccct ccctcttaaa acctccttgc ggatcaaatg 180
ctcccaaaca gatgggaatg gaagtcctgc aaagaggaca gtgcttcatg atctttatga 240
gaaagaaggg cagagtccat ggtatgataa 270

<210> SEQ ID NO 562
<211> LENGTH: 265
<212> TYPE: DNA
<213> ORGANISM: Glycine max

<400> SEQUENCE: 562
cgcctccatt ttcaagctct caacgccatc tccagctgct tccttatcag aagcgcttcg 60
ccccagagat tctcgcttcc tctccttcaa tccttcttcc aacgctatta attacaaaat 120
taacctctcc gcttccctcc gatccattca ctccctccct cttaaaacct ccttgcggat 180
caaatgctcc caaacagatg ggaatggaag tcctgcaaag aggacagtgc ttcatgatct 240
ttatgagaaa gaagggcaga gtcca 265

<210> SEQ ID NO 563
<211> LENGTH: 261
<212> TYPE: DNA
<213> ORGANISM: Glycine max

<400> SEQUENCE: 563

-continued

```
attttcaagc tctcaacgcc atctccagct gcttccttat cagaagcgct tcgccccaga      60

gattctcgct tcctctcctt caatccttct tccaacgcta ttaattacaa aattaacctc     120

tccgcttccc tccgatccat tcactccctc cctcttaaaa cctccttgcg gatcaaatgc     180

tcccaaacag atgggaatgg aagtcctgca aagaggacag tgcttcatga tctttatgag     240

aaagaagggc agagtccatg g                                               261
```

```
<210> SEQ ID NO 564
<211> LENGTH: 282
<212> TYPE: DNA
<213> ORGANISM: Glycine max

<400> SEQUENCE: 564

tccattttca agctctcaac gccatctcca gctgcttcct tatcataagc gcttcgcccc      60

agagattctc gcttcctctc cttcaatcct tcttccaacg ctattaatta cacaattaac     120

ctctccgctt ccctccgatc cattcactcc ctccctctta aaacctcctt gcggatcaaa     180

tgctcccaaa cagatgggaa tggaagtcct gcaaagagga cagtgcttca tgatctttat     240

gagaaagaag ggcagagtcc atggtatgat aatctctgca ga                        282
```

```
<210> SEQ ID NO 565
<211> LENGTH: 290
<212> TYPE: DNA
<213> ORGANISM: Glycine max

<400> SEQUENCE: 565

tccgcttcgt gacttgcagc aattcccaat ggcttccgtt tccaagctct caacgccaaa      60

tccacttgct tccttatcag aagcgcttcg cccccgagat tctcgcttcc tcaccttcaa     120

accttcttcc atcgctttta atcacaaaac taacctatcc gcttccctcc gatccattca     180

ctcgctccct cttaaaacct ccttacggat caaatgctcc caaacagatg ggaatggaag     240

tcctgcaaag aggacagtgc ttcatgatct ttatgagaaa gaagggcaga                290
```

```
<210> SEQ ID NO 566
<211> LENGTH: 256
<212> TYPE: DNA
<213> ORGANISM: Glycine max

<400> SEQUENCE: 566

ccattttcaa gctctcaacg ccatctccag ctgcttcctt atcagaagcg cttcgcccca      60

gagattctcg cttcctctcc ttcaatcctt cttccaacgc tattaattac aaaattaacc     120

tctccgcttc cctccgatcc attcactccc tccctcttaa aacctccttg cggatcaaat     180

gctcccaaac agatgggaat ggaagtcctg caaagaggac agtgcttcat gatctttatg     240

agaaagaagg gcagag                                                     256
```

```
<210> SEQ ID NO 567
<211> LENGTH: 271
<212> TYPE: DNA
<213> ORGANISM: Glycine max

<400> SEQUENCE: 567

gcttcgtgac ttgcagcaat tcccaatggc ttccgtttcc aagctctcaa cgccaaatcc      60

acttgcttcc ttatcagaag cgcttcgccc ccgagattct cgcttcctca ccttcaaacc     120

ttcttccatc gcttttaatc acaaaactaa cctatccgct tccctccgat ccattcactc     180

gctccctctt aaaacctcct tacggatcaa atgctcccaa acagatggga atggaagtcc     240
```

-continued tgcaaagagg acagtgcttc atgatcttta t 271

<210> SEQ ID NO 568
<211> LENGTH: 284
<212> TYPE: DNA
<213> ORGANISM: Glycine max

<400> SEQUENCE: 568
tacttggtgt cttgcaattc ccaatggcct ccattttcaa gctctcaacg ccatctccag 60
ctgcttcctt atcagaagcg cttcgcccca gagattctcg cttcctctcc ttcaatcctt 120
cttccaacgc tattaattac aaaattaacc tctccgcttc cctccgatcc attcactccc 180
tccctcttaa aacctccttg cggatcaaat gctcccaaac agatgggaat ggaagtcctg 240
caaagaggac agtgcttcat gatctttatg agaaagaagg gcag 284

<210> SEQ ID NO 569
<211> LENGTH: 264
<212> TYPE: DNA
<213> ORGANISM: Glycine max

<400> SEQUENCE: 569
ctgacttgca gcaattccca atggcttccg tttccaagct ctcaacgcca aatccacttg 60
cttccttatc agaagcgctt cgcccccgag attctcgctt cctcaccttc aaaccttctt 120
ccatcgcttt taatcacaaa actaacctat ccgcttccct ccgatccatt cactcgctcc 180
ctcttaaaac ctccttacgg atcaaatgct cccaaacaga tgggaatgga agtcctgcaa 240
agaggacatg cttcatgatc ttta 264

<210> SEQ ID NO 570
<211> LENGTH: 250
<212> TYPE: DNA
<213> ORGANISM: Glycine max

<400> SEQUENCE: 570
caatggcctc cattttcaag ctctcaacgc catctccagc tgcttcctta tcagaagcgc 60
ttcgccccag agattctcgc ttcctctcct tcaatccttc ttccaacgct attaattaca 120
aaattaacct ctccgcttcc ctccgatcca ttcactccct ccctcttaaa acctccttgc 180
ggatcaaatg ctcccaaaca gatgggaatg gaagtcctgc aaagaggaca gtgcttcatg 240
atctttatga 250

<210> SEQ ID NO 571
<211> LENGTH: 272
<212> TYPE: DNA
<213> ORGANISM: Glycine max

<400> SEQUENCE: 571
ctcgagccga gcaattccca atggcttccg tttccaagct ctcaacgcca aatccacttg 60
cttccttatc agaagcgctt cgcccccgag attctcgctt cctcaccttc aaacctactc 120
ccatcgcttt taatcacaaa actaacctat ccgcttccct ccgatccatt cactcgctcc 180
ctcttaaaac ctccttacgg atcaaatgct cccaaacaga tgggaatgga agtcctgcaa 240
cgaggacagt gcttcatgat ctttatgaga aa 272

<210> SEQ ID NO 572
<211> LENGTH: 272
<212> TYPE: DNA

-continued

<213> ORGANISM: Glycine max

<400> SEQUENCE: 572
cgcttcgtga cttgcagcaa ttcccaatgg cttccgtttc caagctctca acgccaaatc 60
cacttgcttc cttatcagaa gcgcttcgcc cccgagattc tcgcttcctc accttcaaac 120
cttcttccat cgcttttaat cacaaaacta acctatccgc ttccctccga tccattcact 180
cgctccctct taaaacctcc ttacggatca aatgctccca aacagatggg aatggaagtc 240
ctgcaaagag gacagtgctt catgatcttt at 272

<210> SEQ ID NO 573
<211> LENGTH: 237
<212> TYPE: DNA
<213> ORGANISM: Glycine max

<400> SEQUENCE: 573
ctcaacgcca tctccagctg cttccttatc agaagcgctt cgccccagag attctcgctt 60
cctctccttc aatccttctt ccaacgctat taattacaaa attaacctct ccgcttccct 120
ccgatccatt cactccctcc ctcttaaaac ctccttgcgg atcaaatgct cccaaacaga 180
tgggaatgga agtcctgcaa agaggacagt gcttcatgat ctttatgaga aagaagg 237

<210> SEQ ID NO 574
<211> LENGTH: 251
<212> TYPE: DNA
<213> ORGANISM: Glycine max

<400> SEQUENCE: 574
ccattttcaa gctctcaacg ccatctccag ctgcttcctt atcagaagcg cttcgcccca 60
gagattctcg cttcctctcc ttcaatcctt cttccaacgc tattaattac aaaattaacc 120
tctccgcttc cctccgatcc attcactccc tccctcttaa aacctccttg cggatcaaat 180
gctcccaaac agatgggaat ggaagtcctg caaagaggac agtgcttcat gatctttatg 240
agaaagaagg g 251

<210> SEQ ID NO 575
<211> LENGTH: 233
<212> TYPE: DNA
<213> ORGANISM: Glycine max

<400> SEQUENCE: 575
ctgacttgca gcaattccca atggcttccg tttccaagct ctcaacgcca aatccacttg 60
cttccttatc agaagcgctt cgcccccgag attctcgctt cctcaccttc aaaccttact 120
ccatcgcttt taatcacaaa actaacctat ccgcttccct ccgatccatt cactcgctcc 180
ctcttaaaac ctccttacgg atcaaatgct cccaaacaga tgggaatgga agt 233

<210> SEQ ID NO 576
<211> LENGTH: 279
<212> TYPE: DNA
<213> ORGANISM: Glycine max

<400> SEQUENCE: 576
ccattttcaa gctctcaacg ccatctccag ctgcttcctt atcagaagcg cttcgcccca 60
gagattctcg cttcctctcc ttcaatcctt cttccaacgc tattaattac aaaattaacc 120
tctccgcttc cctccgatcc attcactccc tccctcttaa aacctccttg cggatcaaat 180
gctcccaaac agatgggaat ggaagtcctg caaagaggac agtgcttcat gatctttatg 240

-continued

```
agaaagacgg gcagagtcca tggtatgatc atctctgca                          279


<210> SEQ ID NO 577
<211> LENGTH: 244
<212> TYPE: DNA
<213> ORGANISM: Glycine max

<400> SEQUENCE: 577

ccattttcaa gctctcaacg ccatctccag ctgcttcctt atcagaagcg cttcgcccca     60

gagattctcg cttcctctcc ttcaatcctt cttccaacgc tattaattac aaaattaacc    120

tctccgcttc ctccgatcca ttcactccct ccctcttaaa acctccttgc ggatcaaatg    180

ctcccaaaca gatgggaatg gaagtcctgc aaagaggaca gtgcttcatg atctttatga    240

gaaa                                                                 244


<210> SEQ ID NO 578
<211> LENGTH: 249
<212> TYPE: DNA
<213> ORGANISM: Glycine max

<400> SEQUENCE: 578

caagctctca acgccatctc cagctgcttc cttatcagaa gcgcttcgcc ccagagattc     60

tcgcttcctc tccttcaatc cttcttccaa cgctattaat tacaaaatta acctctccgc    120

ttccctccga tccattcact ccctccctct taaaacctcc ttgcggatca aatgctccca    180

aacagatggg aatggaagtc ctgcaaagag gacagtgctt catgatcttt atgagaaaga    240

gggcagagt                                                            249


<210> SEQ ID NO 579
<211> LENGTH: 245
<212> TYPE: DNA
<213> ORGANISM: Glycine max

<400> SEQUENCE: 579

ccattttcaa gctctcaacg ccatctccag ctgcttcctt atcagaagcg cttcgcccca     60

gagattctcg cttcctctcc ttcaatcctt cttccaacgc tattaattac aaaattaacc    120

tctccgcttc cctccgatcc attcactccc tccctcttaa aacctccttg cggatcaaat    180

gctcccaaac agatgggaat ggaagtcctg caaagaggac agtgcttcat gatctttatg    240

agaaa                                                                245


<210> SEQ ID NO 580
<211> LENGTH: 293
<212> TYPE: DNA
<213> ORGANISM: Glycine max

<400> SEQUENCE: 580

gctatctcat catcgaatgc ttacaatgat cagttcaggg aacttgtgca aacagggaaa     60

gacattgaaa gtgcatattg ggaacttgta gtgaaggata tccaagatgc ttgcagacta    120

tttgaaccaa tctatgatca aacagatggt ggtgatggta tgtttctgtt gaagtatctc    180

ctaggctcgc tgatgacact gagggaacca tagaagctgc aaaatggctt cataaagtgg    240

ttgatcgccc caatgtgtat attaagattc ctgctacaga ggcatgtgtg cct           293


<210> SEQ ID NO 581
<211> LENGTH: 271
<212> TYPE: DNA
```

<213> ORGANISM: Glycine max
<220> FEATURE:
<223> OTHER INFORMATION: unsure at all n locations

<400> SEQUENCE: 581
cgacctgctt cctcttatag caagtggtgt cagangcgtc actagcaacc ctgcgatctt 60
tcagaaagct atctcatcat cgaatgctta caatgatcag ttcagggaac ttgtgcaaac 120
agggaaagac attgaaagtg catattggga acttgtagtg aaggatatcc aagatgcttg 180
cagactattt gaaccaatct atgatcaaac agatggtggt gatgggtatg tttctgtnga 240
agtatctcct aggctcgctg atgacactga g 271

<210> SEQ ID NO 582
<211> LENGTH: 274
<212> TYPE: DNA
<213> ORGANISM: Glycine max

<400> SEQUENCE: 582
ctagatgctt gcaaattatt tgaaccaatc tatgatcaaa cagatggtgg tgatggctat 60
gtttctgttg aagtatctcc caggctcgct gatgacactg agggaaccat agaagctgca 120
aaatggcttc ataaagtggt tgatcgcccc aatgtgtata ttaagattcc tgctacagag 180
gcatgtgtgc cttcaattaa ggaagttatt gctaatggga taagtgtgaa tgtgacgctg 240
atattctctc ttgcaagata tgaagctgta atag 274

<210> SEQ ID NO 583
<211> LENGTH: 267
<212> TYPE: DNA
<213> ORGANISM: Glycine max

<400> SEQUENCE: 583
aagacattga aagtgcatat tgggaacttg tagtgaagga tatccaagat gcttgcaaat 60
tatttgaacc aatctatgat caaacagatg gtggtgatgg ctatgtttct gttgaagtat 120
ctcccaggct cgctgatgac actgagggaa ccatagaagc tgcaaaatgg cttcataaag 180
tggttgatcg ccccaatgtg tatattaaga ttcctgctac agaggcatgt gtgccttcaa 240
ttaaggacgt tattgctaat gggataa 267

<210> SEQ ID NO 584
<211> LENGTH: 248
<212> TYPE: DNA
<213> ORGANISM: Glycine max

<400> SEQUENCE: 584
agaaagtgca tattgggaac ttgtagtgaa ggatatccaa gatgcttgca gactatttga 60
accaatctat gatcaaacag atggtggtga tgggtatgtt tctgttgaag tatctcctag 120
gctcgctgat gacactgagg gaaccataga agctgcaaaa tggcttcata aagtggttga 180
tcgccccaat gtgtatatta agattcctgc tacagaggca tgtgtgcctt caattaagga 240
agttattg 248

<210> SEQ ID NO 585
<211> LENGTH: 253
<212> TYPE: DNA
<213> ORGANISM: Glycine max

<400> SEQUENCE: 585
gcgattactc agaaagctat ctcatcatcg actccttaca atgatcagtt cagggaactt 60

-continued ctgcaagcag ggaaagacat tgaaagtgca tattgggaac ttgtagtgaa ggatatccaa 120
gatgcttgca aattatttga accaatctat gatcaaacag atggtggtga tggctatgtt 180
tctgttgaag tatctcccag gctcgctgat gaacctgagg gaaccatagc agctgcaaaa 240
tggcttcata aag 253

<210> SEQ ID NO 586
<211> LENGTH: 253
<212> TYPE: DNA
<213> ORGANISM: Glycine max

<400> SEQUENCE: 586
gaagctgcaa aatggcttca taaagtggtt gatcgcccca atgtgtatat taagattcct 60
gctacagagg catgtgtgcc ttcaattaag gaagttattg ctaatgggat aagtgtgaat 120
gtgacgctga tattctctct tgcaagatat gaagctgtaa ttgatgcata cttggatggt 180
cttgaggcat ctgagttaaa tgacctctct agagttacaa gtgttgcctc tttcttcgtc 240
agtagagtgg aca 253

<210> SEQ ID NO 587
<211> LENGTH: 264
<212> TYPE: DNA
<213> ORGANISM: Glycine max

<400> SEQUENCE: 587
ctcgagccta agacattgaa agtgcatatt gggaacttgt agtgaaggat atccaagatg 60
cctgcagact atttgaacca atctatgatc aaacagatgg tggtgatggg tatgtttctg 120
ttgaagtatc tcctaggctc gctgatgaca ctgagggaac cattgaagct gcaaaatggc 180
ttcataaagg gttgatcgcc ccaatgtgta tattaagatt cctgctacag aggcatgtgt 240
gccttcaatt aaggaagtta ttgc 264

<210> SEQ ID NO 588
<211> LENGTH: 263
<212> TYPE: DNA
<213> ORGANISM: Glycine max

<400> SEQUENCE: 588
ctgatattct ctcttgcaag atatgaagct gtaatagatg cttacttgga tggtcttgag 60
gcatctgggt taaatgacct ctctagagtt acaagtgttg cctctttctt tgtcagtaga 120
gtggacactc tcattgaaag gcccttgaga aaattggcac cccagaggct cttaatctac 180
gtgggaaggc agcagtagcc caagcagcat tggcttacca gctctaccaa aggaaatttt 240
ctggtccaag gtgggaagct cta 263

<210> SEQ ID NO 589
<211> LENGTH: 244
<212> TYPE: DNA
<213> ORGANISM: Glycine max

<400> SEQUENCE: 589
gggataagtg tgaatgtgac gctgatattc tctcttgcaa gatatgaagc tgtaatagat 60
gcttacttgg atggtcttga ggcatctggg ttaaatgacc tctctagagt tacaagtgtt 120
gcctctttct ttgtcagtag agtggacact ctcattgaca aggcccttga gaaaattggc 180
accccagagg ctcttaatct acgtgggaag gcagcagtag cccaagcagc attggcttac 240

-continued

```
cagc                                                                  244


<210> SEQ ID NO 590
<211> LENGTH: 228
<212> TYPE: DNA
<213> ORGANISM: Glycine max

<400> SEQUENCE: 590

gcttacaatg atcagttcag ggaacttgtg caaacaggga aagacattga aagtgcatat     60

tgggaacttg tagtgaagga tatccaagat gcttgcagac tatttgaacc aatctatgat    120

caaacagatg gtggtgatgg gtatgtttct gttgaagtat ctcctaggct cgctgatgac    180

actgagggaa ccatagaagc tgcaaaatgg cttcataaag tggttgat                 228


<210> SEQ ID NO 591
<211> LENGTH: 265
<212> TYPE: DNA
<213> ORGANISM: Glycine max

<400> SEQUENCE: 591

catagaagct gcaaaatggc ttcataaagt ggttgatcgc cccaatgtgt atattaagat     60

tcctgctaca gaggcatgtg tgccttcaat taaggaagtt attgctaatg ggataagtgt    120

gaatgtgacg ctgatattct ctcttgcaag atatgaagct gtaatagatg cttacttgga    180

tggtcttgag gcatctgggt taaatgacct ctctagagtt acaagtgttg cctctcactt    240

tgtcagtaga gtggacactc tcatt                                          265


<210> SEQ ID NO 592
<211> LENGTH: 281
<212> TYPE: DNA
<213> ORGANISM: Glycine max

<400> SEQUENCE: 592

cctcgagccg attcggctcg agcgaatgct tacaatgatc agttcaacgg aacttgtgca     60

aacagggaaa gacattgaaa gtacatattg ggaacttgta gtgaaggata tccaagatgc    120

ttgcagacta tttgaaccaa tctatgatca aacagatggt ggtgatgggt atgtttctgt    180

tgaagtatct cctaggctcg ctgatgacac tgagggaacc atagaagctg caaaatggct    240

tcataaagtg gttgatcgcc ccaatgtgta tattaagatt c                        281


<210> SEQ ID NO 593
<211> LENGTH: 281
<212> TYPE: DNA
<213> ORGANISM: Glycine max
<220> FEATURE:
<223> OTHER INFORMATION: unsure at all n locations

<400> SEQUENCE: 593

catcatcgaa tgcttaaaat gntcagttca gggnacttgt gnaaacaggg aaagacattg     60

aaagtgcata ttgggaactt gtagtgaagg atatcnaaaa tgcnaaaaan ganGnttgaa    120

accaatctat gancaaacag atggnggtga tgggtatgtt tctgttgaag tatctcctag    180

ggctcgctga tgaacactga gggaaccata gaagctgcaa aatggcttca taaagtggnt    240

gatcggccca atgtgtatat taagattcct gnttacagag g                        281


<210> SEQ ID NO 594
<211> LENGTH: 260
<212> TYPE: DNA
<213> ORGANISM: Glycine max
```

-continued

<400> SEQUENCE: 594
gccttcaatt aaggaagtta ttgctaatgg gataagtgtg aatgtgacgc tgatattctc 60
tcttgcaaga tatgacgctg taatagatgc ttacttggat ggtcttgagg catctgggtt 120
aaatgacctc tctagagtta caagtgttgc ctctttcttt gtcagtagag tggacactct 180
cattgacaag gcccttgaga aaattggcac cccagaggct cttaatctac gtgggaaggc 240
agcagtagcc caagcagcat 260

<210> SEQ ID NO 595
<211> LENGTH: 217
<212> TYPE: DNA
<213> ORGANISM: Glycine max

<400> SEQUENCE: 595
gaagttattg ctaatgggat aagtgtgaat gtgacgctga tattctctct tgcaagatat 60
gaagctgtaa ttgatgcata cttggatggt cttgaggcat ctgagttaaa tgacctctct 120
agagttacaa gtgttgcctc tttcttcgtc agtagagtgg acaccctcat tgacaaggcc 180
cttgagaaaa ttggcacccc agtggccctt aatctac 217

<210> SEQ ID NO 596
<211> LENGTH: 212
<212> TYPE: DNA
<213> ORGANISM: Glycine max

<400> SEQUENCE: 596
ctatgatcaa acagatggtg ctgatggcta tgtttctgtt gaactatctc ccaggctcgc 60
tgatgacact gagggaacca tagaagctgc aaaatggctt cataaagtgg ttgatcgccc 120
caatgtgtat attaagattc ctgctacaga ggcatgtgtg ccttcaatta aggaagttat 180
tgctaatggg ataagtgtga atgtgacgct ga 212

<210> SEQ ID NO 597
<211> LENGTH: 289
<212> TYPE: DNA
<213> ORGANISM: Glycine max
<220> FEATURE:
<223> OTHER INFORMATION: unsure at all n locations

<400> SEQUENCE: 597
ttatagcaag tnngtgtcag angcgtcact ngcaaccctg cgatttttca gaaaggctan 60
cgcatcatcg aaggnttacn atgatcngtt cagggaactt ggtgcaagca gggaaagaca 120
ttgaaagtgc atattgggaa ctngtagtga aggatatcca agatgcttgc aaattatttg 180
aaccantcta tnatcaaaca gatggtggtg atggctatgt ttctgttgaa gtatctccca 240
ggctcgctga tgacactgag gganccatag aactgcaaaa tggcttcat 289

<210> SEQ ID NO 598
<211> LENGTH: 260
<212> TYPE: DNA
<213> ORGANISM: Glycine max

<400> SEQUENCE: 598
gtgaatgtga cgctgatatt ctctcttgca agatatgaag ctgtaattga tgcatacttg 60
gatggtcttg aggcatctga gttaaatgac ctctctagag ttacaagtgt tgcctctttc 120
ttcgtcagta gagtggacac cctcattgac aaggcccttg agaaaattgg caccccagtg 180

-continued gcccttaatc tacgcgggaa ggcagcggta gcccaagcag cattggctta ccagctctac 240
caaaggaaat tttctggtcc 260

<210> SEQ ID NO 599
<211> LENGTH: 229
<212> TYPE: DNA
<213> ORGANISM: Glycine max

<400> SEQUENCE: 599
taaggaagtt attgctaatg gactaagtgt gaatgtgacg ctgatattct ctcttgcaag 60
atatgaagct gtaattgatg catacttgga tggtcttgag gcatctgagt taaatgacct 120
ctctagagtt acaagtgttg cctctttctt cgtcagtaga gtggacaccc tcattgacaa 180
ggcccttgag gaaattggca ccccagtggc ccttaatcta cgcgggaag 229

<210> SEQ ID NO 600
<211> LENGTH: 182
<212> TYPE: DNA
<213> ORGANISM: Glycine max

<400> SEQUENCE: 600
agtgtgaatg tgacgctgat attctctctt gcaagatatg aagctgtaat tttgcgata 60 ctggatggtc ttgaggcatc tgagttaaat gacctctcta gagttacaag tgttgcctct 120
ttcttcgtca gtagagtgga caccctcatt gacaaggccc ttgagaaaat tggcacccca 180
gt 182

<210> SEQ ID NO 601
<211> LENGTH: 399
<212> TYPE: DNA
<213> ORGANISM: Glycine max

<400> SEQUENCE: 601
gatgaatcca tctcttccat gaaggaggtc atttctttgg ggataagtgt aaatgccact 60
ctcatattct gcctccctaa atatgaagca gtgattgatg cttacttgga tggccttgag 120
tcttgtggca tgactgatct ctctaaggtt tcaagtgcag cagcattcta catcagtaga 180
gtggatgtta cacttgacaa gaaacttgag caaattggta ctactgaggc tcttgatctc 240
aaaggaaagg gtgcggttgc tcaagcagtc ttagcatacc aactttacca gaaaaaattt 300
tctggtccaa gatgggaacg cttggagaat agaagtgcca agaagcagag gttgatgtgg 360
gcttcaacaa atgtgaaaaa tccatcttac cctgacaca 399

<210> SEQ ID NO 602
<211> LENGTH: 405
<212> TYPE: DNA
<213> ORGANISM: Glycine max
<220> FEATURE:
<223> OTHER INFORMATION: unsure at all n locations

<400> SEQUENCE: 602
gtcttgaggc atctgggtta aatgacctct ctagagttac aagtgttgcc tctttcttcg 60
tcagtagaat ggacaccctc attgacaagg cccttgagaa aattggcacc ccaatggccc 120
ttaatctacg tgggaaggca acggtagccc aagcagcatt ggcttaacag ctctaccaaa 180
gaaattttct ggtccaaagt gggaagctct agttaaaaag gggggccaaga agcaaaggct 240 cctctgggcc ttaaccagtg taaagaatcc tgcctattct gacaccttat atgttgctcc 300
tcttattgga cccgacactg tatcaacaat gccagaccaa gcccttcaag catttatcga 360
tcatggtacc gtatccagga caatagactc anatgcatct gaagc 405

<210> SEQ ID NO 603
<211> LENGTH: 399
<212> TYPE: DNA
<213> ORGANISM: Glycine max

<400> SEQUENCE: 603
gaacgggcca aagatcaaaa gtacaattct tcaccatctc tatgagaagc agagacagag 60
cccttactat gacaatctct gtcgccctgt ttcagatttg cttccattta ttgccaatgg 120
gatcagaggt gtcactacca acccagcgat ttttgaaaga gctatttcat cctcaaatgc 180
ctacgatgat cagttgaggg aattggtagg ggcagggaag gacatagaaa gtgcttattg 240
ggaattggtt gtgaaggaca tacaggatac ttgcaaactt ctggagccaa tttacaatga 300
aacagatggg gaagatggac atgtatctct tgcagtttcc ccaaagctag caaatgacac 360
caaggggaca attgaggcag caaaatggct tcataatat 399

<210> SEQ ID NO 604
<211> LENGTH: 418
<212> TYPE: DNA
<213> ORGANISM: Glycine max
<220> FEATURE:
<223> OTHER INFORMATION: unsure at all n locations

<400> SEQUENCE: 604
cccacgcgtc cggcccttca agcatttatt gatcatggta ccgtatccag gacaatagac 60
tcaaatgcat ctgaagctga aggaatatac aatgctctcc agaaattggg tattgactgg 120
agctttgttg gttcccagct tgaacttgaa ggagtggact cgtttaagaa gagctttgac 180
agcctcctgg attctctgca agagaaggca aactctctta agttggtcag ccactgaagt 240
ttgaacgtca tggttagtaa tgcagtgctg tgtatgatgg catctatgga ttaataaaag 300
gcagcggctg tgcattttgt gctgctgcan atgtgcttca tggagtcatt tatttagacg 360
atagtgatac aatgtaaatg ggaaaaattg tccgcttcaa gtcaagcgtt ttgttttt 418

<210> SEQ ID NO 605
<211> LENGTH: 396
<212> TYPE: DNA
<213> ORGANISM: Glycine max

<400> SEQUENCE: 605
atctccagct gcttccttat cagaagcgct tcgccccaga gattctcgct tcctctcctt 60
caatccttct tccaacgcta ttaattacaa aattaacctc tccgcttccc tccgatccat 120
tcactccctc cctcttaaaa cctccttgcg gatcaaatgc tccaaacaga tgggaatgaa 180
gtcctgcaaa gaggacagtg cttcatgatc tttatgagaa agaagggcag agtccatggt 240
atgataatct ctgcagacct gttacagacc ttcttcctct tatagcaagt ggtgtcagag 300
gcgtcactag caaccctgcg atttttcaga aagctatctc atcatcgaat gcttacaatg 360
atcagttcag ggaacttgtg caagcaggga aagaca 396

<210> SEQ ID NO 606
<211> LENGTH: 428
<212> TYPE: DNA
<213> ORGANISM: Glycine max

<400> SEQUENCE: 606

-continued

```
ccattttcaa gctctcaacg ccatctccag ctgcttcctt atcagaagcg cttcgcccga     60

gaggttctcg cttcctctcc ttcaatcctt cttccaacgc tattaattac aaaattaacc    120

tctccgcttc cctccgatcc attcactccc tccctcttaa aacctccttg cggatcaaat    180

gctcccaaac agatgggaat ggaagtcctg caaagaggac agtgcttcat gatctttatg    240

agaaagatag gcagagtcca tggtatgata atctctgcag acctgttaca gaccttctta    300

ctcttatagc aagtggtgtc agaggcgtca ctagcaaccc tgcgattttt cagaaagcta    360

tctcatcatc gaatgcttac aatgatcagt tcaaggaact tgtgcaagca tggaaagaca    420

ttgaaagt                                                             428
```

<210> SEQ ID NO 607
<211> LENGTH: 373
<212> TYPE: DNA
<213> ORGANISM: Glycine max

<400> SEQUENCE: 607

```
aacgccatct ccagctgctg ccttatcaga agcgcttcgc cccagagatt ctcgcttagt     60

ctgcttcaat ccttatgcca acgctatcaa ttacaaaatt gacctctccg cttgcctccg    120

atccattcac tccctgccta ttaaaaccta cttgcggatc aaatgctccc aaacagatgg    180

gaatggaagt cctgctaaga ggacagcgct tcatgatctt tatgagaaag aagggcagag    240

tccatggtat gataatctct gcagacctgt tacagagctt gttcctgtta tagcacgtgg    300

tgtcagaggc gtcactagca accctgcgat tttcagaaa gctatctcat catcgaatgc    360

ttacaatgat cag                                                       373
```

<210> SEQ ID NO 608
<211> LENGTH: 405
<212> TYPE: DNA
<213> ORGANISM: Glycine max

<400> SEQUENCE: 608

```
gcaattccca atggcctcca ttttcaagct ctcaacgcca tctccagctg cttccttatc     60

agaagcgctt cgccccagag attctcgctt cctctccttc aatccttctt ccaacgctat    120

taattacaaa attaacctct ccgcttccct ccgatccatt cactccctcc ctcttaaaac    180

ctccttgcgg atcaaatgct cccaaacaga tgggaatgga agtcctgcaa agaggacagt    240

gcttcatgat ctttatgaga aagaaaggca gagtccatgg tatgataatc tctgcagacc    300

tgttacagac cttcttcctc ttatagcaag tggtgtcaga ggcgtcacta gcaaccctgc    360

gatttttcag aaagctatct catcatcgaa tgcttacaat gatca                    405
```

<210> SEQ ID NO 609
<211> LENGTH: 417
<212> TYPE: DNA
<213> ORGANISM: Glycine max

<400> SEQUENCE: 609

```
agtacggctg cgagaagacg acagaagggg gaaccaccta cttggtgtct tgcaattccc     60

aatggcctcc attttcaagc tctcaacgcc atctccagct gcttccttat cagaagcgct    120

tcgccccaga gattctcgct tcctctcctt caatccttct tccaacgcta ttaattacaa    180

aattaacctc tccgcttccc tccgatccat tcactccctc cctcttaaaa cctccttgcg    240

gatcaaatgc tcccaaacag atgggaatgg aagtcctgca aagaggacag tgcttcatga    300

tctttatgag aaagaagggc agagtccatg gtatgataat ctctgcagac ctgttacaga    360
```

-continued

```
ccttcttcct cttatagcaa gtggtgtcag aggcgtcact agcaaccctg cgatttt       417


<210> SEQ ID NO 610
<211> LENGTH: 414
<212> TYPE: DNA
<213> ORGANISM: Glycine max

<400> SEQUENCE: 610

gacccacgcg tcaacccacg cgtccgccca cgcgtccgcc cacgcgtccg tacggctgcg     60

agaagacgac agaaggggac tccatcctcc gcttcgtgac ttgcagcaat tcccaatggc    120

ttccgtttcc aagctctcaa cgccaaatcc acttgcttcc ttatcagaag cgcttcgccc    180

ccgagattct cgcttcctca ccttcaaacc ttcttccatc gcttttaatc acaaaactaa    240

cctatccgct tccctccgat ccattcactc gctccctctt aaaacctcct tacggatcaa    300

atgctcccaa acagatggga atggaagtcc tgcaaagagg acagtgcttc atgatcttta    360

tgagaaagaa gggcagagtc catggtatga taatctctgc agacctgtta caga          414


<210> SEQ ID NO 611
<211> LENGTH: 454
<212> TYPE: DNA
<213> ORGANISM: Glycine max

<400> SEQUENCE: 611

ccattttcaa gctctcaacg ccatctccag ctgcttcctt atcagaagcg cttcggccca     60

gagattctcg cttcctctcc ttcaatcctt cttccaacgc tattaattac aaaattaacc    120

tctccgcttc cctccgatcc attcactccc tccctcttaa aacctccttg cggatcaaat    180

gctcccaaac agatgggaat ggaagtcctg caaagaggac agtgcttcat gatctttatg    240

agaaagaagg gcagagtcca tggtatgata atctctgcag acctgttaca gaccttcttc    300

ctcttatagc aagtggtgtc agaggcgtca ctagcaaccc tgcgattttt cagaaagcta    360

tctcatcatc gaatgcttac aatgatcagt tcacggaact tgtgcaagcg ggaaagacat    420

ttgaagtgca tattgggaac ttgtaatgaa agat                                454


<210> SEQ ID NO 612
<211> LENGTH: 389
<212> TYPE: DNA
<213> ORGANISM: Glycine max

<400> SEQUENCE: 612

aagtcaattt tcaagctctc aacgccatct ccagctgctt ccttatcaga agcgcttcgc     60

cccagagatt ctcgcttcct ctccttcaat ccttcttcga acgctattaa ttacaaaatt    120

aacctctccg cttccctccg atccattcac tccctccctc ttaaaacctc cttgcggatc    180

aaatgctccc aaacagatgg gaatggaagt cctgcaaaga ggacagtgct tcatgatctt    240

tatgagaaag aagggcagag tccatggtat gataatctct gcagacctgt tacagacctt    300

cttcctctta tagcaagtgg tgtcagaggc gtcactagca accctgcgat tttcagaaa     360

gctatctcat catcgaatgc ttacaatga                                      389


<210> SEQ ID NO 613
<211> LENGTH: 384
<212> TYPE: DNA
<213> ORGANISM: Glycine max

<400> SEQUENCE: 613
```

-continued

```
tcaacgccat ctccagctgc ttccttatca gaagcgcttc gccccagaga ttctcgcttg     60

gtctccttca atccttcttc caacgctatt aattacaaaa ttaacctctc cgcttccctc    120

cgatccattc actccctacc tcttaaaacc tacttgcgga tcaaatgctc ccaaacagat    180

gggaatggaa gtcctgcaaa gaggacagtg cttcatgatc tttatgagaa agataggcag    240

aatccatgga atgacaatct ctgcaaacct gttacagacc ttcttcctct tatagcaagt    300

ggtgtcagag gcgtcactag gcaccctgcg atttttcaga aagctatctc atcatcgaat    360

gcttacaatg atcaattcaa ggaa                                           384
```

<210> SEQ ID NO 614
<211> LENGTH: 408
<212> TYPE: DNA
<213> ORGANISM: Glycine max

<400> SEQUENCE: 614

```
agacattgaa agtgcatatt gggaacttgt agtgaaggat atccaagatg cttgcaaatt     60

atttgaacca atctatgatc aaacagatgg tggtgatggc tatgtttctg ttgaagtatc    120

tcccaggctc gctgatgaca ctgagggaac catagaagct gcaaaatggc ttcataaagt    180

ggttgatcgc cccaatgtgt atattaagat tcctgctaca gaggcatgtg tgccttcaat    240

taaggaagtt attgctaatg ggataagtgt gaatgtgacg ctgatattct ctcttgcaag    300

atatgaagct gtaatagatg cttacttgga tggtcttgag gcatctgggt taaatgacct    360

gtctagagtt acaagtgttg cctctttctt tgtcagtaga gtggacac                 408
```

<210> SEQ ID NO 615
<211> LENGTH: 434
<212> TYPE: DNA
<213> ORGANISM: Glycine max

<400> SEQUENCE: 615

```
cccacgcgtc cgggctgcga gaagacgaca gaaggggatc aaacagatgg tggtgatggc     60

tatgtttctg ttgaagtatc tcccaggctc gctgatgaca ctgagggaac catagaagct    120

gcaaaatggc ttcataaagt ggttgatcgc cccaatgtgt atattaagat tcctgctaca    180

gaggcatgtg tgccttcaat taaggaagtt attgctaatg ggataagtgt gaatgtgacg    240

ctgatattct ctcttgcaag atatgaagct gtaatagatg cttacttgga tggtcttgag    300

gcatctgggt taaatgacct ctctagagtt acaagtgttg cctctttctt tgtcagtaga    360

gtggacactc tcattgacaa ggcccttgag aaaattggca ccccagaggc tcttaatcta    420

cgtgggaagg cagc                                                      434
```

<210> SEQ ID NO 616
<211> LENGTH: 417
<212> TYPE: DNA
<213> ORGANISM: Glycine max

<400> SEQUENCE: 616

```
tgcttgcaaa ttatttgaac caatctatga tcaaacagat ggtggtgatg gctatgtgtc     60

tgttgaagta tctcccaggc tcgctgatga cactgaggga accatagaag ctgcaaaatg    120

gcttcataaa gtggttgatc gccccaatgt gtatattaag attcctgcta cagaggcatg    180

tgtgccttca attaaggaag ttattgctaa tgggataagt gtgaatgtga cgctgatatt    240

ctctcttgca agatatgaag ctgtaataga tgcttacttg gatggtcttg aggcatctgg    300

gttaaatgac ctctctagag ttacaagggg ttgcttcttc tttgtcagta gagtggacac    360
```

-continued

```
tctcattgac aaagcccttg agaaaattgg caccccagag gctcttaatc tacgtgg       417


<210> SEQ ID NO 617
<211> LENGTH: 328
<212> TYPE: DNA
<213> ORGANISM: Glycine max

<400> SEQUENCE: 617

tacggctgcg agaagacgac agaagggggg ataagtgtga atgtgacgct gatattctgg     60

cttgcaagat atgaagctgg ggtagatgct tacttggatg gtcttgaggc atctgggtta    120

aatgacctct ctagagttac aagtgttgcc tctttctttg tcagtagagt ggacactctc    180

attgacaagg cccttgagaa aattggcacc ccagaggctc ttaatctacg tgggaaggca    240

gcagtggccc aagcagcatt ggcttaccag cgtctccgaa ggaaatgttc tggtccaagg    300

tgggaagctc tagttaaaaa tggggcca                                       328


<210> SEQ ID NO 618
<211> LENGTH: 290
<212> TYPE: DNA
<213> ORGANISM: Zea mays

<400> SEQUENCE: 618

aacatttgtt tacagtttcg cacaagcggc agcgtcagca caagctggtg catctgtagt     60

acaaatgttt gtgggccgat tgcgggactg ggcaaggcat cactctggtg acccagagat    120

agatgaagct ttgaagaatg gagaagatgc tgggctttct ttggcgaaga aagtatatgc    180

ctatattcac aggattgggt acaaaacaaa gctgatggcc gctgccatac ggaacaagca    240

ggacgtattt agccttctgg ggattgatta cattattgcc cactgaagat               290


<210> SEQ ID NO 619
<211> LENGTH: 300
<212> TYPE: DNA
<213> ORGANISM: Zea mays

<400> SEQUENCE: 619

gatttattga caacaccgat cctgctggga ttgatcatca aattgctcaa ctaggacctg     60

aactggcaac tactcttgta attgtcattt ctaagagcgg aggcacacct gaaacccgca    120

atggtctact agaagtacag aaagccttca gagatgcggg gctgcaattc tcgaaacagg    180

gtgttgcaat tactcaagaa aattctctgt tggataacac tgctagaata gagggatggt    240

tagctcggtt tcctatgttt gattgggttg gtggtaggac ttcagaaatg tctgctgtgg    300


<210> SEQ ID NO 620
<211> LENGTH: 208
<212> TYPE: DNA
<213> ORGANISM: Zea mays

<400> SEQUENCE: 620

cgccaacccc gacgagggtc gcatggtggg ccactactgg ctccgcgacc cggccctcgc     60

tcccaactcc ttcctccgga acaagatcga gaccgcactc gacaaaatcc tcgccttctc    120

ccaagatgtc atctctggaa agattctttc cccatctggt cgtttcactt caattctctc    180

tataggaatc ggagggtcag ctttgggc                                       208


<210> SEQ ID NO 621
<211> LENGTH: 267
<212> TYPE: DNA
```

-continued

<213> ORGANISM: Zea mays

<400> SEQUENCE: 621
cccacgcgtc cgataacact gccagaatag agggatggtt agctcggttt cctatgtttg 60
actgggttgg tggtaggact tcagaaatgt cagctgttgg tttacttcca gctgcattgc 120
agtgtattga tatcaaggaa atgctatttg gtgcagcttt aatggatgag gaaacccgga 180
acactgtggt taaagcaaat ccagcagcat tgcttgcatt atgttggtat tgggcatcgg 240
aagggatagg caaaaaggat atggttg 267

<210> SEQ ID NO 622
<211> LENGTH: 258
<212> TYPE: DNA
<213> ORGANISM: Zea mays

<400> SEQUENCE: 622
agcttctcgc ttttttaacc acagttgtca acctaactgt cggctggaga aatggaatca 60
gagggtctgc ttatgggcct caatttgttg ctaaaccact tgcacctgat aaccctccac 120
tgaaggtaag atttattgac aacatcgatc ctggtgggat tgatcatcaa attgctcaac 180
taggatctca actggcaact agctactctt gtaattgtca tttctaagaa cacttgaggg 240
agggggaact gctgaagc 258

<210> SEQ ID NO 623
<211> LENGTH: 229
<212> TYPE: DNA
<213> ORGANISM: Zea mays

<400> SEQUENCE: 623
gcagaatgtg aacagggcca caactgggat tccttgaaat gttgatccag ttgacgttgc 60
acgaagcatt aaagatttgg atccagaaac cactctggtg gtggctgtat caaagacatt 120
cacaacagct gaaacaatgt taaatgctcg aactcctaag gagtggatcg tttcttctct 180
tgggacacag gctgttgcca tacatatgat tgctgtcagc actaatctt 229

<210> SEQ ID NO 624
<211> LENGTH: 337
<212> TYPE: DNA
<213> ORGANISM: Zea mays

<400> SEQUENCE: 624
aggttggaca gcttttatcc atctatgagc accggattgc agttcagggc ttcatatggg 60
gaattaactc atttgaccca tggggagtgg acctagggaa gtcactcgct tctcaagtga 120
ggaaacagct gcatggaacc cggatggaag gaaagcctgt tgagggtttt aaccacagca 180
cttcaagttt gcttgcacga tatcttgctg tcaagccatc caccccgtat gatactaccg 240
tgctgccgaa ggtgtaatta ctcagttgtt tttgacatgc caattgctga gctctgactt 300
ggcaaggttg agcataagtc tttcttcatt ttgggag 337

<210> SEQ ID NO 625
<211> LENGTH: 248
<212> TYPE: DNA
<213> ORGANISM: Zea mays

<400> SEQUENCE: 625
gcggggctgc aattctcgaa acagggtgtt gcaattactc aagaaaattc tctgttggat 60
aacactgcta gaatagaggg atggttagct cggtttccta tgtttgattg ggttggtggt 120
aggacttcag aaatgtctgc tgtgggttta cttccagctg cattgcaggg tattgatatc 180
aaggaaatgc tagctggtgc agctttaatg gatgaagaaa cccggaacac tgtggttaaa 240
gaaaatcc 248

<210> SEQ ID NO 626
<211> LENGTH: 288
<212> TYPE: DNA
<213> ORGANISM: Zea mays

<400> SEQUENCE: 626
gttgcaatca ctcaagaaaa ttctctgttg gataacactg ccagaataga gggatggtta 60
gctcggtttc ctatgtttga ctgggttggt ggtaggactt cagaaatgtc agctgttggt 120
ttacttccag ctgcattgca gggtattgat atcaaggaaa tgctagttgg tgcagcttta 180
atggatgagg aaacccggaa cactgtggta tcacattatt aataacacgg acaacttgca 240
gtgatggcat gattatctat atgtgtcatg tcaacatgtt tatctttt 288

<210> SEQ ID NO 627
<211> LENGTH: 243
<212> TYPE: DNA
<213> ORGANISM: Zea mays

<400> SEQUENCE: 627
tgatgcgggt ctgcaattct cgaaacaggg tgttgcaatc actcaagaaa attctctgtt 60
ggataacact gccagaatag agggatggtt agctcggttt cctatgtttg actgggttgg 120
tggtaggact tcagaaatgt cagctgttgg tttacttcca gctgcattgc agggtattga 180
tatcaaggaa atgctagttg gtgcagcttt aatggatgag gaaacccgga acactgtggt 240
taa 243

<210> SEQ ID NO 628
<211> LENGTH: 235
<212> TYPE: DNA
<213> ORGANISM: Zea mays

<400> SEQUENCE: 628
cagaaagcct tcagagatgc agggctgcaa ttctcgaaac agggtgttgc aattactcaa 60
gaaaattctc tgttggataa cactgctaga atagagggat ggttagctcg gtttcctatg 120
tttgattggg ttggtggtag gacttcagaa atgtcagctg tgggtttact tccagctgca 180
ttgcagggta ttgatatcaa ggaaatgcta gctggtgcag ctttaatgga tgagg 235

<210> SEQ ID NO 629
<211> LENGTH: 296
<212> TYPE: DNA
<213> ORGANISM: Zea mays

<400> SEQUENCE: 629
cgacagaatc ctcgccttct ctcaagatgt cgtctctgga aagattcttt ccccatctgg 60
tcgtttcact tcaattctct ctataggaat cggagggtca gctttgggcc ctcaatttgt 120
tgctgaggca cttgcgcctg ataaccctcc actgaagata agatttattg acaacaccga 180
tcctgctggg attgatcatc aaattgctca actaggacct gaactggcaa ctactcttgt 240
aattgtcatt tctaagagcg gaggcacacc tgaaacccgc aatgggctac tggaag 296

<210> SEQ ID NO 630

-continued

<211> LENGTH: 228
<212> TYPE: DNA
<213> ORGANISM: Zea mays

<400> SEQUENCE: 630
gaaagattct ttccccatct ggtcgtttca cttcaattct ctctatagga atcggagggt 60
cagctttggg ccctcaattt gttgccgagg cacttgcacc tgataaccct ccactgaaga 120
taagatttat tgacaacaca gatcctgctg ggattgatca tcaaattgct caactaggac 180
ctgaactggc aactactcgt gaaagtgaca tttctaagag cggcggca 228

<210> SEQ ID NO 631
<211> LENGTH: 304
<212> TYPE: DNA
<213> ORGANISM: Zea mays

<400> SEQUENCE: 631
cccacgcgtc cgccgcactc gacagaatcc tcgccttctc tcaagatgtc gtctctggaa 60
agattctttc cccatctggt cgtttcactt caattctctc tataggaatc ggagggtcag 120
ctttgggccc tcaatttgtt gctgaggcac ttgcgcctga taaccctcca ctgaagataa 180
gatttattga caacaccgat cctgctggga ttgatcatca aattgctcaa ctaggacctg 240
aactggcaac tactcttgta attgtcattt ctaagagcgg aggcacacct gaaacccgca 300
atgg 304

<210> SEQ ID NO 632
<211> LENGTH: 273
<212> TYPE: DNA
<213> ORGANISM: Zea mays

<400> SEQUENCE: 632
ctttatgcaa atgaccggga gtctatctct gttactgtgc aagaggtaac tcctagagct 60
gttggagcac tgattgcact ttatgaacgt gctgtgggga tttatgcttc tttggtaaat 120
atcaatgcct atcatcagcc tggtgttgag gctgggaaaa aggcagcagg agaagtattg 180
gcccttcaga aaagggttct gactgtatta aaggaggcca tctgcgagaa ccctactgag 240
ccattgactc tagatgaaat tgcagatcgc tgc 273

<210> SEQ ID NO 633
<211> LENGTH: 322
<212> TYPE: DNA
<213> ORGANISM: Zea mays

<400> SEQUENCE: 633
ctatcatcaa cctggtgttg aggctgggaa aaaggcagca ggagaagtgt tggcccttca 60
gaaaagggtg ctgactgtat taaatgaggc aacctgcaag gacccttgtg agccattgac 120
tatagatgaa attgcagatc gctgccattg ccctgaagat attgagatga tctacaaaat 180
agtccagcac atggctgcta acgacagagc aatcatagca gaaggcagct gtggctctcc 240
tcgcagcgtt aaggtgtacc tcggtgaatg caatgtagac gaagacttgc aggccgcgta 300
ggttccgagc ctggatccgt gt 322

<210> SEQ ID NO 634
<211> LENGTH: 264
<212> TYPE: DNA
<213> ORGANISM: Zea mays

<400> SEQUENCE: 634

-continued atcaacctgg tgttgaggct gggaaaaagg cagcaggaga agtgttggcc cttcagaaaa 60
gggtgctgac tgtattaaat gaggcaacct gcaaggaccc ttgtgagcca ttgactatag 120
atgaaattgc agatcgctgc cattgccctg aagatattga gatgatctac aaaatagtcc 180
agcacatggc tgctaacgac agagcaatca tagcagaagg cagctgtggc tctcctcgca 240
gcgttaaggt gtacctcggt gaat 264

<210> SEQ ID NO 635
<211> LENGTH: 310
<212> TYPE: DNA
<213> ORGANISM: Zea mays

<400> SEQUENCE: 635
cggacgcgtg gtttgagtag atatttgcaa caacttgtca tggaatctct tggaaaagaa 60
ttcgacctgg atggcaaccg tgttaatcaa gggctaactg tatatggtaa caaaggaagc 120
actgaccagc atgcttacat tcagcagctg agagaaggtg tacaaaactt ctttgttacg 180
tttattgagg tcttgcgtga caggcctgct ggacatgatt ggagacttga acctggagtc 240
acgtgtggtg actatttgtt tgggatgttg cagggaaccc gttctgctct ttatgcaaat 300
gaccgggagt 310

<210> SEQ ID NO 636
<211> LENGTH: 295
<212> TYPE: DNA
<213> ORGANISM: Zea mays

<400> SEQUENCE: 636
gttgcttttg agtagatatt tgcaacaact tgtcatggaa tctcttggga aagaatttga 60
tctggatggc aaccgggtaa atcaagggct atctgtatat ggaaacaaag gaagtactga 120
ccagcacgct tacattcagc agctgagaga aggtgtacac aacttctttg ttacttttat 180
cgaggtcttg cgtgacaggc ctgctggtca tgattgggag cttgaacctg gagtcacatg 240
tggtgactat ttgtttggga tgttgcaggg aacacgttct gctctttatg caaat 295

<210> SEQ ID NO 637
<211> LENGTH: 293
<212> TYPE: DNA
<213> ORGANISM: Zea mays

<400> SEQUENCE: 637
acaaaggaag cactgaccag cacgcttaca ttcagcagct gagagaaggt gtacacaact 60
tctttgttac ttttatcgag gtcttgcgtg acaggcctgc tggtcatgat tgggagcttg 120
aacctggagt cacatgtggt gactatttgt ttaggatgtt gcagggaaca cgttctgctc 180
tttatgcaaa tgaccgtgaa tctatctctg ttactgtgca agaggtaact cctagagctg 240
ttggagcact ggttgcactt tatgaacgtg ctgtggggct ttatgcttct ttg 293

<210> SEQ ID NO 638
<211> LENGTH: 281
<212> TYPE: DNA
<213> ORGANISM: Zea mays

<400> SEQUENCE: 638
ggtgtacaaa acttctttgt tacgtttatt gaggtcttgc gtgacaggcc tgctggacat 60
gattgggagc ttgaacctgg agtcacgtgt ggtgactatt tgtttgggat gttgcaggga 120

-continued

```
acccgttctg ctctttatgc aaatgaccgg gagtctatct ctgttactgt gcaagaggta    180

actcctagag ctgttggagc actgattgca ctttatgaac gtgctgtggg gatttatgct    240

tctttggtaa atatcaatgc ctatcatcag cctggtgttg a                        281
```

<210> SEQ ID NO 639
<211> LENGTH: 263
<212> TYPE: DNA
<213> ORGANISM: Zea mays

<400> SEQUENCE: 639

```
ccggaacact gtggttaaag aaaatccagc agcattgctt gcattatgtt ggtattgggc     60

atcagaaggg ataggcaata aggatatggt tgtacttcct tacaaggata gtttgttgct    120

tttgagtaga tatttgcaac aacttgtcat ggaatctctt gggaaagaat ttgatctgga    180

tggcaaccgg gtaaatcaag ggctatctgt atatggaaac aaaggaagca ctgaccagca    240

cgcttacatt cagcagctga gag                                            263
```

<210> SEQ ID NO 640
<211> LENGTH: 300
<212> TYPE: DNA
<213> ORGANISM: Zea mays

<400> SEQUENCE: 640

```
cggacgcgtg gtgctagctg gtgcagcttt aatggatgag gaaacccgga acactgtggt     60

taaagaaaat ccagcagcat tgcttgcatt atgttgctat tgggcatcag aagggatagg    120

caataaggat atggttgtac ttccttacaa ggatagtttg ttgcttttga gtagatattt    180

gcaacaactt gtcatggaat ctcttgggaa agaatttgat ctggatggca accgggtaaa    240

tcaagggcta tctgtatatg gaaacaaagg aagcactgac cagcacgctt acattcagca    300
```

<210> SEQ ID NO 641
<211> LENGTH: 313
<212> TYPE: DNA
<213> ORGANISM: Zea mays

<400> SEQUENCE: 641

```
cccacgcgtc cgcccacgcg tccggggtat tgatatcaag gaaatgctag ctggtgcagc     60

tttaatggat gaagaaaccc ggaacactgt ggttaaagaa aatccagcag cattgcttgc    120

attatgttgg tattgggcat cagaagggat aggcaataag gatatggttg tacttcctta    180

caaggatagt ttgttgcttt tgagtagata tttgcaacaa cttgtcatgg aatctcttgg    240

gaaagaattt gatctggatg gcaaccgggt aaatcaaggg ctatctgtat atggaaacaa    300

aggaagtact gac                                                       313
```

<210> SEQ ID NO 642
<211> LENGTH: 298
<212> TYPE: DNA
<213> ORGANISM: Zea mays

<400> SEQUENCE: 642

```
gatagtttgt tacttttgag tagatatttg cctatccctt ccgatgccca ataccagcag     60

cattgcttgc attatgttgg tattgggcat cggaagggat aggcaaaaag gatatggttg    120

tgcttcctta taaggatagt ttgttacttt tgagtagata tttgcaacaa cttgtcatgg    180

gatctcttgg aaaagaattc gacctggatg gcaaccgtgt taaacaaggg ctaactgtat    240

atggtaacaa aggaagcact gaccagcatg cttacattca gcagctgaga gaaggtgt      298
```

-continued

<210> SEQ ID NO 643
<211> LENGTH: 274
<212> TYPE: DNA
<213> ORGANISM: Zea mays

<400> SEQUENCE: 643
gaggtcttgc gtgacaggcc tgctggtcat gattgggagc ttgaacctgg agtcacgtgt 60
ggtgactatt tgtttgggat gttgcaggga acccgttctg ctctttatgc aaatgaccgg 120
gagtctatct ctgttacgtg caagaggtaa ctcctagagc tgttggagca ctgatttcac 180
tttatgaacg tgctgtgggg atttatgctt ctttggtaaa tatcaatgcc tatcatcagc 240
ctggtgttga ggctgggaaa aaggcagcag gaga 274

<210> SEQ ID NO 644
<211> LENGTH: 284
<212> TYPE: DNA
<213> ORGANISM: Zea mays

<400> SEQUENCE: 644
cagctgcatt gcagggtatt gatatcaagg aaatgctagc tggtgcagct ttaatggatg 60
aggaaacccg gaacactgtg gttaaagaaa atccagcagc attgcttgca ttatgttggt 120
attgggcatc agaagggata ggcaataagg atatggttgt acttccttac aaggatagtt 180
tgttgctttt gagtagatat ttgcaacaac ttgtcatgga atctcttggg aaagaatttg 240
atctggatgg caaccgggta aatcaaggct atctgtatat ggaa 284

<210> SEQ ID NO 645
<211> LENGTH: 306
<212> TYPE: DNA
<213> ORGANISM: Zea mays

<400> SEQUENCE: 645
cggacgcgtg gtgctagctg gtgcagcttt aatggatgag gaaacccgga acactgtggt 60
taaagaaaat ccagcagcat tgcttgcatt atactggtat tgggcatcag aagggatagg 120
caataaggat atggttgtac ttccttacaa ggatagtttg ttgcttttga gtagatattt 180
gcaacaactt gtcatggaat ctcttgggaa agaatttgat ctggatggca accgggtaaa 240
tcaagggcta tctgtatatg gaaacaaagg aagcactgac cagcacgctt acattcagca 300
gctgag 306

<210> SEQ ID NO 646
<211> LENGTH: 271
<212> TYPE: DNA
<213> ORGANISM: Zea mays

<400> SEQUENCE: 646
cccacgcgtc cgcccacgcg tccgcccacg cgtccgcgag gtcttgcgtg acaggcctgc 60
tggtcatgaa tgggagcttg aacctggagt cacatgtggt gactatttgt ttgggatgtt 120
gcagggaaca cgttctgctc tttatgcaaa tgaccgtgaa tctatctctg ttactgtgca 180
agaggtaact cctagagctg ttggagcact ggttgcactt tatgaacgtg ctgtggggct 240
ttatgcttct ttggtaaata tcaatgccta t 271

<210> SEQ ID NO 647
<211> LENGTH: 228
<212> TYPE: DNA

-continued

<213> ORGANISM: Zea mays

<400> SEQUENCE: 647
cggacgcgtg ggggtgtaca caacttcttt gttacgttta ttgaggtctt gcgtgacagg 60
cctgctggtc atgattggga gcttgaacct ggagtcacgt gtggtgacta tttgtttggg 120
atgttgcagg gaacccgttc tgctctttat gcaaatgacc gggagtctat ctctgttact 180
gtgcaagagg taactcctag agctgttgga gcactgattg cactttat 228

<210> SEQ ID NO 648
<211> LENGTH: 275
<212> TYPE: DNA
<213> ORGANISM: Zea mays

<400> SEQUENCE: 648
tggtgtacac aacttctttg ttacttttat cgaggtcttg cgtgacaggc ctgctggtca 60
tgattgggag cttgaacctg gagtcacatg tggtgactat ttgtttggga tgttgcaggg 120
aacacgttct gctctttatg caaatgaccg tgaatctatc tctgttactg tgcaagaggt 180
aactcctaga gctgttggag cactggttgc actttatgaa cgtgctgtgg ggctttatgc 240
ttcttggtaa atatcaatgc tatcatcaac tggtg 275

<210> SEQ ID NO 649
<211> LENGTH: 203
<212> TYPE: DNA
<213> ORGANISM: Zea mays

<400> SEQUENCE: 649
tgttgtactt ccttacaagg atagtttgtt gcttttgagt agatatttgc aacaacttgt 60
catggaatct cttgggaaag aatttgatct ggatggcaac cgggtaaatc aagggctatc 120
tgtatatgga aacaaaggaa gcactgacca gcacgcttac attcagcagc tgagagaagg 180
tgacacaact tctttgttac ttt 203

<210> SEQ ID NO 650
<211> LENGTH: 285
<212> TYPE: DNA
<213> ORGANISM: Zea mays
<220> FEATURE:
<223> OTHER INFORMATION: unsure at all n locations

<400> SEQUENCE: 650
gttgtcaggg tattgatatc aaggaaatgc tagctggtgc agctttaatg gatgaagaaa 60
cccggaacac tgtggttaaa gaaaatccag cagcattgct tgcattatgt tggtattggg 120
catcagaagg gataggcaat aaggatatgg ntgtacttcc ttacaaggat agtttgttgc 180
ttttgagtag atatttgcaa caacttgtca tggaatctct tgggaagaat tgatctggat 240
gcaaccggta aatcaaggct atctgatatg aaacaaagaa gactg 285

<210> SEQ ID NO 651
<211> LENGTH: 267
<212> TYPE: DNA
<213> ORGANISM: Zea mays

<400> SEQUENCE: 651
tatcttgctg tcaagccatc caccccgtat gatactaccg tgctgccgaa gtgtaattac 60
tcagttgttt ttgacatgcc aattgctgag ttctgacttg gcaaggttga gcataagtct 120
ttcttcattt tgggagttat cacagagcca gtttggcagt gctgtagttt tggttttacc 180

-continued tactctttgt agaagaaaag tgaagagtgg atattatgga acaaaatata tacctacggc 240
agcacgcagc atgatgaaac atattta 267

<210> SEQ ID NO 652
<211> LENGTH: 240
<212> TYPE: DNA
<213> ORGANISM: Zea mays

<400> SEQUENCE: 652
gtctcccccg accggcgatc gctatcgact tgtagcggaa gccatggcgt cggcagcgct 60
aatctgcggc acggagcagt ggaaggccct ccaggcgcac gtcggcgcga ttcagaagac 120
gcacctgcgc gacctgatgg ccgacgccga ccgatgcaag gcaatgacgg ctgagtatga 180
agggatcttt ctggattact cgagacagca ggcgactggt gaaacatgga gaagccctta 240

<210> SEQ ID NO 653
<211> LENGTH: 292
<212> TYPE: DNA
<213> ORGANISM: Zea mays

<400> SEQUENCE: 653
caaaatccgg aggaactccc aggaggcgaa aagcagatcc gtctcccccg agccccgacc 60
ggcgatcgct atcgacttgt agcggaagcc atggcgtcgg cagcgctaat ctgcggcacg 120
gagcagtgga aggccctcca ggcgcacgtc ggcgcgattc agaagacgca cctgcgcgac 180
ctgatggccg acgccgaccg atgcaaggca atgacggctg agtatgaagg gatctttctg 240
gattactcga gacagcaggc gactggtgaa acatggagaa gctcttaaat tg 292

<210> SEQ ID NO 654
<211> LENGTH: 320
<212> TYPE: DNA
<213> ORGANISM: Zea mays

<400> SEQUENCE: 654
ggcaagcaaa cgagcggcgg gacggctagc ccgcaataca aaatccggag gaactcccag 60
gaggcgaaaa gcagatccgt ctcccccgag ccccgaccgg cgatcgctat cgacttgtag 120
cggaagccat ggcgtcggca gcgctaatct gcggcacgga gcagtggaag gccctccagg 180
cgcacgtcgg cgcgattcag aagacgcacc tgcgcgacct gatggccgac gccgaccgat 240
gcaaggcaat gacggctgag tatgaaggga tctttctgga ttactcgaga cagcaggcga 300
ctggtgaaac catggagaag 320

<210> SEQ ID NO 655
<211> LENGTH: 278
<212> TYPE: DNA
<213> ORGANISM: Zea mays

<400> SEQUENCE: 655
caccgtcttc cggccgtcca ccgtttccag cacacagggt aaaggcaagc aaacgagcgt 60
ggggacggct agcccgcaat acaaaatccg gaggaactct caggaggcga aaagcagatc 120
tgtctccccc gaccggcgat cgctatcgac ttgtagcgga agccatggcg tcggcagcgc 180
taatctgcgg cacggagcag tggaaggcac tccaggcgca cgtcggcgcg attcagaaga 240
cgcaactgcg cgacctgatg gccgacgccg accgatgc 278

<210> SEQ ID NO 656

-continued

<211> LENGTH: 105
<212> TYPE: DNA
<213> ORGANISM: Zea mays

<400> SEQUENCE: 656
caaaatccgg aggaactccc aggaggcgaa aagcagatcc gtctccccg agccccgacc 60 ggcgatcgct atcgacttgt agcggaagcc atggcgtcgg cagcg 105

<210> SEQ ID NO 657
<211> LENGTH: 267
<212> TYPE: DNA
<213> ORGANISM: Zea mays

<400> SEQUENCE: 657
acccgatcaa gctgtgggag cgctacgtcg agtggctcta ccagcacaag gagctcggca 60
tcttcgtcga cgtcagccgg atggggttca cggaggagtt cctgcggcag atggagccgc 120
ggatgcagca ggccttcgtc gacatgcggg agctcgagaa gggcgccatc gccaaccccg 180
acgagggtcg catggtgggc cactactggc tccgcgaccc ggccctcgct cccaactcct 240
tcctccggaa caagatcgag accgcac 267

<210> SEQ ID NO 658
<211> LENGTH: 325
<212> TYPE: DNA
<213> ORGANISM: Zea mays

<400> SEQUENCE: 658
tgccatattc tcaggcactt gagaagttgg caccacatat acagcagctt agcatggaga 60
gtaacgggaa gggtgtttcc attgatggcg cccaactttc ctttgagaca ggtgaaattg 120
attttggtga acctcgaact aatggccagc acagcttcta tcaattaatc catcagggaa 180
gggttatccc ttgcgacttt attggtgttg ttaaaagtca gcagcctgtt tacttgaaag 240
gggaaactgt gagtaatcat gatgagctta tgtccaattt ctttgcccaa cctgatgctc 300
ttgcttatgg aaagactcct gaaca 325

<210> SEQ ID NO 659
<211> LENGTH: 316
<212> TYPE: DNA
<213> ORGANISM: Zea mays

<400> SEQUENCE: 659
tccagctagg gcaatattgc catattctca ggcacttgag aagttggcac cacatataca 60
gcagcttagc atggagagta acgggaaggg tgtttccatt gatggcgccc aactttcctt 120
tgagacaagt gaaattgatt ttggtgaacc tggaactaat ggccagcaca gcttctatca 180
attaatccat cagggaaggg ttatcccttg cgactttatt ggtgttgtta aaagtcagca 240
gcctgtttac ttgaaagggg aaactgtgag taatcatgat gagcttatgt ccaatttctt 300
tgcccaacct gatgct 316

<210> SEQ ID NO 660
<211> LENGTH: 300
<212> TYPE: DNA
<213> ORGANISM: Zea mays
<220> FEATURE:
<223> OTHER INFORMATION: unsure at all n locations

<400> SEQUENCE: 660
atcaaagaca ttcacaacag ctgnaaacaa tgttaaatgc tcgaactctt aaggagtgga 60

-continued tcgtttcttc tcttgggcca caggctgttg ccaaacatat gattgctgtc agcactaatc 120
ttaagcttgt gaaggagttt ggaattgacc caaacaatgc ttttgccttt tgggactggg 180
ttggcggccg ttatagtgtt tgcagtgctg ttggcgttct gccattatct cttcagtatg 240
gctttccaat tgtccagaaa tttttggagg gagcttccag tatcgacaac cacttctact 300

<210> SEQ ID NO 661
<211> LENGTH: 334
<212> TYPE: DNA
<213> ORGANISM: Zea mays

<400> SEQUENCE: 661
ctcatgatga gcttatgtcc aatttctttg cccaacctga tgctcttgct tatggaaaga 60
ctcctgaaca gttgcacagt gagaaagttc cagataatct tatccctcat aagactttta 120
agggcaaccg gccatcacta agtttgcttc tgcctacact atctgcatat gaggttggac 180
agcttttatc catctatgag caccggattg cagttcaggg cttcatatgg ggaattaact 240
catttgacca ctagggagtg gagctaggga agtcactcgc ttctcaagtg aggaaacagc 300
tgcatggaac ccggatggaa ggacacctgt tgag 334

<210> SEQ ID NO 662
<211> LENGTH: 279
<212> TYPE: DNA
<213> ORGANISM: Zea mays

<400> SEQUENCE: 662
ggtgaacctg gaactaatgg ccagcacagc ttctatcaat taatccatca gggaagggtt 60
atcccttgcg actttattgg tgttgttaaa agtcagcagc ctgtttactt gaaaggggaa 120
actgtgagta atcatgatga gcttatgtcc aatttctttg cccaacctga tgctcttgct 180
tatggaaaga ctcctgaaca gttgcacagt gagaaagttc cagaaaatct tatccctcat 240
aagactttta agggcaaccg gccatcacta agtttgctt 279

<210> SEQ ID NO 663
<211> LENGTH: 274
<212> TYPE: DNA
<213> ORGANISM: Zea mays

<400> SEQUENCE: 663
tgcaaatgtt gatccagttg acgttgcacg aagcattaaa gatttggatc cagaaaccac 60
tctggtggtg gttgtatcaa agacattcac aacagcggaa acaatgttaa atgctcgaac 120
tcttaaggag tggatcgttt cttctcttgg gccacaggct gttgccaaac atatgattgc 180
tgtcagcact aatcttaagc ttgtgaagga gtttggaatt gacccaaaca atgcttttgc 240
cttttgggac tgggttggcg gccgttatag tgtt 274

<210> SEQ ID NO 664
<211> LENGTH: 283
<212> TYPE: DNA
<213> ORGANISM: Zea mays
<220> FEATURE:
<223> OTHER INFORMATION: unsure at all n locations

<400> SEQUENCE: 664
gccacaggct gttgccaaac atatgattgc tgtcagcact aatcttaagc ttgtgaagga 60
gtttggaatt ganccaaaca atgcttntgc ctnttgggac tgggttggcg gccgttatag 120

-continued

```
tgtttgcagt gctgttggcg ttctgccatt atctcttcag tatggcttgc caattgtcca    180

gaaatttttg gagggagctt ccagcattga caaccactnc tactcatctt catgtgagaa    240

naatataccn gtacntcttg gtgctgagtg tgtggaatgt ttc                      283
```

<210> SEQ ID NO 665
<211> LENGTH: 269
<212> TYPE: DNA
<213> ORGANISM: Zea mays

<400> SEQUENCE: 665

```
gccacaggct gttgccaaac atatgattgc tgtcagcact aatcttaagc ttgtgaagga     60

gtttggaatt gacccaaaca atgcttttgc cttttgggac tgggttggcg gccgttatag    120

tgtttgcagt gctgttggcg ttctgccatt atctcttcag tatggctttc caattgtcca    180

gaaatttttg gagggagctt ccagcattga caaccacttc tactcatctt catttgagaa    240

aaatataccg tacttcttgg tttgctgag                                      269
```

<210> SEQ ID NO 666
<211> LENGTH: 299
<212> TYPE: DNA
<213> ORGANISM: Zea mays

<400> SEQUENCE: 666

```
agaagtggat catgggttgg agcaactgga aaaccgttga caaatgttgt gtcagttgga     60

ataggtggta gctttcttgg ccctctattt gtgcatactg cactccagac cgatccagaa    120

gcagcagaat gtgcaaaagg ccggcaactg agattccttg caaatgttga tccagttgac    180

gttgcacgaa gcattaaaga tttggatcca gaaaccactc tggtggtggt tgtatcaaag    240

acattcacaa cagctgaaac aatgttaaat gctcgaactc ttaaggagtg gatcgtttc     299
```

<210> SEQ ID NO 667
<211> LENGTH: 276
<212> TYPE: DNA
<213> ORGANISM: Zea mays

<400> SEQUENCE: 667

```
ttggaattga cccaaacaat gcttttgcct tttgggactg ggttggcggc cgttatagtg     60

tttgcagtgc tgttggcgtt ctgccattat ctcttcagta tggctttcca attgtccaga    120

aatttttgga gggagcttcc agcattgaca accacttcta ctcatcttca tttgagaaaa    180

atatacctgt acttcttggt ttgctgagtg tgtggaatgt tcatttcttg gttatccagc    240

tagggcaata tgccatatct caggcacttg agaagt                              276
```

<210> SEQ ID NO 668
<211> LENGTH: 255
<212> TYPE: DNA
<213> ORGANISM: Zea mays

<400> SEQUENCE: 668

```
ctccaagaga tgcagtcata aacagtgatg ggtgactgt ggtccctgag gtttggagtg      60

ttaaagataa aatcaagcag ttttcagaga cttttagaag tggatcatgg gttggagcaa    120

ctggaaaacc gttgacaaat gttgtgtcgg ttggaatagg tggtagcttt cttggccctc    180

tatttgtgca tactgcactc cagaccgatc cagaagcagc agaatgtgca aaaggccggc    240

aactgagatt ccttg                                                     255
```

-continued

<210> SEQ ID NO 669
<211> LENGTH: 233
<212> TYPE: DNA
<213> ORGANISM: Zea mays

<400> SEQUENCE: 669
gcacgaggtt ctgccattat ctcttcagta tggctttcca attgtccaga aatttttgga 60
gggagcttcc agcattgaca accacttcta ctcatcttca tttgagagaa atatacctgt 120
acttcttggt ttgctgagtg tgtggaatgt ttcatttctt ggttatccag ctagggcaat 180
attgtcatat tctcaggcac ttgagaagtt ggcaccacat atacagcagc tta 233

<210> SEQ ID NO 670
<211> LENGTH: 191
<212> TYPE: DNA
<213> ORGANISM: Zea mays
<220> FEATURE:
<223> OTHER INFORMATION: unsure at all n locations

<400> SEQUENCE: 670
aatttctttg cccaacctga tgctcttgct tatggaaaga ctcctgaaca gttgcacagt 60
gagaaagttc cagaaaatct tatccctcat aagactttta agggcaaccg gccatcacta 120
agtttgcttc tgcctacact atccgcatat gaggtggaca gttttaancc tctatngggc 180
ncggtttnan t 191

<210> SEQ ID NO 671
<211> LENGTH: 115
<212> TYPE: DNA
<213> ORGANISM: Zea mays

<400> SEQUENCE: 671
gtggtagctt tcttggccct ctatttgtgc atactgcact ccagaccgat gcagaagcag 60
cagaatgtgc aaaaggccgg caactgagat tccttgcaaa tgttgatcca gttga 115

<210> SEQ ID NO 672
<211> LENGTH: 113
<212> TYPE: DNA
<213> ORGANISM: Zea mays
<220> FEATURE:
<223> OTHER INFORMATION: unsure at all n locations

<400> SEQUENCE: 672
ggagtttgga attgacccaa acaatgcttt tgccttttgg gactgggttg gcggccgtta 60
tagtgtttgc agtgctgttg gcgntctgcc attatctctt cagtatggct ttc 113

<210> SEQ ID NO 673
<211> LENGTH: 122
<212> TYPE: DNA
<213> ORGANISM: Zea mays

<400> SEQUENCE: 673
tatcttatcc ctcataagac ttttaagggc aaccggccat cactaagttt gcttctgcct 60
acactatctg catacgaggt tacgacagct tttatccatc tatgagcacc ggattgcagt 120
tc 122

<210> SEQ ID NO 674
<211> LENGTH: 443
<212> TYPE: DNA
<213> ORGANISM: Zea mays
<220> FEATURE:

<223> OTHER INFORMATION: unsure at all n locations

<400> SEQUENCE: 674
agtctatctc tgttactgtg caagaggtaa ctcctanagc tgttggagna ctgattgcac 60
tttatgaacg tgctgtgggg atttatgctt ctttggtaaa tatcaatgcc tatcatcagc 120
ctggtgttga ggctgggaaa aaggcancan gagaagtatt ggcccttcag aaaagggttc 180
tgactgtatt aaaggaggcc atctgcnaga accctactga gccattgact ctagatgaaa 240
ttgcagatcg ctgacattgc cctgaagata ttganatgat ctacanaata atccancaca 300
tggcttctaa cgacagatca cttatagcag aaggcatctg cngctttctt ngcagtgtta 360
aggtgtacct nggtgaaatg caattttgga ccnaantatg caggccggga tagattctgn 420
gtcnggancn aagtaacatt ntt 443

<210> SEQ ID NO 675
<211> LENGTH: 420
<212> TYPE: DNA
<213> ORGANISM: Zea mays

<400> SEQUENCE: 675
ctcttgggaa agaatttgat ctggatggca accgggtaaa tcaagggcta tgtgtagatg 60
gaaacaaagg aagcactgac cagcacgctt acattcagca gctgagagaa ggtgtacaca 120
acttctttgt tacttttatc gaggtcttgc gtgacaggcc tgctggtcat gattgggagc 180
ttgaacctgg agtcacatgt ggtgactatt tgtttgggat gttgcaggga acacgttctg 240
ctctttatgc aaatgaccgt gaatctatct ctgttactgt gcaagaggta actcctagag 300
ctgttggagc actggttgca ctttatgaac gtgctgtggg gctttatgct tctttggtaa 360
atatcaatgc ctatcatcaa cctggtgttg aggctgggaa aaaggcagca ggagaagtgt 420

<210> SEQ ID NO 676
<211> LENGTH: 349
<212> TYPE: DNA
<213> ORGANISM: Zea mays

<400> SEQUENCE: 676
tgcggtcaag caatcaaccc cgtatgatac aaccgtgctg ccgaaggtgt aattacccag 60
ttgtttttga catgccaatt gctgagttct gacttggcaa ggttgagcat aagtctttct 120
tcatttggga gttatcacag agccagtttg gcagtgctgt agttttggtt ttacctactc 180
tttgtagaag aaaagtgaag agtggatatt atggaacaaa atatatacct acggcagcac 240
gcagcatgat gaaacatatt taaaaaattt gggtgctcta ccacatgccc gtggaataaa 300
acggatgtaa actcagtgca aaaaaaaaaa aaaaaaaaaa aaacaaaaa 349

<210> SEQ ID NO 677
<211> LENGTH: 376
<212> TYPE: DNA
<213> ORGANISM: Zea mays
<220> FEATURE:
<223> OTHER INFORMATION: unsure at all n locations

<400> SEQUENCE: 677
aacgagcggc gggacggcta gcccgcaata caaaatccgg aggaactccc aggaggcgaa 60
aagcagatcc gtctcccccg agccccgacc ggcgatcgct atcgacttgt agcggaagcc 120
atggcgtcgg cagcgctaat ctgcggcacg gagcagtgga aggccctcca ggcgcacgtc 180
ggcgcgattc agaagacgca cctgcgcgac ctgatggccg acgccgaccg atgcaaggca 240

-continued

```
atgacggctg agtatgaagg gatctttctg gattactcga gacagcaggc gactggtgaa    300

accctggaga agctccttaa atgggctgac gctgcgaagc tcaaggagaa ngatgagaag    360

atgtttaaag gtgaaa                                                    376
```

<210> SEQ ID NO 678
<211> LENGTH: 451
<212> TYPE: DNA
<213> ORGANISM: Zea mays

<400> SEQUENCE: 678

```
ccgtatatag tgtttgcagt gctgttggcg ttctgccatt atctcttcag tatggctttc     60

caattgtcca gaaatttttg gagggagctt ccagcattga caaccacttc tactcatctt    120

catttgagaa aaatatacct gtacttcttg gtttgctgag tgtgtggaat gtttcatttc    180

ttggttatcc agctagggca atattgccat attctcaggc acttgagaag ttggcaccac    240

atatacagca gcttagcatg gagagtaacg ggaagggtgt ttccattgat ggcgcccaac    300

tttcctttga gacaggtgaa attgattttg gtgaacctgg aactaatggc cagcacagct    360

tctatcaatt aatccatcaa ggaagggtta tcccttgcga ctttattggt gttgttaaaa    420

gtcagcagcc tgtttacttg aaaagggaaa c                                   451
```

<210> SEQ ID NO 679
<211> LENGTH: 453
<212> TYPE: DNA
<213> ORGANISM: Zea mays

<400> SEQUENCE: 679

```
gtcatgcact ggagacgttg gcactacata tacagcagct tatcatggat agtaacgggg     60

ggggtgtttc cattgatggc gcccaacttt cctttgagac aggtgaaatt gattttggtg    120

aacctggaac taatggccag cacagcttct atcaattaat ccatcaggga agggttatcc    180

cttgcgactt tattggtgtt gttaaaagtc agcagcctgt ttacttgaaa ggggaaactg    240

tgagtaatca tgatgagctt atgtccaatt tctttgccca acctgatgca cttgcttatg    300

gaaagactcc tgaacagttg cacagtgaga aagttccaga aaatcttatc cctcataaga    360

cttttaaggg caaccggcca tcactaagtt tgcttctgcc tacactatcc gcatatgagg    420

ttggacagct tttatccatc tatgagcacc gga                                 453
```

<210> SEQ ID NO 680
<211> LENGTH: 419
<212> TYPE: DNA
<213> ORGANISM: Zea mays

<400> SEQUENCE: 680

```
aaaatcaagc agttttcaga gacttttaga agtggatcat gggttggagc aactggaaaa     60

ccgttgacaa atgttgtgtc agttggaata ggtggtagct ttcttggccc tctatttgtg    120

catactgcac tccagaccga tccagaagca gcagaatgtg caaaaggccg gcaactgaga    180

ttccttgcaa atgttgatcc agttgacgtt gcacgaagca ttaaagattt ggatccagaa    240

accactctgg tggtggttgt atcaaagaca ttcacaacag ctgaaacaat gttaaatgct    300

cgaactctta aggagtggat cgtttcttct cttgggccac aggctgttgc caaacatatg    360

attgctgtca gcactaatct taagcttgtg aaggagtttg gaattgaccc aaacaatgc     419
```

<210> SEQ ID NO 681

-continued

<211> LENGTH: 426
<212> TYPE: DNA
<213> ORGANISM: Zea mays

<400> SEQUENCE: 681
ctcgcgggcc gacacacgcc tctacatttc ttggttatac agctagggca atattgccat 60
attctcaggc acttgagaag ttggcaccac atatacagca gcttagcatg gagagtaacg 120
ggaagggtgt ttccattgat ggcgcccaac tttcctttga gacaggtgaa attgattttg 180
gtgaacctgg aactaatggc cagcacagct tctatcaatt aatccatcag ggaagggtta 240
tcccttgcga ctttattggt gttgttaaaa gtcagcagcc tgtttacttg aaaggggaaa 300
ctgtgagtaa tcatgatgag cttatgtcca atttctttgc ccaacctgat gctcttgctt 360
atggaaagac tcctgaacag ttgcacagtg agaaagttcc agaaaatctt atccctcata 420
agactt 426

<210> SEQ ID NO 682
<211> LENGTH: 323
<212> TYPE: DNA
<213> ORGANISM: Zea mays

<400> SEQUENCE: 682
gcgaagctca aggagaagat tgagaagatg tttaaaggtg aaaagataaa tagcacagag 60
aacaggtcag tgcttcatgt agctctgagg gctccaagag atgcagtcat aaacagtgat 120
ggggtgaatg tggtccctga ggttcggagt gttaaagata aaatcaagca gttttcagag 180
acttttagaa gtggatcatg ggttggagca actggaaaac cgttgacaaa tgttgtgtcg 240
gttggaatag gtggtagctt tcttggccct ctatttgtgc atactgcact ccagaccgat 300
ccagaagcag cagaatgtgc aaa 323

<210> SEQ ID NO 683
<211> LENGTH: 422
<212> TYPE: DNA
<213> ORGANISM: Zea mays
<220> FEATURE:
<223> OTHER INFORMATION: unsure at all n locations

<400> SEQUENCE: 683
ccaaaactga gtctcattac aaatgtngat cnanttgacg ttgcacnaan cattaaagat 60
ttggntccag aaaccacccn ggtggtggtt gtancaaaga cattcacaac agcggaaaca 120
atgttaaatg ctcgaactct taaggagtgg atcgtttctt ctcttgggcc acaggctgtt 180
gccaaacata tgattgctgt cagcactaat cttaagcttg tgaaggagtt tggaattgac 240
ccaaacaatg cttttgcctt ttgggactgg gttggcggcc gttatagtgt ttgcagtgct 300
gttggcgttc tgccattact cttcagtatg gctttccaat tgtccagaaa tttttggagg 360
gaacttccag ncattgacaa acaacttcna ntcnncctnc attttgagaa aaatatacct 420
gt 422

<210> SEQ ID NO 684
<211> LENGTH: 122
<212> TYPE: DNA
<213> ORGANISM: Glycine max
<220> FEATURE:
<223> OTHER INFORMATION: unsure at all n locations

<400> SEQUENCE: 684
ggtgagtaac catgatgagc taatgtccaa ctattttgca cagtctgatg cccttgcata 60

-continued tnnnaagaca gcagagcagc tgcnaaaggn caatgtttcc ccgcacctta ttccacacaa 120
ga 122

<210> SEQ ID NO 685
<211> LENGTH: 234
<212> TYPE: DNA
<213> ORGANISM: Glycine max

<400> SEQUENCE: 685
tgataatcct ccactcaaga taacatacat ggacaacacg gatcctgctg gaattgatca 60
tcagattgca caacttgggc ctgagctagc ttcaacactt gtgattgtga tatcaaagag 120
tggaggtact cctgagacca gaaatggttt attggaagtg cagaaggcct ttcgtgaagc 180
aggcttggat tttcctaaac agggtgttgc tataacacaa gaaaattctt tgtt 234

<210> SEQ ID NO 686
<211> LENGTH: 205
<212> TYPE: DNA
<213> ORGANISM: Glycine max
<220> FEATURE:
<223> OTHER INFORMATION: unsure at all n locations

<400> SEQUENCE: 686
ttcctatgtt tgatnggnnn ggaggtagaa cgtcagnnat gtctgcagtt ggcctgcttc 60
cagcagccct tccagggatt ganatnanag aaatgcttgc cggtgcatca ttgatggatg 120
angctaanag gagtactgtg nnaaggaata accctgcagc tctgctggct ttatgttggt 180
attgggctac agatggtgna ggatc 205

<210> SEQ ID NO 687
<211> LENGTH: 223
<212> TYPE: DNA
<213> ORGANISM: Glycine max

<400> SEQUENCE: 687
tgcagggcgt tgctataact caagaaaatt ctttgctgga taacactgca agaattgagg 60
gttggttagc tagatttcca atgtttgact gggtgggagg tagaacatca gagatgtctg 120
cagtgggcct gcttccagca gcccttcaga gcattgacat aagagaaatg cttgctggtg 180
cagcattaat ggatgaggcg aataggagta ctgtgataag gaa 223

<210> SEQ ID NO 688
<211> LENGTH: 218
<212> TYPE: DNA
<213> ORGANISM: Glycine max

<400> SEQUENCE: 688
tgcagggcgt tgctataact caagaaaatt ctttgctgga taagactgca agaattgacg 60
gttggttagc tagatttcca atgtttgact gggtgggagg tagaacatca gagatgtctg 120
cagtgggcct gcttccagca gcccttcaga gcattgacat aagagaaatg cttgctggtg 180
cagcattaat ggatgaggcg aataggagta ctgtgata 218

<210> SEQ ID NO 689
<211> LENGTH: 274
<212> TYPE: DNA
<213> ORGANISM: Glycine max

<400> SEQUENCE: 689

-continued

```
gtgctacgtg atagacctcc tggtcatgat tgggaacttg aacctggtgt ccacatgcgg     60

tgactacttg tttggtatgc tacagggaac aagatcagct ctgtatgcca ataaccgaga    120

gtccatcaca gttactgtac aagaagtgac acctagaaca gttggtgctc ttattgcact    180

ctatgaacga gcagtaggaa tttatgcctc ccttgtcaac ataaatgctt atcatcaacc    240

aggtgtggaa gctggtaaaa aagcagcagg tgaa                                274


<210> SEQ ID NO 690
<211> LENGTH: 257
<212> TYPE: DNA
<213> ORGANISM: Glycine max

<400> SEQUENCE: 690

aacaattgag ggaaggtgta cacaatttct ttgtaacatt cattgaggtg ctacgtgata     60

gacctcctgg tcatgattgc gaacttgaac ctggtgtcac atgcggtgac tacttgtttg    120

gtatgctaca gggaacaaga tcagctctgt atgccaataa ccgagagtcc atcacagtta    180

ctgtacaaga agtgacacct agaactgttg gtgctcttat tgcactctat gaacgagcag    240

taggaattta tgcctcc                                                   257


<210> SEQ ID NO 691
<211> LENGTH: 251
<212> TYPE: DNA
<213> ORGANISM: Glycine max
<220> FEATURE:
<223> OTHER INFORMATION: unsure at all n locations

<400> SEQUENCE: 691

gattgggaac ttgaacctgg tgtcacatgt ggtgactact tgtttggtat gctacaggga     60

acaaggtcgg ctttgtatgc caataaccga gagtccatca cagttactgt acaagaaggg    120

acaccaagaa cagttggtgc tcttattggg ctctatgaac gagcagtagg aatttatgcc    180

tcccctgtca acataaatgc ttatctnaac ctgcgtgtgg aagntgacga natnagcagc    240

agngaagtac t                                                         251


<210> SEQ ID NO 692
<211> LENGTH: 245
<212> TYPE: DNA
<213> ORGANISM: Glycine max
<220> FEATURE:
<223> OTHER INFORMATION: unsure at all n locations

<400> SEQUENCE: 692

atcctgcanc tttgcnggct ttatgttggt attgggctac agatggtgta ngatcaaaag     60

atatggttat ccttccatat aaggacagct nganattatn tagtagatac ttgcaacagt    120

nggtcatgga atctctaggc aaggagtttg actgaatggt aatcgggtta atcaaggaat    180

tagtgtctat ggaaataaag gaagcacaga tcagcatgcc tacatccaac aactgaggga    240

aggtg                                                                245


<210> SEQ ID NO 693
<211> LENGTH: 270
<212> TYPE: DNA
<213> ORGANISM: Glycine max

<400> SEQUENCE: 693

cagcatgcct acattcagca actgagggaa ggtgtgcaca atttttttgt gacattcatt     60

gaggtgctac gcgatagacc acctggtcat gattgggagc ttgaaccagg tgtcacatgt    120
```

-continued

```
ggtgactacc tgtttggtat gctacaggga acaaggtcag ccctgtatgc caataaccgt    180

gaatccatca ctgtcacagt gcaagaagtg acacccagat cagttggtgc ccttgtagcc    240

ctttatgaac gggccgttgg aatatatgct                                     270
```

<210> SEQ ID NO 694
<211> LENGTH: 259
<212> TYPE: DNA
<213> ORGANISM: Glycine max

<400> SEQUENCE: 694

```
ggagtttgac ttgaatggta atcgggttaa tcaaggaatt agtgtctatg gaaataaagg     60

aagcacagat cagcatgcct acattcaaca actgagggaa ggtgtgcaca atttttttgt    120

gacattcatt gaggtgctac gcgatagacc acctggtcat gattgggagc ttgaaccagg    180

tgtcacatgt ggtgactacc tgtttggtat gctacaggga acaaggtcag ccctgtatgc    240

caataaccgt gaatccatc                                                 259
```

<210> SEQ ID NO 695
<211> LENGTH: 227
<212> TYPE: DNA
<213> ORGANISM: Glycine max

<400> SEQUENCE: 695

```
atagaagtac tgtgttaagg aataaccctg cagctctgct ggctttatgt tggtattggg     60

ctacagatgg tgtaggatcc aaggatatgg ttattcttcc gtacaaggac agcctgttat    120

tattcagtag atacttgcag cagctggtca tggaatctct aggcaaggag tttgacttgg    180

atggtaatcg ggttaatcaa ggaattagtg tctatggaaa caaagga                  227
```

<210> SEQ ID NO 696
<211> LENGTH: 263
<212> TYPE: DNA
<213> ORGANISM: Glycine max
<220> FEATURE:
<223> OTHER INFORMATION: unsure at all n locations

<400> SEQUENCE: 696

```
ttcagggcat tgatattaga gaaatgcttg cnggtgcatc attgatggat gaggctaata     60

gaagtactgt gttaaggaat aaccctgcag ctntgctggc ttangnaagg tattgggcta    120

cagatggtgt aggaccaagg anatggttat tcttccgtac aaggacagcc tngtattatt    180

cagtagatac ntgcagcagc tggtcatgga atctctaggc aaggagtttg acttggatgg    240

taatcgggtt aatcaaggaa tag                                            263
```

<210> SEQ ID NO 697
<211> LENGTH: 266
<212> TYPE: DNA
<213> ORGANISM: Glycine max

<400> SEQUENCE: 697

```
gcgcgatcgc gaatcccgat gagagtcgca tggtgggaca ctattggctg agggacccta     60

agcgtgcgcc caactcgttc cttaaaacgc agattgagaa cactctcgac gctgtttgca    120

agttcgctaa cgacgtcgtt agtggtaaga ttaagcctcc ttcgtctccg gagggtcgat    180

ttactcaaat attgtctgtg ggaattggag gttctgctct tggaccacag tttgttgcag    240

aagcattggc acctgataat cctcca                                         266
```

-continued

<210> SEQ ID NO 698
<211> LENGTH: 398
<212> TYPE: DNA
<213> ORGANISM: Glycine max
<220> FEATURE:
<223> OTHER INFORMATION: unsure at all n locations

<400> SEQUENCE: 698
gaataaatgg ttaaggcaaa aaggattacg gtgataagga ataatcctgc acctttgctg 60
gctttatgtt ggtattgggc tacagatggt gtaggatcaa aagatatggt tatccttcca 120
tataaggaca gcttgttatt atttagtaga tacttgcaac agttggtcat ggaatctcta 180
agcaaggagt ttgacttgaa tggtaatcgg gttaatcaag gaattagtgt ctatggaaat 240
aaaggaagca cagatcagca tgcctacatt cagcaactga nggaaggtgt gcacaatttt 300
tttgtgacat tcattgangt gctacgcgat agaccacctg gtcatgattg ggagcttgaa 360
caagtgtcac atgtggtgac tacctgtttg gtatgcta 398

<210> SEQ ID NO 699
<211> LENGTH: 362
<212> TYPE: DNA
<213> ORGANISM: Glycine max

<400> SEQUENCE: 699
gttggagaag ggcgcgatcg cgaatcccga tgagagtcgc atggtgggac actattggct 60
gagggaccct aagcgtgcgc ccaactcgtt ccttaaaacg cagattgaga acactctcga 120
cgctgtttgc aagttcgcta acgacgtcgt tagtggtaag attaagcctc cttcgtctcc 180
ggagggtcga tttactcaaa tattgtctgt gggaattgga agttctgctc ttggaccaca 240
gtttgttgca gaagcattgg cacctgataa tcctccactc aagataagat ttgtggacaa 300
cacggatcct gctggaattg atcatcagat tgcacaactt gggcctgagc tagcttcaac 360
ac 362